US008715971B2

(12) United States Patent
Pharkya et al.

(10) Patent No.: US 8,715,971 B2
(45) Date of Patent: May 6, 2014

(54) MICROORGANISMS AND METHODS FOR THE CO-PRODUCTION OF ISOPROPANOL AND 1,4-BUTANEDIOL

(75) Inventors: Priti Pharkya, San Diego, CA (US); Anthony P. Burgard, Bellefonte, PA (US); Robin E. Osterhout, San Diego, CA (US); Mark J. Burk, San Diego, CA (US); Jun Sun, San Diego, CA (US)

(73) Assignee: Genomatica, Inc., San Diego, CA (US)

( * ) Notice: Subject to any disclaimer, the term of this patent is extended or adjusted under 35 U.S.C. 154(b) by 517 days.

(21) Appl. No.: 12/878,980

(22) Filed: Sep. 9, 2010

(65) Prior Publication Data

US 2011/0201068 A1 Aug. 18, 2011

Related U.S. Application Data

(60) Provisional application No. 61/240,959, filed on Sep. 9, 2009, provisional application No. 61/254,650, filed on Oct. 23, 2009.

(51) Int. Cl.
*C12P 7/04* (2006.01)

(52) U.S. Cl.
USPC ........ 435/136; 435/158; 435/146; 435/320.1; 435/69.1

(58) Field of Classification Search
None
See application file for complete search history.

(56) References Cited

U.S. PATENT DOCUMENTS

| | | |
|---|---|---|
| 3,513,209 A | 5/1970 | Clement |
| 3,912,586 A | 10/1975 | Kaneyuki et al. |
| 3,965,182 A | 6/1976 | Worrel |
| 4,048,196 A | 9/1977 | Broecker et al. |
| 4,082,788 A | 4/1978 | Mims |
| 4,167,583 A | 9/1979 | Knott et al. |
| 4,190,495 A | 2/1980 | Curtiss |
| 4,301,077 A | 11/1981 | Pesa et al. |
| 4,624,920 A | 11/1986 | Inoue et al. |
| 4,652,685 A | 3/1987 | Cawse et al. |
| 4,871,667 A | 10/1989 | Imada et al. |
| 5,079,143 A | 1/1992 | Klein et al. |
| 5,143,833 A | 9/1992 | Datta |
| 5,143,834 A | 9/1992 | Glassner et al. |
| 5,168,055 A | 12/1992 | Datta et al. |
| 5,173,429 A | 12/1992 | Gaddy et al. |
| 5,182,199 A | 1/1993 | Hartley |
| 5,192,673 A | 3/1993 | Jain et al. |
| 5,403,721 A | 4/1995 | Ward, Jr. et al. |
| 5,413,922 A | 5/1995 | Matsuyama et al. |
| 5,416,020 A | 5/1995 | Severson et al. |
| 5,457,040 A | 10/1995 | Jarry et al. |
| 5,478,952 A | 12/1995 | Schwartz |
| 5,487,987 A | 1/1996 | Frost et al. |
| 5,504,004 A | 4/1996 | Guettler et al. |
| 5,521,075 A | 5/1996 | Guettler et al. |
| 5,573,931 A | 11/1996 | Guettler et al. |
| 5,616,496 A | 4/1997 | Frost et al. |
| 5,686,276 A | 11/1997 | Lafend et al. |
| 5,700,934 A | 12/1997 | Wolters et al. |
| 5,770,435 A | 6/1998 | Donnelly et al. |
| 5,807,722 A | 9/1998 | Gaddy et al. |
| 5,869,301 A | 2/1999 | Nghiem et al. |
| 5,908,924 A | 6/1999 | Burdette et al. |
| 5,958,745 A | 9/1999 | Gruys et al. |
| 6,117,658 A | 9/2000 | Dennis et al. |
| 6,133,014 A | 10/2000 | Mukouyama et al. |
| 6,136,577 A | 10/2000 | Gaddy et al. |
| 6,159,738 A | 12/2000 | Donnelly et al. |
| 6,194,572 B1 | 2/2001 | Buijs et al. |
| 6,214,592 B1 | 4/2001 | Crouzet et al. |
| 6,274,790 B1 | 8/2001 | Kunst et al. |
| 6,280,986 B1 | 8/2001 | Hespell et al. |
| RE37,393 E | 9/2001 | Donnelly et al. |
| 6,340,581 B1 | 1/2002 | Gaddy et al. |
| 6,353,100 B1 | 3/2002 | Guit et al. |
| 6,432,686 B1 * | 8/2002 | Bulthuis et al. ............... 435/158 |
| 6,448,061 B1 | 9/2002 | Pan et al. |
| 6,455,284 B1 | 9/2002 | Gokarn et al. |
| 6,485,947 B1 | 11/2002 | Rajgarhia et al. |

(Continued)

FOREIGN PATENT DOCUMENTS

| | | |
|---|---|---|
| CN | 1 358 841 | 7/2002 |
| EP | 0 494 078 | 7/1992 |

(Continued)

OTHER PUBLICATIONS

Pharkya et al. (Metabolic Engin., vol. 8 pp. 1-13, 2006).*

(Continued)

*Primary Examiner* — Hope Robinson
(74) *Attorney, Agent, or Firm* — Jones Day

(57) ABSTRACT

The invention provides a non-naturally occurring microbial organism having n-propanol and isopropanol pathways, 1,4-butanediol (14-BDO) and isopropanol pathways, 1,3-butanediol (13-BDO) and isopropanol pathways or methylacrylic acid (MAA) and isopropanolpathways. The microbial organism contains at least one exogenous nucleic acid encoding an enzyme in each of the respective n-propanol, 14-BDO, 13-BDO or MAA and isopropanol pathways. The invention additionally provides a method for co-producing n-propanol and isopropanol, 14-BDO and isopropanol, 13-BDO and isopropanol or MAA and isopropanol. The method can include culturing an n-propanol and an isopropanol co-producing microbial organism, where the microbial organism expresses at least one exogenous nucleic acid encoding an n-propanol, an isopropanol, a 14-BDO, a 13-BDO and/or a MAA pathway enzyme in a sufficient amount to produce each of the respective products, under conditions and for a sufficient period of time to produce each of the respective products.

28 Claims, 8 Drawing Sheets

(56) References Cited

U.S. PATENT DOCUMENTS

| | | | |
|---|---|---|---|
| 6,660,857 B2 | 12/2003 | Agterberg et al. | |
| 6,686,194 B1 | 2/2004 | Mutzel et al. | |
| 6,686,310 B1 | 2/2004 | Kourtakis et al. | |
| 6,743,610 B2 | 6/2004 | Donnelly et al. | |
| 6,852,517 B1 | 2/2005 | Suthers et al. | |
| 6,897,055 B2 * | 5/2005 | Mockel et al. | 435/194 |
| 7,127,379 B2 | 10/2006 | Palsson et al. | |
| 7,186,541 B2 | 3/2007 | Gokarn et al. | |
| 7,223,567 B2 | 5/2007 | Ka-Yiu et al. | |
| 7,241,594 B2 | 7/2007 | Lee et al. | |
| 7,244,610 B2 | 7/2007 | San et al. | |
| 7,256,016 B2 | 8/2007 | San et al. | |
| 7,262,046 B2 | 8/2007 | Ka-Yiu et al. | |
| 7,285,402 B2 | 10/2007 | Gaddy et al. | |
| 7,309,597 B2 | 12/2007 | Liao et al. | |
| 7,371,558 B2 | 5/2008 | Cervin et al. | |
| 7,393,676 B2 | 7/2008 | Gokarn et al. | |
| 7,432,091 B2 | 10/2008 | Yukawa et al. | |
| 7,491,520 B2 | 2/2009 | Raemakers-Franken et al. | |
| 7,569,380 B2 | 8/2009 | San et al. | |
| 7,858,350 B2 | 12/2010 | Burk et al. | |
| 7,947,483 B2 | 5/2011 | Burgard et al. | |
| 8,067,214 B2 * | 11/2011 | Burk et al. | 435/158 |
| 8,129,155 B2 * | 3/2012 | Trawick et al. | 435/146 |
| 2002/0012939 A1 | 1/2002 | Palsson | |
| 2002/0040123 A1 | 4/2002 | Patil et al. | |
| 2002/0106358 A1 | 8/2002 | Hopwood et al. | |
| 2002/0168654 A1 | 11/2002 | Maranas et al. | |
| 2003/0028915 A1 | 2/2003 | Tilton et al. | |
| 2003/0059792 A1 | 3/2003 | Palsson et al. | |
| 2003/0087381 A1 | 5/2003 | Gokarn et al. | |
| 2003/0113886 A1 | 6/2003 | Brzostowicz et al. | |
| 2003/0182678 A1 | 9/2003 | Mitsky et al. | |
| 2003/0224363 A1 | 12/2003 | Park et al. | |
| 2003/0233218 A1 | 12/2003 | Schilling | |
| 2004/0009466 A1 | 1/2004 | Maranas et al. | |
| 2004/0029149 A1 | 2/2004 | Palsson et al. | |
| 2004/0072723 A1 | 4/2004 | Palsson et al. | |
| 2004/0096946 A1 | 5/2004 | Kealey et al. | |
| 2004/0152159 A1 | 8/2004 | Causey et al. | |
| 2005/0042736 A1 | 2/2005 | San et al. | |
| 2005/0079482 A1 | 4/2005 | Maranas et al. | |
| 2005/0250135 A1 | 11/2005 | Klaenhammer et al. | |
| 2005/0287655 A1 | 12/2005 | Tabata et al. | |
| 2006/0035348 A1 | 2/2006 | Gulevich et al. | |
| 2006/0073577 A1 | 4/2006 | Ka-Yiu et al. | |
| 2006/0099578 A1 | 5/2006 | Wallace et al. | |
| 2006/0110810 A1 | 5/2006 | Rajgarhia et al. | |
| 2006/0172399 A1 | 8/2006 | Nomoto et al. | |
| 2006/0281156 A1 | 12/2006 | Aoyama et al. | |
| 2007/0042476 A1 | 2/2007 | Lee et al. | |
| 2007/0072279 A1 | 3/2007 | Meynial-Salles et al. | |
| 2007/0087425 A1 | 4/2007 | Ohto | |
| 2007/0092957 A1 | 4/2007 | Donaldson et al. | |
| 2007/0111294 A1 | 5/2007 | Burgard et al. | |
| 2007/0117191 A1 | 5/2007 | Kamachi et al. | |
| 2007/0184539 A1 | 8/2007 | San et al. | |
| 2007/0190605 A1 | 8/2007 | Bessler et al. | |
| 2007/0259410 A1 | 11/2007 | Donaldson et al. | |
| 2008/0138870 A1 | 6/2008 | Bramucci et al. | |
| 2008/0171371 A1 | 7/2008 | Yukawa et al. | |
| 2008/0182308 A1 | 7/2008 | Donaldson et al. | |
| 2008/0274522 A1 | 11/2008 | Bramucci et al. | |
| 2008/0293125 A1 | 11/2008 | Subbian et al. | |
| 2009/0047718 A1 | 2/2009 | Blaschek et al. | |
| 2009/0047719 A1 | 2/2009 | Burgard et al. | |
| 2009/0068207 A1 | 3/2009 | Breitbart et al. | |
| 2009/0075351 A1 | 3/2009 | Burk et al. | |
| 2009/0081746 A1 | 3/2009 | Liao et al. | |
| 2009/0305364 A1 | 12/2009 | Burgard et al. | |
| 2010/0009419 A1 | 1/2010 | Burk et al. | |
| 2010/0099925 A1 | 4/2010 | Kharas | |
| 2011/0217742 A1 * | 9/2011 | Sun et al. | 435/126 |

FOREIGN PATENT DOCUMENTS

| | | |
|---|---|---|
| EP | 1 473 368 | 11/2004 |
| EP | 2 017 344 | 1/2009 |
| GB | 1230276 | 4/1971 |
| GB | 1314126 | 4/1973 |
| GB | 1344557 | 1/1974 |
| GB | 1512751 | 6/1978 |
| JP | 50 006776 | 1/1975 |
| WO | WO 82/03854 | 11/1982 |
| WO | WO 91/13997 | 9/1991 |
| WO | WO 99/06532 | 2/1999 |
| WO | WO 99/58686 | 11/1999 |
| WO | WO 00/61763 | 4/2000 |
| WO | WO 01/16346 | 3/2001 |
| WO | WO 02/61115 | 1/2002 |
| WO | WO 02/42418 | 5/2002 |
| WO | WO 02/055995 | 7/2002 |
| WO | WO 02/090312 | 11/2002 |
| WO | WO 03/010322 | 2/2003 |
| WO | WO 03/106691 | 12/2003 |
| WO | WO 03/106998 | 12/2003 |
| WO | WO 2005/026338 | 3/2005 |
| WO | WO 2005/047498 | 5/2005 |
| WO | WO 2005/068643 | 7/2005 |
| WO | WO 2006/028063 | 3/2006 |
| WO | WO 2006/031424 | 3/2006 |
| WO | WO 2006/034156 | 3/2006 |
| WO | WO 2007/001982 | 1/2007 |
| WO | WO 2007/030830 | 3/2007 |
| WO | WO 2007/141208 | 12/2007 |
| WO | WO 2008/018930 | 2/2008 |
| WO | WO 2008/024023 | 2/2008 |
| WO | WO 2008/027742 | 3/2008 |
| WO | WO 2008/115840 | 3/2008 |
| WO | WO 2008/080124 | 7/2008 |
| WO | WO 2008/131286 | 10/2008 |
| WO | WO 2008/137403 | 11/2008 |
| WO | WO 2008/152016 | 12/2008 |
| WO | WO 2009/014437 | 1/2009 |
| WO | WO 2009/023493 | 2/2009 |
| WO | WO 2009/028582 | 3/2009 |
| WO | WO 2009/031766 | 3/2009 |
| WO | WO 2009/049274 A2 | 4/2009 |
| WO | WO 2009/094485 A1 | 7/2009 |
| WO | WO 2009/103026 | 8/2009 |
| WO | WO 2009/113853 | 9/2009 |
| WO | WO 2009/113855 | 9/2009 |
| WO | WO 2009/131040 | 10/2009 |

OTHER PUBLICATIONS

Steinbuchel et al. (Biochem. Engin. Journal, vol. 16, 2003, pp. 81-96).*

Hartmanis, "Butyrate kinase from *Clostridium acetobutylicum*," J. Biol. Chem. 262(2):617-621 (1987).

Hugler et al., "Characterization of acetyl-CoA/propionyl-CoA carboxylase in *Metallosphaera sedula*. Carboxylating enzyme in the 3-hydroxypropionate cycle for autotrophic carbon fixation," Eur. J. Biochem. 270(4):736-744 (2003).

Mahadevan et al., "Applications of metabolic modeling to drive bioprocess development for the production of value-added chemicals," Biotechnology and Bioprocess Engineering, Korean Society for Biotechnology and Bioengineering, 10(5):408-417 (2005).

Przybyla-Zawislak et al., "Genes of succinyl-CoA ligase from *Saccharomyces cerevisiae*," Eur. J. Biochem. 258(2):736-743 (1998).

Valentin et al., Journal of Biotechnology, 58:33-38 (1997).

Genbank Accession No. 2QM8_B; GI No. 158430328; Date (Sep. 24, 2008).

Genbank Accession No. AAA23199.2; GI No. 60592974; Date (Mar. 9, 2005).

Genbank Accession No. AAA25892.1; GI No. 151363; Date (Apr. 26, 1993).

Genbank Accession No. AAA34747.1; GI No. 171867; Date (Feb. 12, 2001).

Genbank Accession No. AAA80209; GI No. 687645; Date (Oct. 27, 1995).

(56) References Cited

OTHER PUBLICATIONS

Genbank Accession No. AAB49996.1; GI No. 1899206; Date (Mar. 21, 1997).
Genbank Accession No. AAB58883.2; GI No. 28572162; Date (Feb. 27, 2003).
Genbank Accession No. AAB94931.2; GI No. 157954625; Date (Jun. 20, 2008).
Genbank Accession No. AAB94932.1; GI No. 2746736; Date (Jun. 20, 2008).
Genbank Accession No. AACO2241.1; GI No. 2853226; Date (Jan. 30, 2001).
Genbank Accession No. AAC08713.1; GI No. 3002492; Date (Mar. 31, 1998).
Genbank Accession No. AAC24333.2; GI No. 22711873; Date (Feb. 2, 2005).
Genbank Accession No. AAC25556.1; GI No. 3288810; Date (Jul. 20, 2004).
Genbank Accession No. AAC37147.1; GI No. 141776; Date (Jun. 27, 2003).
Genbank Accession No. AAC45217.1; GI No. 1684886; Date (Dec. 20, 2007).
Genbank Accession No. AAC73823.1; GI No. 1786949; Date (Jul. 28, 2009).
Genbank Accession No. AAC75955.1; GI No. 1789285; Date (Apr. 13, 2009).
Genbank Accession No. AAC76152.1; GI No. 1789505; Date (Jul. 28, 2009).
Genbank Accession No. AAC77492.1; GI No. 1790207; Date (Jul. 28, 2009).
Genbank Accession No. AAD38039.1; GI No. 5020215; Date (Mar. 30, 2000).
Genbank Accession No. AAF89840.1; GI No. 9622535; Date (Aug. 1, 2000).
Genbank Accession No. AAF89841.1; GI No. 9622536; Date (Aug. 1, 2000).
Genbank Accession No. AAK09379.1; GI No. 12958626; Date (Jan. 17, 2002).
Genbank Accession No. AAL26884.1; GI No. 16588720; Date (Nov. 2, 2001).
Genbank Accession No. AAL47820.2; GI No. 29126583; Date (Mar. 20, 2003).
Genbank Accession No. AAL57846.1; GI No. 18042135; Date (Jan. 3, 2002).
Genbank Accession No. AAM21208.1; GI No. 20385191; Date (May 2, 2002).
Genbank Accession No. AAN69545.1; GI No. 24985644; Date (Jan. 10, 2006).
Genbank Accession No. AAO26020.1; GI No. 28136195; Date (Jul. 30, 2003).
Genbank Accession No. AAP08811.1; GI No. 29895524; Date (Mar. 8, 2005).
Genbank Accession No. AAP09256.1; GI No. 29895975; Date (Dec. 30, 2005).
Genbank Accession No. AAP42563.1; GI No. 31075383; Date (Jan. 24, 2007).
Genbank Accession No. AAP42564.1; GI No. 31075384; Date (Jan. 24, 2007).
Genbank Accession No. AAP42565.1; GI No. 31075385; Date (Jan. 24, 2007).
Genbank Accession No. AAP42566.1; GI No. 31075386; Date (Jan. 24, 2007).
Genbank Accession No. AAR19757.1; GI No. 38425288; Date (Mar. 18, 2004).
Genbank Accession No. AAR91477.1; GI No. 40795502; Date (May 27, 2008).
Genbank Accession No. AAR91681.1; GI No. 40796035; Date (Mar. 9, 2004).
Genbank Accession No. AAS20429.1; GI No. 42561982; Date (Feb. 22, 2004).
Genbank Accession No. AAS49166.1; GI No. 44921617; Date (Dec. 27, 2004).
Genbank Accession No. AAT66436.1; GI No. 49473535; Date (Apr. 26, 2006).
Genbank Accession No. AAT92095.1; GI No. 51011368; Date (Mar. 8, 2005).
Genbank Accession No. AAU45405.1; GI No. 52421824; Date (Sep. 27, 2004).
Genbank Accession No. AAU45406.1; GI No. 52421825; Date (Sep. 27, 2004).
Genbank Accession No. AAV66076.1; GI No. 55818563; Date (Jun. 8, 2005).
Genbank Accession No. AAX19660.1; GI No. 60396828; Date (Jan. 5, 2007).
Genbank Accession No. ABB53270.1; GI No. 80973080; Date (Jun. 29, 2007).
Genbank Accession No. ABC88407.1; GI No. 86278275; Date (Aug. 18, 2006).
Genbank Accession No. ABC88408.1; GI No. 86278276; Date (Aug. 18, 2006).
Genbank Accession No. ABC88409.1; GI No. 86278277; Date (Aug. 18, 2006).
Genbank Accession No. ABF82233.1; GI No. 106636093; Date (Aug. 2, 2007).
Genbank Accession No. ABF82234.1; GI No. 106636094; Date (Aug. 2, 2007).
Genbank Accession No. ABI83656.1; GI No. 114848891; Date (Jan. 3, 2007).
Genbank Accession No. ABN80423.1; GI No. 126202187; Date (Oct. 9, 2007).
Genbank Accession No. ABR34203.1; GI No. 149903370; Date (Jun. 27, 2007).
Genbank Accession No. ABS19624.1; GI No. 152002983; Date (Jul. 21, 2007).
Genbank Accession No. ABW05543.1; GI No. 157954626; Date (Jun. 20, 2008).
Genbank Accession No. ABW05544.1; GI No. 157954627; Date (Jun. 20, 2008).
Genbank Accession No. ABW05545.1; GI No. 157954628; Date (Jun. 20, 2008).
Genbank Accession No. ABW05546.1; GI No. 157954629; Date (Jun. 20, 2008).
Genbank Accession No. ABW05547.1; GI No. 157954630; Date (Jun. 20, 2008).
Genbank Accession No. ABW05548.1; GI No. 157954631; Date (Jun. 20, 2008).
Genbank Accession No. ABX24358.1; GI No. 160867735; Date (Jan. 15, 2008).
Genbank Accession No. BAA03892.1; GI No. 425213; Date (Feb. 16, 2008).
Genbank Accession No. BAA09085.1; GI No. 1129082; Date (Feb. 10, 1999).
Genbank Accession No. BAB12273.1; GI No. 9967138; Date (Mar. 18, 2005).
Genbank Accession No. BAB85476.1; GI No. 18857901; Date (Mar. 18, 2005).
Genbank Accession No. BAC55867.1; GI No. 27877097; Date (Dec. 3, 2003).
Genbank Accession No. BAC55868.1; GI No. 27877098; Date (Dec. 3, 2003).
Genbank Accession No. BAC55869.1; GI No. 27877099; Date (Dec. 3, 2003).
Genbank Accession No. CAA03993.1; GI No. 2407931; Date (Apr. 15, 2005).
Genbank Accession No. CAA05137.1; GI No. 2706398; Date (Apr. 15, 2005).
Genbank Accession No. CAA05138.1; GI No. 2706399; Date (Apr. 15, 2005).
Genbank Accession No. CAA05139.1; GI No. 2706400; Date (Apr. 15, 2005).
Genbank Accession No. CAA05140.1; GI No. 2706401; Date (Apr. 15, 2005).

(56) References Cited

OTHER PUBLICATIONS

Genbank Accession No. CAA15502.1; GI No. 3191970; Date (Jan. 13, 2009).
Genbank Accession No. CAA57199.1; GI No. 559392; Date (Mar. 22, 1995).
Genbank Accession No. CAA57200.1; GI No. 559393; Date (Mar. 22, 1995).
Genbank Accession No. CAA70873.1; GI No. 1770208; Date (Sep. 26, 1997).
Genbank Accession No. CAA74300.1; GI No. 3282044; Date (Nov. 14, 2006).
Genbank Accession No. CAA80872.1; GI No. 415915; Date (Apr. 18, 2005).
Genbank Accession No. CAA80873.1; GI No. 415916; Date (Apr. 18, 2005).
Genbank Accession No. CAA80874.1; GI No. 415917; Date (Apr. 18, 2005).
Genbank Accession No. CAA80875.1; GI No. 415918; Date (Apr. 18, 2005).
Genbank Accession No. CAA80876.1; GI No. 415919; Date (Apr. 18, 2005).
Genbank Accession No. CAB40912.1; GI No. 4585853; Date (Apr. 15, 2005).
Genbank Accession No. CAB59633.1; GI No. 6137077; Date (Apr. 15, 2005).
Genbank Accession No. CAB77207.1; GI No. 7242549; Date (Feb. 12, 2002).
Genbank Accession No. CAC07932.1; GI No. 10046659; Date (Jun. 9, 2001).
Genbank Accession No. CAD36475.1; GI No. 21615553; Date (Apr. 15, 2005).
Genbank Accession No. CAE29158.1; GI No. 39650635; Date (Apr. 17, 2005).
Genbank Accession No. CAJ15517.1; GI No. 77019264; Date (Nov. 14, 2006).
Genbank Accession No. CAQ53135.1; GI No. 188027001; Date (May 13, 2008).
Genbank Accession No. EDK33306.1; GI No. 146346770; Date (Feb. 21, 2008).
Genbank Accession No. EDK33307.1; GI No. 146346771; Date (Feb. 21, 2008).
Genbank Accession No. EDK33308.1; GI No. 146346772; Date (Feb. 21, 2008).
Genbank Accession No. EDK33309.1; GI No. 146346773; Date (Feb. 21, 2008).
Genbank Accession No. EDK33310.1; GI No. 146346774; Date (Feb. 21, 2008).
Genbank Accession No. EDK333 11.1; GI No. 146346775; Date (Feb. 21, 2008).
Genbank Accession No. EDK33432.1; GI No. 146346896; Date (Feb. 21, 2008).
Genbank Accession No. EDK35022.1; GI No. 146348486; Date (Feb. 21, 2008).
Genbank Accession No. EDK35586.1; GI No. 146349050; Date (Feb. 21, 2008).
Genbank Accession No. EDP09457.1; GI No. 158283707; Date (Nov. 21, 2007).
Genbank Accession No. EDR98937.1; GI No. 167654808; Date (Feb. 12, 2008).
Genbank Accession No. JC7926; GI No. 60729613; Date (Jul. 14, 2003).
Genbank Accession No. L21902.1; GI No. 146348486; Date (Mar. 15, 1996).
Genbank Accession No. NP_000427.1; GI No. 4557817; Date (Apr. 11, 2009).
Genbank Accession No. NP_000700.1; GI No. 11386135; Date (Oct. 22. 2008).
Genbank Accession No. NP_001004072.2; GI No. 124430510; Date (Mar. 11, 2009).
Genbank Accession No. NP_001020377.2; GI No. 70778822; Date (Jun. 18, 2009).
Genbank Accession No. NP_001099811.1; GI No. 157821869; Date (Aug. 5, 2008).
Genbank Accession No. NP_009362.1; GI No. 6319279; Date (Jun. 16, 2008).
Genbank Accession No. NP_009538.1; GI No. 6319456; Date (Jun. 16, 2008).
Genbank Accession No. NP_009777.1; GI No. 6319695; Date (Jun. 16, 2008).
Genbank Accession No. NP_009780; GI No. 6319698; Date (Jun. 16, 2008).
Genbank Accession No. NP_010140.1; GI No. 6320060; Date (Jun. 16, 2008).
Genbank Accession No. NP_010205.1; GI No. 6320125; Date (Jun. 16. 2008).
Genbank Accession No. NP_010992.1; GI No. 6320913; Date (Jun. 16, 2008).
Genbank Accession No. NP_011105.2; GI No. 37362644; Date (Jun. 16, 2008).
Genbank Accession No. NP_011453.1; GI No. 6321376; Date (Jun. 16, 2008).
Genbank Accession No. NP_011709.1; GI No. 6321632; Date (Jun. 16, 2008).
Genbank Accession No. NP_011760.1; GI No. 6321683; Date (Jun. 16, 2008).
Genbank Accession No. NP_012585.1; GI No. 6322511; Date (Jun. 16, 2008).
Genbank Accession No. NP_012838.1; GI No. 6322765; Date (Jun. 16, 2008).
Genbank Accession No. NP_013023.1; GI No. 6322950; Date (Jun. 16, 2008).
Genbank Accession No. NP_013934.1; GI No. 6323863; Date (Jun. 16, 2008).
Genbank Accession No. NP_014032.1; GI No. 6323961; Date (Jun. 16, 2008).
Genbank Accession No. NP_014328.1; GI No. 6324258; Date (Jun. 16, 2008).
Genbank Accession No. NP_014413.1; GI No. 6324343; Date (Jun. 16, 2008).
Genbank Accession No. NP_014515.2; GI No. 116006499; Date (Jun. 16, 2008).
Genbank Accession No. NP_014785.1; GI No. 6324716; Date (Jun. 16, 2008).
Genbank Accession No. NP_014992.1; GI No. 6324923; Date (Jun. 16, 2008).
Genbank Accession No. NP_015033.1; GI No. 6324964; Date (Jun. 16, 2008).
Genbank Accession No. NP_015061.1; GI No. 6324993; Date (Jun. 16, 2008).
Genbank Accession No. NP_015297.1; GI No. 6325229; Date (Jun. 16, 2008).
Genbank Accession No. NP_070039.1; GI No. 11498810; Date (Apr. 27, 2009).
Genbank Accession No. NP_070807.1; GI No. 11499565; Date (Mar. 26, 2008).
Genbank Accession No. NP_071403.1; GI No. 11545841; Date (May 17, 2009).
Genbank Accession No. NP_076417.2; GI No. 31982927; Date (Oct. 22, 2008).
Genbank Accession No. NP_084486.1; GI No. 21313520; Date (Dec. 28, 2008).
Genbank Accession No. NP_105204.1; GI No. 13473636; Date (Apr. 27, 2009).
Genbank Accession No. NP_112287.1; GI No. 78365255; Date (Oct. 28, 2008).
Genbank Accession No. NP_116635.1; GI No. 14318501; Date (Jun. 16, 2008).
Genbank Accession No. NP_149242.1; GI No. 15004782; Date (Apr. 26, 2009).
Genbank Accession No. NP_149326.1; GI No. 15004866; Date (Jul. 22, 2008).

(56) References Cited

OTHER PUBLICATIONS

Genbank Accession No. NP_149327.1; GI No. 15004867; Date (Apr. 26, 2009).
Genbank Accession No. NP_149328.1; GI No. 15004868; Date (Apr. 26, 2009).
Genbank Accession No. NP_207955.1; GI No. 15645778; Date (Apr. 24, 2009).
Genbank Accession No. NP_231670.1; GI No. 15642038; Date (Apr. 25, 2009).
Genbank Accession No. NP_249708.1; GI No. 15596214; Date (Apr. 26, 2009).
Genbank Accession No. NP_252259.1; GI No. 15598765; Date (Jun. 24, 2009).
Genbank Accession No. NP_343563.1; GI No. 15898958; Date (Apr. 26, 2009).
Genbank Accession No. NP_344510.1; GI No. 15899905; Date (Apr. 26, 2009).
Genbank Accession No. NP_347346.1; GI No. 15893997; Date (Apr. 26, 2009).
Genbank Accession No. NP_349318.1; GI No. 15895969; Date (Apr. 26, 2009).
Genbank Accession No. NP_349476.1; GI No. 15896127; Date (Apr. 26, 2009).
Genbank Accession No. NP_349675; GI No. 15896326; Date (Apr. 26, 2009).
Genbank Accession No. NP_349676.1; GI No. 34540484; Date (Dec. 4, 2007).
Genbank Accession No. NP_349891.1; GI No. 15896542; Date (Apr. 26, 2009).
Genbank Accession No. NP_349892.1; GI No. 15896543; Date (Apr. 26, 2009).
Genbank Accession No. NP_350239.1; GI No. 15896890; Date (Apr. 26, 2009).
Genbank Accession No. NP_376364.1; GI No. 15920695; Date (Apr. 26, 2009).
Genbank Accession No. NP_376686.1; GI No. 15921017; Date (Apr. 26, 2009).
Genbank Accession No. NP_378167.1; GI No. 15922498; Date (May 1, 2009).
Genbank Accession No. NP_389001.1; GI No. 16078184; Date (Apr. 25, 2009).
Genbank Accession No. NP_390273.2; GI No. 255767522; Date (Aug. 12, 2009).
Genbank Accession No. NP_390314.1; GI No. 16079490; Date (Apr. 25, 2009).
Genbank Accession No. NP_390315.1; GI No. 16079491; Date (Aug. 12, 2009).
Genbank Accession No. NP_390798.1; GI No. 16079972; Date (Apr. 25, 2009).
Genbank Accession No. NP_390799.1; GI No. 16079973; Date (Apr. 25, 2009).
Genbank Accession No. NP_390902.2; GI No. 50812281; Date (Apr. 25, 2009).
Genbank Accession No. NP_391777.1; GI No. 16080949; Date (Apr. 25, 2009).
Genbank Accession No. NP_391778.1; GI No. 16080950; Date (Apr. 25, 2009).
Genbank Accession No. NP_414656.1; GI No. 16128107; Date (Jul. 30, 2009).
Genbank Accession No. NP_414657.1; GI No. 16128108; Date (Jul. 30, 2009).
Genbank Accession No. NP_414658.1; GI No. 16128109; Date (Apr. 10, 2009).
Genbank Accession No. NP_414727.1; GI No. 16128178; Date (Jul. 30, 2009).
Genbank Accession No. NP_414777.1; GI No. 16128228; Date (Jul. 30, 2009).
Genbank Accession No. NP_414778.1; GI No. 16128229; Date (Apr. 10, 2009).
Genbank Accession No. NP_414986.1; GI No. 16128437; Date (May 8, 2009).
Genbank Accession No. NP_415027.1; GI No. 16128478; Date (Jul. 30, 2009).
Genbank Accession No. NP_415129.1; GI No. 16128580; Date (Jul. 30, 2009).
Genbank Accession No. NP_415256.1; GI No. 16128703; Date (Jul. 30, 2009).
Genbank Accession No. NP_415264.1; GI No. 16128711; Date (Jul. 30, 2009).
Genbank Accession No. NP_415423.1; GI No. 16128870; Date (Apr. 10, 2009).
Genbank Accession No. NP_415705.1; GI No. 16129150; Date (Apr. 10, 2009).
Genbank Accession No. NP_415757.1; GI No. 16129202; Date (Jul. 30, 2009).
Genbank Accession No. NP_415896.1; GI No. 16129339; Date (Jul. 30, 2009).
Genbank Accession No. NP_415905.1; GI No. 16129348; Date (Apr. 10, 2009).
Genbank Accession No. NP_415911.1; GI No. 16129354; Date (Apr. 10, 2009).
Genbank Accession No. NP_415912.1; GI No. 16129355; Date (Apr. 10, 2009).
Genbank Accession No. NP_415914.1; GI No. 16129357; Date (Jul. 30, 2009).
Genbank Accession No. NP_415991.1; GI No. 16129433; Date (Jul. 30, 2009).
Genbank Accession No. NP_415992.1; GI No. 16129434; Date (Jul. 30, 2009).
Genbank Accession No. NP_415993.1; GI No. 16129435; Date (Jul. 30, 2009).
Genbank Accession No. NP_416128.1; GI No. 16129569; Date (Apr. 10, 2009).
Genbank Accession No. NP_416129.1; GI No. 16129570; Date (Apr. 10, 2009).
Genbank Accession No. NP_416191.1; GI No. 16129632; Date (Apr. 10, 2009).
Genbank Accession No. NP_416293.1; GI No. 71159358; Date (Jul. 30, 2009).
Genbank Accession No. NP_416368.1; GI No. 16129807; Date (Apr. 10, 2009).
Genbank Accession No. NP_416728.1; GI No. 16130161; Date (Jul. 30, 2009).
Genbank Accession No. NP_416799.1; GI No. 16130231; Date (Apr. 10, 2009).
Genbank Accession No. NP_416819.1; GI No. 16130251; Date (Jul. 30, 2009).
Genbank Accession No. NP_416843.1; GI No. 16130274; Date (Apr. 10, 2009).
Genbank Accession No. NP_416844.1; GI No. 16130275; Date (Apr. 10, 2009).
Genbank Accession No. NP_417199.1; GI No. 16130626; Date (Jul. 30, 2009).
Genbank Accession No. NP_417200.1; GI No. 16130627; Date (Jul. 30, 2009).
Genbank Accession No. NP_417201.1; GI No. 16130628; Date (Jul. 30, 2009).
Genbank Accession No. NP_417202.1; GI No. 16130629; Date (Jul. 30, 2009).
Genbank Accession No. NP_417203.1; GI No. 16130630; Date (Jul. 30, 2009).
Genbank Accession No. NP_417204.1; GI No. 16130631; Date (Jul. 30, 2009).
Genbank Accession No. NP_417211.1; GI No. 16130638; Date (Jul. 30, 2009).
Genbank Accession No. NP_417392.1; GI No. 16130818; Date (Jul. 30, 2009).
Genbank Accession No. NP_417394.4; GI No. 90111512; Date (Apr. 10, 2009).
Genbank Accession No. NP_417395.1; GI No. 16130821; Date (Jul. 30, 2009).

(56) References Cited

OTHER PUBLICATIONS

Genbank Accession No. NP_417484.1; GI No. 16130909; Date (Jul. 30, 2009).
Genbank Accession No. NP_417703.1; GI No. 16131126; Date (Apr. 10, 2009).
Genbank Accession No. NP_417721.1; GI No. 16131143; Date (Jul. 30, 2009).
Genbank Accession No. NP_417722.1; GI No. 16131144; Date (Jul. 30, 2009).
Genbank Accession No. NP_417862.1; GI No. 16131280; Date (Apr. 10, 2009).
Genbank Accession No. NP_417891.1; GI No. 16131307; Date (Jul. 30, 2009).
Genbank Accession No. NP_418288.1; GI No. 16131692; Date (Apr. 10, 2009).
Genbank Accession No. NP_418328.1; GI No. 16131732; Date (May 8, 2009).
Genbank Accession No. NP_418329.1; GI No. 16131733; Date (Jul. 30, 2009).
Genbank Accession No. NP_418330.1; GI No. 16131734; Date (Jul. 30, 2009).
Genbank Accession No. NP_418391.1; GI No. 16131794; Date (Apr. 10, 2009).
Genbank Accession No. NP_418393.1; GI No. 16131796; Date (Apr. 10, 2009).
Genbank Accession No. NP_418448.1; GI No. 16131850; Date (Jul. 30, 2009).
Genbank Accession No. NP_418475.1; GI No. 16131877; Date (Jul. 30, 2009).
Genbank Accession No. NP_418503.1; GI No. 16131905; Date (Jul. 30, 2009).
Genbank Accession No. NP_418546.1; GI No. 16131948; Date (Apr. 10, 2009).
Genbank Accession No. NP_418576.1; GI No. 16131977; Date (Apr. 10, 2009).
Genbank Accession No. NP_418577.1; GI No. 16131978; Date (Apr. 10, 2009).
Genbank Accession No. NP_418578.1; GI No. 16131979; Date (Apr. 10, 2009).
Genbank Accession No. NP_446446.1; GI No. 16758900; Date (Mar. 11, 2009).
Genbank Accession No. NP_459319.1; GI No. 16763704; Date (Apr. 30, 2009).
Genbank Accession No. NP_560604.1; GI No. 18313937; Date (Apr. 24, 2009).
Genbank Accession No. NP_570103.1; GI No. 18543355; Date (Oct. 22, 2008).
Genbank Accession No. NP_570112.2; GI No. 51036669; Date (Oct. 24, 2008).
Genbank Accession No. NP_602656.1; GI No. 19705161; Date (Apr. 25, 2009).
Genbank Accession No. NP_602657.1; GI No. 19705162; Date (Apr. 25, 2009).
Genbank Accession No. NP_603179.1; GI No. 19703617; Date (Apr. 25, 2009).
Genbank Accession No. NP_603180.1; GI No. 19703618; Date (Apr. 25, 2009).
Genbank Accession No. NP_622378.1; GI No. 20807207; Date (Apr. 26, 2009).
Genbank Accession No. NP_622379.1; GI No. 20807208; Date (Apr. 26, 2009).
Genbank Accession No. NP_630775.1; GI No. 21224996; Date (Apr. 30, 2009).
Genbank Accession No. NP_630776.1; GI No. 21224997; Date (Apr. 30, 2009).
Genbank Accession No. NP_745426.1; GI No. 26990001; Date (Nov. 30, 2007).
Genbank Accession No. NP_745427.1; GI No. 26990002; Date (Nov. 30, 2007).
Genbank Accession No. NP_745498.1; GI No. 26990073; Date (Apr. 30, 2009).
Genbank Accession No. NP_746082.1; GI No. 26990657; Date (Apr. 30, 2009).
Genbank Accession No. NP_746775.1; GI No. 26991350; Date (Apr. 30, 2009).
Genbank Accession No. NP_767092.1; GI No. 27375563; Date (Apr. 25, 2009).
Genbank Accession No. NP_785996.1; GI No. 28379104; Date (Apr. 25, 2009).
Genbank Accession No. NP_824008.1; GI No. 29829374; Date (Apr. 25, 2009).
Genbank Accession No. NP_824637.1; GI No. 29830003; Date (Apr. 25, 2009).
Genbank Accession No. NP_838397.1; GI No. 30064226; Date (May 1, 2009).
Genbank Accession No. NP_898871.1; GI No. 34101272; Date (Mar. 28, 2009).
Genbank Accession No. NP_904963.1; GI No. 34540484; Date (Apr. 26, 2009).
Genbank Accession No. NP_905281.1; GI No. 34540802; Date (Apr. 26, 2009).
Genbank Accession No. NP_905290.1; GI No. 34540811; Date (Apr. 26, 2009).
Genbank Accession No. NP_955417.1; GI No. 40786469; Date (Apr. 5, 2009).
Genbank Accession No. NP_959974.1; GI No. 41407138; Date (Apr. 25, 2009).
Genbank Accession No. NP_961833.1; GI No. 41408997; Date (Apr. 25, 2009).
Genbank Accession No. O09460.1; GI No. 3122621; Date (Jun. 16, 2009).
Genbank Accession No. O50463.4; GI No. 160395583; Date (Mar. 3, 2009).
Genbank Accession No. O69294.1; GI No. 9789756; Date (Jan. 20, 2009).
Genbank Accession No. P00343.3; GI No. 126063; Date (May 5, 2009).
Genbank Accession No. P02904.1; GI No. 114847; Date (May 26, 2009).
Genbank Accession No. P05042.1; GI No. 120601; Date (Dec. 16, 2008).
Genbank Accession No. P06169.7; GI No. 30923172; Date (Jul. 28, 2009).
Genbank Accession No. P06672.1; GI No. 118391; Date (Jan. 20, 2009).
Genbank Accession No. P0A9B2.2; GI No. 71159358; Date (Jan. 20, 2009).
Genbank Accession No. P0A9M8.2; GI No. 71152910; Date (Jun. 16, 2009).
Genbank Accession No. P0AC33.2; GI No. 81175318; Date (Feb. 10, 2009).
Genbank Accession No. P11178.1; GI No. 129030; Date (Mar. 3, 2009).
Genbank Accession No. P11652.3; GI No. 127549; Date (Jun. 16, 2009).
Genbank Accession No. P11653.3; GI No. 127550; Date (Jun. 16, 2009).
Genbank Accession No. P14407.2; GI No. 33112655; Date (Feb. 10, 2009).
Genbank Accession No. P14408.1; GI No. 120605; Date (Mar. 3, 2009).
Genbank Accession No. P14941.1; GI No. 113443; Date (Jun. 16, 2009).
Genbank Accession No. P16115.2; GI No. 547837; Date (Mar. 3, 2009).
Genbank Accession No. P20906.2; GI No. 3915757; Date (Mar. 3, 2009).
Genbank Accession No. P21839.2; GI No. 115502434; Date (Jul. 28, 2009).
Genbank Accession No. P21880.1; GI No. 118672; Date (Mar. 3, 2009).

(56) References Cited

OTHER PUBLICATIONS

Genbank Accession No. P21881.3; GI No. 3123238; Date (Jun. 16, 2009).
Genbank Accession No. P21882.2; GI No. 129068; Date (Jan. 20, 2009).
Genbank Accession No. P21883.2; GI No. 129054; Date (Mar. 3, 2009).
Genbank Accession No. P22033.3; GI No. 67469281; Date (Jul. 28, 2009).
Genbank Accession No. P28811.1; GI No. 127211; Date (May 5, 2009).
Genbank Accession No. P28817.2; GI No. 2506374; Date (Jul. 28, 2009).
Genbank Accession No. P31937.2; GI No. 12643395; Date (Jul. 28, 2009).
Genbank Accession No. P32185.1; GI No. 416872; Date (Jun. 16, 2009).
Genbank Accession No. P32614.1; GI No. 418423; Date (May 5, 2009).
Genbank Accession No. P38942.2; GI No. 172046066; Date (Feb. 5, 2008).
Genbank Accession No. P38946.1; GI No. 729048; Date (Jun. 16, 2009).
Genbank Accession No. P38947.1; GI No. 172046062; Date (Feb. 5, 2008).
Genbank Accession No. P39646; GI No. 730415; Date (Jun. 16, 2009).
Genbank Accession No. P40976.3; GI No. 13124791; Date (Mar. 3, 2009).
Genbank Accession No. P43923.1; GI No. 1172573; Date (Jun. 16, 2009).
Genbank Accession No. P50113.1; GI No. 1708896; Date (Dec. 16, 2008).
Genbank Accession No. P52643.1; GI No. 1730102; Date (May 5, 2009).
Genbank Accession No. P53000.2; GI No. 9087222; Date (Jan. 20, 2009).
Genbank Accession No. P55792.3; GI No. 84028213; Date (Jan. 20, 2009).
Genbank Accession No. P76458.1; GI No. 2492990; Date (Jun. 16, 2009).
Genbank Accession No. P76459.1; GI No. 2492994; Date (Jun. 16, 2009).
Genbank Accession No. P77445.1; GI No. 2498347; Date (Jun. 16, 2009).
Genbank Accession No. P84067; GI No. 75345323; Date (Oct. 31, 2006).
Genbank Accession No. P84127; GI No. 75427690; Date (Oct. 31, 2006).
Genbank Accession No. Q08987.2; GI No. 88909613; Date (Jul. 28, 2009).
Genbank Accession No. Q10474.1; GI No. 1723561; Date (Nov. 25, 2008).
Genbank Accession No. Q12629.2; GI No. 52788279; Date (Jan. 20, 2009).
Genbank Accession No. Q220N6; GI No. 122479931; Date (Oct. 31, 2006).
Genbank Accession No. Q46MA6; GI No. 123621528; Date (Oct. 31, 2006).
Genbank Accession No. Q58673.1; GI No. 3122345; Date (Jan. 20, 2009).
Genbank Accession No. Q59477.1; GI No. 2842618; Date (Jun. 16, 2009).
Genbank Accession No. Q5XIE6.2; GI No. 146324906; Date (Jul. 28, 2009).
Genbank Accession No. Q6JH32; GI No. 74911026; Date (Nov. 28, 2006).
Genbank Accession No. Q6NVY1.2; GI No. 146324905; Date (Jul. 28, 2009).
Genbank Accession No. Q6TMA2; GI No. 75493131; Date (Nov. 28, 2006).
Genbank Accession No. Q6W6X5; GI No. 75440571; Date (Oct. 31, 2006).
Genbank Accession No. Q70AC7.1; GI No. 62901478; Date (Jan. 20, 2009).
Genbank Accession No. Q84FZ1; GI No. 75486201; Date (Nov. 28, 2006).
Genbank Accession No. Q8GBW6.3; GI No. 62901481; Date (May 26, 2009).
Genbank Accession No. Q8J2Z3; GI No. 74499802; Date (Oct. 31, 2006).
Genbank Accession No. Q8J2Z4; GI No. 74499032; Date (Nov. 28, 2006).
Genbank Accession No. Q8J2Z5; GI No. 74499033; Date (Nov. 14, 2006).
Genbank Accession No. Q94B07; GI No. 75249805; Date (Oct. 31, 2006).
Genbank Accession No. Q96PE7.1; GI No. 50401130; Date (Jul. 28, 2009).
Genbank Accession No. Q97I11.1; GI No. 20137415; Date (Jan. 20, 2009).
Genbank Accession No. Q9HUR2.1; GI No. 81539678; Date (Mar. 3, 2009).
Genbank Accession No. Q9L3F7; GI No. 75416255; Date (Oct. 31, 2006).
Genbank Accession No. Q9X0L4.1; GI No. 6685776; Date (Jun. 16, 2009).
Genbank Accession No. Q9X278.1; GI No. 6685256; Date (Jun. 16, 2009).
Genbank Accession No. XP_001330176.1; GI No. 123975034; Date (Nov. 1, 2008).
Genbank Accession No. XP_636931.1; GI No. 66806417; Date (Oct. 31, 2008).
Genbank Accession No. XP_828352.1; GI No. 71754875; Date (May 15, 2008).
Genbank Accession No. YP_001023546.1; GI No. 124263076; Date (Apr. 29, 2009).
Genbank Accession No. YP_001190808.1; GI No. 146303492; Date (Apr. 29, 2009).
Genbank Accession No. YP_001191508.1; GI No. 146304192; Date (Apr. 29, 2009).
Genbank Accession No. YP_001191537.1; GI No. 146304221; Date (Apr. 29, 2009).
Genbank Accession No. YP_001192065.1; GI No. 146304749; Date (Apr. 29, 2009).
Genbank Accession No. YP_001211906.1; GI No. 147677691; Date (Apr. 28, 2009).
Genbank Accession No. YP_001211907.1; GI No. 147677692; Date (Apr. 28, 2009).
Genbank Accession No. YP_001310906.1; GI No. 150018652; Date (May 7, 2009).
Genbank Accession No. YP_001311608.1; GI No. 150019354; Date (May 7, 2009).
Genbank Accession No. YP_001333808.1; GI No. 152968699; Date (May 1, 2009).
Genbank Accession No. YP_001333809.1; GI No. 152968700; Date (May 1, 2009).
Genbank Accession No. YP_001333810.1; GI No. 152968701; Date (May 1, 2009).
Genbank Accession No. YP_001393856.1; GI No. 153953091; Date (Apr. 29, 2009).
Genbank Accession No. YP_001396399.1; GI No. 153955634; Date (Apr. 29, 2009).
Genbank Accession No. YP_001433009.1; GI No. 156742880; Date (May 7, 2009).
Genbank Accession No. YP_001482096.1; GI No. 157414840; Date (Apr. 30, 2009).
Genbank Accession No. YP_001573497.1; GI No. 161506385; Date (Apr. 30, 2009).
Genbank Accession No. YP_001822177.1; GI No. 182434458; Date (Apr. 28, 2009).

(56) References Cited

OTHER PUBLICATIONS

Genbank Accession No. YP_001825755.1; GI No. 182438036; Date (Apr. 28, 2009).
Genbank Accession No. YP_001825756.1; GI No. 182438037; Date (Apr. 28, 2009).
Genbank Accession No. YP_001828302.1; GI No. 182440583; Date (Apr. 28, 2009).
Genbank Accession No. YP_001850220.1; GI No. 183981929; Date (Apr. 25, 2009).
Genbank Accession No. YP_001850422.1; GI No. 183982131; Date (Apr. 25, 2009).
Genbank Accession No. YP_001851230.1; GI No. 183982939; Date (Apr. 25, 2009).
Genbank Accession No. YP_001928843.1; GI No. 188994591; Date (Apr. 29, 2009).
Genbank Accession No. YP_002270763.1; GI No. 209397911; Date (Apr. 29, 2009).
Genbank Accession No. YP_002301787.1; GI No. 210135348; Date (Apr. 28, 2009).
Genbank Accession No. YP_002938937.1; GI No. 238925420; Date (Jun. 5, 2009).
Genbank Accession No. YP_026272.1; GI No. 49176430; Date (Apr. 10, 2009).
Genbank Accession No. YP_046368.1; GI No. 50084858; Date (Apr. 30, 2009).
Genbank Accession No. YP_047869.1; GI No. 50086359; Date (Apr. 30, 2009).
Genbank Accession No. YP_055310.1; GI No. 50842083; Date (May 1, 2009).
Genbank Accession No. YP_089485.1; GI No. 52426348; Date (Apr. 25, 2009).
Genbank Accession No. YP_118225.1; GI No. 54023983; Date (Apr. 25, 2009).
Genbank Accession No. YP_120266.1; GI No. 54026024; Date (Apr. 25, 2009).
Genbank Accession No. YP_135572.1; GI No. 55377722; Date (May 1, 2009).
Genbank Accession No. YP_158074.1; GI No. 56476485; Date (Apr. 24, 2009).
Genbank Accession No. YP_158075.1; GI No. 56476486; Date (Apr. 24, 2009).
Genbank Accession No. YP_162971.1; GI No. 56552132; Date (Apr. 25, 2009).
Genbank Accession No. YP_224801.1; GI No. 62389399; Date (Apr. 25, 2009).
Genbank Accession No. YP_226809.1; GI No. 62391407; Date (Apr. 25, 2009).
Genbank Accession No. YP_248335.1; GI No. 68249223; Date (Apr. 26, 2009).
Genbank Accession No. YP_255824.1; GI No. 70606954; Date (Apr. 27, 2009).
Genbank Accession No. YP_256941.1; GI No. 70608071; Date (Apr. 27, 2009).
Genbank Accession No. YP_260581.1; GI No. 70730840; Date (Apr. 25, 2009).
Genbank Accession No. YP_384480.1; GI No. 78222733; Date (Apr. 26, 2009).
Genbank Accession No. YP_384481.1; GI No. 78222734; Date (Apr. 26, 2009).
Genbank Accession No. YP_425738.1; GI No. 83591986; Date (May 1, 2009).
Genbank Accession No. YP_427961.1; GI No. 83594209; Date (May 1, 2009).
Genbank Accession No. YP_428946.1; GI No. 83588937; Date (Jul. 22, 2009).
Genbank Accession No. YP_431142.2; GI No. 148283121; Date (Jul. 22, 2009).
Genbank Accession no. YP_431143.1; GI No. 83591134; Date (Jul. 22, 2008).
Genbank Accession No. YP_431144.1; GI No. 83591135; Date (Jul. 22, 2009).
Genbank Accession No. YP_627417.1; GI No. 108563101; Date (Apr. 28, 2009).
Genbank Accession No. YP_627418.1; GI No. 108563102; Date (Apr. 28, 2009).
Genbank Accession No. YP_726053.1; GI No. 113867564; Date (May 7, 2009).
Genbank Accession No. YP_846816.1; GI No. 116750129; Date (Apr. 27, 2009).
Genbank Accession No. YP_846817.1; GI No. 116750130; Date (Apr. 27, 2009).
Genbank Accession No. YP_846818.1; GI No. 116750131; Date (Apr. 27, 2009).
Genbank Accession No. YP_846819.1; GI No. 116750132; Date (Apr. 27, 2009).
Genbank Accession No. YP_878441.1; GI No. 118444181; Date (Apr. 29, 2009).
Genbank Accession No. YP_878442.1; GI No. 118444701; Date (Apr. 29, 2009).
Genbank Accession No. YP_878445.1; GI No. 118444712; Date (Apr. 29, 2009).
Genbank Accession No. YP_886985.1; GI No. 118471293; Date (Apr. 25, 2009).
Genbank Accession No. YP_887275.1; GI No. 118473501; Date (Apr. 25, 2009).
Genbank Accession No. YP_889972.1; GI No. 118469671; Date (Apr. 25, 2009).
Genbank Accession No. YP_890857.1; GI No. 118470447; Date (Apr. 25, 2009).
Genbank Accession No. YP_978699.1; GI No. 121638475; Date (Apr. 29, 2009).
Genbank Accession No. YP_978898.1; GI No. 121638674; Date (Apr. 29, 2009).
Genbank Accession No. ZP_00830776.1; GI No. 77975240; Date (Oct. 20, 2005).
Genbank Accession No. ZP_01039179.1; GI No. 85708113; Date (Jan. 25, 2006).
Genbank Accession No. ZP_01626393.1; GI No. 119504313; Date (Dec. 15, 2006).
Genbank Accession No. ZP_02621214.1; GI No. 168186579; Date (Mar. 4, 2008).
Genbank Accession No. ZP_02621215.1; GI No. 168186580; Date (Mar. 4, 2008).
Genbank Accession No. ZP_02621218.1; GI No. 168186583; Date (Mar. 4, 2008).
Genbank Accession No. ZP_03755203.1; GI No. 225377982; Date (Mar. 19, 2009).
Genbank Accession No. ZP_03838384.1; GI No. 227334728; Date (May 1, 2009).
Genbank Accession No. ZP_04026660.1; GI No. 227979396; Date (Apr. 28, 2009).
Genbank Accession No. ZP_04027864.1; GI No. 227980601; Date (Apr. 28, 2009).
Genbank Accession No. ZP_04635364.1; GI No. 238791727; Date (Jun. 2, 2009).
Genbank Accession No. ZP_04743841.2; GI No. 257413684; Date (Jun. 18, 2009).
Genbank Accession No. ZP_05045132.1; GI No. 254431429; Date (Jul. 20, 2009).
Abadjieva et al., "The Yeast ARG7 Gene Product is Autoproteolyzed to Two Subunit Peptides, Yielding Active Ornithine Acetyltransferase," *J. Biol. Chem.* 275(15):11361-11367 (2000).
Abe et al., "Discovery of amide (peptide) bond synthetic activity in Acyl-CoA synthetase," *J. Biol. Chem.* 283(17):11312-11321 (2008).
Aberhart and Hsu, "Stereospecific hydrogen loss in the conversion of [$^2H_7$] isobutyrate to β-hydroxyisobutyrate in *Pseudomonas putida*. The stereochemistry of β-hydroxyisobutyrate dehydrogenase," *J. Chem. Soc.* [Perkin 1] 6:1404-1406 (1979).
Abiko et al., "Localization of NAD-isocitrate dehydrogenase and glutamate dehydrogenase in rice roots: candidates for providing carbon skeletons to NADH-glutamate synthase," *Plant Cell Physiol.*, 46:1724-1734 (2005).

(56) References Cited

OTHER PUBLICATIONS

Abo-Dalo et al., "A novel member of the GCN5-related N-acetyltransferase superfamily from *Caenorhabditis elegans* preferentially catalyses the N-acetylation of thialysine [S-(2-aminoethyl)-L-cysteine]," *Biochem. J.* 384:129-137 (2004).

Adams and Kletzin, "Oxidoreductase-type enzymes and redox proteins involved in fermentative metabolisms of hyperthermophilic Archaea," *Adv. Protein Chem.* 48:101-180 (1996).

Aevarsson et al., "Crystal structure of 2-oxoisovalerate and dehydrogenase and the architecture of 2-oxo acid dehydrogenase multienzyme complexes," *Nat. Struct. Biol.* 6:785-792 (1999).

Agnihotri and Liu, "Enoyl-CoA Hydratase: Reaction, Mechanism, and Inhibition," *Bioorg. Med. Chem.* 11(1):9-20 (2003).

Ahmed and Lewis, "Fermentation of Biomass-Generated Synthesis Gas: Effects of Nitric Oxide," *Biotechol. Bioeng.* 97:1080-1086 (2007).

Ahmed et al., "Effects of biomass-generated producer gas constituents on cell growth, product distribution and hydrogenase activity of *Clostridium*carboxidivorans $P7^T$," *Biomass Bioenergy* 30(7):665-672 (2006).

Akashi et al., "Molecular and biochemical Characterization of 2-Hydroxyisoflavanone Dehydratase. Involvement of Carboxylesterase-Like Proteins in Leguminous Isoflavone Biosynthesis," *Plant. Physiol.* 137:882-891 (2005).

Akatsuka et al., "The Serratia marcescens bioH gene encodes an esterase," *Gene* 302(1-2):185-192 (2003).

Akhtar and Jones, "Construction of a synthetic YdbK-dependent pyruvate:$H_2$ pathway in *Escherichia coli* BL21(DE3)," *Metab. Eng.* 11(3):139-147 (2009).

Alam et al., "Anaerobic Fermentation Balance of *Escherichia coli* as Observed by In Vivo Nuclear Magnetic Resonance Spectroscopy," *J. Bacteriol.* 171(11):6213-6217.

Alber et al., "3-Hydroxypropionyl-Coenzyme A synthetase from *Metallosphaera sedula*, an enzyme involved in autotrophic $CO_2$ fixation," *J. Bacteriol.* 190:1383-1389.

Alber et al., "Malonyl-Coenzyme A reductase in the modified 3-hydroxypropionate cycle for autotrophic carbon fixtion in archaeal *Metallosphaera* and *Sulfolobus* spp.," *J. Bacteriol.* 188(24):8551-8559 2006.

Alber et al., "Propionyl-Coenzyme A synthase from *Chloroflexus aurantiacus*, a key enzyme of the 3-hydroxypropionate cycle for autotrophic $CO_2$ fixation," *J. Biol. Chem.* 277:12137-12143 (2002).

Alber et al., "Study of an alternate glyoxylate cycle for acetate assimilation by *Rhodobacter sphaerbides*," *Mol. Microbiol.* 61(2):297-309 (2006).

Alberty, Biochemical thermodynamics. *Biochim. Biophys. Acta* 1207:1-11 (1994).

Aldor and Keasling, "Metabolic engineering of poly(3-hydroxybutyrate-co-3-hydroxyvalerate) composition in recombinant *Salmonella enterica* serovar typhimurium," *Biotechnol. Bioeng*, 76(2):108-114 (2001).

Aldor et al., "Metabolic Engineering of a Novel Propionate-Independent Pathway for the Production of Poly(3-Hydroxybutyrate-co-3-Hydroxyvalerate) in Recombinant *Salmonella enterica* Serovar Typhimurium," *Appl. Environ. Microbiol.* 68(8):3848-3854 (2002).

Aldrich Catalog, Sigma-Aldrich Company, Milwaukee, WI, p. 481 (2002).

Aldrich et al., "Cloning and complete nucleotide sequence determination of the catB gene encoding cis,cis-muconate lactonizing enzyme," *Gene* 52:185-195 (1987).

Alexeeva et al., "Requirement of ArcA for redox regulation in *Escherichia coli* under microaerobic but not anaerobic or aerobic conditions," *J. Bacteriol.* 185(1):204-209 (2003).

Alexson et al., "NADH-sensitive propionyl-CoA hydrolase in brown-adipose-tissue mitochondria of the rat," *Biochim. Biophys. Acta* 1005(1):13-19 (1989).

Alhapel et al., "Molecular and functional analysis of nicotinate catabolism in *Eubacterium barkeri*," *Proc. Natl. Acad. Sci. U.S.A.* 103(33):12341-12346 (2006).

Alper et al., "Construction of lycopene-overproducing *E. coli* strains by combining systematic and combinatorial gene knockout targets," *Nat. Biotechnol.* 23(5):612-616 (2005).

Alper et al., "Identifying gene targets for the metabolic engineering of lycopene biosynthesis in *Escherichi coli*," *Metab. Eng*, 7(3):155-164 (2005).

Alper et al., "Engineering yeast transcription machinery for improved ethanol tolerance and production," *Science* 314(5805):1565-1568 (2006).

Altamirano et al., "Decoupling cell growth and product formation in Chinese hamster ovary cells throguh metabolic control," *Biotechnol. Bioeng*, 76(4):351-360 (2001).

Altmiller and Wanger, "Purification and properties of dihydroxy acid dehydratase from soluble and mitochondrial fractions of *Neurospora crassa*," *Arch. Biochem. Biophys.* 138:160-170 (1970).

Amann et al., "Tightly regulated tac promoter vectors useful for the expression of unfused and fused proteins in *Escherichia coli*," *Gene* 69:301-315 (1988).

Andersen and Hansen, "Cloning of the lysA gene from *Mycobacterium tuberculosis*," *Gene* 124(1):105-109 (1993).

Andersen et al., "A gene duplication led to specialized γ-aminobutyrate and β-alanine aminotransferase in yeast," *FEBS J.* 274:1804-1817 (2007).

Anderson and Dawes, "Occurrence, metabolism, metabolic role, and industrial uses of bacterial polyhydroxyalkanoates," *Microbiol. Rev.* 54(4):450-472 (1990).

Anderson et al., "Evaluation of 5-enolpyruvoylshikimate-3-phosphate synthase substrate and inhibitor binding by stopped-flow and equilibrium fluorescence measurements," *Biochemistry* 27:1604-1610 (1988).

Andersson et al., "Effect of different carbon sources on the production of succinic acid using metabolically engineered *Escherichia coli*," *Biotechnol. Prog.* 23(2):381-388 (2007).

Andreesen and Ljungdahl, "Formate Dehydrogenase of *Clostridium thermoaceticum*: Incorporation of Selenium-75, and the Effects of Selenite, Molybate, and Tungstate on the Enzyme," *J. Bacteriol.* 116(2):867-873 (1973).

Aneja and Charles, "Poly-3-hydroxybutyrate degradation in *Rhizobium* (Sinorhizobium) meliloti: isolation and characterization of a gene encoding 3-hydroxybutryate dehydrogenase," *J. Bacteriol.* 181(3):849-857 (1999).

Angrand et al., "Simplified generation of targeting constructs using ET recombination," *Nucleic Acids Res.* 27(17):e16 (1999).

Ansorge and Kula, "Production of Recombinant L-Leucine Dehydrogenase from *Bacillus cereus* in Pilot Scale Using the Runaway Replication System *E. coli*[plET98]," *Biotechnol. Bioeng*, 68:557-562 (2000).

Aoshima and Igarashi, "A novel biotin protein required for reductive carboxylation of 2-oxoglutarate by isocitrate dehydrogenase in *Hydrogenobacter thermophilus* TK-6," *Mol. Microbiol.* 51(3):791-798 (2004).

Aoshima and Igarshi, "Nondecarboxylating and decarboxylating isocitrate dehydrogenases: oxalosuccinate reductase as an ancestral form of isocitrate dehydrogenase," *J. Bacteriol.* 190(6):2050-2055 (2008).

Aoshima et al., "A novel enzyme, citryl-CoA lyase, catalysing the second step of the citrate cleavage reaction in *Hydrogenobacter thermophilus* TK-6," *Mol. Microbiol.* 52(3):763-770 (2004).

Aoshima et al., "A novel enzyme, citryl-CoA synthetase, catalysing the first step of the citrate cleavage reaction in *Hydrogenobacter thermophilus* TK-6," *Mol. Microbiol.* 52(3):751-761 (2004).

Aoshima et al., "A novel oxalosuccinate-forming enzyme involved in the reductive carboxylation of 2-oxoglutarate in *Hydrogenobacter thermophilus* TK-6," *Mol. Microbiol.* 62(3):748-759 (2006).

Aoshima, "Novel enzyme reactions related to the tricarboxylic acid cycle: phylogenetic/functional implications and biotechnological applications," *Appl. Microbiol. Biotechnol.* 75(2):249-255 (2007).

Aragon and Lowenstein, "A survey of Enzymes Which Generate or Use Acetoacetyl Thioesters in Rat Liver," *J. Biol. Chem.* 258(8):4725-4733 1983.

Arendsen et al., "Nitrate-Dependent Regulation of Acetate Biosynthesis and Nitrate Respiration by *Clostridium thermoaceticum*," *J. Bacteriol.* 181:1489-1495 (1999).

(56) References Cited

OTHER PUBLICATIONS

Argyrou and Blanchard, "Kinetic and chemical mechanism of *Mycobacterium tuberculosis* 1-deoxy-D-xylulose-5-phosphate isomeroreductase," *Biochemistry* 43:4375-4384 (2004).
Arikawa et al., "Soluble fumarate reductase isoenzymes from *Saccharomyces cerevisiae* are required for anaerobic growth," *FEMS Microbiol. Lett.* 165:111-116 (1998).
Aristidou et al., "Metabolic Engineering of *Escherichia coli* to Enhance Recombinant Protein Production through Acetate Reduction," *Biotechnol. Prog.* 11(4):475-478 (1995).
Aristidou et al., "Metabolic flux analysis of *Escherichia coli* expressing the *Bacillus subtilis* Acetolactate Synthase in Batch and Continuous Cultures," *Biotechnol. Bioeng.* 63(6):737-749 (1999).
Armstrong et al., "Steroselectivity and sterospecificity of the α, β-dihydroxyacid dehydratase from *Salmonella typhimurium*" *Biochim. Biophys. Acta* 498:282-293 (1977).
Arps et al., "Genetics of serine pathway enzymes in *Methylobacterium extorquens* AM1: phosphoenolpyruvate carboxylase and malyl Coenzyme A lyase," *J. Bacteriol.* 175:3776-3783 (1993).
Asano and Kato, "Crystalline 3-methylaspartase from a facultative anaerobe, *Escherichia coli* strain YG1002," *FEMS Microbiol. Lett.* 118(3):255-258 (1994).
Asano et al., "Alteration of substrate specificity of aspartase by directed evolution," *Biomol. Eng.* 22(1-3):95-101 (2005).
Asanuma et al., "Characterization and transcription of the genes encoding enzymes involved in butyrate production in *Butyrivibrio fibrisolvens*," *Curr. Microbiol.* 45:203-207 (2003).
Asuncion et al., "Overexpression, purification, crystallization and data collection of 3-methylaspartase from *Clostridium tetanomorphum*," *Acta. Crystallogr. D. Biol. Crystallogr.* 57(Pt 5):731-733 (2001).
Asuncion et al., "The structure of 3-methylaspartase from *Clostridium tetanomorphum* functions via the common enolase chemical step," *J. Biol. Chem.* 277(10):8306-8311 (2002).
Atsumi et al., "Metabolic engineering of *Escherichia coli* for 1-butanol production," *Metab. Eng.* 10(6):305-311 (2007).
Atsumi et al., "Non-fermentative pathways for synthesis of branched-chain higher alcohols as biofuels," *Nature* 451(7174):86-89 (2008).
Atteia et al., "Pyruvate formate-lyase and a novel route of eukaryotic ATP synthesis in *Chlamydomonas* mitochondria," *J. Biol. Chem.* 281:9909-9918 (2006).
Auerbach et al., "Lactate dehydrogenase from the hyperthermophilic bacterium thermotoga maritima: the crystal structure at 2.1 Å resolution reveals strategies for intrinsic protein stabilization," *Structure* 6:769-781 (1998).
Baba et al., "Construction of *Escherichia coli* K-12 in-frame, single-gene knockout mutants: the Keio collection," *Mol. Syst. Biol.* 2:2006. 0008 (2006).
Bachmann and Townsend, "β-Lactam synthetase: a new biosynthetic enzyme," *Proc. Natl. Acad. Sci. U.S.A.* 95(16):9082-9086 (1998).
Bai et al., "Lewis-acid assisted cross metathesis of acrylonitrile with functionalized olefins catalyzed by phosphine-free ruthenium carbene complex," *Org. Biomol. Chem.* 3:4139-4142 (2005).
Bailey et al., "Identification, cloning, purification, and enzymatic characterization of *Mycobacterium tuberculosis* 1-deoxy-D-xylulose 5-phosphate synthase," *Glycobiology* 12:813-820 (2002).
Baird et al., "Enzymes involved in acetoacetate formation in various bovine tissues," *Biochem. J.* 117(4):703-709 (1970).
Baker and van der Drift, "Purification and properties of L-erythro-3,5-diaminohexanoate dehydrogenase from *Clostridium sticklandii*," *Biochemistry* 13(2):292-299 (1974).
Baker et al., "Purification and properties of L-erythro-3,5-diaminohexanoate dehydrogenase from a lysine-fermenting *Clostridium*," *J. Biol. Chem.* 247:7724-7734 (1972).
Bakker et al., "Stoichiometry and compartmentation of NADH metabolism in *Saccharomyces cerevisiae*," *FEMS Microbiol. Rev.* 25:15-37 (2001).
Banerji et al., "The cloning and characterization of the arom gene of *Pneumocystis carinii*," *J. Gen. Microbiol.* 139:2901-2914 (1993).
Barber et al., "Structure and regulation of acetyl-CoA carboxylase genes of metazoa," *Biochimica. Biophysica. Acta* 1733:1-28 (2005).
Barker and Frost, "Microbial synthesis of *p*-hydroxybenzoic acid from glucose," *Biotechnol. Bioeng.* 76:376-390 (2001).
Barker et al., "Butyryl-CoA:Acetoacetate CoA-transferase from Lysine-fermenting *Clostridium*," *J. Biol. Chem.* 253(4):1219-1225 (1978).
Barker et al., "Pathway of Lysine Degradation in *Fusobacterium nucleatum*," *J. Bacteriol.* 152(1):201-207 (1982).
Barrick et al., "Quantitative analysis of ribosome binding sites in *E. coli*," *Nucleic Acid Res.* 22(7):1287-1295 (1994).
Barrowman et al., "Immunological comparison of microbial TPP-dependent non-oxidative α-keto acid decarboxylase," *FEMS Microbiol. Lett.* 34:57-60 (1986).
Barthelmebs et al., "Expression of *Escherichia coli* of Native and chimeric Phenolic Acid Decarboxylases with Modified Enzymatic Activities and Method for Screening Recombinant *E. coli* Strains Expressing These Enzymes," *Appl. Environ. Microbiol.* 67:1063-1069 (2001).
Barthelmebs et al., "Inducible metabolism of phenolic acids in *Pedicoccus pentosaecus* is encoded by an autoregulated operon which involves a new class of negative transcriptional regulator," *J. Bacteriol.* 182:6724-6731 (2000).
Bartsch et al., "Molecular analysis of two genes of the *Escherichia coli* gab cluster: nucleotide sequence of the glutamate:succinic semialdehyde transaminase gene (gabT) and characterization of the succinic semialdehyde dehydrogenase gene (gabD)," *J. Bacteriol.* 172(12):7035-7042 (1990).
Basset et al., "Folate synthesis in plants: the p-aminobenzoate branch is initiated by a bifunctional PabA-PabB protein that is targeted to plastids," *Proc. Natl. Acad. Sci. U. S. A* 101:1496-1501 (2004).
Battaile et al., "Structures of isobutyryl-CoA dehydrogenase and enzyme-product complex: Comparison with isovaleryl- and short-chain acyl-CoA dehydrogenases," *J. Biol. Chem.* 279:16526-16534 (2004).
Baudin et al., "A simple and efficient method for direct gene deletion in *Saccharomyces cerevisiae*," *Nucleic Acids Res.* 21(14):3329-3330 (1993).
Bauer et al., "Improved Expression of Human Interleukin-2 in High-Cell-Density Fermentor Cultures of *Escherichia coli* K-12 by a Phosphotransacetylase Mutant," *Appl. Environ. Microbiol.* 56:1296-1302 (1990).
Beatrix et al., "The biotin-dependent sodium ion pump glutaconyl-CoA decarboxylase from *Fusobactevium nucleatum* (subsp. *nucleatum*). Comparison with the glutaconyl-CoA decarboxylases from gram-positive bacteria," *Arch. Microbiol.* 154(4):362-369 (1990).
Beckers et al., "Large-scale mutational analysis for the annotation of the mouse genome," *Curr. Opin. Chem. Biol.* 6:17-23 (2001).
Benner et al., "Stereospecificity and sterochemical infidelity of acetoacetate decarboxylase (AAD)," *J. Am. Chem. So.* 103:993-994 (1981).
Benning et al., "New reactions in the crotonase superfamily: Structure of methylmalonyl CoA decarboxylase from *Escherichia coli*," *Biochemistry* 39:4630-4639 (2000).
Berg et al., "A 3-Hydroxypropionate/4-Hydroxybutyrate Autotrophic Carbon Dioxide Assimilation Pathway in Archaea," *Science* 318(5857) 1782-1786 (2007).
Bergquist and Gibbs, "Degenerate oligonucleotide gene shuffling," *Meth. Mol. Biol.* 352:191-204 (2007).
Bergquist et al., "Degenerate oligonucleotide gene shuffling (DOGS) and random drift mutagenesis (RNDM): Two complementary techniques for enzyme evolution," *Biomol. Eng.* 22:63-72 (2005).
Berkovitch et al., "A locking mechanism preventing radical damage in the absence of substrate, as revealed by the x-ray structure of lysine 5,6-aminomutase," *Proc. Natl. Acad. Sci. U.S.A.* 101:15870-15875 (2004).
Berman and Magasanik, "The pathway of myo-inositol degradation in *Aerobacter aerogenes*," *J. Biol. Chem.* 241(4):800-806 (1966).

(56) References Cited

OTHER PUBLICATIONS

Bermejo et al., "Expression of *Clostridium acetobutylicum* ATCC 824 Genes in *Escherichia coli* for Acetone Production and Acetate Detoxification," *Appl. Environ. Microbiol.* 64(3):1079-1085 (1998).
Berrios-Rivera et al., "Metabolic Engineering of *Escherichia coli*: Increase of NADH Availability by Overexpressing an $NAD^+$-Dependent Formate Dehydrogenase," *Metab Eng.* 4(3):217-229 (2002).
Berthold et al., "Structure of the branched-chain keto acid decarboxylase (KdcA) from *Lactococcus lacti* prvides insights into structural basis for the chemoselective enantioselective carboligation reaction," *Acta. Crystalloqr. D. Biol. Crystallogr.* 63(Pt 12):1217-1224 (2007).
Biellmann et al., "Aspartate-β-semialdehyde dehydrogenase from *Escherichia coli*. Purification and general properties," *Eur. J. Biochem.* 104(1):53-58 (1980).
Binieda et al., "Purification, characterization, DNA sequence and cloning of a pimeloyl-CoA synthetase from *Pseudomonas mendocina* 35," *Biochem. J.* 340:793-801 (1999).
Binstock and Schulz, "Fatty acid oxidation complex from *Escherichia coli*," *Methods Enzymol.* 71(Pt C):403-411 (1981).
Birch et al., "Cloning, sequencing, and expression of the gene encoding methylmalonyl-Coenzyme A mutase from *Streptomyces cinnamonensis*," *J. Bacteriol.* 175(11):3511-3519 (1993).
Birrer et al., "Electro-transformation of *Clostridium beijerinckii* NRRL B-592 with shuttle plasmid pHR106 and recombinant derivatives," *Appl. Microbiol. Biotechnol.* 41(1):32-38 (1994).
Bisswanger, "Substrate specificity of the Pyruvate Dehydrogenase Complex from *Escherichia coli*," *J. Biol. Chem.* 256(2):815-822 (1981).
Blanco et al., "Critical catalytic functional groups in the mechanism of aspartate-β-semialdehyde dehydrogenase," *Acta. Crystallogr. D. Biol. Crystallogr.* 60(Pt 10):1808-1815 (2004).
Blanco et al., "The role of substrate-binding groups in the mechanism of aspartate-β-semialdehyde dehydrogenase," *Acta. Crystallogr. D. Biol. Crystallogr.* 60(Pt 8):1388-1395 (2004).
Blaschkowski et al., "Routes of flavodoxin and ferredoxin reduction in *Escherichia coli*. CoA-acylating pyruvate: flavodoxin and NADPH: flavodoxin oxidoreductases participating in the activation of pyruvate formate-lyase," *Eur. J. Biochem.* 123(3):563-569 (1982).
Blazquez et al., "Identification and analysis of a glutaryl-CoA dehydrogenase-encoding gene and its cognate transcriptional regulator from *Azoarcus* sp. CIB," *Environ. Microbiol.* 10(2):474-482 (2008).
Blombach et al., "*Corynebacterium glutamicum* tailored for high-yield L-valine production," *Appl. Microbiol. Biotechnol.* 79(3):471-479 (2008).
Blomqvist et al., "Characterization of the genes of the 2,3-butanediol operons from *Klebsiella terrigena* and *Enterobacter aerogenes*," *J. Bacteriol.* 175:1392-1404 (1993).
Bobik and Rasche, "HPLC assay for methylmalonyl-CoA epimerase," *Anal. Bioanal. Chem.* 375(3):344-349 (2003).
Bobik and Rasche, "Identification of the human methylmalonyl-CoA racemase gene based on the analysis of prokaryotic gene arrangements. Implications for decoding the human genome," *J. Biol. Chem.* 276(40):37194-37198 (2001).
Bobik et al., "Propanediol Utilization Genes (pdu) of *Salmonella typhimurium*: Three Genes for the Propanediol Dehydratase," *J. Bacteriol.* 179(21):6633-6639 (1997).
Bock et al., "Purification and characterization of two extremely thermostable enzymes, phosphate acetyltransferase and acetate kinase, from the hyperthermophilic eubacterium *Thermotoga maritima*," *J. Bacteriol.* 181:1861-1867 (1999).
Boiangiu et al., "Sodium Ion Pumps and Hydrogen Production in Glutamate Fermenting Anaerobic Bacteria," *J. Mol. Microbiol. Biotechnol.* 10:105-119 (2005).
Boles et al., "Characterization of a glucose-repressed pyruvate kinase (Pyk2p) in *Saccharomyces cerevisiae* that is catalytically insensitive to fructose-1,6-bisphosphate," *J. Bacteriol.* 179:2987-2993 (1997).
Bonnarme et al., "Itaconate biosynthesis in *Aspergillus terreus*," *J. Bacteriol.* 177(12):3573-3578 (1995).

Bonner and Bloch, "Purification and properties of fatty acyl thioesterase I from *Escherichia coli*," *J. Biol. Chem.* 247(10):3123-3133 (1972).
Boronin et al., "Plasmids specifying ε-caprolactam degradation in Pseudomonas strains," *FEMS Microbiol Lett.* 22(3):167-170 (1984).
Bose et al., "Genetic analysis of the methanol- and methylamine-specific methyltransferase 2 genes of *Methanosarcina acetivorans* C2A," *J. Bacteriol.* 190(11):4017-4026 (2008).
Bott et al., "Methylmalonyl-CoA decarboxylase from *Propionigenium modestum*. Cloning and sequencing of the structural genes and purification of the enzyme complex," *Eur. J. Biochem.* 250:590-599 (1997).
Botting et al., "Substrate Specificity of the 3-Methylaspartate Ammonia-Lyase Reactin: Observation of Differential relative Reaction Rates for Substrate-Product Pairs," *Biochemistry* 27:2953-2955 (1988).
Bottomley et al., "Cloning, sequencing, expression, purification and preliminary characterization of type II dehydroquinase from *Helicobacter pylori*," *Biochem. J.* 319:559-565 (1996).
Bower et al., "Cloning, sequencing, and characterization of the *Bacillus subtilis* biotin biosynthetic operon," *J. Bacteriol.* 178(14):4122-4130 (1996).
Boylan and Dekker, "L-Threonine Dehydrogenase of *Escherichia coli* K-12," *Biochem. Biophys. Res. Commun.* 85(1):190-197 (1978).
Boynton et al., "Cloning, sequencing, and expression of clustered genes encoding β-hydroxybutyryl-Coenzyme A (CoA) dehydrogenase, crotonase, and butyryl-CoA dehydrogenase from *Clostridium acetobutylicum* ATCC 824," *J. Bacteriol.* 178(11):3015-3024 (1996).
Brachmann et al., "Designer deletion strains derived from *Saccharomyces cerevisiae* S288C: a useful set of strains and plasmids for PCR-mediated gene disruption and other applications," *Yeast* 14(2):115-132 (1998).
Bradford, "A rapid and sensitive method for the quantitation of microgram quantities of protein utilizing the principle of protein-dye binding," *Anal. Biochem.* 72:248-254 (1976).
Branlant, "Nucleotide sequence of *Escherichia coli* gap gene. Different evolutionary behavior of the $NAD^+$-binding domain and of the catalytic domain of D-glyceraldehyde-3-phosphate dehydrogenase," *Eur. J. Biochem.* 150:61-66 (1985).
Bräsen and Schönheit, "Unusual ADP-forming acetyl-Coenzyme A synthetases from the mesophilic halophilic euryarchaeon *Haloarcula marismortui* and from the hyperthermophilic crenarchaeon *Pyrobaculum aerophilum*," *Arch. Microbiol.* 182(4):277-287 (2004).
Braune et al., "The sodium ion translocating glutaconyl-CoA decarboxylase from *Acidaminococcus fermentans*: cloning and function on the genes forming a second operon," *Mol. Microbiol.* 31(2):473-487 (1999).
Bravo et al., "Reliable, sensitive, rapid and quantitative enzyme-based assay for gamma-hydroxybutyric acid (GHB)," *J. Forensic Sci.* 49:379-387 (2004).
Bredwell et al., "Reactor Design Issues for Synthesis-Gas Fermentations," *Biotechnol. Prog.* 15(5):834-844 (1999).
Breese et al., "Genes coding for the benzoyl-CoA pathway of anaerobic aromatic metabolism in the bacterium *Thauera aromatica*," *Eur. J. Biochem.* 256(1):148-154.
Breitkruez et al., "A novel γ-hydroxybutyrate dehydrogenase: Identification and expression of an Arabidopsis cDNA and potential role under oxygen deficiency," *J. Biol. Chem.* 278:41552-41556 (2003).
Bremer, "Pyruvate Dehydrogenase, Substrate Specificity and Product Inhibition," *Eur. J. Biochem.* 8:535-540 (1969).
Brey et al., "Cloning of multiple genes involved with cobalamin (Vitamin $B_{12}$) biosynthesis in *Bacillus megaterium*," *J. Bacteriol.* 167:623-630 (1986).
Bro et al., "In silico aided metabloic engineering of *Saccharomyces cerevisiae* for improved bioethanol production," *Metab. Eng*, 8(2):102-111 (2006).
Brooke et al., "GAMS: A User's Guide. GAMS Development Corporation," (1998).
Broun et al., "Catalytic plasticity of fatty acid modification enzymes underlying chemical diversity of plant lipids," *Science* 282:1315-1317 (1998).

(56) References Cited

OTHER PUBLICATIONS

Brown et al., "A role for pabAB, a p-aminobenzoate synthase gene of *Streptomyces venezuelae* ISP5230, in chloramphenicol biosynthesis," *Microbiol.* 142 ( Pt 6):1345-1355 (1996).
Brown et al., "Comparative structural analysis and kinetic properties of lactate dehydrogenases from the four species of human malarial parasites," *Biochemistry.* 43:6219-6229 (2004).
Browner et al., "Sequence analysis, biogenesis, and mitochondrial import of the α-subunit of rat liver propionyl-CoA carboxylase," *J. Biol. Chem.* 264:12680-12685 (1989).
Bu and Tobin, "The exon-intron organization of the genes (GAD1 and GAD2) encoding two human glutamate decarboxylases ($GAD_{67}$ and $GAD_{65}$) suggests that they derive from a common ancestral GAD," *Genomics* 21:222-228 (1994).
Bu et al., "Two human glutamate decarboxylases, 65-kDa GAD and 67-kDa GAD, are each encoded by a single gene," *Proc. Natl. Acad. Sci. U.S.A.* 89:2115-2119 (1992).
Buchanan et al., "An extremely thermostable aldolase from *Sulfolobus solfataricus* with specificity for non-phosphorylated substrates," *Biochem. J.* 343:563-570 (1999).
Buck et al., "Primary structure of the succinyl-CoA synthetase of *Escherichia coli*," *Biochem.* 24(22):6245-6252 (1985).
Buckel and Barker, "Two pathways of glutamate fermentation by anaerobic bacteria," *J. Bacteriol.* 117(3):1248-1260 (1974).
Buckel and Golding, "Radical enzymes in anaerobes," *Annu. Rev. Microbiol.* 60:27-49 (2006).
Buckel and Golding, "Radical species in the catalytic pathways of enzymes from anaerobes," *FEMS Microbiol. Rev.* 22(5):523-541 (1999).
Buckel et al., "ATP-Driven electron transfer in enzymatic radical reactions," *Curr. Opin. Chem. Biol.* 8:462-467 (2004).
Buckel et al., "Glutaconate CoA-Transferase from *Acidaminococcus fermentans*," *Eur. J. Biochem.* 118:315-321 (1981).
Buckel et al., "Radical-mediated dehydration reactions in anaerobic bacteria," *Biol. Chem.* 386:951-959 (2005).
Buckel, "Sodium ion-translocating decarboxylases," *Biochimica. Biophysica. Acta.* 1505:15-27 (2001).
Bueding and Yale, "Production of α-methylbutyric acid by bacteria-free *Ascaris lumbricoides*," *J. Biol. Chem.* 193:411-423 (1951).
Bühler and Simon, "On the kinetics and mechanism of enoate reductase," *Hoppe Seylers Z. Physiol. Chem.* 363(6):609-625 (1982).
Bunch et al., "The ldhA gene encoding the fermentative lactate dehydrogenase of *Escherichia coli*," *Microbiol.* 143:187-195 (1997).
Burgard and Maranas, "Probing the performance limits of the *Escherichia coli* metabolic network subject to gene additions or deletions," *Biotechnol. Bioeng.* 74:364-375 (2001).
Burgard et al., "Minimal Reaction Sets for *Escherichia coli* Metabolism under Different Growth Requirements and Uptake Environments," *Biotechnol. Prog.* 17:791-797 (2001).
Burgard et al., "Optknock: a bilevel programming framework for identifying gene knockout strategies for microbial strain optimization," *Biotechnol. Bioeng.* 84(6):647-657 (2003).
Burke et al., "The Isolation, Characterization, and Sequence of the Pyruvate Kinase Gene of *Saccharomyces cerevisiae*," *J. Biol. Chem.* 258(4):2193-2201 (1983).
Burks et al., "Stereochemical and Isotopic Labeling Studies of 2-Oxo-hept-4-ene-1,7-dioate Hydratase: Evidence for an Enzyme-Catalyzed Ketonization Step in the Hydration Reaction," *J. Am. Chem. Soc.* 120(31):7665-7675 (1998).
Buu et al., "Functional characterization and localization of acetyl-CoA hydrolase, Ach1p, in *Saccharomyces cerevisiae*," *J. Biol. Chem.* 278:17203-17209 (2003).
Buzenet et al., "Purification and properties of 4-Aminobutyrate 2-Ketoglutarate Aminotransferase From Pig Liver," *Biochimica. Biophvsica. Acta* 522:400-411 (1978).
Byrnes et al., "Thermodynamics of reactions catalyzed by anthranilate synthase," *Biophys. Chem.* 84:45-64 (2000).
Cahyanto et al., "Regulation of aspartokinase, asparate semialdehyde dehydrogenase, dihydrodipicolinate synthase and dihydropdipicolinate reductase in *Lactobacillus plantarum*," *Microbiology.* 152 (Pt 1): 105-112 (2006).
Caldovic and Tuchman, "N-Acetylglutamate and its changing role through evolution," *Biochem. J.* 372:279-290 (2003).
Calhoun et al., "Threonine deaminase from *Eschericiha coli*. I. Purification and properties," *J. Biol. Chem.* 248(10):3511-3516 (1973).
Camara et al., "Characterization of a Gene Cluster Involved in 4-Chlorocatechol Degradation by *Pseudomonas reinekei* MT1," *J. Bacteriol.* 191(15):4905-4915.
Campbell and Cronan, Jr., "The enigmatic *Escherichia coli* fadE gene is yafH," *J. Bacteriol.* 184(13):3759-3764 (2002).
Campbell et al., "A complete shikimate pathway in *Toxoplasma gondii*: an ancient eukaryotic innovation," *Int. J. Parasitol.* 34:5-13 (2004).
Campbell et al., "A new *Escherichia coli* metabolic competency: growth on fatty acids by a novel anaerobic β-oxidation pathway," *Mol. Microbiol.* 47(3):793-805.
Canovas et al., "Characterization of the genes for the biosynthesis of the compatible solute ectoine in the moderately haliphilic bacterium *Halomonas elongata* DSM 3043," *Syst. Appl. Microbiol.* 21:487-497 (1998).
Cao et al., "Simultaneous Production and recovery of Fumaric Acid from Immobilized *Rhizopus oryzae* with a Rotary biofilm Contactor and an Adsorption Column," *Appl. Environ. Microbiol.* 62(8):2926-2931 (1996).
Carlini et al., "Guerbet condensation of methanol with n-propanol to isobutyl alcohol over heterogeneous copper chromite/MG—Al mixed oxides catalysts," *J. Mol. Catal. A. Chem.* 220:215-220 (2004).
Carlini et al., "Selective synthesis of isobutanol by means of the Guerbet reaction Part 3: Methanol/n-propanol condensation by using bifunctional catalytic systems based on *nickel, rhodium* and *ruthenium* species with basic components," *J. Mol. Catal. A. Chem.* 206:409-418 (2003).
Carlini et al., "Selective synthesis of isobutanol by means of the Guebet reaction Part 1. Methanol/n-propanol condensation by using copper based catalytic systems," *J. Mol. Catal. A. Chem.* 184:273-280 (2002).
Carlini et al., "Selective synthesis of isobutanol by means of the Guerbet reaction Part 2. Reaction of methanol/ethanol and methanol/ethanol/n-propanol mixtures over copper based MeONa catalytic systems," *J. Mol. Catal. A. Chem.* 200:137-146 (2003).
Carpenter et al., "Structure of dehydroquinate synthase reveals an active site capable of multistep catalysis," *Nature* 394:299-302 (1998).
Carretero-Paulet et al., "Expression and molecular analysis of the Arabidopsis DXR gene encoding1-deoxy-D-xylulose 5-phosphate reductoisomerase, the firszt committed enzyme of the 2-C-methyl-D-erythritiol 4-phosphate pathway," *Plant. Physiol.* 129:1581-1591 (2002).
Carta et al., "Production of fumaric acid by fermentation of enzymatic hydrolysates derived from *Cassava bagasse*," *Biores. Tech.* 68:23-28 (1999).
Cary et al., "Cloning and Expression of *Clostridium acetobutylicum* ATCC 824 Acetoacetyl-Coenzyme A:Acetate/Butyrate:Coenzyme A-Transferase in *Escherichia coli*," *App. Environ. Microbiol.* 56(6):1576-1583 (1990).
Cary et al., "Cloning and expression of *Clostridium acetobutylicum* phosphotransbutyrylase and butyrate kinase genes in *Escherichia coli*," *J. Bacteriol* 170(10):4613-4618 (1988).
Casero and Pegg, "Spermidine/spermine $N^1$-acetyltransferase-the turning point in polyamine metabolism," *FASEB J.* 7:653-661 (1993).
Caspi et al., "MetaCyc: a multiorganism database of metabolic pathways and enzymes," *Nucleic Acids Res.* 34(Database issue):D511-D516 (2006).
Cavin et al., "Gene cloning, transcriptional analysis, purification, and characterization of phenolic acid decarboxylase from bacillus subtilis," *Appl. Environ. Microbiol.* 64(4):1466-1471 (1998).
Cha and Bruce, "Stereo- and regiospecific cis,cis-muconate cycloisomerization by *Rhodococcus rhodochrous* N75," *FEMS Microbiol. Lett.* 224:29-34 (2003).
Cha and Parks, Jr., "Succinic Thiokinase. I. Purification of the Enzyme from Pig Heart," *J. Biol. Chem.* 239:1961-1967 (1964).

(56) References Cited

OTHER PUBLICATIONS

Chandra et al. "Pyruvate decarboxylase: a key enzyme for the oxidative metabolism of lactic acid by *Acetobacter pasteurianus*," *Arch. Microbiol.* 176:443-451 (2001).

Chang et al., "p-Aminobenzoic acid and chloramphenicol biosynthesis in *Streptomyces venezuelae*: gene sets for a key enzyme, 4-amino-4-deoxychorismate synthase," *Microbiology* 147:2113-2126 (2001).

Chang et al., "Effects of deletions at the carboxyl terminus of *Zymomonas mobills* pyruvate decarboxylase on the kinetic properties and substrate specificity," *Biochemisty* 39(31):9430-9437 (2000).

Chao and Ramsdell, "The effects of wall populations on coexistence of bacteria in the liquid phase of chemostat cultures," *J. Gen. Microbiol.* 131(5):1229-1236 (1985).

Chaparro-Riggers et al., "Comparison of Three Enoate Reductases and their Potential Use for Biotransformations," *Adv. Synth. Catal.* 349:1521-1531 (2007).

Charles et al., "The isolation and nucleotide sequence of the complex AROM locus of *Aspergillus nidulans*," *Nucleic Acids Res.* 14:2201-2213 (1986).

Charrier et al., "A novel class of CoA-transferase involved in short-chain fatty acid metabolism in butyrate-producing human colonic bacteria," *Microbiology* 152:179-185 (2006).

Chatterjee et al., "A general model for selectively in olefin cross methathesis," *J. Am Chem. Soc.* 125(37):11360-11370 (2003).

Chatterjee et al., "Mutation of the ptsG Gene Results in Increased Production of Succinate in Fermentation of Glucose by *Escherichia coli*," *Appl. Env. Microbiol.* 67:148-154 (2001).

Chaudhuri et al., "Identification of the active-site lysine residues of two biosynthetic 3-dehydroquinases," *Biochem. J.* 275:1-6 (1991).

Chen and Hiu, "Acetone-Butanol-Isopropanol Production by *Clostridium beijerinckii* (Synonym, *Clostridium butylicum*)," *Biotechnology Letters* 8(5):371-376 (1986).

Chen et al., "A novel lysine 2,3-aminomutase encoded by the yodO gene of *Bacillus subtilis*: characterization and the observation of organic radical intermediates," *Biochem. J.* 348:539-549 (2000).

Chen et al., "Cloning, Sequencing, Heterologous Expression, Purification, and Characterization of Adenosylcobalamin-dependent D-Ornithine Aminomutase from *Clostridium sticklandii*," *J. Biol. Chem.* 276:44744-44750 (2001).

Chen et al., "The control region of the pdu/cob regulon in *Salmonella typhimurium*," *J. Bacteriol.* 176:5474-5482 (1994).

Cheng et al., "Genetic Analysis of a Gene Cluser for Cyclohexanol Oxidation in *Acinetobacter* sp. Strain SE19 by In Vitro Transportation," *J. Bacteriol.* 182:(17):4744-4751 (2000).

Cheng et al., "Mammalian Wax Biosynthesis. I. Identification of two fatty acyl-Coenzyme A reductases with different substrate specificities and tissue distributions," *J. Biol. Chem.* 279(36):37789-37797 (2004).

Cheng et al., "Mammalian Wax Biosynthesis. II. Expression cloning of wax synthase cDNAs encoding a member of the acyltransferase enzyme family," *J. Biol. Chem.* 279(36):37798-37807 (2004).

Cheng et al., "Structural basis for shikimate-binding specificity of *Helicobacter pylori* shikimate kinase," *J. Bacteriol.* 187:8156-8163 (2005).

Chicco et al., "Regulation of Gene Expression of Branched-chain Keto Acid Dehydrogenase Complex in Primary Cultured Hepatocytes by Dexamethasone and a cAMP Analog," *J. Biol. Chem.* 269(30):19427-19434 (1994).

Chirpich et al., "Lysine 2,3-Aminomutase. Purification and Properties of Pyridoxal Phosphate and S-Adenosylmethionine-Activated Enzyme," *J. Biol. Chem.* 245(7):1778-1789 (1970).

Cho et al., "Critical residues for the Coenzyme specificity of $NAD^+$-dependent 15-hydroxyprostaglandin dehydrogenase," *Arch. Biochem. Biophys.* 419:139-146 (2003).

Choi et al, "Olefin Metathesis Involving Ruthenium Enoic Carbene Complexes," *J. Am. Chem. Soc.* 123(42):10417-10418 (2001).

Choi et al., "Enhanced production of cis,cis-muconate in a cell-recycle bioreactor," *J. Ferment. Bioenq.* 84:70-76 (1997).

Choi-Rhee and Cronan, "The biotin carboxylase-biotin carboxyl carrier protein complex of *Escherichia coli* acetyl-CoA carboxylase," *J. Biol. Chem .* 278:30806-30812 (2003).

Chopra et al., "Expression, purification, and biochemical characterization of Mycobacterium tuberculosis aspartate decarboxylase, PanD," *Protein Expr. Purif.* 25:533-540 (2002).

Chou et al., "Effect of Modulated Glucose Uptake on High-Level Recombinant Protein Production in a Dense *Escherichia coli* Culture," *Biotechnol. Prog.* 10:644-647 (1994).

Chowdhury et al., "3-Hydroxyisobutyrate dehydrogenase from *Pseudomonas putida* E23: purification and characterization," *Biosci. Biotechnol. Biochem.* 60(12):2043-2047 (1996).

Chowdhury et al., "Cloning and overexpression of the 3-hydroxyisobutyrate dehydrogenase gene from pseudomonas putida E23," *Biosci. Biotechnol. Biochem.* 67(2):438-441 (2003).

Christenson et al., "Kinetic analysis of the 4-methylideneimidazole-5-one-containing tyrosine aminomutase in enediyne antitumor antibiotic C-1027 biosynthesis," *Biochemistry* 42:12708-12718 (2003).

Chuakrut et al., "Characterization of a bifunctional archael acyl Coenzyme A carboxylase," *J. Bacteriol.* 185:938-947 (2003).

Clark and Ljungdahl, "Purification and properties of 5,10-methylenetetrahydrofolate reductase from *Clostridium formicoaceticum*," *Methods Enzymol.* 122:392-399. (1986).

Clark and Ljungdahl, "Purification and Properties of 5,10-Methylenetetrahydrofolate Reductase, an Iron-sulfur Flavoprotein from *Clostridium formicoaceticum*," *J. Biol. Chem.* 259(17)10845-10849 (1984).

Clark et al., "Mutants of *Escherichia coli* defective in acid fermentation," *Appl. Biochem. Biotechnol.* 17:163-173 (1988).

Clark, Progress Report for Department of Energy Grant DE-FG02-88ER13941, "Regulation of Alcohol Fermentation in *Escherichia coli*," pp. 1-7 for the period: Jul. 1991-Jun. 1994.

Clarke et al., "Rational construction of a 2-Hydroxyacid Dehydrogenase With New Substrate Specificity," *Biochem. Bioghys. Res. Commun.* 148:15-23 (1987).

Clausen et al., "PAD1 encodes phenylarcrylic acid decarboxylase which confers resistance to cinnamic acid in *Saccharomyces cerevisiae*," *Gene* 142:107-112 (1994).

Coco et al., "DNA shuffling method for generating highly recombined genes and evolved enzymes," *Nat. Biotechnol.* 19:354-359 (2001).

Coggins et al., "The arom multifunctional enzyme from *Neurospora crassa*," *Methods Enzymol.* 142:325-341 (1987).

Colby and Chen, "Purification and properties of 3-hydroxybutyryl-Coenzyme A dehydrogenase from *Clostridium beijerinckii* ("*Clostridium butylicum* ") NRRL B593," *Appl. Environ. Microbiol.* 58:3297-3302 (1992).

Coleman, "Expression of a glutamate decarboxylase homologue is required for normal oxidative stress tolerance in *Saccharomyces cerevisiae*," *J. Biol. Chem.* 276:244-250 (2001).

Conrad et al., "D- and L-Isoleucine Metabolism and Regulation of Their Pathways in *Pseudomonas Putida*," *J. Bacteriol.* 118(1):103-111 (1974).

Cooper, "Glutamate-γ-aminobutyrate transaminase," *Methods Enzymol.* 113:80-82 (1985).

Corthesy-Theulaz et al., "Cloning and Characterization of *Helicobacter pylori* Succinyl CoA:Acetoacetate CoA-transferase, a Novel Prokaryotic Member of the CoA-transferase Family," *J. Biol. Chem.* 272(41):25659-25667 (1997).

Couturier et al., "A Cyclometalated Aryloxy(chloro)neopentylidenetungsten Complex: A Highly Active and Stereoselective Catalyst for the Metathesis of cis- and trans-2-Pentene, Norbornene, 1-Methyl-norbornene, and Ethyl Oleate," *Angew. Chem Int. Ed. Engl.* 31(5):628-631 (1992).

Cox et al., "Development of a metabolic network design and optimization framework incorporating implementation constraints: A succinate production case study," *Metab. Eng*, 8(1):46-57 (2006).

Craney et al., "A synthetic luxCDABE gene cluster optimized for expression in high-GC bacteria," *Nucleic Acids Res.* 35(6):e46 (2007).

Cukalovic et al., "Feasibility of production method for succinic acid derivatives: a marriage of renewable resources and chemical technology," *Biofuels Bioprod. Bioref.* 2:505-529 (2008).

(56) References Cited

OTHER PUBLICATIONS

Cunningham et al., "Transcriptional regulation of the aconitase genes (acnA and acnB) of *Escherichia coli*," *Microbiology* 143(Pt 12):3795-3805 (1997).
Dai et al., "Highly Selective Diels-Alder Reactions of directly Connected Enzyne Dienphiles," *J. Am. Chem. Soc.* 129:645-657 (2007).
Dakoji et al., "Studies on the inactivation of bovine liver enoyl-CoA hydratase by (methylenecyclopropyl)formyl-CoA: elucidation of the inactivation mechanism and identification of cysteine-114 as the entrapped nucleophile," *J. Am. Chem. Soc.* 123(4):9749-9759 (2001).
Dal et al., "Transcriptional Organization of Genes for Protocatechuate and quinate Degradation from *Acinetobacter* sp. Strain ADP1," *Appl. Environ. Microbiol.* 71(2):1025-1034 (2005).
Dangel et al., "Anaerobic metabolism of cyclohexanol by denitrifying bacteria," *Arch. Microbiol.* 150(4):358-362 (1988).
Dangel et al., "Enzyme reactions involved in anaerobic cyclohexanol metabolism by a dentitrifying *Psedomonas* species," *Arch. Microbiol.* 152:273-279 (1989).
D'Ari and Rabinowitz, "Purification Characterization, cloning, and Amino Acid Sequence of the Bifundtional Enzyme 5,10-Methylenetetrahydrofolate Dehydrogenase/5,10-Methenyltetrahydrofolate Cyclohydrolase from *Escherichia coli*," *J. Biol. Chem.* 266(35):23953-23958 (1991).
Das et al., "Characterization of a corrinoid protein involved in the Cl metabolism of strict anaerobic bacterium *Moorella thermoacetica*," *Proteins* 67(1):167-176 (2007).
Datar et al., "Fermentation of biomass-generated producer gas to ethanol," *Biotechnol. Bioeng.* 86(5):587-594 (2004).
Datsenko et al., "One-step inactivation of chromosomal genes in *Escherichia coli* K12 using PCR products," *Proc. Natl. Acad. Sci. U.S.A.* 97:6640-6645 (2000).
Datta et al., "Covalent structure of biodegradative threonine dehydratase of *Escherichi coli*: homology with other dehydratases," *Proc. Natl. Acad. Sci. U.S.A.* 84(2):393-397 (1987).
Davey and Trudgill, "The metabolism of trans-cyclohexan-1,2-diol by an *Acinetobacter* species," *Eur. J. Biochem.* 74(1):115-127 (1977).
Davids et al, "Characterization of the *N*-acetyltransferases respectively responsible for arylalkylamine and diamine acetylation in *Ascaris suum*," *Mol. Biochem. Parasitol.* 64(2):341-344 (1994).
Davie et al., "Expression and assembly of a functional E1 component ($\alpha_2\beta_2$) of mammalian branched-chain α-ketoacid dehydrogenase complex in *Escherichia coli*," *J. Biol. Chem.* 267:16601-16606 (1992).
De Biase et al., "Isolation, overexpression, and biochemical characterization of the two isoforms of glutamic acid decarboxylase from *Escherichia coli*," *Protein Expr. Purif.* 8:430-438 (1996).
de Bok et al., "Two W-containing formate dehydrogenases ($CO_2$-reductases) involving syntrophic propionate oxidation by *Syntrophobacter fumaroxidans*," *Eur. J. Biochem.* 270:2476-2485 (2003).
de Crecy et al., "Development of a novel continuous culture device for experimental evolution of bacterial populations," *Appl. Microbiol. Biotechnol.* 77(2): 489-496 (2007).
de la Torre et al., "Identification and functional analysis of a prokaryotic-type aspartate aminotransferase: implications for plant amino acid metabolism," *Plant. J.* 43(3):414-425 (2006).
de Mata and Rabinowitz, "Formyl-methenyl-methylenetetrahydrofolate synthetase (combined) from yeast. Biochemical characterization of the protein from an ADE3 mutant lacking the formyltetrahydrofolate synthetase function," *J. Biol Chem.* 255:2569-2577 (1980).
de Mendonca et al., "Functional characterization by genetic complementation of aroB-encoded dehydroquinate synthase from *Mycobacterium tuberculosis* H37Rv and its heterologous expression and purification," *J. Bacteriol.* 189:6246-6252 (2007).
de Smidt et al., "The alcohol dehydrogenases of *Saccharomyces cerevisiae*: a comprehensive review," *FEMS Yeast Rev.* 7:967-978 (2008).

Deana, "Substrate specificity of a dicarboxyl-CoA: dicarboxylic acid Coenzyme A transferase from rat liver mitochondria," *Biochem. Int.* 26(4):767-773 (1992).
DeFeyter and Pittard, "Purification and properties of shikimate kinase II from *Escherichia coli* K-12," *J. Bacteriol.* 165:331-333 (1986).
Del Campillo-Campbell et al., "Biotin-requiring Mutants of *Escherichia coli* K-12," *J. Bacteriol.* 94(6):2065-2066 (1967).
Deno, "The Diels-Alder Reaction with α, β, γ, δ-Unsaturated Acids," *J. Am. Chem. Soc.* 72:4057-4059 (1950).
Department of Energy, "Top value added chemicals from biomass. vol. I—Results of Screening for Potential Candidates from Sugars and Synthesis Gas," *Biomass*, Aug. 2004.
Desvaux, "*Clostridium cellulolyticum*: model organism of mesophilic cellulolytic clostridia," *FEMS Microbiol. Rev.* 29(4):741-764 (2005).
Devos et al., "Practical limits of function prediction," *Proteins* 41:98-107 (2000).
Di Gennaro, "Styrene lower catabolic pathway in *Pseudomonas fluorescens* ST: identification and characterization of genes for phenylacetic acid degradation," *Arch. Microbiol.* 188(2):117-125 (2007).
Diao et al., "Crystal structure of butyrate kinase 2 from *Thermotoga maritima*, a member of the Askha superfamily of phosphotransferases," *J. Bacteriol.* 191:2521-2529 (2009).
Diao et al., "Crystallization of the butyrate kinase 2 from *Thermotoga maritima* mediated by vapor diffusion of acetic acid," *Acta. Crystallogr D. Biol. Crystallogr.* 59(Pt 6):1100-1102 (2003).
Dias et al., "Well-Defined Ruthenium Olefin Metathesis Catalyst: Mechanism and Activity," *J. Am. Chem. Soc.* 119(17):3887-3897 (1997).
Diaz et al., "Gene cloning, heterologous overexpression and optimized refolding of the NAD-glutamate dehydrogenase from *Haloferax mediterranei*," *Extremophiles* 10:105-115 (2006).
Diderichsen et al., "Cloning of aldB, Which Encodes α-Acetolactate Decarboxylase, an Exoenzyme from *Bacillus brevis*," *J. Bacteriol.* 172(8):4315-4321 (1990).
Dittrich et al., "Redistribution of Metabolic Fluxes in the Central Aerobic Metabolic Pathway of *E.coli* Mutant Strains with Deletion of the *ackA-pta* and *pox*βPathways for the Synthesis of Isoamyl Acetate," *Biotechnol Prog.* 21(2):627-631 (2005).
Do et al., "Engineering *Escherichia coli* for fermentative dihydrogen production: potential role of NADH-ferredoxin oxidoreductase from the hydrogenosome of anaerobic protozoa," *Appl. Biochem. Biotechnol.* 153(1-3):21-33 (2009).
Do et al., "Growth of rhodospirillum rubrum on synthesis gas: conversion of CO to $H_2$ and Poly-β-hydroxyalkanoate," *Biotechnol. Bioeng.* 97(2):279-286 (2007).
Dobbek et al., "Crystal structure of a carbon monoxide dehydrogenase reveals a [Ni-4Fe-5S] cluster," *Science* 293(5533):1281-1285 (2001).
Dombek and Ingram, "Ethanol production during batch fermentation with *Saccharomyces cerevisiae*: Changes in glycolytic enzymes and internal pH," *Appl. Environ. Microbiol.* 53:1286-1291 (1987).
Donnelly and Cooper, "Succinic semialdehyde dehydrogenases of *Escherichia coli*: Their role in the degradation of p-hydroxyphenylacetate and γ-aminobutyrate," *Eur. J. Biochem.* 113:555-561 (1981).
Donnelly and Cooper, "Two succinic semialdehyde dehydrogenases are induced when *Escherichia coli* K-12 Is grown on γ-aminobutyrate," *J. Bacteriol.* 145:1425-1427 (1981).
Donnelly et al., "A novel fermentation pathway in an *Escherichia coli* mutant producing succinic acid, acetic acid, and ethanol," *App. Biochem. Biotech.* 70-72:187-198 (1998).
Doten et al., "Cloning and Genetic Organization of the pca Gene cluster from *Acinetobacter calcoaceticus*," *J. Bacteriol.* 169(7):3168-3174 (1987).
Doyle et al., "Structural Basis for a Change in substrate Specificity: Crystal Structure of S113E Isocitrate Dehydrogenase in a Complex with Isopropylmalate, $Mg^{2+}$ and NAPD," *Biochemistry* 40:4234-4241 (2001).
Drake and Daniel, "Physiology of the thermophilic acetogen *Moorella thermoacetica*," *Res. Microbiol.* 155(10):869-883 (2004).

(56) References Cited

OTHER PUBLICATIONS

Drake, "Acetogenesis, acetogenic bacteria, and the acetyl-CoA "Wood/Ljungdahl" pathway: past and current perspectives," in *Acetogenesis*, H. L. Drake, (ed.), Chapman & Hall, New York, p. 3-60 (1994).
Drake, "Demonstration of hydrogenase in extracts of the homoacetate-fermenting bacterium *Clostridium thermoaceticum*," *J. Bacteriol.* 150(2):702-709 (1982).
Draths and Frost, "Environmentally compatible synthesis of adipic acid from D-glucose," *J. Am. Chem. Soc.* 116:399-400 (1994).
Drevland et al., "Enzymology and Evolution of the Pyruvate Pathway to 2-Oxobutyrate in *Methanocaldococcus jannachii*," *J. Bacteriol.* 189(12):4391-4400 (2007).
Drewke et al., "4-O-Phosphoryl-L-threonine, a substrate of the pdxC(serC) gene product involved in vitamin $B_6$ biosynthesis," *FEBS Lett.* 390:179-182 (1996).
Drewke et al., "Ethanol formation in adh) mutants reveals the existence of a novel acetaldehyde-reducing activity in *Saccharomyces cerevisiae*," *J. Bacteriol.* 172:3909-3917 (1990).
Driscoll and Taber, "Sequence Organization and Regulation of the *Bacillus subtilis* menBE Operon," *J. Bacteriol.* 174(15):5063-5071 (1992).
Drummond and Stern, "Enzymes of ketone body metabolism. II. Properties of an acetoacetate-synthesizing enzyme prepared from ox liver," *J. Biol. Chem.* 235:318-325 (1960).
Du et al., "Succinic acid production from wheat using a biorefining strategy," *Appl. Microbiol. Biotechnol.* 76:1263-1270 (2007).
Duarte et al., "Reconstruction and validation of *Saccharomyces cerevisiae* iND750, a fully compartmentalized genome-scale metabolic model," *Genome Res.* 14(7):1298-1309 (2004).
Duckworth et al., "The Binding of Reduced Nicotinamide Adenine Dinucleotide to Citrate Synthase of *Escherichia coli* K12," *Biochemistry* 15(1):108-114 (1976).
Duncan et al., "The pentafunctional arom enzyme of *Saccharomyces cerevisiae* is a mosaic of monofunctional domains," *Biochem. J.* 246:375-386 (1987).
Duncan et al., "Acetate utilization and butyryl Coenzyme A (CoA):acetate-CoA transferase in butyrate-producing bacteria from the human large intestine," *Appl. Environ. Microbiol.* 68(10):5186-5190 (2002).
Duncombe and Frerman, "Molecular and catalytic properties of the acetoacetyl-Coenzyme A thiolase of *Escherichia coli*," *Arch. Biochem. Biophys.* 176(1):159-170 (1976).
Duran et al., "Characterization of cDNA clones for the 2-methyl branched-chain enoyl-CoA reductase. An enzyme involved in branched-chain fatty acid synthesis in anerobic mitochondria of the parasitic nematode *Ascaris suum*," *J. Biol. Chem.* 268(30):22391-22396 (1993).
Durner et al., "Accumulation of Poly[(R)-3-Hydroxyalkanoates] *Pseudomonas oleovorans* during Growth with Octanoate in continuous culture at Different Dilution Rates," *Appl. Environ. Microbiol.* 66(8):3408-3414 (2000).
Durre and Bahl, "Microbial Production of Acetone/Butanol/Isopropanol," In Biotechnology vol. 6: "Products of Primary Metabolism", Second edition pp. 229-268, M. Roehr, ed. Published jointly by: VCH Verlagsgesellschaft mbH, Weinheim, Federal Republic of Germany and VCH Publishers Inc., New York, NY (1996).
Dürre et al., "Solventogenic enzymes of *Clostridium acetobutylicum*: catalytic properties, genetic organization, and transcriptional regulation," *FEMS Microbiol. Rev.* 17:251-262 (1995).
Dürre, "Biobutanol: an attractive biofuel," *Biotechnol. J.* 2(12):1525-1534 (2007).
Dürre, "New insights and novel developments in clostridial acetone/butanol/isopropanol fermentation," *Appl. Microbiol. Biotechnol.* 49:639-648 (1998).
Dusch et al., "Expression of the *Corynebacterium glutamicum* panD gene encoding L-aspartate-α-decarboxylase leads to pantothenate overproduction in *Escherichia coli*," *Appl. Environ. Microbiol.* 65(4)1530-1539 (1999).
Dutscho et al., "Cloning and sequencing of the genes of 2-hydoxyglutaryl-CoA dehydratase from *Acidaminococcus fermentans*," *Eur. J. Biochem.* 181(3):741-746 (1989).
Dwiarti et al., "Purification and characterization of cis-aconitic acid decarboxylase from *Aspergillus terreus* TN484-M1," *J. Biosci Bioeng.* 94(1):29-33 (2002).
Dwyer et al., "Proton Abstraction reaction, Steady-State kinetics, and Oxidation-Reduction Potential of Human Glutaryl-CoA Dehydrogenase," *Biochemistry* 39:11488-11499 (2000).
Dykhuizen, "Chemostats used for studying natural selection and adaptive evolution," *Methods. Enzymol.* 224:613-631 (1993).
Eberhard and Gerlt, "Evolution of Function in the Crotonase Superfamily: The Stereochemical course of the Reaction catalyzed by 2-Ketocyclohexanecarboxyl-CoA Hydrolase," *J. Am. Chem. Soc.* 126:7188-7189 (2004).
Edegger et al., "Biocatalytic deuterium- and hydrogen-transfer using over-expressed ADH-'A': enhanced steroselectivity and $^2$H-labeled chiral alcohols," *Chem. Commun.* 22:2402-2404 (2006).
Eden et al., "Involvement of branched-chain amino acid aminotransferases in the production of fusel alcohols during fermentation in yeast," *Appl. Microbiol. Biotechnol.* 55:296-300 (2001).
Edwards and Palsson, "Metabolic flux balance analysis and the in silico analysis of *Escherichia coli* K-12 gene deletions," *BMC Bioinform.* 1:1 (2000).
Edwards and PalsSon, "Systems properties of the Haemophilus influenzae Rd metabolic genotype," *J. Biol. Chem.* 274(25):17410-17416 (1999).
Edwards and Palsson, "The *Escherichia coli* MG1655 in silico Metabolic Genotype: Its Definition, Characteristics, and Capabilities," *Proc. Natl. Acad. Sci. U.S.A.* 97(10):5528-5533 (2000).
Edwards et al., "Metabolic modelling of microbes: the flux-balance approach," *Environ. Microbiol.* 4(3):133-140 (2002).
Edwards et al., "In Silico Predictions of *Escherichia coli* metabolic capabilities are Consistent with Experimental Data," *Nat. Biotechnol.* 19(2):125-130 (2001).
Efe et al., "Options for biochemical production of 4-hydroxybutyrate and its lactone as a substitute for petrochemical production," *Biotechnol. Bioeng.* 99:1392-1406 (2008).
Egland et al., "A cluster of bacterial genes for anaerobic benzene ring biodegradation," *Proc. Natl. Acad. Sci. U.S.A.* 94:6484-6489 (1997).
Eikmanns et al., "The phosphoenolpyruvate carboxylase gene of *Corynebacterium glutamicum*: Molecular cloning, nucleotide sequence, and expression." *Mol. Gen. Genet.* 218:330-339 (1989).
Elshahed et al., "Metabolism of Benzoate, Cyclohex-1-ene Carboxylate, and Cyclohexane Carboxylate by "Syntrophus aciditrophicus" Strain SB in Syntrophic Association with $H_2$-Using Microorganisms," *Appl. Environ. Microbiol.* 67(4):1728-1738 (2001).
Engel, "Butyryl-CoA Dehydrogenase from *Megasphaera elsdenii*," *Methods. Enzymol.* 71:359-366 (1981).
Enomoto et al., "Cloning and sequencing of the gene encoding the soluble fumarate reductase from *Saccharomyces cerevisiae*," *DNA Res.* 3:263-267 (1996).
Ensign and Ludden, "Characterization of the CO Oxidation/$H_2$ Evolution System of *Rhodospirillum rubrum*. Role of a 22-κDa iron-sulfur protein in mediating electron transfer between carbon monoxide dehydrogenase and hydrogenase," *J. Biol. Chem.* 266(27)18395-18403 (1991).
Estévez et al., "X-ray crystallographic and kinetic correlation of a clinically observed human fumarase mutation," *Protein Sci.* 11(6):1552-1557 (2002).
Eulberg et al., "Characterization of a protocatechuate catabolic gene cluster from *Rhodococcus opacus* 1CP: evidence for a merged enzyme with 4-carboxymuconolactone-cecarboxylating and 3-oxoadipate enol-lactone-hydrolyzing activity," *J. Bacteriol.* 180:1072-1081 (1998).
Evans et al., "[$^{13}$C]propionate oxidatin in wild-type and citrate synthase mutant *Escherichia coli*: evidence for multiple pathways of propionate utilization," *Biochem. J.* 291(Pt 3):927-932 (1993).
Ezeji et al., "Butanol fermentation research: upstream and downstream manipulations," *Chem. Rec.* 4(5):305-314 (2004).

(56) References Cited

OTHER PUBLICATIONS

Faehnle et al., "A New Branch in the Family: Structure of Aspartate-β-semialdehyde Dehydrogenase from *Methanococcus jannaschii*," *J. Mol. Biol.* 353:1055-1068 (2005).
Feist et al., "The growing scope of applications of genome-scale metabolic reconstructions using *Escherichia coli*," *Nat. Biotechnol.* 26(6):659-667 (2008).
Feldberg and Datta, "L-threonine deaminase of *Rhodospirillum rubrum*. Purification and characterization," *Eur. J. Biochem.* 21(3):438-446 (1971).
Fell and Small, "Fat Synthesis in Adipose Tissue. An Examination of Stoichiometric Constraints," *Biochem. J.* 238(3):781-786 (1986).
Fernandez-Canon and Penalva, "Characterization of a fungal maleylacetoacetate isomerase gene and indentification of its human homologue," *J. Biol. Chem.* 273:329-337 (1998).
Fernandez-Valverde et al., "Purification of *Pseudomonas putida* Acyl Coenzyme A Ligase Active with a Range of aliphatic and Aromatic substrates," *Appl. Environ. Microbiol.* 59(4):1149-1154 (1993).
Fischer and Sauer, "Metabolic flux profiling of *Escherichi coli* mutants in central carbon metabolism using GC-MS," *Eur. J. Biochem.* 270(5):880-891 (2003).
Fish and Blumenthal, "2-Keto-3-deoxy-o-glucarate aldolase," *Methods Enzymol.* 9:529-534 (1966).
Fishbein and Bessman, "Purification and properties of an enzyme in human blood and rat liver microsomes catalyzing the formation and hydrolysis of γ-lactones. I. Tissue localization, stoichiometry, specificity, distinction from esterase," *J. Biol. Chem.* 241:4835-4841 (1966).
Fishbein and Bessman, "Purification and properties of an enzyme in human blood and rat liver microsomes catalyzing the formation and hydrolysis of γ-lactones. II. Metal ion effects, kinetics, and equilibria," *J. Biol. Chem.* 241:4842-4847 (1966).
Fitzgerald and Flanagan, "Characterization and sequence analysis of the human ornithine decarboxylase gene," *DNA* 8:(9):623-634 (1989).
Flint et al., "The role and properties of the iron-sulfur cluster in *Escherichia coli* dihydroxy-acid dehydratase," *J. Biol. Chem.* 268:14732-14742 (1993).
Flint, "Initial kinetic and mechanistic characterization of *Escherichia coli* fumarase A," *Arch. Biochem. Biophys.* 311(2):509-516 (1994).
Fochi, "Selective catalytic dehydrogenation of 1,4-cyclohexadiene to benzene. 1. Radical anions derived from stransition-metal arene complexes as promoters," *Organometallics* 7:2255-2256 (1988).
Fomine and Tlenkopatchev, "Cross-methathesis of dimethyl maleate and ethylene catalyzed by second generation ruthenium carbene complexes: B3LYP and MPW1K comparison study," *J. Org. Chem.* 691:5189-5196 (2006).
Fong and Palsson, "Metabolic gene-deletion strains of *Escherichia coli* evolve to computationally predicted growth phenotypes," *Nat. Genet.* 36(10):1056-1058 (2004).
Fong et al., "Description and Interpretation of Adaptive Evolution of *Escherichia coli* K-12 MG1655 by Using a Genome-Scale In Silico Metabolic Model," *J. Bacteriol.* 185(21):6400-6408 (2003).
Fong et al., "In Silico design and adaptive evolution of *Escherichia coli* for production of lactic acid," *Biotechnol. Bioeng.* 91(5):643-648 (2005).
Fonknechten et al., "A conserved gene cluster rules anaerobic oxidative degradation of L-ornithine," *J. Bacteriol.* 191(9):3162-3167 (2009).
Fontaine et al., "Molecular charcterization and transcriptional analysis of adhE2, the gene encoding the NADH-dependent aldehyde/alcohol dehydrogenase responsible for butanol production in alcohologenic cultures of *Clostridium acetobutylicum* ATCC 824," *J. Bacteriol.* 184:821-830 (2002).
Fontaine et al., "A New Type of Glucose Fermentation by *Clostridium thermoaceticum* N.Sp.," *J. Bacteriol.* 43(6):701-715 (1942).
Ford et al., "Molecular properties of the lyst1+ gene and the regulation of α-aminoadipate reductase in Schizosaccharomyces pombe," *Curr. Genet.* 28:131-137 (1995).

Forouhar et al., "Structural and Functional Evidence for *Bacillus subtilis* PaiA as a Novel $N^1$-Spermidine/spermine Acetyltransferase," *J. Biol. Chem.* 280(48):40328-40336 (2005).
Forster et al., "Genome-scale reconstruction of the *Saccharomyces cerevisiae* metabolic network," *Genome Res.* 13(2):244-253 (2003).
Fox et al., "Characterization of the region encoding the CO-induced hydrogenase of *Rhodospirillum rubrum*," *J. Bacteriol.* 178(21):6200-6208 (1996).
Freiberg et al., "Identification and characterization of the first class of potent bacterial acetyl-CoA carboxylase inhibitors with antibacterial activity," *J. Biol. Chem.* 279:26066-26073 (2004).
Freidrich et al., "The complete stereochemistry of the enzymatic dehydration of 4-hydroxybutyryl Coenzyme A to crotonyl Coenzyme A," *Angew. Chem. Int. Ed.* 47:3254-3257 (2008).
Frerman and Duncombe, "Studies on the subunits of *Escherichia coli* Coenzyme A transferase. Reconstitution of an active enzyme," *Biochim. Biophys. Acta* 580(2):289-297 (1979).
Fries et al., "Reaction Mechanism of the heterotetrameric ($\alpha_2\beta_2$) El Component of 2-Oxo Acid Dehydrogenase Multienzyme Complexes," *Biochemistry* 42:6996-7002 (2003).
Frost and Draths, "Synthesis of adipic acid from biomass-derived carbon sources," *Biotechnol Adv.* 15(1):294 (1997).
Frost et al., "Dehydroquinate synthase from *Escherichia coli*: purification, cloning, and construction of overproducers of the enzyme," *Biochemistry* 23:4470-4475 (1984).
Frost, "Redefining chemical manufacture. Replacing petroleum with plant-derived feedstocks," *Ind. Biotechnol.* 1(1):23-24 (2005).
Fu et al., "Crystal structures of human glutaryl-CoA dehydrogenase with and without an alternate substrate: structural bases of dehydrogenation and decarboxylation reactions," *Biochemistry* 43(30):9674-9684 (2004).
Fujii et al., "Characterization of L-lysine 6-aminotransferase and its structural gene from *Flavobacterium lutescens* IFO3084," *J. Biochem.* 128:391-397 (2000).
Fujii et al., "Error-prone rolling circle amplification: the simplest random mutagenesis protocol," *Nat. Protoc.* 1:2493-2497 (2006).
Fujii et al., "One-step random mutagenesis by error-prone rolling circle amplification," *Nucleic Acids Res.* 32:e145 2004.
Fujii, T. et al. "Molecular Cloning, Sequence Analysis, and Expression of the Yeast Alcohol Acetyltransferase Gene," *Appl. Environ. Microbiol.* 60:2786-2792 (1994).
Fujishiro et al., "Crystallization and Some Properties of Acetylpolyamine Amidohydrolase From Mycoplana Bullata," *Biochem. Biophys. Res. Commun.* 157(3):1169-1174 (1988).
Fujita et al., "Novel Substrate Specificity of Designer 3-Isopropylmalate Dehydrogenase Derived from *Thermus thermophilus* HB8," *Biosci. Biotechnol. Biochem.* 65(12):2695-2700 (2001).
Fukao et al., "Succinyl-CoA:3-ketoacid CoA transferase (SCOT): cloning of the human SCOT gene, tertiary structural modeling of the human SCOT monomer, and characterization of three pathogenic mutations," *Genomics* 68:144-151 (2000).
Fukuda and Wakagi, "Substrate recognition by 2-oxoacid:ferredoxin oxidoreductase from *Sulfolobus* sp. Strain 7," *Biochim. Biophys. Acta* 1597:74-80 (2002).
Fukuda et al., "Role of a highly conserved YPITP motif in 2-oxoacid:ferredoxin oxidoreductase Heterologous expression of the gene from *Sulfolobus* sp. Strain 7, and characterization of the recombinant and variant enzymes," *Eur. J. Biochem.* 568:5639-5646 (2001).
Fukui et al., "Engineering of *Ralstonia eutropha* for production of poly(3-hydroxybutyrate-co-3-hydroxyhexanoate) from fructose and solid-state properties of the copolymer," *Biomacromolecules* 3(3):618-624 (2002).
Fukumura et al, "Hydrolysis of cyclic and linear oligomers of 6-aminocaproic acid by a bacterial cell extract," *J. Biochem.* 59(6):531-536 (1966).
Fukumura et al., "Purification and properties of a novel enzyme, L-α-amino-ε-caprolactamase from *Cryptococcus laurentii*," *FEBS Lett.* 89(2):298-300 (1978).

(56) References Cited

OTHER PUBLICATIONS

Fuller and Leadlay, "Proton transfer in methylmalonyl-CoA epimerase from *Propionibacterium shermanii*. The reaction of (2R)-methylmalonyl-CoA in tritiated water," *Biochem. J.* 213(3):643-650 (1983).
Furdui and Ragsdale, "The role of pyruvate ferredoxin oxidoreductase in pyruvate synthesis during autotrophic growth by the Wood-Ljungdahl pathway," *J. Biol. Chem.* 275(37):28494-28499 (2000).
Furukawa et al., "Increased alcohol acetyltransferase activity by inositol limitation in *Saccharomyces cerevisiae* in sake mash," *J. Biosci. Bioeng.*96(4):380-386 (2003).
Galagan et al., "The genome of *M. acetivorans* reveals extensive metabolic and physiological diversity," *Genome Res.* 12(4):532-542 (2002).
Gallagher et al., "The crystal structure of chorismate lyase shows a new fold and a tightly retained product," *Proteins* 44:304-311 (2001).
Gangloff et al., "Molecular cloning of the Yeast Mitochondrial Aconitase Gene (ACO1) and Evidence of a Synergistic Regulation of Expression by Glucose plus Glutamate," *Mol. Cell. Biol.* 10(7):3551-3561 (1990).
Garras et al., "Subcellular localisation and induction of NADH-sensitive acetyl-CoA hydrolase and propionyl-CoA hydrolase activities in rat liver under lipogenic conditions after treatment with sulfur-substituted fatty acids," *Biochim. Biophys Acta.* 1255(2):154-160 (1995).
Garvie, "Bacterial lactate dehydrogenases," *Microbiol. Rev.* 44:106-139 (1980).
Gay et al., "Cloning Structural Gene sacB, Which Codes for Exoenzyme Levansucrase of *Bacillus subtilis*: Expression of the Gene in *Escherichia coli*," *J. Bacteriol.* 153(3):1424-1431 (1983).
Genda et al., "Purification and characterization of fumarase from *Corynebacterium glutamicum*," *Biosci. Biotechnol. Biochem.* 70:1102-1109 (2006).
Gerhardt et al. "Fermentation of 4-aminobutyrate by *Clostridium aminobutyricum*: cloning of two genes involved in the formation dehydration of 4-hydroxybutyrl-CoA," *Arch. Microbiol.* 174:189-199 (2000).
Gerischer and Dürre, "mRNA Analysis of the *adc* Gene Region of *Clostridium acetobutylicum* during the Shift to Solventogenesis," *J. Bacteriol.* 174(2):426-433 (1992).
Gescher et al., "Genes coding for a new pathway of aerobic benzoate metabolism in *Azoarcus evansii*," *J Bacteriol.* 184(22):6301-6315 (2002).
Giaever et al., "Functional profiling of the *Saccharomyces cerevisiae* genome," *Nature* 418(6896):387-391 (2002).
Gibbs et al., "Degenerate olignucleotide gene shuffling (DOGS): a method for enhancing the frequence of recombination with family shuffling," *Gene* 271:13-20 (2001).
Gibson (née Thomas) et al., "Cross metathesis of the amino acid homoallylglycine," *Chem. Commun.* 1107-1108 (1997).
Gibson and McAlister-Henn, "Physical and genetic interactions of cytosolic malate dehydrogenase with other gluconeogenic enzymes," *J. Biol. Chem.* 278:25628-25636 (2003).
Giesel and Simon, "On the occurrence of enoate reductase and 2-oxo-carboxylate reductase in clostridia and some observations on the amino acid fermentation by *Peptostreptococcus anaerobius*," *Arch. Microbiol.* 135(1):51-57 (1983).
Gillyon et al., "Putrescine Breakdown in the *Yeast Candida boidinii*: Subcellular Location of Some of the Enzymes Involved and Properties of Two Acetamidoaldehyde Dehydrogenases," *J. of Gen. Microbiol.* 133:2477-2485 (1987).
Glasemacher et al., "Purification and properties of acetyl-CoA synthetase (ADP-forming), an archael enzyme of acetate formation and ATP synthesis, from the hyperthermophile *Pyrococcus furiosus*," *Eur. J. Biochem.* 244:561-567 (1997).
Göbel et al., "Degradation of Aromatics and Chloroaromatics by *Pseudomonas* sp. Strain B13: Cloning, Characterization, and analysis of Sequences Encoding 3-Oxoadipate:Succinyl-Coenzyme A (CoA) Transferase and 3-oxoaipyl-CoA Thiolase," *J. Bacteriol.* 184(1):216-223 (2002).
Goda et al., "Cloning, sequencing, and expression in *Escherichia coli* of the *Clostridium tetanomorphum* gene encoding 13-methylaspartase and characterization of the recombinant protein," *Biochemistry* 31(44):10747-10756 (1992).
Gokarn et al., "Expression of pyruvate carboxylase enhances succinate production in *Escherichia coli* without affecting glucose uptake," *Biotechnol. Lett.* 20:795-798 (1998).
Gokarn et al., "Metabolic Analysis of *Escherichia coli* in the Presence and Absence of the Carboxylating Enzymes Phosphoenolpyruvate Carboxylase and Pyruvate Carboxylase," *Appl. Environ. Microbiol.* 66:1844-1850 (2000).
Gokarn, et al., "The physiological effects and metabolic alterations caused by the expression of *Rhizobium etli* pyruvate carboxylase in *Escherichia coli*," *Appl. Microbiol. Biotechnol.* 56(1-2):188-195 (2001).
Gokulan et al., "Crystal structure of *Mycobacterium tuberculosis* diaminipimelate decarboxylase, an essential enzyme in bacterial lysine biosynthesis," *J. Biol. Chem.* 278(20):18588-18596 (2003).
Goldberg et al., "Improved Conversion of Fumarate to Succinate by *Escherichia coli* Strains Amplified for Fumarate Reductase," *Appl. Environ. Microbiol.* 45:1838-1847 (1983).
Gong et al., "Specificity Determinants for the Pyruvate Dehydrogenase Component Reaction Mapped with Mutated and Prosthetic Group Modified Lipoyl Domains," *J. Biol. Chem.* 275(18):13645-13653 (2000).
González and Robb, "Genetic analysis of Carboxydothermus hydrogenoformans carbon monoxide dehydrogenase genes cooF and cooS," *FEMS Microbiol. Lett.* 191(2):243-247 (2000).
Gonzalez et al., "Characterization of a (2R,3R)-2,3-Butanediol Dehydrogenase as the *Saccharomyces cerevisiae* YAL060W Gene Product," *J. Biol. Chem.* 275(46):35876-35885 (2000).
Gonzalez-Pajuelo et al., "Metabolic engineering of *Clostridium acetobutylicum* for the industrial production of 1,3-propanediol from glycerol," *Met. Eng.* 7:329-336 (2005).
Gordon and Doelle, "Purification, properties and immunological relationship of L(+)-lactate dehydrogenase from *Lactobacillus casei*," *Eur. J. Biochem.* 67:543-555 (1976).
Goupil et al., "Imbalance of Leucine Flux in *Lactococcus lactis* and Its Use for the Isolation of Diacetyl-Overproducting Strains," *Appl. Environ. Microbiol.* 62(7):2636-2640 (1996).
Goupil-Feuillerat et al., "Transcriptional and Translational Regulation of α-Acetolactate Decarboxylase of *Lactococcus lactis* subsp. *Lactis*," *J. Bacteriol.* 182(19):5399-5408 (2000).
Gourley et al., "The two types of 3-dehydroquinase have distinct structures but catalyze the same overall reaction," *Nat. Struct. Biol.* 6:521-525 (1999).
Grant and Patel. "The non-oxidative decarboxylation of p-hydroxybenzoic acid, gentisic acid, protocatechuic acid and gallic acid by *Klebsiella aerogenes* (*Aerobacter aerogenes*)," *Antonie Van Leeuwenhoek* 35:325-343 (1969).
Green and Bennett, "Genetic manipulation of acid and solvent formation in *Clostridium acetobutylicum* ATCC 824," *Biotechnol. Bioeng.* 58(2-3):215-221 (1998).
Green and Nichols, "p-Aminobenzoate biosynthesis in *Escherichia coli*. Purification of aminodeoxychorismate lyase and cloning of pabC," *J. Biol. Chem.* 266:12971-12975 (1991).
Green et al., "Catabolism of α-ketoglutarate by a sucA mutant of *Bradyrhizobium japonicum*: evidence for an alternative tricarboxylic acid cycle," *J. Bacteriol.* 182:2838-2844 (2000).
Green et al., "Characterization and sequence of *Escherichia coli* pabC, the gene encoding aminodeoxychorismate lyase, a pyridoxal phosphate-containing enzyme," *J. Bacteriol.* 174:5317-5323 (1992).
Grethlein and Jain, "Bioprocessing of coal-derived synthesis gases by anaerobic bacteria," *Trends Biotech.* 10:418-423 (1992).
Grolle et al., "Isolation of the dxr gene of *Zymomonas mobilis* and characterization of the 1-deoxy-D-xylulose 5-phosphate reductoisomerase," *FEMS Microbiol. Lett.* 191:131-137 (2000).
Grubbs, "Olefin Meethathesis " *Tetrahedron* 60:7117-7140 (2004).

(56) References Cited

OTHER PUBLICATIONS

Gu et al., "Crystal structure of shikimate kinase from *Mycobacterium tuberculosis* reveals the dynamic role of the LID domain in catalysiS," *J. Mol. Biol.* 319:779-789 (2002).
Gueldener et al., "A second set of *loxP* marker cassettes for Cre-mediated multiple gene knockouts in budding yeast," *Nucleic Acids Res.* 30(6):e23 (2002).
Guerra et al., "Role of transmembrane segment M8 in the biogenesis and function of yeast plasma-membrane H+-ATPase," *Biochim. Biophys. Acta* 1768:2383-2392 (2007).
Guest et al., "The fumarase genes of *Escherichia coli*: location of the fumB gene and discovery of a new gene (fumC)," *J. Gen. Microbiol.* 131(11):2971-2984 (1985).
Guettler et al., "*Actinobacillus succinogenes* sp. nov., a novel succinic-acidproducing strain from the bovine rumen," *Int. J. Syst. Bacteriol.* 49:207-216 (1999).
Guirard and Snell, "Purification and properties of ornithine decarboxylase from *Lactobacillus* sp. 30a," *J. Biol. Chem.* 255:5960-5964 (1980).
Guo and Bhattacharjee, "Posttranslational activation, site-directed mutation and phylogenetic analyses of the lysine biosynthesis enzymes α-aminoadipate reductase Lys1p (AAR) and the phosphopantetheinyl transferase Lys7p (PPTase) from *Schizosaccharomyces pombe*," *Yeast* 21:1279-1288 (2004).
Guo and Bhattacharjee, "Site-directed mutational analysis of the novel catalytic domains of α-aminoadipate reductase (Lys2p) from *Candida albicans*," *Mol. Gen. Gemonics.* 269:271-279 (2003).
Guterman et al., "Generation of phenylpropanoid pathway-derived volatiles in transgenic plants: rose alcohol acetyltransferase produces phenylethyl acetate and benzyl acetate in petunia flowers," *Plant Mol. Biol.* 60(4):555-563 (2006).
Gutierrez et al., "A mutant D-amino acid aminotransferase with broad substrate specificity: construction by replacement of the interdoman loop Pro119-Arg120-Pro121 by Gly-Gly-Gly," *Protein Eng.* 11:53-58 (1998).
Gutknecht et al., "The dihydroxyacetone kinase of *Escherichia coli* utilizes a phosphoprotein instead of ATP as phosphoryl donor," *Embo J.* 20(10):2480-2486 (2001).
Guyer et al., "Identification of a sex-factor-affinity site in *E. coli* as γδ," *Cold Spring Harbor Symp. Quant. Biol.* 45:135-140 (1981).
Guzman et al., "Tight regulation, modulation, and high-level expression by vectors containing the arabinose $P_{BAD}$ promoter," *J. Bacteriol.* 177:4121-4130 (1995).
Haarasilta and Oura, "On the activity and regulation of anaplerotic and gluconeogenetic enzymes during the growth process of baker's yeast. The biphasic growth," *Eur. J. Biochem.* 52:1-7 (1975).
Hadfield et al., "Active Site Analysis of the Potential Antimicrobial Target Aspartate Semialdehyde Dehydrogenase," *Biochemistry* 40:14475-14483 (2001).
Hadfield et al., "Structure of Aspartate-β-semialdehyde Dehydrogenase from *Escherichia coli*, A Key Enzyme in the Aspartate Family of Amino Acid Biosynthesis," *J. Mol. Biol.* 289:991-1002 (1999).
Hagemeier et al., "Insight into the mechanism of biological methanol activation based on the crystal structure of the methanol-cobalamin methyltransferase complex," *Proc. Natl. Acad. Sci. U.S.A.* 103(50):18917-18922 (2006).
Hahm et al., "Characterization and evaluation of a *pta* (phosphotransacetylase) negative mutant of *Escherichia coli* HB101 as a production host of foreign lipase," *Appl. Microbiol. Biotechnol.* 42:100-107 (1994).
Haller et al., "Discovering new enzymes and metabolic pathways: conversion of succinate to propionate by *Escherichia coli*," *Biochem.* 39(16):4622-4629 (2000).
Hambraeus and Nyberg, "Enzymatic Hydrogenation of trans-2-Nonenal in Barley," *J. Agric. Food Chem.* 53:8714-8721 (2005).
Hamilton-Kemp et al., "Production of the long-chain alcohols octanol, decanol, and dodecanol by *Escherichia coli*," *Curr. Microbiol.* 51:82-86 (2005).

Hammer and Bode, "Purification and characterization of an inducible L-lysine:2-oxoglutarate 6-aminotransferase from *Candida utilis*," *J. Basic Microbiol.* 32:21-27 (1992).
Han et al., "Biochemical characterization and inhibitor discovery of shikimate dehydrogenase from *Helicobacter pylori*," *FEBS J.* 273:4682-4692 (2006).
Hanai et al., "Engineered synthetic pathway for isopropanol production in *Escherichia coli*," *Appl. Environ. Microbiol.* 73(24):7814-7818 (2007).
Hansford, "Control of mitochondrial substrate oxidation," *Curr. Top Bioenergy.* 10:217-278 (1980).
Harder, "Anaerobic degradation of cyclohexane-1,2-diol by a new *Azoarcus* species," *Arch. Microbiol.* 168:199-204 (1997).
Hardison et al., "Globin Gene Server: A prototype E-Mail Database Server Featuring Extensive Multiple Alignments and Data Compilation for Electronic Genetic Analysis," *Genomics* 21:344-353 (1994).
Harker and Bramley, "Expression of prokaryotic 1-deoxy-D-xylulose-5-phosphatases in *Escherichia coli* increases carotenoid and ubiquinone biosynthesis," *FEBS Lett.* 448:115-119 (1999).
Harms and Thauer, "Methylcobalamin: Coenzyme M methyltransferase isoenzymes MtaA and MtbA from *Methanosarcina barkeri*. Cloning, sequencing and differential transcription of the encoding genes, and functional overexpression of the mtaA gene in *Escherichia coli*," *Eur. J. Biochem.* 235(3):653-659 (1996).
Harrison and Harwood, "The pimFABCDE operon from *Rhodopseudomonas palustris* mediates dicarboxylic acid degradation and participates in anaerobic benzoate degradation," *Microbiology* 151:727-736 (2005).
Hartel et al., "Purification of glutaryl-CoA dehydrogenase from *Pseudomonas* sp., an enzyme involved in the anaerobic degradation of benzoate," *Arch. Mirobiol.* 159:174-181 (1993).
Harwood and Parales, "The β-ketoadipate pathway and the biology of self-identity," Annu. Rev. Microbiol. 50:553-590 (1996).
Harwood et al., "Anaerobic metabolism of aromatic compounds via the benzoyl-CoA pathway," *FEMS Microbiol. Rev.* 22:439-458 (1999).
Harwood et al., "Identification of the pcaRKF Gene cluster from *Pseudomonas putida*: Involvement in Chemotaxis, Biodegradation, and Transport of 4- Hydroxybenzoate," *J. Bacteriol.* 176(21):6479-6488 (1994).
Hasan and Nester, "Dehydroquinate synthase in *Bacillus subtilis*. An enzyme associated with chorismate synthase and flavin reductase," *J. Biol. Chem.* 253:4999-5004 (1978).
Hasegawa et al., "Transcriptional regulation of ketone body-utilizing enzyme, acetoacetyl-CoA synthetase, by C/EBPα during adipocyte differentiation," *Biochim. Biophys. Acta.* 1779(6-7):414-419 (2008).
Haselbeck and McAlister-Henn, "Isolation, nucleotide sequence, and disruption of the *Saccharomyces cerevisiae* gene encoding mitochondrial NADP(H)-specific isocitrate dehydrogenase," *J. Biol. Chem.* 266(4):2339-2345 (1991).
Hashidoko et al., "Cloning of a DNA fragment carrying the 4-hydroxycinnamate decarboxylase (pofK) gene from *Klebsielss oxytoca* and its constitutive expression in *Escherichia coli* JM109 cells," *Biosci. Biotech. Biochem.* 58(1):217-218 (1994).
Hashimoto et al., "Activation of L-Lysine ε-Dehydrogenase from *Agrobacterium tumefaciens* by Several Amino Acids and Monocarboxylates," *J. Biochem.* 106:76-80 (1989).
Hasson et al., "The crystal structure of benzoylfomate decarboxylase at 1.6 Å resolution: diversity of catalytic residues in thiamin diphosphate-dependent enzymes," *Biochemistry* 37:9918-9930 (1998).
Hatakeyama et al., "Analysis of oxidation sensitivity of maleate cis-trans isomerase from *Serratia marcescens*," *Biosci. Biotechnol. Biochem.* 64:1477-1485 (2000).
Hatakeyama et al., "Gene Cloning and Characterization of Maleate cis-trans Isomerase from *Alcaligenes faecalis*," *Biochem. Biophys. Res. Comm.* 239:74-79 (1997).
Hawes et al., "Primary structure and tissue-specific expression of human β-hydroxyisobutyryl-Coenzyme A hydrolase," *J. Biol. Chem.* 271:26430-26434 (1996).
Hawes et al., "Mammalian 3-hydroxyisobutyrate dehydrogenase," *Methods Enzymol.* 324:218-228 (2000).

(56) References Cited

OTHER PUBLICATIONS

Hayashi et al., "Properties of 2-hydroxyglutarate dehydrogenase from *Fusobacterium*," *J. Nihon. Univ. Sch. Dent.* 28(1):12-21 (1986).
Hayden et al., "Glutamate dehydrogenase of *Halobacterium salinarum*: evidence that the gene sequence currently assigned to the $NADP^+$-dependent enzyme is in fact that of the $Nad^+$-dependent glutamate dehydrogenase," *FEMS Microbiol. Lett.* 211:37-41 (2002).
Hayes et al., "Combining computational and experimental screening for rapid optimization of protein properties," *Proc. Natl. Acad. Sci. U.S.A.* 99(25):15926-15931 (2002).
Hayes et al., "The Biofine Process: Production of Levulinic Acid, Furfural and Formic Acid from Lignocellulosic Feedstocks," In *Biorefineries: Industrial Proceses and Products*, Wiley, Weinheim, Germany, 139-164, (2006).
Haywood and Large, "4-Acetamidobutyrate Deacetylase in the Yeast *Candida boidinii* Grown on Putrescine or Spermidine as Sole Nitrogen, Source and Its Probable Role in Polyamine Catabolism," *J. Gen. Microbiol.* 132:7-14 (1986).
Haywood et al., "Characterization of two 3-ketothiolases possessing differing substrate specificities in the polyhydroxyalkanoate synthesizing organism *Alcaligenes eutrophus*," *FEMS Microbiol. Lett.* 52:91-96 (1988).
He and Wiegel. "Purification and characterization of an oxygen-sensitive reversible 4-hydroxybenzoate decarboxylase from *Clostridium hydroxybenzoicum*," *Eur. J. Biochem.* 229:77-82 (1995).
Heidlas and Tressi, "Purification and Properties of two oxidoreductases catalyzing the enantioselective reduction of diacetyl and other diketones from baker's yeast," *Eur. J. Biochem.* 188:165-174 (1990).
Heipieper and Isken, "Ethanol tolerance and membrane fatty acid adaptation in adh multiple and null mutants of *Kluyveromyces lactis*," *Res. Microbiol.* 151:(9):777-784 (2000).
Helin et al.,. "The refined x-ray structure of muconate lactonizing enzyme from *Pseudomonas putida* PRS2000 at 1.85 Å resolution," *J. Mol. Biol.* 254:918-941 (1995).
Heller et al., "Cloning and expression of the gene for the vitamin $B_{12}$ receptor protein in the outer membrane of *Escherichia coli*," *J. Bacteriol.* 161:896-903 (1985).
Hemschemeier et al., "Biochemical and physiological characterization of the pyruvate formate-lyase Pfl1 of *Chlamydomonas reinhardtii*, a typically bacterial enzyme in eukaryotic alga, " *Eukaryot. Cell* 7:518-526 (2008).
Henne et al., "Construction of environmental DNA libraries in *Escherichia coli* and screening for the presence of genes conferring utilization of 4-hydroxybutyrate," *Appl. Environ. Microbiol.* 65(9):3901-3907 (1999).
Hennessy et al., "The reactivity of gamma-hydroxybutyric acid (GHB) and gamma-butyrolactone (GBL) in alcoholic solutions," *J. Forensic. Sci.* 49(6):1220-1229 (2004). (provided electronically by publisher as pp. 1-10).
Henning et al., "Identification of novel benzoylformate decarboxylases by growth selection," *Appl. Environ. Microbiol.* 72:7510-7517 (2006).
Henriksson et al., "The 1.9 Å resolution structure of *Mycobacterium tuberculosis* 1-deoxy-D-xylulose 5-phosphate reductoisomerase, a potential drug target," *Acta. Crystallogr. D. Biol. Crystallogr.* 62(Pt 7):807-813 (2006).
Henstra et al., "Microbiology of synthesis gas fermentation for biofuel production," *Curr. Opin. Biotechnol.* 18:200-206 (2007).
Hermes et al., "Searching sequence space by definably random mutagenesis: Improving the catalytic potency of an enzyme," *Proc. Natl. Acad. Sci U.S.A.* 87:696-700 (1990).
Herrmann et al., "Energy Conservation via Electron-Transferring Flavoprotein in Anaerobic Bacteria," *J. Bacteriol.* 190(3):784-791 (2008).
Herrmann et al., "Two β-alanyl-CoA:ammonia lyases in *Clostridium propionicum*," *FEBS J.* 272:813-821 (2005).
Hespell et al., "Stabilization of *pet* Operon Plasmids and Ethanol Production in *Escherichia coli* Strains Lacking Lactate Dehydrogenase and Pyruvate Formate-Lyase Activities," *Appl. Environ. Microbiol.* 62:4594-4597 (Dec. 1996).
Hesslinger et al., "Novel keto acid formate-lyase and propionate kinase enzymes are components of an anaerobic pathway in *Escherichia coli* that degrades L-threonine to propionate," *Mol. Microbiol.* 27(2):477-492 (1998).
Hester et al., "Purification of active El $\alpha_2\beta_2$ of *Pseudomonas putida* branched-chainoxoacid dehydrogenase," *Eur. J. Biochem.* 233:828-836 (1995).
Hetzel et al., "Acryloyl-CoA reductase from clostridium propionicum. An enzyme complex of pripionyl-CoA dehydrogenase and electron-transferring flavoprotein," *Eur. J. Biochem.* 270:902-910 (2003).
Heydari et al., "Highly Stable L-Lysine 6-Dehydrogenase from the thermophile *Geobacillus stearothermophilus* Isolated from a Japanese Hot Spring: characterization, Gene Cloning and sequencing, and Expression," *Appl. Environ. Microbiol.* 70(2):937-942 (2004).
Hibbert et al., "Directed evolution of biocatalytic processes," *Biomol. Eng.* 22:11-19 (2005).
Highbarger et al., "Mechanism of the reaction catalyzed by acetoacetate decarboxylase. Importance of lysine 116 in determining the $pK_a$ of active-site lysine 115," *Biochemistry* 35(1):41-46 (1996).
Hijarrubia et al., "Domain Structure Characterization of the Multifunctional α-Aminoadipate Reductase from *Penicillium chrysogenum* by Limited Proteolysis," *J. Biol. Chem.* 278(10):8250-8256 (2003).
Hill et al., "PCR based gene engineering of the *Vibrio harveyi* lux operon and the *Escherichia coli* trp operon provides for biochemically functional native and fused gene products," *Mol. Gen. Genet.* 226:41-48 (1991).
Hillmer and Gottschalk, "Particulate Nature of Enzymes Involved in the Fermentation of Ethanol and Acetate by *Clostridium Kluyveri*," *FEBS Lett.* 21(3):351-354 (1974).
Hillmer and Gottschalk, "Solubilization and partial characterization of particulate dehydrogenases from *Clostridium kluyveri*," *Biochim. Biophys. Acta* 334:12-23 (1974).
Hirano et al., "Purification and characerization of the Alcohol Dehydrogenase with a Broad Substrate Specificy Originated from 2-Phenylethanol-Assimilating *Brevibacterium* sp. KU 1309," *J. Biosci. Bioeng.* 100(3): 318-322 (2005).
Hirata et al., "Stereochemistry of reduction of the endocyclic double bond of (-)-carvone with the enzyme preparation from cultured cells of *Nicotiana tabacum*," *Phytochemistry* 28(12):3331-3333 (1989).
Hiser et al., "ERG10 from *Saccharomyces cerevisiae* encodes acetoacetyl-CoA thiolase," *J. Biol. Chem.* 269:31383-31389 (1994).
Ho et al., "Regulation of serine biosynthesis in Arabidopsis. Crucial role of plastidic 3-phosphoglycerate dehydrogenase in non-photosynthetic tissues," *J. Biol. Chem.* 274:397-402 (1999).
Hoang et al., "A broad-host-range Flp-FRT recombination system for site-specific excision of chromosomally-located DNA sequences: application for isolation of unmarked *Pseudomonas aeruginosa* mutants," *Gene* 212(1):77-86 (1998).
Hoffmann and Dimroth, "Sterochemistry of the methylmalonyl-CoA decarboxylation reaction," *FEBS Lett.* 220:121-125 (1987).
Hoffmeister et al., "Mitochondrial trans-2-enoyl-CoA reductase of wax ester fermentation from *Euglena gracilis* defines a new family of enzymes involved in lipid synthesis," *Biol. Chem.* 280(6):4329-4338 (2005).
Hofmeister and Buckel, "(R)-lactyl-CoA dehydratase from *Clostridium propionicum*. Stereochemistry of the dehydration of (R)-2-hydroxybutyryl-CoA to crotonly-CoA," *Eur. J. Biochem.* 206(2):547-552 (1992).
Hofmeister et al., "Cloning and expression of the two genes coding for L-serine dehydratase from *Peptostreptococcus asaccharolyticus*: relationship of the iron-sulfur protein to both L-serine dehydratases from *Escherichia coli*," *J. Bacteriol.* 179(15):4937-4941 (1997).
Hogan et al., "Improved Specificity toward Substrates with Positively Charged Side chains by Site-Directed Mutagenesis of the L-Lactate Dehydrogenase of *Bacillus stearothermophilus*," *Biochemistry* 34:4225-4230 (1995).
Holloway and Marsh, "Adenosylcobalamin-dependent glutamate mutase from *Clostridium tetanomorphum*. Overexpression in

(56) References Cited

OTHER PUBLICATIONS

*Escherichia coli*, purification, and characterization of the recombinant enzyme," *J. Biol. Chem.* 269(32):20425-20430 (1994).

Holms, "The central metabolic pathways in *Escherichia coli*: relationship between flux and control at a branch point, efficiency of conversion to biomass, and excretion of acetate," *Curr. Top. Cell. Regul.* 28:69-105 (1986).

Hong and Lee, "Metabolic flux analysis for succinic acid production by recombinant *Escherichia coli* with amplified malic enzyme activity," *Biotechnol. Bioeng.* 74(2):89-95 (2001).

Hong and Lee, "Enhanced Production of Succinic Acid by Metabolically Engineered *Escherichia coli* with Amplified Activities of Malic Enzyme and Fumarase," *Biotechnol. Bioprocess. Eng.* 9:4:252-255 (2004).

Hong et al., "The genome sequence of the capnophilic rumen bacterium *Mannheimia succiniciproducens*." *Nat. Biotechnol.* 22(10):1275-1281 (2004).

Hong et al., "Importance of redox balance on the production of succinic acid by metabolically engineered *Escherichia coli*," *Appl. Microbiol. Biotechnol.* 58:286-290 (2002).

Horswill and Escalante-Semerena, "In vitro conversion of propionate to pyruvate by *Salmonella enterica* enzymes: 2-methylcitrate dehydratase (PrpD) and aconitas Enzymes catalyze the conversion of 2-methylcitrate to 2-methylisocitrate," *Biochemistry* 40(15):4703-4713 (2001).

Horton et al., "Heterologous expression of the *Saccharomyces cerevisiae* alcohol acetyltransferase genes in *Clostridium acetobutylicum* and *Escherichia coli* for the production of isoamyl acetate," *J. Ind. Microbiol. Biotechnol.* 30(7):427-432 (2003).

Howard et al., "Titanium Metallacarbene-Metallacylobutane Reactions: Stepwise Metathesis," *J. Am. Chem. Soc.* 102:6876-6878 (1980).

Hsu et al., "Expression of an aromatic-dependent decarboxylase which provides growth-essential $CO_2$ equivalents for the acetogenic (Wood) pathway of *Clostridium thermoaceticum*," *J. Bacteriol.* 172:5901-5907 (1990).

Hu et al., "The catalytic intermediate stabilized by a "down" active site loop for diaminopimelate decarboxylase from *Helicobacter pylori*. Enzymatic characterization with crystal structure analysis," *J. Biol. Chem.* 283(30):21284-21293 (2008).

Huang et al., "Genetic characterization of the resorcinol catabolic pathway in *Corynebacterium glutamicum*," *Appl. Environ. Microbiol.* 72:7245 (2006).

Huang et al., "Purification and characterization of a ferulic acid decarboxylase from *Pseudomonas fluorescens*," *J. Bacteriol.* 176:5912-5918 (1994).

Huang et al., "Identification and characterization of a second butyrate kinase from *Clostridium acetobutylicum* ATCC 824," *J. Mol. Microbiol. Biotechnol.* 2(1):33-38 (2000).

Hübner et al., "The mechanism of substrate activation of pyruvate decarboxylase: A first approach," *Eur. J. Biochem.* 92:175-181 (1978).

Huder and Dimroth, "Sequence of the sodium ion pump methylmalonyl-CoA decarboxylase from *Veillonella parvula*," *J. Biol. Chem.* 268:24564-24571 (1993).

Hughes et al., "Cloning and expression of pca genes from *Pseudomonas putida* in *Escherichia coli*," *J. Gen. Microbiol.* 134:2877-2887 (1988).

Hughes et al., "Evidence for isofunctional enzymes in the degradation of phenol, m- and p-toluate, and p-cresol via catechol meta-cleavage pathways in *Alcaligenes eutrophus*," *J. Bacteriol.* 158(1):79-83 (1984).

Hugler et al., "Malonyl-Coenzyme A Reductase from *Chloroflexus aurantiacus*, a Key Enzyme of the 3-Hydroxypropionate Cycle for Autotrophic CO2 Fixation," *J. Bacteriol.* 184(9):2404-2410 (2002).

Huh et al., "Global analysis of protein localization in budding yeast," *Nature* 425:686-691 (2003).

Huisman and Lalonde, "Enzyme evolution for chemical process applications," In R.N. Patel (ed.), *Biocatalysis in the pharmaceutical and biotechnology industries*, CRC Press, p. 717-742 (2007).

Huo and Viola, "Substrate Specificity and Identification of Functional Groups of Homoserine Kinase from *Escherichia coli*," *Biochemistry* 35:16180-16185 (1996).

Husain and Steenkamp, "Partial purification and characterization of glutaryl-Coenzyme A dehydrogenase, electron transfer flavoprotein, and electron transfer flavoprotein-Q oxidoreductase from *Paracoccus denitrificans*," *J. Bacteriol.* 163:709-715 (1985).

Hustede et al., "Cloning of poly(3-hydroxybutyric acid) synthase genes of *Rhodobacter sphaeroides* and *Rhodospirillum rubum* and heterologous expression in *Alcaligenes eutrophys*," *FEMS Microbiol. Lett.* 93:285-290 (1992).

Ibarra et al., "*Escherichia coli* K-12 undergoes adaptive evolution to achieve in silico predicted optimal growth," *Nature* 420(6912):186-189 (2002).

Ichikawa et al., "Catalytic reaction of 1,3-butanediol over solid acids," *J. Mol. Catalysis A Chem.* 256:106-112 (2006).

Ichikawa et al., "PIO study on 1,3-butanediol dehydration over $CeO_2$ (1 1 1) surface," *J. Mol. Catalysis A Chem.* 231:181-189 (2005).

Iffland et al., "Directed Molecular Evolution of Cytochrome *c* Peroxidase," *Biochemistry* 39:10790-10798 (2000).

Ikai and Yamamoto, "Identification and analysis of a gene encoding L-2,4-diaminobutyrate:2-ketoglutarate 4-aminotransferase involved in the 1,3-diaminopropane production pathway in *Acinetobacter baummanni*," *J. Bacteriol.* 179:5118-5125 (1997).

Imai and Ohno, "Measurement of yeast intracellular pH by image processing and the change it undergoes during growth phase," *J.Biotechnol.* 38:165-172 (1995).

Ingoldsby et al., "The discovery of four distinct glutamate dehydrogenase genes in a strain of *Halobacterium salinarum*," *Gene* 349:237-244 (2005).

Ingram and Vreeland, "Differential-Effects of Ethanol and Hexanol on the *Escherichia-coli* Cell-Envelope," *J. Bacteriol.* 144:481-488 (1980).

Inui et al., "Occurrence of Oxygen-Sensitive, $NADP^+$-Dependent Pyruvate-Dehydrogenase in Mitochondria of *Euglena-gracilis*," *J. Biochem.* 96:931-934 (1984).

Inui et al., "Pyruvate-$NADP^+$ Oxidoreductase from *Euglena-gracilis*—the Kinetic-Properties of the Enzyme," *Arch. Biochem Bipophys.* 274:434-442 (1989).

Inui et al., "Wax Ester Fermentation in *Euglena-gracilis*," *FEBS Lett.* 150:89-93 (1982).

Inui et al., "Fatty acid synthesis in mitochondria of *Euglena gracilis*," *Euro. J. Biochem.* 142(1):121-126 (1984).

Inui et al., "Production and Composition of Wax Esters by Fermentation of *Euglena gracilis*," *Agr. Biol. Chem.* 47(11):2669-2671 (1983).

Inui et al., "Purification and characterization of pyruvate:$NADP^+$ oxidoreductase in *Euglena gracilis*," *J. Biol. Chem.* 262(19):9130-9135 (1987).

Inui et al., "Pyruvate:$NADP^+$ oxidoreductase from *Euglena gracilis*: mechanism of $O_2$-inactivation of the enzyme and its stability in the aerobe," *Arch. Biochem. Biophys.* 280:292-298 (1990).

Inui et al., "The physiological role of oxygen-sensitive pyruvate dehydrogenase in mitochondrial fatty acid synthesis in *Euglena gracilis*," *Arch. Biochem. Biophys.* 237(2):423-429 (1985).

Ishida et al., "Efficient production of L-Lactic acid by metabolically engineered *Saccharomyces cerevisiae* with a genome-integrated L-lactate dehydrogenase gene," *Appl. Envirom. Microbiol.* 71:1964-1970 (2005).

Ishige et al, "Long-chain aldehyde dehydrogenase that participates in n-alkane utilization and wax ester synthesis in *Acinetobacter* sp. strain M-1," *Appl. Environ. Microbiol.* 66:3481-3486 (2000).

Ishige et al., "Wax ester production from n-alkanes by *Acinetobacter* sp. strain M-1: ultrastructure of cellular inclusions and role of acyl Coenzyme A reductase," *Appl. Environ. Microbiol.* 68(3):1192-1195 (2002).

Ismaiel et al., "Purification and Characterization of a Primary-Secondary Alcohol Dehydrogenase from Two Strains of *Clostridium beijerinckii*," *J. Bacteriol.* 175(16):5097-5105 (1993).

Ismail et al., "Functional genomics by NMR spectroscopy. Phenylacetate catabolism in *Escherichia coli*," *Eur. J. Biochem.* 270(14):3047-3054 (2005).

(56) References Cited

OTHER PUBLICATIONS

Ito and Yanofsky, "Anthranilate synthetase, an enzyme specified by the tryptophan operon of *Escherichia coli*: Comparative studies on the complex and the subunits," *J. Bacteriol.* 97:734-742 (1969).

Ito et al., "Colistin nephrotoxicity: report of a case with light and electron microscopic studies," *Acta. Pathol. Jpn.* 19:55-67 (1969).

Ito et al., "D -3-hydroxybutyrate dehydrogenase from *Pseudomonas fragi*: molecular cloning of the enzyme gene and crystal structure of the enzyme," *J. Mol. Biol.* 355(4):722-733 (2006).

Iverson et al., "Structure of the *Escherichia coli* fumarate reductase respiratory complex," *Science* 284(5422):1961-1966 (1999).

Iwakura et al., "Studies on regulatory functions of malic enzymes. VI. Purification and molecular properties of NAPD-linked malic enzyme from *Escherichia coli* W," *J. Biochem.* 85:1355-1365 (1979).

Izard and Blackwell, "Crystal structures of the metal-dependent 2-dehydro-3-deoxy-galacarate aldolase suggest a novel reaction mechanism," *EMBO J.* 19:3849-3856 (2000).

Izumi et al., "Structure and Mechanism of HpcG, a Hydratase in the Homoprotocatechuate Degradation Pathway of *Escherichia coli*," *J. Mol. Biol.* 370:899-911 (2007).

Jacobi et al., "The hyp operon gene products are required for the maturation of catalytically active hydrogenase isoenzymes in *Escherichia coli*," *Arch. Microbiol.* 158(6):444-451 (1992).

Jacques et al., "Characterization of yeast homoserine dehydrogenase, an antifungal target: the invariant histidine 309 is important for enzyme integrity," *Biochem. Biophys. Acta* 1544:28-41 (2001).

Jäger and Färber, "Die Alanatreduktion von β-Carbonyl-oxalylsäureestern," *Chem. Ber.* 92:2492-2499 (1959).

James and Cronan, "Expression of two *Escherichia coli* acetyl-CoA carboxylase subunits is autoregulated," *J. Biol. Chem.* 279:2520-2527 (2004).

James and Viola, "Production and characterization of bifunctional enzymes. Domain swapping to produce new bifunctional enzymes in the aspartate pathway," *Biochemistry* 41(11) 3720-3725 (2002).

Jansen and Wanders, "L-2-hydroxyglutarate dehydrogenase: identification of a novel enzyme activity in rat and human liver. Implications for L-2-hydroxyglutaric academia," *Biochim. Biophys. Acta* 1225(1):53-56 (1993).

Janssen, "Propanol as an end product of theonine fermentation," *Arch. Microbiol.* 182:482-486 (2004).

Jantama et al., "Combining metabolic engineering and metabolic evolution to develop nonrecombinant strains of *Escherichia coli* C that produce succinate and malate," *Biotechnol. Bioeng.* 99(5):1140-1153 (2008).

Jantama et al., "Eliminating Side Products and Increasing succinate Yields in Engineered Strains of *Escherichia coli* C," *Biotechnol. Bioeng.* 101(5) 881-893 (2008).

Javid-Majd and Blanchard, "Mechanistic Analysis of the argE-Encoded N-Acetylornithine Deacetylase," *Biochemistry* 39:1285-1293 (2000).

Jeng et al., "Ornithine degradation in *Clostridium sticklandii*; pyridoxial phosphate and Coenzyme A dependent thiolytic cleavage of 2-amino-4-ketopentanoate to alanine and acetyl Coenzyme A," *Biochemistry* 13(14):2898-2903 (1974).

Jenkins and Nunn, "Genetic and molecular characterization of the genes involved in short-chain fatty acid degradation in *Escherichia coli*: the ato system," *J. Bacteriol.* 169(1):42-52 (1987).

Jennert et al., "Gene transfer to *Clostridium cellulolyticum* ATCC 35319," *Microbiol.* 146:3071-3080 (2000).

Jenssen et al., "A literature network of human genes for high-throughput analysis of gene expression," *Nat. Gene.* 28:21-28 (2001).

Jeon et al., "Heterologous expression of the alcohol dehydrogenase (adhI) gene from *Geobacillius thermoglucosidasius* strain M10EXG," *J. Biotechnol.* 135:127-133 (2008).

Jewell et al., "Bioconversion of propionic, valeric and 4-hydroxybutyric acids into the corresponding alcohols by *Clostridium acetobutylicum* NRRL 527," *Curr. Microbiol.* 13(4):215-219 (1986).

Jiang et al., "De Novo Computational Design of Retro-Aldol Enzymes," *Science* 319:1387-1391 (2008).

Jin and Sonenshein, "Characterization of the major citrate synthase of *Bacillus subtilis*," *J. Bacteriol.* 178(12):3658-3660 (1996).

Johanson et al., "Strain engineering for steroselective bioreduction of dicarbonyl compounds by yeast reductases," *FEMS Yeast Res.* 5:513-525 (2005).

Johnson et al., "Alteration of a single amino acid changes the substrate specificity of dihydroflavonol 4-reductase," *Plant J.* 25(3):325-333 (2001).

Johnston et al., "Structure of naphthoate synthase (MenB) from *Mycobacterium tuberculosis* in both native and product-bound forms," *Acta. Crystallogr. D. Biol. Crystallogr.* 61(Pt 9):1199-1206 (2005).

Jojima et al., "Production of isopropanol by metabolically engineered *Escherichia coli*," *Appl. Microbiol. Biotechnol.* 77:1219-1224 (2008).

Jones and Woods, "Acetone-butanol fermentation revisited," *Microbiol. Rev.* 50(4):484-524 (1986).

Junker and Ramos, "Involvement of the cis/trans isomerase Cti in solvent resistance of *Pseudomonas putida* DOT-T1E," *J. Bacteriol.* 181:5693-5700 (1999).

Kaclikova et al., "Fumaric acid overproduction in yeast mutants deficient in fumarase," *FEMS Microbiol. Lett.* 91(2):101-106 (1992).

Kahng et al., "Characterization of strain HY99, a novel microorganism capable of aerobic and anaerobic degradation of aniline," *FEMS Microbiol. Lett.* 190:215-221 (2000).

Kai et al., "Phosphoeno/pyruvate carboxylase: three-dimensional structure and molecular mechanisms," *Arch. Biochem. Biophys.* 414:170-179 (2003).

Kakimoto et al., "β-aminoisobutyrate-α-ketoglutarate transaminase in relation to β-aminoisobutyric aciduria," *Biochim. Biophys. Acta* 156(2):374-380 (1968).

Kalousek et al., "Isolation and characterization of propionyl-CoA carboxylase from normal human liver. Evidence for a protomeric tetramer of nonidentical subunits," *J. Biol. Chem.* 255:60-65 (1980).

Kalpos, "On the mammalian acetone metabolism: from chemistry to clinical implications," *Biochim. Biophys. Acta* 1621(2):122-139 (2003).

Kalscheuer and Steinbuchel, "A novel bifunctional wax ester synthase/acyl-CoA:diacylglycerol acyltransferase mediates wax ester and triacylglycerol biosynthesis in *Acinetobacter calcoaceticus* ADP1," *J. Biol. Chem.* 278(10):8075-8082 (2003).

Kalscheuer et al., "Analysis of storage lipid accumulation in *Alcanivorax borkumensis*: Evidence for alternative triacylglycerol biosynthesis routes in bacteria," *J. Bacteriol.* 189(3):918-928 (2007).

Kanagawa et al., "Characterization of the 6-aminohexanoate-dimer hydrolase from *Pseudomonas* sp. NK87," *J. Gen. Microbiol.* 139(4):787-795 (1993).

Kanamasa et al., "Cloning and functional characterization of the cis-aconitic acid decarboxylase (CAD) gene from *Aspergillus terreus*," *Appl. Microbiol. Biotechnol.* 80(2):223-229 (2008).

Kanao et al., "Characterization of isocitrate dehydrogenase from the green sulfur bacterium *Chlorbium limicola*. A carbon dioxide-fixing enzyme in the reductive tricarboxylic acid cycle," *Eur. J. Biochem.* 269(7):1926-1931 (2002).

Kanaujia et al., "Cloning, expression, purification, crystallization and preliminary X-ray crystallographic study of DHNA synthetase from *Geobacillus kaustophilus*," *Acta. Crystallogr. Sect. F. Struct. Biol. Cryst. Commun.* 63(Pt 2):103-105 (2007).

Kanehisa and Goto, "KEGG: Kyoto Encyclopedia of Genes and Genomes database," *Nucleic Acids Res.* 28(1):27-30 (2000).

Kapatral et al., "Genome Sequence and Analysis of the Oral Bacterium *Fusobacterium nucleatum* Strain ATCC 25586," *J. Bacteriol.* 184(7):2005-2018 (2002).

Karyakin et al., "Kinetic properties of L-lysine-2-monooxygenase from *Pseufomonas putida* and its application to biosensors for L-lysine," *Prikladnaya Biokhimiya I Mikrobiologiya* 27:825-832 (1991).

Kasberg et al., "Cloning, characterization, and sequence analysis of the clcE gene encoding the maleylacetate reductase of *Pseufomonas* sp. Strain B13," *J. Bacteriol.* 179:3801-3803 (1997).

Kaschabek and Reineke, "Degradation of chloroaromatics: purification and characterization of maleylacetate reductase from *Pseudomonas* sp. Strain B13," *J. Bacteriol.* 175:6075-6081 (1993).

(56) References Cited

OTHER PUBLICATIONS

Kaschabek and Reineke, "Maleylacetate reductase of *Pseufomonas* sp. Strain B13: specificity of substrate conversion and halide elimination," *J. Bacteriol.* 177:320-325 (1995).
Kaschabek et al., "Degradation of aromatics and chloroaromatics by *Pseudomonas* sp. strain B13: purification and characterization of 3-oxoadipate:succinyl-Coenzyme A (CoA) transferase and 3-oxoadipyl-CoA thiolase," *J. Bacteriol.* 184(1):207-215 (2002).
Kashket and Cao, "Isolation of a Degeneration-Resistant Mutant of *Clostridium acetobutylicum* NCIMB 8052," *Appl. Environ. Microbiol.* 59:4198-4202 (1993).
Kato and Asano, "3-Methylaspartate ammonia-lyase as a marker enzyme of the mesaconate pathway for (S)-glutamate fermentation in Enterobacteriaceae," *Arch. Microbiol.* 168(6):457-463 (1997).
Katti et al., "Crystal structure of muconolactone isomerase at 3.3 Å resolution," *J. Mol. Biol.* 205:557-571 (1989).
Katz et al., "Screening of two complementary collections of *Saccharomyces cerevisiae* to identify enzymes involved in stereo-selective reductions of specific carbonyl compounds: an alternative to protein purification," *Enzyme Microb. Technol.* 33:163-172 (2003).
Kawabata et al., "The Effect of Growth Temperature on Wax Ester Content and Composition of *Euglena gracilis*," *J. Gen. Microbiol.* 135: 1461-1467 (1989).
Kazahaya et al, "Aerobic Dissimilation of Glucose by Heterolactic Bacteria III. Aldehyde dehydrogenase and alcohol dehydrogenase of luconostoc mesenteroids," *J. Gen. Appl. Microbiol.* 18(1):43-55 (1972).
Kefala et al., "Cloning, expression, purification, crystallization and preliminary x-ray diffraction analysis of LysA (Rv1293) from *Mycobacterium tuberculosis*," *Acta. Crystallogr. Sect. F. Struct. Biol. Cryst. Commun.* 61(Pt 8):782-784 (2005).
Kellum and Drake, "Effects of cultivation gas phase on hydrogenase of the acetogen *Clostridium thermoaceticum*," *J. Bacteriol.* 160(1):466-469 (1984).
Kenealy et al., "Biochemical Aspects of Fumaric Acid Accumulation by *Rhizopus arrhizus*," *Appl. Environ. Microbiol.* 52:128-133 (1986).
Keng and Viola, "Specificity of Aspartokinase III from *Escherichia coli* and Examination of Important Catalytic Residues," *Arch. Biochem. Biophys.* 335(1):73-81 (1996).
Kenklies et al., "Proline biosynthesis from L-ornithine in *Clostridium sticklandii*: purification of $\Delta^1$-pyrroline-5-carboxylate reductase, and sequence and expression of encoding gene, proC," *Microbiology* 145(Pt 4):819-826 (1999).
Kerby et al., "Carbon Monoxide-Dependent Growth of *Rhodospirillum rubrum*," *J. Bacteriol.* 177:2241-2244 (1995).
Kerby et al., "Genetic and physiological characterization of the *Rhodospirillum rubrum* carbon monoxide dehydrogenase system," *J. Bacteriol.* 174(16):5284-5294.
Kern et al., "Isoamyl alcohol-induced morphological change in *Saccharomyces cerevisiae* involves increases in mitochondria and cell wall chitin content," *FEMS Yeast Res.* 5:43-49 (2004).
Kessler et al., "Pyruvate-formate-lyase-deactivase and acetyl-CoA reductase activities of *Escherichia coli* reside on a polymeric protein particle encoded by adhE," *FEBS Lett.* 281(1-2):59-63 (1991).
Khan et al., "Molecular Properties and Enhancement of Thermostability by Random Mutagenesis of Glutamate Dehydrogenase from *Bacillus subtilis*," *Biosci. Biotechnol. Biochem.* 69(10):1861-1870 (2005).
Killenberg-Jabs et al., "Active oligomeric states of pyruvate decarboxylase and their functional characterization," *Eur. J. Biochem.* 268:1698-1704 (2001).
Kim et al, "Effect of Overexpression of *Actinobacillus succinogenes* Phosphoenolpyruvate Carboxykinase on Succinate Production in *Escherichia coli*," *Appl. Env. Microbiol.* 70(2) 1238-1241 (2004).
Kim et al., "2-Hydroxyisocaproyl-CoA dehydratase and its activator from *Clostridium difficile*," *FEBS J.* 272:550-561 (2005).
Kim et al., "Construction of an *Escherichia coli* K-12 Mutant for Homoethanologic Fermentation of Glucose or Xylose without Foreign Genes," *Appl. Environ. Microbiol.* 73(6):1766-1771 (2007).

Kim et al., "Dehydration of (R)-2-hydroxyacyl-CoA to enoyl-CoA in the fermentation of a-amino acids by anaerobic bacteria," *FEMS Microbiol. Rev.* 28:455-468 (2004).
Kim et al., "Dihydrolipoamide dehydrogenase mutation alters the NADH sensitivity of pyruvate dehydrogenase complex of *Escherichia coli* K-12," *J. Bacteriol.* 190:3851-3858 (2008).
Kim et al., "Studies of the hyperthermophile *Thermotoga maritime* by random sequencing of cDNA and genomic libraries. Identification and sequencing of the trpEG (D) operon," *J. Mol. Biol.* 231:960-981 (1993).
Kim, "Purification and Properties of a diamine α-Ketoglutarate Transminase from *Escherichia coli*," *J. Biol. Chem.* 239(3):783-786 (1964).
Kino et al. Synthesis of DL-tryptophan by modified broad specificity amino acid racemase from *Pseudomonas putida* IFO 12996, *Appl. Microbiol. Biotechnol.* 73:1299-1305 (2007).
Kinoshita et al., "Purification and characterization of 6-aminohexanoic-acid-oligomer hydrolase of *Flavobacterium* sp. KI72," *Eur. J. Biochem.* 116(3):547-551 (1981).
Kinoshita, "Purification of two alcohol dehydrogenases from *Zymomonas mobilis* and their properties," *Appl. Microbiol. Biotechnol.* 22:249-254 (1985).
Kisselev L., "Polypeptide release factors in prokaryotes and eukaryotes: same function, different structure," *Structure* 10:8-9 (2002).
Klasson, et al., "Biological conversion of coal and coal-derived synthesis gas," *Fuel* 72(12):1673-1678 (1993).
Klatt et al., "Comparative genomics provides evidence for the 3-hydroxypropionate autotrophic pathway in filamentous anoxygenic phototrophic bacteria and in hot spring microbial mats," *Environ. Microbiol.* 9:2067-2078 (2007).
Kleanthous et al., "A comparison of the enzymological and biophysical properties of two distinct classes of dehydroquinase enzymes," *Biochem. J.* 282(Pt3):687-695 (1992).
Klyosov, "Kinetics and specificity of human liver aldehyde dehydrogenases toward aliphatic, aromatic, and fused polycyclic aldehydes," *Biochemistry* 35(14):4457-4467 (1996).
Knapp et al., "Crystal Structure of the Truncated Cubic Core component of the *Escherichia coli* 2-Oxoglutarate Dehydrogenase Multienzyme Complex," *J. Mol. Biol.* 280:655-668 (1998).
Knappe and Sawers, "A radical-chemical route to acetyl-CoA: the anaerobically induced pyruvate formate-lyase system of *Escherichia coli*," *FEMS. Microbiol. Rev.* 75:383-398 (1990).
Knappe et al., "Post-translational activation introduces a free radical into pyruvate formate-lyase," *Proc. Natl. Acad. Sci. U.S.A.* 81:1332-1335 (1984).
Knothe, "'Designer' Biodiesel: Optimizing Fatty Ester Composition to Improve Fuel Properties," *Energy Fuels* 22:1358-1364 (2008).
Kobayashi et al., "Physicochemical, catalytic, and immunochemical properties of fumarases crystallized separately from mitochondrial and cytosolic fractions of rat liver," *J. Biochem.* 89(6):1923-1931 (1981).
Koch and Fuchs, "Enzymatic reduction of benzoyl-CoA to alicyclic compounds, a key reaction in anaerobic aromatic metabolism," *Eur. J. Biochem.* 205:195-202 (1992).
Koch et al., "Products of enzymatic reduction of benzoyl-CoA, a key reaction in anaerobic aromatic metabolism," *Eur. J. Biochem.* 211:649-661 (1993).
Koland and Gennis, "Proximity of Reactive Cysteine Residue and Flavin in *Escherichia coli* Pyruvate Oxidase As Estimated by Flourescence Energy Transfer," *Biochemistry* 21:4438-4442 (1982).
Kollmann-Koch et al.,"Nicotinic acid metabolism. Dimethylmaleate hydratase," *Hoppe Seylers Z Physiol Chem.* 365:s.847-857 (1984).
Koo et al., "Cloning and characterization of the bifunctional alcohol/ acetaldehyde dehydrogenase gene (adhE) in *Leuconostoc mesenteroides* isolated from kimchi," *Biotechnol. Lett.* 27(7):505-510 (2005).
Korbert et al., "Crystallization of the $NADP^+$-dependent Glutamate Dehydrogenase from *Escherichia coli*," *J. Mol. Biol.* 234:1270-1273 (1993).
Kornberg, "The role and control of the glyoxylate cycle in *Escherichia coli*," *Biochem. J.* 99:1-11 (1966).

(56) References Cited

OTHER PUBLICATIONS

Korolev et al., "Autotracing of *Escherichia coli* acetate CoA-transferase α-subunit structure using 3.4 Å MAD and 1.9 Å native data," *Acta. Crystallogr. D. Biol. Crystallogr.* 58 (Pt 12):2116-2121 (2002).
Korotkova and Lidstrom, "Connection between poly-β-hydroxybutyrate biosynthesis and growth on $C_1$ and $C_2$ compounds in the methylotroph *Methylobacterium extorquens* AM1," *J. Bacteriol.* 183(3):1038-1046 (2001).
Korotkova and Lidstrom, "MeaB is a component of the methylmalonyl-CoA mutase complex required for protection of the enzyme from inactivation," *J. Biol. Chem.* 279(14):13652-13658 (2004).
Kort et al., "Glutamate dehydrogenase from the hyperthermophilic bacterium *Thermotoga maritima*: molecular characterization and phylogenetic implication," *Extremophiles* 1:52-60 (1997).
Kosaka et al., "Characterization of the sol operon in butanol-hyperproducing *Clostridium saccharoperbutylacetonicum* strain N1-4 and its degeneration mechanism," *Biosci. Biotechnol. Biochem.* 71:58-68 (2007).
Kosjek et al., "Purification and characterization of a chemotolerant alcohol dehydrogenase applicable to coupled redox reactions," *Biotechnol. Bioeng.* 86(1):55-62 (2004).
Kouzarides, "Acetylation: a regulatory modification to rival phosphorylation?" *EMBO J.* 19(6):1176-1179 (2000).
Kovachy et al., "Recognition, Isolation, and Characterization of Rat Liver D-Methylmalonyl Coenzyme A Hydrolase," *J. Biol. Chem.* 258(18):11415-11421 (1983).
Kowalchuk et al., "Contrasting patterns of evolutionary divergence within the *Acinetobacter calcoaceticus* pca operon," *Gene* 146:23-30 (1994).
Kraus et al., "Biosynthesis and mitochondrial processing of the β subunit of propionyl Coenzyme A carboxylase from rat liver," *J. Biol. Chem.* 258:7245-7248 (1983).
Kreimeyer et al., "Identification of the Last Unknown Genes in the Fermentation Pathway of Lysine," *J. Biol. Chem.* 282(10):7191-7197 (2007).
Kress et al., "First direct observation of the simultaneous presence and of the interconversion of chain-propagating metal-carbene and metallacyclobutane complexes in a catalytic olefin metathesis reaction: the ring-opening polymerization of norbornene," *J. Am. Chem. Soc.* 109(3):899-901 (1987).
Kress et al., "Tungsten(VI) and molybdenum(VI) oxo-alkyl species. Their role in the metathesis of olefins," *J. Chem. Soc. Chem. Commun.* 431-432 (1980).
Kretz et al., "Gene site saturation mutagenesis: a comprehensive mutagenesis approach," *Methods Enzymol.* 388:3-11 (2004).
Krieger et al., "Pyruvate decarboxylase from *Kluyveromyces lactis* an enzyme with an extraordinary substrate activation behaviour," *Eur. J. Biochem.* 269:3256-3263 (2002).
Krishna et al., "Enzymatic synthesis of isoamyl acetate using immobilized lipase from *Rhizomucor miehei*," *J. Biotechnol.* 87:193-201 (2001).
Kuchta and Abeles, "Lactate Reduction in *Clostridium propionicum* Purification and properties of lactyl-CoA dehydratase," *J. Biol. Chem.* 260(24):13181-13189 (1985).
Kühnl et al., "Functional analysis of the methylmalonyl-CoA epimerase from *Caenorhabditis elegans*," *FEBS J.* 272(6):1465-1477 (2005).
Kulkarni and Kanekar, "Bioremediation of ε-caprolactum from nylon-6 waste water by use of *Pseudomonas aeruginosa* MCM B-407," *Curr. Microbiol.* 37(3):191-194 (1998).
Kumamaru et al., "Enhanced degradation of polychlorinated biphenyls by directed evolution of biphenyl dioxygenase," *Nat. Biotechnol.* 16:663-666 (1998).
Kumari et al., "Cloning, Characterization, and Functional Expression of acs, the Gene Which Encodes Acetyl Coenzyme A Synthetase in *Escherichia coli*," *J. Bacteriol.* 177(10): 2878-2886 (1995).
Kuntze et al., "6-Oxocyclohex-1-ene-1-carbonyl-Coenzyme A hydrolases from obligately anaerobic bacteria: characterization and indentification of its gene as a functional marker for aromatic compounds degrading anaerobes," *Environ. Microbiol.* 10(6):1547-1556 (2008).
Kurihara et al., "γ-Glutamyputrescine synthetase in the putrescine utilization pathway of *Escherichia coli* K-12," *J. Biol. Chem.* 283(29)19981-19990 (2008).
Kurihara et al., "A Novel Putrescine Utilization Pathway Involves γ-Glutamylated Intermediates of *Escherichia coli* K-12," *J. Biol. Chem.* 280(6):4602-4608 (2005).
Kuznetsova et al., "Enzyme genomics: Application of general enzymatic screens to discover new enzymes," *FEMS Microbiol. Rev.* 29(2):263-279 (2005).
Kwok and Hanson, "GFP-labelled Rubisco and aspartate aminotransferase are present in plastid stromules and traffic between plastids," *J. Exp. Bot.* 55(397):595-604 (2004).
Kwon et al., "Influence of gluconegoenic phosphoenolpyruvate carbosykinase (PCK) expression on succinic acid fermentation in *Escherichi coli* under high bicarbonate condition," *J. Microbiol. Biotechnol.* 16(9):1448-1452 (2006).
Laempe et al., "6-Hydroxycyclohex-1-ene-1-carbonyl-CoA dehydrogenase and 6-oxocyclohex-1-ene-1-carbonyl-CoA hydrolase, enzymes of the benzoyl-CoA pathway of anaerobic aromatic metabolism in the denitrifying bacterium *Thauera aromatica*," *Eur. J. Biochem.* 263(2):420-429 (1999).
Laivenieks et al., "Cloning sequencing, and overexpression of the *Anaerobiospirillum succiniciproducens* phosphoenolpyruvate carboxykinase (*pckA*) gene," *Appl. Environ. Microbiol.* 63:2273-2280 (1997).
Lam and Winkler, "Metabolic Relationships between Pyridoxine (Vitamin $B_6$) and Serine Biosynthesis in *Escherichia coli* K-12," *J. Bacteriol.* 171(11):6518-6528 (1990).
Lamas-Maceiras et al., "Amplification and disruption of the phenylacetyl-CoA ligase gene of *Penicillium chrysogenum* encoding an aryl-capping enzyme that supplies phenylacetic acid to the isopenicillin N-acyltransferase," *Biochem. J.* 395(1):147-155 (2006).
Lamed and Zeikus, "Novel NADP-linked alcohol-aldehyde/ketone oxidoreductase in thermophilic ethanologenic bacteria," *Biochem. J.* 195:183-190 (1981).
Lardizabal et al., "Purification of a jojoba embryo wax synthase, cloning of its cDNA, and production of high levels of wax in seeds of transgenic arabidopsis," *Plant Physiol.* 122(3):645-655 (2000).
Lawrence and Roth, "Evolution of Coenzyme $B_{12}$ synthesis among enteric bacteria: evidence for loss and reacquisition of a multigene complex," *Genetics* 142(1):11-24 (1996).
Lawrence and Roth, "The cobalamin (Coenzyme $B_{12}$) biosynthetic genes of *Escherichia coli*," *J. Bacteriol.* 177(22):6371-6380 (1995).
Lebbink et al., "Engineering activity and stability of *Thermotoga maritima* glutamate dehydrogenase I. Introduction of a six-residue ion-pair network in the hinge region," *J. Mol. Biol.* 280:287-296 (1998).
Lebbink et al., "Engineering Activity and Stability of *Thermotoga maritima* glutamate Dehydrogenase. II: construction of a 16-Residue Ion-pair Network at the Subunit Interface," *J. Mol. Biol.* 289:357-369 (1999).
Leduc et al., "The hotdog thioesterase EntH (YbdB) plays a role in vivo in optimal enterobactin biosynthesis by interacting with the ArCP domain of EntB," *J. Bacteriol.* 189(19):7112-7126 (2007).
Lee and Cho, "Identification of essential active-site residues in ornithine decarboxylase of *Nicotiana glutinosa* decarboxylating both L-ornithine and L-lysine," *Biochem. J.* 360:657-665 (2001).
Lee et al., "A new approach to directed gene evolution by recombined extension on truncated templates (RETT)," *J. Molec. Catalysis* 26:119-129 (2003).
Lee et al., "Batch and continuous cultivation of *Anaerobiospirillum succiniciproducens* for the production of succinic acid from whey," *Appl. Microbiol. Biotechnol.* 54(1):23-27 (2000).
Lee et al., "Biological conversion of wood hydrolysate to succinic acid by *Anaerobiospirillum succiniciproducens*," *Biotechnol. Lett.* 25(2):111-114 (2003).
Lee et al., "Biosynthesis of enantiopure (S)-3-hydroxybutyric acid in metabolically engineered *Escherichia coli*," *App. Microbiol. Biotechnol.* 79:633-641 (2008).

(56) References Cited

OTHER PUBLICATIONS

Lee et al., "Chaperonin GroESL mediates the protein folding of human liver mitochondrial aldehyde dehydrogenase in *Escherichia coli*," *Biochem. Biophys. Res. Commun.* 298(2):216-224 (2002).
Lee et al., "Cloning and Characterization of *Mannheimia succiniciproducens* MBEL55E Phosphoenolpyruvate Carboxykinase (*pckA*) Gene," *Biotechnol. Bioprocess Eng.* 7:95-99 (2002).
Lee et al., "Fermentative production of chemicals that can be used for polymer synthesis," *Macromol. Biosci.* 4:157-164 (2004).
Lee et al., "Genome-based metabolic engineering of *Mannheimia succiniciproducens* for succinic acid productiion," *Appl. Environ. Microbiol.* 72(3):1939-1948 (2006).
Lee et al., "Isolation and characterization of a new succinic acid-producing bacterium, *Mannheimia succiniciproducens* MBEL55E, from bovine rumen," *Appl. Microbiol. Biotechnol.* 58(5):663-668 (2002).
Lee et al., "Phylogenetic diversity and the structural basis of substrate specificity in the β/α-barrel fold basic amino acid decarboxylases," *J. Biol. Chem.* 282:27115-27125 (2007).
Lee et al., "Metabolic engineering of *Escherichia coli* for enhanced production of succinic acid, based on genome comparison and in silico gene knockout simulation," *Appl Environ Microbiol.* 71(12):7880-7887 (2005).
Lehtio and Goldman, "The pyruvate format lyase family: sequences, structures and activation," Protein Eng. Des.Sel. 17:545-552 (2004).
Lehtio et al., "Crystal structure of glycyl radical enzyme from *Archaeoglobus fulgidus*," *J. Mol. Biol.* 357(1):221-235 (2006).
Lei et al., "A shared binding site for NAD$^+$ and Coenzyme A in an acetaldehyde dehydrogenase involved in bacterial degradation of aromatic compounds," *Biochemistry* 47:6870-6882 (2008).
Lemoine et al., "Microcorrespondence: Monofunctional biosynthetic peptidoglycan transglycosylases," *Mol. Microbiol.* 19(3):639-647 (1996).
Lemonnier and Lane, "Expression of the second lysine decarboxylase gene of *Escherichia coli*," *Microbiology* 144(Pt 3):751-760 (1998).
Lenski and Travisano, "Dynamics of adaptation and diversification: a 10,000-generation experiment with bacterial populations," *Proc. Natl. Acad. Sci. U.S.A.* 91(15):6808-6814 (1994).
Leonardo et al., "Anaerobic Regulation of the adhE gene, Encoding the Fermentative Alcohol Dehydrogenase of *Escherichia coli*," *J. Bacteriol.* 175(3):870-878 (1993).
Lepore et al., "The x-ray crystal structure of lysine-2,3-aminomutase from *Clostridium subterminale*," *Proc. Natl. Acad. Sci U.S.A.* 102:13819-13824 (2005).
Leppänen et al., "Pyruvate formate lyase is structurally homologous to type I ribonucleotide reductase," *Structure* 7:733-744 (1999).
Lessner et al., "An unconventional pathway for reduction of $CO_2$ to methane in CO-grown *Methanosarcina acetivorans* revealed by proteomics," *Proc. Natl. Acad. Sci. U.S.A.* 103(47):17921-17926 (2006).
Leutwein and Heider, "Succinyl-CoA(R)-benzylsuccinate CoA-Transferase: an enzyme of the anaerobic toluene catabolic pathway in denitrifying bacteria," *J. Bacteriol.* 183(14):4288-4295 (2001).
Levanon et al., "Effect of Oxygen on the *Escherichia coli* ArcA and FNR Regulation Systems and Metabolic Responses," *Biotechnol. Bioeng.* 89(5):556-564 (2005).
Li and Jordan, "Effects of substitution of tryptophan 412 in the substrate activation pathway of yeast pyruvate decarboxylase," *Biochemistry* 38:10004-10012 (1999).
Li et al., "Properties of Nicotinamide Adenine Dinucleotide Phosphate-Dependent Formate Dehydrogenase from *Clostridium thermoaceticum*," *J. Bacteriol.* 92(2):405-412 (1996).
Li et al., "Purification, crystallization and preliminary crystallographic studies on 2-dehydro-3-deoxygalactarate aldolase from *Leptospira interrogans*," *Acta. Crystallogr. Sect. Struct. Biol. Cryst. Commun.* 62(Pt 12):1269-1270 (2006).
Li, Guang-Shan, "Development of a reporter system for the study of gene expression for solvent production in *Clostridium beijerinckii* NRRL B592 and *Clostridium acetobutylicum* ATCC 824," Dissertation, Department of Biochemistry, Virginia Polytechnic Institute and State University (Sep. 1998).
Lian et al., "Stereochemical and Isotopic Labeling Studies of 4-Oxalocrotonate Decarboxylase and Vinylpyruvate hydratase: Analysis and Mechanistic Implications," *J. Am. Chem Soc.* 116:10403-10411 (1994).
Lin et al., "Chemostat culture characterization of *Escherichia coli* mutant strains metabolically engineered for aerobic succinate production: A study of the modified metabolic network based on metabolite profile, enzyme activity, and gene expression profile," *Metab. Eng.* 7(5-6):337-352 (2005).
Lin et al., "Functional Expression of Horseradish Peroxidase in *E. coli* by Directed Evolution," *Biotechnol. Prog.* 15:467-471 (1999).
Lin et al., "Effect of carbon sources differing in oxidation state and transport route on succinate production in metabolically engineered *Escherichia coli*," *J. Ind. Microbiol. Biotechnol.* 32:87-93 (2005).
Lin et al., "Fed-batch culture of a metabolically engineered *Escherichia coli* strain designed for high-level succinate production and yield under aerobic conditions," *Biotechnol. Bioeng.* 90:775-779 (2005).
Lin et al., "Genetic Reconstruction of the Aerobic Central Metabolism in *Escherichia coli* for the Absolute Aerobic Production of Succinate," *Biotechnol. Bioeng.* 89(2):148-156 (2005).
Lin et al., "Increasing the Acetyl-CoA pool in the Presence of Overexpressed Phosphoenolpyruvate Carboxylase or Pyruvate Carboxylase Enhances Succinate Production in *Escherichia coli*," *Biotechnol. Prog.* 20(5):1599-1604 (2004).
Lin et al., "Metabolic engineering of aerobic succinate production systems in *Escherichia coli* to improve process productivity and achieve the maximum theoretical succinate yield," *Metab. Eng.* 7(2):116-127 (2005).
Lin, "Metabolic Network Design and Engineering in *Escherichia coli*" Ph.D. Thesis, Rice University, Dept. of Bioengineering (2005).
Lin, H et al., "Effect of *Sorghum vulgare* phosphoenolpyruvate carboxylase and *Lactococcus lactis* pyruvate carboxylase coexpression on succinate production in mutant strains of *Escherichia coli*," *Appl. Microbiol. Biotechnol.* 67(4): 515-523 (2005).
Lingen et al., "Alteration of the substrate specificity of benzoylformate decarboxylase from *Pseudomonas putida* by directed evolution," *Chembiochem.* 4:721-726 (2003).
Lingen et al., "Improving the carboligase activity of benzoylformate decarboxylase from *Pseudomonas putida* by a combination of directed evolution and site-directed mutagenesis," *Protein Eng.* 15:585-593 (2002).
Link et al., "Methods for generating precise deletions and insertions in the genome of wild-type *Eshcerichia coli*: application to open reading frame characterization," *J. Bacteriol.* 179:6228-6237 (1997).
Liou et al., "*Clostridium carboxidivorans* sp. nov., a solvent-producing *clostridium* isolated from an agricultural settling lagoon, and reclassification of the acetogen *Clostridium scatologenes* strain SL1 as *Clostridium drakei* sp. nov," *Int. J. Syst. Evol. Microbiol.* 55(Pt 5):2085-2091 (2005).
Liu et al., "Kinetic and crystallographic analysis of active site mutants of *Escherichia coli* γ-aminobutyrate aminotransferase," *Biochemistry* 44:(8):2982-2992 (2005).
Liu et al., "Microbial production of R-3-hydroxybutyric acid by recombinant *E. coli* harboring genes of phbA, phbB, and tesB," *Appl. Microbiol. Biotechnol.* 76:811-818 (2007).
Liu et al., "Purification and characterization of ornithine acetyltransferase from *Saccharomyces cerevisiae*," *Eur. J. Biochem.* 228:291-296 (1995).
Liu et al., "Crystal structures of unbound and aminooxyacetate-bound *Escherichia coli* γ-aminobutyrate aminotransferase," *Biochemistry* 43(34):10896-10905 (2004).
Liu et al., "Economical succinic acid production from cane molasses by *Actinobacillus succinogenes*," *Bioresour Technol* 99(6):1736-1742 (2008).
Ljungdahl and Andreesen, "Formate dehydrogenase, a selenium-tungsten enzyme from *Clostridium thermoaceticum*," *Methods Enzymol.* 53:360-372 (1978).

(56) References Cited

OTHER PUBLICATIONS

Ljungdahl and Andreesen, "Tungsten, a component of active formate dehydrogenase from *Clostridium thermoacetium*," *FEBS Lett.* 54:279-282 (1975).

Ljungdahl, "The Autotrophic Pathway of Acetate Synthesis in Acetogenic Bacteria," *Ann. Rev. Microbiol.* 40:415-450 (1986).

Lloyd-Jones et al., "Rate Enhancement by Ethylene in the Ru-Catalyzed Ring-Closing Metathesis of Enynes: Evidence for an "Ene-then-Yne" Pathway that Diverts through a Second Catalytic Cycle," *Angew Chem Int Ed.* 44(45):7442-7447 (2005).

Lokanath et al., "Crystal structure of novel NADP-dependent 3-hydroxyisobutyrate dehydrogenase from *Thermus thermophilus* HB8," *J. Mol. Biol.* 352(4):905-917 (2005).

Loke et al., "Active acetyl-CoA synthase from *Clostridium thermoaceticum* obtained by cloning and heterologous expression of acsAB in *Escherichia coli*," *Proc. Natl. Acad. Sci. U.S.A.* 97:12503-12535 (2000).

Longtine et al., "Additional modules for versatile and economical PCR-based gene deletion and modification in *Saccharomyces cerevisiae*," *Yeast* 14(10): 953-961 (1998).

Lopez-Barragan et al., "The *bzd* gene cluster, coding for anaerobic benzoate catabolism, in *Azoarcus* sp. Strain CIB," *J. Bacteriol.* 186(17):5762-5774 (2004).

Louie and Chan, "Cloning and characterization of the gamma-glutamyl phosphate reductase gene of *Campylobacter jejuni*," *Mol. Gen. Genet.* 240:29-35 (1993).

Louis et al., "Restricted distribution of the butyrate kinase pathway among butyrate-producing bacteria from the human colon," *J. Bacteriol.* 186:2099-2106 (2004).

Lovell et al., "Cloning and expression in *Escherichia coli* of the *Clostridium thermoaceticum* gene encoding thermostable formyltetrahydrofolate synthetase," *Arch. Microbiol.* 149(4):280-285 (1988).

Lovell et al., "Primary structure of the thermostable formyltetrahydrofolate synthetase from *Clostridium thermoaceticum*," *Biochemistry* 20(29):5687-5694 (1990).

Low et al., "Mimicking somatic hypermutation: Affinity maturation of antibodies displayed on baceriophage using a bacterial mutator strain," *J. Mol. Biol.* 260(3):359-368 (1996).

Lu et al., "Controlled Poetntial Enzymology of Methyl Transfer Reactions Involved in Acetyl-CoA Synthesis by CO Dehydrogenase and the Corrinoid/Iron-Sulfur Protein from *Clostridium thermoaceticum*," *J. Biol. Chem.* 265(6):3124-3133 (1990).

Lu et al., "Functional Analysis and Regulation of the Divergent spuABCDEFGH-spuI Operons for Polyamine Uptake and Utilization in *Pseudomonas aeruginosa* PAO1," *J. Bacteriol.* 184(14):3765-3773 (2002).

Lu et al., "Sequence and expression of the gene encoding the corrinoid/iron-sulfur protein from *Clostridium thermoaceticum* and reconstitution of the recombinant protein to full-activity," *J. Biol. Chem.* 268(8):5605-5614 (1993).

Luersen, "Leishmania major thialsine $N^\beta$-acetyltransferase: Identification of amino acid residues crucial for substrate binding," *FEBS Lett.* 579:5347-5352 (2005).

Luli and Strohl, "Comparison of Growth, Acetate Production, and Acetate Inhibition of *Escherichia coli* Strains in Batch and Fed-Batch Fermentations," *Appl. Environ. Microbiol.* 56:1004-1011 (1990).

Lupa et al., "Distribution of genes encoding the microbial non-oxidative reversible hydroxyarylic acid decarboxylases/phenol carboxylases," *Genomics* 86:342-351 (2005).

Lupa et al., "Properties of the reversible nonoxidative vanillate/4-hydroxybenzoate decarboxylase from *Bacillus subtilis*," *Can. J. Microbiol* 54:75-81 (2008).

Lütke-Eversloh and Steinbüchel, "Biochemical and molecular characterization of a succinate semialdehyde dehydrogenase involved in the catabolism of 4-hydroxybutyric acid in *Ralstonia eutropha*," *FEMS Microbiol. Lett.* 181(1):63-71 (1999).

Lutz and Bujard, "Independent and tight regulation of transcriptional units in *Escherichia coli* via the LacR/O, the TetR/O and AraC/$l_1$-$l_2$ regulatory elements," *Nucleic Acids Res.* 25(6):1203-1210 (1997).

Lutz et al., "Creating multiple-crossover DNA libraries independent of sequence identity," *Proc. Natl. Acad. Sci U.S.A.* 98:11248-11253 (2001).

Lutz et al., "Dissecting the functional program of *Escherichia coli* promoters: the combined mode of action of Lac repressor and AraC activator," *Nucleic Acids Res.* 29(18):3873-3881 (2001).

Lutz et al., "Rapid generation of incremental truncation libraries for protein enginering using $\alpha$-phosphothioate nucleotides," *Nucleic Acids Res.* 29:E16 (2001).

Lynch et al., "SCALEs: multiscale analysis of library enrichment," *Nat. Methods.* 4(1):87-93 (2007).

Lynd et al., "Microbial Cellulose Utilization: Fundamentals and Biotechnology," *Microbiol. Mol. Biol. Rev.* 66:506-577 (2002).

Lynn et al., "Living Ring-Opening Metathesis Polymerization in Aqueous Media Catalyzed by Well-Defined Ruthenium Carbene Complexes," *J. Am. Chem. Soc.* 118(4):784-790 (1996).

Lynn et al., "Living Ring-Opening Metathesis Polymerization in Water," *J. Am. Chem. Soc.* 120(7):1627-1628 (1998).

Ma et al., "Induced rebuilding of aspartase conformation," *Ann. NY Acad. Sci.* 672:60-65 (1992).

Macis et al., "Properties and sequence of the Coenzyme $B_{12}$-dependent glycerol dehydratase of *Clostridium pasteruianum*," *FEMS Microbiol. Lett.* 164:21-28 (1998).

Mack and Buckel, "Conversion of glutaconate CoA-transferase from *Acidaminococcus fermentans* into an acyl-CoA hydrolase by site-directed mutagenesis," *FEBS Lett.* 405(2):209-212 (1997).

Mack et al., "Location of the two genes encoding glutaconate Coenzyme A-transferase at the beginning of the hydroxyglutarate operon in *Acidaminococcus fermentans*," *Eur. J. Biochem.* 226:41-51 (1994).

Maeda et al., "Enhanced hydrogen production from glucose by metabolically engineered *Escherichia coli*," *Appl. Microbiol. Biotechnol.* 77:879-890 (2007).

Maeder et al., "The *Methanosarcina barkeri* genome: comparative analysis with *Methanosarcina acetivorans* and *Methanosarcina mazei* reveals extensive rearrangement within methanosarcinal genomes," *J. Bacteriol.* 188(22):7922-7931 (2006).

Maes et al., "Crystallization of ornithine acetyltransferase from yeast by counter-diffusion and preliminary x-ray study," *Acta. Crystallogr. Sect. F. Struct. Biol. Cryst. Commun.* 62(Pt 12):1294-1297 (2006).

Mahadevan and Schilling, "The effects of alternate optimal solutions in constraint-based genome-scale metabolic models," *Metab. Eng.* 5(4):264-276 (2003).

Mahan and Csonka, "Genetic analysis of the proBA genes of *Salmonella typhimurium*: physical and genetic analyses of the cloned proB$^+$A$^+$ genes of *Escherichia coli* and of a mutant allele that confers proline overproduction and enhanced osmotolerance," *J. Bacteriol.* 156:1249-1262 (1983).

Mai and Adams, "Purification and characterization of two reversible and ADP-dependent acetyl Coenzyme A synthetases from the hyperthermophilic archaeon *Pyrococcus furiosus*," *J. Bacteriol.* 178:5897-5903 (1996.).

Maicas, S. et al., "NAD(P)H regeneration is the key for heterolactic fermentation of hexoses in *Oenococcus oeni*," *Microbiology* 148: 325-332 (2002).

Maitra and Sprinson, "5-Dehydro-3-deoxy-D-arabino-heptulosonic acid 7-phosphate. An intermediate in the 3-dehydroquinate synthase reaction," *J Biol. Chem.* 253:5426-2430 (1978).

Majewski and Domach, "Simple Constrained-Optimization View of Acete Overflow in *E. Coli*," *Biotechnol. Bioeng.* 35(7):732-738 (1990).

Maklashina et al., "Anaerobic expression of *Escherichia coli* succinate dehydrogenase: functional replacement of fumarate-reductase in the respiratory chain during anaerobic growth," *J. Bacteriol.* 180(22):5989-5996 (1998).

Manjasetty et al., "Crystallization and preliminary X-ray analysis of dmpFG-encoded 4-hydroxy-2-ketovalerate aldolase-aldehyde dehydrogenase (acylating) from *Pseudomonas* sp strain CF600," *Acta. Crystallogr. D. Biol. Crystallogr.* 57(Pt 4):582-585 (2001).

Manning and Pollitt, "Tracer studies of the interconversion of R- and S-methylmalonic semialdehydes in man," *Biochem. J.* 231(2):481-484 (1985).

(56) References Cited

OTHER PUBLICATIONS

Marco-Mann et al., "Site-directed Mutagenesis of *Escherichia coli* Acetylglutamate Kinase and Aspartokinase III Probes the Catalytic and Substrate-binding Mechanisms of these Amino Acid Kinase Family Enzymes and Allows Three-dimensional Modelling of Aspartokinase," *J. Mol. Biol.* 334:459-476 (2003).

Marek and Henson, "Cloning and expression of the *Escherichia coli* K-12 sad gene," *J. Bacteriol.* 170:991-994 (1988).

Marks et al., "Molecular cloning and characterization of (R)-3-hydroxybutyrate dehydrogenase from human heart," *J. Biol. Chem.* 267(22):15459-15463 (1992).

Martin et al., "Engineering a mevalonate pathway in *Escherichia coli* for production of terpenoids," *Nat. Biotechnol.* 21:796-802 (2003).

Martin et al., "Nematode.net update 2008: improvements enabling more efficient data mining and comparative nematode genomics," *Nucleic Acids Res.* 37:D571-D578 (2009).

Martinez-Blanco et al., "Purification and biochemical characterization of phenylacetyl-CoA ligase from *Pseudomonas putida*. A specific enzyme for the catabolism of phenylacetic acid," *J. Biol. Chem.* 265(12):7084-7090 (1990).

Martinez-Carrion and Jenkins, "D-Alanine-D-glutamate transminase. I. Purification and characterization," *J. Biol. Chem.* 240(9):3538-3546 (1965).

Martins et al., "Crystal structure of 4-hydroxybutyryl-CoA dehydratase: radical catalysis involving a [4Fe-4S] cluster and flavin," *Proc. Natl. Acad. Sci. U.S.A.* 101(44):15645-15649 (2004).

Mason and Dufour, "Alcohol acetyltransferases and the significance of ester synthesis in yeast," *Yeast* 16(14):1287-1298 (2000).

Matiasek et al., "Volatile ketone formation in bacteria: release of 3-oxopentanoate by soil pseudomonads during growth on heptanoate," *Curr. Microbiol.* 42:276-281 (2001).

Mat-Jan et al., "Mutants of *Escherichia coli* Deficient in the Fermentative Lactate Dehydrogenase," *J. Bacteriol.* 171(1):342-348 (1989).

Matsumura et al., "Constitutive expression of catABC genes in the aniline-assimilating bacterium *Rhodococcus* species AN-22: production, purification, characterization and gene analysis of CatA, CatB and CatC," *Biochem. J.* 393:219-226 (2006).

Matsushima et al., "An enone reductase from *Nicotiana tabacum*: cDNA cloning, expression in *Escherichia coli*, and reduction of enones with the recombinant proteins," *Bioorg. Chem.* 36:23-28 (2008).

Matta et al., "Interactions of the antizyme AtoC with regulatory elements of the *Escherichia coli* atoDAEB operon," *J. Bacteriol.* 189(17):6324-6332 (2007).

Mattevi et al., "Atomic structure of the cubic core of the pyruvate dehydrogenase multienzyme complex," *Science* 255(5051):1544-1550 (1992).

Matthies and Schink, "Reciprocal Isomerization of Butyrate and Isobutyrate by the Strictly Anaerobic Bacterium Strain WoG13 and Methanogenic Isobutyrate Degradation by a Defined Triculture," *Appl. Environ. Microbiol.* 58(5):1435-1439 (1992).

Maurus et al., "Insights into the Evolution of Allosteric Properties. The NADH Binding Site of Hexameric Type II Citrate Synthases," *Biochemistry* 42:5555-5565 (2003).

Mavrovouniotis, Estimation of standard Gibbs energy changes of biotransformations, *J. Biol. Chem.* 266:14440-14445 (1991).

Maynard et al., "Autocatalytic activation of acetyl-CoA synthase," *J. Biol. Inorg. Chem.* 9:316-322 (2004).

Mazur et al., "Cis,cis-muconate lactonizing enzyme from *Trichosporon cutaneum*: evidence for a novel class of cycloisomerases in eucaryotes," *Biochemistry* 33:1961-1970 (1994).

McAlister-Henn and Thompson, "Isolation and expression of the gene encoding yeast mitochondrial malate dehydrogenase," *J. Bacteriol.* 169:5157-5166 (1987).

McCarthy et al., "Crystal structure of methylmalonyl-Coenzyme A epimerase from *P. shermanii*: a novel enzymatic function on an ancient metal binding scaffold," *Structure* 9(7):637-646 (2001).

McCullough et al., "Enzymatic decarboxylation of the aminobenzoates," *J. Am. Chem. Soc.* 79:628-630 (1957).

McGregor et al., "argE-Encoded N-Acetyl-L-Ornithine Deacetylase from *Escherchia coli* Contains a Dinuclear Metalloactive Site," *J. Am. Chem. Soc.* 127:14100-14107 (2005).

McInerney et al., "The genome of *Syntrophus aciditrophicus*: Life at the thermodynamic limit of microbial growth," *Proc. Natl. Acad. Sci U.S.A.* 104:7600-7605 (2007).

McKinlay et al., "Prospects for a bio-based succinate industry," *Appl. Microbiol. Biotechnol.* 76(4):727-740 (2007).

McPherson and Wootton, "Complete nucleotide sequence of the *Escherichia coli* gdhA gene," *Nucleic Acids Res.* 11:5257-5266 (1983).

McPherson et al., "Multiple interactions of lysine-128 of *Escherichia coli* glutamate dehydrogenase revealed by site-directed mutagenesis studies," *Protein Eng.* 2(2):147-152 (1988).

Meagher, "Purification and partial amino acid sequence of the cyanogen bromide fragments of muconolactone isomerase from *Pseudomonas putida*," *Biochim. Biophys Acta* 494:33-47 (1977).

Mechichi et al., "*Alicycliphilus denitrificans* gen. nov., sp. nov., a cyclohexanoldegrading, nitrate-reducing β-proteobacterium," *Int. J. Syst. Evol. Microbiol.* 53:147-152 (2003).

Megraw et al., "Formation of lactyl-Coenzyme A and pyruvyl-Coenzyme A from lactic acid by *Escherichia coli*," *J. Bacteriol.* 90(4):984-988 (1965).

Meinnel et al., "Structural and Biochemical Characterization of the *Escherichia coli* argE Gene Product," *J. Bacteriol.* 174(7):2323-2331 (1992).

Melchiorsen et al., "The level of pyruvate-formate lyase controls the shift from homolactic to mixed-acid product formation in *Lactococcus lactis*," *Appl. Microbiol. Biotechnol.* 58:338-344 (2002).

Meng and Chuang, "Site-directed Mutagenesis and Functional Analysis of the Active-Site Residues of the E2 Component of Bovine Branched-Chain α-Keto Acid Dehydrogenase Complex," *Biochemist* 33:12879-12885 (1994).

Meng and Li, "Cloning, expression and characterization of a thiolase gene from *Clostridium pasteurianum*," *Biotechnol. Lett.* 28(16):1227-1232 (2006).

Menon and Ragsdale, "Mechanism of the *Clostridium thermoaceticum* pyruvate:ferredoxin oxidoreductase: evidence for the common catalytic intermediacy of the hydroxyethylthiamine pyropyrosphate radical," *Biochemistry* 36(28):8484-8494 (1997).

Menzel et al., "Enzymatic evidence for an involvement of pyruvate dehydrogenase in the anaerobic glycerol metabolism of *Klebsiella pneumoniae*," *J. Biotech.* 56:135-142 (1997).

Menzel et al., "Kinetic, dynamic, and pathway studies of glycerol metabolism by *Klebsiella pneumoniae* in anaerobic continuous culsutre: IV. Enzymes and fluxes of pyruvate metabolism," *Botechnol. Bioeng.* 60(5):617-626 (1998).

Merkel and Nichols, "Characterization and sequence of the *Escherichia coli* panBCD gene cluster," *FEMS Microbiol. Lett.* 143(2-3):247-252 (1996).

Mermelstein et al., "Metabolic Engineering of *Clostridium acetobutylicum* ATCC 824 for Increased Solvent Production by Enhancement of Acetone Formation Enzyme Activities Using a Synthetic Acetone Operon," *Biotechnol. Bioeng.* 42(9):1053-1060 (1993).

Metz et al., "Purification of a jojoba embryo fatty acyl-Coenzyme A reductase and expression of its cDNA in high erucic acid rapeseed," *Plant Phys.* 122:635-644 (2000).

Meynial-Salles, I., et al., "A new process for the continuous production of succinic acid from glucose at high yield, titer and productivity," *Biotechnol. Bioeng.* 99(1):129-135 (2008).

Millard et al., "Enhanced production of succinic acid by overexpression of phosphoenolpryuvate carbosylase in *Escherichia coli*," *Appl. Environ. Microbiol.* 62(5):1808-1810 (1996).

Miller and Jenesel, "Enzymology of butyrate Formation by Butyrivibrio-Fibrisolvens," *J. Bacteriol.* 138:99-104 (1979).

Miller et al., "Structure of β-lactam synthetase reveals how to synthesize antibiotics instead of asparagine," *Nat. Struct. Biol.* 8(8):684-689 (2001).

Miller et al., "The catalytic cycle of β-lactam synthetase observed by x-ray crystallographic snapshots," *Proc. Natl. Acad. Sci. U.S.A.* 99(23):14752-41757 (2002).

(56) References Cited

OTHER PUBLICATIONS

Minard and McAlister-Henn, "Isolation, nucleotide sequence analysis, and disruption of the MDH2 gene from *Saccharomyces cerevisiae*: evidence for three isozymes of yeast malate dehydrogenase," *Mol. Cell. Biol.* 11:370-380 (1991).
Misono and Nagasaki, "Occurrence of L-Lysine ε-Dehydrogenase in *Agrobacterium tumefaciens*," *J. Bacteriol.* 150(1):398-401 (1982).
Misono et al., "Properties of L-lysine epsilon-dehydrogenase from *Agrobacterium tumefaciens*," *J. Biochem.* 105(6):1002-1008 (1989).
Miura et al., "Molecular Cloning of the *nemA* Gene Encoding N-Ethylmaleimide Reductase from *Escherichia coli*," *Biol. Pharm. Bull.* 20(1):110-112 (1997).
Miyazaki et al., "α-Aminoadipate aminotransferase from an extremely thermophilic bacterium, *Thermus thermophilus*," *Microbiology* 150:2327-2334 (2004).
Mizobata et al., "Purification and characterization of a thermostable class II fumarase from *Thermus thermophilus*," *Arch. Biochem. Biophys.* 355(1):49-55 (1998).
Mizugaki et al. "Studies on the metabolism of unsaturated fatty acids. IX. Stereochemical studies of the reaction catalyzed by trans-2-enoyl-Coenzyme A reductase of *Escherichia coli*," *J. Biochem.* 92(5):1649-1654 (1982).
Mizugaki et al., "Studies on the Metabolism of Unsaturated Fatty Acids. V. Isomerization of Thiol Esters of cis-2-Alkenoic Acids during Their Preparation and Alkaline Hydrolysis," *Chem. Pharm. Bull.* 30(1):206-213 (1982).
Momany et al., "Crystallization of diaminopimelate decarboxylase from *Escherichia coli*, a stereo specific a-amino-acid decarboxylase," *Acta. Crystallogr. D. Biol. Crystallogr.* 58(Pt 3):549-552 (2002).
Momany et al., "Crystallographic Structure of PLP-Dependent Ornithine Decarboxylase from *Lactobacillus* 30a to 3.0 Å Resolution," *J. Mol. Biol.* 252:643-655 (1995).
Monnet et al., "Regulation of branched-chain amino acid biosynthesis by α-acetolactate decarboxylase in *Streptococcus thermophilus*," *Lett. Appl. Microbiol.* 36(6):399-405 (2003).
Moon et al., "Metabolic engineering of *Escherichia coli* for the production of malic acid," *Biochem. Eng. J.* 40(2):312-320 (2008).
Moore et al., "Expression and Purification of Aspartate β-Semialdehyde Dehydrogenase from Infectious Microorganisms," *Protein Expr. Purif.* 25:189-194 (2002).
Moresi et al., "Fumaric acid production from hydrolysates of starch-based substrates," *J. Chem. Technol. Biotechnol.* 54(3):283-290 (1992).
Mori et al., "Characterization, Sequencing, and Expression of the Genes Encoding a Reactivating Factor for Glycerol-inactivated Adenosylcobalamin-dependent Diol Dehydratase," *J. Biol. Chem.* 272(51):32034-32041 (1997).
Morris and Jinks-Robertson, "Nucleotide sequence of the LYS2 gene of *Saccharomyces cerevisiae*: homology to *Bacillus brevis* tyrocidine synthetase 1," *Gene* 98:141-145 (1991).
Morsomme et al., "Single point mutations in various domains of a plant plasma membrane H+-ATPase expressed in *Saccharomyces cerevisiae* increase H+-pumping and permit yeast growth at low pH," *EMBO. J.* 15(20):5513-5526 (1996).
Morton et al., "Cloning, sequencing, and expressions of genes encoding enzymes of the autotrophic acetyl-CoA pathway in the acetogen *Clostridium thermoaceticum*," In M. Sebald (ed.), *Genetics and molecular biology of anaerobic bacteria*, Springer Verlag, New York, 389-406 (1992).
Morton et al., "The primary structure of the subunits of carbon monoxide dehydrogenase/acetyl-CoA synthase from *Clostridium thermoaceticum*," *J. Biol. Chem.* 266(35):23824-23828 (1991).
Moskowitz et al., "Metabolism of poly-β-hydroxybutyrate. II. Enzymatic synthesis of D-(−)-β-hydroxybutyryl Coenzyme A by an enoyl hydrase from *Rhodospirillum rubrum*," *Biochemistry* 8:2748-2755 (1969).
Moszer, "The complete genome of *Bacillus subtilis*: from sequence annotation to data management and analysis," *FEBS Lett.* 430:28-36 (1998).

Mouttaki et al., "Cyclohexane Carboxylate and Benzoate Formation from Crotonate in *Syntrophus aciditrophicus*," *Appl. Environl. Microbiol.* 73(3):930-938 (2007).
Müh et al., "4-Hydroxybutyryl-CoA dehydratase from *Clostridium aminobutyricum*: characterization of FAD and iron-sulfur clusters involved in an overall non-redox reaction," *Biochemistry* 35:11710-11718 (1996).
Müh et al., "Mössbauer study of 4-hydroxybutyryl-CoA dehydratase probing the role of an iron-sulfur cluster in an overall non-redox reaction," *Eur. J. Biochem.* 248:380-384 (1997).
Mukhopadhyay and Purwantini, "Pyruvate carboxylase from *Mycobacterium smegmatis*: stabilization, rapid purification, moleculare and biochemical characterization and regulation of the cellular level," *Biochim. Biophys. Acta* 1475(3):191-206 (2000).
Muller and Buckel, "Activation of (R)-2-hydroxyglutaryl-CoA dehydratase from *Acidaminococcus fermentans*," *Eur. J. Biochem.* 230(2):698-704 (1995).
Muller et al., "Nucleotide exchange and excisiion technology (NExT) DNA shuffling; a robust method for DNA fragmentation and directed evolution," *Nucleic Acids Res.* 33:e117 (2005).
Müller, "Energy Conservation in Acetogenic Bacteria," *Appl. Environ. Microbiol.* 69:6345-6353 (2003).
Murakami et al., "Purification and characterization of two muconate cycloisomerase isozymes from aniline-assimilating Frateuria species ANA-18," *Biosci. Biotechnol. Biochem.* 62:1129-1133 (1998).
Muratsubaki and Enomoto, "One of the fumarate reductase isoenzymes from *Saccharomyces cerevisiae* is encoded by the OSM1 gene," *Arch. Biochem. Biophys.* 352:175-181 (1998).
Musfeldt and Schönheit, "Novel type of ADP-forming acetyl Coenzyme A synthetase in hyperthermophilic archaea: heterologous expression and characterization of isoenzymes from the sulfate reducer *Archaeoglobus fulgidus* and the methanogen *Methanococcus jannaschii*," *J. Bacteriol.* 184(3):636-644 (2002).
Muyrers et al., "Rapid modification of bacterial artificial chromosomes by ET-recombination," recombination, *Nucleic Acids Res.* 27:1555-1557 (1999).
Nagasawa et al., "Cloning and Nucleotide Sequence of the Alcohol Acetyltransferase II gene (*ATF2*) from *Saccharomyces cerevisiae* Kyokai No. 7," *Biosci. Biotechnol. Biochem.* 62:1852-1857 (1998).
Nagata et al., "Gene cloning, purification, and characterization of thermostable and halophilic leucine dehydrogenase from a halophilic thermophile, *Bacillus licheniformis* TSN9," *Appl. Microbiol. Biotechnol.* 44:432-438 (1995).
Naggert et al., "Cloning, sequencing, and characterization of *Escherichia coli* thioesterase II," *J. Biol. Chem.* 266(17):11044-11050 (1991).
Nahvi et al., "Genetic Control by a Metabolite Binding mRNA," *Chem. Biol.* 9:1043-1049 (2002).
Naidu and Ragsdale, "Characterization of a three-component vanillate O-demethylase from *Moorella thermoacetica*," *J. Bacteriol.* 183(11):3276-3281 (2001).
Najafpour and Younesi, "Ethanol and acetate synthesis from waste gas using batch culture of *Clostridium ljungdahlii*," *Enzyme Microb. Technol.* 38:223-228 (2006).
Najmudin et al., "Purification, crystallization and preliminary X-ray crystallographic studies on acetolactate decarboxylase," *Acta. Crystallogr. D. Biol. Crystallogr.* 59(Pt 6):1073-1075 (2003).
Nakahigashi and Inokuchi, "Nucleotide sequence of the fadA and fadB genes from *Escherichia coli*," *Nucleic Acids Res.* 18(16):4937 (1990).
Nakano et al., "Characterization of Anaerobic Fermentative Growth of *Bacillus subtilis*: Identification of Fermentation End Products and Genes Required for Growth," *J. Bacteriol.* 179(21):6749-6755 (1997).
Nakazawa et al., "Studies on monooxygenases. V. Manifestation of amino acid oxidase activity by L-lysine monooxygenase," *J. Biol. Chem.* 247:3439-3444 (1972).
Namba et al., "Coenzyme A- and Nicotinamide Adenine Dinucleotide-dependent Branched Chain α-Keto Acid Dehydrogenase," *J. Biol. Chem.* 244(16):4437-4447 (1969).
Neidhart et al., "Mandelate racemase and muconate lactonizing enzyme are mechanistically distinct and structurally homologous," *Nature* 347:692-694 (1990).

(56) References Cited

OTHER PUBLICATIONS

Ness et al., "Synthetic shuffling expands functional protein diversity by allowing amino acids to recombine independently," *Nat. Biotechnol.* 20:1251-1255 (2002).
Nicolaou et al., "The Diels-Alder Reaction in Total Synthesis," *Angew Chemie Int Ed.* 41:1668-1698 (2002).
Niegemann et al., "Molecular organization of the *Escherichia coli* gab cluster: nucleotide sequence of the structural genes gabD and gabP and expression of the GABA permease gene," *Arch.Microbiol* 160:454-460 (1993).
Nimmo, "Kinetic mechanism of *Escherichia coli* isocitrate dehydrogenase and its inhibition by glyoxylate and oxaloacetate," *Biochem. J.* 234(2):317-323 (1986).
Nishimaki et al., "Studies on the Metabolism of Unsaturated Fatty Acids. XIV. Purification and Properties of NADPH-Dependent trans-2-Enoyl-CoA Reductase of *Escherichia coli* K-12," *J. Biochem.* 95(5):1315-1321 (1984).
Nishizawa et al., "Gene expression and characterization of two 2-oxoacid:ferredoxin oxidoreductases from *Aeropyrum pernix* K1," *FEBS Lett.* 579:2319-2322 (2005).
Nissen et al., "Expression of a cytoplasmic transhydrogenase in *Saccharomyces cerevisiae* results in formation of 2-oxoglutarate due to depletion of the NADPH pool," *Yeast* 18:19-32 (2001).
Nogales et al., "Characterization of the last step of the aerobic phenylacetic acid degradation pathway," *Microbiology* 153(Pt 2):357-365 (2007).
Noichinda et al., "Subcellular Localization of Alcohol Acetyltransferase in Strawberry Fruit," *Food Sci. Technol. Res.* 5(3):239-242 (1999).
Nölling et al., "Genome sequence and comparative analysis of the solvent-producing bacterium *Clostridium acetobutylicum*," *J. Bacteriol.* 183(16):4823-4838 (2001).
Norton, "The Diels-Alder Diene Synthesis," *Chem. Rev.* 31:319-523 (1942).
Nowicki et al., "Recombinant tyrosine aminotransferase from *Trypanosoma cruzi*: structural characterization and site directed mutagenesis of a broad substrate specificity enzyme," *Biochim. Biophysica Acta* 1546:268-281 (2001).
O'Brien and Gennis, "Studies of the Thiamin Pyrophosphate Binding Site of *Escherichia coli* Pyruvate Oxidase," *J. Biol. Chem.* 255(8):3302-3307 (1980).
O'Brien et al, "Regulation by Lipids of Cofactor Binding to a Peripheral Membrane. Pyrophosphate to Pyruvate Oxidase," *Biochemistry* 16(14):3105-3109 (1977).
O'Brien et al., "Chemical, physical and enzymatic comparisons of formyltetrahydrofolate synthetases from thermo- and mesophilic clostridia," *Experientia. Suppl.* 26:249-262 (1976).
O'Brien et al., "Insight into the Mechanism of the $B_{12}$-Independent Glycerol Dehydratase from *Clostridium butyricum*: Preliminary Biochemical and Structural Characterization," *Biochemistry* 43:4635-4645 (2004).
Ofman et al., "2-Methyl-3-hydroxybutyryl-CoA dehydrogenase deficiency is caused by mutations in the HADH2 gene," *Am. J. Hum. Genet.* 72:1300-1307 (2003).
Ohgami et al., "Expression of acetoacetyl-CoA synthetase, a novel cytosolic ketone body-utilizing enzyme, in human brain," *Biochem. Pharmacol.* 65:989-994 (2003).
Ohsugi et al., "Metabolism of L-β-Lysine by *Pseudomonas*. Purification and Properties of a Deacetylase-Thiolestrerase Utilizing 4-Acetamidobutyryl CoA and Related Compounds," *J. Biol. Chem.* 256(14):7642-7651 (1981).
Okino et al., "An effeicient succinic acid production process in a metabolically engineered *Corynebacterium glutamicum* strain," *Appl. Microbiol. Biotechnol.* 81(3):459-464 (2008).
Oku and Kaneda, "Biosynthesis of branched-chain fatty acids in *Bacillus subtilis*. A decarboxylase is essental for branched-chain fatty acid synthetase," *J. Biol. Chem.* 263:18386-18396 (1998).
Okuno et al., "2-Aminoadipate-2-oxoglutarate aminotransferase isoenzymes in human liver: a plausible physiological role in lysine and tryptophan metabolism," *Enzyme Protein* 47:136-148 (1993).

Olivera et al., "Molecular characterization of the phenylacetic acid catabolic pathway in *Pseudomonas putida* U: the phenylacetyl-CoA catabolon," *Proc. Natl. Acad. Sci. U.S.A.* 95(11):6419-6424 (1998).
Onuffer and Kirsch, "Redesign of the substrate specificity of *Escherichia coli* aspartate aminotransferase to that of *Escherichia coli* tyrosine aminotransferase by homology modeling and site-directed mutagenesis," *Protein Sci.* 4:1750-1757 (1995).
O'Reilly and Devine, "Sequence and analysis of the citrulline biosynthetic operon argC-F from *Bacillus subtilis*," *Microbiology* 140:1023-1025 (1994).
Orencio-Trejo et al., "Metabolic regluation analysis of an ethanologenic *Escherichia coli* strain based on RT-PCR and enzymatic activities," *Biotechnol. Biofuels* 1:8 (2008). (provided electronically by publisher as pp. 1-13).
Ostermeier et al., "A Combinatorial approach to hybrid enzymes independent of DNA homology," *Nat. Biotechnol.* 17:1205-1209 (1999).
Ostermeier et al., "Combinatorial protein engineering by incremental truncation," *Proc. Natl. Acad. Sci. U.S.A.* 96:3562-3567 (1999).
O'Sullivan et al., "Purification and characterisation of acetolactate decarboxylase from *Leuconostoc lactis* NCW1," *FEMS Microbiol. Lett* 194(2):245-249 (2001).
Otten and Quax, "Directed evolution:selecting today's biocatalysts," *Biomol. Eng.* 22:1-9 (2005).
Overkamp et al., "Functional analysis of structural genes for $NAD^+$-dependent formate dehydrogenase in *Saccharomyces cerevisiae*," *Yeast* 19:509-520 (2002).
Overkamp et al., "In vivo analysis of the mechanism for oxidation of cytosolic NADH by *Saccharomyces cerevisiae* mitochondria," *J. Bacteriol.* 182:2823-2830 (2000).
Padovani and Banerjee, "Assembly and protection of the radical enzyme, methylmalonyl-CoA mutase, by its chaperone," *Biochem.* 45(30):9300-9306 (2006).
Paik and Kim, "Enzymic syntehsis of δ-N-Acetyl-L-Lysine," *Arch. Biochem. Biophys.* 108:221-229 (1964).
Palosaari and Rogers, "Purification and Properties of the Inducible Coenzyme A-Linked Butyraldehyde Dehydrogenase from *Clostridium acetobutylicum*," *J. Bacteriol.* 170(7):2971-2976 (1988).
Parales and Harwood, "Characterization of the Genes Encoding β-Ketoadipate: Succinyl-Coenzyme A Transferase in *Pseudomonas putida*," *J. Bacteriol.* 174(14):4657-4666 (1992).
Park and Lee, "Biosynthesis of poly(3-hydroxybutyrate- co-3-hydroxyalkanoates) by metabolically engineered *Escherichia coli* strains," *Appl. Biochem. Biotechnol.* 113-116:335-346 (2004).
Park and Lee, "Identification and characterization of a new enoyl Coenzyme A hydratase involved in biosynthesis of medium-chain-length polyhydroxyalkanoates in recombinant *Escherichia coli*," *J. Bacteriol.* 185(18):5391-5397 (2003).
Park and Lee, "New FadB homologous enzymes and their use in enhanced biosynthesis of medium-chain-length polyhydroxyalkanoates in FadB mutant *Escherichia coli*," *Biotechnol. Bioeng.* 86(6):681-686 (2004).
Park et al., "Metabolic engineering of *Escherichia coli* for the production of L-valine based on transcriptome analysis and in silico gene knockout simulation," *Proc. Natl. Acad. Sci. U.S.A.* 104(19):7797-7802 (2007).
Park et al., "Regulation of succinate dehydrogenase (sdhCDAB) operon expression in *Escherichia coli* in response to carbon supply and anaerobiosis: role of ArcA and Fnr," *Mol. Microbiol.* 15(3):473-482 (1995).
Park et al., "Utilization of Electrically Reduced Neutral Red by *Actinobacillus succinogenes*: Physiological Function of Neutral Red in Membrane-Driven Fumarate Reduction and Energy Conservation," *J. Bacteriol* 181(8):2403-2410 (1999).
Parkin et al., "Rapid and efficient electrocatalytic $CO_2$/CO interconversions by *Carboxydothermus hydrogenoformans* CO dehydrogenase I on an electrode," *J. Am. Chem. Soc.* 129(34):10328-10329 (2007).
Parsot et al., "Nucleotide sequence of *Escherichia coli* argB and argC genes: comparison of N-acetylglutamate kinase and N-acetylglutamate-γ-semialdehyde dehydrogenase with homologous and analogous enzymes," *Gene* 68:275-283 (1988).

(56) References Cited

OTHER PUBLICATIONS

Patel and Clark, "Acetoacetate metabolism in rat brain. Development of acetoacetyl-Coenzyme A deacylase and 3-hydroxy-3-methylglutaryl-Coenzyme A synthase," *Biochem. J.* 176(3):951-958 (1978).

Patel et al., "β-ketoadipate enol-lactone hydrolases I and II from *Acinetobacter calcoaceticus*," *J. Biol. Chem.* 250:6567-6577 (1975).

Patil et al., "Use of genome-scale microbial models for metabolic engineering," *Curr. Opin. Biotechnol.* 15(1):64-69 (2004).

Patnaik et al., "Genome shuffling of *Lactobacillus* for improved acid tolerance," *Nat. Biotechnol.* 20:707-712 (2002).

Pauli and Overath, "ato Operon: a Highly Inducible System for Acetoacetate and Butyrate Degradation in *Escherichia coli*," *Eur. J. Biochem.* 29:553-562 (1972).

Pauwels et al., "The N-acetylglutamate synthase/N-acetylgltamate kinase metabolon of *Saccharomyces cerevisiae* allows co-ordinated feedback regulation of the first two steps in arginine biosynthesis," *Eur. J. Biochem.* 270:1014-1024 (2003).

Paxton et al., "Role of branched-chain 2-oxo acid dehydrogenase and pyruvate dehydrogenase in 2-oxobutyrate metabolism," *Biochem. J.* 234:295-303 (1986).

Peisach et al., "Crystallographic study of steps along the reaction pathway of D-amino acid aminotransferase," *Biochemistry* 37(14)4958-4967 (1998).

Pelletier and Harwood, "2-Ketocyclohexanecarboxyl Coenzyme A Hydrolase, the Ring cleavage Enzyme Required for Anaerobic Benzoate Degradation of *Rhodpseudomonas palustris*," *J. Bacteriol.* 180(9):2330-2336 (1998).

Peoples and Sinskey, "Fine structural analysis of the *Zoogloea ramigera* phbA-phbB locus encoding β-ketothiolase and acetoacetyl-CoA reductase: nucleotide sequence of phbB," *Mol. Microbiol.* 3:349-357 (1989).

Pereira et al:, "Active site mutants of *Escherichia coli* citrate synthase. Effects of mutations on catalytic and allosteric properties," *J. Biol. Chem.* 269:412-417 (1994).

Peretz and Burstein, "Amino acid sequence of alcohol dehydrogenase from the thermophilic bacterium *Thermoanaerobium brockii*," *Biochemistry* 28(16):6549-6555 (1989).

Peretz et al., "Molecular cloning, nucleotide sequencing, and expression of genes encoding alcohol dehydrogenases from the thermophile *Thermoanaerobacter brockii* and the mesophile *Clostridium beijerinckii*," *Anaerobe*. 3:259-270 (1997).

Perez et al., "*Escherichia coli* YqhD exhibits aldehyde reductase activity and protects from the harmful effect of lipid peroxidation-derived aldehydes," *J. Biol. Chem.* 283(12):7346-7353 (2008).

Perez-Prior et al., "Reactivity of lactones and GHB formation," *J. Org. Chem.* 70:420-426 (2005).

Petersen and Bennett, "Purification of acetoacetate decarboxylase from *Clostridium acetobutylicum* ATCC 824 and cloning of the acetoacetate decarboxylase gene in *Escherichia coli*," *Appl. Environ. Microbiol.* 56:3491-3498 (1990).

Petitdemange et al., "Regulation of the NADH and NADPH-ferredoxin oxidoreductases in clostridia of the butyric group," *Biochim. Biophys. Acta.* 421(2):334-347 (1976).

Pfanner and Geissler, "Versatility of the mitochondrial protein import machinery," *Nat. Rev. Mol. Cell. Biol.* 2(5):339-349 (2001).

Pfluger et al., "Lysine-2,3-Aminomutase and β-Lysine Acetyltransferase Genes of Methanogenic Archaea Are Salt Induced and Are Essential for the Biosynthesis of $N^\epsilon$-Acetyl-β-Lysine and Growth at High Salinity," *Appl. Environ. Microbiol.* 69(10):6047-6055 (2003).

Phalip et al., "Purification and properties of the α-acetolactate decarboxylase from *Lactococcus lactis* subsp. *Lactis* NCDO 2118," *FEBS Lett.* 351(1):95-99 (1994).

Pharkya et al., "OptiStrain: A computational Framework for redesign of microbial production systems," *Genome Res.* 14(11):2367-2376 (2004).

Pharkya et al., "Exploring the overproduction of amino acids using the bilevel optimization framework OptKnock," *Biotechnol. Bioeng.* 84(7):887-899 (2003).

Phillips et al., "High Copy Number Plasmids Compatible with Commonly Used Cloning Vectors," *Biotechniques* 28:400, 402, 404, 406, 408 (2000).

Pierce et al., "The Complete Genome Sequence of *Moorella thermoacetia* (f. *Clostridum thermoaceticum*)," *Environ. Microbiol.* 10(10):2550-2573 (2008).

Pieulle et al., "Isolation and analysis of the gene encoding the pyruvate-ferredoxin oxidoreductase of *Desulfovibrio africanus*, production of the recombinant enzyme in *Escherichia coli*, and effect of carboxy-terminal deletions on its stability," *J. Bacteriol.* 179(18):5684-5692 (1997).

Pine et al., "Titanium-Mediated Methylene-Transfer Reactions. Direct Conversion of Esters into Vinyl Ethers," *J. Am. Chem. Soc.* 102:3270-3272 (1980).

Ploux et al., "Investigation of the first step of biotin biosynthesis in *Bacillus sphericus*," *Biochem. J.* 287:685-690 (1992).

Ploux et al., "The NADPH-linked acetoacetyl-CoA reductase from *Zoogloea ramigera*, Characterization and mechanistic studies of the cloned enzyme over-produced in *Escherichia coli*," *Eur. J. Biochem.* 174:177-182 (1988).

Pohl et al., "Remarkably broad Sutstrate Tolerance of Malonyl-CoA Synthetase, an Enzyme Capable of Intracellular Synthesis of Polyketide Precursors," *J. Am. Chem. Soc.* 123:5822-5823 (2001).

Pohlmann et al., "Genome sequence of the bioplastic-producing "Knallgas" bacterium *Ralstonia eutropha* H16," *Nat. Biotechnol.* 24(10):1257-1262 (2006).

Pollard et al., "Purification, characterisation and reaction mechanisms of monofunctional 2-hydroxypentadienoic acid hydratase from *Escherichia coli*," *Eur. J. Biochem. FEBS.* 251:98-106 (1998).

Pollard et al., "Substrate Selectivity and biochemical Properties of 4-Hydroxy-2-Keto-Pentanoic Acid Aldolase from *Escherichia coli*," *Appl. Environ. Microbiol.* 64(10):4093-4094 (1998).

Polovnikova et al., "Structural and kinetic analysis of catalysis by a thiamine diphosphate-deptendent enzyme, benzoylformate decarboxylase," *Biochemistry* 42:1820-1830 (2003).

Ponce, E., et al., "Cloning of the two pyruvate kinase isoenzyme structural genes from *Escherichia coli*: the relative roles of these enzymes in pyruvate biosynthesis," *J. Bacteriol.* 177(19):5719-5722 (1995).

Postma et al., "Phosphoenolpyruvate Carbohydrate Phosphotransferase Systems of Bacteria," *Microbiol Rev.* 57(3):543-594 (1993).

Poston, "Assay of leucine 2,3-aminomutase," *Methods Enzymol.* 166:130-135 (1998).

Powlowski et al., "Purification and properties of the physically associated meta-cleavage pathway enzymes 4-hydroxy-2-ketovalerate aldolase and aldehyde dehydrogenase (acylating) from *Pseudomonas* sp. strain CF600," *J. Bacteriol.* 175(2):377-385 (1993).

Price et al., "Genome-scale microbial in silico models: the constraints-based approach," *Trends Biotechnol.* 21(4):162-169 (2003).

Price et al., "Genome-scale models of microbial cells: evaluating the consequences of constraints," *Nat. Rev. Microbiol.* 2(11):886-897 (2004).

Prieto et al., "Molecular Characterization of the 4-Hydroxyphenylacetate Catabolic Pathway of *Escherichia coli* W: Engineering a Mobile Aromatic Degradative Cluster," *J. Bacteriol.* 178(1):111-120 (1996).

Pritchard et al., "A general model of error-prone PCR," *J. Theor. Biol.* 234:497-509 (2005).

Pritchett and Metcalf, "Genetic, physiological and biochemical characterization of multiple methanol methyltransferase isozymes in *Methanosarcina acetivorans* C2A," *Mol. Microbiol.* 56(5):1183-1194 (2005).

Pronk et al., "Pyruvate metabolism in *Saccharomyces cerevisiae*," *Yeast* 12:1607-1633 (1996).

Pucci et al., "*Staphylococcus haemolyticus* contains two D-glutamic acid biosynthetic activities, a glutamate racemase and a D-amino acid transminase," *J. Bacteriol.* 177(2):336-342 (1995).

Purnell et al., "Modulation of higher-plant NAD(H)-dependent glutamate dehydrogenase activity in transgenic tobacco via alteration of β subunit levels," *Planta* 222:167-180 (2005).

(56) References Cited

OTHER PUBLICATIONS

Qi et al., "Functional expression of prokaryotic and eukaryotic genes in *Escherichia coli* for conversion of glucose to p-hydroxystyrene," *Metab. Eng.* 9:268-276 (2007).

Qian et al., "Metabolic engineering of *Escherichia coli* for the production of putrescine: a four carbon diamine," *Biotechnol. Bioeng.* 104(4)651-662 (2009).

Qiu et al., "Metabolic engineering of Aeromonas hydrophila for the enhanced production of poly(3-hydroxybutyrate-co-3-hydroxyhexanoate)," *Appl. Microbiol. Biotechnol.* 69(5):537-542 (2006).

Qu et al., "Inhibition of human ornthine decarboxylase activity by enantiomers of difluoromethylornithine," *Biochem. J.* 375:465-470 (2003).

Quail and Guest, "Purification, characterization and mode of action of pdhR, the transcriptional repressor of the PdhR-aceEF-Ipd operon of *Escherichia coli*," *Mol. Microbiol.* 15(3):519-529 (1995).

Rado and Hoch, "Phosphotransacetylase from *Bacillus subtilis*: purification and physiological studies," *Biochim. Biophys. Acta* 321:114-125 (1973).

Ragsdale et al., "Acetogenesis and the Wood-Ljungdahl pathway of $CO_2$ fixation," *Biochimica. Biophysica. Acta* 1784(12):1873-1898 (2008).

Ragsdale, "Enzymology of the wood-Ljungdahl pathway of acetogenesis," *Ann. NY Acad. Sci.* 1125:129-136 (2008).

Ragsdale, "Life with carbon monoxide," *Crit. Rev. Biochem. Mol. Biol.* 39(3):165-195 (2004).

Ragsdale, "Pyruvate ferredoxin oxidoreductase and its radical intermediate," *Chem. Rev.* 103(6):2333-2346 (2003).

Rajpal et al., "A general method for greatly improving the affinity of antibodies by using combinatorial libraries," *Proc. Natl. Acad. Sci. U.S.A.* 102:8466-8471 (2005).

Ramjee et al., "*Escherichia coli* L-aspartate-α-decarboxylase: preprotein processing and observation of reaction intermediates by electrospray mass spectrometry," *Biochem. J.* 323(Pt 3):661-669 (1997).

Ramon-Maiques et al., "Structure of Acetylglutamate Kinase, a Key Enzyme for Arginine Biosynthesis and Prototype for the Amino Acid Kinase Enzyme Family, during Catalysis," *Structure* 10:329-342 (2002).

Ramos et al., "Mutations affecting the enzymes involved in the utilization of 4-aminobutyric acid as nitrogen source by the yeast *Saccharomyces cerevisiae*," *Eur.J. Biochem.* 149:401-404 (1985).

Rangarajan et al., "Structure of [NiFe] hydrogenase maturation protein HypE from *Escherichia coli* and its interaction with HypF," *J. Bacteriol.* 190(4):1447-1458 (2008).

Rasmussen, L.J., et al. "Carbon Metabolism Regulates Expression of the *pfl* (Pyruvate-Formate-Lyase) Gene in *Escherichia coli*," *J. Bacteriol.* 173(20):6390-6397 (1991).

Rathinasabapathi, "Propionate, a source of β-alanine, is an inhibitor of β-alanine methylation in *Limonium latifoilium* Plunbaginaces," *J. Plant Physiol.* 159:671-674 (2002).

Ratnatilleke et al., "Cloning and sequencing of the Coenzyme $B_{12}$-binding domain of isobutyryl-CoA mutase from *Streptomyces cinnamonensis*, reconstitution of mutase activity, and characterization of the recombinant enzyme produced in *Escherichia coli*," *J. Biol. Chem.* 274(44):31679-31685 (1999).

Raux et al., "The role of *Saccharomyces cerevisiae* Met1p and Met8p in sirohaem and cobalamin biosynthesis," *Biochem. J.* 338 (pt. 3):701-708 (1999).

Raux et al., "*Salmonella typhimurium* cobalamin (vitamin $B_{12}$) biosynthetic genes: functional studies in *S. typhimurium* and *Escherichia coli*," *J. Bacteriol.* 178(3):753-767 (1996).

Ravagnani et al., "Spo0A directly controls the switch from acid to solvent production in solvent-forming clostridia," *Mol. Microbiol.* 37(5):1172-1185 (2000).

Raybuck et al., "Kinetic characterization of the carbon monoxide-acetyl-CoA (carbonyl group) exchange activity of the acetyl-CoA synthesizing CO dehydrogenase from *Clostridium thermoaceticum*," *Biochemistry* 27(20):7698-7702 (1988).

Raynaud et al., "Molecular characterization of the 1,3-propanediol (1,3-PD) operon of *Clostridium butyricum*," *Proc. Natl. Acad. Sci. U.S.A.* 100:5010-5015 (2003).

Rea et al., "Structure and Mechanism of HpcH: A Metal Ion Dependent Class II Aldolase from the Homoprotocatechuate Degradation Pathway of *Escherichia coli*," *J. Mol. Biol.* 373:866-876 (2007).

Recasens et al., "Cystein Sulfinate Aminotransferase and Aspartate Aminotransferase Isoenzymes of Rat Brain. Purification, Characterization, and Further Evidence of Identity," *Biochemistry* 19:4583-4589 (1980).

Reda et al., "Reversible interconversion of carbon dioxide and formate by an electroactive enzyme," *Proc. Natl. Acad. Sci. U.S.A.* 105:10654-10658 (2008).

Reetz and Carballeira, "Iterative saturation mutagenesis (ISM) for rapid directed evolution of functional enzymes," *Nat. Protoc.* 2:891-903 (2007).

Reetz et al., "Creation of Enantioselective Biocatalysts for Organic Chemistry by In Vitro Evolution," *Angew. Chem. Int. Ed. Engl.* 36:2830-2832 (1997).

Reetz et al., "Directed Evolution of an Enantioselective Enzyme through Combinatorial Multiple-Cassette Mutagenesis, " *Angew. Chem. Int. Ed. Engl.* 40:3589-3591 (2001).

Reetz et al., "Expanding the Range of Substrate Acceptance Enzymes: Corninatorial Active-Site Saturation Test," *Angew. Chem. Int. Ed. Engl.* 117:4264-4268 (2005).

Reetz et al., "Iterative saturation mutagenesis on the basis of B factors as a strategy for incresing protein thermostability," *Angew. Chem. Int. Ed.* 45:7745-7751 (2006).

Regev-Rudzki et al., "Yeast Aconitase in Two Locations and Two Metabolic Pathways: Seeing Small Amounts Is Believing," *Mol. Biol. Cell* 16:4163-4171 (2005).

Reidhaar-Olson and Sauer, "Combinatorial cassette mutagenesis as a probe of the informational content of protein sequences," *Science* 241:53-57 (1988).

Reidhaar-Olson et al., "Random mutagenesis of protein sequences using oligonucleotide cassettes," *Methods Enzymmol.* 208:564-586 (1991).

Reiser and Somerville, "Isolation of mutants of *Acinetobacter calcoaceticus* deficient in wax ester synthesis and complementation of one mutation with a gene encoding a fatty acyl Coenzyme A reductase," *J. Bacteriol.* 179(9):2969-2975 (1997).

Reitzer et al., "Crystallization and preliminary X-ray analysis of recombinant glutamate mutase and of the isolated component S from *Clostridium cochlearium*," *Acta. Crystallogr. D. Biol. Crystallogr.* 54(Pt 5):1039-1042 (1998).

Repetto and Tzagoloff, "Structure and Regulation of KGD1, the Structural Gene for Yeast α-Ketoglutarate Dehydrogenase," *Mol. Cell. Biol.* 9(6):2695-2705 (1989).

Reshetnikov, et al., "Characterization of the ectoine biosynthesis genes of haloalkalotolerant obligate methanotroph 'Methylomicrobium alcaliphilum 20Z'," *Arch. Microbiol.* 184:286-297 (2006).

Resnekov et al., "Organization and regulation of the *Bacillus subtilis* odhAB operon, which encodes two of the subenzymes of the 2-oxoglutarate dehydrogenase complex," *Mol. Gen. Genet.* 234:285-296 (1992).

Rhodes et al., "Production of fumaric acid by *Rhizopus arrhuzus*," *Appl. Microbiol.* 7:74-80 (1959).

Rhodes et al., "Production of Fumaric Acid in 20-Liter Fermentors," *Appl. Microbiol.* 10(1)9-15 (1962).

Rigden et al., "A cofactor-dependent phosphoglycerate mutase homolog from *Bacillus stearothermophilus* is actually a broad specificity phosphatase," *Protein Sci.* 10:1835-1846 (2001).

Ringer et al., "Monoterpene double-bond reductases of the (−)-menthol biosynthetic pathway: isolation and characterization of cDNAs encoding (−)-isopiperitenone reductase and (+)-pulegone reductase of peppermint," *Arch. Biochem. Biophys.* 418(1):80-92 (2003).

Ringquist et al., "Translation initiation in *Escherichia coli*: sequences within the ribosome-binding site," *Mol. Microbiol.* 6(9):1219-1229 (1992).

(56) References Cited

OTHER PUBLICATIONS

Riondet et al., "Measurement of the intracellular pH in *Escherichia coli* with the internally conjugated fluorescent probe 5- (and 6-)carboxyfluorescein succinimidyl ester." *Biotechnol. Tech.* 11:735-738 (1997).
Rioux et al.: "Two outer membrane transport systems for vitamin $B_{12}$ in *Salmonella typhimurium*," *J. Bacteriol.* 171:2986-2993 (1989).
Rioux et al., "Vitamin $B_{12}$ transportin *Escherichia coli* K12 does not require the *btuE* gene of the *btuCED* operon," *Mol. Gen. Genet.* 217:301-308 (1989).
Riviere et al., "Acetyl:succinate CoA-transferase in procyclic *Trypanosoma brucei*. Gene identificatibn and role in carbohydrate metabolism." *J. Biol. Chem.* 279:45337-45346 (2004).
Roa Engel et al., "Fumaric acid production by fermentation," *Appl. Microbiol. Biotechnol.* 78(3):379-389 (2008).
Roberts et al, "The Role of Enoyl-CoA Hydratase in the Metabolism of Isoleucine by *Pseudomonas putida*," *Arch. Microbiol.* 117:99-108 (1978).
Roberts et al., "Acetyl-Coenzyme a synthesis from methyltetrahydrofolate, CO, and Coenzyme A by enzymes purified from *Clostridium thermoaceticum*: attainment of in vivo rates and identification of rate-limiting steps," *J. Bacteriol.* 174(14):4667-4676 (1992).
Roberts et al., "Cloning and expression of the gene cluster encoding key proteins involved in acetyl-CoA synthesis in *Clostridium thermoaceticum*: CO dehydrogenase, the corrinoid/Fe-S protein, and methyltransferase," *Proc. Natl. Acad. Sci. U.S.A.* 86(1):32-36 (1989).
Robinson et al., "Studies on Rat Brain Acyl-Coenzyme A Hydrolase (Short Chain)," *Biochem. Biophys. Res. Commun.* 71(4):959-965 (1976).
Roca et al., "Metabolic engineering of ammonium assimilation in xylose-fermenting *Saccharomyces cerevisiae* improves ethanol production," *Appl. Environ. Microbiol.* 69:4732-4736 (2003).
Rodriguez et al., "Characterization of the p-Coumaric Acid Decarboxylase from *Lactobacillus plantarium* CECT $748^T$," *J. Agric. Food Chem.* 56:3068-3072 (2008).
Roffia et al., "Byproduct Identification in the Terepthalic Acid Production Process and Possible Mechanisms of their Formation," *Ind. Eng. Chem. Prod. Res. Dev.* 23:629-634 (1984).
Rohdich et al., "Enoate reductases of Clostridia. Cloning, sequencing, and expression," *J. Biol. Chem.* 276(8):5779-5787 (2001).
Rohwerder et al., "The alkyl tert-butyl ether intermediate 2-hydroxyisobutyrate is degraded via a novel cobalamin-dependent mutase pathway," *Appl. Environ. Microbiol.* 72(6):4128-4135 (2006).
Romero et al., "Partial purification and characterization and nitrogen regulation of the lysine ε-aminotransferase of *Streptomyces clavuligers*," *J. Ind. Microbiol. Biotechnol.* 18:241-246 (1997).
Roper et al., "Sequence of the hpcC and hpcG genes of the meta-fission homoprotocatechuic acid pathway of *Escherichia coli* C: nearly 40% amino-acid identity with the analogues enzymes of the catechol pathway," *Gene* 156:47-51 (1995).
Rose and Weaver, "The role of the allosteric B site in the fumarase reaction," *Proc. Natl. Sci. U.S.A.* 101(10):3393-3397 (2004).
Rose et al., "Enzymatic phosphorylation of acetate," *J. Biol. Chem.* 211(2):737-756 (1954).
Rosenberg, "A Comparison of Lipid Patterns in Photosynthesizing and Nonphotosynthesizing Cells of *Euglena gracilis*," *Biochem.* 2:1148-1154 (1963).
Roszak et al., "The Structure and Mechanism of the Type II Dehydroquinase from *Streptomyces coelicolor*," *Structure* 10:493-503 (2002).
Roth et al., "Characterization of the cobalamin (vitamin $B_{12}$) biosynthetic genes of *Salmonella typhimurium*," *J. Bacteriol.* 175:3303-3316 (1993).
Rother and Metcalf, "Anaerobic growth of *Methanosarcina acetivorans* C2A on carbon monoxide: an unusual way of life for a methanogenic archaeon," *Proc. Natl. Acad. Sci. U.S.A.* 101(48):16929-16934 (2004).
Rother et al., "Genetic and proteomic analyses of CO utilization by *Methanosarcina acetivorans*," *Arch. Microbiol.* 188(5):463-472 (2007).
Rous, "On the occurrence of enzymes of ketone-body metabolism in human adipose tissue," *Biochem. Biophys. Res. Commun.* 69(1):74-78 (1976).
Roux and Walsh, "p-aminobenzoate synthesis in *Escherichia coli*: kinetic and mechanistic characterization of the amidotransferase PabA," *Biochemistry* 31:6904-6910 (1992).
Roux and Walsh, "p-Aminobenzoate synthesis in *Escherichia coli*: mutational analysis of three conserved amino acid residues of the amidotransferase PabA," *Biochemistry* 32:3763-3768 (1993).
Roy and Dawes, "Cloning and Characterization of the gene Encoding Lipoamide Dehydrogenase in *Saccharomyces cerevisiae*," *J. Gen. Microbiol.* 133:925-933 (1987).
Roymoulik et al., "Rearrangement of L-2-hydroxyglutarate to L-threo-3-methylmalate catalyzed by adenosylcobalamin-dependent glutamate mutase," *Biochem.* 39(33):10340-10346 (2000).
Rozell and Benner, "Stereochemical Imperative in Enzymic Decarboxylations. Stereochemical Course of Decarboxylation Catalyzed by Acetoacetate Decarboxylase," *J. Am. Chem. Soc.* 106:4937-4941 (1984).
Rudman and Meister, "Transamination in *Escherichia coli*," *J. Biol. Chem.* 200(2):591-604 (1953).
Ruldeekulthamrong et al., "Molecular characterization of lysine 6-dehydrogenase from *Achromobacter denitrificans*," *BMB Reports* 790-795 (2008).
Sabo et al., "Purification and physical properties of inducible *Escherichia coli* lysine decarboxylase," *Biochemistry* 13:622-670 (1974).
Sadowski, "The Flp recombinase of the 2-μm plasmid of *Saccharomyces cerevisiae*," *Prog. Nucleic Acid Res. Mol. Biol.* 51:53-91 (1995).
Saegesser et al., "Stability of broad host range cloning vectors in the phototrophic bacterium *Rhodospirillum rubrum*," *FEMS Microbiol. Lett.* 95:7-11 (1992).
Saito and Doi, "Microbial synthesis and properties of poly(3-hydroxybutyrate-co-4-hydroxybutyrate) in *Comamonas acidovorans*," *Int. J Biol Macromol.* 16:99-104 (1994).
Sakai et al, "Acetate and Ethanol Production from $H_2$ and $CO_2$ by *Morrella* sp. Using a Repeated Batch Culture," *J. Biosci. Bioeng.* 99:252-258 (2005).
Sakanyan et al., "A re-examination of the pathway for ornithine biosynthesis in a thermophilic and two mesophilic *Bacillus* species," *J. Gen. Microbiol.* 138:125-130 (1992).
Sakurada et al., "Acetylpolyamine Amidohydrolase from *Mycoplana ramosa*: Gene Cloning and Characterization of the Metal-Substituted Enzyme," *J. Bacteriol.* 178(19):5781-5786 (1996).
Salmon et al., "Global gene expression profiling in *Escherichia coli* K12. Effects of oxygen availability and ArcA," *J. Biol. Chem.* 280(15):15084-15096 (2005).
Saltzgaber-Muller et al., "Nuclear genes coding the yeast mitochondrial adenosine triphosphatase complex. Isolation of ATP2 coding the $F_1$-ATPase β subunit," *J. Bio. Chem.* 258(19):11465-11470 (1983).
Samanta and Harwood, "Use of *Rhodopseudomonas palustris* genome sequence to identify a single amino acid that contributes to the activity of Coenzyme A ligase with chlorinated substrates," *Mol. Microbiol.* 55(4):1151-1159 (2005).
Samsonova et al., "Molecular cloning and characterization of *Escherichia coli* K12 ygjG gene," *BMC Microbiol.* 3:2 (2003).
Samuelov et al., "Whey fermentation by *Anaerobiospirillum succiniciproducens* for production of a succinate-based animal feed additive," *Appl. Environ. Microbiol.* 65(5):2260-2263 (1999).
San et al., "Metabolic Engineering through Cofactor Manipulation and its Effects on Metabolic Flux Redistribution in *Escherichia coli*," *Metab Eng.* 4(2):182-192 (2002).
Sanchez et al., "Efficient succinic acid production from glucose through overexpression of pyruvate carboxylase in an *Escherichia coli* alcohol dehydrogenase and lactate dehydrogenase mutant," *Biotechnol. Prog.* 21(2):358-365 (2005).

(56) References Cited

OTHER PUBLICATIONS

Sanchez et al., "Novel pathway engineering design of the anaerobic central metabolic pathway in *Escherichia coli* to increase succinate yield and productivity," *Metab. Eng.* 7(3): 229-239 (2005).

Sanchez et al., "Batch culture characterization and metabolic flux analysis of succinate-producing *Escherichia coli* strains," *Metab Eng.* 8(3):209-226 (2006).

Sanchez et al., "Effect of different levels of NADH availability on metabolic fluxes of *Escherichia coli* chemostat cultures in defined medium," *J. Biotechnol.* 117(4):395-405 (2005).

Sankaranarayanan et al., "Preliminary x-ray crystallographic analysis of ornithine acetyltransferase (Rv1653) from *Mycobacterium tuberculosis*," *Acta. Crystallogr. Sect. F. Struct. Biol. Cryst. Commun.* 65(Pt 2):173-176 (2009).

Sanyal et al., "Biosyntehsis of pimeloyl-CoA, a biotin precursor in *Escherichia coli*, follows a modified fatty acid synthesis pathway: $^{13}$C-labeling studies," *J. Am. Chem. Soc.* 116:2637-2638 (1994).

Sariaslani, "Development of a Combined biological and Chemical Process for Production of Industrial aromatics from Renewable Resources," *Annu. Rev. Microbiol.* 61:51-69 (2007).

Sass et al., "Folding of fumarase during mitochondrial import determines its dual targeting in yeast," *J. Biol. Chem.* 278(46):45109-45116 (2003).

Sato et al., "Poly[(R)-3-hydroxybutyrate] formation in *Escherichia coli* from glucose through an enoyl-CoA hydratase-mediated pathway," *J. Biosci. Bioeng.* 103(1):38-44 (2007).

Sauer and Thauer, "Methanol:Coenzyme M methyltransferase from *Methanosarcina barkeri*. Identification of the active-site histidine in the corrinoid-harboring subunit MtaC by site-directed mutagenesis," *Eur. J. Biochem.* 253(3):698-705 (1998).

Sauer et al., "Methanol:Coenzyme M methyltransferase from *Methanosarcina barkeri*. Purification, properties and encoding genes of the corrinoid protein MT1," *Eur. J. Biochem.* 243(3):670-677 (1997).

Sauer, "Diels-Alder Reactions II: The Reaction Mechanism," *Angew. Chem. Int. Ed.* 6:16-33 (1967).

Sauvageot et al., "Characterisation of the diol dehydratase pdu operon of *Lactobacillus collinoides*," *FEMS Microbiol. Lett.* 209:69-74 (2002).

Sawers and Boxer, "Purification and properties of membrane-bound hydrogenase isoenzyme 1 from anaerobically grown *Escherichia coli* K12," *Eur. J. Biochem.* 156(2):265-275 (1986).

Sawers et al., "Characterization and physiological roles of membrane-bound hydrogenase isoenzymes from *Salmonella typhimurium*," *J. Bacteriol.* 168(1):398-404 (1986).

Sawers et al., "Differential expression of hydrogenase isoenzymes in *Escherichia coli* K-12: evidence for a third isoenzyme," *J. Bacteriol.* 164(3):1324-1331 (1985).

Sawers, "The hydrogenases and formate dehydrogenases of *Escherichia coli*," *Antonie Van Leeuwenhoek* 66(1-3):57-88 (1994).

Saz and Weil, "The mechanism of the formation of α-methylbutyrate from carbohydrate by *Ascaris lumbricoides* muscle," *J. Biol. Chem.* 235:914-918 (1960).

Schadt et al., "2-Amino-2-deoxyisochorismate is a key intermediate in *Bacillus subtilis* p-aminobenzoic acid biosynthesis," *J. Am. Chem. Soc.* 131:3481-3483 (2009).

Scher and Jakoby, "Maleate isomerase," *J. Biol. Chem.* 244:1878-1882 (1969).

Scherf and Buckel, "Purification and properties of 4-hydroxybutyrate Coenzyme A transferase from *Clostridium aminobutyricum*," *Appl. Environ. Microbiol.* 57(9):2699-2702 (1991).

Scherf and Bucket, "Purification and properties of an iron-sulfur and FAD-containing 4-hydroxybutyryl-CoA dehadratase/vinylacetyl-CoA $\Delta^3$—$\Delta^2$-isomerase from *Clostridium aminobutricum*," *Eur. J. Biochem.* 215:421-429 (1993).

Scherf et al, "Succinate-ethanol fermentation in *Clostridium kluyveri*: purification and characterisation of 4-hydroxybutyryl-CoA dehydratase/vinylacetyl-CoA $\Delta^3$—$\Delta^2$-isomerase," *Arch. Microbiol.* 161(3):239-245 (1994).

Schilling et al., "Genome-Scale Metabolic Model of *Helicobacter pylori* 26695," *J. Bacteriol.* 184:4582-4593 (2002).

Schilling et al., "Combining Pathway Analysis with Flux Balance Analysis for the Comprehensive Study of Metabolic Systems," *Biotechnol. Bioeng.* 71(4):286-306 (2000/2001).

Schilling et al., "Theory for the Systematic Definition of Metabolic Pathways and Their Use in Interpreting Metabolic Function from a Pathway-Oriented Perspective," *J. Theor. Biol.* 203(3):229-248 (2000).

Schilling et al., "Toward Metabolic Phenomics: Analysis of Genomic Data Using Flux Balances," *Biotechnol. Prog.* 15(3):288-295 (1999).

Schmid et al., "Plasmid-mediated uptake and metabolism of sucrose by *Escherichia coli* K-12," *J. Bacteriol.* 151(1):68-76 (1982).

Schmitzberger et al., "Structural constraints on protein self-processing in L-aspartate-α-decarboxylase," *EMBO J.* 22:6193-6204 (2003).

Schneider and Betz, "Waxmonoester Fermentation in *Euglena-gracilis* T Factors Favoring the Synthesis of Odd-Numbered Fatty-Acids and Alcohols," *Planta.* 166:67-73 (1985).

Schneider et al., "The *Escherichia coli* gabDTPC operon: specific γ-aminobutyrate catabolism and nonspecific induction," *J. Bacteriol.* 184:6976-6986 (2002).

Schnell et al., "Anaerobic degradation of aniline and dihydroxybehienes by newly isolated sulfate-reducing bacteria and description of *Desulfobacterium anilini*," *Arch. Microbiol.* 152:556-563 (1989).

Schousboe et al., "Purification and Characterization of the 4-Aminobutyrate-2-Ketoglurate Transminase from Mouse Brain," *Biochem.* 2(15):2868-2873 (1973).

Schrock et al., "Preparation and Reactivity of Several Alkylidene Complexes of the Type W(CHR')(N-2, 6-$C_6H_3$-i-$Pr_2$)(OR)$_2$ and Related Tungstacyclobutane complexes. Controlling Metathesis Activity through the Choice of Alkoxide Ligand," *J. Am. Chem. Soc.* 110:1423-1435 (1988).

Schulz et al., "Stereospecific production of the herbicide phosphinothricin (glufosinate) by transamination: isolation and characterization of a phosphinothricin-specific transaminase from *Escherichia coli*," *Appl. Environ. Microbiol.* 56(1):1-6 (1990).

Schurmann and Sprenger, "Fructose-6-phosphate aldolase is a novel class I aldolase from *Escherichia coli* and is related to a novel group of bacterial transaldolases," *J. Biol. Chem.* 276(14): p. 11055-11061 (2001).

Schwarzer et al., "Nonribosomal peptides: from genes to products," *Nat. Prod. Rep.* 20:275-287 (2003).

Schweiger and Buckel, "On the dehydration of (R)-lactate in the fermentation of alanine to propionat by *Clostridium propionicum*," *FEBS Lett.* 171:79-84 (1984).

Schweiger et al., "Purification of 2-hydroxyglutaryl-CoA dehydratase from *Acidaminococcus fermentans*. An iron-sulfur protein," *Eur. J. Biochem.* 169(2):441-448 (1987).

Scott and Jakoby, "Soluble γ-Aminobutyric-Glutamic Transaminase from *Pseudomonas fluorescens*," *J. Biol. Chem.* 234:932-936 (1959).

Scott, a.I., "Discovering nature's diverse pathways to vitamin $B_{12}$: a 35-year odyssey," *J. Org. Chem.* 68:2529-2539 (2003).

Seedorf et al., "The genome of *Clostridium kluyveri*, a strict anaerobe with unique metabolic features," *Proc. Natl. Acad. Sci. U.S.A.* 105(6):2128-2133 (2008).

Seffernick et al., "Melamine deaminase and Atrazine chlorohydrolase: 98 percent identical but functionally different," *J. Bacteriol.* 183 (8):2405-2410 (2001).

Segre et al., "Analysis of optimality in natural and perturbed metabolic networks," *Proc. Natl. Acad. Sci. U.S.A.* 99:15112-15117 (2002).

Seibert et al., "Characterization of a gene cluster encoding the maleylacetate reductase from Ralstonia eutropha 335T, and enzyme recruited for growth with 4-fluorobenzoate," *Microbiology* 150:463-472 (2004).

Seibert et al., "Characterization of the maleylacteate reductase MacA of *Rhodococcus* opacus 1CP and evidence for the presence of an isofunctional enzyme," *J. Bacteriol.* 180:3503-3508 (1998).

Seibert et al., "Purification and characterization of maleylacetate reductase from *Alcaligenes eutrophys* JMP134(pJP4)," *J. Bacteriol.* 175:6745-6754 (1993).

(56) References Cited

OTHER PUBLICATIONS

Selifonova et al., "Rapid evolution of novel traits in microorganisms," *Appl Environ. Microbiol.* 67:3645-3649 (2001).
Selmer et al., "Propionate CoA-transferase from *Clostridium propionicum*. Cloning of gene identification of glutamate 324 at the active site," *Eur. J. Biochem.* 269:372-380 (2002).
Seltzer, "Purification and properties of maleylacetone cis-trans isomerase from Vibrio 01," *J. Biol. Chem.* 248:215-222 (1973).
Sen et al., "Developments in directed evolution for improving enzyme functions," *Appl. Biochem. Biotechnol.* 143:212-223 (2007).
Sennett et al., "Transmembrane transport of cobalamin in prokaryotic and eukaryotic cells," *Ann. Rev. Biochem.* 50:1053-1086 (1981).
Seravalli et al., "Evidence that NiNi acetyl-CoA synthase is active and that the CuNi enzyme is not," *Biochemistry* 43(13):3944-3955 (2004).
Seravalli et al., "Mechanism of transfer of the methyl group from (6S)-methyltetrahydrofolate to the corrinoid/iron-sulfur protein catalyzed by the methyltransferase from *Clostridium thermoaceticum*: a key step in the Wood-Ljungdahl pathway of acetyl-CoA synthesis," *Biochemistry* 38(18):5728-5735 (1999).
Seyfried et al., "Cloning, Sequencing, and Overexpression of the Genes Encoding Coenzyme $B_{12}$-Dependent Glycerol Dehydratase of *Citrobacter freundii*," *J. Bacteriol.* 178(19):5793-5796 (1996).
Shafiani et al., "Cloning and characterization of aspartate-β-semialdehyde dehydrogenase from *Mycobacterium tuberculosis* H37 Rv," *J. Appl. Microbiol.* 98:832-838 (2005).
Shalel-Levanon et al., "Effect of ArcA and FNR on the expression of genes related to the oxygen regulation and the glycolysis pathway in *Escherichia coli* under microaerobic growth conditions," *Biotechnol. Bioeng.* 92(2):147-159 (2005).
Shames et al., "Interaction of Aspartate and Aspartate-derived Antimetabolites with the Enzymes of the Threonine Biosynthetic Pathway of *Escherichia coli*," *J. Biol. Chem.* 258(24):15331-15339 (1984).
Shanley et al., "Cloning and expression of *Acinetobacter calcoaceticus* catBCDE genes in *Pseudomonas putida* and *Escherichia coli*," *J. Bacteriol.* 165:557-563 (1986).
Shao et al., "Random-priming in vitro recombination: an effective tool for directed evolution," *Nucleic Acids Res.* 26:681-683 (1998).
Sharma et al., "Menaquinone (Vitamin $K_2$) Biosynthesis: Nucleotide Sequence and Expression of themenB Gene from *Escherichia coli*," *J. Bacteriol.* 174(15): 5057-5062 (1992).
Sheppard et al., "Purification and Properties of NADH-Dependent 5,10-Methylenetetrahydrofolate Reductase (MetF) from *Escherichia coli*," *J. Bacteriol.* 181(3):718-725 (1999).
Shi et al., "The Structure of I-Aspartate Ammonia-Lyase from *Escherichia coli*," *Biochemistry* 36:9136-9144 (1997).
Shiba et al., "Engineering of the pyruate dehydrogenase bypass in *Saccharomyces cerevisiae* for high-level production of isoprenoids," *Metab. Eng.* 9:160-168 (2007).
Shibata et al., "Purification, characterization, and immunological properties of fumarase from *Euglena gracilis* var. bacillaris," *J. Bacteriol.* 164(2):762-768 (1985).
Shigeoka and Nakano, "Characterization and molecular properties of 2-oxoglutarate decarboxylase from *Euglena gracilis*," *Arch. Biochem. Biophys.* 288:22-28 (1991).
Shigeoka and Nakano, "The effect of thiamin on the activation of thiamin pyrophosphate-dependent 2-oxoglutarate decarboxylase in *Euglena gracilis*," *Biochem. J.* 292 (Pt 2):463-467 (1993).
Shigeoka et al., "Effect of L-glutamate on 2-oxoglutarate decarboxylase in *Euglena gracilis*," *Biochem. J.* 282 ( Pt 2):319-323 (1992).
Shimaoka et al, "Effects of edd and pgi Disruptions on Inosine Accumulation in *Escherichia coli*," *Biosci. Boitechnol. Biochem.* 69(7):1248-1255 (2005).
Shimoda et al., "Asymmetric Transformation of Enones with *Synechococcus* sp. PCC 7943," *Bulletin of the Chemical Society of Japan* 77(12):2269-2272 (2004).
Shimomura et al., "3-hydroxyisobutyryl-CoA hydrolase," *Methods Enzymol.* 324:229-240 (2000).

Shimomura et al., "Purification and partial characterization of 3-hydroxyisobutyryl-Coenzyme A hydrolase of rat liver," *J. Biol. Chem.* 269(19):14248-14253 (1994).
Shimoyama et al., "MmcBC in *Pelotomaculum thermopropionicum* represents a novel group of prokaryotic fumarases," *FEMS Microbiol Lett.* 270(2):207-213 (2007).
Shingler et al., "Nucleotide sequence and functional analysis of the complete phenol/3,4-dimethylphenol catabolic pathway of *Pseudomonas* sp. strain CF600," *J. Bacteriol.* 174(3):711-724 (1992).
Shlomi et al., "Regulatory on/off minimization of metabolic flux changes after genetic perturbations " *Proc. Natl. Acad. Sci. U.S.A.* 102:7695-7700 (2005).
Shukla et al., "Production of D(-)-lactate from sucrose and molasses," *Biotechnol. Lett.* 26(9):68-693 (2004).
Shuler and Kargi, Operating Considerations for Bioreactors for Suspension and Immobilized Cultures, in *Bioprocess Engineering: Basic Concepts*, Prentice Hall, Inc., Upper Saddle River, NJ., p. 245-247 (2002).
Sibilli et al., "Two regions of the bifunctional protein aspartokinase I-homoserine dehydrogenase I are connected by a short hinge," *J. Biol. Chem.* 256 (20):10228-10230 (1981).
Sieber et al., "Libraries of hybrid proteins from distantly related sequences," *Nat. Biotechnol.* 19:456-460 (2001).
Siegert et al., "Exchanging the substrate specificities of pyruvate decarboxylase from *Zymomonas mobilis* and benzoylformate decarboxylase from *Pseudomonas putida*," *Protein. Eng. Des. Sel.* 18:345-357 (2005).
Siew et al., "Localization and characteristics of rat liver mitochondrial aldehyde dehydrogenases," *Arch. Biochem. Biophys.*, 176(2):638-649 (1976).
Sikorski and Heiter, "A system of shuttle vectors and yeast host strains designed for efficient manupulation of DNA in *Saccharomyces cerevisiae*," *Genetics* 122(1):19-27 (1989).
Simanshu et al., "Structure and function of enzymes involved in the anaerobic degradation of L-threonine to propionate," *J. Biosci.* 32(6):1195-1206 (2007).
Siminov et al., "Application of Gas Chromatography and Gas Chromatography-Mass Spectrometry to the Detection of γ-Hydroxybutyric Acid and Its Precursors in Various Materials," *J. Anal. Chem.* 59:965-971 (2004).
Simon et al., "Chiral Compounds Synthesized by Biocatalytic Reductions," *Angew. Chem. Int. Ed. Engl.* 24:539-553 (1985).
Sinclair et al., "Purification and characterization of the branched chain α-ketoacid dehydrogenase complex from *Saccharomyces cerevisiae*," *Biochem. Mol. Biol. Int.* 31(5):911-922 (1993).
Sipma et al., "Microbial CO conversions with applications in synthesis gas purification and bio-desulfurization," *Crit. Rev. Biotechnol.* 26:41-65 (2006).
Sivaraman et al., "Codon choice in genes depends on flanking sequence information—implications for theoretical reverse translation," *Nucleic Acids Res.*36(3):e16 (2008).
Sjöström et al., "Purification and characterisation of a plasminogen-binding protein from Haemophilus influenzae. Sequence determination reveals identity with aspartase," *Biochim. Biophys. Acta* 1324(2):182-190 (1997).
Skarstedt and Silverstein, "*Escherichia coli* acetate kinase mechanism studied by net initial rate, equilibrium, and independent isotopic exchange kinetics," *J. Biol. Chem.* 251:6775-6783 (1976).
Slater et al., "Multiple β-ketothiolaset mediate poly(β-hydroxyalkanoate) copolymer synthesis in *Ralstonia eutropha*," *J. Bacteriol.* 180(8):1979-1987 (1998).
Sloane et al., "Studies on the metabolism of p-aminobenzoic acid by *Mycobacterium smegmatis*," *J Biol. Chem.* 193:453-458 (1951).
Slock et al., "An apparent *Bacillus subtilis* folic acid biosynthetic operon containing pab, an amphibolic *trpG* gene, a third gene required for synthesis of paraaminobenzoic acid, and the dihydropteroate synthase gene," *J. Bacteriol.* 172:7211-7226 (1990).
Smit et al., "Identification, cloning and characterization of *Lactococcus* lactic branched-chain α-keto acid decarboxylase involved in flavor formation," *Appl. Environ. Microbiol.* 71:303-311 (2005).

(56) References Cited

OTHER PUBLICATIONS

Smith and Gray, "Catalysis of the oxidation of 1,4-cyclohexadiene to benzene by electroactive binuclear rhodium complexes," *Catalysis Lett.* 6:195-199 (1990).
Smith and Kaplan, "Purification, properties and kinetic mechanism of Coenzyme A-linked aldehyde dehydrogenase from *Clostridium kluyveri*," *Arch. Biochem. Biophys.* 203:663-675 (1980).
Smith et al., "Purification and characteristics of a γ-glutamyl kinase involved in *Escherichia coli* proline biosynthesis," *J. Bacteriol.* 157:545-551 (1984).
Smith et al., "Fumarate metabolism and the microaerophily of *Campylobacter* species," *Int. J. Biochem. Cell Biol.* 31(9):961-975 (1999).
Smith et al., "Structural and functional organization of the animal fatty acid synthase," *Prop. Lipid. Res.* 42(4):289-317 (2003).
Sobue et al., "Actin polymerization induced by calspectin, a calmodulin-binding spectrin-like protein," *FEBS Lett* 148(2):221-225 (1982).
Soda and Misono, "L-Lysine:α-ketoglutarate aminotransferase. II. Purification, crystallization, and properties," *J. Bacteriol.* 7:4110-4119 (1968).
Söhling and Gottschalk, "Molecular analysis of the anaerobic succinate degradation pathway in *Clostridium kluyveri*," *J. Bacteriol.* 178:871-880 (1996).
Söhling and Gottschalk, "Purification and characterization of a Coenzyme-A-dependent succinate-semialdehyde dehydrogenase from *Clostridium kluyveri*," *Eur. J. Biochem.* 212:121-127 (1993).
Soini et al., "High cell density media for *Escherichia coli* are generally designed for aerobic cultivations—consequences for large-scale bioprocesses and shake flask cultures," *Microb. Cell. Fact.* 7:26 (2008).
Sokatch et al., "Purification of a Branched-Chain Keto Acid Dehydrogenase from *Pseudomonas putida*," *J. Bacteriol.* 148(2):647-652 (1981).
Somerville, "The Billion-Ton Biofuels Vision," *Science* 312(5778):1277 (2006).
Sone et al., "Nucleotide sequence and expression of the Enterobacter aerogenes α-acetolactate decarboxylase gene in brewer's yeast, " *Appl. Environ. Microbiol.* 54:38-42 (1988).
Song et al, "Effects of dissolved $CO_2$ levels on the growth of *Mannheimia succinicproducens* and succinic acid production," *Biotechnol. Bioeng.* 98(6):1296-1304 (2007).
Song et al., "Construction of recombinant *Escherichia coli* strains producing poly (4-hydroxybutyric acid) homopolyester from glucose," *Wei Sheng Wu Xue.Bao.* 45:382-386 (2005).
Song et al., "Ultrasound-mediated DNA transfer for bacteria," *Nucl. Acids Res.* 35:e129 (2007).
Song et al., "Recovery of succinic acid produced by fermentation of a metabolically engineered *Mannheimia succiniciproducens* strain," *J. Biotechnol.* 132:445-452 (2007).
Song et al., "Structure, function, and mechanism of the phenylacetate pathway hot dog-fold thioesterase PaaI," *J. Biol. Chem.* 281(16):11028-11038 (2006).
Soucaille et al., "Butanol tolerance and autobacteriocin production by *Clostridium acetobutylicum*," *Curr. Microbiol.* 14:295-299 (1987).
Sovik, "Mitochondrial 2-methylacetoacetyl-CoA thiolase deficiency: an inborn error of isoleucine and ketone body metabolism," *J. Inherit. Metab. Dis.* 16:46-54 (1993).
Sramek and Frerman, "Purification and properties of *Escherichia coli* Coenzyme A-transferase," *Arch. Biochem. Biophys.* 171(1):14-26 (1975).
St. Maurice et al., "Flavodoxin:quinone reductase (FgrB): a redox partner of pyruvate:ferredoxin oxidoreductase that reversibly couples pyruvate oxidation to NADPH production in *Helicobacter pylori* and *Campylobacter jejuni*," *J. Bacteriol.* 189:4764-4773 (2007).
Stadtman, "The enzyme synthesis of β-alanyl Coenzyme A," *J. Plant Chem. Soc.* 77:5765-5766 (1955).
Stanley et al., "Expression and stereochemical and isotope effect studies of active 4-oxalocrotonate decarboxylase," *Biochemistry* 39:718-726 (2000).
Starai et al., "Acetate excretion during growth of salmonella enerica on ethanolamine requires phosphotransacetylase (EutD) activity, and acetate recapture requires acetyl-CoA synthetase (Acs) and phosphotransacetylase (Pta) activities," *Microbiology* 151:3793-3801 (2005).
Starai et al., "Residue Leu-641 of Acetyl-CoA synthetase is critical for the acetylation of residue Lys-609 by the Protein acetyltransferase enzyme of *Salmonella enterica*," *J. Biol. Chem.* 280(28):26200-26205 (2005).
Starnes et al., "Threonine-sensitive aspartokinase-homoserine dehydrogenase complex, amino acid composition, molecular weight, and subunit composition of the complex," *Biochemistry* 11:677-687 (1973).
Steen et al., "Metabolic engineering of *Saccharomyces cerevisiae* for the production of n-butanol," *Microb. Cell Fact.* 7:36 (provided electronically by publisher as pp. 1-8) (2008).
Steffan and McAlister-Henn, "Isolation and characterization of the yeast gene encoding the MDH3 isozyme of malate dehydrogenase," *J. Biol. Chem.* 267:24708-24715 (1992).
Steinbacher et al., "Enoate reductase family," in Flavins and Flavoproteins, Proceedings of the Fourteenth International Symposium, St. John's College, University of Cambridge, UK, Jul. 14-18, 2002, Chapman et al., pp. 941-949, Rudolf Weber, Agency for Scientific Publications Berlin.
Steinbüchel and Schlegel, "NAD-linked L(+)-lactate dehydrogenase from the strict aerobe alcaligenes eutrophus. 2. Kinetic properties and inhibition by oxaloacetate," *Eur. J. Biochem.* 130(2):329-334 (1983).
Steinbuchel and Schlegel, "A multifunctional fermentative alcohol dehydrogenase from the strict aerobe Alcaligenes eutrophus: purification and properties," *Eur. J. Biochem.* 141:555-564 (1984).
Steiner and Sauer, "Long-term continuous evolution of acetate resistant *Acetobacter aceti*," *Biotechnol. Bioeng.* 84:40-44 (2003).
Stemmer, "DNA shuffling by random fragmentation and reassembly: in vitro recombination for molecular evolution," *Proc. Natl. Acad. Sci. U.S.A.* 91:10747-10751 (1994).
Stemmer, "Rapid evolution of a protein in vitro by DNA shuffling," *Nature* 370:389-391 (1994).
Stim-Herndon et al., "Characterization of an acetyl-CoA C-acetyltransferase (thiolase). gene from *Clostridium acetobutylicum* ATCC 824," *Gene* 154(1):81-85 (1995).
Stirling and Perry, "Purification and Properties of a Nicotinamide Adenine Dinucleotide-Linked Cyclohexanol Dehydrogenase from a *cocardia* Species," *Curr. Microbiol.* 4:37-40 (1980).
Stokell et al., "Probing the roles of key residues in the unique regulatory NADH binding site of type II citrate synthase of *Escherichia coli*," *J. Biol. Chem.* 278:35435-35443 (2003).
Stols and Donnelly, "Production of succinic acid through overexpression of $Nad^+$-dependent malic enzyme in an *Escherichia coli* mutant," *Appl. Environ. Microbiol.* 63(7):2695-2701 (1997).
Stols et al., "Expression of *Ascaris suum* malic enzyme in a mutant *Escherichia coli* allows production of succinic acid from glucose," *Appl. Biochem. Biotechnol.* 63-65: 153-158 (1997).
Stols et al., "New vectors for co-expression of proteins: Structure of *Bacillus subtilis* ScoAB obtained by High-throughput protocols," *Protein Expr. Purif.* 53:396-403 (2007).
Stoyan et al., "Cloning, sequencing and overexpression of the leucine dehydrogenase gene from *Bacillus cereus*," *J. Biotechnol.* 54:77-80 (1997).
Straathof et al., "Feasibility of acrylic acid production by fermentation," *Appl. Microbiol. Biotechnol.* 67:727-734 (2005).
Strauss and Fuchs, "Enzymes of a novel autotrophic $CO_2$ fixation pathway in the phototrophic bacterium *Chloroflexus aurantiacus*, the 3-hydroxypropionate cycle," *Eur. J. Biochem.* 215:633-643 (1993).
Streit and Entcheva, "Biotin in microbes, the genes involved in its biosynthesis, its biochemical role and perspectives for biotechnological production," *Appl. Microbiol. Biotechnol.* 61:21-31 (2003).
Stringfellow et al., "Sequence of the *Escherichia coli* C homoprotocatechuic acid degradative operon completed with that of the 2,4-dihydroxyhept-2-ene-1,7-dioicic acide aldolase-encoding gene (hpdH)," *Gene* 166:73-76 (1995).

(56) References Cited

OTHER PUBLICATIONS

Stryer, *Biochemistry*. 3rd Ed. New York: W.H. Freeman and Company, pp. 374-376 (1988).
Suarez de Mata et al., "Propionyl-CoA condensing enzyme from Ascaris muscle mitochondria. I. Isolation and characterization of multiple forms," *Arch. Biochem. Biophys.* 285(1):158-165 (1991).
Suarez de Mata et al., "Propionyl-CoA condensing enzyme from Ascaris muscle mitochondria. II. Coenzyme A modulation," *Arch. Biochem. Biophys.* 285:166-171 (1991).
Suda et al., "Purification and properties of α-ketoadipate reductase, a newly discovered enzyme from human placenta," *Arch. Biochem. Biophys.* 176(2):610-620 (1976).
Suda et al., "Subcellular localization and tissue distribution of α-ketoadipate reduction and oxidation in the rat," *Biochem. Biophys. Res. Commun.* 77(2):586-591 (1977).
Suematsu et al., "Molecular cloning and functional expression of rat liver cytosolic acetyl-CoA hydrolase," *Eur. J. Biochem.* 268(9):2700-2709 (2001).
Sulzenbacher et al., "Crystal structure of *E.coli* alcohol dehydrogenase YqhD: evidence of a covalently modified NADP Coenzyme," *J. Mol. Biol.* 342(2):489-502 (2004).
Suthers et al., "Metabolic flux elucidation for large-scale models using $^{13}$C labeled isotopes," *Metab. Eng.* 9:387-405 (2007).
Suzuki et al., "Acetylputrescine deacetylase from *Micrococcus luteus* K-11," *Biochim. Biophys. Acta* 882:140-142 (1986).
Suzuki et al., "GriC and GriD Constitute a carboxylic acid reductase involved in grixazone biosynthesis in streptomyces griseus," *J. Antibiot.* 60(6):380-387 (2007).
Suzuki et al., "Properties and metabolic, role of mesaconate hydratase of an aerobic bacterium," *J. Biochem.* 81:1917-1925 (1977).
Suzuki, "Phospotransacetylase of *Escherichia coli* B., activation by pyruvate and inhibition by NADH and certain nucleotides," *Biochem. Biophys. Acta* 191:559-569 (1969).
Svensson et al., "Characterization and isolation of enzymes that hydrolyze short-chain acyl-CoA in rat-liver mitochondria," *Eur. J. Biochem.* 238(2):526-531 (1996).
Svetlitchnyi et al., "A functional Ni-Ni-[4Fe-4S] cluster in the monomeric acetyl-CoA synthase from *Carboxydothermus hydrogenoformans*," *Proc. Natl. Acad. Sci. U.S.A.* 101(2):446-451 (2004).
Svetlitchnyi et al., "Two membrane-associated NiFeS-carbon monoxide dehydrogenases from the anaerobic carbon-monoxide-utilizing eubacterium *Carboxydothermus hydrogenoformans*," *J. Bacteriol.* 183(17):5134-5144 (2001).
Switzer, "Glutamate mutase," In Dolphin, D. ed., Vitamin B$_{12}$ (vol. 2: Biochemistry and Medicine), Wiley-Interscience: New York, p. 289-305 (1982).
Tae-Kang et al., "Purification and characterization of a cyclohexanol dehydrogenase from *Rhodococcus* sp. TK6," *J. Microbiol. Biotechnol.* 12:39-45 (2002).
Tahlan et al., "Two sets of paralogous genes encode the enzymes involved in the early stages of clavulanic acid and clavam metabolite biosynthesis in *Streptomyces clavuligerus*," *Antimicrob. Agents Chemother.* 48(3):930-939 (2004).
Takacs et al., "Formate hydrogenlyase in the hyperthermophilic archaeon, *Thermococcus litoralis*," *BMC Microbiol.* 8:88 (2008).
Takagi et al, "Purification, crystallization, and molecular properties of aspartase from *Pseudomonas fluorescens*," *J. Biochem.* 96(2):545-552 (1984).
Takagi et al., "Isolation of a versatile *Serratia marcescens* mutant as a host and molecular cloning of the aspartase gene," *J. Bacteriol.* 161:1-6 (1985).
Takagi et al., "Cloning and nucleotide sequence of the aspartase gene of *Pseudomonas fluorescens*," *J. Biochem.* 100(3):697-705 (1986).
Takahashi and Yamada, "Metabolic pathways for cytoxic and end product formation from glutamate- and aspartate-containing peptides by *Porphyromonas gingivalis*," *J. Bacteriol.* 182:4704-4710 (2000).
Takahashi-Abbe et al., "Biochemical and functional properties of a pyruvate formate-lyase (PFL)-activating system in *Streptococcus mutans*," *Oral Microbiol. Immunol.* 18:293-297 (2003).
Takanashi et al., "Characterization of a novel 3-hydroxybutyrate dehydrogenase from *Ralstonia-pickettii* T1," *Antonie van Leeuwnhoek* 95(3):249-262 (2009).
Takatsuka et al., "Gene cloning and molecular characterization of lysine decarboxylase from *Selenomonas ruminantium* delineate its evolutionary relationship to ornithine decarboxylases from eukaryotes," *J. Bacteriol.* 182:6732-6741 (2000).
Takatsuka et al., "Identification of the amino acid residues conferring substrate specificity upon *Selenomonas ruminantium* lysine decarboxylase," *Bioxci. Biotechnol Biochem.* 63:1843-1846 (1999).
Takeo, "Existence and Properties of Two Malic Enzymes in *Escherichia coli* Especially of NAD-linked Enzyme," *J. Biochem.* 66:379-387 (1969).
Takigawa et al., "Probabilistic path ranking based on adjacent pairwise coexpression for metabolic transcripts analysis," *Bioinform.* 24(2):250-257 (2008).
Tallant and Krzycki, "Coenzyme M methylase activity of the 480-kilodalton corrinoid protein from *Methanosarcina barkeri*," *J. Bacteriol.* 178(5):1295-1301 (1996).
Tallant and Krzycki, "Methylthiol:Coenzyme M Methyltransferase from *Methanosarcina barkeri*, an enzyme of methanogenesis from dimethylsulfide and methylmercaptopropionate," *J. Bacteriol.* 179(22):6902-6911 (1997).
Tallant et al., "The MtsA subunit of the methylthiol:Coenzyme M methyltransferase of *Methanosarcina barkeri* catalyses both half-reactions of corrinoid-dependent dimethylsulfide: Coenzyme M methyl transfer," *J. Biol. Chem.* 276(6):4485-4493 (2001).
Tamaki et al., "Purification, properties, and sequencing of aminoisobutyrate aminotransferases from rat liver," *Methods Enzymol.* 324:376-389 (2000).
Tanaka et al., "Cloning and characterization of a human orthologue of testis-specific succinyl CoA: 3-oxo acid CoA transferase (Scot-t) cDNA," *Mol. Hum. Reprod.* 8:16-23 (2002).
Tanaka et al., "Lysine decarboxylase of *Vibrio parahaemolyticus*: kinetics of transcription and role in acid resistance," *J. Appl. Microbiol.* 104:1283-1293 (2008).
Tang et al., "Identification of a novel pyridoxal 5'-phosphaste binding site in adenosylcobalamin-dependent lysine 5,6-aminomutase from *Porphyromonas gingivalis*," *Biochemistry* 41(27):8767-8776 (2002).
Tani et al., "Thermostable NADP$^+$-dependent medium-chain alcohol dehydrogenase from *Acinetobacter* sp. strain M-1: purification and characterization and gene expression in *Escherichia coli*," *Appl. Environ. Microbiol.* 66(12):5231-5235 (2000).
Tanizawa et al., "The primary structure of thermostable D-amino acid aminotransferase from a thermophilic *Bacillus* species and its correlation with L-amino acid aminotransferases," *J. Biol. Chem.* 264(5):2450-2454 (1989).
Tanous et al., "Glutamate dehydrogenase activity can be transmitted naturally to *Lactococcus lactis* strains to stimulate amino acid conversion to aroma compounds," *Appl. Environ. Microbiol.* 72(2):1402-1409 (2006).
Tardif et al., "Electrotransformation studies in *Clostridium cellulolyticum*," *J. Ind. Microbiol. Biotechnol.* 27(5):271-274 (2001).
Taylor and Fotheringham, "Nucleotide sequence of the *Bacillus licheniformis* ATCC 10716 dat gene and comparison of the predicted amino acid sequence with those of other bacterial species," *Biochim. Biophys. Acta* 1350(1):38-40 (1997).
Tebbe et al., "Titanium-Catalyzed Olefin Metathesis," *J. Am. Chem. Soc.* 101(17):5074-5075 (1979).
Teipel et al., "The substrate specificity of fumarase," *J. Biol. Chem.* 243:5684-5694 (1968).
ter Schure et al., "Pyruvate decarboxylase catalyzes decarboxylation of branchedchain 2-oxo acids but is not essential for fusel alcohol production by *Saccharomyces cerevisiae*," *Appl. Environ. Microbiol.* 64:1303-1307 (1998).
Teufel et al., "3-hydroxypropionyl-Coenzyme A dehydratase and acryloyl-Coenzyme A reductase, enzymes of the autotrophic 3-hydroxypropionate/4-hydroxybutyrate cycle in the Sulfolbales," *J. Bacteriol.* 191:4572-4581 (2009).

(56) References Cited

OTHER PUBLICATIONS

Thanos and Simon, "Electro-enzymic viologen-mediated stereospecific reduction of 2-enoates with free and immobilized enoate reductase on cellulose filters or modified carbon electrodes," *J. Biotechnol.* 6:13-29 (1987).
Thauer, "Microbiology. A Fifth Pathway of Carbon Fixation," *Science* 318:1732-1733 (2007).
Thomas et al., "Bimetallic nanocatalysts for the conversion of muconic acid to adipic acid," *Chem. Commun.* 21:1126-1127 (2003).
Thornton et al.; "Primary structure of the monomer of the 12S subunit of transcarboxylase as deduced from DNA and characterizatio not the product expressed in *Escherichia coli*," *J. Bacteriol.* 175:5301-5308 (1993).
Thykaer et al., "Metabolic network analysis of an adipoyl-7-ADCA-producing strain of *Penicillium chrysogenum*: elucidation of adipate degradation," *Metab. Eng.* 4(2):151-158 (2002).
Tian et al., "Variant tricarboxylic acid cycle in *Mycobacterium tuberculosis*: identification of α-ketoglutarate decarboxylase," *Proc. Natl. Acad. Sci. U.S.A.* 102:10670-10675 (2005).
Tischer et al., "Purification and Some Properties of a Hitherto-Unknown Enzyme Reducing the Carbon-Carbon Double Bond of α, β-Unsaturated Carboxylate Anions," *Eur. J. Biochem.* 97(1):103-112 (1979).
Tobimatsu et al., "Molecular cloning, Sequencing and Characterization of the Genes for Adenosylcobalamin-deptendent Diol Dehydratase of *Klebsiella pneumoniae*," *Biosci. Biotechnol. Biochem.* 62(9):1744-1777 (1998).
Tobimatsu et al., "Molecular cloning, Sequencing and Expression of the Genes Encoding Adenosylcobalamin-dependent Diol Dehydrase of *Klebsiella oxytoca*," *J. Biol. Chem.* 270(13):7142-7148 (1995).
Tobin et al., "Localization of the Lysine ϵ-Aminotransferase (lat) and σ-Aminoadipyl)- L-Cysteinyl-D-Valine Synthetase (pcbAB) Genes from *Streptomyces clavuligerus* and Production of Lysine ϵ-Aminotransferase Activity in *Escherichia coli*," *J. Bacteriol.* 173(19):6223-6229 (1991).
Tolentino et al., "A pH-regulated promoter for the expression of recombinant proteins in *Escherichia coli*," *Biotechnol. Lett.* 14:157-162. (1992).
Tomas et al., "Overexpression of groESL in *Clostridium acetobutylicum* Results in Increased Solvent Production and Tolerance, Prolonged Metabolism, and Changes in the Cell's Transcriptional Program," *Appl. Environ. Microbiol.* 69:4951-4965 (2003).
Toraya et al., "Substrate Specificity of Coenzyme $B_{12}$-Dependent Diol Dehydrase: Glycerol as Both a Good Substrate and a Potent Inactivator," *Biochem. Biophys. Res. Commun.* 69:475-480 (1976).
Toth et al., "The ald Gene, Encoding a Coenzyme A-Acylating Aldehyde Dehydrogenase, Distinguishes *Clostridium beijerinckii* and Two Other Solvent-Producing Clostridia from *Clostridium acetobutylicum*," *App. Environ. Microbiol.* 65(11):4973-4980 (1999).
Tretter and Adam-Vizi, "Alpha-ketoglutarate dehydrogenase: a target and generator of oxidative stress," *Philos. Trans. R. Soc. B* 360:2335-2345 (2006).
Trower et al., "Isolation and Characterization of a Cyclohexane-Metabolizing *Xanthobacter* sp.," *Appl. Environ. Microbiol.* 49(5):1282-1289 (1985).
Truscott et al., "Mechanisms of protein import into mitochondria," *Curr. Biol.* 13(8):R326-R337 (2003).
Tsao et al., "Production of multifunctional organic acids from renewable resources," *Adv. Biochem. Eng. Biotechnol.* 65:243-280 (1999).
Tseng et al., "Metabolic Engineering of *Escherichia coli* for Enhanced Production of (R)- and (S)-3-Hydroxybutyrate," *App. Environ. Microbiol.* 75(10):3137-3145 (2009).
Tseng et al., "Oxygen- and growth rate-dependent regulation of *Escherichia coli* fumarase (FumA, FumB, and BumC) activity," *J. Bacteriol.* 183(2):461-467 (2001).
Tsujimoto et al., "L-Lysine biosynthetic pathway of *Methylophilus methylotrophus* and construction of an L-Lysine producer," *J. Biotechnol.* 124:327-337 (2006).

Tucci and Martin, "A novel prokaryotic trans-2-enoyl-CoA reductase from the spirochete *Treponema denticola*," *FEBS Lett.* 581(8):1561-1566 (2007).
Tutino et al., "Expression of *Sulfolobus solfataricus* trpE and trpG genes in *E. coli*," *Biochem. Biophys. Res. Commun.* 230:306-310 (1997).
Twarog and Wolfe, "Role of butyryl phosphate in the energy metabolism of *Clostridium tetanomorphum*," *J. Bacteriol.* 86:112-117 (1963).
Tyurin et al., "Electrotransformation of *Clostridum acetobutylicum* ATCC 824 using high-voltage radio frequency modulated square pulses," *J. Appl. Microbiol.* 88(2):220-227 (2000).
Tyurin et al., "Electrotransformation of *Clostridium thermocellum*," *Appl. Environ. Microbiol.* 70(2):883-890 (2004).
Tzagoloff and Dieckmann, "PET genes of *Saccharomyces cerevisiae*," *Microbiol. Rev.* 54(3):211-225 (1990).
Uchiyama et al., "Identification of the 4-Hydroxycinnamate Decarboxylase (PAD) Gene of *Klebsiella oxytocia*," *Biosci. Biotechnol. Biochem.* 72: 116-123 (2008).
Ulaganathan et al., "Structure of Staphylococcus aureus1,4-dihydroxy-2-naphthoyl-CoA synthase (MenB) in complex with acetoacetyl-CoA," *Acta. Crystallogr. Sect. F. Struct. Biol. Cryst. Commun.* 63(Pt 11):908-913 (2007).
Umbarger and Brown, "Threonine deamination in *Escherichia coli*. II. Evidence fro two L -threonine deaminases," *J. Bacteriol.* 73(1):105-112 (1957).
Underwood et al., "Genetic Changes to Optimize Carbon Partitioning between Ethanol and Biosynthesis in Ethanologenic *Escherichia coli*," *App. Environ. Microbiol.* 68(12):6263-6372 (2002).
Urbance et al., "Evaluation of succinic acid continuous and repeat-batch biofilm fermentation by *Actinobacillus succinogenes* using plastic composite support bioreactors," *Appl. Microbiol. Biotechnol.* 65(6):664-670 (2004).
Uttaro and Opperdoes, "Purification and characterisation of a novel isopropanol dehydrogenase from *Phytomonas* sp.," *Mol. Biochem. Parasitol.* 85:213-219 (1997).
Vadali et al., "Enhanced Isoamyl Acetate Production upon Manipulation of the Acetyl-CoA node in *Escherichia coli*," *Biotech. Prog.* 20:692-697 (2004).
Vadali et al., "Production of isoamyl acetate in ackA-pta and/or ldh mutants of *E. coli* with overexpression of yeast ATF2," *Appl. Microbiol. Biotechnol.* 63:698-704 (2004).
Vadali et al., "Cofactor engineering of intercellular CoA/acetyl-CoA and its effect on metabolic flux redistribution in *Escherichia coli*," *Metab Eng.* 6(2): 133-139 (2004).
Valdes-Hevia and Gancedo, "Isolation and characterization of the gene encoding phosphoenolpyruvate carboxykinase from *Saccharomyces cerevisiae*," *FEBS Lett.* 258:313-316 (1989).
Valentin et al., "Metabolic pathway for biosynthesis of poly(3-hydroxybutyrate-co-4-hydroxybutyrate) from 4-hydroxybutyrate by *Alcaligenes eutrophus*," *Eur. J. Biochem.* 227(1-2):43-60 (1995).
Valentine and Wolfe, "Purification and role of phosphotransbutyrylase," *J. Biol. Chem.* 235:1948-1952 (1960).
Vamecq et al., "The microsomal dicarboxylyl-CoA synthetase," *Biochem. J.* 230(3):683-693 (1985).
Van Beilen et al., "Cloning of Baeyer-Villiger monooxygenases from comamonas, Xantherobacter and Rhodococcus using polymerase chain reaction with highly degenerate primers," *Environ. Microbiol.* 5(3):174-182 (2003).
van der Voorhorst et al., "Genetic and biochemcial characterization of a short-chain alcohol dehydrogenase from the hyperthermophilic archaeon *Pyrococcus furiosus*," *Eur. J. Biochem.* 268:3062-3068 (2001).
Van Der Westhuizen, et al., "Autolytic Activity and Butanol tolerance of *Clostridium acetobutylicum*," *Appl. Environ. Microbiol.* 44:1277-1281 (1982).
van Grinsven et al., "Acetate:succinate CoA-transferase in the hydrogenosomes of *Trichomonas vaginalis*: identification and characterization," *J. Biol. Chem.* 283:1411-1418 (2008).
van Loon and Young, "Intracellular sorting of alcohol dehydregenase isoenzymes in yeast: a cytosolic location oreflects absence of an amino-terminal targeting sequence for the mitochondrion," *EMBO J.* 5:161-165 (1986).

(56) References Cited

OTHER PUBLICATIONS van Maris et al., "Directed evolution of pyruvate decarboxylase-negative *Saccharomyces cerevisiae*, yielding a $C_2$-independent, glucose-tolerant, and pyruvate-hyperproducing yeast," *Appl. Environ. Microbiol.* 7:159-166 (2004).
Van Mullem et al., "Construction of a set of *Saccharomyces cerevisiae* vectors designed for recombinational cloning," *Yeast* 20(8):739-746 (2003).
Vanderwinkel et al., "Growth of *Escherichia coli* on fatty acids: requirement for Coenzyme A transferase activity," *Biochem. Biophys. Res. Commun.* 33(6):902-908 (1968).
Vanrolleghem et al., "Validation of a Metabolic Network for *Saccharomyces cerevisiae* Using Mixed Substrate Studies," *Biotechnol. Prog.* 12(4):434-448 (1996).
Varadarajan and Miller, "Catalytic Upgrading of Fermentation-Derived Organic Acids," *Biotechnol. Prog.* 15:845-854 (1999).
Vardar-Schara et al., "Metabolically engineered bacteria for producing hydrogen via fermentation," *Microbio. Biotechnol.* 1:107-125 (2008).
Varma and Palsson, "Stoichiometric Flux Balance Models Quantitatively Predict Growth and Metabolic By-Product Secretion in Wild-Type *Escherichia coli* W3110," *Appl Env. Microbiol.* 60(10):3724-3731 (1994).
Varma and Palsson, "Metabolic Flux Balancing: Basic Concepts, Scientific and Practical Use," *Biotechnology* 12:994-998 (1994).
Varma et al., "Biochemical Production Capabilities of *Escherichia coli*," *Biotechnol. Bioeng.* 42:59-73 (1993).
Varma et al., "Stoichiometric Interpretation of *Escherichia coli* Glucose Catabolism under Various Oxygenation Rates," *Appl. Environ. Microbiol.* 59:2465-2473 (1993).
Vazquez et al., "Phosphtransbutyrylase expression in *Bacillus megaterium*," *Curr. Microbiol.* 42:345-349 (2001).
Vega et al., "The Biological Production of Ethanol from Synthesis Gas," *Appl. Biochem. Biotechnol.* 20/21:781-797 (1989).
Vellanki et al., "Expression of hepatitis B surface antigen in *Saccharomyces cerevisiae* utilizing glyceraldehyde-3-phosphate dehydrogenase promoter of *Pichia pastoris*," *Biotechnol. Lett.* 29(2):313-318 (2007).
Vemuri et al. "Succinate production in dual-phase *Escherichia coli* fermentations depends on the time of transition from aerobic to anaerobic conditions," *J. Ind. Microbiol. Biotechnol.* 28:325-332 (2002).
Vemuri et al., "Effects of growth mode and pyruvate carboxylase on succinic acid production by metabolically engineered strains of *Escherichia coli*," *Appl. Environ. Microbiol.* 68(4):1715-1727 (2002).
Venkitasubramanian et al. Biocatalysis in the Pharmaceutical and Biotechnology Industires, ed. R.N. Patel, Chapter 15, pp. 425-440, CRC Press LLC, Boca Raton, FL. 2007.
Venkitasubramanian et al., "Reduction of Carboxylic Acids by Nocardia Aldehyde Oxidoreductase Requires a Phosphopantetheinylated Enzyme," *J. Biol. Chem.* 282(1):478-485 (2007).
Verhaert et al., "Enzyme kinetics in reversed micelles. 2. Behaviour of enoate reductase," *Eur. J. Biochem.* 187:73-79 (1990).
Vernal et al., "Cloning and heterologous expression of a broad specificity aminotransferase of *Leishmania mexicana* promastigotes," *FEMS Microbiol. Lett.* 229:217-222 (2003).
Vernal et al., "Isolation partial characterization of a broad specificity aminotransferase from *Leishmania mexicana* promastigotes," *Mol. Biochem. Parasitol.* 96:83-92 (1998).
Vey et al., "Structural basis for glycyl radical formation by pyruvate formate-lyase activating enzyme," *Proc. Natl. Acad. Sci. U.S.A.* 105:16137-16141 (2008).
Vijay et al., "Diels-Alder reactions between cyclic five-membered dienes and acetylene," *J. Mol. Struc.* 589-590:291-299 (2002).
Viola, "L-Aspartase: New Tricks From an Old Enzyme," *Adv. Enzymol. Relat. Areas. Mol. Biol.* 74:295-341 (2000).

Voellmy and Leisinger, "Role of 4-Aminobutyrate Aminotransferase in the Arginine Metabolism of *Pseudomonas aeruginosa*," *J. Bacteriol.* 128(3):722-729 (1976).
Voets et al., "Reduced intracellular ionic strength as the initial trigger for activation of endothelial volume-regulated anion channels," *Proc. Natl. Acad. Sci. U.S.A.* 96:5298-5303 (1999).
Volkert, et al., "The Δ(*argF-lacZ*)205(U169) Deletion Greatly Enhances Resistance to Hydrogen Peroxide in Stationary-Phase *Escherichia coli*," *J. Bact.* 176(3):1297-1302 (1994).
Volkov et al., "Random chimeragenesis by heteroduplex recombination," *Methods Enzymol.* 328:456-463 (2000).
Volkov et al., "Recombination and chimeragenesis by in vitro heteroduplex formation and in vivo repair," *Nucleic Acids Res.* 27:e18 (1999).
Vrijbloed et al., "Insertional inactivation of methylmalonyl Coenzyme A (CoA) mutase and isobutyryl-CoA mutase genes in *Streptomyces cinnamonensis*: influence on polyketide antibiotic biosynthesis," *J. Bacteriol.* 181(18):5600-5605 (1999).
Wakil et al., "Studies on the fatty acid oxidizing system of animal tissues. VI. β-Hydroxyacyl Coenzyme A dehydrogenase," *J. Biol. Chem.* 207(2):631-638 (1954).
Walker et al., "Yeast pyruvate carboxylase: identification of two genes encoding isoenzymes," *Biochem. Biophys. Res. Commun.* 176:1210-1217 (2007).
Walter et al., "Molecular characterization of two *Clostridium acetobutylicum* ATCC 824 butanol dehydrogenase isozyme genes," *J. Bacteriol.* 174(22):7149-7158 (1992).
Walter et al., "Sequence and arrangement of two genes of the butyrate-synthesis pathway of *Clostridium acetobutylicum* ATCC 824," *Gene* 134(1):107-111 (1993).
Wang and Barker, "Purification and Properties of L-citramalate hydrolase," *J. Biol. Chem.* 244(10):2516-2526 (1969).
Wang and Seah, "Determination of the metal ion dependence and substrate specificty of a hydratase involve din the degradation pathway of biphenyl/chlorobiphenyl," *FEBS J.* 272: 966-974 (2005).
Wang et al, "Molecular cloning and functional identification of a novel phenylacetylCoA ligase gene from *Penicillium chrysogenum*," *Biochem. Biopyhs. Res. Commun.* 360(2):453-458 (2007).
Wang et al., "The primary structure of branched-chain α-oxo acid dehydrogenase from *Bacillus subtilis* and its similarity to other α-oxo acid dehydrogenases," *Eur. J. Biochem.* 213:1091-1099 (1993).
Wang et al., "Bioconversion of fumaric acid to succinic acid by recombinant *E. coli*," *App. Biochem. Biotechnol.* 70-72: 919-928 (1998).
Wang et al., "Cloning, Sequencing, and Expression of the Pyruvate Carboxylase Gene in *Lactococcus lactis* subsp. *lactis* C2," *App. Environ. Microbiol.* 66(3):1223-1227 (2000).
Wang et al., "Expression of galactose permease and pyruvate carboxylase in *Escherichia coli* ptsG mutant increases the growth rate and succinate yield under anaerobic conditions," *Biotechnol. Lett.* 28(2):89-93 (2006).
Wang et al., "Genome-scale in silico aided metabolic analysis and flux comparisons of *Escherichia coli* to improve succinate production," *Appl. Microbiol. Biotechnol.* 73(4):887-894 (2006).
Wang et al., "Screening microorganisms for utilization of furfural and possible intermediates in its degradative pathway," *Biotechnol. Lett.* 16(9):977-982 (1994).
Wang et al., "Site-directed mutagenesis of the phosphorylatable serine (Ser[8]) in $C_4$ phosphoenolpyruvate carboxylase from sorghum. The effect of negative charge at position 8," *J. Biol. Chem.* 267:16759-16762. (1992).
Wanner and Tressl, "Purification and characterization of two enone reductases from *Saccharomyces cerevisia*," *Eur. J. Biochem.* 255(1):271-278 (1998).
Ward et al., "Molecular analysis of the rele of two aromatic aminotransferases and a broad-specificity aminotransferase in the aromatic amino acid metabolism of *Pyococcus furiosus*," *Archaea* 1:133-141 (2002).
Weaver, "Structure of free fumarase C from *Escherichia coli*," *Acta. Crystallogr. D. Biol. Crystallogr.* 61(Pt 10):1395-1401 (2005).
Weber and Falbe, "Oxo Synthesis Technology," *Ind. Eng. Chem. Res.* 62:33-37 (1970).

(56) References Cited

OTHER PUBLICATIONS

Weidner and Sawers, "Molecular characterization of the Genes Encoding Pyruvate Formate-Lyase and Its Activating enzyme of *Clostridium pasteruianum*," *J. Bacteriol.* 178(8):2440-2444 (1996).
Welch et al., "Purification and Characterization of the NADH-Dependent Butanol Dehydrogenase from *Clostridium acetobutylicum* (ATCC 824)," *Arch. Biochem. Biophys.* 273(2):309-318 (1989).
Wengrovius et al., "Tungsten-Oxo Alkylidene Complexes as Olefin Metathesis Catalysts and the Crystal Structure of W(O)(CHCMe$_3$)(PEt$_3$)Cl$_2$$^1$" *J. Am. Chem. Soc.* 102:4515-4516 (1980).
Westin et al., "The identification of a succinyl-CoA thioesterase suggests a novel pathway for succinate production in peroxisomes," *J. Biol. Chem.* 280(46):38125-38132 (2005).
Wexler et al., "A wide host-range metagenomic library from a waste water treatment plant yields a novel alcohol/aldehyde dehdrogenase," *Environ. Microbiol.* 7:1917-1926 (2006).
Whalen and Berg, "Analysis of an avtA::Mu d1(Ap lac) Mutant: Metabolic Role of Transaminase C," *J. Bacteriol.* 150(2):739-746 (1982).
Whalen and Berg, "Gratuitous repression of avtA in *Escherichia coli* and *Salmonella typhimurium*," *J. Bacteriol.* 158(2):571-574 (1984).
Whelan et al., "Nylon 6 (PA6)," *Kunststof en Rubber*, Wyt en Zonen Uitgevers. Rotterdam, NL, 39(3):38-39 (1986).
Whisstock et al., "Prediction of protein function from protein sequence and structure," *Q. Rev. Biophysics.* 36(3):307-340 (2003).
White et al., "Long-chain alcohol production by yeasts," *7th Int. Symp. Yeasts* S465-S470 (1989).
White et al., "The structural biology of type II fatty acid biosynthesis," *Ann. Rev. Biochem.* 74:791-831 (2005).
Whitehead and Rabinowitz, "Cloning and expression in *Escherichia coli* of the gene for 10-formyltetrahydrofolate synthetase from *Clostridium acidiurici* ("*Clostridium acidi-urici*")," *J. Bacteriol.* 167:205-209 (1986).
Whitehead and Rabinowitz, "Nucleotide Sequence of the *Clostridium acidiurici* ("*Clostridium acidi-urici*") Gene for 10-Formyltetrahydrofolate Synthetase Shows Extensive Amino Acid Homology with the Trifunctional Enzyme C$_1$-Tetrahydrofolate Synthase from *Saccharomyces cerevisiae*," *J. Bacteriol.* 170(7):3255-3261 (1988).
Wiesenborn et al., "Coenzyme A Transferase from *Clostridium acetobutylicum* ATCC 824 and Its Role in the Uptake of Acids," *Appl. Environ. Microbiol.* 55(2):323-329 (1989).
Wiesenborn et al., "Phosphotransbutyrylase from *Clostridium acetobutylicum* ATCC 824 and its role in acidogenesis," *Appl. Environ. Microbiol.* 55:317-322 (1989).
Wilkie and Warren, "Recombinant expression, purification, and characterization of three isoenzymes of aspartate aminotransferase from *Arabidopsis thaliana*," *Protein Expr. Purif.* 12:381-389 (1998).
Wilks et al., "A specific, Highly Active Malate Dehydrogenase by Redesign of a Lactate Dehydrogenase Framework," *Science* 242:1541-1544 (1988).
Wilks et al., "Design of a Specific Phenyllactate Dehydrogenase by Peptide Loop Exchange on the *Bacillus stearothermophilus* Lactate Dehydrogenase Framework," *Biochemistry* 31:7802-7806 (1992).
Wilks et al., "Designs for a Broad Substrate Specificity Keto Acid Dehydrogenase," *Biochemistry* 29:8587-8591 (1990).
Willke and Vorlop, "Biotechnological production of itaconic acid," *Appl. Microbiol. Biotechnol.* 56(3-4):289-295 (2001).
Willke and Vorlop, "Industrial bioconversion of renewable resources as an alternative to conventional chemistry," *Appl. Microbiol. Biotechnol.* 66(2):131-142 (2004).
Winkler et al., "A new type of a multifunctional β-oxidation enzyme in euglena," *Plant. Physiol.* 131(2):753-762 (2003).
Winzeler et al., "Functional Characterization of *S. cerevisiae* Genome by Gene Deletion and Parallel Analysis," *Science* 285:901-906 (1999).
Winzer et al., "Differential regulation of two thiolase genes from *Clostridium acetobutylicum* DSM 792," *J. Mol. Microbiol. Biotechnol.* 2(4):531-541 (2000).
Witkowski et al., "Conversion of β-ketoacyl synthase to a Malonyl Decarboxylase by replacement of the active cysteine with glutamine," *Biochemistry* 38:11643-11650 (1999).
Wittich and Walter, "Putrescine *N*-acetyltransferase in *Onchocerca volvulus* and *Ascaris suum*, an enzyme which is involved in polyamine degradation and release of *N*-acetylputrescine," *Mol. Biochem. Parasitol.* 38:13-17 (1990).
Wolff and Kenealy, "Purification and characterization of the oxygen-sensitive 4-hydroxybutanoate dehydrogenase from *Clostridium kluyveri*," *Protein Expr. Purif.* 6:206-212 (1995).
Wong et al., "Molecular Properties of Pyruvate Formate-Lyase Activating Enzyme," *Biochemistry* 32:14102-14110 (1993).
Wong et al., "Sequence saturation mutagenesis (SeSaM): a novel method for directed evolution," *Nucleic Acids Res* 32:e26 (2004).
Wong et al., "Sequence saturation mutagenesis with tunable mutation frequencies," *Anal. Biochem.* 341:187-189 (2005).
Wong et al., "Transversion-enriched sequence saturation mutagenesis (SeSaM-Tv$^+$): a random mutagenesis method with consecutive nucleotide exchanges that complements the bias of error-prone PCR," *Biotechnol. J.* 3:74-82 (2008).
Wood, "Life with CO or CO$_2$ and H$_2$ as a source of carbon and energy," *Fed. Amer. Societies Experi. Biol. J.* 5:156-163 (1991).
Woods, "Two biochemically distinct classes of fumarase in *Escherichia coli*," *Biochim. Biophys. Acta* 954(1):14-26 (1988).
Wu and Woodard, "New insights into the evolutionary links relating to the 3-deoxy-D-arabino-heptulosonate 7-phosphate synthase subfamilies," *J. Biol. Chem.* 281:4042-4048 (2006).
Wu et al., "Microbial synthesis of cis-cis-muconic acid by *Sphingobacterium* sp. GcG generated from effluent of a styrene monomer (SM) production plant," *Enzyme Microbial Tech.* 35:598-604 (2004).
Wu et al., "Thermotoga maritima 3-deoxy-D-arabino-heptulosonate 7-phosphate (DAHP) synthase: the ancestral eubacterial DAHP synthase?" *J. Biol. Chem.* 278:27525-27531 (2003).
Wu et al., "Life in hot carbon monoxide: the complete genome sequence of Carboxydothermus hydrogenoformans Z-2901," *PLoS Genet.* 1(5):e65 (2005).
Wylie et al., "Nematode.net: a tool for navigating sequences from parasitic and free-living nematodes," *Nucleic Acids Res.* 32:D423-D426 (2004).
Wynn et al., "Chaperonins GroEL and GroES promote assembly of heterotetramers ($\alpha_2\beta_2$) of mammalian mitochondrial branched-chain α-keto acid decarboxylase in *Escherichia coli*," *J. Biol. Chem.* 267:12400-12403 (1992).
Wynn et al., "Cloning and expression in *Escherichia coli* of mature E1 β subunit of bovine mitochondrial branched-chain α-keto acid dehydrogenase complex. Mapping of the E1 β-binding region on E2," *J. Biol. Chem.* 267:1881-1887 (1992).
Yabutani et al., "Analysis of β-ketothiolase and acetoacetyl-CoA reductase genes of a methylotrophic bacterium, Paracoccus denitrificans, and their expression in *Escherichia coli*," *FEMS Microbiol. Lett.* 133:85-90 (1995).
Yagi et al., "Aspartate: 2-oxoglutarate aminotransferase from bakers' yeast: crystallization and characterization," *J. Biochem.* 92(1):35-43 (1982).
Yagi et al., "Crystallization and properties of aspartate aminotransferase from *Escherichia coli* B," *FEBS Lett.* 100(1):81-84 (1979).
Yagi et al., "Glutamate-aspartate transaminase from microorganisms," *Methods Enzymol.* 113:83-89 (1985).
Yamamoto et al., "Carboxylation reaction catalyzed by 2-oxoglutarate:ferredoxin oxidoreductases from *Hydrogenobacter thermophilus*," *Extremophiles* 14:79-85 (2010).
Yamamoto et al., "Purification and Properties of NADP-dependent Formate Dehydrogenase from *Clostridium thermoaceticum*, a tungsten—Selenium—Iron Protein," *J. Biol. Chem.* 258(3):1826-1832 (1983).
Yamano et al., "Construction of a brewer's yeast having β-acetolactate decarboxylase gene from *Acetobacter aceti* ssp. *xylinum* integrated in the genome," *J. Biotechnol.* 32:173-178 (1994).
Yan and Chen, "Coenzyme A-acylating aldehyde dehydrogenase from *Clostridium beijerinckii* NRRL B592," *Appl. Environ. Microbiol.* 56:2591-2599 (1990).

(56) References Cited

OTHER PUBLICATIONS

Yang et al., "Aspartate Dehydrogenase, a Novel Enzyme Identified from Structural and Functional Studies of TM1643," *J. Biol. Chem.* 278(10):8804-8808 (2003).

Yang et al., "Effect of inactivation of *nuo* and *ackA-pta* on redistribution of metabolic fluxes in *Escherichia coli*," *Biotechnol Bioeng.* 65(3):291-297 (1999).

Yang et al., "Effect of Variation of *Klebsiella pneumonaie* Acetolactate Synthase Expression on Metabolic Flux Redistribution in *Escherichia coli*," *Biotechnol. Bioeng.* 69(2)150-159 (2000).

Yang et al., "Metabolic Flux Analysis of *Escherichia coli* Deficient in the Acetate Production Pathway and Expressing the *Bacillus subtilis* Acetolactate Synthase," *Metab. Eng.* 1(1):26-34 (1999).

Yang et al., "Nucleotide sequence of the fadA gene. Primary structure of 3-ketoacyl-Coenzyme A thiolase from *Escherichia coli* and the structural organization of the fadAB operon," *J. Biol. Chem.* 265(18):10424-10429 (1990).

Yang et al., "Nucleotide sequence of the fadA gene. Primary structure of 3-ketoacyl-Coenzyme A thiolase from *Escherichia coli* and the structural organization of the fadAB operon," *J. Biol. Chem.* 266(24):16255 (1991).

Yang et al., "Nucleotide sequence of the promoter and fadB gene of the fadBA operon and primary structure of the multifunctional fatty acid oxidation protein from *Escherichia coli*," *Biochem.* 30(27):6788-6795 (1991).

Yang et al., "Redistribution of Metabolic Fluxes in *Escherichia coli* with Fermentative Lactate Dehydrogenase Overexpression and Deletion," *Metab. Eng.* 1:141-152 (1999).

Yang et al., "The effects of feed and intracellular pyruvate levels on the redistribution of metabolic fluxes in *Escherichia coli*," *Metab Eng.* 3(2):115-123 (2001).

Yang, "Location of the fadBA operon on the physical map of *Escherichia coli*," *J. Bacteriol.* 173(23):7405-7406 (1991).

Yanisch-Perron et al., "Improved M13 phage cloning vectors and host strains: nucleotide sequences of the M13mp18 and pUC19 vectors," *Gene* 33:103-119 (1985).

Yano et al., "Directed evolution of an aspartate aminotransferase with new substrate specificities," *Proc. Natl. Acad. Sci U.S.A.* 95:5511-5515 (1998).

Yarlett et al., "*Trichomonas vaginalis*: characterization of ornithine decarboxylase," *Biochem. J.* 293(Pt2):487-493 (1993).

Yeh and Ornston, Evolutionarily Homologous $\alpha_2$ $\beta_2$ Oligomeric Structures in β-Ketoadipate Succinyl-CoA Transferases from *Acinetobacter calcoaceticus* and *Pseudomonas putida*, *J. Biol. Chem.* 256(4):1565-1569 (1981).

Ylianttila et al., "Crystal Structure of Yeast Peroxisomal Multifunctional Enzyme:.Structural BaSis for Substrate Specificity of (3R)-hydroxyacyl-CoA Dehydrogenase Units," *J. Mol. Biol.* 258:1286-1295 (2006).

Ylianttila et al., "Site-directed mutagenesis to enable and improve crystallizability of candida tropicalis (3R)-hydroxyacyl-CoA dehydrogenase," *Biochem. Biophys. Res. Commun.* 324:25-30 (2004).

Yoshida et al., "The Structures of L-Rhamnose Isomerase from *Pseudomonas stutzeri* in Complexes with L-Rhamnose and D-Allose Provide Insights into Broad Substrate Specificity," *J. Mol. Biol.* 365:1505-1516 (2007).

Yoshimoto, et al., "Isolation and Characterization of the *ATF2* Gene Encoding Alcohol Acetyltransferase II in the Bottom Fermenting Yeast *Saccharomyces pastorianus*," *Yeast* 15:409-417 (1999).

Yoshioka and Hashimoto, "Ester formation by Alcohol Acetyltransferase from Brewer's Yeast," *Agric. Biol. Chem.* 45: 2183-2190 (1981).

Youngleson et al., "Homology between hydroxybutyryl and hydroxyacyl Coenzyme A dehydrogenase enzymes from *Clostridium acetobutylicum* fermentation and vertebrate fatty acid β-oxidation pathways," *J. Bacteriol.* 171(12):6800-6807 (1989).

Yun et al., "The genes for anabolic 2-oxoglutarate: ferredoxin oxidoreductse from hydrogenobacter thermophilus TK-6," *Biochem. Biophys. Res. Commun.* 282(2):589-594 (2001).

Yun et al., "ω-Amino acid:pyruvate transaminase from Alcaligenes denitrificans Y2k-2: a new catalyst for kinetic resolution of β-amino acids and amines," *Appl. Environ. Microbiol.* 70(4):2529-2534 (2004).

Yun et al., "Enhancement of lactate and succinate formation in adhE or pta-ackA mutants of NADH dehydrogenase-deficient *Escherichia coli*," *J. Appl. Microbiol.* 99(6):1404-1412 (2005).

Zeiher and Randall, "Identification and characterization of Mitochondrial Acetyl-Coenzyme A Hydrolase from *Pisum sativum* L. Seedlings," *Plant. Physiol.* 94:20-27 (1990).

Zeikus et al., "Biotechnology of succinic acid production and markets for derived industrial products," *Appl. Microbiol. Biotechnol.* 51: 545-552 (1999).

Zelle et al., "Malic acid production by *Saccharomyces cerevisiae*: engineering of pyruvate carboxylation, oxaloacetate reduction, and malate export," *Appl. Environ. Microbiol.* 74(9):2766-2777 (2008).

Zerbe-Burkhardt et al., "Cloning, sequencing, expression, and insertional inactivation of the gene for the large subunit of the Coenzyme $B_{12}$-dependent isobutyryl-CoA mutase from *Streptomyces cinnamonensis*," *J. Biol. Chem.* 273(11):6508-6517 (1998).

Zhang et al., "2-Oxoacid:Ferredoxin Oxidoreductase from the Thermoacidophilic archaeon, sulfolobus sp. Strain 7," *J. Biochem.* 120:587-599 (1996).

Zhang et al., "A new logic for DNA engineering using recombination in *Escherichia coli*," *Nat. Genet.* 20:123-128 (1998).

Zhang et al., "Directed evolution of a fucosidase from a galactosidase by DNA shuffling and screening," *Proc. Natl. Acad. Sci. U.S.A.* 94(9):4504-4509 (1997).

Zhang et al., "Functional characterization of the first two actinomycete 4-amino-4-deoxychorismate lyase genes," *Microbiology* 155:2450-2459 (2009).

Zhang et al., "Genes encoding acyl-CoA dehydrogenase (AcdH) homologues from *Streptomyces coelicolor* and *Streptomyces avermitilis* provide insights into the metabolism of small branched-chain fayy acids and marcrolide antibiotic production," *Microbiol.* 145 (Pt 9):2323-2334 (1999).

Zhang et al., "Isolation and properties of a levo-lactonase from *Fusarium proliferatum* ECU2002: a robust biocatalyst for production of chiral lactones," *Appl. Microbiol. Biotechnol.* 75:1087-1094 (2007).

Zhang et al., "Molecular basis for the inhibition of the carboxyltransferase domain of acetyl-Coenzyme-A carboxylase by haloxfop and dicofop," *Proc. Natl. Acad. Sci. U.S.A.* 101:5910-5915 (2004).

Zhao and Winkler, "A novel α-ketoglutarate reductase activity of the serA-encoded 3-phosphoglycerate dehydrogenase of *Escherichia coli* K-12 and its possible implications for human 2-hydroxyglutaric aciduria," *J. Bacteriol.* 178(1):232-239 (1996).

Zhao et al., "Molecular evolution by staggered extension process (StEP) in vitro recombination," *Nat. Biotechnol.* 16:258-261 (1998).

Zhou et al., "Comparison of fumaric acid production by *Rhizopus oryzae* using different neutralizing agents," *Bioproc. Biosyst. Eng.* 25(3):179-181 (2002).

Zhou et al., "Engineering a native homoethanol pathway in *Escherichia coli* B for ethanol production," *Biotechnol. Lett.* 30:335-342 (2008).

Zhou et al., "Mycelial pellet formation by *Rhizopus oryzae* ATCC 20344," *Appl. Biochem. Biotechnol.* 84-86:779-789 (2000).

Zhou et al., "The remarkable structural and functional organization of the eukaryotic pyruvate dehydrogenase complexes," *Proc. Natl. Acad. Sci. U.S.A.* 98:14802-14807 (2001).

Zhou et al., "Isolation, crystallization and preliminary X-ray analysis of a methanol-induced corrinoid protein from *Moorella thermoacetica*," *Acta. Crystallogr. Sect. F. Struct. Biol. Cryst. Commun.* 61(Pt 5):537-540 (2005).

Zhu and Sadowski, "Cleavage-dependent ligation by the FLP recombinase. Characterization of a mutant FLP protein with an alteration in a catalytic amino acid," *J. Biol. Chem.* 270(39):23044-23054 (1995).

Zhuang et al., "The YbgC protein encoded by the ybgC gene of the tol-pal gene cluster of Haemophilus influenzae catalyzes acyl-Coenzyme A thioester hydrolysis," *FEBS Lett.* 516(1-3):161-163 (2002).

(56) References Cited

OTHER PUBLICATIONS

Zou et al., "Metabolic engineering for microbial production and applications of copolyesters consisting of 3-hydroxybutyrate and medium-chain-length 3-hydroxyalkanoates," *Macromol. Biosci.* 7:174-182 (2007).

One page from URL: 1.eee.energy.gov/biomass/information_resources.html (printed Apr. 19, 2010).

One page from URL: expressys.de/ (Printed Dec. 21, 2009).

Two pages from URL: toxnet.nlm.nih.gov/cgi-bin/sis/search/f?./temp/~FwAsma:1:BASIC (printed Feb. 17, 2010).

Two pages from URL: web.archive.org/web/20080302001450/http://www.verenium.com/Pages/Technology/EnzymeTech/TechEnzyTGR.html (printed Apr. 12, 2010).

Gene Bridges, "Quick & Easy BAC Modification Kit by Red®/ET® Recombination," Technical Protocol, Cat. No. K001, Version 2.6 (2007).

Ferreira-Torres et al., "Microscale process evaluation of recombinant biocatalyst libraries: application to Baeyer-Villiger monooxygenase catalysed lactone synthesis," *Bioprocess Biosyst. Eng.* 28(2):83-93 (2005).

Locher et al., "Crystal structure of the Acidaminococcus fermentans 2-hydroxyglutaryl-CoA dehydratase component A," *J. Mol. Biol.* 307(1):297-308 (2001).

Niu et al., "Benzene-free synthesis of adipic acid," *Biotechnol. Prog.* 18:201-211 (2002).

Reed et al., "An expanded genome-scale model of *Escherichia coli* K-12 (iJR904 GSM/GPR)," *Genome. Biol.* 4(9):R54 (2003).

Asaoka et al., "Production of 1,4-butancdiol from bacillus which is fermented on sugar substrate, from which production is recovered," *Chiyoda Chem. Eng. Constr. Co.* (Official Publication Date 1987). Database WPI Week Apr. 1988 Thomson Scientific, London, GB; AN 1988-025175.

Biomass Program: Information Resources [online], Aug. 2007 [retrieved on Apr. 19, 2010]. Retrieved from the Internet: <URL: http://www1.eere.energy.gov/biomass/information_resources.html>.

ESPRESSYS—Tools for Gene Expression: Welcome to EXPRESSYS [online], Oct. 2009 [retrieved on Dec. 21, 2009]. Retrieved from the Internet: <URL: http://www.expressys.de/>.

Acrylic Acid (CASRN: 79-10-7) Human Health Effects [online], [retrieved on Feb. 17, 2010]. Retrieved from the Internet: <URL: http://www.toxnet.nlm.nih.gov/cgi-bin/sis/search/f?./temp/~FwAsma:1:BASIC>.

Tunable Genereassembly™ (TGR™) Technology [online], [retrieved on Apr. 12, 2010]. Retrieved from the Internet: <URL: http://web.archive.org/web/20080302001450/http://www.verenium.com/Pages/Technology/EnzymeTech/TechEnzyTGR.html>.

\* cited by examiner

MICROORGANISMS AND METHODS FOR THE CO-PRODUCTION OF ISOPROPANOL AND 1,4-BUTANEDIOL

This application claims the benefit of priority to U.S. provisional patent application Ser. No. 61/240,959, filed Sep. 9, 2009 and U.S. provisional application Ser. No. 61/254,650, filed Oct. 23, 2009, which are herein incorporated by reference in their entirety.

BACKGROUND OF THE INVENTION

The present invention relates generally to biosynthetic processes, and more specifically to organisms having n-propanol and isopropanol, 1,4-butanediol and isopropanol, 1,3-butanediol and isopropanol or methylacrylic and isopropanol biosynthetic capability.

Isopropanol (IPA) is a colorless, flammable liquid that mixes completely with most solvents, including water. The largest use for IPA is as a solvent, including its well known yet small use as "rubbing alcohol," which is a mixture of IPA and water. As a solvent, IPA is found in many everyday products such as paints, lacquers, thinners, inks, adhesives, general-purpose cleaners, disinfectants, cosmetics, toiletries, de-icers, and pharmaceuticals. Low-grade IPA is also used in motor oils. The second largest use is as a chemical intermediate for the production of isopropylamines, isopropylethers, and isopropyl esters. Isopropanol can potentially be dehydrated to form propylene, a polymer precursor with an annual market of more than 2 million metric tons.

Current global production capacity of isopropanol (IPA) is approximately 6 B lb/yr, with approximately 74% of global IPA capacity concentrated in the US, Europe, and Japan. Isopropanol is manufactured by two petrochemical routes. The predominant process entails the hydration of propylene either with or without sulfuric acid catalysis. Secondarily, IPA is produced via hydrogenation of acetone, which is a by-product formed in the production of phenol and propylene oxide. High-priced propylene is currently driving costs up and margins down throughout the chemical industry motivating the need for an expanded range of low cost feedstocks.

n-Propanol can be potentially used as a gasoline substitute. It is currently used as a multi-purpose solvent in the pharmaceutical industry, for surface coatings and in ink formulations. It is used as a building block for resins and esters, propyl amines and halides. It is also used for packaging and food contact applications. Global production of n-propanol in 2005 was more than 140,000 metric tonnes.

n-Propanol is manufactured by the catalytic hydrogenation of propionaldehyde. Propionaldehyde is itself produced via the oxo process, by hydroformylation of ethylene using carbon monoxide and hydrogen in the presence of a catalyst such as cobalt octacarbonyl or a rhodium complex. It is formed naturally in small amounts in many fermentation processes. For example, microbial production of very small quantities of n-propanol has been detected from certain species of *Clostridium* via threonine catabolism and from yeast in beer fermentation. No existing microorganism has been reported to produce 1-propanol from sugars in significant amounts.

1,4-Butanediol (14-BDO) is a polymer intermediate and industrial solvent with a global market of about 3 billion lb/year. BDO is currently produced from petrochemical precursors, primarily acetylene, maleic anhydride, and propylene oxide. For example, acetylene is reacted with 2 molecules of formaldehyde in the Reppe synthesis reaction (Kroschwitz and Grant, *Encyclopedia of Chem. Tech.*, John Wiley and Sons, Inc., New York (1999)), followed by catalytic hydrogenation to form 1,4-butanediol. Downstream, 14-BDO can be further transformed; for example, by oxidation to gamma-butyrolactone, which can be further converted to pyrrolidone and N-methyl-pyrrolidone, or hydrogenolysis to tetrahydrofuran. These compounds have varied uses as polymer intermediates, solvents, and additives, and have a combined market of nearly 2 billion lb/year. 1,3-Butanediol (13-BDO) is a four carbon diol commonly used as an organic solvent for food flavoring agents. It is also used as a co-monomer for polyurethane and polyester resins and is widely employed as a hypoglycaemic agent. Optically active 13-BDO is a useful starting material for the synthesis of biologically active compounds and liquid crystals. A substantial commercial use of 1,3-butanediol is subsequent dehydration to afford 1,3-butadiene (Ichikawa, *J. Mol. Catalysis.* 256:106-112 (2006)), a 25 billion lb/yr petrochemical used to manufacture synthetic rubbers (e.g., tires), latex, and resins. 13-BDO is traditionally produced from acetylene via its hydration. The resulting acetaldehyde is then converted to 3-hydroxybutyraldehdye which is subsequently reduced to form 1,3-BDO. In more recent years, acetylene has been replaced by ethylene as a source of acetaldehyde.

Methylacrylic acid (MAA) is a key precursor of methyl methacrylate (MMA), a chemical intermediate with a global demand in excess of 4.5 billion pounds per year, much of which is converted to polyacrylates. The conventional process for synthesizing methyl methacrylate (i.e., the acetone cyanohydrin route) involves the conversion of hydrogen cyanide (HCN) and acetone to acetone cyanohydrin which then undergoes acid assisted hydrolysis and esterification with methanol to give MAA. Difficulties in handling potentially deadly HCN along with the high costs of byproduct disposal (1.2 tons of ammonium bisulfate are formed per ton of MAA) have sparked a great deal of research aimed at cleaner and more economical processes. As a starting material, MAA can easily be converted into MAA via esterification with methanol. No existing microorganism has been reported to produce MAA from sugars in significant amounts.

Microbial organisms and methods for effectively co-producing commercial quantities of n-propanol and isopropanol, 14-BDO and isopropanol, 13-BDO and isopropanol or MAA and isopropanol are described herein and include related advantages.

SUMMARY OF THE INVENTION

The invention provides non-naturally occurring microbial organisms having an n-propanol pathway and an isopropanol pathway. In one aspect, the embodiments disclosed herein relate to a non-naturally occurring microbial organism that includes a microbial organism having an n-propanol and an isopropanol pathway, where the n-propanol pathway includes at least one exogenous nucleic acid encoding an n-propanol pathway enzyme expressed in a sufficient amount to produce n-propanol and where the isopropanol pathway includes at least one exogenous nucleic acid encoding an isopropanol pathway enzyme expressed in a sufficient amount to produce isopropanol. In one aspect, the n-propanol pathway includes a propionaldehyde dehydrogenase, a propanol dehydrogenase, a propionyl-CoA:phosphate propanoyltransferase, a propionyl-CoA hydrolase, a propionyl-CoA transferase, a propionyl-CoA synthetase, a propionate kinase, a propionate reductase or a propionyl phosphate reductase and the isopropanol pathway includes an acetyl-CoA acetyl thiolase, an acetoacetyl-CoA transferase, an acetoacetyl-CoA hydrolase, an acetoacetyl-CoA synthetase, an acetoacetyl-CoA synthetase, an acetoacetate decarboxylase or an isopropanol dehydrogenase.

In another embodiment, the invention provides a non-naturally occurring microbial organism that includes a microbial organism having an n-propanol and an isopropanol pathway, where the n-propanol pathway includes a first set of exogenous nucleic acids encoding n-propanol pathway enzymes expressed in a sufficient amount to produce n-propanol and where the isopropanol pathway includes a second set of exogenous nucleic acids encoding isopropanol pathway enzymes expressed in a sufficient amount to produce isopropanol. In one aspect, the first set encodes n-propanol pathway enzymes including a propionaldehyde dehydrogenase and a propanol dehydrogenase; or a propionyl-CoA:phosphate propanoyltransferase, a propionyl phosphate reductase and a propanol dehydrogenase; or a propionyl-CoA hydrolase or a propionyl-CoA transferase or a propionyl-CoA synthetase, a propionate kinase, a propionyl phosphate reductase and a propanol dehydrogenase; or a propionyl-CoA hydrolase or a propionyl-CoA transferase or a propionyl-CoA synthetase, a propionate reductase and a propanol dehydrogenase. In another aspect, the second set encodes isopropanol pathway enzymes including an acetyl-CoA acetyl thiolase; an acetoacetyl-CoA transferase, an acetoacetyl-CoA hydrolase, an acetoacetyl-CoA synthetase or an acetoacetyl-CoA synthetase; an acetoacetate decarboxylase; and an isopropanol dehydrogenase.

In another aspect, the invention provides a non-naturally occurring microbial organism having a first set of exogenous nucleic acids encoding n-propanol pathway enzymes and a second set of exogenous nucleic acids encoding isopropanol pathway enzymes, where the first set encodes a PEP carboxykinase or a PEP carboxylase; a malate dehydrogenase; a fumarase; a fumarate reductase; a succinyl-CoA transferase or a succinyl-CoA synthetase; a methylmalonyl-CoA mutase; a methylmalonyl-CoA decarboxylase; and a propionaldehyde dehydrogenase and a propanol dehydrogenase; or a propionyl-CoA:phosphate propanoyltransferase and a propionyl phosphate reductase; or a propionyl-CoA hydrolase or a propionyl-CoA transferase or a propionyl-CoA synthetase, a propionate kinase, a propionyl phosphate reductase and a propanol dehydrogenase; or a propionyl-CoA hydrolase or a propionyl-CoA transferase or a propionyl-CoA synthetase, a propionate reductase and a propanol dehydrogenase, and the second set encodes a pyruvate kinase; a pyruvate dehydrogenase or a pyruvate ferredoxin oxidoreductase; or a pyruvate formate lyase, a pyruvate formate lyase activating enzyme and a formate dehydrogenase; an acetyl-CoA acetyl thiolase; an acetoacetyl-CoA transferase or an acetoacetyl-CoA hydrolase or an acetoacetyl-CoA synthetase, an acetoacetate decarboxylase; and an isopropanol dehydrogenase.

In another aspect, the invention provides a non-naturally occurring microbial organism having a first set of exogenous nucleic acids encoding n-propanol pathway enzymes and a second set of exogenous nucleic acids encoding isopropanol pathway enzymes, where the first set encodes a PEP carboxykinase or a PEP carboxylase; a threonine deaminase; and a 2-oxobutanoate decarboxylase and a propanol dehydrogenase; or a 2-oxobutanoate dehydrogenase, a propionaldehyde dehydrogenase and a propanol dehydrogenase; or a 2-oxobutanoate dehydrogenase, a propionyl-CoA:phosphate propanoyltransferase, a propionyl phosphate reductase and a propanol dehydrogenase; or a 2-oxobutanoate dehydrogenase, a propionyl-CoA hydrolase or a propionyl-CoA transferase or a propionyl-CoA synthetase, a propionate kinase, a propionyl phosphate reductase and a propanol dehydrogenase; or a 2-oxobutanoate dehydrogenase, a propionyl-CoA hydrolase or a propionyl-CoA transferase or a propionyl-CoA synthetase, a propionate reductase and a propanol dehydrogenase, and the second set encodes a pyruvate kinase; a pyruvate dehydrogenase or a pyruvate ferredoxin oxidoreductase; or a pyruvate formate lyase, a pyruvate formate lyase activating enzyme and a formate dehydrogenase; an acetyl-CoA acetyl thiolase; an acetoacetyl-CoA transferase or an acetoacetyl-CoA hydrolase or an acetoacetyl-CoA synthetase, an acetoacetate decarboxylase; and an isopropanol dehydrogenase.

In another aspect, the invention provides a non-naturally occurring microbial organism having a first set of exogenous nucleic acids encoding n-propanol pathway enzymes and a second set of exogenous nucleic acids encoding isopropanol pathway enzymes, where the first set encodes a pyruvate kinase; a pyruvate dehydrogenase or a pyruvate ferredoxin oxidoreductase; or a pyruvate formate lyase, a pyruvate formate lyase activating enzyme and a formate dehydrogenase; an acetyl-CoA carboxylase; a malonyl-CoA reductase; a malonate semialdehyde reductase; propionyl-CoA synthase; and a propionaldehyde dehydrogenase and a propanol dehydrogenase; or a propionyl-CoA:phosphate propanoyltransferase, a propionyl phosphate reductase and propanol dehydrogenase; or a propionyl-CoA hydrolase or a propionyl-CoA transferase or a propionyl-CoA synthetase, a propionate kinase, a propionyl phosphate reductase and a propanol dehydrogenase; or a propionyl-CoA hydrolase or a propionyl-CoA transferase or a propionyl-CoA synthetase, a propionate reductase and a propanol dehydrogenase and the second set encodes an acetyl-CoA acetyl thiolase; an acetoacetyl-CoA transferase or an acetoacetyl-CoA hydrolase or an acetoacetyl-CoA synthetase, an acetoacetate decarboxylase; and an isopropanol dehydrogenase.

In another aspect, the invention provides a non-naturally occurring microbial organism having a first set of exogenous nucleic acids encoding n-propanol pathway enzymes and a second set of exogenous nucleic acids encoding isopropanol pathway enzymes, where the first set encodes a lactate dehydrogenase; a lactate-CoA transferase; a lactyl-CoA dehydratase; acryloyl CoA reductase; and a propionaldehyde dehydrogenase and a propanol dehydrogenase; or a propionyl-CoA:phosphate propanoyltransferase, a propionyl phosphate reductase and a propanol dehydrogenase; or a propionyl-CoA hydrolase or a propionyl-CoA transferase or a propionyl-CoA synthetase, a propionate kinase, a propionyl phosphate reductase and a propanol dehydrogenase; or a propionyl-CoA hydrolase or a propionyl-CoA transferase or a propionyl-CoA synthetase, a propionate reductase and a propanol dehydrogenase and the second set encodes a pyruvate dehydrogenase or a pyruvate ferredoxin oxidoreductase; or a pyruvate formate lyase, a pyruvate formate lyase activating enzyme and a formate dehydrogenase; an acetyl-CoA acetyl thiolase; an acetoacetyl-CoA transferase or an acetoacetyl-CoA hydrolase or an acetoacetyl-CoA synthetase, an acetoacetate decarboxylase; and an isopropanol dehydrogenase.

In another embodiment, the invention provides a non-naturally occurring microbial organism having an n-propanol pathway, the n-propanol pathway including at least one exogenous nucleic acid encoding an n-propanol pathway enzyme expressed in a sufficient amount to produce n-propanol. In one aspect the n-propanol pathway includes a propionaldehyde dehydrogenase, a propanol dehydrogenase, a propionyl-CoA:phosphate propanoyltransferase, a propionyl-CoA hydrolase, a propionyl-CoA transferase, a propionyl-CoA synthetase, a propionate kinase, a propionate reductase or a propionyl phosphate reductase.

In another embodiment, the invention provides a non-naturally occurring microbial organism having an n-propanol pathway, the n-propanol pathway including a set of exogenous nucleic acids encoding n-propanol pathway enzymes expressed in a sufficient amount to produce n-propanol, the set of exogenous nucleic acids encoding a propionaldehyde dehydrogenase and a propanol dehydrogenase; or a propionyl-CoA:phosphate propanoyltransferase, a propionyl phosphate reductase and a propanol dehydrogenase; or a propionyl-CoA hydrolase or a propionyl-CoA transferase or a propionyl-CoA synthetase, a propionate kinase, a propionyl phosphate reductase and a propanol dehydrogenase; or a propionyl-CoA hydrolase or a propionyl-CoA transferase or a propionyl-CoA synthetase, a propionate reductase and a propanol dehydrogenase.

In still other aspects, embodiments disclosed herein relate to a method for producing n-propanol and isopropanol that includes culturing the aforementioned non-naturally occurring microbial organisms. In still other aspect, embodiments disclosed herein relate to a method for producing n-propanol that includes culturing the aforementioned non-naturally occurring micribial organisms.

In one embodiment, the invention provides non-naturally occurring microbial organisms having an isopropanol pathway and a 1,4-butanediol (14-BDO) pathway, a 1,3-butanediol (13-BDO) pathway or a methylacrylic acid (MAA) pathway. In one aspect, the embodiments disclosed herein relate to a non-naturally occurring microbial organism that includes a microbial organism having a 1,4-butanediol and an isopropanol pathway, where the 1,4-butanediol pathway includes at least one exogenous nucleic acid encoding a 1,4-butanediol pathway enzyme expressed in a sufficient amount to produce 1,4-butanediol and where the isopropanol pathway includes at least one exogenous nucleic acid encoding an isopropanol pathway enzyme expressed in a sufficient amount to produce isopropanol. In one aspect, the embodiments disclosed herein relate to a non-naturally occurring microbial organism that includes a microbial organism having a 1,3-butanediol and an isopropanol pathway, where the 1,3-butanediol pathway includes at least one exogenous nucleic acid encoding a 1,3-butanediol pathway enzyme expressed in a sufficient amount to produce 1,3-butanediol and where the isopropanol pathway includes at least one exogenous nucleic acid encoding an isopropanol pathway enzyme expressed in a sufficient amount to produce isopropanol. In one aspect, the embodiments disclosed herein relate to a non-naturally occurring microbial organism that includes a microbial organism having a methylacrylic acid and an isopropanol pathway, where the methylacrylic acid pathway includes at least one exogenous nucleic acid encoding a methylacrylic acid pathway enzyme expressed in a sufficient amount to produce methylacrylic acid and where the isopropanol pathway includes at least one exogenous nucleic acid encoding an isopropanol pathway enzyme expressed in a sufficient amount to produce isopropanol.

In one embodiment, the isopropanol pathway comprises an acetyl-CoA acetyl thiolase, an acetoacetyl-CoA transferase, an acetoacetyl-CoA hydrolase, an acetoacetyl-CoA synthetase, an acetoacetate decarboxylase or an isopropanol dehydrogenase.

In one embodiment, the 14-BDO pathway comprises a succinyl-CoA reductase, a succinate reductase, a 4-hydroxybutyrate dehydrogenase, a 4-hydroxybutyryl-CoA transferase, a 4-hydroxybutyryl-CoA synthetase, a 4-hydroxybutyryl-CoA reductase (aldehyde-forming), a 4-hydroxybutyraldehyde reductase, a 4-hydroxybutyrate reductase; a 4-hydroxybutyrate kinase, a phosphotrans-4-hydroxybutyrylase, 4-hydroxybutyryl-phosphate reductase, or a 4-hydroxybutyryl-CoA reductase (alcohol-forming).

In one embodiment, the 13-BDO pathway comprises a succinyl-CoA reductase, a succinate reductase, a 4-hydroxybutyrate dehydrogenase, a 4-hydroxybutyryl-CoA transferase, a 4-hydroxybutyryl-CoA synthetase, a 4-hydroxybutyrate kinase, a phosphotrans-4-hydroxybutyrylase, a 4-hydroxybutyryl-CoA dehydratase, a crotonase, a 3-hydroxybutyryl-CoA reductase (aldehyde forming), a 3-hydroxybutyraldehyde reductase, a 3-hydroxybutyryl-CoA reductase (alcohol-forming), a 3-hydroxybutyryl-CoA transferase, a 3-hydroxybutyryl-CoA synthetase, a 3-hydroxybutyryl-CoA hydrolase, or a 3-hydroxybutyrate reductase.

In one embodiment, the MAA pathway comprises a succinyl-CoA reductase, a succinate reductase, a 4-hydroxybutyrate dehydrogenase, a 4-hydroxybutyryl-CoA transferase, a 4-hydroxybutyryl-CoA synthetase, a 4-hydroxybutyrate kinase, a phosphotrans-4-hydroxybutyrylase, a 4-hydroxybutyryl-CoA mutase, a 3-hydroxyisobutyryl-CoA dehydratase, a methacrylyl-CoA transferase, a methacrylyl-CoA synthetase, a methacrylyl-CoA hydrolase, a 3-hydroxyisobutyryl-CoA transferase, a 3-hydroxyisobutyryl-CoA synthetase, a 3-hydroxyisobutyryl-CoA hydrolase, a 3-hydroxyisobutyrate dehydratase, a methylmalonyl-CoA mutase, a methylmalonyl-CoA transferase, a methylmalonyl-CoA synthetase, a methylmalonyl-CoA hydrolase, a methylmalonate reductase, a methylmalonyl-CoA reductase (aldehyde forming), a 3-hydroxyisobutyrate dehydrogenase, a methylmalonyl-CoA reductase (alcohol forming) or a 3-hydroxyisobutyrate dehydratase.

In one embodiment, the invention provides a non-naturally occurring microbial organism that includes a microbial organism having an 14-BDO and an isopropanol pathway, where the 14-BDO pathway includes a first set of exogenous nucleic acids encoding 14-BDO pathway enzymes expressed in a sufficient amount to produce 14-BDO and where the isopropanol pathway includes a second set of exogenous nucleic acids encoding isopropanol pathway enzymes expressed in a sufficient amount to produce isopropanol.

In one embodiment, the invention provides a non-naturally occurring microbial organism that includes a microbial organism having an 13-BDO and an isopropanol pathway, where the 13-BDO pathway includes a first set of exogenous nucleic acids encoding 13-BDO pathway enzymes expressed in a sufficient amount to produce 13-BDO and where the isopropanol pathway includes a second set of exogenous nucleic acids encoding isopropanol pathway enzymes expressed in a sufficient amount to produce isopropanol.

In one embodiment, the invention provides a non-naturally occurring microbial organism that includes a microbial organism having an methylacrylic acid and an isopropanol pathway, where the methylacrylic acid pathway includes a first set of exogenous nucleic acids encoding methylacrylic acid pathway enzymes expressed in a sufficient amount to produce methylacrylic acid and where the isopropanol pathway includes a second set of exogenous nucleic acids encoding isopropanol pathway enzymes expressed in a sufficient amount to produce isopropanol.

It is understood that methylacrylic acid pathways passing through a 3-hydroxyisobutyrate intermediate can be applied for 3-hydroxyisobutyrate production as opposed to methylacrylic acid production if the downstream enzyme, that is, a dehydratase, is omitted (see FIGS. 7 and 8). In this case, the non-naturally occurring organism would produce 3-hydroxyisobutyrate instead of methylacrylic acid. The non-naturally occurring organism could alternatively produce a mixture of 3-hydroxyisobutyate and methylacrylic acid. The maximum molar yields of ATP and product will be unchanged regardless of whether methylacrylic acid or 3-hydroxyisobutyrate is produced.

It is further understood that, if desired, 3-hydroxyisobutyric acid expressed by a microbial organism of the invention can be chemically converted to methylacrylic acid. For example, 3-hydroxyisobutyric acid, or β-hydroxyisobutyric acid, can be dehydrated to form methylacrylic acid as described, for example, in U.S. Pat. No. 7,186,856.

In still other aspects, embodiments disclosed herein relate to a method for producing 14-BDO and isopropanol, 13-BDO and isopropanol or MAA and isopropanol that includes culturing the aforementioned non-naturally occurring microbial organisms.

DETAILED DESCRIPTION THE INVENTION

Figure 1:
FIG. 1 shows an exemplary pathway for co-production of n-propanol and isopropanol from glucose. Abbreviations: Glc—glucose, PEP—phosphoenolpyruvate, PYR—pyruvate, FOR—formate, ACCOA—acetyl-CoA, AACOA—acetoacetyl-CoA, ACAC—acetoacetate, AC—acetone, PPOH-2—isopropanol, OAA—oxaloacetate, MAL—malate, FUM—fumarate, SUCC—succinate, SUCCOA—succinyl-CoA, MMCOA—methylmalonyl-CoA, PPCOA—propionyl-CoA, PPA—propionate, PPAL—propionaldehyde, PPPi—propionyl phosphate, PPOH-1—n-propanol.

Embodiments of the present invention provide non-naturally occurring microbial organisms having redox-balanced anaerobic pathways for co-production of n-propanol and isopropanol from 3 phosphoenolpyruvate (PEP) molecules as exemplified in FIGS. 1-4. Some advantages of this co-production strategy include: (1) the co-production affords the maximum theoretical yield of n-propanol and isopropanol at 1.33 moles total/mole of glucose; and (2) the pathway for co-production is completely redox balanced and has a net positive yield of ATP. This facilitates a completely anaerobic production of the C3 alcohols as opposed to culturing microbial organisms having the isopropanol pathway alone, which requires aeration for regeneration of NAD.

Embodiments of the present invention also provide non-naturally occurring microbial organisms that can co-produce n-propanol and isopropanol from renewable resources as shown in FIGS. 1-4. Specifically, the organisms include all enzymes utilized in the co-production of n-propanol and isopropanol from acetyl-CoA and propionyl-CoA. Formate can be converted to carbon dioxide by a formate dehydrogenase that provides an additional reducing equivalent that can be used for n-propanol and isopropanol syntheses. Additionally, reducing equivalents can be obtained from other steps in the pathway, such as, the glycolysis pathway during conversion of glucose to phospheonolpyruvate, pyruvate dehydrogenase or pyruvate ferredoxin oxidoreductase during conversion of pyruvate to acetyl-CoA, or 2-oxobutanoate dehydrogenase during conversion of 2-oxobutanoate to propionyl-CoA.

Embodiments of the present invention also provide non-naturally occurring microbial organisms that can produce n-propanol via propionyl-CoA. This conversion is carried out by two different enzymes: an aldehyde and alcohol dehydrogenase or in one step by a bifunctional aldehyde/alcohol dehydrogenase. Alternatively, propionyl-CoA can be converted into propionyl phosphate and then transformed into propionaldehyde by an acyl phosphate reductase. Alternatively, propionyl-CoA can be converted to propionate then to propionyl phosphate by a propionyl-CoA hydrolase, transferase, or synthetase and a propionate dinase, respectively. Alternatively, propionate can be converted to propionaldehyde by a propionate reductase. Pathways for production of propionyl-CoA are exemplified in FIGS. 1-4. In one embodiment, the pathway for production of propionyl-CoA proceeds via oxaloacetate as exemplified in FIG. 1. Oxaloacetate is converted to propionyl-CoA by means of the reductive TCA cycle, a methylmutase, a decarboxylase, and a decarboxylase. An epimerase may be required to convert the (R) stereoisomer of methylmalonyl-CoA to the (S) configuration. In another embodiment, the pathway for production of propionyl-CoA proceeds via threonine as exemplified in FIG. 2. Oxaloacetate is converted into threonine by the native threonine pathway engineered for high yields. It is then deaminated to form 2-oxobutanoate and subsequently converted into propionyl-CoA. In one alternative, 2-oxobutanoate is converted to propionaldehyde by a decarboxylase, which is then reduced to n-propanol by a propanol dehydrogenase. In yet another embodiment, the pathway for production of propionyl-CoA proceeds via malonyl-CoA as exemplified in FIG. 3. Acetyl-CoA is carboxylated to form malonyl-CoA. This is then reduced to malonate semialdehyde, and subsequently transformed into 3-hydroxypropionate (3HP). 3HP is converted into propionyl-CoA via propionyl-CoA synthase. In yet another embodiment, the pathway for production of propionyl-CoA proceeds via lactate as exemplified in FIG. 4. Pyruvate is reduced to form lactate which is then activated to form lactoyl-CoA. The lactoyl-CoA is dehydrated to form acryloyl-CoA and then reduced to generate propionyl-CoA.

Embodiments of the present invention also provide non-naturally occurring microbial organisms that can produce isopropanol via acetyl-CoA. Isopropanol production is achieved via conversion of acetyl-CoA by an acetoacetyl-CoA thiolase, an acetoacetyl-CoA transferase or an acetoacetyl-CoA hydrolase or an acetoacetyl-CoA synthetase, an acetoacetate decarboxylase, and an isopropanol dehydrogenase as exemplified in FIGS. 1-4. In one embodiment the pathway for production of acetyl-CoA from glucose proceeds via phosphoenolpyruvate (PEP). Glucose is converted into PEP by the native glycolysis pathway of the microbial organism. PEP is converted to pyruvate by pyruvate kinase and then to acetyl-CoA by pyruvate dehydrogenase or pyruvate ferredoxin oxidoreductase. Alternatively, pyruvate is converted to acetyl-CoA and formate by pyruvate formate lyase. The formate is then converted to carbon dioxide and hydrogen by a formate dehydrogenase.

Embodiments of the present invention provide alternate methods for coproduction of isopropanol with the compounds 14-BDO, 13-BDO and MAA. The production of isopropanol proceeds via acetyl-CoA as described above. Alone this route is not redox-balanced and thus requires aeration to achieve high isopropanol yields. Embodiments described herein use this route and combine it with pathways for synthesizing the coproducts 1,4-butanediol (14-BDO), 1,3-butanediol (13-BDO) and methylacrylic acid (MAA). Coproduction routes are redox-balanced under anaerobic conditions as opposed to the requirement of oxygen if isopropanol is produced solely through acetone. Coproduction also provides related advantages, such as, the ease of separating isopropanol from other fermentation products due it its low boiling point (82° C.) relative to 14-BDO (230° C.), 13-BDO (203° C.) and MAA (163° C.) and the coproduction using any of the microbial organisms described herein provides that maximum theoretical yield of the carbon from glucose is afforded.

Embodiments of the present invention provide non-naturally occurring microbial organisms that can produce 14-BDO via succinyl-CoA or in some aspects via succinate. For production of 14-BDO, succinyl-CoA is converted to succinic semialdehyde by a succinyl-CoA reductase. Alternatively, succinate can be converted to succinic semialdehyde by a succinate reductase. Next, succinic semialdehyde is reduced to 4-hydroxybutyrate by 4-hydroxybutyrate dehydrogenase. Activation of 4-HB to its acyl-CoA is catalyzed by a CoA transferase or synthetase. Alternatively, 4-HB can be converted into 4-hydroxybutyryl-phosphate and subsequently transformed into 4-HB-CoA by a phosphotrans-4-hydroxybutyrylase. 4-HB-CoA is then converted to 14-BDO by either a bifunctional CoA-dependent aldehyde/alcohol dehydrogenase, or by two separate enzymes with aldehyde and alcohol dehydrogenase activity. Yet another alternative that bypasses the 4-HB-CoA intermediate is direct reduction of 4-HB to 4-hydroxybutyrylaldehyde by a carboxylic acid reductase. 4-Hydroxybutyrylaldehyde is subsequently reduced to 14-BDO by an alcohol dehydrogenase. Yet another route that bypasses 4-HB-CoA entails reducing 4-hydroxybutyryl-phosphate to 4-hydroxybutyraldehyde by a phosphate reductase.

Embodiments of the present invention provide non-naturally occurring microbial organisms that can produce 13-BDO via succinyl-CoA or in some aspects via succinate. Production of 13-BDO also proceeds through 4-hydroxybutyryl-CoA, formed as described above. In this route, 4-hydroxybutyryl-CoA is dehydrated and isomerized to form crotonyl-CoA. The dehydration and vinylisomerisation reactions are catalyzed by a bifunctional enzyme, 4-hydroxybutyryl-CoA dehydratase. Crotonyl-CoA is then hydrated to 3-hydroxybutyryl-CoA. Removal of the CoA moiety and concurrent reduction yields 3-hydroxybutyraldehyde. Alternatively, 3-hydroxybutyryl-CoA is converted to 3-hydroxybutyrate by a 3-hydroxybutyryl-CoA transferase, hydrolase, or synthetase and then reduced by a 3-hydroxybutyrate reductase to yield 3-hydroxybutyraldehyde. Finally reduction of the aldehyde by 3-hydroxybutyraldehyde reductase yields 13-BDO.

Embodiments of the present invention provide non-naturally occurring microbial organisms that can produce MAA via two alternative routes. The first route proceeds through 4-hydroxybutyryl-CoA, formed as described above. 4-Hydroxybutyryl-CoA is converted to 3-hydroxyisobutyryl-CoA by a methyl mutase. The CoA moiety of 3-Hydroxyisobutyryl-CoA is then removed by a CoA transferase, hydrolase or synthetase. Finally, dehydration of the 3-hydroxy group yields MAA. Alternatively, 3-hydroxyisobutyryl-CoA is converted to methyacrylyl-CoA by a 3-hydroxyisobutyryl-CoA dehydratase and then the CoA moiety is removed by a CoA transferase, hydrolase or synthetase to yield MAA. In the alternate MAA production route, succinyl-CoA is converted to methylmalonyl-CoA by methylmalonyl-CoA mutase. An epimerase may be required to convert the (R) stereoisomer of methylmalonyl-CoA to the (S) configuration. A CoA-dependent aldehyde dehydrogenase then converts methylmalonyl- CoA to methylmalonate semialdehyde. Alternatively, the CoA moiety of (R)-methylmalonyl-CoA or (S)-methylmalonyl-CoA is removed by a CoA transferase, hydrolase or synthetase to form methylmalonate, which is then converted to the semialdehyde by a reductase. Reduction of the aldehyde to 3-hydroxyisobutyrate, followed by dehydration, yields MAA. Alternately, methylmalonyl-CoA is converted to 3-hydroxyisobutyrate by an alcohol-forming CoA reductase.

Embodiments of the present invention provide non-naturally occurring microbial organisms having pathways for production of succinyl-CoA as exemplified in FIGS. 5-8. In one embodiment, the pathway for production of succinyl-CoA proceeds via oxaloacetate. Oxaloacetate is converted to succinyl-CoA by means of the reductive TCA cycle, including a malate dehydrogenase, a fumerase, a fumarate reductatase and a succinyl-CoA transferase or alternatively a succinyl-CoA synthetase.

Engineering these pathways into a microorganism involves cloning an appropriate set of genes encoding a set of enzymes into a production host described herein, optimizing fermentation conditions, and assaying product formation following fermentation. To engineer a production host for the production of n-propanol and isopropanol, 14-BDO and isopropanol, 13-BDO and isopropanol or MAA and isopropanol, one or more exogenous DNA sequence(s) can be expressed in a microorganism. In addition, the microorganism can have endogenous gene(s) functionally disrupted, deleted or overexpressed. The metabolic modifications disclosed herein enable the production of n-propanol and isopropanol, 14-BDO and isopropanol, 13-BDO and isopropanol or MAA and isopropanol using renewable feedstock.

In some embodiments, the invention provides non-naturally occurring microbial organisms that include at least one exogenous nucleic acid that encode an n-propanol pathway enzyme expressed in a sufficient amount to produce n-propanol.

In another embodiment, the invention provides non-naturally occurring microbial organisms that include at least one exogenous nucleic acid that encode an isopropanol pathway enzyme expressed in a sufficient amount to produce isopropanol.

In still other embodiments, the invention provides methods for co-producing n-propanol and isopropanol, 14-BDO and isopropanol, 13-BDO and isopropanol or MAA and isopropanol. Such methods involve culturing the microbial organisms described herein.

As used herein, the term "non-naturally occurring" when used in reference to a microbial organism or microorganism of the invention is intended to mean that the microbial organism has at least one genetic alteration not normally found in a naturally occurring strain of the referenced species, including wild-type strains of the referenced species. Genetic alterations include, for example, modifications introducing expressible nucleic acids encoding metabolic polypeptides, other nucleic acid additions, nucleic acid deletions and/or other functional disruption of the microbial organism's genetic material. Such modifications include, for example, coding regions and functional fragments thereof, for heterologous, homologous or both heterologous and homologous polypeptides for the referenced species. Additional modifications include, for example, non-coding regulatory regions in which the modifications alter expression of a gene or operon. Exemplary metabolic polypeptides include enzymes or proteins within an n-propanol, an isopropanol, a 14-BDO, a 13-BDO and/or MAA biosynthetic pathways.

A metabolic modification refers to a biochemical reaction that is altered from its naturally occurring state. Therefore, non-naturally occurring microorganisms can have genetic modifications to nucleic acids encoding metabolic polypeptides or, functional fragments thereof. Exemplary metabolic modifications are disclosed herein.

As used herein, the term "isolated" when used in reference to a microbial organism are intended to mean an organism that is substantially free of at least one component as the referenced microbial organism is found in nature. The term includes a microbial organism that is removed from some or all components as it is found in its natural environment. The term also includes a microbial organism that is removed from some or all components as the microbial organism is found in non-naturally occurring environments. Therefore, an isolated microbial organism is partly or completely separated from other substances as it is found in nature or as it is grown, stored or subsisted in non-naturally occurring environments. Specific examples of isolated microbial organisms include partially pure microbes, substantially pure microbes and microbes cultured in a medium that is non-naturally occurring.

As used herein, the terms "microbial," "microbial organism" or "microorganism" is intended to mean any organism that exists as a microscopic cell that is included within the domains of archaea, bacteria or eukarya. Therefore, the term is intended to encompass prokaryotic or eukaryotic cells or organisms having a microscopic size and includes bacteria, archaea and eubacteria of all species as well as eukaryotic microorganisms such as yeast and fungi. The term also includes cell cultures of any species that can be cultured for the production of a biochemical.

As used herein, "n-propanol" is intended to mean a primary alcohol with the molecular formula of $C_3H_8O$ and a molecular mass of 60.1 g/mol. N-propanol is also known in the art as 1-propanol, 1-propyl alcohol, n-propyl alcohol, propan-1-ol, or simply propanol. N-propanol is an isomer of isopropanol.

As used herein, "isopropanol" is intended to mean a secondary alcohol, with the molecular formula of $C_3H_8O$ and a molecular mass of 60.1 g/mol, wherein the alcohol carbon is attached to two other carbons. This attachment is sometimes shown as $(CH_3)_2CHOH$. Isopropanol is also known in the art as propan-2-ol, 2-propanol or the abbreviation IPA. Isopropanol is an isomer of n-propanol.

As used herein, the term "1,4-butanediol" is intended to mean an alcohol derivative of the alkane butane, carrying two hydroxyl groups which has the chemical formula $C_4H_{10}O_2$ and a molecular mass of 90.12 g/mol. The chemical compound 1,4-butanediol also is known in the art as 1,4-BDO and is a chemical intermediate or precursor for a family of compounds commonly referred to as the BDO family of compounds.

As used herein, the term "1,3-butanediol" is intended to mean one of four stable isomers of butanediol having the chemical formula $C_4H_{10}O_2$ and a molecular mass of 90.12 g/mol. The chemical compound 1,3-butanediol is known in the art as 13-BDO or β-butane glycol and is also a chemical intermediate or precursor for a family of compounds commonly referred to as the BDO family of compounds.

As used herein, "methylacrylic acid," having the chemical formula $CH_2=C(CH_3)CO_2$ (also known as methacrylic acid and IUPAC name 2-methyl-2-propenoic acid), is the acid form of methylacrylate, and it is understood that methylacrylic acid and methylacrylate can be used interchangebly throughout to refer to the compound in any of its neutral or ionized forms, including any salt forms thereof. It is understood by those skilled understand that the specific form will depend on the pH. Similarly, 3-hydroxyisobutyrate and 3-hydroxyisobutyric acid can be used interchangebly throughout to refer to the compound in any of its neutral or ionized forms, including any salt forms thereof.

As used herein, the term "CoA" or "coenzyme A" is intended to mean an organic cofactor or prosthetic group (nonprotein portion of an enzyme) whose presence is required for the activity of many enzymes (the apoenzyme) to form an active enzyme system. Coenzyme A functions in certain condensing enzymes, acts in acetyl or other acyl group transfer and in fatty acid synthesis and oxidation, pyruvate oxidation and in other acetylation.

As used herein, the term "substantially anaerobic" when used in reference to a culture or growth condition is intended to mean that the amount of oxygen is less than about 10% of saturation for dissolved oxygen in liquid media. The term also is intended to include sealed chambers of liquid or solid medium maintained with an atmosphere of less than about 1% oxygen.

"Exogenous" as it is used herein is intended to mean that the referenced molecule or the referenced activity is introduced into the host microbial organism. The molecule can be introduced, for example, by introduction of an encoding nucleic acid into the host genetic material such as by integration into a host chromosome or as non-chromosomal genetic material such as a plasmid. Therefore, the term as it is used in reference to expression of an encoding nucleic acid refers to introduction of the encoding nucleic acid in an expressible form into the microbial organism. When used in reference to a biosynthetic activity, the term refers to an activity that is introduced into the host reference organism. The source can be, for example, a homologous or heterologous encoding nucleic acid that expresses the referenced activity following introduction into the host microbial organism. Therefore, the term "endogenous" refers to a referenced molecule or activity that is present in the host. Similarly, the term when used in reference to expression of an encoding nucleic acid refers to expression of an encoding nucleic acid contained within the microbial organism. The term "heterologous" refers to a molecule or activity derived from a source other than the referenced species whereas "homologous" refers to a molecule or activity derived from the host microbial organism. Accordingly, exogenous expression of an encoding nucleic acid of the invention can utilize either or both a heterologous or homologous encoding nucleic acid.

The non-naturally occurring microbial organisms of the invention can contain stable genetic alterations, which refers to microorganisms that can be cultured for greater than five generations without loss of the alteration. Generally, stable genetic alterations include modifications that persist greater than 10 generations, particularly stable modifications will persist more than about 25 generations, and more particularly, stable genetic modifications will be greater than 50 generations, including indefinitely.

Those skilled in the art will understand that the genetic alterations, including metabolic modifications exemplified herein, are described with reference to a suitable host organism such as E. coli and their corresponding metabolic reactions or a suitable source organism for desired genetic material such as genes for a desired metabolic pathway. However, given the complete genome sequencing of a wide variety of organisms and the high level of skill in the area of genomics, those skilled in the art will readily be able to apply the teachings and guidance provided herein to essentially all other organisms. For example, the E. coli metabolic alterations exemplified herein can readily be applied to other species by incorporating the same or analogous encoding nucleic acid from species other than the referenced species. Such genetic alterations include, for example, genetic alterations of species homologs, in general, and in particular, orthologs, paralogs or nonorthologous gene displacements.

An ortholog is a gene or genes that are related by vertical descent and are responsible for substantially the same or identical functions in different organisms. For example, mouse epoxide hydrolase and human epoxide hydrolase can be considered orthologs for the biological function of hydrolysis of epoxides. Genes are related by vertical descent when, for example, they share sequence similarity of sufficient amount to indicate they are homologous, or related by evolution from a common ancestor. Genes can also be considered orthologs if they share three-dimensional structure but not necessarily sequence similarity, of a sufficient amount to indicate that they have evolved from a common ancestor to the extent that the primary sequence similarity is not identifiable. Genes that are orthologous can encode proteins with sequence similarity of about 25% to 100% amino acid sequence identity. Genes encoding proteins sharing an amino acid similarity less that 25% can also be considered to have arisen by vertical descent if their three-dimensional structure also shows similarities. Members of the serine protease family of enzymes, including tissue plasminogen activator and elastase, are considered to have arisen by vertical descent from a common ancestor.

Orthologs include genes or their encoded gene products that through, for example, evolution, have diverged in structure or overall activity. For example, where one species encodes a gene product exhibiting two functions and where such functions have been separated into distinct genes in a second species, the three genes and their corresponding products are considered to be orthologs. For the production of a biochemical product, those skilled in the art will understand that the orthologous gene harboring the metabolic activity to be introduced or disrupted is to be chosen for construction of the non-naturally occurring microorganism. An example of orthologs exhibiting separable activities is where distinct activities have been separated into distinct gene products between two or more species or within a single species. A specific example is the separation of elastase proteolysis and plasminogen proteolysis, two types of serine protease activity, into distinct molecules as plasminogen activator and elastase. A second example is the separation of mycoplasma 5'-3' exonuclease and Drosophila DNA polymerase III activity. The DNA polymerase from the first species can be considered an ortholog to either or both of the exonuclease or the polymerase from the second species and vice versa.

In contrast, paralogs are homologs related by, for example, duplication followed by evolutionary divergence and have similar or common, but not identical functions. Paralogs can originate or derive from, for example, the same species or from a different species. For example, microsomal epoxide hydrolase (epoxide hydrolase I) and soluble epoxide hydrolase (epoxide hydrolase II) can be considered paralogs because they represent two distinct enzymes, co-evolved from a common ancestor, that catalyze distinct reactions and have distinct functions in the same species. Paralogs are proteins from the same species with significant sequence similarity to each other suggesting that they are homologous, or related through co-evolution from a common ancestor. Groups of paralogous protein families include HipA homologs, luciferase genes, peptidases, and others.

A nonorthologous gene displacement is a nonorthologous gene from one species that can substitute for a referenced gene function in a different species. Substitution includes, for example, being able to perform substantially the same or a similar function in the species of origin compared to the referenced function in the different species. Although generally, a nonorthologous gene displacement will be identifiable as structurally related to a known gene encoding the referenced function, less structurally related but functionally similar genes and their corresponding gene products nevertheless will still fall within the meaning of the term as it is used herein. Functional similarity requires, for example, at least some structural similarity in the active site or binding region of a nonorthologous gene product compared to a gene encoding the function sought to be substituted. Therefore, a nonorthologous gene includes, for example, a paralog or an unrelated gene.

Therefore, in identifying and constructing the non-naturally occurring microbial organisms of the invention having n-propanol and isopropanol, 14-BDO and isopropanol, 13-BDO and isopropanol or MAA and isopropanol biosynthetic capability, those skilled in the art will understand with applying the teaching and guidance provided herein to a particular species that the identification of metabolic modifications can include identification and inclusion or inactivation of orthologs. To the extent that paralogs and/or non-orthologous gene displacements are present in the referenced microorganism that encode an enzyme catalyzing a similar or substantially similar metabolic reaction, those skilled in the art also can utilize these evolutionarily related genes.

Orthologs, paralogs and nonorthologous gene displacements can be determined by methods well known to those skilled in the art. For example, inspection of nucleic acid or amino acid sequences for two polypeptides will reveal sequence identity and similarities between the compared sequences. Based on such similarities, one skilled in the art can determine if the similarity is sufficiently high to indicate the proteins are related through evolution from a common ancestor. Algorithms well known to those skilled in the art, such as Align, BLAST, Clustal W and others compare and determine a raw sequence similarity or identity, and also determine the presence or significance of gaps in the sequence which can be assigned a weight or score. Such algorithms also are known in the art and are similarly applicable for determining nucleotide sequence similarity or identity. Parameters for sufficient similarity to determine relatedness are computed based on well known methods for calculating statistical similarity, or the chance of finding a similar match in a random polypeptide, and the significance of the match determined. A computer comparison of two or more sequences can, if desired, also be optimized visually by those skilled in the art. Related gene products or proteins can be expected to have a high similarity, for example, 25% to 100% sequence identity. Proteins that are unrelated can have an identity which is essentially the same as would be expected to occur by chance, if a database of sufficient size is scanned (about 5%). Sequences between 5% and 24% may or may not represent sufficient homology to conclude that the compared sequences are related. Additional statistical analysis to determine the significance of such matches given the size of the data set can be carried out to determine the relevance of these sequences.

Exemplary parameters for determining relatedness of two or more sequences using the BLAST algorithm, for example, can be as set forth below. Briefly, amino acid sequence alignments can be performed using BLASTP version 2.0.8 (Jan. 5, 1999) and the following parameters: Matrix: 0 BLOSUM62; gap open: 11; gap extension: 1; x_dropoff: 50; expect: 10.0; wordsize: 3; filter: on. Nucleic acid sequence alignments can be performed using BLASTN version 2.0.6 (Sep. 16, 1998) and the following parameters: Match: 1; mismatch: −2; gap open: 5; gap extension: 2; x_dropoff: 50; expect: 10.0; wordsize: 11; filter: off. Those skilled in the art will know what modifications can be made to the above parameters to either increase or decrease the stringency of the comparison, for example, and determine the relatedness of two or more sequences.

In one embodiment, the invention provides a non-naturally occurring microbial organism, including a microbial organism having an n-propanol pathway and an isopropanol pathway, the n-propanol pathway having at least one exogenous nucleic acid encoding an n-propanol pathway enzyme expressed in a sufficient amount to produce n-propanol, the n-propanol pathway including a propionaldehyde dehydrogenase, a propanol dehydrogenase, a propionyl-CoA:phosphate propanoyltransferase, a propionyl-CoA hydrolase, a propionyl-CoA transferase, a propionyl-CoA synthetase, a propionate kinase, a propionate reductase or a propionyl phosphate reductase, the isopropanol pathway comprising at least one exogenous nucleic acid encoding an isopropanol pathway enzyme expressed in a sufficient amount to produce isopropanol, the isopropanol pathway including an acetyl-CoA acetyl thiolase, an acetoacetyl-CoA transferase, an acetoacetyl-CoA hydrolase, an acetoacetyl-CoA synthetase, an acetoacetate decarboxylase or an isopropanol dehydrogenase.

In a further aspect of the above embodiment, the microbial organism has an acetyl-CoA pathway having at least one exogenous nucleic acid encoding an acetyl-CoA pathway enzyme expressed in a sufficient amount to produce acetyl-CoA, the acetyl-CoA pathway including a pyruvate kinase, a pyruvate dehydrogenase, a pyruvate ferredoxin oxidoreductase, a pyruvate formate lyase, a pyruvate formate lyase activating enzyme, or a formate dehydrogenase.

In further embodiment, the microbial organism has a propionyl-CoA pathway having at least one exogenous nucleic acid encoding a propionyl-CoA pathway enzyme expressed in a sufficient amount to produce propionyl-CoA, the propionyl-CoA pathway including a PEP carboxykinase, a PEP carboxylase, a malate dehydrogenase, a fumarase, a fumarate reductase, a succinyl-CoA transferase, a succinyl-CoA synthetase, a methylmalonyl-CoA mutase, a methylmalonyl-CoA epimerase or a methylmalonyl-CoA decarboxylase. In a further aspect, the propionyl-CoA pathway includes a pyruvate carboxylase or a methylmalonyl-CoA carboxytransferase.

In another further embodiment, the microbial organism has a propionyl-CoA pathway having at least one exogenous nucleic acid encoding a propionyl-CoA pathway enzyme expressed in a sufficient amount to produce propionyl-CoA, the propionyl-CoA pathway including a PEP carboxykinase, a PEP carboxylase, a threonine deaminase, or a 2-oxobutanoate dehydrogenase. In a further aspect, the n-propanol pathway includes 2-oxobutanoate decarboxylase.

In another further embodiment, the microbial organism has a propionyl-CoA pathway having at least one exogenous nucleic acid encoding a propionyl-CoA pathway enzyme expressed in a sufficient amount to produce propionyl-CoA, the propionyl-CoA pathway including an acetyl-CoA carboxylase, a malonyl-CoA reductase, a malonate semialdehyde reductase or propionyl-CoA synthase.

In another further embodiment, the microbial organism has a propionyl-CoA pathway having at least one exogenous nucleic acid encoding a propionyl-CoA pathway enzyme expressed in a sufficient amount to produce propionyl-CoA, the propionyl-CoA pathway including a lactate dehydrogenase, a lactate-CoA transferase, a lactyl-CoA dehydratase or acryloyl CoA reductase.

In yet another embodiment, the invention provides a non-naturally occurring microbial organism, including a microbial organism having an n-propanol pathway and an isopropanol pathway, the n-propanol pathway having a first set of exogenous nucleic acids encoding n-propanol pathway enzymes expressed in a sufficient amount to produce n-propanol, the first set of exogenous nucleic acids encoding a propionaldehyde dehydrogenase and a propanol dehydrogenase; or a propionyl-CoA:phosphate propanoyltransferase, a propionyl phosphate reductase and a propanol dehydrogenase; or a propionyl-CoA hydrolase or a propionyl-CoA transferase or a propionyl-CoA synthetase, a propionate kinase, a propionyl phosphate reductase and a propanol dehydrogenase; or a propionyl-CoA hydrolase or a propionyl-CoA transferase or a propionyl-CoA synthetase, a propionate reductase and a propanol dehydrogenase, and the isopropanol pathway having a second set of exogenous nucleic acids encoding isopropanol pathway enzymes expressed in a sufficient amount to produce isopropanol, the second set of exogenous nucleic acids encoding an acetyl-CoA acetyl thiolase; an acetoacetyl-CoA transferase or an acetoacetyl-CoA hydrolase or an acetoacetyl-CoA synthetase, an acetoacetate decarboxylase; and an isopropanol dehydrogenase.

In a further aspect of the above embodiment, the microbial organism has an acetyl-CoA pathway having a third set of exogenous nucleic acids encoding acetyl-CoA pathway enzymes expressed in a sufficient amount to produce acetyl-CoA, the third set of exogenous nucleic acids encoding a pyruvate kinase; and a pyruvate dehydrogenase or a pyruvate ferredoxin oxidoreductase; or a pyruvate formate lyase, a pyruvate formate lyase activating enzyme and a formate dehydrogenase.

In another further embodiment, the microbial organism has a propionyl-CoA pathway having a third set of exogenous nucleic acids encoding propionyl-CoA pathway enzymes expressed in a sufficient amount to produce propionyl-CoA, the third set of exogenous nucleic acids encoding a PEP carboxykinase or a PEP carboxylase; a malate dehydrogenase; a fumarase; a fumarate reductase; a succinyl-CoA transferase or a succinyl-CoA synthetase; a methylmalonyl-CoA mutase; and a methylmalonyl-CoA decarboxylase. In a further aspect, the third set of exogenous nucleic acids further encodes a methylmalonyl-CoA epimerase, a pyruvate carboxylase or a methylmalonyl-CoA carboxytransferase.

In another further embodiment, the microbial organism has a propionyl-CoA pathway having a third set of exogenous nucleic acids encoding propionyl-CoA pathway enzymes expressed in a sufficient amount to produce propionyl-CoA, said third set of exogenous nucleic acids encoding a PEP carboxykinase or a PEP carboxylase; a threonine deaminase; and a 2-oxobutanoate dehydrogenase. In a further aspect, the third set of exogenous nucleic acids further encodes a methylmalonyl-CoA decarboxylase or a pyruvate carboxylase. In yet another aspect, the second set of exogenous nucleic acids further encodes a 2-oxobutanoate decarboxylase.

In another further embodiment, the microbial organism has a propionyl-CoA pathway having a third set of exogenous nucleic acids encoding propionyl-CoA pathway enzymes expressed in a sufficient amount to produce propionyl-CoA, the third set of exogenous nucleic acids encoding an acetyl-CoA carboxylase; a malonyl-CoA reductase; a malonate semialdehyde reductase; and propionyl-CoA synthase.

In another further embodiment, the microbial organism has a propionyl-CoA pathway having a third set of exogenous nucleic acids encoding a lactate dehydrogenase; a lactate-CoA transferase; a lactyl-CoA dehydratase; and acryloyl CoA reductase.

In one embodiment, the invention provides a non-naturally occurring microbial organism including a microbial organism having an n-propanol pathway and an isopropanol pathway, the n-propanol pathway comprising a first set of exogenous nucleic acids encoding n-propanol pathway enzymes expressed in a sufficient amount to produce n-propanol, the first set of exogenous nucleic acids encoding a PEP carboxykinase or a PEP carboxylase; a malate dehydrogenase; a fumarase; a fumarate reductase; a succinyl-CoA transferase or a succinyl-CoA synthetase; a methylmalonyl-CoA mutase; a methylmalonyl-CoA decarboxylase; and a propionaldehyde dehydrogenase and a propanol dehydrogenase; or a propionyl-CoA:phosphate propanoyltransferase and a propionyl phosphate reductase; or a propionyl-CoA hydrolase or a propionyl-CoA transferase or a propionyl-CoA synthetase, a propionate kinase, a propionyl phosphate reductase and a propanol dehydrogenase; or a propionyl-CoA hydrolase or a propionyl-CoA transferase or a propionyl-CoA synthetase, a propionate reductase and a propanol dehydrogenase, and the isopropanol pathway comprising a second set of exogenous nucleic acids encoding isopropanol pathway enzymes expressed in a sufficient amount to produce isopropanol, the second set of exogenous nucleic acids encoding a pyruvate kinase; a pyruvate dehydrogenase or a pyruvate ferredoxin oxidoreductase; or a pyruvate formate lyase, a pyruvate formate lyase activating enzyme and a formate dehydrogenase; an acetyl-CoA acetyl thiolase; an acetoacetyl-CoA transferase or an acetoacetyl-CoA hydrolase or an acetoacetyl-CoA synthetase, an acetoacetate decarboxylase; and an isopropanol dehydrogenase.

In one embodiment, the invention provides a non-naturally occurring microbial organism including a microbial organism having an n-propanol pathway and an isopropanol pathway, the n-propanol pathway comprising a first set of exogenous nucleic acids encoding n-popanol pathway enzymes expressed in a sufficient amount to produce n-propanol, the first set of exogenous nucleic acids encoding a PEP carboxykinase or a PEP carboxylase; a threonine deaminase; and a 2-oxobutanoate decarboxylase and a propanol dehydrogenase; or a 2-oxobutanoate dehydrogenase, a propionaldehyde dehydrogenase and a propanol dehydrogenase; or a 2-oxobutanoate dehydrogenase, a propionyl-CoA:phosphate propanoyltransferase, a propionyl phosphate reductase and a propanol dehydrogenase; a 2-oxobutanoate dehydrogenase, a propionyl-CoA hydrolase or a propionyl-CoA transferase or a propionyl-CoA synthetase, a propionate kinase, a propionyl phosphate reductase and a propanol dehydrogenase; or a 2-oxobutanoate dehydrogenase, a propionyl-CoA hydrolase or a propionyl-CoA transferase or a propionyl-CoA synthetase, a propionate reductase and a propanol dehydrogenase, and the isopropanol pathway comprising a second set of exogenous nucleic acids encoding isopropanol pathway enzymes expressed in a sufficient amount to produce isopropanol, the second set of exogenous nucleic acids encoding a pyruvate kinase; a pyruvate dehydrogenase or a pyruvate ferredoxin oxidoreductase; or a pyruvate formate lyase, a pyruvate formate lyase activating enzyme and a formate dehydrogenase; an acetyl-CoA acetyl thiolase; an acetoacetyl-CoA transferase or an acetoacetyl-CoA hydrolase or an acetoacetyl-CoA synthetase, an acetoacetate decarboxylase; and an isopropanol dehydrogenase. In a further aspect, the second set of exogenous nucleic acids further encodes a pyruvate carboxylase or a methylmalonyl-CoA carboxytransferase.

In one embodiment, the invention provides a non-naturally occurring microbial organism including a microbial organism having an n-propanol pathway and an isopropanol pathway, the n-propanol pathway comprising a first set of exogenous nucleic acids encoding n-propanol pathway enzymes expressed in a sufficient amount to produce n-propanol, the first set of exogenous nucleic acids encoding a pyruvate kinase; a pyruvate dehydrogenase or a pyruvate ferredoxin oxidoreductase; or a pyruvate formate lyase, a pyruvate formate lyase activating enzyme and a formate dehydrogenase; an acetyl-CoA carboxylase; a malonyl-CoA reductase; a malonate semialdehyde reductase; propionyl-CoA synthase; and a propionaldehyde dehydrogenase and a propanol dehydrogenase; or a propionyl-CoA:phosphate propanoyltransferase, a propionyl phosphate reductase and propanol dehydrogenase; or a propionyl-CoA hydrolase or a propionyl-CoA transferase or a propionyl-CoA synthetase, a propionate kinase, a propionyl phosphate reductase and a propanol dehydrogenase; or a propionyl-CoA hydrolase or a propionyl-CoA transferase or a propionyl-CoA synthetase, a propionate reductase and a propanol dehydrogenase, and the isopropanol pathway comprising a second set of exogenous nucleic acids encoding isopropanol pathway enzymes expressed in a sufficient amount to produce isopropanol, the second set of exogenous nucleic acids encoding an acetyl-CoA acetyl thiolase; an acetoacetyl-CoA transferase or an acetoacetyl-CoA hydrolase or an acetoacetyl-CoA synthetase, an acetoacetate decarboxylase; and an isopropanol dehydrogenase.

In one embodiment, the invention provides a non-naturally occurring microbial organism including a microbial organism having an n-propanol pathway and an isopropanol pathway, the n-propanol pathway including a first set of exogenous nucleic acids encoding n-propanol pathway enzymes expressed in a sufficient amount to produce n-propanol, the first set of exogenous nucleic acids encoding a lactate dehydrogenase; a lactate-CoA transferase; a lactyl-CoA dehydratase; acryloyl CoA reductase; and a propionaldehyde dehydrogenase and a propanol dehydrogenase; or a propionyl-CoA:phosphate propanoyltransferase, a propionyl phosphate reductase and a propanol dehydrogenase; or a propionyl-CoA hydrolase or a propionyl-CoA transferase or a propionyl-CoA synthetase, a propionate kinase, a propionyl phosphate reductase and a propanol dehydrogenase; or a propionyl-CoA hydrolase or a propionyl-CoA transferase or a propionyl-CoA synthetase, a propionate reductase and a propanol dehydrogenase, and the isopropanol pathway comprising a second set of exogenous nucleic acids encoding isopropanol pathway enzymes expressed in a sufficient amount to produce isopropanol, the second set of exogenous nucleic acids encoding a pyruvate dehydrogenase or a pyruvate ferredoxin oxidoreductase; or a pyruvate formate lyase, a pyruvate formate lyase activating enzyme and a formate dehydrogenase; an acetyl-CoA acetyl thiolase; an acetoacetyl-CoA transferase or an acetoacetyl-CoA hydrolase or an acetoacetyl-CoA synthetase, an acetoacetate decarboxylase; and an isopropanol dehydrogenase.

In one embodiment, the invention provides a non-naturally occurring microbial organism including a microbial organism having an n-propanol pathway, the n-propanol pathway comprising at least one exogenous nucleic acid encoding an n-propanol pathway enzyme expressed in a sufficient amount to produce n-propanol, the n-propanol pathway including a propionaldehyde dehydrogenase, a propanol dehydrogenase, a propionyl-CoA:phosphate propanoyltransferase, a propionyl-CoA hydrolase, a propionyl-CoA transferase, a propionyl-CoA synthetase, a propionate kinase, a propionate reductase, or a propionyl phosphate reductase.

In another embodiment, the invention provides a non-naturally occurring microbial organism including a microbial organism having an n-propanol pathway, the n-propanol pathway comprising a set of exogenous nucleic acids encoding n-propanol pathway enzymes expressed in a sufficient amount to produce n-propanol, the set of exogenous nucleic acids encoding a propionaldehyde dehydrogenase and a propanol dehydrogenase; or a propionyl-CoA:phosphate propanoyltransferase, a propionyl phosphate reductase and a propanol dehydrogenase; or a propionyl-CoA hydrolase or a propionyl-CoA transferase or a propionyl-CoA synthetase, a propionate kinase, a propionyl phosphate reductase and a propanol dehydrogenase; or a propionyl-CoA hydrolase or a propionyl-CoA transferase or a propionyl-CoA synthetase, a propionate reductase and a propanol dehydrogenase.

In a further aspect of the above embodiment, the non-naturally occurring microbial organism having an n-propanol pathway also has a propionyl-CoA pathway including exogenous nucleic acids encoding propionyl-CoA pathway enzymes expressed in a sufficient amount to produce propionyl-CoA as exemplified herein. For example, in some aspects the exogenous nucleic acids encode a PEP carboxykinase, a PEP carboxylase, a malate dehydrogenase, a fumarase, a fumarate reductase, a succinyl-CoA transferase, a succinyl-CoA synthetase, a methylmalonyl-CoA mutase or a methylmalonyl-CoA decarboxylase. In another aspect, the exogenous nucleic acids further encode a methylmalonyl-CoA epimerase. Additionally, in yet another aspect of the above embodiment, the non-naturally occurring microbial organism having an n-propanol pathway can have a first set of exogenous nucleic acids encoding n-propanol pathway enzymes expressed in a sufficient amount to produce n-propanol, wherein the first set of exogenous nucleic acids encode a PEP carboxykinase or a PEP carboxylase; a malate dehydrogenase; a fumarase; a fumarate reductase; a succinyl-CoA transferase or a succinyl-CoA synthetase; a methylmalonyl-CoA mutase; a methylmalonyl-CoA epimerase, a methylmalonyl-CoA decarboxylase; a propionaldehyde dehydrogenase and a propanol dehydrogenase.

In one embodiment, the invention provides a non-naturally occurring microbial organism, including a microbial organism having an 14-BDO pathway and an isopropanol pathway, the 14-BDO pathway having at least one exogenous nucleic acid encoding an 14-BDO pathway enzyme expressed in a sufficient amount to produce 14-BDO, the 14-BDO pathway including a succinyl-CoA reductase, a succinate reductase, a 4-hydroxybutyrate dehydrogenase, a 4-hydroxybutyryl-CoA transferase, a 4-hydroxybutyryl-CoA synthetase, a 4-hydroxybutyryl-CoA reductase (aldehyde-forming), a 4-hydroxybutyraldehyde reductase, a 4-hydroxybutyrate reductase; a 4-hydroxybutyrate kinase, a phosphotrans-4-hydroxybutyrylase, a 4-hydroxybutyryl-phosphate reductase or a 4-hydroxybutyryl-CoA reductase (alcohol-forming), the isopropanol pathway including at least one exogenous nucleic acid encoding an isopropanol pathway enzyme expressed in a sufficient amount to produce isopropanol, the isopropanol pathway including an acetyl-CoA acetyl thiolase, an acetoacetyl-CoA transferase, an acetoacetyl-CoA hydrolase, an acetoacetyl-CoA synthetase, an acetoacetate decarboxylase or an isopropanol dehydrogenase.

In one embodiment, the invention provides a non-naturally occurring microbial organism, including a microbial organism having an 13-BDO pathway and an isopropanol pathway, the 13-BDO pathway having at least one exogenous nucleic acid encoding an 13-BDO pathway enzyme expressed in a sufficient amount to produce 13-BDO, the 13-BDO pathway including a succinyl-CoA reductase, a succinate reductase, a 4-hydroxybutyrate dehydrogenase, a 4-hydroxybutyryl-CoA transferase, a 4-hydroxybutyryl-CoA synthetase, a 4-hydroxybutyrate kinase, a phosphotrans-4-hydroxybutyrylase, a 4-hydroxybutyryl-CoA dehydratase, a crotonase, a 3-hydroxybutyryl-CoA reductase (aldehyde forming), a 3-hydroxybutyraldehyde reductase, a 3-hydroxybutyryl-CoA transferase, a 3-hydroxybutyryl-CoA synthetase, a 3-hydroxybutyryl-CoA hydrolase, or a 3-hydroxybutyrate reductase, or a 3-hydroxybutyryl-CoA reductase (alcohol-forming), the isopropanol pathway including at least one exogenous nucleic acid encoding an isopropanol pathway enzyme expressed in a sufficient amount to produce isopropanol, the isopropanol pathway including an acetyl-CoA acetyl thiolase, an acetoacetyl-CoA transferase, an acetoacetyl-CoA hydrolase, an acetoacetyl-CoA synthetase, an acetoacetate decarboxylase or an isopropanol dehydrogenase.

In one embodiment, the invention provides a non-naturally occurring microbial organism, including a microbial organism having an MAA pathway and an isopropanol pathway, the MAA pathway having at least one exogenous nucleic acid encoding an MAA pathway enzyme expressed in a sufficient amount to produce MAA, the MAA pathway including a succinyl-CoA reductase, a succinate reductase, a 4-hydroxybutyrate dehydrogenase, a 4-hydroxybutyryl-CoA transferase, a 4-hydroxybutyryl-CoA synthetase, a 4-hydroxybutyrate kinase, a phosphotrans-4-hydroxybutyrylase, a 4-hydroxybutyryl-CoA mutase, a 3-hydroxyisobutyryl-CoA dehydratase, a methacrylyl-CoA transferase, a methacrylyl-CoA synthetase, a methacrylyl-CoA hydrolase, a 3-hydroxyisobutyryl-CoA transferase, a 3-hydroxyisobutyryl-CoA synthetase, a 3-hydroxyisobutyryl-CoA hydrolase, a 3-hydroxyisobutyrate dehydratase, a methylmalonyl-CoA mutase, a methylmalonyl-CoA epimerase, a methylmalonyl-CoA transferase, a methylmalonyl-CoA synthetase, a methylmalonyl-CoA hydrolase, a methylmalonate reductase, a methylmalonyl-CoA reductase (aldehyde forming), a 3-hydroxyisobutyrate dehydrogenase, a methylmalonyl-CoA reductase (alcohol forming) or a 3-hydroxyisobutyrate dehydratase, the isopropanol pathway including at least one exogenous nucleic acid encoding an isopropanol pathway enzyme expressed in a sufficient amount to produce isopropanol, the isopropanol pathway including an acetyl-CoA acetyl thiolase, an acetoacetyl-CoA transferase, an acetoacetyl-CoA hydrolase, an acetoacetyl-CoA synthetase, an acetoacetate decarboxylase or an isopropanol dehydrogenase.

In a further aspect of the above embodiments, the microbial organism has an acetyl-CoA pathway having at least one exogenous nucleic acid encoding an acetyl-CoA pathway enzyme expressed in a sufficient amount to produce acetyl-CoA, the acetyl-CoA pathway including a pyruvate kinase, a pyruvate dehydrogenase, a pyruvate ferredoxin oxidoreductase, a pyruvate formate lyase, a pyruvate formate lyase activating enzyme, or a formate dehydrogenase.

In further aspect of the above embodiments, the microbial organism has a succinyl-CoA pathway having at least one exogenous nucleic acid encoding a succinyl-CoA pathway enzyme expressed in a sufficient amount to produce succinyl-CoA, the succinyl-CoA pathway including a PEP carboxykinase, a PEP carboxylase, a malate dehydrogenase, a fumarase, a fumarate reductase, a succinyl-CoA transferase or a succinyl-CoA synthetase. In a further aspect, the succinyl-CoA pathway includes a pyruvate carboxylase or a methylmalonyl-CoA carboxytransferase.

In one embodiment, the invention provides a non-naturally occurring microbial organism including a microbial organism having an 14-BDO pathway and an isopropanol pathway, the 14-BDO pathway including a first set of exogenous nucleic acids encoding 14-BDO pathway enzymes expressed in a sufficient amount to produce 14-BDO, the first set of exogenous nucleic acids encoding a succinyl-CoA reductase; a 4-hydroxybutyrate dehydrogenase; a 4-hydroxybutyryl-CoA transferase or a 4-hydroxybutyryl-CoA synthetase; a 4-hydroxybutyryl-CoA reductase (aldehyde-forming); and a 4-hydroxybutyraldehyde reductase, and the isopropanol pathway comprising a second set of exogenous nucleic acids encoding isopropanol pathway enzymes expressed in a sufficient amount to produce isopropanol, the second set of exogenous nucleic acids encoding an acetyl-CoA acetyl thiolase; an acetoacetyl-CoA transferase or an acetoacetyl-CoA hydrolase or an acetoacetyl-CoA synthetase; an acetoacetate decarboxylase; and an isopropanol dehydrogenase.

In one embodiment, the invention provides a non-naturally occurring microbial organism including a microbial organism having an 14-BDO pathway and an isopropanol pathway, the 14-BDO pathway including a first set of exogenous nucleic acids encoding 14-BDO pathway enzymes expressed in a sufficient amount to produce 14-BDO, the first set of exogenous nucleic acids encoding a succinyl-CoA reductase; a 4-hydroxybutyrate dehydrogenase; a 4-hydroxybutyrate reductase; and a 4-hydroxybutyraldehyde reductase, and the isopropanol pathway comprising a second set of exogenous nucleic acids encoding isopropanol pathway enzymes expressed in a sufficient amount to produce isopropanol, the second set of exogenous nucleic acids encoding an acetyl-CoA acetyl thiolase; an acetoacetyl-CoA transferase or an acetoacetyl-CoA hydrolase or an acetoacetyl-CoA synthetase; an acetoacetate decarboxylase; and an isopropanol dehydrogenase.

In one embodiment, the invention provides a non-naturally occurring microbial organism including a microbial organism having an 14-BDO pathway and an isopropanol pathway, the 14-BDO pathway including a first set of exogenous nucleic acids encoding 14-BDO pathway enzymes expressed in a sufficient amount to produce 14-BDO, the first set of exogenous nucleic acids encoding a succinyl-CoA reductase; a 4-hydroxybutyrate dehydrogenase; a 4-hydroxybutyrate kinase; a phosphotrans-4-hydroxybutyrylase; a 4-hydroxybutyryl-CoA reductase (aldehyde-forming); and a 4-hydroxybutyraldehyde reductase, and the isopropanol pathway comprising a second set of exogenous nucleic acids encoding isopropanol pathway enzymes expressed in a sufficient amount to produce isopropanol, the second set of exogenous nucleic acids encoding an acetyl-CoA acetyl thiolase; an acetoacetyl-CoA transferase or an acetoacetyl-CoA hydrolase or an acetoacetyl-CoA synthetase; an acetoacetate decarboxylase; and an isopropanol dehydrogenase.

In one embodiment, the invention provides a non-naturally occurring microbial organism including a microbial organism having an 14-BDO pathway and an isopropanol pathway, the 14-BDO pathway including a first set of exogenous nucleic acids encoding 14-BDO pathway enzymes expressed in a sufficient amount to produce 14-BDO, the first set of exogenous nucleic acids encoding a succinyl-CoA reductase; a 4-hydroxybutyrate dehydrogenase; a 4-hydroxybutyrate kinase; a 4-hydroxybutyryl-phosphate reductase; and a 4-hydroxybutyraldehyde reductase, and the isopropanol pathway comprising a second set of exogenous nucleic acids encoding isopropanol pathway enzymes expressed in a sufficient amount to produce isopropanol, the second set of exogenous nucleic acids encoding an acetyl-CoA acetyl thiolase; an acetoacetyl-CoA transferase or an acetoacetyl-CoA hydrolase or an acetoacetyl-CoA synthetase; an acetoacetate decarboxylase; and an isopropanol dehydrogenase.

In one embodiment, the invention provides a non-naturally occurring microbial organism including a microbial organism having an 14-BDO pathway and an isopropanol pathway, the 14-BDO pathway including a first set of exogenous nucleic acids encoding 14-BDO pathway enzymes expressed in a sufficient amount to produce 14-BDO, the first set of exogenous nucleic acids encoding a succinyl-CoA reductase; a 4-hydroxybutyrate dehydrogenase; a 4-hydroxybutyrate kinase; a phosphotrans-4-hydroxybutyrylase; and a 4-hydroxybutyryl-CoA reductase (alcohol-forming), and the isopropanol pathway comprising a second set of exogenous nucleic acids encoding isopropanol pathway enzymes expressed in a sufficient amount to produce isopropanol, the second set of exogenous nucleic acids encoding an acetyl-CoA acetyl thiolase; an acetoacetyl-CoA transferase or an acetoacetyl-CoA hydrolase or an acetoacetyl-CoA synthetase; an acetoacetate decarboxylase; and an isopropanol dehydrogenase.

In one embodiment, the invention provides a non-naturally occurring microbial organism including a microbial organism having an 14-BDO pathway and an isopropanol pathway, the 14-BDO pathway including a first set of exogenous nucleic acids encoding 14-BDO pathway enzymes expressed in a sufficient amount to produce 14-BDO, the first set of exogenous nucleic acids encoding a succinyl-CoA reductase; a 4-hydroxybutyrate dehydrogenase; a 4-hydroxybutyryl-CoA transferase or a 4-hydroxybutyryl-CoA synthetase; and a 4-hydroxybutyryl-CoA reductase (alcohol-forming), and the isopropanol pathway comprising a second set of exogenous nucleic acids encoding isopropanol pathway enzymes expressed in a sufficient amount to produce isopropanol, the second set of exogenous nucleic acids encoding an acetyl-CoA acetyl thiolase; an acetoacetyl-CoA transferase or an acetoacetyl-CoA hydrolase or an acetoacetyl-CoA synthetase; an acetoacetate decarboxylase; and an isopropanol dehydrogenase.

In one embodiment, the invention provides a non-naturally occurring microbial organism including a microbial organism having an 14-BDO pathway and an isopropanol pathway, the 14-BDO pathway including a first set of exogenous nucleic acids encoding 14-BDO pathway enzymes expressed in a sufficient amount to produce 14-BDO, the first set of exogenous nucleic acids encoding a succinate reductase; a 4-hydroxybutyrate dehydrogenase; a 4-hydroxybutyryl-CoA transferase or a 4-hydroxybutyryl-CoA synthetase; a 4-hydroxybutyryl-CoA reductase (aldehyde-forming); and a 4-hydroxybutyraldehyde reductase, and the isopropanol pathway comprising a second set of exogenous nucleic acids encoding isopropanol pathway enzymes expressed in a sufficient amount to produce isopropanol, the second set of exogenous nucleic acids encoding an acetyl-CoA acetyl thiolase; an acetoacetyl-CoA transferase or an acetoacetyl-CoA hydrolase or an acetoacetyl-CoA synthetase; an acetoacetate decarboxylase; and an isopropanol dehydrogenase.

In one embodiment, the invention provides a non-naturally occurring microbial organism including a microbial organism having an 14-BDO pathway and an isopropanol pathway, the 14-BDO pathway including a first set of exogenous nucleic acids encoding 14-BDO pathway enzymes expressed in a sufficient amount to produce 14-BDO, the first set of exogenous nucleic acids encoding a succinate reductase; a 4-hydroxybutyrate dehydrogenase; a 4-hydroxybutyrate reductase; and a 4-hydroxybutyraldehyde reductase, and the isopropanol pathway comprising a second set of exogenous nucleic acids encoding isopropanol pathway enzymes expressed in a sufficient amount to produce isopropanol, the second set of exogenous nucleic acids encoding an acetyl-CoA acetyl thiolase; an acetoacetyl-CoA transferase or an acetoacetyl-CoA hydrolase or an acetoacetyl-CoA synthetase; an acetoacetate decarboxylase; and an isopropanol dehydrogenase.

In one embodiment, the invention provides a non-naturally occurring microbial organism including a microbial organism having an 14-BDO pathway and an isopropanol pathway, the 14-BDO pathway including a first set of exogenous nucleic acids encoding 14-BDO pathway enzymes expressed in a sufficient amount to produce 14-BDO, the first set of exogenous nucleic acids encoding a succinate reductase; a 4-hydroxybutyrate dehydrogenase; a 4-hydroxybutyrate kinase; a phosphotrans-4-hydroxybutyrylase; a 4-hydroxybutyryl-CoA reductase (aldehyde-forming); and a 4-hydroxybutyraldehyde reductase, and the isopropanol pathway comprising a second set of exogenous nucleic acids encoding isopropanol pathway enzymes expressed in a sufficient amount to produce isopropanol, the second set of exogenous nucleic acids encoding an acetyl-CoA acetyl thiolase; an acetoacetyl-CoA transferase or an acetoacetyl-CoA hydrolase or an acetoacetyl-CoA synthetase; an acetoacetate decarboxylase; and an isopropanol dehydrogenase.

In one embodiment, the invention provides a non-naturally occurring microbial organism including a microbial organism having an 14-BDO pathway and an isopropanol pathway, the 14-BDO pathway including a first set of exogenous nucleic acids encoding 14-BDO pathway enzymes expressed in a sufficient amount to produce 14-BDO, the first set of exogenous nucleic acids encoding a succinate reductase; a 4-hydroxybutyrate dehydrogenase; a 4-hydroxybutyrate kinase; a 4-hydroxybutyryl-phosphate reductase; and a 4-hydroxybutyraldehyde reductase, and the isopropanol pathway comprising a second set of exogenous nucleic acids encoding isopropanol pathway enzymes expressed in a sufficient amount to produce isopropanol, the second set of exogenous nucleic acids encoding an acetyl-CoA acetyl thiolase; an acetoacetyl-CoA transferase or an acetoacetyl-CoA hydrolase or an acetoacetyl-CoA synthetase; an acetoacetate decarboxylase; and an isopropanol dehydrogenase.

In one embodiment, the invention provides a non-naturally occurring microbial organism including a microbial organism having an 14-BDO pathway and an isopropanol pathway, the 14-BDO pathway including a first set of exogenous nucleic acids encoding 14-BDO pathway enzymes expressed in a sufficient amount to produce 14-BDO, the first set of exogenous nucleic acids encoding a succinate reductase; a 4-hydroxybutyrate dehydrogenase; a 4-hydroxybutyrate kinase; a phosphotrans-4-hydroxybutyrylase; and a 4-hydroxybutyryl-CoA reductase (alcohol-forming), and the isopropanol pathway comprising a second set of exogenous nucleic acids encoding isopropanol pathway enzymes expressed in a sufficient amount to produce isopropanol, the second set of exogenous nucleic acids encoding an acetyl-CoA acetyl thiolase; an acetoacetyl-CoA transferase or an acetoacetyl-CoA hydrolase or an acetoacetyl-CoA synthetase; an acetoacetate decarboxylase; and an isopropanol dehydrogenase.

In one embodiment, the invention provides a non-naturally occurring microbial organism including a microbial organism having an 14-BDO pathway and an isopropanol pathway, the 14-BDO pathway including a first set of exogenous nucleic acids encoding 14-BDO pathway enzymes expressed in a sufficient amount to produce 14-BDO, the first set of exogenous nucleic acids encoding a succinate reductase; a 4-hydroxybutyrate dehydrogenase; a 4-hydroxybutyryl-CoA transferase or a 4-hydroxybutyryl-CoA synthetase; and a 4-hydroxybutyryl-CoA reductase (alcohol-forming), and the isopropanol pathway comprising a second set of exogenous nucleic acids encoding isopropanol pathway enzymes expressed in a sufficient amount to produce isopropanol, the second set of exogenous nucleic acids encoding an acetyl-CoA acetyl thiolase; an acetoacetyl-CoA transferase or an acetoacetyl-CoA hydrolase or an acetoacetyl-CoA synthetase, an acetoacetate decarboxylase; and an isopropanol dehydrogenase.

In one embodiment, the invention provides a non-naturally occurring microbial organism including a microbial organism having an 13-BDO pathway and an isopropanol pathway, the 13-BDO pathway including a first set of exogenous nucleic acids encoding 13-BDO pathway enzymes expressed in a sufficient amount to produce 13-BDO, the first set of exogenous nucleic acids encoding a succinyl-CoA reductase; a 4-hydroxybutyrate dehydrogenase; a 4-hydroxybutyryl-CoA transferase or a 4-hydroxybutyryl-CoA synthetase; a 4-hydroxybutyryl-CoA dehydratase; a crotonase; a 3-hydroxybutyryl-CoA reductase (aldehyde forming); and a 3-hydroxybutyraldehyde reductase, and the isopropanol pathway comprising a second set of exogenous nucleic acids encoding isopropanol pathway enzymes expressed in a sufficient amount to produce isopropanol, the second set of exogenous nucleic acids encoding an acetyl-CoA acetyl thiolase; an acetoacetyl-CoA transferase or an acetoacetyl-CoA hydrolase or an acetoacetyl-CoA synthetase, an acetoacetate decarboxylase; and an isopropanol dehydrogenase.

In one embodiment, the invention provides a non-naturally occurring microbial organism including a microbial organism having an 13-BDO pathway and an isopropanol pathway, the 13-BDO pathway including a first set of exogenous nucleic acids encoding 13-BDO pathway enzymes expressed in a sufficient amount to produce 13-BDO, the first set of exogenous nucleic acids encoding a succinyl-CoA reductase; a 4-hydroxybutyrate dehydrogenase; a 4-hydroxybutyryl-CoA transferase or a 4-hydroxybutyryl-CoA synthetase; a 4-hydroxybutyryl-CoA dehydratase; a crotonase; a 3-hydroxybutyryl-CoA transferase or a 3-hydroxybutyryl-CoA synthetase or a 3-hydroxybutyryl-CoA hydrolase; a 3-hydroxybutyrate reductase; and a 3 hydroxybutyraldehyde reductase, and the isopropanol pathway comprising a second set of exogenous nucleic acids encoding isopropanol pathway enzymes expressed in a sufficient amount to produce isopropanol, the second set of exogenous nucleic acids encoding an acetyl-CoA acetyl thiolase; an acetoacetyl-CoA transferase or an acetoacetyl-CoA hydrolase or an acetoacetyl-CoA synthetase, an acetoacetate decarboxylase; and an isopropanol dehydrogenase.

In one embodiment, the invention provides a non-naturally occurring microbial organism including a microbial organism having an 13-BDO pathway and an isopropanol pathway, the 13-BDO pathway including a first set of exogenous nucleic acids encoding 13-BDO pathway enzymes expressed in a sufficient amount to produce 13-BDO, the first set of exogenous nucleic acids encoding a succinyl-CoA reductase; a 4-hydroxybutyrate dehydrogenase; a 4-hydroxybutyrate kinase; a phosphotrans-4-hydroxybutyrylase; a 4-hydroxybutyryl-CoA dehydratase; a crotonase; a 3-hydroxybutyryl-CoA reductase (aldehyde forming); and a 3-hydroxybutyraldehyde reductase, and the isopropanol pathway comprising a second set of exogenous nucleic acids encoding isopropanol pathway enzymes expressed in a sufficient amount to produce isopropanol, the second set of exogenous nucleic acids encoding an acetyl-CoA acetyl thiolase; an acetoacetyl-CoA transferase or an acetoacetyl-CoA hydrolase or an acetoacetyl-CoA synthetase; an acetoacetate decarboxylase; and an isopropanol dehydrogenase.

In one embodiment, the invention provides a non-naturally occurring microbial organism including a microbial organism having an 13-BDO pathway and an isopropanol pathway, the 13-BDO pathway including a first set of exogenous nucleic acids encoding 13-BDO pathway enzymes expressed in a sufficient amount to produce 13-BDO, the first set of exogenous nucleic acids encoding a succinyl-CoA reductase; a 4-hydroxybutyrate dehydrogenase; a 4-hydroxybutyrate kinase; a phosphotrans-4-hydroxybutyrylase; a 4-hydroxybutyryl-CoA dehydratase; a crotonase; a 3-hydroxybutyryl-CoA transferase or a 3-hydroxybutyryl-CoA synthetase or a 3-hydroxybutyryl-CoA hydrolase; a 3-hydroxybutyrate reductase; and a 3-hydroxybutyraldehyde reductase, and the isopropanol pathway comprising a second set of exogenous nucleic acids encoding isopropanol pathway enzymes expressed in a sufficient amount to produce isopropanol, the second set of exogenous nucleic acids encoding an acetyl-CoA acetyl thiolase; an acetoacetyl-CoA transferase or an acetoacetyl-CoA hydrolase or an acetoacetyl-CoA synthetase; an acetoacetate decarboxylase; and an isopropanol dehydrogenase.

In one embodiment, the invention provides a non-naturally occurring microbial organism including a microbial organism having an 13-BDO pathway and an isopropanol pathway, the 13-BDO pathway including a first set of exogenous nucleic acids encoding 13-BDO pathway enzymes expressed in a sufficient amount to produce 13-BDO, the first set of exogenous nucleic acids encoding a succinyl-CoA reductase; a 4-hydroxybutyrate dehydrogenase; a 4-hydroxybutyrate kinase; a phosphotrans-4-hydroxybutyrylase; a 4-hydroxybutyryl-CoA dehydratase; a crotonase; and a 3-hydroxybutyryl-CoA reductase (alcohol-forming), and the isopropanol pathway comprising a second set of exogenous nucleic acids encoding isopropanol pathway enzymes expressed in a sufficient amount to produce isopropanol, the second set of exogenous nucleic acids encoding an acetyl-CoA acetyl thiolase; an acetoacetyl-CoA transferase or an acetoacetyl-CoA hydrolase or an acetoacetyl-CoA synthetase, an acetoacetate decarboxylase; and an isopropanol dehydrogenase.

In one embodiment, the invention provides a non-naturally occurring microbial organism including a microbial organism having an 13-BDO pathway and an isopropanol pathway, the 13-BDO pathway including a first set of exogenous nucleic acids encoding 13-BDO pathway enzymes expressed in a sufficient amount to produce 13-BDO, the first set of exogenous nucleic acids encoding a succinyl-CoA reductase; a 4-hydroxybutyrate dehydrogenase; a 4-hydroxybutyryl-CoA transferase or a 4-hydroxybutyryl-CoA synthetase; a 4-hydroxybutyryl-CoA dehydratase; a crotonase; and a 3-hydroxybutyryl-CoA reductase (alcohol-forming), and the isopropanol pathway comprising a second set of exogenous nucleic acids encoding isopropanol pathway enzymes expressed in a sufficient amount to produce isopropanol, the second set of exogenous nucleic acids encoding an acetyl-CoA acetyl thiolase; an acetoacetyl-CoA transferase or an acetoacetyl-CoA hydrolase or an acetoacetyl-CoA synthetase, an acetoacetate decarboxylase; and an isopropanol dehydrogenase.

In one embodiment, the invention provides a non-naturally occurring microbial organism including a microbial organism having an 13-BDO pathway and an isopropanol pathway, the 13-BDO pathway including a first set of exogenous nucleic acids encoding 13-BDO pathway enzymes expressed in a sufficient amount to produce 13-BDO, the first set of exogenous nucleic acids encoding a succinate reductase; a 4-hydroxybutyrate dehydrogenase; a 4-hydroxybutyryl-CoA transferase or a 4-hydroxybutyryl-CoA synthetase; a 4-hydroxybutyryl-CoA dehydratase; a crotonase; a 3-hydroxybutyryl-CoA reductase (aldehyde forming); and a 3-hydroxybutyraldehyde reductase, and the isopropanol pathway comprising a second set of exogenous nucleic acids encoding isopropanol pathway enzymes expressed in a sufficient amount to produce isopropanol, the second set of exogenous nucleic acids encoding an acetyl-CoA acetyl thiolase; an acetoacetyl-CoA transferase or an acetoacetyl-CoA hydrolase or an acetoacetyl-CoA synthetase; an acetoacetate decarboxylase; and an isopropanol dehydrogenase.

In one embodiment, the invention provides a non-naturally occurring microbial organism including a microbial organism having an 13-BDO pathway and an isopropanol pathway, the 13-BDO pathway including a first set of exogenous nucleic acids encoding 13-BDO pathway enzymes expressed in a sufficient amount to produce 13-BDO, the first set of exogenous nucleic acids encoding a succinate reductase; a 4-hydroxybutyrate dehydrogenase; a 4-hydroxybutyryl-CoA transferase or a 4-hydroxybutyryl-CoA synthetase; a 4-hydroxybutyryl-CoA dehydratase; a crotonase; a 3-hydroxybutyryl-CoA transferase or a 3-hydroxybutyryl-CoA synthetase or a 3-hydroxybutyryl-CoA hydrolase; a 3-hydroxybutyrate reductase; and a 3 hydroxybutyraldehyde reductase, and the isopropanol pathway comprising a second set of exogenous nucleic acids encoding isopropanol pathway enzymes expressed in a sufficient amount to produce isopropanol, the second set of exogenous nucleic acids encoding an acetyl-CoA acetyl thiolase; an acetoacetyl-CoA transferase or an acetoacetyl-CoA hydrolase or an acetoacetyl-CoA synthetase; an acetoacetate decarboxylase; and an isopropanol dehydrogenase.

In one embodiment, the invention provides a non-naturally occurring microbial organism including a microbial organism having an 13-BDO pathway and an isopropanol pathway, the 13-BDO pathway including a first set of exogenous nucleic acids encoding 13-BDO pathway enzymes expressed in a sufficient amount to produce 13-BDO, the first set of exogenous nucleic acids encoding a succinate reductase; a 4-hydroxybutyrate dehydrogenase; a 4-hydroxybutyrate kinase; a phosphotrans-4-hydroxybutyrylase; a 4-hydroxybutyryl-CoA dehydratase; a crotonase; a 3-hydroxybutyryl-CoA reductase (aldehyde forming); and a 3-hydroxybutyraldehyde reductase, and the isopropanol pathway comprising a second set of exogenous nucleic acids encoding isopropanol pathway enzymes expressed in a sufficient amount to produce isopropanol, the second set of exogenous nucleic acids encoding an acetyl-CoA acetyl thiolase; an acetoacetyl-CoA transferase or an acetoacetyl-CoA hydrolase or an acetoacetyl-CoA synthetase; an acetoacetate decarboxylase; and an isopropanol dehydrogenase.

In one embodiment, the invention provides a non-naturally occurring microbial organism including a microbial organism having an 13-BDO pathway and an isopropanol pathway, the 13-BDO pathway including a first set of exogenous nucleic acids encoding 13-BDO pathway enzymes expressed in a sufficient amount to produce 13-BDO, the first set of exogenous nucleic acids encoding a succinate reductase; a 4-hydroxybutyrate dehydrogenase; a 4 hydroxybutyrate kinase; a phosphotrans-4-hydroxybutyrylase; a 4-hydroxybutyryl-CoA dehydratase; a crotonase; a 3-hydroxybutyryl-CoA transferase or a 3-hydroxybutyryl-CoA synthetase or a 3-hydroxybutyryl-CoA hydrolase; a 3-hydroxybutyrate reductase; and a 3 hydroxybutyraldehyde reductase, and the isopropanol pathway comprising a second set of exogenous nucleic acids encoding isopropanol pathway enzymes expressed in a sufficient amount to produce isopropanol, the second set of exogenous nucleic acids encoding an acetyl-CoA acetyl thiolase; an acetoacetyl-CoA transferase or an acetoacetyl-CoA hydrolase or an acetoacetyl-CoA synthetase; an acetoacetate decarboxylase; and an isopropanol dehydrogenase.

In one embodiment, the invention provides a non-naturally occurring microbial organism including a microbial organism having an 13-BDO pathway and an isopropanol pathway, the 13-BDO pathway including a first set of exogenous nucleic acids encoding 13-BDO pathway enzymes expressed in a sufficient amount to produce 13-BDO, the first set of exogenous nucleic acids encoding a succinate reductase; a 4-hydroxybutyrate dehydrogenase; a 4-hydroxybutyrate kinase; a phosphotrans-4-hydroxybutyrylase; a crotonase; and a 3-hydroxybutyryl-CoA reductase (alcohol-forming), and the isopropanol pathway comprising a second set of exogenous nucleic acids encoding isopropanol pathway enzymes expressed in a sufficient amount to produce isopropanol, the second set of exogenous nucleic acids encoding an acetyl-CoA acetyl thiolase; an acetoacetyl-CoA transferase or an acetoacetyl-CoA hydrolase or an acetoacetyl-CoA synthetase, an acetoacetate decarboxylase; and an isopropanol dehydrogenase.

In one embodiment, the invention provides a non-naturally occurring microbial organism including a microbial organism having an 13-BDO pathway and an isopropanol pathway, the 13-BDO pathway including a first set of exogenous nucleic acids encoding 13-BDO pathway enzymes expressed in a sufficient amount to produce 13-BDO, the first set of exogenous nucleic acids encoding a succinate reductase; a 4-hydroxybutyrate dehydrogenase; a 4-hydroxybutyryl-CoA transferase or a 4-hydroxybutyryl-CoA synthetase; a 4-hydroxybutyryl-CoA dehydratase; a crotonase; and a 3-hydroxybutyryl-CoA reductase (alcohol-forming), and the isopropanol pathway comprising a second set of exogenous nucleic acids encoding isopropanol pathway enzymes expressed in a sufficient amount to produce isopropanol, the second set of exogenous nucleic acids encoding an acetyl-CoA acetyl thiolase; an acetoacetyl-CoA transferase or an acetoacetyl-CoA hydrolase or an acetoacetyl-CoA synthetase, an acetoacetate decarboxylase; and an isopropanol dehydrogenase.

In one embodiment, the invention provides a non-naturally occurring microbial organism including a microbial organism having an MAA pathway and an isopropanol pathway, the MAA pathway including a first set of exogenous nucleic acids encoding MAA pathway enzymes expressed in a sufficient amount to produce MAA, the first set of exogenous nucleic acids encoding a succinyl-CoA reductase; a 4-hydroxybutyrate dehydrogenase; a 4-hydroxybutyryl-CoA transferase or a 4-hydroxybutyryl-CoA synthetase; a 4-hydroxybutyryl-CoA mutase; a 3-hydroxyisobutyryl-CoA transferase, a 3-hydroxyisobutyryl-CoA synthetase or a 3-hydroxyisobutyryl-CoA hydrolase; and a 3-hydroxyisobutyrate dehydratase, and the isopropanol pathway comprising a second set of exogenous nucleic acids encoding isopropanol pathway enzymes expressed in a sufficient amount to produce isopropanol, the second set of exogenous nucleic acids encoding an acetyl-CoA acetyl thiolase; an acetoacetyl-CoA transferase or an acetoacetyl-CoA hydrolase or an acetoacetyl-CoA synthetase; an acetoacetate decarboxylase; and an isopropanol dehydrogenase.

In one embodiment, the invention provides a non-naturally occurring microbial organism including a microbial organism having an MAA pathway and an isopropanol pathway, the MAA pathway including a first set of exogenous nucleic acids encoding MAA pathway enzymes expressed in a sufficient amount to produce MAA, the first set of exogenous nucleic acids encoding a succinyl-CoA reductase; a 4-hydroxybutyrate dehydrogenase; a 4-hydroxybutyryl-CoA transferase or a 4-hydroxybutyryl-CoA synthetase; a 4-hydroxybutyryl-CoA mutase; a 3-hydroxyisobutyryl-CoA dehydratase; and a methacrylyl-CoA transferase, a methacrylyl-CoA synthetase or a methacrylyl-CoA hydrolase, and the isopropanol pathway comprising a second set of exogenous nucleic acids encoding isopropanol pathway enzymes expressed in a sufficient amount to produce isopropanol, the second set of exogenous nucleic acids encoding an acetyl-CoA acetyl thiolase; an acetoacetyl-CoA transferase or an acetoacetyl-CoA hydrolase or an acetoacetyl-CoA synthetase; an acetoacetate decarboxylase; and an isopropanol dehydrogenase.

In one embodiment, the invention provides a non-naturally occurring microbial organism including a microbial organism having an MAA pathway and an isopropanol pathway, the MAA pathway including a first set of exogenous nucleic acids encoding MAA pathway enzymes expressed in a sufficient amount to produce MAA, the first set of exogenous nucleic acids encoding a succinyl-CoA reductase; a 4-hydroxybutyrate dehydrogenase; a 4-hydroxybutyrate kinase; a phosphotrans-4-hydroxybutyrylase; a 4-hydroxybutyryl-CoA mutase; a 3-hydroxyisobutyryl-CoA transferase, a 3-hydroxyisobutyryl-CoA synthetase or a 3-hydroxyisobutyryl-CoA hydrolase; and a 3-hydroxyisobutyrate dehydratase, and the isopropanol pathway comprising a second set of exogenous nucleic acids encoding isopropanol pathway enzymes expressed in a sufficient amount to produce isopropanol, the second set of exogenous nucleic acids encoding an acetyl-CoA acetyl thiolase; an acetoacetyl-CoA transferase or an acetoacetyl-CoA hydrolase or an acetoacetyl-CoA synthetase; an acetoacetate decarboxylase; and an isopropanol dehydrogenase.

In one embodiment, the invention provides a non-naturally occurring microbial organism including a microbial organism having an MAA pathway and an isopropanol pathway, the MAA pathway including a first set of exogenous nucleic acids encoding MAA pathway enzymes expressed in a sufficient amount to produce MAA, the first set of exogenous nucleic acids encoding a succinyl-CoA reductase; a 4-hydroxybutyrate dehydrogenase; a 4 hydroxybutyrate kinase; a phosphotrans-4-hydroxybutyrylase; a 4-hydroxybutyryl-CoA mutase; a 3-hydroxyisobutyryl-CoA dehydratase; and a methacrylyl-CoA transferase, a methacrylyl-CoA synthetase or a methacrylyl-CoA hydrolase, and the isopropanol pathway comprising a second set of exogenous nucleic acids encoding isopropanol pathway enzymes expressed in a sufficient amount to produce isopropanol, the second set of exogenous nucleic acids encoding an acetyl-CoA acetyl thiolase; an acetoacetyl-CoA transferase or an acetoacetyl-CoA hydrolase or an acetoacetyl-CoA synthetase; an acetoacetate decarboxylase; and an isopropanol dehydrogenase.

In one embodiment, the invention provides a non-naturally occurring microbial organism including a microbial organism having an MAA pathway and an isopropanol pathway, the MAA pathway including a first set of exogenous nucleic acids encoding MAA pathway enzymes expressed in a sufficient amount to produce MAA, the first set of exogenous nucleic acids encoding a succinate reductase; a 4-hydroxybutyrate dehydrogenase; a 4-hydroxybutyryl-CoA transferase or a 4-hydroxybutyryl-CoA synthetase; a 4-hydroxybutyryl-CoA mutase; a 3-hydroxyisobutyryl-CoA transferase, a 3-hydroxyisobutyryl-CoA synthetase or a 3-hydroxyisobutyryl-CoA hydrolase; and a 3-hydroxyisobutyrate dehydratase, and the isopropanol pathway comprising a second set of exogenous nucleic acids encoding isopropanol pathway enzymes expressed in a sufficient amount to produce isopropanol, the second set of exogenous nucleic acids encoding an acetyl-CoA acetyl thiolase; an acetoacetyl-CoA transferase or an acetoacetyl-CoA hydrolase or an acetoacetyl-CoA synthetase; an acetoacetate decarboxylase; and an isopropanol dehydrogenase.

In one embodiment, the invention provides a non-naturally occurring microbial organism including a microbial organism having an MAA pathway and an isopropanol pathway, the MAA pathway including a first set of exogenous nucleic acids encoding MAA pathway enzymes expressed in a sufficient amount to produce MAA, the first set of exogenous nucleic acids encoding a succinate reductase; a 4-hydroxybutyrate dehydrogenase; a 4-hydroxybutyryl-CoA transferase or a 4-hydroxybutyryl-CoA synthetase; a 4-hydroxybutyryl-CoA mutase; a 3-hydroxyisobutyryl-CoA dehydratase; and a methacrylyl-CoA transferase, a methacrylyl-CoA synthetase or a methacrylyl-CoA hydrolase, and the isopropanol pathway comprising a second set of exogenous nucleic acids encoding isopropanol pathway enzymes expressed in a sufficient amount to produce isopropanol, the second set of exogenous nucleic acids encoding an acetyl-CoA acetyl thiolase; an acetoacetyl-CoA transferase or an acetoacetyl-CoA hydrolase or an acetoacetyl-CoA synthetase; an acetoacetate decarboxylase; and an isopropanol dehydrogenase.

In one embodiment, the invention provides a non-naturally occurring microbial organism including a microbial organism having an MAA pathway and an isopropanol pathway, the MAA pathway including a first set of exogenous nucleic acids encoding MAA pathway enzymes expressed in a sufficient amount to produce MAA, the first set of exogenous nucleic acids encoding a succinate reductase; a 4-hydroxybutyrate dehydrogenase; a 4-hydroxybutyrate kinase; a phosphotrans-4-hydroxybutyrylase; a 4-hydroxybutyryl-CoA mutase; a 3-hydroxyisobutyryl-CoA transferase, a 3-hydroxyisobutyryl-CoA synthetase or a 3-hydroxyisobutyryl-CoA hydrolase; and a 3-hydroxyisobutyrate dehydratase, and the isopropanol pathway comprising a second set of exogenous nucleic acids encoding isopropanol pathway enzymes expressed in a sufficient amount to produce isopropanol, the second set of exogenous nucleic acids encoding an acetyl-CoA acetyl thiolase; an acetoacetyl-CoA transferase or an acetoacetyl-CoA hydrolase or an acetoacetyl-CoA synthetase; an acetoacetate decarboxylase; and an isopropanol dehydrogenase.

In one embodiment, the invention provides a non-naturally occurring microbial organism including a microbial organism having an MAA pathway and an isopropanol pathway, the MAA pathway including a first set of exogenous nucleic acids encoding MAA pathway enzymes expressed in a sufficient amount to produce MAA, the first set of exogenous nucleic acids encoding a succinate reductase; a 4-hydroxybutyrate dehydrogenase; a 4 hydroxybutyrate kinase; a phosphotrans-4-hydroxybutyrylase; a 4-hydroxybutyryl-CoA mutase; a 3-hydroxyisobutyryl-CoA dehydratase; and a methacrylyl-CoA transferase, a methacrylyl-CoA synthetase or a methacrylyl-CoA hydrolase, and the isopropanol pathway comprising a second set of exogenous nucleic acids encoding isopropanol pathway enzymes expressed in a sufficient amount to produce isopropanol, the second set of exogenous nucleic acids encoding an acetyl-CoA acetyl thiolase; an acetoacetyl-CoA transferase or an acetoacetyl-CoA hydrolase or an acetoacetyl-CoA synthetase; an acetoacetate decarboxylase; and an isopropanol dehydrogenase.

In one embodiment, the invention provides a non-naturally occurring microbial organism including a microbial organism having an MAA pathway and an isopropanol pathway, the MAA pathway including a first set of exogenous nucleic acids encoding MAA pathway enzymes expressed in a sufficient amount to produce MAA, the first set of exogenous nucleic acids encoding a methylmalonyl-CoA mutase; a methylmalonyl-CoA reductase (aldehyde forming); a 3-hydroxyisobutyrate dehydrogenase; and a 3-hydroxyisobutyrate dehydratase, and the isopropanol pathway comprising a second set of exogenous nucleic acids encoding isopropanol pathway enzymes expressed in a sufficient amount to produce isopropanol, the second set of exogenous nucleic acids encoding an acetyl-CoA acetyl thiolase; an acetoacetyl-CoA transferase or an acetoacetyl-CoA hydrolase or an acetoacetyl-CoA synthetase; an acetoacetate decarboxylase; and an isopropanol dehydrogenase.

In one embodiment, the invention provides a non-naturally occurring microbial organism including a microbial organism having an MAA pathway and an isopropanol pathway, the MAA pathway including a first set of exogenous nucleic acids encoding MAA pathway enzymes expressed in a sufficient amount to produce MAA, the first set of exogenous nucleic acids encoding a methylmalonyl-CoA mutase; a methylmalonyl-CoA epimerase; a methylmalonyl-CoA transferase, a methylmalonyl-CoA synthetase, or a methylmalonyl-CoA hydrolase; a methylmalonate reductase; a 3-hydroxyisobutyrate dehydrogenase; and a 3-hydroxyisobutyrate dehydratase, and the isopropanol pathway comprising a second set of exogenous nucleic acids encoding isopropanol pathway enzymes expressed in a sufficient amount to produce isopropanol, the second set of exogenous nucleic acids encoding an acetyl-CoA acetyl thiolase; an acetoacetyl-CoA transferase or an acetoacetyl-CoA hydrolase or an acetoacetyl-CoA synthetase; an acetoacetate decarboxylase; and an isopropanol dehydrogenase.

In one embodiment, the invention provides a non-naturally occurring microbial organism including a microbial organism having an MAA pathway and an isopropanol pathway, the MAA pathway including a first set of exogenous nucleic acids encoding MAA pathway enzymes expressed in a sufficient amount to produce MAA, the first set of exogenous nucleic acids encoding a methylmalonyl-CoA mutase; a methylmalonyl-CoA transferase, a methylmalonyl-CoA synthetase or a methylmalonyl-CoA hydrolase; a methylmalonate reductase; a 3-hydroxyisobutyrate dehydrogenase; and a 3-hydroxyisobutyrate dehydratase, and the isopropanol pathway comprising a second set of exogenous nucleic acids encoding isopropanol pathway enzymes expressed in a sufficient amount to produce isopropanol, the second set of exogenous nucleic acids encoding an acetyl-CoA acetyl thiolase; an acetoacetyl-CoA transferase or an acetoacetyl-CoA hydrolase or an acetoacetyl-CoA synthetase; an acetoacetate decarboxylase; and an isopropanol dehydrogenase.

In one embodiment, the invention provides a non-naturally occurring microbial organism including a microbial organism having an MAA pathway and an isopropanol pathway, the MAA pathway including a first set of exogenous nucleic acids encoding MAA pathway enzymes expressed in a sufficient amount to produce MAA, the first set of exogenous nucleic acids encoding a methylmalonyl-CoA mutase; a methylmalonyl-CoA epimerase; a methylmalonyl-CoA reductase (alcohol forming); and a 3-hydroxyisobutyrate dehydratase, and the isopropanol pathway comprising a second set of exogenous nucleic acids encoding isopropanol pathway enzymes expressed in a sufficient amount to produce isopropanol, the second set of exogenous nucleic acids encoding an acetyl-CoA acetyl thiolase; an acetoacetyl-CoA transferase or an acetoacetyl-CoA hydrolase or an acetoacetyl-CoA synthetase, an acetoacetate decarboxylase; and an isopropanol dehydrogenase.

In a further aspect of the above embodiments, the microbial organism has an acetyl-CoA pathway having a third set of exogenous nucleic acids encoding acetyl-CoA pathway enzymes expressed in a sufficient amount to produce acetyl-CoA, the third set of exogenous nucleic acids encoding a pyruvate kinase; and a pyruvate dehydrogenase or a pyruvate ferredoxin oxidoreductase; or a pyruvate formate lyase, a pyruvate formate lyase activating enzyme and a formate dehydrogenase.

In another further embodiment, the microbial organism has a succinyl-CoA pathway having a third set of exogenous nucleic acids encoding succinyl-CoA pathway enzymes expressed in a sufficient amount to produce succinyl-CoA, the third set of exogenous nucleic acids encoding a PEP carboxykinase, a PEP carboxylase, a malate dehydrogenase, a fumarase, a fumarate reductase, a succinyl-CoA transferase and a succinyl-CoA synthetase. In a further aspect, the third set of exogenous nucleic acids further encodes a pyruvate carboxylase or a methylmalonyl-CoA carboxytransferase.

In one embodiment, the invention provides a non-naturally occurring microbial organism including a microbial organism having an 14-BDO pathway and an isopropanol pathway, the 14-BDO pathway including a first set of exogenous nucleic acids encoding 14-BDO pathway enzymes expressed in a sufficient amount to produce 14-BDO, the first set of exogenous nucleic acids encoding a PEP carboxykinase, a PEP carboxylase, a malate dehydrogenase, a fumarase, a fumarate reductase, a succinyl-CoA transferase, a succinyl-CoA synthetase, a pyruvate carboxylase, a methylmalonyl-CoA carboxytransferase, a succinyl-CoA reductase, a succinate reductase, a 4-hydroxybutyrate dehydrogenase, a 4-hydroxybutyryl-CoA transferase, a 4-hydroxybutyryl-CoA synthetase, a 4-hydroxybutyryl-CoA reductase (aldehyde-forming), a 4-hydroxybutyraldehyde reductase, a 4-hydroxybutyrate reductase; a 4-hydroxybutyrate kinase, a phosphotrans-4-hydroxybutyrylase, a 4-hydroxybutyryl-phosphate reductase, a 4-hydroxybutyryl-CoA reductase (alcohol-forming), and a 4-hydroxybutyraldehyde reductase, and the isopropanol pathway comprising a second set of exogenous nucleic acids encoding isopropanol pathway enzymes expressed in a sufficient amount to produce isopropanol, the second set of exogenous nucleic acids encoding a pyruvate kinase, a pyruvate dehydrogenase, a pyruvate ferredoxin oxidoreductase, a pyruvate formate lyase, a pyruvate formate lyase activating enzyme, a formate dehydrogenase, an acetyl-CoA acetyl thiolase, an acetoacetyl-CoA transferase, an acetoacetyl-CoA hydrolase, an acetoacetyl-CoA synthetase, an acetoacetate decarboxylase, and an isopropanol dehydrogenase.

In one embodiment, the invention provides a non-naturally occurring microbial organism including a microbial organism having an 13-BDO pathway and an isopropanol pathway, the 13-BDO pathway including a first set of exogenous nucleic acids encoding 13-BDO pathway enzymes expressed in a sufficient amount to produce 13-BDO, the first set of exogenous nucleic acids encoding a PEP carboxykinase, a PEP carboxylase, a malate dehydrogenase, a fumarase, a fumarate reductase, a succinyl-CoA transferase, a succinyl-CoA synthetase, a pyruvate carboxylase, a methylmalonyl-CoA carboxytransferase, a succinyl-CoA reductase, a succinate reductase, a 4-hydroxybutyrate dehydrogenase, a 4-hydroxybutyryl-CoA transferase, a 4-hydroxybutyryl-CoA synthetase, a 4-hydroxybutyrate kinase, a phosphotrans-4-hydroxybutyrylase, a 4-hydroxybutyryl-CoA dehydratase, a crotonase, a 3-hydroxybutyryl-CoA reductase (aldehyde forming), a 3-hydroxybutyraldehyde reductase, a 3-hydroxybutyryl-CoA transferase, a 3-hydroxybutyryl-CoA synthetase, a 3-hydroxybutyryl-CoA hydrolase, a 3-hydroxybutyrate reductase, and a 3-hydroxybutyryl-CoA reductase (alcohol-forming), and the isopropanol pathway comprising a second set of exogenous nucleic acids encoding isopropanol pathway enzymes expressed in a sufficient amount to produce isopropanol, the second set of exogenous nucleic acids encoding a pyruvate kinase, a pyruvate dehydrogenase, a pyruvate ferredoxin oxidoreductase, a pyruvate formate lyase, a pyruvate formate lyase activating enzyme, a formate dehydrogenase, an acetyl-CoA acetyl thiolase, an acetoacetyl-CoA transferase, an acetoacetyl-CoA hydrolase, an acetoacetyl-CoA synthetase, an acetoacetate decarboxylase, and an isopropanol dehydrogenase.

In one embodiment, the invention provides a non-naturally occurring microbial organism including a microbial organism having an MAA pathway and an isopropanol pathway, the MAA pathway including a first set of exogenous nucleic acids encoding MAA pathway enzymes expressed in a sufficient amount to produce MAA, the first set of exogenous nucleic acids encoding a PEP carboxykinase, a PEP carboxylase, a malate dehydrogenase, a fumarase, a fumarate reductase, a succinyl-CoA transferase, a succinyl-CoA synthetase, a pyruvate carboxylase, a methylmalonyl-CoA carboxytransferase, a succinyl-CoA reductase, a succinate reductase, a 4-hydroxybutyrate dehydrogenase, a 4-hydroxybutyryl-CoA transferase, a 4-hydroxybutyryl-CoA synthetase, a 4-hydroxybutyrate kinase, a phosphotrans-4-hydroxybutyrylase, a 4-hydroxybutyryl-CoA mutase, a 3-hydroxyisobutyryl-CoA transferase, a 3-hydroxyisobutyryl-CoA synthetase, a 3-hydroxyisobutyryl-CoA hydrolase, 3-hydroxyisobutyryl-CoA dehydratase, methacrylyl-CoA transferase, methacrylyl-CoA synthetase, methacrylyl-CoA hydrolase and a 3-hydroxyisobutyrate dehydratase, and the isopropanol pathway comprising a second set of exogenous nucleic acids encoding isopropanol pathway enzymes expressed in a sufficient amount to produce isopropanol, the second set of exogenous nucleic acids encoding a pyruvate kinase, a pyruvate dehydrogenase, a pyruvate ferredoxin oxidoreductase, a pyruvate formate lyase, a pyruvate formate lyase activating enzyme, a formate dehydrogenase, an acetyl-CoA acetyl thiolase, an acetoacetyl-CoA transferase, an acetoacetyl-CoA hydrolase, an acetoacetyl-CoA synthetase, an acetoacetate decarboxylase, and an isopropanol dehydrogenase.

In one embodiment, the invention provides a non-naturally occurring microbial organism including a microbial organism having an MAA pathway and an isopropanol pathway, the MAA pathway including a first set of exogenous nucleic acids encoding MAA pathway enzymes expressed in a sufficient amount to produce MAA, the first set of exogenous nucleic acids encoding a PEP carboxykinase, a PEP carboxylase, a malate dehydrogenase, a fumarase, a fumarate reductase, a succinyl-CoA transferase, a succinyl-CoA synthetase, a pyruvate carboxylase, a methylmalonyl-CoA carboxytransferase, a methylmalonyl-CoA mutase, a methylmalonyl-CoA epimerase, a methylmalonyl-CoA transferase, a methylmalonyl-CoA synthetase, a methylmalonyl-CoA hydrolase, a methylmalonate reductase, a methylmalonyl-CoA reductase (aldehyde forming), a 3-hydroxyisobutyrate dehydrogenase, a methylmalonyl-CoA reductase (alcohol forming) and a 3-hydroxyisobutyrate dehydratase, and the isopropanol pathway comprising a second set of exogenous nucleic acids encoding isopropanol pathway enzymes expressed in a sufficient amount to produce isopropanol, the second set of exogenous nucleic acids encoding a pyruvate kinase, a pyruvate dehydrogenase, a pyruvate ferredoxin oxidoreductase, a pyruvate formate lyase, a pyruvate formate lyase activating enzyme, a formate dehydrogenase, an acetyl-CoA acetyl thiolase, an acetoacetyl-CoA transferase, an acetoacetyl-CoA hydrolase, an acetoacetyl-CoA synthetase, an acetoacetate decarboxylase, and an isopropanol dehydrogenase.

In a further aspect of each of the above embodiments, the exogenous nucleic acid is a heterologous nucleic acid.

In a further aspect of each of the above embodiments, the non-naturally occurring microbial organism is in a substantially anaerobic culture medium.

In an additional embodiment, the invention provides a non-naturally occurring microbial organism having an n-propanol and isopropanol pathway, wherein the non-naturally occurring microbial organism comprises at least one exogenous nucleic acid encoding an enzyme or protein that converts a substrate to a product selected from the group consisting of phosphoenolpyruvate to oxaloacetate, oxaloacetate to malate, malate to fumarate, fumarate to succinate, succinate to succinyl-CoA, succinyl-CoA to (R)-methylmalonyl-CoA, (R)-methylmalonyl-CoA to (S)-methylmalonyl-CoA, (S)-methylmalonyl-CoA to propionyl-CoA, propionyl-CoA to propionaldehyde, propionaldehyde to n-propanol, propionyl-CoA to propionyl phosphate, propionyl-CoA to propionate, propionate to propionyl phosphate, propionate to propionaldehyde, propionyl phosphate to propionaldehyde, phosphoenolpyruvate to pyruvate, pyruvate to oxaloacetate, pyruvate to acetyl-CoA, pyruvate to acetyl-CoA and formate, formate to $CO_2$, 2 acetyl-CoA substrates to 1 acetoacetyl-CoA product, acetoacetyl-CoA to acetoacetate, acetoacetate to acetone, acetone to isopropanol. One skilled in the art will understand that these are merely exemplary and that any of the substrate-product pairs disclosed herein suitable to produce a desired product and for which an appropriate activity is available for the conversion of the substrate to the product can be readily determined by one skilled in the art based on the teachings herein. Thus, the invention provides a non-naturally occurring microbial organism containing at least one exogenous nucleic acid encoding an enzyme or protein, where the enzyme or protein converts the substrates and products of an n-propanol and isopropanol pathway, such as that shown in FIG. 1.

In an additional embodiment, the invention provides a non-naturally occurring microbial organism having an n-propanol and isopropanol pathway, wherein the non-naturally occurring microbial organism comprises at least one exogenous nucleic acid encoding an enzyme or protein that converts a substrate to a product selected from the group consisting of phosphoenolpyruvate to oxaloacetate, oxaloacetate to threonine, threonine to 2-oxobutanoate, 2-oxobutanoate to propionyl-CoA, propionyl-CoA to propionaldehyde, propionaldehyde to n-propanol, 2-oxobutanoate to propionaldehyde, propionyl-CoA to propionyl phosphate, propionyl-CoA to propionate, propionate to propionyl phosphate, propionate to propionaldehyde, propionyl phosphate to propionaldehyde, phosphoenolpyruvate to pyruvate, pyruvate to oxaloacetate, pyruvate to acetyl-CoA, pyruvate to acetyl-CoA and formate, formate to $CO_2$, 2 acetyl-CoA substrates to 1 acetoacetyl-CoA product, acetoacetyl-CoA to acetoacetate, acetoacetate to acetone, acetone to isopropanol. One skilled in the art will understand that these are merely exemplary and that any of the substrate-product pairs disclosed herein suitable to produce a desired product and for which an appropriate activity is available for the conversion of the substrate to the product can be readily determined by one skilled in the art based on the teachings herein. Thus, the invention provides a non-naturally occurring microbial organism containing at least one exogenous nucleic acid encoding an enzyme or protein, where the enzyme or protein converts the substrates and products of an n-propanol and isopropanol pathway, such as that shown in FIG. 2.

In an additional embodiment, the invention provides a non-naturally occurring microbial organism having an n-propanol and isopropanol pathway, wherein the non-naturally occurring microbial organism comprises at least one exogenous nucleic acid encoding an enzyme or protein that converts a substrate to a product selected from the group consisting of phosphoenolpyruvate to pyruvate, pyruvate to acetyl-CoA, pyruvate to acetyl-CoA and formate, formate to CO$_2$, acetyl-CoA to malonyl-CoA, malonyl-CoA to malonate semialdehyde, malonate semialdehyde to 3-hydroxypropionate, 3-hydroxypropionate to propionyl-CoA, propionyl-CoA to propionaldehyde, propionaldehyde to n-propanol, propionyl-CoA to propionyl phosphate, propionyl-CoA to propionate, propionate to propionyl phosphate, propionate to propionaldehyde, propionyl phosphate to propionaldehyde, 2 acetyl-CoA substrates to 1 acetoacetyl-CoA product, acetoacetyl-CoA to acetoacetate, acetoacetate to acetone, acetone to isopropanol. One skilled in the art will understand that these are merely exemplary and that any of the substrate-product pairs disclosed herein suitable to produce a desired product and for which an appropriate activity is available for the conversion of the substrate to the product can be readily determined by one skilled in the art based on the teachings herein. Thus, the invention provides a non-naturally occurring microbial organism containing at least one exogenous nucleic acid encoding an enzyme or protein, where the enzyme or protein converts the substrates and products of an n-propanol and isopropanol pathway, such as that shown in FIG. 3.

In an additional embodiment, the invention provides a non-naturally occurring microbial organism having an n-propanol and isopropanol pathway, wherein the non-naturally occurring microbial organism comprises at least one exogenous nucleic acid encoding an enzyme or protein that converts a substrate to a product selected from the group consisting of pyruvate to D-lactate, D-lactate to lactoyl-CoA, lactoyl-CoA to acryloyl-CoA, acryloyl-CoA to propionyl-CoA, propionyl-CoA to propionaldehyde, propionaldehyde to n-propanol, propionyl-CoA to propionyl phosphate, propionyl-CoA to propionate, propionate to propionyl phosphate, propionate to propionaldehyde, propionyl phosphate to propionaldehyde, pyruvate to acetyl-CoA, pyruvate to acetyl-CoA and formate, formate to CO$_2$, 2 acetyl-CoA substrates to 1 acetoacetyl-CoA product, acetoacetyl-CoA to acetoacetate, acetoacetate to acetone, acetone to isopropanol. One skilled in the art will understand that these are merely exemplary and that any of the substrate-product pairs disclosed herein suitable to produce a desired product and for which an appropriate activity is available for the conversion of the substrate to the product can be readily determined by one skilled in the art based on the teachings herein. Thus, the invention provides a non-naturally occurring microbial organism containing at least one exogenous nucleic acid encoding an enzyme or protein, where the enzyme or protein converts the substrates and products of an n-propanol and isopropanol pathway, such as that shown in FIG. 4.

In an additional embodiment, the invention provides a non-naturally occurring microbial organism having an n-propanol pathway, wherein the non-naturally occurring microbial organism comprises at least one exogenous nucleic acid encoding an enzyme or protein that converst a strabstrate to a product selected from the group consisting of propionyl-CoA to propionaldehyde, propionaldehyde to n-propanol, propionyl-CoA to propionyl phosphate, propionyl-CoA to propionate, propionate to propionyl phosphate, propionate to propionaldehyde, and propionyl phosphate to propionaldehyde. One skilled in the art will understand that these are merely exemplary and that any of the substrate-product pairs disclosed herein suitable to produce a desired product and for which an appropriate activity is available for the conversion of the substrate to the product can be readily determined by one skilled in the art based on the teachings herein. Thus, the invention provides a non-naturally occurring microbial organism containing at least one exogenous nucleic acid encoding an enzyme or protein, where the enzyme or protein converts the substrates and products of an n-propanol pathway, such as that shown in FIGS. 1-4.

In an additional embodiment, the invention provides a non-naturally occurring microbial organism having an 14-BDO and an isopropanol pathway, wherein the non-naturally occurring microbial organism comprises at least one exogenous nucleic acid encoding an enzyme or protein that converts a substrate to a product selected from the group consisting of phosphoenolpyruvate to oxaloacetate, oxaloacetate to malate, malate to fumarate, fumarate to succinate, succinate to succinyl-CoA, succinyl-CoA to succinic semialdehyde, succinic semialdehyde to 4-hydroxybutyrate, 4-hydroxybutyrate to 4-hydroxybutyryl-CoA, 4-hydroxybutyryl-CoA to 4-hydroxybutyraldehyde, 4-hydroxybutyraldehyde to 14-BDO, succinate to succinic semialdehyde, 4-hydroxybutyrate to 4-hydroxybutyraldehyde, 4-hydroxybutyrate to 4-hydroxybutyryl-phosphate, 4-hydroxybutyryl-phosphate to 4-hydroxybutyryl-CoA, 4-hydroxybutyryl-phosphate to 4-hydroxybutyraldehyde, 4-hydroxybutyryl-CoA to 14-BDO, propionyl-CoA to propionyl phosphate, propionyl phosphate to propionaldehyde, phosphoenolpyruvate to pyruvate, pyruvate to oxaloacetate, pyruvate to acetyl-CoA, pyruvate to acetyl-CoA and formate, formate to CO$_2$, 2 acetyl-CoA substrates to 1 acetoacetyl-CoA product, acetoacetyl-CoA to acetoacetate, acetoacetate to acetone, acetone to isopropanol. One skilled in the art will understand that these are merely exemplary and that any of the substrate-product pairs disclosed herein suitable to produce a desired product and for which an appropriate activity is available for the conversion of the substrate to the product can be readily determined by one skilled in the art based on the teachings herein. Thus, the invention provides a non-naturally occurring microbial organism containing at least one exogenous nucleic acid encoding an enzyme or protein, where the enzyme or protein converts the substrates and products of an n-propanol and isopropanol pathway, such as that shown in FIG. 5.

In an additional embodiment, the invention provides a non-naturally occurring microbial organism having an 13-BDO and an isopropanol pathway, wherein the non-naturally occurring microbial organism comprises at least one exogenous nucleic acid encoding an enzyme or protein that converts a substrate to a product selected from the group consisting of phosphoenolpyruvate to oxaloacetate, oxaloacetate to malate, malate to fumarate, fumarate to succinate, succinate to succinyl-CoA, succinyl-CoA to succinic semialdehyde, succinic semialdehyde to 4-hydroxybutyrate, 4-hydroxybutyrate to 4-hydroxybutyryl-CoA, succinate to succinic semialdehyde, 4-hydroxybutyrate to 4-hydroxybutyryl-phosphate, 4-hydroxybutyryl-phosphate to 4-hydroxybutyryl-CoA, 4-hydroxybutyryl-CoA to crotonyl-CoA, crotonyl-CoA to 3-hydroxybutyryl-CoA, 3-hydroxybutyryl-CoA to 3-hydroxybutyraldehyde, 3-hydroxybutyryl-CoA to 3-hydroxybutyrate, 3-hydroxybutyrate to 3-hydroxybutyraldehyde, 3-hydroxybutyraldehyde to 13-BDO, 3-hydroxybutyryl-CoA to 13-BDO, propionyl-CoA to propionyl phosphate, propionyl phosphate to propionaldehyde, phosphoenolpyruvate to pyruvate, pyruvate to oxaloacetate, pyruvate to acetyl-CoA, pyruvate to acetyl-CoA and formate, formate to $CO_2$, 2 acetyl-CoA substrates to 1 acetoacetyl-CoA product, acetoacetyl-CoA to acetoacetate, acetoacetate to acetone, acetone to isopropanol. One skilled in the art will understand that these are merely exemplary and that any of the substrate-product pairs disclosed herein suitable to produce a desired product and for which an appropriate activity is available for the conversion of the substrate to the product can be readily determined by one skilled in the art based on the teachings herein. Thus, the invention provides a non-naturally occurring microbial organism containing at least one exogenous nucleic acid encoding an enzyme or protein, where the enzyme or protein converts the substrates and products of an n-propanol and isopropanol pathway, such as that shown in FIG. 6.

In an additional embodiment, the invention provides a non-naturally occurring microbial organism having an MAA and an isopropanol pathway, wherein the non-naturally occurring microbial organism comprises at least one exogenous nucleic acid encoding an enzyme or protein that converts a substrate to a product selected from the group consisting of phosphoenolpyruvate to oxaloacetate, oxaloacetate to malate, malate to fumarate, fumarate to succinate, succinate to succinyl-CoA, succinyl-CoA to succinic semialdehyde, succinic semialdehyde to 4-hydroxybutyrate, 4-hydroxybutyrate to 4-hydroxybutyryl-CoA, succinate to succinic semialdehyde, 4-hydroxybutyrate to 4-hydroxybutyryl-phosphate, 4-hydroxybutyryl-phosphate to 4-hydroxybutyryl-CoA, 4-hydroxybutyryl-CoA to 3-hydroxyisobutyryl-CoA, 3-hydroxyisobutyryl-CoA to 3-hydroxyisobutyrate, 3-hydroxyisobutyryl-CoA to methyacrylyl-CoA, methyacrylyl-CoA to MAA, 3-hydroxyisobutyrate to MAA, succinyl-CoA to (R)-methylmalonyl-CoA, (R)-methylmalonyl-CoA to (S)-methylmalonyl-CoA, (S)-methylmalonyl-CoA to methylmalonate semialdehyde, (S)-methylmalonyl-CoA to 3-hydroxyisobutyrate, methylmalonate semialdehyde to 3-hydroxyisobutyrate, propionyl-CoA to propionyl phosphate, propionyl phosphate to propionaldehyde, phosphoenolpyruvate to pyruvate, pyruvate to oxaloacetate, pyruvate to acetyl-CoA, pyruvate to acetyl-CoA and formate, formate to $CO_2$, 2 acetyl-CoA substrates to 1 acetoacetyl-CoA product, acetoacetyl-CoA to acetoacetate, acetoacetate to acetone, acetone to isopropanol. One skilled in the art will understand that these are merely exemplary and that any of the substrate-product pairs disclosed herein suitable to produce a desired product and for which an appropriate activity is available for the conversion of the substrate to the product can be readily determined by one skilled in the art based on the teachings herein. Thus, the invention provides a non-naturally occurring microbial organism containing at least one exogenous nucleic acid encoding an enzyme or protein, where the enzyme or protein converts the substrates and products of an n-propanol and isopropanol pathway, such as that shown in FIGS. 7 and 8.

While generally described herein as a microbial organism that contains an n-propanol and an isopropanol, a 14-BDO and an isopropanol, a 13-BDO and an isopropanol or a MAA and an isopropanol pathway, it is understood that the invention additionally provides a non-naturally occurring microbial organism comprising at least one exogenous nucleic acid encoding an n-propanol, an isopropanol, a 14-BDO, a 13-BDO and/or MAA pathway enzyme expressed in a sufficient amount to produce an intermediate of an n-propanol, an isopropanol, a 14-BDO, a 13-BDO and/or MAA pathway. For example, as disclosed herein, an n-propanol, an isopropanol, a 14-BDO, a 13-BDO and/or MAA pathway is exemplified in FIGS. 1-8. Therefore, in addition to a microbial organism containing an n-propanol and an isopropanol, a 14-BDO and an isopropanol, a 13-BDO and an isopropanol or a MAA and an isopropanol pathway that produces n-propanol and isopropanol, 14-BDO and isopropanol, 13-BDO and isopropanol or MAA and isopropanol, the invention additionally provides a non-naturally occurring microbial organism comprising at least one exogenous nucleic acid encoding an n-propanol, an isopropanol, a 14-BDO, a 13-BDO and/or MAA pathway enzyme, where the microbial organism produces an n-propanol, an isopropanol, a 14-BDO, a 13-BDO and/or MAA pathway intermediate, for example, acetone, methylmalonyl-CoA, propionyl phosphate, 2-oxobutanoate, 3-hydroxypropionate, lactoyl-CoA, 4-hydroxybutyrate, 4-hydroxybutyryl-phosphate, crotonyl-CoA, succinyl-CoA, succinic semialdehyde or 3-hydroxyisobutyryl-CoA.

It is understood that any of the pathways disclosed herein, as described in the Examples and exemplified in the Figures, including the pathways of FIGS. 1-8, can be utilized to generate a non-naturally occurring microbial organism that produces any pathway intermediate or product, as desired. As disclosed herein, such a microbial organism that produces an intermediate can be used in combination with another microbial organism expressing downstream pathway enzymes to produce a desired product. However, it is understood that a non-naturally occurring microbial organism that produces an n-propanol, an isopropanol, a 14-BDO, a 13-BDO and/or MAA intermediate can be utilized to produce the intermediate as a desired product.

The invention is described herein with general reference to the metabolic reaction, reactant or product thereof, or with specific reference to one or more nucleic acids or genes encoding an enzyme associated with or catalyzing, or a protein associated with, the referenced metabolic reaction, reactant or product. Unless otherwise expressly stated herein, those skilled in the art will understand that reference to a reaction also constitutes reference to the reactants and products of the reaction. Similarly, unless otherwise expressly stated herein, reference to a reactant or product also references the reaction, and reference to any of these metabolic constituents also references the gene or genes encoding the enzymes that catalyze or proteins involved in the referenced reaction, reactant or product. Likewise, given the well known fields of metabolic biochemistry, enzymology and genomics, reference herein to a gene or encoding nucleic acid also constitutes a reference to the corresponding encoded enzyme and the reaction it catalyzes or a protein associated with the reaction as well as the reactants and products of the reaction.

The non-naturally occurring microbial organisms of the invention can be produced by introducing expressible nucleic acids encoding one or more of the enzymes or proteins participating in one or more n-propanol, isopropanol, 14-BDO, 13-BDO and/or MAA biosynthetic pathways. Depending on the host microbial organism chosen for biosynthesis, nucleic acids for some or all of a particular n-propanol, isopropanol, 14-BDO, 13-BDO and/or MAA biosynthetic pathway can be expressed. For example, if a chosen host is deficient in one or more enzymes or proteins for a desired biosynthetic pathway, then expressible nucleic acids for the deficient enzyme(s) or protein(s) are introduced into the host for subsequent exogenous expression. Alternatively, if the chosen host exhibits endogenous expression of some pathway genes, but is deficient in others, then an encoding nucleic acid is needed for the deficient enzyme(s) or protein(s) to achieve n-propanol, isopropanol, 14-BDO, 13-BDO and/or MAA biosynthesis. Thus, a non-naturally occurring microbial organism of the invention can be produced by introducing exogenous enzyme or protein activities to obtain a desired biosynthetic pathway or a desired biosynthetic pathway can be obtained by introducing one or more exogenous enzyme or protein activities that, together with one or more endogenous enzymes or proteins, produces a desired product such as n-propanol, isopropanol, 14-BDO, 13-BDO and/or MAA.

Depending on the n-propanol, isopropanol, 14-BDO, 13-BDO and/or MAA biosynthetic pathway constituents of a selected host microbial organism, the non-naturally occurring microbial organisms of the invention will include at least one exogenously expressed n-propanol, isopropanol, 14-BDO, 13-BDO and/or MAA pathway-encoding nucleic acid and up to all encoding nucleic acids for one or more n-propanol, isopropanol, 14-BDO, 13-BDO and/or MAA biosynthetic pathways. For example, n-propanol, isopropanol, 14-BDO, 13-BDO and/or MAA biosynthesis can be established in a host deficient in a pathway enzyme or protein through exogenous expression of the corresponding encoding nucleic acid. In a host deficient in all enzymes or proteins of an n-propanol, an isopropanol, a 14-BDO, a 13-BDO and/or a MAA pathway, exogenous expression of all enzyme or proteins in the pathway can be included, although it is understood that all enzymes or proteins of a pathway can be expressed even if the host contains at least one of the pathway enzymes or proteins. For example, exogenous expression of all enzymes or proteins in a pathway for production of n-propanol and isopropanol can be included, such as a PEP carboxykinase or a PEP carboxylase; a malate dehydrogenase; a fumarase; a fumarate reductase; a succinyl-CoA transferase or a succinyl-CoA synthetase; a methylmalonyl-CoA mutase; a methylmalonyl-CoA epimerase; a methylmalonyl-CoA decarboxylase; and a propionaldehyde dehydrogenase and a propanol dehydrogenase; or a propionyl-CoA:phosphate propanoyltransferase and a propionyl phosphate reductase, a pyruvate kinase; a pyruvate dehydrogenase or a pyruvate ferredoxin oxidoreductase; or a pyruvate formate lyase, a pyruvate formate lyase activating enzyme and a formate dehydrogenase; an acetyl-CoA acetyl thiolase; an acetoacetyl-CoA transferase or an acetoacetyl-CoA hydrolase or an acetoacetyl-CoA synthetase, an acetoacetate decarboxylase; and an isopropanol dehydrogenase, as exemplified in FIG. 1.

Given the teachings and guidance provided herein, those skilled in the art will understand that the number of encoding nucleic acids to introduce in an expressible form will, at least, parallel the n-propanol, isopropanol, 14-BDO, 13-BDO and/or MAA pathway deficiencies of the selected host microbial organism. Therefore, a non-naturally occurring microbial organism of the invention can have one, two, three, four, five, six, seven, eight, nine, ten, eleven, twelve, thirteen, fourteen, fifteen, sixteen, seventeen, eighteen, nineteen, twenty or twenty one, up to all nucleic acids encoding the enzymes or proteins constituting an n-propanol, an isopropanol, a 14-BDO, a 13-BDO and/or a MAA biosynthetic pathway disclosed herein. In some embodiments, the non-naturally occurring microbial organisms also can include other genetic modifications that facilitate or optimize n-propanol, isopropanol, 14-BDO, 13-BDO and/or MAA biosynthesis or that confer other useful functions onto the host microbial organism. One such other functionality can include, for example, augmentation of the synthesis of one or more of the n-propanol, isopropanol, 14-BDO, 13-BDO and/or MAA pathway precursors such as phosphoenolpyruvate or pyruvate.

Generally, a host microbial organism is selected such that it produces the precursor of an n-propanol, an isopropanol, a 14-BDO, a 13-BDO and/or a MAA pathway, either as a naturally produced molecule or as an engineered product that either provides de novo production of a desired precursor or increased production of a precursor naturally produced by the host microbial organism. For example, phosphoenolpyruvate and pyruvate are produced naturally in a host organism such as E. coli. A host organism can be engineered to increase production of a precursor, as disclosed herein. In addition, a microbial organism that has been engineered to produce a desired precursor can be used as a host organism and further engineered to express enzymes or proteins of an n-propanol, an isopropanol, a 14-BDO, a 13-BDO and/or a MAA pathway.

In some embodiments, a non-naturally occurring microbial organism of the invention is generated from a host that contains the enzymatic capability to synthesize n-propanol, isopropanol, 14-BDO, 13-BDO and/or MAA. In this specific embodiment it can be useful to increase the synthesis or accumulation of an n-propanol, an isopropanol, a 14-BDO, a 13-BDO and/or a MAA pathway product to, for example, drive n-propanol, isopropanol, 14-BDO, 13-BDO and/or MAA pathway reactions toward n-propanol, isopropanol, 14-BDO, 13-BDO and/or MAA production. Increased synthesis or accumulation can be accomplished by, for example, overexpression of nucleic acids encoding one or more of the above-described n-propanol and/or isopropanol pathway enzymes or proteins. Over expression of the enzyme or enzymes and/or protein or proteins of the n-propanol, isopropanol, 14-BDO, 13-BDO and/or MAA pathway can occur, for example, through exogenous expression of the endogenous gene or genes, or through exogenous expression of the heterologous gene or genes. Therefore, naturally occurring organisms can be readily generated to be non-naturally occurring microbial organisms of the invention, for example, producing n-propanol, isopropanol, 14-BDO, 13-BDO and/or MAA, through overexpression of one, two, three, four, five, six, seven, eight, nine, ten, eleven, twelve, thirteen, fourteen, fifteen, sixteen, seventeen, eighteen, nineteen, twenty or twenty one, that is, up to all nucleic acids encoding n-propanol, isopropanol, 14-BDO, 13-BDO and/or MAA biosynthetic pathway enzymes or proteins. In addition, a non-naturally occurring organism can be generated by mutagenesis of an endogenous gene that results in an increase in activity of an enzyme in the n-propanol, isopropanol, 14-BDO, 13-BDO and/or MAA biosynthetic pathway.

In particularly useful embodiments, exogenous expression of the encoding nucleic acids is employed. Exogenous expression confers the ability to custom tailor the expression and/or regulatory elements to the host and application to achieve a desired expression level that is controlled by the user. However, endogenous expression also can be utilized in other embodiments such as by removing a negative regulatory effector or induction of the gene's promoter when linked to an inducible promoter or other regulatory element. Thus, an endogenous gene having a naturally occurring inducible promoter can be up-regulated by providing the appropriate inducing agent, or the regulatory region of an endogenous gene can be engineered to incorporate an inducible regulatory element, thereby allowing the regulation of increased expression of an endogenous gene at a desired time. Similarly, an inducible promoter can be included as a regulatory element for an exogenous gene introduced into a non-naturally occurring microbial organism.

It is understood that, in methods of the invention, any of the one or more exogenous nucleic acids can be introduced into a microbial organism to produce a non-naturally occurring microbial organism of the invention. The nucleic acids can be introduced so as to confer, for example, an n-propanol and isopropanol, 14-BDO and isopropanol, 13-BDO and isopropanol or MAA and isopropanol biosynthetic pathway onto the microbial organism. Alternatively, encoding nucleic acids can be introduced to produce an intermediate microbial organism having the biosynthetic capability to catalyze some of the required reactions to confer n-propanol, isopropanol, 14-BDO, 13-BDO and/or MAA biosynthetic capability. For example, a non-naturally occurring microbial organism having an n-propanol and an isopropanol, a 14-BDO and an isopropanol, a 13-BDO and an isopropanol or a MAA and an isopropanol biosynthetic pathway can comprise at least two exogenous nucleic acids encoding desired enzymes or proteins, such as the combination of propionaldehyde dehydrogenase and isopropanol dehydrogenase, or alternatively propionyl-CoA synthase and acetyl-CoA acetyl thiolase, or alternatively lactate dehydrogenase and acetyl-CoA thiolase, or alternatively a succinyl-CoA reductase and 4-hydroxybutyryl-CoA reductase (alcohol-forming), or alternatively crotonase and acetoacetate decarboxylase, or alternatively 4-hydroxybutyrate kinase and phosphotrans-4-hydroxybutyrylase or alternatively methylmalonyl-CoA reductase (alcohol forming) and pyruvate kinase and the like. Thus, it is understood that any combination of two or more enzymes or proteins of a biosynthetic pathway can be included in a non-naturally occurring microbial organism of the invention. Similarly, it is understood that any combination of three or more enzymes or proteins of a biosynthetic pathway can be included in a non-naturally occurring microbial organism of the invention, for example, PEP carboxykinase, acetyl-CoA acetyl thiolase and propanol dehydrogenase, or alternatively pyruvate kinase, acetoacetate decarboxylase and 2-oxobutanoate dehydrogenase, or alternatively propionyl-CoA:phosphate propanoyltransferase, propionyl phosphate reductase and isopropanol dehydrogenase, or alternatively lactate-CoA transferase and lactyl-CoA dehydratase and pyruvate formate lyase, or alternatively succinyl-CoA dehydrogenase, 4-hydroxybutyrate reductase and 4-hydroxybutyraldehyde reductase, or alternatively crotonase, PEP carboxylase and acetoacetate decarboxylase, or alternatively 3-hydroxyisobutyryl-CoA synthetase, fumarase and isopropanol dehydrogenase, or alternatively acetyl-CoA acetyl thiolase, acetoacetate decarboxylase and methylmalonyl-CoA reductase (alcohol forming) and so forth, as desired, so long as the combination of enzymes and/or proteins of the desired biosynthetic pathway results in production of the corresponding desired product. Similarly, any combination of four or more enzymes or proteins of a biosynthetic pathway as disclosed herein, for example, pyruvate carboxylase, malate dehydrogenase, methylmalonyl-CoA epimerase and acetoacetyl-CoA hydrolase, or alternatively acetyl-CoA acetyl thiolase, isopropanol dehydrogenase, propionaldehyde dehydrogenase and propanol dehydrogenase, or alternatively acetyl-CoA carboxylase, malonyl-CoA reductase, malonate semialdehyde and acetoacetate decarboxylase, or alternatively, acryloyl CoA reductase, acetoacetyl-CoA transferase, acetoacetate decarboxylase, and isopropanol dehydrogenase, or alternatively succinyl-CoA dehydrogenase, 4-hydroxybutyrate dehydrogenase, 4-hydroxybutyryl-CoA transferase, and isopropanol dehydrogenase, or alternatively succinate reductase, 3-hydroxyisobutyryl-CoA synthetase, 3-hydroxyisobutyrate dehydratase and pyruvate ferredoxin oxidoreductase, or alternatively acetyl-CoA acetyl thiolase, acetoacetyl-CoA transferase, methylmalonyl-CoA mutase and hydroxyisobutyrate dehydratase, can be included in a non-naturally occurring microbial organism of the invention, as desired, so long as the combination of enzymes and/or proteins of the desired biosynthetic pathway results in production of the corresponding desired product.

It is understood that when more than one exogenous nucleic acid is included in a microbial organism that the more than one exogenous nucleic acids refers to the referenced encoding nucleic acid or biosynthetic activity, as discussed above. It is further understood, as disclosed herein, that more than one exogenous nucleic acids can be introduced into the host microbial organism on separate nucleic acid molecules, on polycistronic nucleic acid molecules, or a combination thereof, and still be considered as more than one exogenous nucleic acid. For example, as disclosed herein a microbial organism can be engineered to express two or more exogenous nucleic acids encoding a desired pathway enzyme or protein. In the case where two exogenous nucleic acids encoding a desired activity are introduced into a host microbial organism, it is understood that the two exogenous nucleic acids can be introduced as a single nucleic acid, for example, on a single plasmid, on separate plasmids, can be integrated into the host chromosome at a single site or multiple sites, and still be considered as two exogenous nucleic acids. Similarly, it is understood that more than two exogenous nucleic acids can be introduced into a host organism in any desired combination, for example, on a single plasmid, on separate plasmids, can be integrated into the host chromosome at a single site or multiple sites, and still be considered as two or more exogenous nucleic acids, for example three exogenous nucleic acids. Thus, the number of referenced exogenous nucleic acids or biosynthetic activities refers to the number of encoding nucleic acids or the number of biosynthetic activities, not the number of separate nucleic acids introduced into the host organism.

In addition to the biosynthesis of n-propanol, isopropanol, 14-BDO, 13-BDO and/or MAA as described herein, the non-naturally occurring microbial organisms and methods of the invention also can be utilized in various combinations with each other and with other microbial organisms and methods well known in the art to achieve product biosynthesis by other routes. For example, one alternative to produce n-propanol, isopropanol, 14-BDO, 13-BDO and/or MAA other than use of the n-propanol, isopropanol, 14-BDO, 13-BDO and/or MAA producers is through addition of another microbial organism capable of converting an n-propanol, an isopropanol, a 14-BDO, a 13-BDO and/or a MAA pathway intermediate to n-propanol, isopropanol, 14-BDO, 13-BDO and/or MAA. One such procedure includes, for example, the fermentation of a microbial organism that produces an n-propanol, an isopropanol, a 14-BDO, a 13-BDO and/or a MAA pathway intermediate. The n-propanol and isopropanol, 14-BDO and isopropanol, 13-BDO and isopropanol or MAA and isopropanol pathway intermediate can then be used as a substrate for a second microbial organism that converts the n-propanol, isopropanol, 14-BDO, 13-BDO and/or MAA pathway intermediate to n-propanol, isopropanol, 14-BDO, 13-BDO and/or MAA. The n-propanol, isopropanol, 14-BDO, 13-BDO and/or MAA pathway intermediate can be added directly to another culture of the second organism or the original culture of the n-propanol, isopropanol, 14-BDO, 13-BDO and/or MAA pathway intermediate producers can be depleted of these microbial organisms by, for example, cell separation, and then subsequent addition of the second organism to the fermentation broth can be utilized to produce the final product without intermediate purification steps.

In other embodiments, the non-naturally occurring microbial organisms and methods of the invention can be assembled in a wide variety of subpathways to achieve biosynthesis of, for example, n-propanol and isopropanol, 14-BDO and isopropanol, 13-BDO and isopropanol or MAA and isopropanol. In these embodiments, biosynthetic pathways for a desired product of the invention can be segregated into different microbial organisms, and the different microbial organisms can be co-cultured to produce the final product. In such a biosynthetic scheme, the product of one microbial organism is the substrate for a second microbial organism until the final product is synthesized. For example, the biosynthesis of n-propanol, isopropanol, 14-BDO, 13-BDO and/or MAA can be accomplished by constructing a microbial organism that contains biosynthetic pathways for conversion of one pathway intermediate to another pathway intermediate or the product. Alternatively, n-propanol, isopropanol, 14-BDO, 13-BDO and/or MAA also can be biosynthetically produced from microbial organisms through co-culture or co-fermentation using two organisms in the same vessel, where the first microbial organism produces a propionyl-CoA, succinyl-CoA and/or an acetyl-CoA intermediate and the second microbial organism converts the intermediate(s) to n-propanol, isopropanol, 14-BDO, 13-BDO and/or MAA.

Given the teachings and guidance provided herein, those skilled in the art will understand that a wide variety of combinations and permutations exist for the non-naturally occurring microbial organisms and methods of the invention together with other microbial organisms, with the co-culture of other non-naturally occurring microbial organisms having subpathways and with combinations of other chemical and/or biochemical procedures well known in the art to produce n-propanol, isopropanol, 14-BDO, 13-BDO and/or MAA.

Sources of encoding nucleic acids for an n-propanol, an isopropanol, a 14-BDO, a 13-BDO and/or a MAA pathway enzyme or protein can include, for example, any species where the encoded gene product is capable of catalyzing the referenced reaction. Such species include both prokaryotic and eukaryotic organisms including, but not limited to, bacteria, including archaea and eubacteria, and eukaryotes, including yeast, plant, insect, animal, and mammal, including human. Exemplary species for such sources include, for example, *Escherichia coli, Acetobacter pasteurians, Acidanus brierleyi, Acinetobacter baylyi Acinetobacter calcoaceticus, Acinetobacter* sp. Strain M-1, *Actinobacillus succinogenes, Anaerobiospirillum succiniciproducens, Anaerostipes caccae* DSM 14662, *Arabidopsis thaliana, Bacillus cereus* ATCC 14579, *Bacillus subtilis, Bacillus subtilis* subsp. *subtilis* str. 168, *Bos taurus, Bradyrhizobium japonicum* USDA110, *Caenorhabditis elegans, Campylobacter jejuni, Chlamydomonas reinhardtii, Chloroflexus aurantiacus, Clostridium acetobutylicum, Clostridium acetobutylicum* ATCC 824, *Clostridium beijerinckii, Clostridium botulinum* C str. *Eklund, Clostridium kluyveri, Clostridium kluyveri* DSM 555, *Clostridium novyi-*NT, *Clostridium propionicum, Clostridium saccharobutylicum, Clostridium saccharoperbutylacetonicum, Corynebacterium glutamicum, Desulfovibrio africanus, Erythrobacter* sp. NAP1, *Escherichia coli* K12, *Escherichia coli* K12 str. MG1655, *Escherichia coli* O157:H7, *Geobacillus thermoglucosidasius* M10EXG, *Haemophilus influenza, Helicobacter pylori, Homo sapiens, Klebsiella pneumonia* MGH78578, *Kluyveromyces lactis, Lactobacillus casei, Lactobacillus plantarum* WCFS1, *Lactococcus lactis, Leuconostoc mesenteroides, Mannheimia succiniciproducens,* marine gamma proteobacterium HTCC2080, *Mesorhizobium loti, Metallosphaera sedula, Methylobacterium extorquens, Moorella thermoacetica, Mycobacterium smegmatis, Mycobacterium tuberculosis, Oryctolagus cuniculus, Plasmodium ovale, Porphyromonas gingivalis, Propionibacterium acnes, Propionibacterium fredenreichii* sp. *shermanii, Propionibacterium freudenreichii, Propionigenium modestum, Pseudomonas aeruginosa, Pseudomonas aeruginosa* PA01, *Pseudomonas fluorescens, Pseudomonas putida, Pseudomonas putida* E23, *Pseudomonas putida* KT2440, *Pseudomonas* sp, *Pseudomonas stutzeri, Ralstonia eutropha, Ralstonia eutropha* H16, *Rattus norvegicus, Rhodobacter spaeroides, Rhodoferax ferrireducens* DSM 15236, *Rhodospirillum rubrum, Roseiflexus castenholzii, Saccharomyces cerevisiae, Salmonella enterica, Salmonella typhimurium, Shigella flexneri, Simmondsia chinensis, Streptococcus mutans, Sulfolobus acidocaldarius, Sulfolobus solfataricus, Sulfolobus tokodaii, Syntrophobacter fumaroxidans, Thermococcus litoralis, Thermotoga maritime, Thermus thermophilus, Trichomonas vaginalis* G3, *Trypanosoma brucei, Veillonella parvula, Yersinia frederiksenii, Zymomonas mobilis, Bacillus megaterium,* butyrate-producing bacterium L2-50, *Clostridium aminobutyricum, Geobacillus thermoglucosidasius, Mycobacterium bovis* BCG, *Nocardia farcinica* IFM 10152, *Nocardia iowensis* (sp. NRRL 5646), *Penicillium chrysogenum, Porphyromonas gingivalis* ATCC 33277, *Pseudomonas mendocina, Streptomyces griseus* subsp. *griseus* NBRC 13350 as well as other exemplary species disclosed herein are available as source organisms for corresponding genes. However, with the complete genome sequence available for now more than 550 species (with more than half of these available on public databases such as the NCBI), including 395 microorganism genomes and a variety of yeast, fungi, plant, and mammalian genomes, the identification of genes encoding the requisite n-propanol, isopropanol, 14-BDO, 13-BDO and/or MAA biosynthetic activity for one or more genes in related or distant species, including for example, homologues, orthologs, paralogs and nonorthologous gene displacements of known genes, and the interchange of genetic alterations between organisms is routine and well known in the art. Accordingly, the metabolic alterations allowing biosynthesis of n-propanol, isopropanol, 14-BDO, 13-BDO and/or MAA described herein with reference to a particular organism such as *E. coli* can be readily applied to other microorganisms, including prokaryotic and eukaryotic organisms alike. Given the teachings and guidance provided herein, those skilled in the art will know that a metabolic alteration exemplified in one organism can be applied equally to other organisms.

In some instances, such as when an alternative n-propanol, isopropanol, 14-BDO, 13-BDO and/or MAA biosynthetic pathway exists in an unrelated species, n-propanol, isopropanol, 14-BDO, 13-BDO and/or MAA biosynthesis can be conferred onto the host species by, for example, exogenous expression of a paralog or paralogs from the unrelated species that catalyzes a similar, yet non-identical metabolic reaction to replace the referenced reaction. Because certain differences among metabolic networks exist between different organisms, those skilled in the art will understand that the actual gene usage between different organisms may differ. However, given the teachings and guidance provided herein, those skilled in the art also will understand that the teachings and methods of the invention can be applied to all microbial organisms using the cognate metabolic alterations to those exemplified herein to construct a microbial organism in a species of interest that will synthesize n-propanol, isopropanol, 14-BDO, 13-BDO and/or MAA.

Host microbial organisms can be selected from, and the non-naturally occurring microbial organisms generated in, for example, bacteria, yeast, fungus or any of a variety of other microorganisms applicable to fermentation processes. Exemplary bacteria include species selected from *Escherichia coli, Klebsiella oxytoca, Anaerobiospirillum succiniciproducens, Actinobacillus succinogenes, Mannheimia succiniciproducens, Rhizobium etli, Bacillus subtilis, Corynebacterium glutamicum, Gluconobacter oxydans, Zymomonas mobilis, Lactococcus lactis, Lactobacillus plantarum, Streptomyces coelicolor, Clostridium acetobutylicum,*

*Pseudomonas fluorescens*, and *Pseudomonas putida*. Exemplary yeasts or fungi include species selected from *Saccharomyces cerevisiae, Schizosaccharomyces pombe, Kluyveromyces lactis, Kluyveromyces marxianus, Aspergillus terreus, Aspergillus niger* and *Pichia pastoris*. *E. coli* is a particularly useful host organism since it is a well characterized microbial organism suitable for genetic engineering. Other particularly useful host organisms include yeast such as *Saccharomyces cerevisiae*. Other particularly useful host organisms include microbial organisms which naturally produce sufficient quantities of propionyl-CoA and/or acetyl-CoA for co-production of n-propanol and isopropanol. Examples of such organisms include, but are not limited to, *Clostrium propionicum, Escherichia coli* and *Propionibacterium freudenreichii* subsp. *shermanii*.

Methods for constructing and testing the expression levels of a non-naturally occurring n-propanol-, isopropanol-, 14-BDO-, 13-BDO- and/or MAA-producing host can be performed, for example, by recombinant and detection methods well known in the art. Such methods can be found described in, for example, Sambrook et al., *Molecular Cloning: A Laboratory Manual*, Third Ed., Cold Spring Harbor Laboratory, New York (2001); and Ausubel et al., *Current Protocols in Molecular Biology*, John Wiley and Sons, Baltimore, Md. (1999).

Exogenous nucleic acid sequences involved in a pathway for production of n-propanol and isopropanol, 14-BDO and isopropanol, 13-BDO and isopropanol or MAA and isopropanol can be introduced stably or transiently into a host cell using techniques well known in the art including, but not limited to, conjugation, electroporation, chemical transformation, transduction, transfection, and ultrasound transformation. For exogenous expression in *E. coli* or other prokaryotic cells, some nucleic acid sequences in the genes or cDNAs of eukaryotic nucleic acids can encode targeting signals such as an N-terminal mitochondrial or other targeting signal, which can be removed before transformation into prokaryotic host cells, if desired. For example, removal of a mitochondrial leader sequence led to increased expression in *E. coli* (Hoffmeister et al., *J. Biol. Chem.* 280:4329-4338 (2005)). For exogenous expression in yeast or other eukaryotic cells, genes can be expressed in the cytosol without the addition of leader sequence, or can be targeted to mitochondrion or other organelles, or targeted for secretion, by the addition of a suitable targeting sequence such as a mitochondrial targeting or secretion signal suitable for the host cells. Thus, it is understood that appropriate modifications to a nucleic acid sequence to remove or include a targeting sequence can be incorporated into an exogenous nucleic acid sequence to impart desirable properties. Furthermore, genes can be subjected to codon optimization with techniques well known in the art to achieve optimized expression of the proteins.

An expression vector or vectors can be constructed to include one or more n-propanol, isopropanol, 14-BDO, 13-BDO and/or MAA biosynthetic pathway encoding nucleic acids as exemplified herein operably linked to expression control sequences functional in the host organism. Expression vectors applicable for use in the microbial host organisms of the invention include, for example, plasmids, phage vectors, viral vectors, episomes and artificial chromosomes, including vectors and selection sequences or markers operable for stable integration into a host chromosome. Additionally, the expression vectors can include one or more selectable marker genes and appropriate expression control sequences. Selectable marker genes also can be included that, for example, provide resistance to antibiotics or toxins, complement auxotrophic deficiencies, or supply critical nutrients not in the culture media. Expression control sequences can include constitutive and inducible promoters, transcription enhancers, transcription terminators, and the like which are well known in the art. When two or more exogenous encoding nucleic acids are to be co-expressed, both nucleic acids can be inserted, for example, into a single expression vector or in separate expression vectors. For single vector expression, the encoding nucleic acids can be operationally linked to one common expression control sequence or linked to different expression control sequences, such as one inducible promoter and one constitutive promoter. The transformation of exogenous nucleic acid sequences involved in a metabolic or synthetic pathway can be confirmed using methods well known in the art. Such methods include, for example, nucleic acid analysis such as Northern blots or polymerase chain reaction (PCR) amplification of mRNA, or immunoblotting for expression of gene products, or other suitable analytical methods to test the expression of an introduced nucleic acid sequence or its corresponding gene product. It is understood by those skilled in the art that the exogenous nucleic acid is expressed in a sufficient amount to produce the desired product, and it is further understood that expression levels can be optimized to obtain sufficient expression using methods well known in the art and as disclosed herein.

Directed evolution is a powerful approach that involves the introduction of mutations targeted to a specific gene in order to improve and/or alter the properties of an enzyme. Improved and/or altered enzymes can be identified through the development and implementation of sensitive high-throughput screening assays that allow the automated screening of many enzyme variants (e.g., >$10^4$). Iterative rounds of mutagenesis and screening typically are performed to afford an enzyme with optimized properties. Computational algorithms that can help to identify areas of the gene for mutagenesis also have been developed and can significantly reduce the number of enzyme variants that need to be generated and screened.

Numerous directed evolution technologies have been developed (for reviews, see Hibbert et al., *Biomol. Eng* 22:11-19 (2005); Huisman and Lalonde, In Biocatalysis in the pharmaceutical and biotechnology industries pgs. 717-742 (2007), Patel (ed.), CRC Press; Otten and Quax. *Biomol. Eng* 22:1-9 (2005); and Sen et al., *Appl Biochem. Biotechnol* 143: 212-223 (2007)) to be effective at creating diverse variant libraries and these methods have been successfully applied to the improvement of a wide range of properties across many enzyme classes.

Enzyme characteristics that have been improved and/or altered by directed evolution technologies include, for example, selectivity/specificity—for conversion of non-natural substrates; temperature stability—for robust high temperature processing; pH stability—for bioprocessing under lower or higher pH conditions; substrate or product tolerance—so that high product titers can be achieved; binding ($K_m$)—broadens substrate binding to include non-natural substrates; inhibition ($K_i$)—to remove inhibition by products, substrates, or key intermediates; activity (kcat)—increases enzymatic reaction rates to achieve desired flux; expression levels—increases protein yields and overall pathway flux; oxygen stability—for operation of air sensitive enzymes under aerobic conditions; and anaerobic activity—for operation of an aerobic enzyme in the absence of oxygen.

The following exemplary methods have been developed for the mutagenesis and diversification of genes to target desired properties of specific enzymes. Any of these can be used to alter/optimize activity of a decarboxylase enzyme.

EpPCR (Pritchard et al., *J Theor. Biol* 234:497-509 (2005)) introduces random point mutations by reducing the fidelity of DNA polymerase in PCR reactions by the addition of $Mn^{2+}$ ions, by biasing dNTP concentrations, or by other conditional variations. The five step cloning process to confine the mutagenesis to the target gene of interest involves: 1) error-prone PCR amplification of the gene of interest; 2) restriction enzyme digestion; 3) gel purification of the desired DNA fragment; 4) ligation into a vector; 5) transformation of the gene variants into a suitable host and screening of the library for improved performance. This method can generate multiple mutations in a single gene simultaneously, which can be useful. A high number of mutants can be generated by EpPCR, so a high-throughput screening assay or a selection method (especially using robotics) is useful to identify those with desirable characteristics.

Error-prone Rolling Circle Amplification (epRCA) (Fujii et al., *Nucleic Acids Res* 32:e145 (2004); and Fujii et al., *Nat. Protoc.* 1:2493-2497 (2006)) has many of the same elements as epPCR except a whole circular plasmid is used as the template and random 6-mers with exonuclease resistant thiophosphate linkages on the last 2 nucleotides are used to amplify the plasmid followed by transformation into cells in which the plasmid is re-circularized at tandem repeats. Adjusting the $Mn^{2+}$ concentration can vary the mutation rate somewhat. This technique uses a simple error-prone, single-step method to create a full copy of the plasmid with 3-4 mutations/kbp. No restriction enzyme digestion or specific primers are required. Additionally, this method is typically available as a kit.

DNA or Family Shuffling (Stemmer, *Proc Natl Acad Sci U.S.A.* 91:10747-10751 (1994); and Stemmer, *Nature* 370:389-391 (1994)) typically involves digestion of two or more variant genes with nucleases such as Dnase I or EndoV to generate a pool of random fragments that are reassembled by cycles of annealing and extension in the presence of DNA polymerase to create a library of chimeric genes. Fragments prime each other and recombination occurs when one copy primes another copy (template switch). This method can be used with >1 kbp DNA sequences. In addition to mutational recombinants created by fragment reassembly, this method introduces point mutations in the extension steps at a rate similar to error-prone PCR. The method can be used to remove deleterious, random and neutral mutations that might confer antigenicity.

Staggered Extension (StEP) (Zhao et al., *Nat. Biotechnol* 16:258-261 (1998)) entails template priming followed by repeated cycles of 2 step PCR with denaturation and very short duration of annealing/extension (as short as 5 sec). Growing fragments anneal to different templates and extend further, which is repeated until full-length sequences are made. Template switching means most resulting fragments have multiple parents. Combinations of low-fidelity polymerases (Taq and Mutazyme) reduce error-prone biases because of opposite mutational spectra.

In Random Priming Recombination (RPR) random sequence primers are used to generate many short DNA fragments complementary to different segments of the template. (Shao et al., *Nucleic Acids Res* 26:681-683 (1998)) Base misincorporation and mispriming via epPCR give point mutations. Short DNA fragments prime one another based on homology and are recombined and reassembled into full-length by repeated thermocycling. Removal of templates prior to this step assures low parental recombinants. This method, like most others, can be performed over multiple iterations to evolve distinct properties. This technology avoids sequence bias, is independent of gene length, and requires very little parent DNA for the application.

In Heteroduplex Recombination linearized plasmid DNA is used to form heteroduplexes that are repaired by mismatch repair. (Volkov et al, *Nucleic Acids Res* 27:e18 (1999); and Volkov et al., *Methods Enzymol.* 328:456-463 (2000)) The mismatch repair step is at least somewhat mutagenic. Heteroduplexes transform more efficiently than linear homoduplexes. This method is suitable for large genes and whole operons.

Random Chimeragenesis on Transient Templates (RACHITT) (Coco et al., *Nat. Biotechnol* 19:354-359 (2001)) employs Dnase I fragmentation and size fractionation of ssDNA. Homologous fragments are hybridized in the absence of polymerase to a complementary ssDNA scaffold. Any overlapping unhybridized fragment ends are trimmed down by an exonuclease. Gaps between fragments are filled in, and then ligated to give a pool of full-length diverse strands hybridized to the scaffold (that contains U to preclude amplification). The scaffold then is destroyed and is replaced by a new strand complementary to the diverse strand by PCR amplification. The method involves one strand (scaffold) that is from only one parent while the priming fragments derive from other genes; the parent scaffold is selected against. Thus, no reannealing with parental fragments occurs. Overlapping fragments are trimmed with an exonuclease. Otherwise, this is conceptually similar to DNA shuffling and StEP. Therefore, there should be no siblings, few inactives, and no unshuffled parentals. This technique has advantages in that few or no parental genes are created and many more crossovers can result relative to standard DNA shuffling.

Recombined Extension on Truncated templates (RETT) entails template switching of unidirectionally growing strands from primers in the presence of unidirectional ssDNA fragments used as a pool of templates. (Lee et al., *J. Molec. Catalysis* 26:119-129 (2003)) No DNA endonucleases are used. Unidirectional ssDNA is made by DNA polymerase with random primers or serial deletion with exonuclease. Unidirectional ssDNA are only templates and not primers. Random priming and exonucleases don't introduce sequence bias as true of enzymatic cleavage of DNA shuffling/RACHITT. RETT can be easier to optimize than StEP because it uses normal PCR conditions instead of very short extensions. Recombination occurs as a component of the PCR steps—no direct shuffling. This method can also be more random than StEP due to the absence of pauses.

In Degenerate Oligonucleotide Gene Shuffling (DOGS) degenerate primers are used to control recombination between molecules; (Bergquist and Gibbs, *Methods Mol. Biol.* 352:191-204 (2007); Bergquist et al., *Biomol. Eng* 22:63-72 (2005); Gibbs et al., *Gene* 271:13-20 (2001)) this can be used to control the tendency of other methods such as DNA shuffling to regenerate parental genes. This method can be combined with random mutagenesis (epPCR) of selected gene segments. This can be a good method to block the reformation of parental sequences. No endonucleases are needed. By adjusting input concentrations of segments made, one can bias towards a desired backbone. This method allows DNA shuffling from unrelated parents without restriction enzyme digests and allows a choice of random mutagenesis methods.

Incremental Truncation for the Creation of Hybrid Enzymes (ITCHY) creates a combinatorial library with 1 base pair deletions of a gene or gene fragment of interest. (Ostermeier et al., *Proc Natl Acad Sci U.S.A.* 96:3562-3567 (1999); and Ostermeier et al., *Nat. Biotechnol* 17:1205-1209 (1999)) Truncations are introduced in opposite direction on pieces of 2 different genes. These are ligated together and the fusions are cloned. This technique does not require homology between the 2 parental genes. When ITCHY is combined with DNA shuffling, the system is called SCRATCHY (see below). A major advantage of both is no need for homology between parental genes; for example, functional fusions between an *E. coli* and a human gene were created via ITCHY. When ITCHY libraries are made, all possible crossovers are captured.

Thio-Incremental Truncation for the Creation of Hybrid Enzymes (THIO-ITCHY) is similar to ITCHY except that phosphothioate dNTPs are used to generate truncations. (Lutz et al., *Nucleic Acids Res* 29:E16 (2001)) Relative to ITCHY, THIO-ITCHY can be easier to optimize, provide more reproducibility, and adjustability.

SCRATCHY combines two methods for recombining genes, ITCHY and DNA shuffling. (Lutz et al., *Proc Natl Acad Sci U.S.A.* 98:11248-11253 (2001)) SCRATCHY combines the best features of ITCHY and DNA shuffling. First, ITCHY is used to create a comprehensive set of fusions between fragments of genes in a DNA homology-independent fashion. This artificial family is then subjected to a DNA-shuffling step to augment the number of crossovers. Computational predictions can be used in optimization. SCRATCHY is more effective than DNA shuffling when sequence identity is below 80%.

In Random Drift Mutagenesis (RNDM) mutations made via epPCR followed by screening/selection for those retaining usable activity. (Bergquist et al., *Biomol. Eng* 22:63-72 (2005)) Then, these are used in DOGS to generate recombinants with fusions between multiple active mutants or between active mutants and some other desirable parent. Designed to promote isolation of neutral mutations; its purpose is to screen for retained catalytic activity whether or not this activity is higher or lower than in the original gene. RNDM is usable in high throughput assays when screening is capable of detecting activity above background. RNDM has been used as a front end to DOGS in generating diversity. The technique imposes a requirement for activity prior to shuffling or other subsequent steps; neutral drift libraries are indicated to result in higher/quicker improvements in activity from smaller libraries. Though published using epPCR, this could be applied to other large-scale mutagenesis methods.

Sequence Saturation Mutagenesis (SeSaM) is a random mutagenesis method that: 1) generates pool of random length fragments using random incorporation of a phosphothioate nucleotide and cleavage; this pool is used as a template to 2) extend in the presence of "universal" bases such as inosine; 3) replication of a inosine-containing complement gives random base incorporation and, consequently, mutagenesis. (Wong et al., *Biotechnol J* 3:74-82 (2008); Wong et al., *Nucleic Acids Res* 32:e26 (2004); and Wong et al., *Anal. Biochem.* 341:187-189 (2005)) Using this technique it can be possible to generate a large library of mutants within 2-3 days using simple methods. This technique is non-directed in comparison to the mutational bias of DNA polymerases. Differences in this approach make this technique complementary (or an alternative) to epPCR.

In Synthetic Shuffling, overlapping oligonucleotides are designed to encode "all genetic diversity in targets" and allow a very high diversity for the shuffled progeny. (Ness et al., Nat. Biotechnol 20:1251-1255 (2002)) In this technique, one can design the fragments to be shuffled. This aids in increasing the resulting diversity of the progeny. One can design sequence/codon biases to make more distantly related sequences recombine at rates approaching those observed with more closely related sequences. Additionally, the technique does not require physically possessing the template genes.

Nucleotide Exchange and Excision Technology NexT exploits a combination of dUTP incorporation followed by treatment with uracil DNA glycosylase and then piperidine to perform endpoint DNA fragmentation. (Muller et al., *Nucleic Acids Res* 33:e117 (2005)) The gene is reassembled using internal PCR primer extension with proofreading polymerase. The sizes for shuffling are directly controllable using varying dUPT::dTTP ratios. This is an end point reaction using simple methods for uracil incorporation and cleavage. Other nucleotide analogs, such as 8-oxo-guanine, can be used with this method. Additionally, the technique works well with very short fragments (86 bp) and has a low error rate. The chemical cleavage of DNA used in this technique results in very few unshuffled clones.

In Sequence Homology-Independent Protein Recombination (SHIPREC) a linker is used to facilitate fusion between two distantly/unrelated genes. Nuclease treatment is used to generate a range of chimeras between the two genes. These fusions result in libraries of single-crossover hybrids. (Sieber et al., *Nat. Biotechnol* 19:456-460 (2001)) This produces a limited type of shuffling and a separate process is required for mutagenesis. In addition, since no homology is needed this technique can create a library of chimeras with varying fractions of each of the two unrelated parent genes. SHIPREC was tested with a heme-binding domain of a bacterial CP450 fused to N-terminal regions of a mammalian CP450; this produced mammalian activity in a more soluble enzyme.

In Gene Site Saturation Mutagenesis™ (GSSM™) the starting materials are a supercoiled dsDNA plasmid containing an insert and two primers which are degenerate at the desired site of mutations. (Kretz et al., Methods Enzymol. 388:3-11 (2004)) Primers carrying the mutation of interest, anneal to the same sequence on opposite strands of DNA. The mutation is typically in the middle of the primer and flanked on each side by ~20 nucleotides of correct sequence. The sequence in the primer is NNN or NNK (coding) and MNN (noncoding) (N=all 4, K=G, T, M=A, C). After extension, DpnI is used to digest dam-methylated DNA to eliminate the wild-type template. This technique explores all possible amino acid substitutions at a given locus (i.e., one codon). The technique facilitates the generation of all possible replacements at a single-site with no nonsense codons and results in equal to near-equal representation of most possible alleles. This technique does not require prior knowledge of the structure, mechanism, or domains of the target enzyme. If followed by shuffling or Gene Reassembly, this technology creates a diverse library of recombinants containing all possible combinations of single-site up-mutations. The utility of this technology combination has been demonstrated for the successful evolution of over 50 different enzymes, and also for more than one property in a given enzyme.

Combinatorial Cassette Mutagenesis (CCM) involves the use of short oligonucleotide cassettes to replace limited regions with a large number of possible amino acid sequence alterations. (Reidhaar-Olson et al. *Methods Enzymol*. 208: 564-586 (1991); and Reidhaar-Olson et al. *Science* 241:53-57 (1988)) Simultaneous substitutions at two or three sites are possible using this technique. Additionally, the method tests a large multiplicity of possible sequence changes at a limited range of sites. This technique has been used to explore the information content of the lambda repressor DNA-binding domain.

Combinatorial Multiple Cassette Mutagenesis (CMCM) is essentially similar to CCM except it is employed as part of a larger program: 1) Use of epPCR at high mutation rate to 2) ID hot spots and hot regions and then 3) extension by CMCM to cover a defined region of protein sequence space. (Reetz, M. T., S. Wilensek, D. Zha, and K. E. Jaeger, 2001, Directed Evolution of an Enantioselective Enzyme through Combinatorial Multiple-Cassette Mutagenesis. Angew. Chem. Int. Ed Engl. 40:3589-3591.) As with CCM, this method can test virtually all possible alterations over a target region. If used along with methods to create random mutations and shuffled genes, it provides an excellent means of generating diverse, shuffled proteins. This approach was successful in increasing, by 51-fold, the enantioselectivity of an enzyme.

In the Mutator Strains technique conditional is mutator plasmids allow increases of 20- to 4000-X in random and natural mutation frequency during selection and block accumulation of deleterious mutations when selection is not required. (Selifonova et al., *Appl Environ Microbiol* 67:3645-3649 (2001)) This technology is based on a plasmid-derived mutD5 gene, which encodes a mutant subunit of DNA polymerase III. This subunit binds to endogenous DNA polymerase III and compromises the proofreading ability of polymerase III in any strain that harbors the plasmid. A broad-spectrum of base substitutions and frameshift mutations occur. In order for effective use, the mutator plasmid should be removed once the desired phenotype is achieved; this is accomplished through a temperature sensitive origin of replication, which allows for plasmid curing at 41° C. It should be noted that mutator strains have been explored for quite some time (e.g., see Low et al., *J. Mol. Biol.* 260:359-3680 (1996)). In this technique very high spontaneous mutation rates are observed. The conditional property minimizes non-desired background mutations. This technology could be combined with adaptive evolution to enhance mutagenesis rates and more rapidly achieve desired phenotypes.

"Look-Through Mutagenesis (LTM) is a multidimensional mutagenesis method that assesses and optimizes combinatorial mutations of selected amino acids." (Rajpal et al., *Proc Natl Acad Sci U.S.A.* 102:8466-8471 (2005)) Rather than saturating each site with all possible amino acid changes, a set of nine is chosen to cover the range of amino acid R-group chemistry. Fewer changes per site allows multiple sites to be subjected to this type of mutagenesis. A >800-fold increase in binding affinity for an antibody from low nanomolar to picomolar has been achieved through this method. This is a rational approach to minimize the number of random combinations and can increase the ability to find improved traits by greatly decreasing the numbers of clones to be screened. This has been applied to antibody engineering, specifically to increase the binding affinity and/or reduce dissociation. The technique can be combined with either screens or selections.

Gene Reassembly is a DNA shuffling method that can be applied to multiple genes at one time or to creating a large library of chimeras (multiple mutations) of a single gene. (Tunable GeneReassembly™ (TGR™) Technology supplied by Verenium Corporation) Typically this technology is used in combination with ultra-high-throughput screening to query the represented sequence space for desired improvements. This technique allows multiple gene recombination independent of homology. The exact number and position of cross-over events can be pre-determined using fragments designed via bioinformatic analysis. This technology leads to a very high level of diversity with virtually no parental gene reformation and a low level of inactive genes. Combined with GSSM™, a large range of mutations can be tested for improved activity. The method allows "blending" and "fine tuning" of DNA shuffling, e.g. codon usage can be optimized.

In Silico Protein Design Automation (PDA) is an optimization algorithm that anchors the structurally defined protein backbone possessing a particular fold, and searches sequence space for amino acid substitutions that can stabilize the fold and overall protein energetics. (Hayes et al., *Proc Natl Acad Sci U.S.A.* 99:15926-15931 (2002)) This technology uses in silico structure-based entropy predictions in order to search for structural tolerance toward protein amino acid variations. Statistical mechanics is applied to calculate coupling interactions at each position. Structural tolerance toward amino acid substitution is a measure of coupling. Ultimately, this technology is designed to yield desired modifications of protein properties while maintaining the integrity of structural characteristics. The method computationally assesses and allows filtering of a very large number of possible sequence variants ($10^{50}$). The choice of sequence variants to test is related to predictions based on the most favorable thermodynamics. Ostensibly only stability or properties that are linked to stability can be effectively addressed with this technology. The method has been successfully used in some therapeutic proteins, especially in engineering immunoglobulins. In silico predictions avoid testing extraordinarily large numbers of potential variants. Predictions based on existing three-dimensional structures are more likely to succeed than predictions based on hypothetical structures. This technology can readily predict and allow targeted screening of multiple simultaneous mutations, something not possible with purely experimental technologies due to exponential increases in numbers.

Iterative Saturation Mutagenesis (ISM) involves: 1) use knowledge of structure/function to choose a likely site for enzyme improvement; 2) saturation mutagenesis at chosen site using Stratagene QuikChange (or other suitable means); 3) screen/select for desired properties; and 4) with improved clone(s), start over at another site and continue repeating. (Reetz et al., *Nat. Protoc.* 2:891-903 (2007); and Reetz et al., *Angew. Chem. Int. Ed Engl.* 45:7745-7751 (2006)) This is a proven methodology, which assures all possible replacements at a given position are made for screening/selection.

Any of the aforementioned methods for mutagenesis can be used alone or in any combination. Additionally, any one or combination of the directed evolution methods can be used in conjunction with adaptive evolution techniques.

In one embodiment, the invention provides a method for producing n-propanol and isopropanol that includes culturing a non-naturally occurring microbial organism, including a microbial organism having an n-propanol pathway and an isopropanol pathway, the n-propanol pathway having at least one exogenous nucleic acid encoding an n-propanol pathway enzyme expressed in a sufficient amount to produce n-propanol, the n-propanol pathway including a propionaldehyde dehydrogenase, a propanol dehydrogenase, a propionyl-CoA:phosphate propanoyltransferase, a propionyl-CoA hydrolase, a propionyl-CoA transferase, a propionyl-CoA synthetase, a propionate kinase, a propionate reductase or a propionyl phosphate reductase, the isopropanol pathway comprising at least one exogenous nucleic acid encoding an isopropanol pathway enzyme expressed in a sufficient amount to produce isopropanol, the isopropanol pathway including an acetyl-CoA acetyl thiolase, an acetoacetyl-CoA transferase, an acetoacetyl-CoA hydrolase, an acetoacetyl-CoA synthetase, an acetoacetate decarboxylase or an isopropanol dehydrogenase.

In a further aspect of the above embodiment, the method includes a microbial organism having an acetyl-CoA pathway having at least one exogenous nucleic acid encoding an acetyl-CoA pathway enzyme expressed in a sufficient amount to produce acetyl-CoA, the acetyl-CoA pathway including a pyruvate kinase, a pyruvate dehydrogenase, a pyruvate ferredoxin oxidoreductase, a pyruvate formate lyase, a pyruvate formate lyase activating enzyme, or a formate dehydrogenase.

In further embodiment, the method includes a microbial organism having a propionyl-CoA pathway having at least one exogenous nucleic acid encoding a propionyl-CoA pathway enzyme expressed in a sufficient amount to produce propionyl-CoA, the propionyl-CoA pathway including a PEP carboxykinase, a PEP carboxylase, a malate dehydrogenase, a fumarase, a fumarate reductase, a succinyl-CoA transferase, a succinyl-CoA synthetase, a methylmalonyl-CoA mutase, a methylmalonyl-CoA epimerase or a methylmalonyl-CoA decarboxylase. In a further aspect, the propionyl-CoA pathway includes a pyruvate carboxylase or a methylmalonyl-CoA carboxytransferase.

In another further embodiment, the method includes a microbial organism having a propionyl-CoA pathway having at least one exogenous nucleic acid encoding a propionyl-CoA pathway enzyme expressed in a sufficient amount to produce propionyl-CoA, the propionyl-CoA pathway including a PEP carboxykinase, a PEP carboxylase, a threonine deaminase, or a 2-oxobutanoate dehydrogenase. In a further aspect, the n-propanol pathway includes 2-oxobutanoate decarboxylase.

In another further embodiment, the method includes a microbial organism having a propionyl-CoA pathway having at least one exogenous nucleic acid encoding a propionyl-CoA pathway enzyme expressed in a sufficient amount to produce propionyl-CoA, the propionyl-CoA pathway including an acetyl-CoA carboxylase, a malonyl-CoA reductase, a malonate semialdehyde reductase or propionyl-CoA synthase.

In another further embodiment, the method includes a microbial organism having a propionyl-CoA pathway having at least one exogenous nucleic acid encoding a propionyl-CoA pathway enzyme expressed in a sufficient amount to produce propionyl-CoA, the propionyl-CoA pathway including a lactate dehydrogenase, a lactate-CoA transferase, a lactyl-CoA dehydratase or acryloyl CoA reductase.

In yet another embodiment, the invention provides a method for producing n-propanol and isopropanol that includes culturing a non-naturally occurring microbial organism, including a microbial organism having an n-propanol pathway and an isopropanol pathway, the n-propanol pathway having a first set of exogenous nucleic acids encoding n-propanol pathway enzymes expressed in a sufficient amount to produce n-propanol, the first set of exogenous nucleic acids encoding a propionaldehyde dehydrogenase and a propanol dehydrogenase; or a propionyl-CoA:phosphate propanoyltransferase, a propionyl phosphate reductase and a propanol dehydrogenase; or a propionyl-CoA hydrolase or a propionyl-CoA transferase or a propionyl-CoA synthetase, a propionate kinase, a propionyl phosphate reductase and a propanol dehydrogenase; or a propionyl-CoA hydrolase or a propionyl-CoA transferase or a propionyl-CoA synthetase, a propionate reductase and a propanol dehydrogenase, and the isopropanol pathway having a second set of exogenous nucleic acids encoding isopropanol pathway enzymes expressed in a sufficient amount to produce isopropanol, the second set of exogenous nucleic acids encoding an acetyl-CoA acetyl thiolase; an acetoacetyl-CoA transferase or an acetoacetyl-CoA hydrolase or an acetoacetyl-CoA synthetase, an acetoacetate decarboxylase; and an isopropanol dehydrogenase.

In a further aspect of the above embodiment, the method includes a microbial organism having an acetyl-CoA pathway having a third set of exogenous nucleic acids encoding acetyl-CoA pathway enzymes expressed in a sufficient amount to produce acetyl-CoA, the third set of exogenous nucleic acids encoding a pyruvate kinase; and a pyruvate dehydrogenase or a pyruvate ferredoxin oxidoreductase; or a pyruvate formate lyase, a pyruvate formate lyase activating enzyme and a formate dehydrogenase.

In another further embodiment, the method includes a microbial organism having a propionyl-CoA pathway having a third set of exogenous nucleic acids encoding propionyl-CoA pathway enzymes expressed in a sufficient amount to produce propionyl-CoA, the third set of exogenous nucleic acids encoding a PEP carboxykinase or a PEP carboxylase; a malate dehydrogenase; a fumarase; a fumarate reductase; a succinyl-CoA transferase or a succinyl-CoA synthetase; a methylmalonyl-CoA mutase; and a methylmalonyl-CoA decarboxylase. In a further aspect, the third set of exogenous nucleic acids further encodes a methylmalonyl-CoA epimerase or a pyruvate carboxylas.

In another further embodiment, the method includes a microbial organism having a propionyl-CoA pathway having a third set of exogenous nucleic acids encoding propionyl-CoA pathway enzymes expressed in a sufficient amount to produce propionyl-CoA, said third set of exogenous nucleic acids encoding a PEP carboxykinase or a PEP carboxylase; a threonine deaminase; and a 2-oxobutanoate dehydrogenase. In a further aspect, the third set of exogenous nucleic acids further encodes a methylmalonyl-CoA decarboxylase or a pyruvate carboxylase. In yet another aspect, the second set of exogenous nucleic acids further encodes a 2-oxobutanoate decarboxylase.

In another further embodiment, the method includes a microbial organism having a propionyl-CoA pathway having a third set of exogenous nucleic acids encoding propionyl-CoA pathway enzymes expressed in a sufficient amount to produce propionyl-CoA, the third set of exogenous nucleic acids encoding an acetyl-CoA carboxylase; a malonyl-CoA reductase; a malonate semialdehyde reductase; and propionyl-CoA synthase.

In another further embodiment, the method includes a microbial organism having a propionyl-CoA pathway having a third set of exogenous nucleic acids encoding a lactate dehydrogenase; a lactate-CoA transferase; a lactyl-CoA dehydratase; and acryloyl CoA reductase.

In one embodiment, the invention provides a method for producing n-propanol and isopropanol that includes culturing a non-naturally occurring microbial organism including a microbial organism having an n-propanol pathway and an isopropanol pathway, the n-propanol pathway comprising a first set of exogenous nucleic acids encoding n-propanol pathway enzymes expressed in a sufficient amount to produce n-propanol, the first set of exogenous nucleic acids encoding a PEP carboxykinase or a PEP carboxylase; a malate dehydrogenase; a fumarase; a fumarate reductase; a succinyl-CoA transferase or a succinyl-CoA synthetase; a methylmalonyl-CoA mutase; a methylmalonyl-CoA decarboxylase; and a propionaldehyde dehydrogenase and a propanol dehydrogenase; or a propionyl-CoA:phosphate propanoyltransferase and a propionyl phosphate reductase; or a propionyl-CoA hydrolase or a propionyl-CoA transferase or a propionyl-CoA synthetase, a propionate kinase, a propionyl phosphate reductase and a propanol dehydrogenase; or a propionyl-CoA hydrolase or a propionyl-CoA transferase or a propionyl-CoA synthetase, a propionate reductase and a propanol dehydrogenase, and the isopropanol pathway comprising a second set of exogenous nucleic acids encoding isopropanol pathway enzymes expressed in a sufficient amount to produce isopropanol, the second set of exogenous nucleic acids encoding a pyruvate kinase; a pyruvate dehydrogenase or a pyruvate ferredoxin oxidoreductase; or a pyruvate formate lyase, a pyruvate formate lyase activating enzyme and a formate dehydrogenase; an acetyl-CoA acetyl thiolase; an acetoacetyl-CoA transferase or an acetoacetyl-CoA hydrolase or an acetoacetyl-CoA synthetase, an acetoacetate decarboxylase; and an isopropanol dehydrogenase.

In one embodiment, the invention provides a method for producing n-propanol and isopropanol that includes culturing a non-naturally occurring microbial organism including a microbial organism having an n-propanol pathway and an isopropanol pathway, the n-propanol pathway comprising a first set of exogenous nucleic acids encoding n-propanol pathway enzymes expressed in a sufficient amount to produce n-propanol, the first set of exogenous nucleic acids encoding a PEP carboxykinase or a PEP carboxylase; a threonine deaminase; and a 2-oxobutanoate decarboxylase and a propanol dehydrogenase; or a 2-oxobutanoate dehydrogenase, a propionaldehyde dehydrogenase and a propanol dehydrogenase; or a 2-oxobutanoate dehydrogenase, a propionyl-CoA:phosphate propanoyltransferase, a propionyl phosphate reductase and a propanol dehydrogenase; or a 2-oxobutanoate dehydrogenase, a propionyl-CoA hydrolase or a propionyl-CoA transferase or a propionyl-CoA synthetase, a propionate kinase, a propionyl phosphate reductase and a propanol dehydrogenase; or a 2-oxobutanoate dehydrogenase, a propionyl-CoA hydrolase or a propionyl-CoA transferase or a propionyl-CoA synthetase, a propionate reductase and a propanol dehydrogenase, and the isopropanol pathway comprising a second set of exogenous nucleic acids encoding isopropanol pathway enzymes expressed in a sufficient amount to produce isopropanol, the second set of exogenous nucleic acids encoding a pyruvate kinase; a pyruvate dehydrogenase or a pyruvate ferredoxin oxidoreductase; or a pyruvate formate lyase, a pyruvate formate lyase activating enzyme and a formate dehydrogenase; an acetyl-CoA acetyl thiolase; an acetoacetyl-CoA transferase or an acetoacetyl-CoA hydrolase or an acetoacetyl-CoA synthetase, an acetoacetate decarboxylase; and an isopropanol dehydrogenase. In a further aspect, the second set of exogenous nucleic acids further encodes a pyruvate carboxylase or a methylmalonyl-CoA carboxytransferase.

In one embodiment, the invention provides a method for producing n-propanol and isopropanol that includes culturing a non-naturally occurring microbial organism including a microbial organism having an n-propanol pathway and an isopropanol pathway, the n-propanol pathway comprising a first set of exogenous nucleic acids encoding n-propanol pathway enzymes expressed in a sufficient amount to produce n-propanol, the first set of exogenous nucleic acids encoding a pyruvate kinase; a pyruvate dehydrogenase or a pyruvate ferredoxin oxidoreductase; or a pyruvate formate lyase, a pyruvate formate lyase activating enzyme and a formate dehydrogenase; an acetyl-CoA carboxylase; a malonyl-CoA reductase; a malonate semialdehyde reductase; propionyl-CoA synthase; and a propionaldehyde dehydrogenase and a propanol dehydrogenase; or a propionyl-CoA:phosphate propanoyltransferase, a propionyl phosphate reductase and propanol dehydrogenase; or a propionyl-CoA hydrolase or a propionyl-CoA transferase or a propionyl-CoA synthetase, a propionate kinase, a propionyl phosphate reductase and a propanol dehydrogenase; or a propionyl-CoA hydrolase or a propionyl-CoA transferase or a propionyl-CoA synthetase, a propionate reductase and a propanol dehydrogenase, and the isopropanol pathway comprising a second set of exogenous nucleic acids encoding isopropanol pathway enzymes expressed in a sufficient amount to produce isopropanol, the second set of exogenous nucleic acids encoding an acetyl-CoA acetyl thiolase; an acetoacetyl-CoA transferase or an acetoacetyl-CoA hydrolase or an acetoacetyl-CoA synthetase, an acetoacetate decarboxylase; and an isopropanol dehydrogenase.

In one embodiment, the invention provides a method for producing n-propanol and isopropanol that includes culturing a non-naturally occurring microbial organism including a microbial organism having an n-propanol pathway and an isopropanol pathway, the n-propanol pathway including a first set of exogenous nucleic acids encoding n-propanol pathway enzymes expressed in a sufficient amount to produce n-propanol, the first set of exogenous nucleic acids encoding a lactate dehydrogenase; a lactate-CoA transferase; a lactyl-CoA dehydratase; acryloyl CoA reductase; and a propionaldehyde dehydrogenase and a propanol dehydrogenase; or a propionyl-CoA:phosphate propanoyltransferase, a propionyl phosphate reductase and a propanol dehydrogenase; or a propionyl-CoA hydrolase or a propionyl-CoA transferase or a propionyl-CoA synthetase, a propionate kinase, a propionyl phosphate reductase and a propanol dehydrogenase; or a propionyl-CoA hydrolase or a propionyl-CoA transferase or a propionyl-CoA synthetase, a propionate reductase and a propanol dehydrogenase, and the isopropanol pathway comprising a second set of exogenous nucleic acids encoding isopropanol pathway enzymes expressed in a sufficient amount to produce isopropanol, the second set of exogenous nucleic acids encoding a pyruvate dehydrogenase or a pyruvate ferredoxin oxidoreductase; or a pyruvate formate lyase, a pyruvate formate lyase activating enzyme and a formate dehydrogenase; an acetyl-CoA acetyl thiolase; an acetoacetyl-CoA transferase or an acetoacetyl-CoA hydrolase or an acetoacetyl-CoA synthetase, an acetoacetate decarboxylase; and an isopropanol dehydrogenase.

In one embodiment, the invention provides a method for producing n-propanol that includes culturing a non-naturally occurring microbial organism including a microbial organism having an n-propanol pathway, the n-propanol pathway comprising at least one exogenous nucleic acid encoding an n-propanol pathway enzyme expressed in a sufficient amount to produce n-propanol, the n-propanol pathway including a propionaldehyde dehydrogenase, a propanol dehydrogenase, a propionyl-CoA:phosphate propanoyltransferase, a propionyl-CoA hydrolase, a propionyl-CoA transferase, a propionyl-CoA synthetase, a propionate kinase, a propionate reductase, or a propionyl phosphate reductase.

In a further aspect of the above embodiment, the method for producing an propanol includes culturing the non-naturally occurring microbial organism having an n-propanol pathway that also has a propionyl-CoA pathway including exogenous nucleic acids encoding propionyl-CoA pathway enzymes expressed in a sufficient amount to produce propionyl-CoA as exemplified herein. For example, in some aspects the exogenous nucleic acids encode a PEP carboxykinase, a PEP carboxylase, a malate dehydrogenase, a fumarase, a fumarate reductase, a succinyl-CoA transferase, a succinyl-CoA synthetase, a methylmalonyl-CoA mutase, or a methylmalonyl-CoA decarboxylase. In another aspect, the exogenous nucleic acids further encode a methylmalonyl-CoA epimerase. Additionally, in yet another aspect of the above embodiment, the method for producing an propanol includes culturing the non-naturally occurring microbial organism having an n-propanol pathway that has a first set of exogenous nucleic acids encoding n-propanol pathway enzymes expressed in a sufficient amount to produce n-propanol, wherein the first set of exogenous nucleic acids encode a PEP carboxykinase or a PEP carboxylase; a malate dehydrogenase; a fumarase; a fumarate reductase; a succinyl-CoA transferase or a succinyl-CoA synthetase; a methylmalonyl-CoA mutase; a methylmalonyl-CoA epimerase; a methylmalonyl-CoA decarboxylase; a propionaldehyde dehydrogenase and a propanol dehydrogenase.

In another embodiment, the invention provides a method for producing n-propanol that includes culturing a non-naturally occurring microbial organism including a microbial organism having an n-propanol pathway, the n-propanol pathway comprising a set of exogenous nucleic acids encoding n-propanol pathway enzymes expressed in a sufficient amount to produce n-propanol, the set of exogenous nucleic acids encoding a propionaldehyde dehydrogenase and a propanol dehydrogenase; or a propionyl-CoA:phosphate propanoyltransferase, a propionyl phosphate reductase and a propanol dehydrogenase; or a propionyl-CoA hydrolase or a propionyl-CoA transferase or a propionyl-CoA synthetase, a propionate kinase, a propionyl phosphate reductase and a propanol dehydrogenase; or a propionyl-CoA hydrolase or a propionyl-CoA transferase or a propionyl-CoA synthetase, a propionate reductase and a propanol dehydrogenase.

In one embodiment, the invention provides a method for producing 14-BDO and isopropanol that includes culturing a non-naturally occurring microbial organism, including a microbial organism having an 14-BDO pathway and an isopropanol pathway, the 14-BDO pathway having at least one exogenous nucleic acid encoding an 14-BDO pathway enzyme expressed in a sufficient amount to produce 14-BDO, the 14-BDO pathway including a succinyl-CoA reductase, a succinate reductase, a 4-hydroxybutyrate dehydrogenase, a 4-hydroxybutyryl-CoA transferase, a 4-hydroxybutyryl-CoA synthetase, a 4-hydroxybutyryl-CoA reductase (aldehyde-forming), a 4-hydroxybutyraldehyde reductase, a 4-hydroxybutyrate reductase; a 4-hydroxybutyrate kinase, a phosphotrans-4-hydroxybutyrylase, a 4-hydroxybutyryl-phosphate reductase or a 4-hydroxybutyryl-CoA reductase (alcohol-forming), the isopropanol pathway including at least one exogenous nucleic acid encoding an isopropanol pathway enzyme expressed in a sufficient amount to produce isopropanol, the isopropanol pathway including an acetyl-CoA acetyl thiolase, an acetoacetyl-CoA transferase, an acetoacetyl-CoA hydrolase, an acetoacetyl-CoA synthetase, an acetoacetate decarboxylase or an isopropanol dehydrogenase.

In one embodiment, the invention provides a method for producing 13-BDO and isopropanol that includes culturing a non-naturally occurring microbial organism, including a microbial organism having an 13-BDO pathway and an isopropanol pathway, the 13-BDO pathway having at least one exogenous nucleic acid encoding an 13-BDO pathway enzyme expressed in a sufficient amount to produce 13-BDO, the 13-BDO pathway including a succinyl-CoA reductase, a succinate reductase, a 4-hydroxybutyrate dehydrogenase, a 4-hydroxybutyryl-CoA transferase, a 4-hydroxybutyryl-CoA synthetase, a 4-hydroxybutyrate kinase, a phosphotrans-4-hydroxybutyrylase, a 4-hydroxybutyryl-CoA dehydratase, a crotonase, a 3-hydroxybutyryl-CoA reductase (aldehyde forming), a 3-hydroxybutyraldehyde reductase, a 3-hydroxybutyryl-CoA transferase, a 3-hydroxybutyryl-CoA synthetase, a 3-hydroxybutyryl-CoA hydrolase, or a 3-hydroxybutyrate reductase, or a 3-hydroxybutyryl-CoA reductase (alcohol-forming), the isopropanol pathway including at least one exogenous nucleic acid encoding an isopropanol pathway enzyme expressed in a sufficient amount to produce isopropanol, the isopropanol pathway including an acetyl-CoA acetyl thiolase, an acetoacetyl-CoA transferase, an acetoacetyl-CoA hydrolase, an acetoacetyl-CoA synthetase, an acetoacetate decarboxylase or an isopropanol dehydrogenase.

In one embodiment, the invention provides a method for producing MAA and isopropanol that includes culturing a non-naturally occurring microbial organism, including a microbial organism having an MAA pathway and an isopropanol pathway, the MAA pathway having at least one exogenous nucleic acid encoding an MAA pathway enzyme expressed in a sufficient amount to produce MAA, the MAA pathway including a succinyl-CoA reductase, a succinate reductase, a 4-hydroxybutyrate dehydrogenase, a 4-hydroxybutyryl-CoA transferase, a 4-hydroxybutyryl-CoA synthetase, a 4-hydroxybutyrate kinase, a phosphotrans-4-hydroxybutyrylase, a 4-hydroxybutyryl-CoA mutase, a 3-hydroxyisobutyryl-CoA dehydratase, a methacrylyl-CoA transferase, a methacrylyl-CoA synthetase, a methacrylyl-CoA hydrolase, a 3-hydroxyisobutyryl-CoA transferase, a 3-hydroxyisobutyryl-CoA synthetase, a 3-hydroxyisobutyryl-CoA hydrolase, a 3-hydroxyisobutyrate dehydratase, a methylmalonyl-CoA mutase, a methylmalonyl-CoA epimerase, a methylmalonyl-CoA transferase, a methylmalonyl-CoA synthetase, a methylmalonyl-CoA hydrolase, a methylmalonate reductase, a methylmalonyl-CoA reductase (aldehyde forming), a 3-hydroxyisobutyrate dehydrogenase, a methylmalonyl-CoA reductase (alcohol forming) or a 3-hydroxyisobutyrate dehydratase, the isopropanol pathway including at least one exogenous nucleic acid encoding an isopropanol pathway enzyme expressed in a sufficient amount to produce isopropanol, the isopropanol pathway including an acetyl-CoA acetyl thiolase, an acetoacetyl-CoA transferase, an acetoacetyl-CoA hydrolase, an acetoacetyl-CoA synthetase, an acetoacetate decarboxylase or an isopropanol dehydrogenase.

In a further aspect of the above embodiments, the microbial organism has an acetyl-CoA pathway having at least one exogenous nucleic acid encoding an acetyl-CoA pathway enzyme expressed in a sufficient amount to produce acetyl-CoA, the acetyl-CoA pathway including a pyruvate kinase, a pyruvate dehydrogenase, a pyruvate ferredoxin oxidoreductase, a pyruvate formate lyase, a pyruvate formate lyase activating enzyme, or a formate dehydrogenase.

In further aspect of the above embodiments, the microbial organism has a succinyl-CoA pathway having at least one exogenous nucleic acid encoding a succinyl-CoA pathway enzyme expressed in a sufficient amount to produce succinyl-CoA, the succinyl-CoA pathway including a PEP carboxykinase, a PEP carboxylase, a malate dehydrogenase, a fumarase, a fumarate reductase, a succinyl-CoA transferase or a succinyl-CoA synthetase. In a further aspect, the succinyl-CoA pathway includes a pyruvate carboxylase or a methylmalonyl-CoA carboxytransferase.

In one embodiment, the invention provides a method for producing 14-BDO and isopropanol that includes culturing a non-naturally occurring microbial organism including a microbial organism having an 14-BDO pathway and an isopropanol pathway, the 14-BDO pathway including a first set of exogenous nucleic acids encoding 14-BDO pathway enzymes expressed in a sufficient amount to produce 14-BDO, the first set of exogenous nucleic acids encoding a succinyl-CoA reductase; a 4-hydroxybutyrate dehydrogenase; a 4-hydroxybutyryl-CoA transferase or a 4-hydroxybutyryl-CoA synthetase; a 4-hydroxybutyryl-CoA reductase (aldehyde-forming); and a 4-hydroxybutyraldehyde reductase, and the isopropanol pathway comprising a second set of exogenous nucleic acids encoding isopropanol pathway enzymes expressed in a sufficient amount to produce isopropanol, the second set of exogenous nucleic acids encoding an acetyl-CoA acetyl thiolase; an acetoacetyl-CoA transferase or an acetoacetyl-CoA hydrolase or an acetoacetyl-CoA synthetase, an acetoacetate decarboxylase; and an isopropanol dehydrogenase.

In one embodiment, the invention provides a method for producing 14-BDO and isopropanol that includes culturing a non-naturally occurring microbial organism including a microbial organism having an 14-BDO pathway and an isopropanol pathway, the 14-BDO pathway including a first set of exogenous nucleic acids encoding 14-BDO pathway enzymes expressed in a sufficient amount to produce 14-BDO, the first set of exogenous nucleic acids encoding a succinyl-CoA reductase; a 4-hydroxybutyrate dehydrogenase; a 4-hydroxybutyrate reductase; and a 4-hydroxybutyraldehyde reductase, and the isopropanol pathway comprising a second set of exogenous nucleic acids encoding isopropanol pathway enzymes expressed in a sufficient amount to produce isopropanol, the second set of exogenous nucleic acids encoding an acetyl-CoA acetyl thiolase; an acetoacetyl-CoA transferase or an acetoacetyl-CoA hydrolase or an acetoacetyl-CoA synthetase, an acetoacetate decarboxylase; and an isopropanol dehydrogenase.

In one embodiment, the invention provides a method for producing 14-BDO and isopropanol that includes culturing a non-naturally occurring microbial organism including a microbial organism having an 14-BDO pathway and an isopropanol pathway, the 14-BDO pathway including a first set of exogenous nucleic acids encoding 14-BDO pathway enzymes expressed in a sufficient amount to produce 14-BDO, the first set of exogenous nucleic acids encoding a succinyl-CoA reductase; a 4-hydroxybutyrate dehydrogenase; a 4-hydroxybutyrate kinase; a phosphotrans-4-hydroxybutyrylase; a 4-hydroxybutyryl-CoA reductase (aldehyde-forming); and a 4-hydroxybutyraldehyde reductase, and the isopropanol pathway comprising a second set of exogenous nucleic acids encoding isopropanol pathway enzymes expressed in a sufficient amount to produce isopropanol, the second set of exogenous nucleic acids encoding an acetyl-CoA acetyl thiolase; an acetoacetyl-CoA transferase or an acetoacetyl-CoA hydrolase or an acetoacetyl-CoA synthetase, an acetoacetate decarboxylase; and an isopropanol dehydrogenase.

In one embodiment, the invention provides a method for producing 14-BDO and isopropanol that includes culturing a non-naturally occurring microbial organism including a microbial organism having an 14-BDO pathway and an isopropanol pathway, the 14-BDO pathway including a first set of exogenous nucleic acids encoding 14-BDO pathway enzymes expressed in a sufficient amount to produce 14-BDO, the first set of exogenous nucleic acids encoding a succinyl-CoA reductase; a 4-hydroxybutyrate dehydrogenase; a 4-hydroxybutyrate kinase; a 4-hydroxybutyryl-phosphate reductase; and a 4-hydroxybutyraldehyde reductase, and the isopropanol pathway comprising a second set of exogenous nucleic acids encoding isopropanol pathway enzymes expressed in a sufficient amount to produce isopropanol, the second set of exogenous nucleic acids encoding an acetyl-CoA acetyl thiolase; an acetoacetyl-CoA transferase or an acetoacetyl-CoA hydrolase or an acetoacetyl-CoA synthetase; an acetoacetate decarboxylase; and an isopropanol dehydrogenase.

In one embodiment, the invention provides a method for producing 14-BDO and isopropanol that includes culturing a non-naturally occurring microbial organism including a microbial organism having an 14-BDO pathway and an isopropanol pathway, the 14-BDO pathway including a first set of exogenous nucleic acids encoding 14-BDO pathway enzymes expressed in a sufficient amount to produce 14-BDO, the first set of exogenous nucleic acids encoding a succinyl-CoA reductase; a 4-hydroxybutyrate dehydrogenase; a 4-hydroxybutyrate kinase; a phosphotrans-4-hydroxybutyrylase; and a 4-hydroxybutyryl-CoA reductase (alcohol-forming), and the isopropanol pathway comprising a second set of exogenous nucleic acids encoding isopropanol pathway enzymes expressed in a sufficient amount to produce isopropanol, the second set of exogenous nucleic acids encoding an acetyl-CoA acetyl thiolase; an acetoacetyl-CoA transferase or an acetoacetyl-CoA hydrolase or an acetoacetyl-CoA synthetase, an acetoacetate decarboxylase; and an isopropanol dehydrogenase.

In one embodiment, the invention provides a method for producing 14-BDO and isopropanol that includes culturing a non-naturally occurring microbial organism including a microbial organism having an 14-BDO pathway and an isopropanol pathway, the 14-BDO pathway including a first set of exogenous nucleic acids encoding 14-BDO pathway enzymes expressed in a sufficient amount to produce 14-BDO, the first set of exogenous nucleic acids encoding a succinyl-CoA reductase; a 4-hydroxybutyrate dehydrogenase; a 4-hydroxybutyryl-CoA transferase or a 4-hydroxybutyryl-CoA synthetase; and a 4-hydroxybutyryl-CoA reductase (alcohol-forming); and a 4-hydroxybutyryl-CoA reductase (alcohol-forming), and the isopropanol pathway comprising a second set of exogenous nucleic acids encoding isopropanol pathway enzymes expressed in a sufficient amount to produce isopropanol, the second set of exogenous nucleic acids encoding an acetyl-CoA acetyl thiolase; an acetoacetyl-CoA transferase or an acetoacetyl-CoA hydrolase or an acetoacetyl-CoA synthetase, an acetoacetate decarboxylase; and an isopropanol dehydrogenase.

In one embodiment, the invention provides a method for producing 14-BDO and isopropanol that includes culturing a non-naturally occurring microbial organism including a microbial organism having an 14-BDO pathway and an isopropanol pathway, the 14-BDO pathway including a first set of exogenous nucleic acids encoding 14-BDO pathway enzymes expressed in a sufficient amount to produce 14-BDO, the first set of exogenous nucleic acids encoding a succinate reductase; a 4-hydroxybutyrate dehydrogenase; a 4-hydroxybutyryl-CoA transferase or a 4-hydroxybutyryl-CoA synthetase; a 4-hydroxybutyryl-CoA reductase (aldehyde-forming); and a 4-hydroxybutyraldehyde reductase, and the isopropanol pathway comprising a second set of exogenous nucleic acids encoding isopropanol pathway enzymes expressed in a sufficient amount to produce isopropanol, the second set of exogenous nucleic acids encoding an acetyl-CoA acetyl thiolase; an acetoacetyl-CoA transferase or an acetoacetyl-CoA hydrolase or an acetoacetyl-CoA synthetase, an acetoacetate decarboxylase; and an isopropanol dehydrogenase.

In one embodiment, the invention provides a method for producing 14-BDO and isopropanol that includes culturing a non-naturally occurring microbial organism including a microbial organism having an 14-BDO pathway and an isopropanol pathway, the 14-BDO pathway including a first set of exogenous nucleic acids encoding 14-BDO pathway enzymes expressed in a sufficient amount to produce 14-BDO, the first set of exogenous nucleic acids encoding a succinate reductase; a 4-hydroxybutyrate dehydrogenase; a 4-hydroxybutyrate reductase; and a 4-hydroxybutyraldehyde reductase, and the isopropanol pathway comprising a second set of exogenous nucleic acids encoding isopropanol pathway enzymes expressed in a sufficient amount to produce isopropanol, the second set of exogenous nucleic acids encoding an acetyl-CoA acetyl thiolase; an acetoacetyl-CoA transferase or an acetoacetyl-CoA hydrolase or an acetoacetyl-CoA synthetase, an acetoacetate decarboxylase; and an isopropanol dehydrogenase.

In one embodiment, the invention provides a method for producing 14-BDO and isopropanol that includes culturing a non-naturally occurring microbial organism including a microbial organism having an 14-BDO pathway and an isopropanol pathway, the 14-BDO pathway including a first set of exogenous nucleic acids encoding 14-BDO pathway enzymes expressed in a sufficient amount to produce 14-BDO, the first set of exogenous nucleic acids encoding a succinate reductase; a 4-hydroxybutyrate dehydrogenase; a 4-hydroxybutyrate kinase; a phosphotrans-4-hydroxybutyrylase; a 4-hydroxybutyryl-CoA reductase (aldehyde-forming); and a 4-hydroxybutyraldehyde reductase, and the isopropanol pathway comprising a second set of exogenous nucleic acids encoding isopropanol pathway enzymes expressed in a sufficient amount to produce isopropanol, the second set of exogenous nucleic acids encoding an acetyl-CoA acetyl thiolase; an acetoacetyl-CoA transferase or an acetoacetyl-CoA hydrolase or an acetoacetyl-CoA synthetase, an acetoacetate decarboxylase; and an isopropanol dehydrogenase.

In one embodiment, the invention provides a method for producing 14-BDO and isopropanol that includes culturing a non-naturally occurring microbial organism including a microbial organism having an 14-BDO pathway and an isopropanol pathway, the 14-BDO pathway including a first set of exogenous nucleic acids encoding 14-BDO pathway enzymes expressed in a sufficient amount to produce 14-BDO, the first set of exogenous nucleic acids encoding a succinate reductase; a 4-hydroxybutyrate dehydrogenase; a 4-hydroxybutyrate kinase; a 4-hydroxybutyryl-phosphate reductase; and a 4-hydroxybutyraldehyde reductase, and the isopropanol pathway comprising a second set of exogenous nucleic acids encoding isopropanol pathway enzymes expressed in a sufficient amount to produce isopropanol, the second set of exogenous nucleic acids encoding an acetyl-CoA acetyl thiolase; an acetoacetyl-CoA transferase or an acetoacetyl-CoA hydrolase or an acetoacetyl-CoA synthetase; an acetoacetate decarboxylase; and an isopropanol dehydrogenase.

In one embodiment, the invention provides a method for producing 14-BDO and isopropanol that includes culturing a non-naturally occurring microbial organism including a microbial organism having an 14-BDO pathway and an isopropanol pathway, the 14-BDO pathway including a first set of exogenous nucleic acids encoding 14-BDO pathway enzymes expressed in a sufficient amount to produce 14-BDO, the first set of exogenous nucleic acids encoding a succinate reductase; a 4-hydroxybutyrate dehydrogenase; a 4-hydroxybutyrate kinase; a phosphotrans-4-hydroxybutyrylase; and a 4-hydroxybutyryl-CoA reductase (alcohol-forming), and the isopropanol pathway comprising a second set of exogenous nucleic acids encoding isopropanol pathway enzymes expressed in a sufficient amount to produce isopropanol, the second set of exogenous nucleic acids encoding an acetyl-CoA acetyl thiolase; an acetoacetyl-CoA transferase or an acetoacetyl-CoA hydrolase or an acetoacetyl-CoA synthetase, an acetoacetate decarboxylase; and an isopropanol dehydrogenase.

In one embodiment, the invention provides a method for producing 14-BDO and isopropanol that includes culturing a non-naturally occurring microbial organism including a microbial organism having an 14-BDO pathway and an isopropanol pathway, the 14-BDO pathway including a first set of exogenous nucleic acids encoding 14-BDO pathway enzymes expressed in a sufficient amount to produce 14-BDO, the first set of exogenous nucleic acids encoding a succinate reductase; a 4-hydroxybutyrate dehydrogenase; a 4-hydroxybutyryl-CoA transferase or a 4-hydroxybutyryl-CoA synthetase; and a 4-hydroxybutyryl-CoA reductase (alcohol-forming), and the isopropanol pathway comprising a second set of exogenous nucleic acids encoding isopropanol pathway enzymes expressed in a sufficient amount to produce isopropanol, the second set of exogenous nucleic acids encoding an acetyl-CoA acetyl thiolase; an acetoacetyl-CoA transferase or an acetoacetyl-CoA hydrolase or an acetoacetyl-CoA synthetase, an acetoacetate decarboxylase; and an isopropanol dehydrogenase.

In one embodiment, the invention provides a method for producing 13-BDO and isopropanol that includes culturing a non-naturally occurring microbial organism including a microbial organism having an 13-BDO pathway and an isopropanol pathway, the 13-BDO pathway including a first set of exogenous nucleic acids encoding 13-BDO pathway enzymes expressed in a sufficient amount to produce 13-BDO, the first set of exogenous nucleic acids encoding a succinyl-CoA reductase; a 4-hydroxybutyrate dehydrogenase; a 4-hydroxybutyryl-CoA transferase or a 4-hydroxybutyryl-CoA synthetase; a 4-hydroxybutyryl-CoA dehydratase; a crotonase; a 3-hydroxybutyryl-CoA reductase (aldehyde forming); and a 3-hydroxybutyraldehyde reductase, and the isopropanol pathway comprising a second set of exogenous nucleic acids encoding isopropanol pathway enzymes expressed in a sufficient amount to produce isopropanol, the second set of exogenous nucleic acids encoding an acetyl-CoA acetyl thiolase; an acetoacetyl-CoA transferase or an acetoacetyl-CoA hydrolase or an acetoacetyl-CoA synthetase, an acetoacetate decarboxylase; and an isopropanol dehydrogenase.

In one embodiment, the invention provides a method for producing 13-BDO and isopropanol that includes culturing a non-naturally occurring microbial organism including a microbial organism having an 13-BDO pathway and an isopropanol pathway, the 13-BDO pathway including a first set of exogenous nucleic acids encoding 13-BDO pathway enzymes expressed in a sufficient amount to produce 13-BDO, the first set of exogenous nucleic acids encoding a succinyl-CoA reductase; a 4-hydroxybutyrate dehydrogenase; a 4-hydroxybutyryl-CoA transferase or a 4-hydroxybutyryl-CoA synthetase; a 4-hydroxybutyryl-CoA dehydratase; a crotonase; a 3-hydroxybutyryl-CoA transferase or a 3-hydroxybutyryl-CoA synthetase or a 3-hydroxybutyryl-CoA hydrolase; a 3-hydroxybutyrate reductase; and a 3 hydroxybutyraldehyde reductase, and the isopropanol pathway comprising a second set of exogenous nucleic acids encoding isopropanol pathway enzymes expressed in a sufficient amount to produce isopropanol, the second set of exogenous nucleic acids encoding an acetyl-CoA acetyl thiolase; an acetoacetyl-CoA transferase or an acetoacetyl-CoA hydrolase or an acetoacetyl-CoA synthetase, an acetoacetate decarboxylase; and an isopropanol dehydrogenase.

In one embodiment, the invention provides a method for producing 13-BDO and isopropanol that includes culturing a non-naturally occurring microbial organism including a microbial organism having an 13-BDO pathway and an isopropanol pathway, the 13-BDO pathway including a first set of exogenous nucleic acids encoding 13-BDO pathway enzymes expressed in a sufficient amount to produce 13-BDO, the first set of exogenous nucleic acids encoding a succinyl-CoA reductase; a 4-hydroxybutyrate dehydrogenase; a 4-hydroxybutyrate kinase; a phosphotrans-4-hydroxybutyrylase; a 4-hydroxybutyryl-CoA dehydratase; a crotonase; a 3-hydroxybutyryl-CoA reductase (aldehyde forming); and a 3-hydroxybutyraldehyde reductase, and the isopropanol pathway comprising a second set of exogenous nucleic acids encoding isopropanol pathway enzymes expressed in a sufficient amount to produce isopropanol, the second set of exogenous nucleic acids encoding an acetyl-CoA acetyl thiolase; an acetoacetyl-CoA transferase or an acetoacetyl-CoA hydrolase or an acetoacetyl-CoA synthetase, an acetoacetate decarboxylase; and an isopropanol dehydrogenase.

In one embodiment, the invention provides a method for producing 13-BDO and isopropanol that includes culturing a non-naturally occurring microbial organism including a microbial organism having an 13-BDO pathway and an isopropanol pathway, the 13-BDO pathway including a first set of exogenous nucleic acids encoding 13-BDO pathway enzymes expressed in a sufficient amount to produce 13-BDO, the first set of exogenous nucleic acids encoding a succinyl-CoA reductase; a 4-hydroxybutyrate dehydrogenase; a 4-hydroxybutyrate kinase; a phosphotrans-4-hydroxybutyrylase; a 4-hydroxybutyryl-CoA dehydratase; a crotonase; a 3-hydroxybutyryl-CoA transferase or a 3-hydroxybutyryl-CoA synthetase or a 3-hydroxybutyryl-CoA hydrolase; a 3-hydroxybutyrate reductase; and a 3-hydroxybutyraldehyde reductase, and the isopropanol pathway comprising a second set of exogenous nucleic acids encoding isopropanol pathway enzymes expressed in a sufficient amount to produce isopropanol, the second set of exogenous nucleic acids encoding an acetyl-CoA acetyl thiolase; an acetoacetyl-CoA transferase or an acetoacetyl-CoA hydrolase or an acetoacetyl-CoA synthetase; an acetoacetate decarboxylase; and an isopropanol dehydrogenase.

In one embodiment, the invention provides a method for producing 13-BDO and isopropanol that includes culturing a non-naturally occurring microbial organism including a microbial organism having an 13-BDO pathway and an isopropanol pathway, the 13-BDO pathway including a first set of exogenous nucleic acids encoding 13-BDO pathway enzymes expressed in a sufficient amount to produce 13-BDO, the first set of exogenous nucleic acids encoding a succinyl-CoA reductase; a 4-hydroxybutyrate dehydrogenase; a 4-hydroxybutyrate kinase; a phosphotrans-4-hydroxybutyrylase; a 4-hydroxybutyryl-CoA dehydratase; a crotonase; and a 3-hydroxybutyryl-CoA reductase (alcohol-forming), and the isopropanol pathway comprising a second set of exogenous nucleic acids encoding isopropanol pathway enzymes expressed in a sufficient amount to produce isopropanol, the second set of exogenous nucleic acids encoding an acetyl-CoA acetyl thiolase; an acetoacetyl-CoA transferase or an acetoacetyl-CoA hydrolase or an acetoacetyl-CoA synthetase; an acetoacetate decarboxylase; and an isopropanol dehydrogenase.

In one embodiment, the invention provides a method for producing 13-BDO and isopropanol that includes culturing a non-naturally occurring microbial organism including a microbial organism having an 13-BDO pathway and an isopropanol pathway, the 13-BDO pathway including a first set of exogenous nucleic acids encoding 13-BDO pathway enzymes expressed in a sufficient amount to produce 13-BDO, the first set of exogenous nucleic acids encoding a succinyl-CoA reductase; a 4-hydroxybutyryl-CoA transferase or a 4-hydroxybutyryl-CoA synthetase; a 4-hydroxybutyryl-CoA dehydratase; a crotonase; and a 3-hydroxybutyryl-CoA reductase (alcohol-forming), and the isopropanol pathway comprising a second set of exogenous nucleic acids encoding isopropanol pathway enzymes expressed in a sufficient amount to produce isopropanol, the second set of exogenous nucleic acids encoding an acetyl-CoA acetyl thiolase; an acetoacetyl-CoA transferase or an acetoacetyl-CoA hydrolase or an acetoacetyl-CoA synthetase; an acetoacetate decarboxylase; and an isopropanol dehydrogenase.

In one embodiment, the invention provides a method for producing 13-BDO and isopropanol that includes culturing a non-naturally occurring microbial organism including a microbial organism having an 13-BDO pathway and an isopropanol pathway, the 13-BDO pathway including a first set of exogenous nucleic acids encoding 13-BDO pathway enzymes expressed in a sufficient amount to produce 13-BDO, the first set of exogenous nucleic acids encoding a succinate reductase; a 4-hydroxybutyrate dehydrogenase; a 4-hydroxybutyryl-CoA transferase or a 4-hydroxybutyryl-CoA synthetase; a 4-hydroxybutyryl-CoA dehydratase; a crotonase; a 3-hydroxybutyryl-CoA reductase (aldehyde forming); and a 3-hydroxybutyraldehyde reductase, and the isopropanol pathway comprising a second set of exogenous nucleic acids encoding isopropanol pathway enzymes expressed in a sufficient amount to produce isopropanol, the second set of exogenous nucleic acids encoding an acetyl-CoA acetyl thiolase; an acetoacetyl-CoA transferase or an acetoacetyl-CoA hydrolase or an acetoacetyl-CoA synthetase, an acetoacetate decarboxylase; and an isopropanol dehydrogenase.

In one embodiment, the invention provides a method for producing 13-BDO and isopropanol that includes culturing a non-naturally occurring microbial organism including a microbial organism having an 13-BDO pathway and an isopropanol pathway, the 13-BDO pathway including a first set of exogenous nucleic acids encoding 13-BDO pathway enzymes expressed in a sufficient amount to produce 13-BDO, the first set of exogenous nucleic acids encoding a succinate reductase; a 4-hydroxybutyrate dehydrogenase; a 4-hydroxybutyryl-CoA transferase or a 4-hydroxybutyryl-CoA synthetase; a 4-hydroxybutyryl-CoA dehydratase; a crotonase; a 3-hydroxybutyryl-CoA transferase or a 3-hydroxybutyryl-CoA synthetase or a 3-hydroxybutyryl-CoA hydrolase; a 3-hydroxybutyrate reductase; and a 3 hydroxybutyraldehyde reductase, and the isopropanol pathway comprising a second set of exogenous nucleic acids encoding isopropanol pathway enzymes expressed in a sufficient amount to produce isopropanol, the second set of exogenous nucleic acids encoding an acetyl-CoA acetyl thiolase; an acetoacetyl-CoA transferase or an acetoacetyl-CoA hydrolase or an acetoacetyl-CoA synthetase; an acetoacetate decarboxylase; and an isopropanol dehydrogenase.

In one embodiment, the invention provides a method for producing 13-BDO and isopropanol that includes culturing a non-naturally occurring microbial organism including a microbial organism having an 13-BDO pathway and an isopropanol pathway, the 13-BDO pathway including a first set of exogenous nucleic acids encoding 13-BDO pathway enzymes expressed in a sufficient amount to produce 13-BDO, the first set of exogenous nucleic acids encoding a succinate reductase; a 4-hydroxybutyrate dehydrogenase; a 4-hydroxybutyrate kinase; a phosphotrans-4-hydroxybutyrylase; a 4-hydroxybutyryl-CoA dehydratase; a crotonase; a 3-hydroxybutyryl-CoA reductase (aldehyde forming); and a 3-hydroxybutyraldehyde reductase, and the isopropanol pathway comprising a second set of exogenous nucleic acids encoding isopropanol pathway enzymes expressed in a sufficient amount to produce isopropanol, the second set of exogenous nucleic acids encoding an acetyl-CoA acetyl thiolase;

an acetoacetyl-CoA transferase or an acetoacetyl-CoA hydrolase or an acetoacetyl-CoA synthetase, an acetoacetate decarboxylase; and an isopropanol dehydrogenase.

In one embodiment, the invention provides a method for producing 13-BDO and isopropanol that includes culturing a non-naturally occurring microbial organism including a microbial organism having an 13-BDO pathway and an isopropanol pathway, the 13-BDO pathway including a first set of exogenous nucleic acids encoding 13-BDO pathway enzymes expressed in a sufficient amount to produce 13-BDO, the first set of exogenous nucleic acids encoding a succinate reductase; a 4-hydroxybutyrate dehydrogenase; a 4 hydroxybutyrate kinase; a phosphotrans-4-hydroxybutyrylase; a 4-hydroxybutyryl-CoA dehydratase; a crotonase; a 3-hydroxybutyryl-CoA transferase or a 3-hydroxybutyryl-CoA synthetase or a 3-hydroxybutyryl-CoA hydrolase; a 3-hydroxybutyrate reductase; and a 3 hydroxybutyraldehyde reductase, and the isopropanol pathway comprising a second set of exogenous nucleic acids encoding isopropanol pathway enzymes expressed in a sufficient amount to produce isopropanol, the second set of exogenous nucleic acids encoding an acetyl-CoA acetyl thiolase; an acetoacetyl-CoA transferase or an acetoacetyl-CoA hydrolase or an acetoacetyl-CoA synthetase; an acetoacetate decarboxylase; and an isopropanol dehydrogenase.

In one embodiment, the invention provides a method for producing 13-BDO and isopropanol that includes culturing a non-naturally occurring microbial organism including a microbial organism having an 13-BDO pathway and an isopropanol pathway, the 13-BDO pathway including a first set of exogenous nucleic acids encoding 13-BDO pathway enzymes expressed in a sufficient amount to produce 13-BDO, the first set of exogenous nucleic acids encoding a succinate reductase; a 4-hydroxybutyrate dehydrogenase; a 4-hydroxybutyrate kinase; a phosphotrans-4-hydroxybutyrylase; a crotonase; and a 3-hydroxybutyryl-CoA reductase (alcohol-forming), and the isopropanol pathway comprising a second set of exogenous nucleic acids encoding isopropanol pathway enzymes expressed in a sufficient amount to produce isopropanol, the second set of exogenous nucleic acids encoding an acetyl-CoA acetyl thiolase; an acetoacetyl-CoA transferase or an acetoacetyl-CoA hydrolase or an acetoacetyl-CoA synthetase, an acetoacetate decarboxylase; and an isopropanol dehydrogenase.

In one embodiment, the invention provides a method for producing 13-BDO and isopropanol that includes culturing a non-naturally occurring microbial organism including a microbial organism having an 13-BDO pathway and an isopropanol pathway, the 13-BDO pathway including a first set of exogenous nucleic acids encoding 13-BDO pathway enzymes expressed in a sufficient amount to produce 13-BDO, the first set of exogenous nucleic acids encoding a succinate reductase; a 4-hydroxybutyrate dehydrogenase; a 4-hydroxybutyryl-CoA transferase or a 4-hydroxybutyryl-CoA synthetase; a 4-hydroxybutyryl-CoA dehydratase; a crotonase; and a 3-hydroxybutyryl-CoA reductase (alcohol-forming), and the isopropanol pathway comprising a second set of exogenous nucleic acids encoding isopropanol pathway enzymes expressed in a sufficient amount to produce isopropanol, the second set of exogenous nucleic acids encoding an acetyl-CoA acetyl thiolase; an acetoacetyl-CoA transferase or an acetoacetyl-CoA hydrolase or an acetoacetyl-CoA synthetase, an acetoacetate decarboxylase; and an isopropanol dehydrogenase.

In one embodiment, the invention provides a method for producing MAA and isopropanol that includes culturing a non-naturally occurring microbial organism including a microbial organism having an MAA pathway and an isopropanol pathway, the MAA pathway including a first set of exogenous nucleic acids encoding MAA pathway enzymes expressed in a sufficient amount to produce MAA, the first set of exogenous nucleic acids encoding a succinyl-CoA reductase; a 4-hydroxybutyrate dehydrogenase; a 4-hydroxybutyryl-CoA transferase or a 4-hydroxybutyryl-CoA synthetase; a 4-hydroxybutyryl-CoA mutase; a 3-hydroxyisobutyryl-CoA transferase, a 3-hydroxyisobutyryl-CoA synthetase or a 3-hydroxyisobutyryl-CoA hydrolase; and a 3-hydroxyisobutyrate dehydratase, and the isopropanol pathway comprising a second set of exogenous nucleic acids encoding isopropanol pathway enzymes expressed in a sufficient amount to produce isopropanol, the second set of exogenous nucleic acids encoding an acetyl-CoA acetyl thiolase; an acetoacetyl-CoA transferase or an acetoacetyl-CoA hydrolase or an acetoacetyl-CoA synthetase, an acetoacetate decarboxylase; and an isopropanol dehydrogenase.

In one embodiment, the invention provides a method for producing MAA and isopropanol that includes culturing a non-naturally occurring microbial organism including a microbial organism having an MAA pathway and an isopropanol pathway, the MAA pathway including a first set of exogenous nucleic acids encoding MAA pathway enzymes expressed in a sufficient amount to produce MAA, the first set of exogenous nucleic acids encoding a succinyl-CoA reductase; a 4-hydroxybutyrate dehydrogenase; a 4-hydroxybutyryl-CoA transferase or a 4-hydroxybutyryl-CoA synthetase; a 4-hydroxybutyryl-CoA mutase; a 3-hydroxyisobutyryl-CoA dehydratase; and a methacrylyl-CoA transferase, a methacrylyl-CoA synthetase or a methacrylyl-CoA hydrolase, and the isopropanol pathway comprising a second set of exogenous nucleic acids encoding isopropanol pathway enzymes expressed in a sufficient amount to produce isopropanol, the second set of exogenous nucleic acids encoding an acetyl-CoA acetyl thiolase; an acetoacetyl-CoA transferase or an acetoacetyl-CoA hydrolase or an acetoacetyl-CoA synthetase; an acetoacetate decarboxylase; and an isopropanol dehydrogenase.

In one embodiment, the invention provides a method for producing MAA and isopropanol that includes culturing a non-naturally occurring microbial organism including a microbial organism having an MAA pathway and an isopropanol pathway, the MAA pathway including a first set of exogenous nucleic acids encoding MAA pathway enzymes expressed in a sufficient amount to produce MAA, the first set of exogenous nucleic acids encoding a succinyl-CoA reductase; a 4-hydroxybutyrate dehydrogenase; a 4-hydroxybutyrate kinase; a phosphotrans-4-hydroxybutyrylase; a 4-hydroxybutyryl-CoA mutase; a 3-hydroxyisobutyryl-CoA transferase, a 3-hydroxyisobutyryl-CoA synthetase or a 3-hydroxyisobutyryl-CoA hydrolase; and a 3-hydroxyisobutyrate dehydratase, and the isopropanol pathway comprising a second set of exogenous nucleic acids encoding isopropanol pathway enzymes expressed in a sufficient amount to produce isopropanol, the second set of exogenous nucleic acids encoding an acetyl-CoA acetyl thiolase; an acetoacetyl-CoA transferase or an acetoacetyl-CoA hydrolase or an acetoacetyl-CoA synthetase, an acetoacetate decarboxylase; and an isopropanol dehydrogenase.

In one embodiment, the invention provides a method for producing MAA and isopropanol that includes culturing a non-naturally occurring microbial organism including a microbial organism having an MAA pathway and an isopropanol pathway, the MAA pathway including a first set of exogenous nucleic acids encoding MAA pathway enzymes expressed in a sufficient amount to produce MAA, the first set of exogenous nucleic acids encoding a succinyl-CoA reductase; a 4-hydroxybutyrate dehydrogenase; a 4 hydroxybutyrate kinase; a phosphotrans-4-hydroxybutyrylase; a 4-hydroxybutyryl-CoA mutase; a 3-hydroxyisobutyryl-CoA dehydratase; and a methacrylyl-CoA transferase, a methacrylyl-CoA synthetase or a methacrylyl-CoA hydrolase, and the isopropanol pathway comprising a second set of exogenous nucleic acids encoding isopropanol pathway enzymes expressed in a sufficient amount to produce isopropanol, the second set of exogenous nucleic acids encoding an acetyl-CoA acetyl thiolase; an acetoacetyl-CoA transferase or an acetoacetyl-CoA hydrolase or an acetoacetyl-CoA synthetase; an acetoacetate decarboxylase; and an isopropanol dehydrogenase.

In one embodiment, the invention provides a method for producing MAA and isopropanol that includes culturing a non-naturally occurring microbial organism including a microbial organism having an MAA pathway and an isopropanol pathway, the MAA pathway including a first set of exogenous nucleic acids encoding MAA pathway enzymes expressed in a sufficient amount to produce MAA, the first set of exogenous nucleic acids encoding a succinate reductase; a 4-hydroxybutyrate dehydrogenase; a 4-hydroxybutyryl-CoA transferase or a 4-hydroxybutyryl-CoA synthetase; a 4-hydroxybutyryl-CoA mutase; a 3-hydroxyisobutyryl-CoA transferase, a 3-hydroxyisobutyryl-CoA synthetase or a 3-hydroxyisobutyryl-CoA hydrolase; and a 3-hydroxyisobutyrate dehydratase, and the isopropanol pathway comprising a second set of exogenous nucleic acids encoding isopropanol pathway enzymes expressed in a sufficient amount to produce isopropanol, the second set of exogenous nucleic acids encoding an acetyl-CoA acetyl thiolase; an acetoacetyl-CoA transferase or an acetoacetyl-CoA hydrolase or an acetoacetyl-CoA synthetase, an acetoacetate decarboxylase; and an isopropanol dehydrogenase.

In one embodiment, the invention provides a method for producing MAA and isopropanol that includes culturing a non-naturally occurring microbial organism including a microbial organism having an MAA pathway and an isopropanol pathway, the MAA pathway including a first set of exogenous nucleic acids encoding MAA pathway enzymes expressed in a sufficient amount to produce MAA, the first set of exogenous nucleic acids encoding a succinate reductase; a 4-hydroxybutyrate dehydrogenase; a 4-hydroxybutyryl-CoA transferase or a 4-hydroxybutyryl-CoA synthetase; a 4-hydroxybutyryl-CoA mutase; a 3-hydroxyisobutyryl-CoA dehydratase; and a methacrylyl-CoA transferase, a methacrylyl-CoA synthetase or a methacrylyl-CoA hydrolase, and the isopropanol pathway comprising a second set of exogenous nucleic acids encoding isopropanol pathway enzymes expressed in a sufficient amount to produce isopropanol, the second set of exogenous nucleic acids encoding an acetyl-CoA acetyl thiolase; an acetoacetyl-CoA transferase or an acetoacetyl-CoA hydrolase or an acetoacetyl-CoA synthetase; an acetoacetate decarboxylase; and an isopropanol dehydrogenase.

In one embodiment, the invention provides a method for producing MAA and isopropanol that includes culturing a non-naturally occurring microbial organism including a microbial organism having an MAA pathway and an isopropanol pathway, the MAA pathway including a first set of exogenous nucleic acids encoding MAA pathway enzymes expressed in a sufficient amount to produce MAA, the first set of exogenous nucleic acids encoding a succinate reductase; a 4-hydroxybutyrate dehydrogenase; a 4-hydroxybutyrate kinase; a phosphotrans-4-hydroxybutyrylase; a 4-hydroxybutyryl-CoA mutase; a 3-hydroxyisobutyryl-CoA transferase, a 3-hydroxyisobutyryl-CoA synthetase or a 3-hydroxyisobutyryl-CoA hydrolase; and a 3-hydroxyisobutyrate dehydratase, and the isopropanol pathway comprising a second set of exogenous nucleic acids encoding isopropanol pathway enzymes expressed in a sufficient amount to produce isopropanol, the second set of exogenous nucleic acids encoding an acetyl-CoA acetyl thiolase; an acetoacetyl-CoA transferase or an acetoacetyl-CoA hydrolase or an acetoacetyl-CoA synthetase, an acetoacetate decarboxylase; and an isopropanol dehydrogenase.

In one embodiment, the invention provides a method for producing MAA and isopropanol that includes culturing a non-naturally occurring microbial organism including a microbial organism having an MAA pathway and an isopropanol pathway, the MAA pathway including a first set of exogenous nucleic acids encoding MAA pathway enzymes expressed in a sufficient amount to produce MAA, the first set of exogenous nucleic acids encoding a succinate reductase; a 4-hydroxybutyrate dehydrogenase; a 4 hydroxybutyrate kinase; a phosphotrans-4-hydroxybutyrylase; a 4-hydroxybutyryl-CoA mutase; a 3-hydroxyisobutyryl-CoA dehydratase; and a methacrylyl-CoA transferase, a methacrylyl-CoA synthetase or a methacrylyl-CoA hydrolase, and the isopropanol pathway comprising a second set of exogenous nucleic acids encoding isopropanol pathway enzymes expressed in a sufficient amount to produce isopropanol, the second set of exogenous nucleic acids encoding an acetyl-CoA acetyl thiolase; an acetoacetyl-CoA transferase or an acetoacetyl-CoA hydrolase or an acetoacetyl-CoA synthetase; an acetoacetate decarboxylase; and an isopropanol dehydrogenase.

In one embodiment, the invention provides a method for producing MAA and isopropanol that includes culturing a non-naturally occurring microbial organism including a microbial organism having an MAA pathway and an isopropanol pathway, the MAA pathway including a first set of exogenous nucleic acids encoding MAA pathway enzymes expressed in a sufficient amount to produce MAA, the first set of exogenous nucleic acids encoding a methylmalonyl-CoA mutase; a methylmalonyl-CoA reductase (aldehyde forming); a 3-hydroxyisobutyrate dehydrogenase; and a 3-hydroxyisobutyrate dehydratase, and the isopropanol pathway comprising a second set of exogenous nucleic acids encoding isopropanol pathway enzymes expressed in a sufficient amount to produce isopropanol, the second set of exogenous nucleic acids encoding an acetyl-CoA acetyl thiolase; an acetoacetyl-CoA transferase or an acetoacetyl-CoA hydrolase or an acetoacetyl-CoA synthetase; an acetoacetate decarboxylase; and an isopropanol dehydrogenase.

In one embodiment, the invention provides a method for producing MAA and isopropanol that includes culturing a non-naturally occurring microbial organism including a microbial organism having an MAA pathway and an isopropanol pathway, the MAA pathway including a first set of exogenous nucleic acids encoding MAA pathway enzymes expressed in a sufficient amount to produce MAA, the first set of exogenous nucleic acids encoding a methylmalonyl-CoA mutase; a methylmalonyl-CoA epimerase; a methylmalonyl-CoA transferase, a methylmalonyl-CoA synthetase, or a methylmalonyl-CoA hydrolase; a methylmalonate reductase; a 3-hydroxyisobutyrate dehydrogenase; and a 3-hydroxyisobutyrate dehydratase, and the isopropanol pathway comprising a second set of exogenous nucleic acids encoding isopropanol pathway enzymes expressed in a sufficient amount to produce isopropanol, the second set of exogenous nucleic acids encoding an acetyl-CoA acetyl thiolase; an acetoacetyl-CoA transferase or an acetoacetyl-CoA hydrolase or an acetoacetyl-CoA synthetase; an acetoacetate decarboxylase; and an isopropanol dehydrogenase.

In one embodiment, the invention provides a method for producing MAA and isopropanol that includes culturing a non-naturally occurring microbial organism including a microbial organism having an MAA pathway and an isopropanol pathway, the MAA pathway including a first set of exogenous nucleic acids encoding MAA pathway enzymes expressed in a sufficient amount to produce MAA, the first set of exogenous nucleic acids encoding a methylmalonyl-CoA mutase; a methylmalonyl-CoA transferase, a methylmalonyl-CoA synthetase or a methylmalonyl-CoA hydrolase; a methylmalonate reductase; a 3-hydroxyisobutyrate dehydrogenase; and a 3-hydroxyisobutyrate dehydratase, and the isopropanol pathway comprising a second set of exogenous nucleic acids encoding isopropanol pathway enzymes expressed in a sufficient amount to produce isopropanol, the second set of exogenous nucleic acids encoding an acetyl-CoA acetyl thiolase; an acetoacetyl-CoA transferase or an acetoacetyl-CoA hydrolase or an acetoacetyl-CoA synthetase; an acetoacetate decarboxylase; and an isopropanol dehydrogenase.

In one embodiment, the invention provides a method for producing MAA and isopropanol that includes culturing a non-naturally occurring microbial organism including a microbial organism having an MAA pathway and an isopropanol pathway, the MAA pathway including a first set of exogenous nucleic acids encoding MAA pathway enzymes expressed in a sufficient amount to produce MAA, the first set of exogenous nucleic acids a methylmalonyl-CoA mutase; a methylmalonyl-CoA reductase (alcohol forming); and a 3-hydroxyisobutyrate dehydratase, and the isopropanol pathway comprising a second set of exogenous nucleic acids encoding isopropanol pathway enzymes expressed in a sufficient amount to produce isopropanol, the second set of exogenous nucleic acids encoding an acetyl-CoA acetyl thiolase; an acetoacetyl-CoA transferase or an acetoacetyl-CoA hydrolase or an acetoacetyl-CoA synthetase; an acetoacetate decarboxylase; and an isopropanol dehydrogenase.

In a further aspect of the above embodiments, the microbial organism has an acetyl-CoA pathway having a third set of exogenous nucleic acids encoding acetyl-CoA pathway enzymes expressed in a sufficient amount to produce acetyl-CoA, the third set of exogenous nucleic acids encoding a pyruvate kinase; and a pyruvate dehydrogenase or a pyruvate ferredoxin oxidoreductase; or a pyruvate formate lyase, a pyruvate formate lyase activating enzyme and a formate dehydrogenase.

In another further embodiment, the microbial organism has a succinyl-CoA pathway having a third set of exogenous nucleic acids encoding succinyl-CoA pathway enzymes expressed in a sufficient amount to produce succinyl-CoA, the third set of exogenous nucleic acids encoding a PEP carboxykinase, a PEP carboxylase, a malate dehydrogenase, a fumarase, a fumarate reductase, a succinyl-CoA transferase and a succinyl-CoA synthetase. In a further aspect, the third set of exogenous nucleic acids further encodes a methylmalonyl-CoA epimerase, a pyruvate carboxylase or a methylmalonyl-CoA carboxytransferase.

In one embodiment, the invention provides a method for producing 14-BDO and isopropanol that includes culturing a non-naturally occurring microbial organism including a microbial organism having an 14-BDO pathway and an isopropanol pathway, the 14-BDO pathway including a first set of exogenous nucleic acids encoding 14-BDO pathway enzymes expressed in a sufficient amount to produce 14-BDO, the first set of exogenous nucleic acids encoding a PEP carboxykinase, a PEP carboxylase, a malate dehydrogenase, a fumarase, a fumarate reductase, a succinyl-CoA transferase, a succinyl-CoA synthetase, a pyruvate carboxylase, a methylmalonyl-CoA carboxytransferase, a succinyl-CoA reductase, a succinate reductase, a 4-hydroxybutyrate dehydrogenase, a 4-hydroxybutyryl-CoA transferase, a 4-hydroxybutyryl-CoA synthetase, a 4-hydroxybutyryl-CoA reductase (aldehyde-forming), a 4-hydroxybutyraldehyde reductase, a 4-hydroxybutyrate reductase; a 4-hydroxybutyrate kinase, a phosphotrans-4-hydroxybutyrylase, a 4-hydroxybutyryl-phosphate reductase, a 4-hydroxybutyryl-CoA reductase (alcohol-forming), and a 4-hydroxybutyraldehyde reductase, and the isopropanol pathway comprising a second set of exogenous nucleic acids encoding isopropanol pathway enzymes expressed in a sufficient amount to produce isopropanol, the second set of exogenous nucleic acids encoding a pyruvate kinase, a pyruvate dehydrogenase, a pyruvate ferredoxin oxidoreductase, a pyruvate formate lyase, a pyruvate formate lyase activating enzyme, a formate dehydrogenase, an acetyl-CoA acetyl thiolase, an acetoacetyl-CoA transferase, an acetoacetyl-CoA hydrolase, an acetoacetyl-CoA synthetase, an acetoacetate decarboxylase, and an isopropanol dehydrogenase.

In one embodiment, the invention provides a method for producing 13-BDO and isopropanol that includes culturing a non-naturally occurring microbial organism including a microbial organism having an 13-BDO pathway and an isopropanol pathway, the 13-BDO pathway including a first set of exogenous nucleic acids encoding 13-BDO pathway enzymes expressed in a sufficient amount to produce 13-BDO, the first set of exogenous nucleic acids encoding PEP carboxykinase, a PEP carboxylase, a malate dehydrogenase, a fumarase, a fumarate reductase, a succinyl-CoA transferase, a succinyl-CoA synthetase, a pyruvate carboxylase, a methylmalonyl-CoA carboxytransferase, a succinyl-CoA reductase, a succinate reductase, a 4-hydroxybutyrate dehydrogenase, a 4-hydroxybutyryl-CoA transferase, a 4-hydroxybutyryl-CoA synthetase, a 4-hydroxybutyrate kinase, a phosphotrans-4-hydroxybutyrylase, a 4-hydroxybutyryl-CoA dehydratase, a crotonase, a 3-hydroxybutyryl-CoA reductase (aldehyde forming), a 3-hydroxybutyraldehyde reductase, a 3-hydroxybutyryl-CoA transferase, a 3-hydroxybutyryl-CoA synthetase, a 3-hydroxybutyryl-CoA hydrolase, a 3-hydroxybutyrate reductase, and a 3-hydroxybutyryl-CoA reductase (alcohol-forming), and the isopropanol pathway comprising a second set of exogenous nucleic acids encoding isopropanol pathway enzymes expressed in a sufficient amount to produce isopropanol, the second set of exogenous nucleic acids encoding a pyruvate kinase, a pyruvate dehydrogenase, a pyruvate ferredoxin oxidoreductase, a pyruvate formate lyase, a pyruvate formate lyase activating enzyme, a formate dehydrogenase, an acetyl-CoA acetyl thiolase, an acetoacetyl-CoA transferase, an acetoacetyl-CoA hydrolase, an acetoacetyl-CoA synthetase, an acetoacetate decarboxylase, and an isopropanol dehydrogenase.

In one embodiment, the invention provides a method for producing MAA and isopropanol that includes culturing a non-naturally occurring microbial organism including a microbial organism having an MAA pathway and an isopropanol pathway, the MAA pathway including a first set of exogenous nucleic acids encoding MAA pathway enzymes expressed in a sufficient amount to produce MAA, the first set of exogenous nucleic acids encoding a PEP carboxykinase, a PEP carboxylase, a malate dehydrogenase, a fumarase, a fumarate reductase, a succinyl-CoA transferase, a succinyl-CoA synthetase, a pyruvate carboxylase, a methylmalonyl-CoA carboxytransferase, a succinyl-CoA reductase, a succinate reductase, a 4-hydroxybutyrate dehydrogenase, a 4-hydroxybutyryl-CoA transferase, a 4-hydroxybutyryl-CoA synthetase, a 4-hydroxybutyrate kinase, a phosphotrans-4-hydroxybutyrylase, a 4-hydroxybutyryl-CoA mutase, a 3-hydroxyisobutyryl-CoA transferase, a 3-hydroxyisobutyryl-CoA synthetase, a 3-hydroxyisobutyryl-CoA hydrolase, 3-hydroxyisobutyryl-CoA dehydratase, methacrylyl-CoA transferase, methacrylyl-CoA synthetase, methacrylyl-CoA hydrolase and a 3-hydroxyisobutyrate dehydratase, and the isopropanol pathway comprising a second set of exogenous nucleic acids encoding isopropanol pathway enzymes expressed in a sufficient amount to produce isopropanol, the second set of exogenous nucleic acids encoding a pyruvate kinase, a pyruvate dehydrogenase, a pyruvate ferredoxin oxidoreductase, a pyruvate formate lyase, a pyruvate formate lyase activating enzyme, a formate dehydrogenase, an acetyl-CoA acetyl thiolase, an acetoacetyl-CoA transferase, an acetoacetyl-CoA hydrolase, an acetoacetyl-CoA synthetase, an acetoacetate decarboxylase, and an isopropanol dehydrogenase.

In one embodiment, the invention provides a method for producing MAA and isopropanol that includes culturing a non-naturally occurring microbial organism including a microbial organism having an MAA pathway and an isopropanol pathway, the MAA pathway including a first set of exogenous nucleic acids encoding MAA pathway enzymes expressed in a sufficient amount to produce MAA, the first set of exogenous nucleic acids encoding a PEP carboxykinase, a PEP carboxylase, a malate dehydrogenase, a fumarase, a fumarate reductase, a succinyl-CoA transferase, a succinyl-CoA synthetase, a pyruvate carboxylase, a methylmalonyl-CoA carboxytransferase, a methylmalonyl-CoA mutase, a methylmalonyl-CoA epimerase, a methylmalonyl-CoA transferase, a methylmalonyl-CoA synthetase, a methylmalonyl-CoA hydrolase, a methylmalonate reductase, a methylmalonyl-CoA reductase (aldehyde forming), a 3-hydroxyisobutyrate dehydrogenase, a methylmalonyl-CoA reductase (alcohol forming) and a 3-hydroxyisobutyrate dehydratase, and the isopropanol pathway comprising a second set of exogenous nucleic acids encoding isopropanol pathway enzymes expressed in a sufficient amount to produce isopropanol, the second set of exogenous nucleic acids encoding a pyruvate kinase, a pyruvate dehydrogenase, a pyruvate ferredoxin oxidoreductase, a pyruvate formate lyase, a pyruvate formate lyase activating enzyme, a formate dehydrogenase, an acetyl-CoA acetyl thiolase, an acetoacetyl-CoA transferase, an acetoacetyl-CoA hydrolase, an acetoacetyl-CoA synthetase, an acetoacetate decarboxylase, and an isopropanol dehydrogenase.

In a further aspect of each of the above embodiments, the exogenous nucleic acid is a heterologous nucleic acid.

In a further aspect of each of the above embodiments, the conditions include substantially anaerobic culture conditions.

Suitable purification and/or assays to test for the production of n-propanol, isopropanol, 14-BDO, 13-BDO and/or MAA can be performed using well known methods. Suitable replicates such as triplicate cultures can be grown for each engineered strain to be tested. For example, product and byproduct formation in the engineered production host can be monitored. The final product and intermediates, and other organic compounds, can be analyzed by methods such as HPLC (High Performance Liquid Chromatography), GC-MS (Gas Chromatography-Mass Spectroscopy) and LC-MS (Liquid Chromatography-Mass Spectroscopy) or other suitable analytical methods using routine procedures well known in the art. The release of product in the fermentation broth can also be tested with the culture supernatant. Byproducts and residual glucose can be quantified by HPLC using, for example, a refractive index detector for glucose and alcohols, and a UV detector for organic acids (Lin et al., *Biotechnol. Bioeng.* 90:775-779 (2005)), or other suitable assay and detection methods well known in the art. The individual enzyme or protein activities from the exogenous DNA sequences can also be assayed using methods well known in the art. Various alcohols can be quantified by gas chromatography by using a flame ionization detector as described in Atsumi et al. *Metab Eng* (2007) and Hanai et al. *Appl Environ Microbiol* 73:7814-7818 (2007).

The n-propanol, isopropanol, 14-BDO, 13-BDO and/or MAA can be separated from other components in the culture using a variety of methods well known in the art. Such separation methods include, for example, extraction procedures as well as methods that include continuous liquid-liquid extraction, pervaporation, membrane filtration, membrane separation, reverse osmosis, electrodialysis, distillation, crystallization, centrifugation, extractive filtration, ion exchange chromatography, size exclusion chromatography, adsorption chromatography, and ultrafiltration. All of the above methods are well known in the art.

Any of the non-naturally occurring microbial organisms described herein can be cultured to produce and/or secrete the biosynthetic products of the invention. For example, the n-propanol, isopropanol, 14-BDO, 13-BDO and/or MAA producers can be cultured for the biosynthetic production of n-propanol, isopropanol, 14-BDO, 13-BDO and/or MAA.

For the production of n-propanol, isopropanol, 14-BDO, 13-BDO and/or MAA, the recombinant strains are cultured in a medium with a carbon source and other essential nutrients. It is highly desirable to maintain anaerobic conditions in the fermenter to reduce the cost of the overall process. Such conditions can be obtained, for example, by first sparging the medium with nitrogen and then sealing the flasks with a septum and crimp-cap. For strains where growth is not observed anaerobically, microaerobic conditions can be applied by perforating the septum with a small hole for limited aeration. Exemplary anaerobic conditions have been described previously and are well-known in the art. Exemplary aerobic and anaerobic conditions are described, for example, in U.S. publication 2009/0047719, filed Aug. 10, 2007. Fermentations can be performed in a batch, fed-batch or continuous manner, as disclosed herein.

If desired, the pH of the medium can be maintained at a desired pH, in particular neutral pH, such as a pH of around 7 by addition of a base, such as NaOH or other bases, or acid, as needed to maintain the culture medium at a desirable pH. The growth rate can be determined by measuring optical density using a spectrophotometer (600 nm), and the glucose uptake rate by monitoring carbon source depletion over time.

The growth medium can include, for example, any carbohydrate source which can supply a source of carbon to the non-naturally occurring microorganism. Such sources include, for example, sugars such as glucose, xylose, arabinose, galactose, mannose, fructose, sucrose and starch. Other sources of carbohydrate include, for example, renewable feedstocks and biomass. Exemplary types of biomasses that can be used as feedstocks in the methods of the invention include cellulosic biomass, hemicellulosic biomass and lignin feedstocks or portions of feedstocks. Such biomass feedstocks contain, for example, carbohydrate substrates useful as carbon sources such as glucose, xylose, arabinose, galactose, mannose, fructose and starch. Given the teachings and guidance provided herein, those skilled in the art will understand that renewable feedstocks and biomass other than those exemplified above also can be used for culturing the microbial organisms of the invention for the production of n-propanol, isopropanol, 14-BDO, 13-BDO and/or MAA.

In addition to renewable feedstocks such as those exemplified above, the n-propanol and isopropanol, 14-BDO and isopropanol, 13-BDO and isopropanol or MAA and isopropanol microbial organisms of the invention also can be modified for growth on syngas as its source of carbon. In this specific embodiment, one or more proteins or enzymes are expressed in the n-propanol, isopropanol, 14-BDO, 13-BDO and/or MAA producing organisms to provide a metabolic pathway for utilization of syngas or other gaseous carbon source.

Synthesis gas, also known as syngas or producer gas, is the major product of gasification of coal and of carbonaceous materials such as biomass materials, including agricultural crops and residues. Syngas is a mixture primarily of $H_2$ and CO and can be obtained from the gasification of any organic feedstock, including but not limited to coal, coal oil, natural gas, biomass, and waste organic matter. Gasification is generally carried out under a high fuel to oxygen ratio. Although largely $H_2$ and CO, syngas can also include $CO_2$ and other gases in smaller quantities. Thus, synthesis gas provides a cost effective source of gaseous carbon such as CO and, additionally, $CO_2$.

The Wood-Ljungdahl pathway catalyzes the conversion of CO and $H_2$ to acetyl-CoA and other products such as acetate. Organisms capable of utilizing CO and syngas also generally have the capability of utilizing $CO_2$ and $CO_2/H_2$ mixtures through the same basic set of enzymes and transformations encompassed by the Wood-Ljungdahl pathway. $H_2$-dependent conversion of $CO_2$ to acetate by microorganisms was recognized long before it was revealed that CO also could be used by the same organisms and that the same pathways were involved. Many acetogens have been shown to grow in the presence of $CO_2$ and produce compounds such as acetate as long as hydrogen is present to supply the necessary reducing equivalents (see for example, Drake, *Acetogenesis*, pp. 3-60 Chapman and Hall, New York, (1994)). This can be summarized by the following equation:

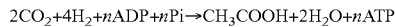

$$2CO_2 + 4H_2 + n\text{ADP} + n\text{Pi} \rightarrow CH_3COOH + 2H_2O + n\text{ATP}$$

Hence, non-naturally occurring microorganisms possessing the Wood-Ljungdahl pathway can utilize $CO_2$ and $H_2$ mixtures as well for the production of acetyl-CoA and other desired products.

The Wood-Ljungdahl pathway is well known in the art and consists of 12 reactions which can be separated into two branches: (1) methyl branch and (2) carbonyl branch. The methyl branch converts syngas to methyl-tetrahydrofolate (methyl-THF) whereas the carbonyl branch converts methyl-THF to acetyl-CoA. The reactions in the methyl branch are catalyzed in order by the following enzymes or proteins: ferredoxin oxidoreductase, formate dehydrogenase, formyltetrahydrofolate synthetase, methenyltetrahydrofolate cyclodehydratase, methylenetetrahydrofolate dehydrogenase and methylenetetrahydrofolate reductase. The reactions in the carbonyl branch are catalyzed in order by the following enzymes or proteins: methyltetrahydrofolate:corrinoid protein methyltransferase (for example, AcsE), corrinoid iron-sulfur protein, nickel-protein assembly protein (for example, AcsF), ferredoxin, acetyl-CoA synthase, carbon monoxide dehydrogenase and nickel-protein assembly protein (for example, CooC). Following the teachings and guidance provided herein for introducing a sufficient number of encoding nucleic acids to generate an n-propanol, an isopropanol, a 14-BDO, a 13-BDO and/or a MAA pathway, those skilled in the art will understand that the same engineering design also can be performed with respect to introducing at least the nucleic acids encoding the Wood-Ljungdahl enzymes or proteins absent in the host organism. Therefore, introduction of one or more encoding nucleic acids into the microbial organisms of the invention such that the modified organism contains the complete Wood-Ljungdahl pathway will confer syngas utilization ability.

Additionally, the reductive (reverse) tricarboxylic acid cycle is and/or hydrogenase activities can also be used for the conversion of CO, $CO_2$ and/or $H_2$ to acetyl-CoA and other products such as acetate. Organisms capable of fixing carbon via the reductive TCA pathway can utilize one or more of the following enzymes: ATP citrate-lyase, citrate lyase, aconitase, isocitrate dehydrogenase, alpha-ketoglutarate:ferredoxin oxidoreductase, succinyl-CoA synthetase, succinyl-CoA transferase, fumarate reductase, fumarase, malate dehydrogenase, NAD(P)H:ferredoxin oxidoreductase, carbon monoxide dehydrogenase, and hydrogenase. Specifically, the reducing equivalents extracted from CO and/or $H_2$ by carbon monoxide dehydrogenase and hydrogenase are utilized to fix $CO_2$ via the reductive TCA cycle into acetyl-CoA or acetate. Acetate can be converted to acetyl-CoA by enzymes such as acetyl-CoA transferase, acetate kinase/phosphotransacetylase, and acetyl-CoA synthetase. Acetyl-CoA can be converted to an n-propanol, an isopropanol, a 14-BDO, a 13-BDO and/or a MAA precursors, glyceraldehyde-3-phosphate, phosphoenolpyruvate, and pyruvate, by pyruvate:ferredoxin oxidoreductase and the enzymes of gluconeogenesis. Following the teachings and guidance provided herein for introducing a sufficient number of encoding nucleic acids to generate an n-propanol, an isopropanol, a 14-BDO, a 13-BDO and/or a MAA pathway, those skilled in the art will understand that the same engineering design also can be performed with respect to introducing at least the nucleic acids encoding the reductive TCA pathway enzymes or proteins absent in the host organism. Therefore, introduction of one or more encoding nucleic acids into the microbial organisms of the invention such that the modified organism contains the complete reductive TCA pathway will confer syngas utilization ability.

Accordingly, given the teachings and guidance provided herein, those skilled in the art will understand that a non-naturally occurring microbial organism can be produced that secretes the biosynthesized compounds of the invention when grown on a carbon source such as a carbohydrate. Such compounds include, for example, n-propanol, isopropanol, 14-BDO, 13-BDO and/or MAA and any of the intermediate metabolites in the n-propanol, isopropanol, 14-BDO, 13-BDO and/or MAA pathway. All that is required is to engineer in one or more of the required enzyme or protein activities to achieve biosynthesis of the desired compound or intermediate including, for example, inclusion of some or all of the n-propanol, isopropanol, 14-BDO, 13-BDO and/or MAA biosynthetic pathways. Accordingly, the invention provides a non-naturally occurring microbial organism that produces and/or secretes n-propanol, isopropanol, 14-BDO, 13-BDO and/or MAA when grown on a carbohydrate or other carbon source and produces and/or secretes any of the intermediate metabolites shown in the n-propanol, isopropanol, 14-BDO, 13-BDO and/or MAA pathway when grown on a carbohydrate or other carbon source. The n-propanol and isopropanol, 14-BDO and isopropanol, 13-BDO and isopropanol or MAA and isopropanol producing microbial organisms of the invention can initiate synthesis from an intermediate, for example, succinyl-CoA, propionyl-CoA and/or acetyl-CoA.

The non-naturally occurring microbial organisms of the invention are constructed using methods well known in the art as exemplified herein to exogenously express at least one nucleic acid encoding an n-propanol, an isopropanol, a 14-BDO, a 13-BDO and/or a MAA pathway enzyme or protein in sufficient amounts to produce n-propanol, isopropanol, 14-BDO, 13-BDO and/or MAA. It is understood that the microbial organisms of the invention are cultured under conditions sufficient to produce n-propanol, isopropanol, 14-BDO, 13-BDO and/or MAA. Following the teachings and guidance provided herein, the non-naturally occurring microbial organisms of the invention can achieve biosynthesis of n-propanol, isopropanol, 14-BDO, 13-BDO and/or MAA resulting in intracellular concentrations between about 0.1-200 mM or more. Generally, the intracellular concentration of n-propanol, isopropanol, 14-BDO, 13-BDO and/or MAA is between about 3-150 mM, particularly between about 5-125 mM and more particularly between about 8-100 mM, including about 10 mM, 20 mM, 50 mM, 80 mM, or more. Intracellular concentrations between and above each of these exemplary ranges also can be achieved from the non-naturally occurring microbial organisms of the invention.

In some embodiments, culture conditions include anaerobic or substantially anaerobic growth or maintenance conditions. Exemplary anaerobic conditions have been described previously and are well known in the art. Exemplary anaerobic conditions for fermentation processes are described herein and are described, for example, in U.S. publication 2009/0047719, filed Aug. 10, 2007. Any of these conditions can be employed with the non-naturally occurring microbial organisms as well as other anaerobic conditions well known in the art. Under such anaerobic conditions, the n-propanol, isopropanol, 14-BDO, 13-BDO and/or MAA producers can synthesize n-propanol, isopropanol, 14-BDO, 13-BDO and/or MAA at intracellular concentrations of 5-10 mM or more as well as all other concentrations exemplified herein. It is understood that, even though the above description refers to intracellular concentrations, n-propanol, isopropanol, 14-BDO, 13-BDO and/or MAA producing microbial organisms can produce n-propanol, isopropanol, 14-BDO, 13-BDO and/or MAA intracellularly and/or secrete the product into the culture medium.

The culture conditions can include, for example, liquid culture procedures as well as fermentation and other large scale culture procedures. As described herein, particularly useful yields of the biosynthetic products of the invention can be obtained under anaerobic or substantially anaerobic culture conditions.

As described herein, one exemplary growth condition for achieving biosynthesis of n-propanol and isopropanol, 14-BDO and isopropanol, 13-BDO and isopropanol or MAA and isopropanol includes anaerobic culture or fermentation conditions. In certain embodiments, the non-naturally occurring microbial organisms of the invention can be sustained, cultured or fermented under anaerobic or substantially anaerobic conditions. Briefly, anaerobic conditions refers to an environment devoid of oxygen. Substantially anaerobic conditions include, for example, a culture, batch fermentation or continuous fermentation such that the dissolved oxygen concentration in the medium remains between 0 and 10% of saturation. Substantially anaerobic conditions also includes growing or resting cells in liquid medium or on solid agar inside a sealed chamber maintained with an atmosphere of less than 1% oxygen. The percent of oxygen can be maintained by, for example, sparging the culture with an $N_2/CO_2$ mixture or other suitable non-oxygen gas or gases.

The culture conditions described herein can be scaled up and grown continuously for manufacturing of n-propanol and isopropanol, 14-BDO and isopropanol, 13-BDO and isopropanol or MAA and isopropanol. Exemplary growth procedures include, for example, fed-batch fermentation and batch separation; fed-batch fermentation and continuous separation, or continuous fermentation and continuous separation. All of these processes are well known in the art. Fermentation procedures are particularly useful for the biosynthetic production of commercial quantities of n-propanol, isopropanol, 14-BDO, 13-BDO and/or MAA. Generally, and as with non-continuous culture procedures, the continuous and/or near-continuous production of n-propanol, isopropanol, 14-BDO, 13-BDO and/or MAA will include culturing a non-naturally occurring n-propanol and isopropanol, 14-BDO and isopropanol, 13-BDO and isopropanol or MAA and isopropanol producing organism of the invention in sufficient nutrients and medium to sustain and/or nearly sustain growth in an exponential phase. Continuous culture under such conditions can be include, for example, growth for 1 day, 2, 3, 4, 5, 6 or 7 days or more. Additionally, continuous culture can include longer time periods of 1 week, 2, 3, 4 or 5 or more weeks and up to several months. Alternatively, organisms of the invention can be cultured for hours, if suitable for a particular application. It is to be understood that the continuous and/or near-continuous culture conditions also can include all time intervals in between these exemplary periods. It is further understood that the time of culturing the microbial organism of the invention is for a sufficient period of time to produce a sufficient amount of product for a desired purpose.

Fermentation procedures are well known in the art. Briefly, fermentation for the biosynthetic production of n-propanol and isopropanol, 14-BDO and isopropanol, 13-BDO and isopropanol or MAA and isopropanol can be utilized in, for example, fed-batch fermentation and batch separation; fed-batch fermentation and continuous separation, or continuous fermentation and continuous separation. Examples of batch and continuous fermentation procedures are well known in the art.

In addition to the above fermentation procedures using the n-propanol, isopropanol, 14-BDO, 13-BDO and/or MAA producers of the invention for continuous production of substantial quantities of n-propanol and isopropanol, 14-BDO and isopropanol, 13-BDO and isopropanol or MAA and isopropanol, the n-propanol, isopropanol, 14-BDO, 13-BDO and/or MAA producers also can be, for example, simultaneously subjected to chemical synthesis procedures to convert the product to other compounds or the product can be separated from the fermentation culture and sequentially subjected to chemical conversion to convert the product to other compounds, if desired.

In addition to the culturing and fermentation conditions described herein, growth condition for achieving biosynthesis of n-propanol and isopropanol, 14-BDO and isopropanol, 13-BDO and isopropanol or MAA and isopropanol can include the addition of an osmoprotectant to the culturing conditions. In certain embodiments, the non-naturally occurring microbial organisms of the invention can be sustained, cultured or fermented as described herein in the presence of an osmoprotectant. Briefly, an osmoprotectant means a compound that acts as an osmolyte and helps a microbial organism as described herein survive osmotic stress. Osmoprotectants include, but are not limited to, betaines, amino acids, and the sugar trehalose. Non-limiting examples of such are glycine betaine, praline betaine, dimethylthetin, dimethylsulfonioproprionate, 3-dimethylsulfonio-2-methylproprionate, pipecolic acid, dimethylsulfonioacetate, choline, L-carnitine and ectoine. In one aspect, the osmoprotectant is glycine betaine. It is understood to one of ordinary skill in the art that the amount and type of osmoprotectant suitable for protecting a microbial organism described herein from osmotic stress will depend on the microbial organism used. The amount of osmoprotectant in the culturing conditions can be, for example, no more than about 0.1 mM, no more than about 0.5 mM, no more than about 1.0 mM, no more than about 1.5 mM, no more than about 2.0 mM, no more than about 2.5 mM, no more than about 3.0 mM, no more than about 5.0 mM, no more than about 7.0 mM, no more than about 10 mM, no more than about 50 mM, no more than about 100 mM or no more than about 500 mM.

To generate better producers, metabolic modeling can be utilized to optimize growth conditions. Modeling can also be used to design gene knockouts that additionally optimize utilization of the pathway (see, for example, U.S. patent publications US 2002/0012939, US 2003/0224363, US 2004/0029149, US 2004/0072723, US 2003/0059792, US 2002/0168654 and US 2004/0009466, and U.S. Pat. No. 7,127,379). Modeling analysis allows reliable predictions of the effects on cell growth of shifting the metabolism towards more efficient production of n-propanol, isopropanol, 14-BDO, 13-BDO and/or MAA.

One computational method for identifying and designing metabolic alterations favoring biosynthesis of a desired product is the OptKnock computational framework (Burgard et al., *Biotechnol. Bioeng.* 84:647-657 (2003)). OptKnock is a metabolic modeling and simulation program that suggests gene deletion or disruption strategies that result in genetically stable microorganisms which overproduce the target product. Specifically, the framework examines the complete metabolic and/or biochemical network of a microorganism in order to suggest genetic manipulations that force the desired biochemical to become an obligatory byproduct of cell growth. By coupling biochemical production with cell growth through strategically placed gene deletions or other functional gene disruption, the growth selection pressures imposed on the engineered strains after long periods of time in a bioreactor lead to improvements in performance as a result of the compulsory growth-coupled biochemical production. Lastly, when gene deletions are constructed there is a negligible possibility of the designed strains reverting to their wild-type states because the genes selected by OptKnock are to be completely removed from the genome. Therefore, this computational methodology can be used to either identify alternative pathways that lead to biosynthesis of a desired product or used in connection with the non-naturally occurring microbial organisms for further optimization of biosynthesis of a desired product.

Briefly, OptKnock is a term used herein to refer to a computational method and system for modeling cellular metabolism. The OptKnock program relates to a framework of models and methods that incorporate particular constraints into flux balance analysis (FBA) models. These constraints include, for example, qualitative kinetic information, qualitative regulatory information, and/or DNA microarray experimental data. OptKnock also computes solutions to various metabolic problems by, for example, tightening the flux boundaries derived through flux balance models and subsequently probing the performance limits of metabolic networks in the presence of gene additions or deletions. OptKnock computational framework allows the construction of model formulations that allow an effective query of the performance limits of metabolic networks and provides methods for solving the resulting mixed-integer linear programming problems. The metabolic modeling and simulation methods referred to herein as OptKnock are described in, for example, U.S. publication 2002/0168654, filed Jan. 10, 2002, in International Patent No. PCT/US02/00660, filed Jan. 10, 2002, and U.S. publication 2009/0047719, filed Aug. 10, 2007.

Another computational method for identifying and designing metabolic alterations favoring biosynthetic production of a product is a metabolic modeling and simulation system termed SimPheny®. This computational method and system is described in, for example, U.S. publication 2003/0233218, filed Jun. 14, 2002, and in International Patent Application No. PCT/US03/18838, filed Jun. 13, 2003. SimPheny® is a computational system that can be used to produce a network model in silico and to simulate the flux of mass, energy or charge through the chemical reactions of a biological system to define a solution space that contains any and all possible functionalities of the chemical reactions in the system, thereby determining a range of allowed activities for the biological system. This approach is referred to as constraints-based modeling because the solution space is defined by constraints such as the known stoichiometry of the included reactions as well as reaction thermodynamic and capacity constraints associated with maximum fluxes through reactions. The space defined by these constraints can be interrogated to determine the phenotypic capabilities and behavior of the biological system or of its biochemical components.

These computational approaches are consistent with biological realities because biological systems are flexible and can reach the same result in many different ways. Biological systems are designed through evolutionary mechanisms that have been restricted by fundamental constraints that all living systems must face. Therefore, constraints-based modeling strategy embraces these general realities. Further, the ability to continuously impose further restrictions on a network model via the tightening of constraints results in a reduction in the size of the solution space, thereby enhancing the precision with which physiological performance or phenotype can be predicted.

Given the teachings and guidance provided herein, those skilled in the art will be able to apply various computational frameworks for metabolic modeling and simulation to design and implement biosynthesis of a desired compound in host microbial organisms. Such metabolic modeling and simulation methods include, for example, the computational systems exemplified above as SimPheny® and OptKnock. For illustration of the invention, some methods are described herein with reference to the OptKnock computation framework for modeling and simulation. Those skilled in the art will know how to apply the identification, design and implementation of the metabolic alterations using OptKnock to any of such other metabolic modeling and simulation computational frameworks and methods well known in the art.

The methods described above will provide one set of metabolic reactions to disrupt. Elimination of each reaction within the set or metabolic modification can result in a desired product as an obligatory product during the growth phase of the organism. Because the reactions are known, a solution to the bilevel OptKnock problem also will provide the associated gene or genes encoding one or more enzymes that catalyze each reaction within the set of reactions. Identification of a set of reactions and their corresponding genes encoding the enzymes participating in each reaction is generally an automated process, accomplished through correlation of the reactions with a reaction database having a relationship between enzymes and encoding genes.

Once identified, the set of reactions that are to be disrupted in order to achieve production of a desired product are implemented in the target cell or organism by functional disruption of at least one gene encoding each metabolic reaction within the set. One particularly useful means to achieve functional disruption of the reaction set is by deletion of each encoding gene. However, in some instances, it can be beneficial to disrupt the reaction by other genetic aberrations including, for example, mutation, deletion of regulatory regions such as promoters or cis binding sites for regulatory factors, or by truncation of the coding sequence at any of a number of locations. These latter aberrations, resulting in less than total deletion of the gene set can be useful, for example, when rapid assessments of the coupling of a product are desired or when genetic reversion is less likely to occur.

To identify additional productive solutions to the above described bilevel OptKnock problem which lead to further sets of reactions to disrupt or metabolic modifications that can result in the biosynthesis, including growth-coupled biosynthesis of a desired product, an optimization method, termed integer cuts, can be implemented. This method proceeds by iteratively solving the OptKnock problem exemplified above with the incorporation of an additional constraint referred to as an integer cut at each iteration. Integer cut constraints effectively prevent the solution procedure from choosing the exact same set of reactions identified in any previous iteration that obligatorily couples product biosynthesis to growth. For example, if a previously identified growth-coupled metabolic modification specifies reactions 1, 2, and 3 for disruption, then the following constraint prevents the same reactions from being simultaneously considered in subsequent solutions. The integer cut method is well known in the art and can be found described in, for example, Burgard et al., *Biotechnol. Prog.* 17:791-797 (2001). As with all methods described herein with reference to their use in combination with the OptKnock computational framework for metabolic modeling and simulation, the integer cut method of reducing redundancy in iterative computational analysis also can be applied with other computational frameworks well known in the art including, for example, SimPheny®.

The methods exemplified herein allow the construction of cells and organisms that biosynthetically produce a desired product, including the obligatory coupling of production of a target biochemical product to growth of the cell or organism engineered to harbor the identified genetic alterations. Therefore, the computational methods described herein allow the identification and implementation of metabolic modifications that are identified by an in silico method selected from OptKnock or SimPheny®. The set of metabolic modifications can include, for example, addition of one or more biosynthetic pathway enzymes and/or functional disruption of one or more metabolic reactions including, for example, disruption by gene deletion.

As discussed above, the OptKnock methodology was developed on the premise that mutant microbial networks can be evolved towards their computationally predicted maximum-growth phenotypes when subjected to long periods of growth selection. In other words, the approach leverages an organism's ability to self-optimize under selective pressures. The OptKnock framework allows for the exhaustive enumeration of gene deletion combinations that force a coupling between biochemical production and cell growth based on network stoichiometry. The identification of optimal gene/reaction knockouts requires the solution of a bilevel optimization problem that chooses the set of active reactions such that an optimal growth solution for the resulting network overproduces the biochemical of interest (Burgard et al., *Biotechnol. Bioeng.* 84:647-657 (2003)).

An in silico stoichiometric model of *E. coli* metabolism can be employed to identify essential genes for metabolic pathways as exemplified previously and described in, for example, U.S. patent publications US 2002/0012939, US 2003/0224363, US 2004/0029149, US 2004/0072723, US 2003/0059792, US 2002/0168654 and US 2004/0009466, and in U.S. Pat. No. 7,127,379. As disclosed herein, the OptKnock mathematical framework can be applied to pinpoint gene deletions leading to the growth-coupled production of a desired product. Further, the solution of the bilevel OptKnock problem provides only one set of deletions. To enumerate all meaningful solutions, that is, all sets of knockouts leading to growth-coupled production formation, an optimization technique, termed integer cuts, can be implemented. This entails iteratively solving the OptKnock problem with the incorporation of an additional constraint referred to as an integer cut at each iteration, as discussed above.

It is understood that modifications which do not substantially affect the activity of the various embodiments of this invention are also provided within the definition of the invention provided herein. Accordingly, the following examples are intended to illustrate but not limit the present invention.

Example I

Pathways for Co-Production of N-Propanol and Isopropanol from Glucose

This example describes exemplary pathways for co-production of n-propanol and isopropanol.

Novel pathways for co-producing n-propanol and isopropanol and related products are described herein. This invention provides four alternate methods for co-production of n-propanol and isopropanol. The production of isopropanol in *E. coli* has been described previously (Hanai et al., *Appl Environ Microbiol* 73:7814-7818 (2007)). Briefly, acetyl CoA is converted into acetoacetyl CoA, transformed into acetoacetate, decarboxylated to form acetone and then reduced to form isopropanol (FIGS. 1-4). The microbial organisms and methods described herein combine this known route with four novel pathways for synthesizing n-propanol. This co-production will provide completely redox balanced routes for production of the C3 alcohols, i.e. n-propanol and isopropanol, allowing for anaerobic production as opposed to the requirement of oxygen if isopropanol is produced solely via acetone as described by Hanai et al., supra. One advantage to the co-production of n-propanol and isopropanol using any of the pathways described herein is that the maximum theoretical yield of the C3 alcohols is afforded:

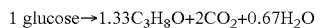

Furthermore, all of these pathways have a net positive yield of ATP.

Production of Isopropanol Utilizing Acetyl-CoA

Isopropanol production is achieved via conversion of acetyl-CoA by an acetoacetyl-CoA thiolase, an acetoacetyl-CoA transferase or an acetoacetyl-CoA hydrolase or an acetoacetyl-CoA synthetase, an acetoacetate decarboxylase, and an isopropanol dehydrogenase as exemplified in FIGS. 1-4. Isopropanol production has been described for recombinant *E. coli* following expression of two heterologous genes from *C. acetobutylicum* (thl and adc encoding acetoacetyl-CoA thiolase and acetoacetate decarboxylase, respectively) and one from *C. beijerinckii* (adh encoding a secondary alcohol dehydrogenase), along with the increased expression of the native atoA and atoD genes which encode acetoacetyl-CoA:acetate:CoA transferase activity (Hanai et al., *Appl Environ Microbiol* 73:7814-7818 (2007)). The conversion of acetoacetyl-CoA to acetoacetate can alternately be catalyzed by an enzyme with acetoacetyl-CoA hydrolase or acetoacetyl-CoA synthetase activities.

Acetoacetyl-CoA Thiolase

Acetoacetyl-CoA thiolase (also known as acetyl-CoA acetyltransferase) converts two molecules of acetyl-CoA into one molecule each of acetoacetyl-CoA and CoA. Exemplary acetoacetyl-CoA thiolase enzymes include the gene products of atoB from *E. coli* (Martin et al., *Nat. Biotechnol* 21:796-802 (2003)), thlA and thlB from *C. acetobutylicum* (Hanai et al., *Appl Environ Microbiol* 73:7814-7818 (2007); Winzer et al., *J. Mol. Microbiol Biotechnol* 2:531-541 (2000), and ERG10 from *S. cerevisiae* Hiser et al., *J. Biol. Chem.* 269: 31383-31389 (1994)). These genes/proteins are identified below in Table 1.

TABLE 1

| Gene | GenBank ID | GI Number | Organism |
|---|---|---|---|
| AtoB | NP_416728 | 16130161 | *Escherichia coli* |
| ThlA | NP_349476.1 | 15896127 | *Clostridium acetobutylicum* |
| ThlB | NP_149242.1 | 15004782 | *Clostridium acetobutylicum* |
| ERG10 | NP_015297 | 6325229 | *Saccharomyces cerevisiae* |

Acetoacetyl-CoA Transferase

Acetoacetyl-CoA transferase catalyzes the conversion of acetoacetyl-CoA to acetoacetate while transferring the CoA moiety to a CoA acceptor molecule. Many transferases have broad specificity and thus may utilize CoA acceptors as diverse as acetate, succinate, propionate, butyrate, 2-methylacetoacetate, 3-ketohexanoate, 3-ketopentanoate, valerate, crotonate, 3-mercaptopropionate, propionate, vinylacetate, butyrate, among others.

Acetoacetyl-CoA:acetate:CoA transferase converts acetoacetyl-CoA and acetate to acetoacetate and acetyl-CoA. Exemplary enzymes include the gene products of atoAD from *E. coli* (Hanai et al., Appl Environ Microbiol 73:7814-7818 (2007), ctfAB from *C. acetobutylicum* (Jojima et al., Appl Microbiol Biotechnol 77:1219-1224 (2008), and ctfAB from *Clostridium saccharoperbutylacetonicum* (Kosaka et al., *Biosci. Biotechnol Biochem.* 71:58-68 (2007)) are shown below in Table 2. A succinyl-CoA:3-ketoacid CoA transferase (SCOT) can also catalyze the conversion of the 3-ketoacyl-CoA, acetoacetyl-CoA, to the 3-ketoacid, acetoacetate. As opposed to acetoacetyl-CoA:acetate:CoA transferase, SCOT employs succinate as the CoA acceptor instead of acetate. Exemplary succinyl-CoA:3:ketoacid-CoA transferases are present in *Helicobacter pylori* (Corthesy-Theulaz et al., *J Biol Chem* 272:25659-25667 (1997)), *Bacillus subtilis* (Stols et al., Protein Expr Purif 53:396-403 (2007)), and *Homo sapiens* (Fukao et al., Genomics 68:144-151 (2000); Tanaka et al., *Mol Hum Reprod* 8:16-23 (2002)). Yet another transferase capable of this conversion is butyryl-CoA:acetoacetate CoA-transferase. Exemplary enzymes can be found in *Fusobacterium nucleatum* (Barker et al., *J Bacteriol* 152(1):201-7 (1982)), *Clostridium* SB4 (Barker et al., *J Biol Chem* 253(4):1219-25 (1978)), and *Clostridium acetobutylicum* (Wiesenborn et al., *Appl Environ Microbiol* 55(2): 323-9 (1989)). Although specific gene sequences were not provided for butyryl-CoA:acetoacetate CoA-transferase in these references, the genes FN0272 and FN0273 have been annotated as a butyrate-acetoacetate CoA-transferase (Kapatral et al., J Bact 184(7) 2005-2018 (2002)). Homologs in *Fusobacterium nucleatum* such as FN1857 and FN1856 also likely have the desired acetoacetyl-CoA transferase activity. FN1857 and FN1856 are located adjacent to many other genes involved in lysine fermentation and are thus very likely to encode an acetoacetate:butyrate CoA transferase (Kreimeyer, et al., *J Biol Chem* 282 (10) 7191-7197 (2007)). Additional candidates from *Porphyrmonas gingivalis* and *Thermoanaerobacter tengcongensis* can be identified in a similar fashion (Kreimeyer, et al., *J Biol Chem* 282 (10) 7191-7197 (2007)). These genes/proteins are identified below in Table 2.

TABLE 2

| Gene | GenBank ID | GI Number | Organism |
|---|---|---|---|
| AtoA | NP_416726.1 | 2492994 | *Escherichia coli* |
| AtoD | NP_416725.1 | 2492990 | *Escherichia coli* |
| CtfA | NP_149326.1 | 15004866 | *Clostridium acetobutylicum* |
| CtfB | NP_149327.1 | 15004867 | *Clostridium acetobutylicum* |
| CtfA | AAP42564.1 | 31075384 | *Clostridium saccharoperbutylacetonicum* |
| CtfB | AAP42565.1 | 31075385 | *Clostridium saccharoperbutylacetonicum* |
| HPAG1_0676 | YP_627417 | 108563101 | *Helicobacter pylori* |
| HPAG1_0677 | YP_627418 | 108563102 | *Helicobacter pylori* |
| ScoA | NP_391778 | 16080950 | *Bacillus subtilis* |
| ScoB | NP_391777 | 16080949 | *Bacillus subtilis* |
| OXCT1 | NP_000427 | 4557817 | *Homo sapiens* |
| OXCT2 | NP_071403 | 11545841 | *Homo sapiens* |
| FN0272 | NP_603179.1 | 19703617 | *Fusobacterium nucleatum* |
| FN0273 | NP_603180.1 | 19703618 | *Fusobacterium nucleatum* |
| FN1857 | NP_602657.1 | 19705162 | *Fusobacterium nucleatum* |
| FN1856 | NP_602656.1 | 19705161 | *Fusobacterium nucleatum* |
| PG1066 | NP_905281.1 | 34540802 | *Porphyromonas gingivalis* W83 |
| PG1075 | NP_905290.1 | 34540811 | *Porphyromonas gingivalis* W83 |
| TTE0720 | NP_622378.1 | 20807207 | *Thermoanaerobacter tengcongensis* MB4 |
| TTE0721 | NP_622379.1 | 20807208 | *Thermoanaerobacter tengcongensis* MB4 |

Acetoacetyl-CoA Synthetase

A CoA synthetase can also catalyze the removal of the CoA moiety from acetoacetyl-CoA. One candidate enzyme, ADP-forming acetyl-CoA synthetase (ACD, EC 6.2.1.13), couples the conversion of acyl-CoA esters to their corresponding acids with the concurrent synthesis of ATP. Several enzymes with broad substrate specificities have been described in the literature. ACD I from *Archaeoglobus fulgidus*, encoded by AF1211, was shown to operate on a variety of linear and branched-chain substrates including acetyl-CoA, propionyl-CoA, butyryl-CoA, acetate, propionate, butyrate, isobutyryate, isovalerate, succinate, fumarate, phenylacetate, indoleacetate (Musfeldt et al., *J Bacteriol* 184:636-644 (2002)). The enzyme from *Haloarcula marismortui* (annotated as a succinyl-CoA synthetase) accepts propionate, butyrate, and branched-chain acids (isovalerate and isobutyrate) as substrates, and was shown to operate in the forward and reverse directions (Brasen et al., *Arch Microbiol* 182:277-287 (2004)). The ACD encoded by PAE3250 from hyperthermophilic crenarchaeon *Pyrobaculum aerophilum* showed the broadest substrate range of all characterized ACDs, reacting with acetyl-CoA, isobutyryl-CoA (preferred substrate) and phenylacetyl-CoA (Brasen et al., supra). The enzymes from *A. fulgidus, H. marismortui* and *P. aerophilum* have all been cloned, functionally expressed, and characterized in *E. coli* (Musfeldt et al., supra; Brasen et al., supra). These genes/proteins are identified below in Table 3.

TABLE 3

| Gene | GenBank ID | GI Number | Organism |
| --- | --- | --- | --- |
| AF1211 | NP_070039.1 | 11498810 | Archaeoglobus fulgidus DSM 4304 |
| scs | YP_135572.1 | 55377722 | Haloarcula marismortui ATCC 43049 |
| PAE3250 | NP_560604.1 | 18313937 | Pyrobaculum aerophilum str. IM2 |

Another candidate CoA synthetase is succinyl-CoA synthetase. The sucCD genes of *E. coli* form a succinyl-CoA synthetase complex which naturally catalyzes the formation of succinyl-CoA from succinate with the concaminant consumption of one ATP, a reaction which is reversible in vivo (Buck et al., *Biochem.* 24:6245-6252 (1985)). These genes/proteins are identified below in Table 4.

TABLE 4

| Protein | GenBank ID | GI Number | Organism |
| --- | --- | --- | --- |
| sucC | NP_415256.1 | 16128703 | Escherichia coli |
| sucD | AAC73823.1 | 1786949 | Escherichia coli |

Additional exemplary CoA-ligases include the rat dicarboxylate-CoA ligase for which the sequence is yet uncharacterized (Vamecq et al., *Biochemical Journal* 230:683-693 (1985)), either of the two characterized phenylacetate-CoA ligases from *P. chrysogenum* (Lamas-Maceiras et al., *Biochem. J.* 395:147-155 (2005); Wang et al., *Biochem Biophy Res Commun* 360(2):453-458 (2007)), the phenylacetate-CoA ligase from *Pseudomonas putida* (Martinez-Blanco et al., *J. Biol. Chem.* 265:7084-7090 (1990)), and the 6-carboxyhexanoate-CoA ligase from *Bacilis subtilis* (Bower et al., *J. Bacteriol.* 178(14):4122-4130 (1996)). Additional candidate enzymes are acetoacetyl-CoA synthetases from *Mus musculus* (Hasegawa et al., *Biochim Biophys Acta* 1779:414-419 (2008)) and *Homo sapiens* (Ohgami et al., *Biochem Pharmacol* 65:989-994 (2003)) which naturally catalyze the ATP-dependant conversion of acetoacetate into acetoacetyl-CoA. These genes/proteins are identified below in Table 5.

TABLE 5

| Gene | GenBank ID | GI Number | Organism |
| --- | --- | --- | --- |
| phl | CAJ15517.1 | 77019264 | Penicillium chrysogenum |
| phlB | ABS19624.1 | 152002983 | Penicillium chrysogenum |
| paaF | AAC24333.2 | 22711873 | Pseudomonas putida |
| bioW | NP_390902.2 | 50812281 | Bacillus subtilis |
| AACS | NP_084486.1 | 21313520 | Mus musculus |
| AACS | NP_076417.2 | 31982927 | Homo sapiens |

Acetoacetyl-CoA Hydrolase

Acetoacetyl-CoA can also be converted to acetoacetate by a CoA hydrolase. Acetoacetyl-CoA hydrolase enzyme candidates include acyl-CoA hydrolase, 3-hydroxyisobutyryl-CoA hydrolase, acetyl-CoA hydrolase, and dicarboxylic acid thioesterase. A short-chain acyl-CoA hydrolase in rat liver mitochondria was found to accept acetoacetyl-CoA as a substrate; however, the gene associated with this enzyme has not been identified to date (Svensson et al. *Eur. J. Biochem.*, 239:526-531 (1996)).

3-Hydroxyisobutyryl-CoA hydrolase efficiently catalyzes the conversion of 3-hydroxyisobutyryl-CoA to 3-hydroxyisobutyrate during valine degradation (Shimomura et al., *J Biol Chem.* 269:14248-14253 (1994)). Genes encoding this enzyme include hibch of *Rattus norvegicus* (Shimomura et al., supra; Shimomura et al., *Methods Enzymol.* 324:229-240 (2000)) and *Homo sapiens* (Shimomura et al., supra). The *H. sapiens* enzyme also accepts 3-hydroxybutyryl-CoA and 3-hydroxypropionyl-CoA as substrates (Shimomura et al., supra). Candidate genes by sequence homology include hibch of *Saccharomyces cerevisiae* and BC_2292 of *Bacillus cereus*. These genes/proteins are identified below in Table 6.

TABLE 6

| Gene | GenBank ID | GI Number | Organism |
| --- | --- | --- | --- |
| hibch | Q5XIE6.2 | 146324906 | Rattus norvegicus |
| hibch | Q6NVY1.2 | 146324905 | Homo sapiens |
| hibch | P28817.2 | 2506374 | Saccharomyces cerevisiae |
| BC_2292 | AP09256 | 29895975 | Bacillus cereus |

Several eukaryotic acetyl-CoA hydrolases (EC 3.1.2.1) have broad substrate specificity and thus represent suitable candidate enzymes. For example, the enzyme from *Rattus norvegicus* brain (Robinson et al., *Res. Commun.* 71:959-965 (1976)) can react with butyryl-CoA, hexanoyl-CoA and malonyl-CoA. Though its sequence has not been reported, the enzyme from the mitochondrion of the pea leaf also has a broad substrate specificity, with demonstrated activity on acetyl-CoA, propionyl-CoA, butyryl-CoA, palmitoyl-CoA, oleoyl-CoA, succinyl-CoA, and crotonyl-CoA (Zeiher et al., *Plant. Physiol.* 94:20-27 (1990)). The acetyl-CoA hydrolase, ACH1, from *S. cerevisiae* represents another candidate hydrolase (Buu et al., *J. Biol. Chem.* 278:17203-17209 (2003)). These genes/proteins are identified below in Table 7.

TABLE 7

| Gene | GenBank ID | GI Number | Organism |
| --- | --- | --- | --- |
| acot12 | NP_570103.1 | 18543355 | Rattus norvegicus |
| ACH1 | NP_009538 | 6319456 | Saccharomyces cerevisiae |

Another candidate hydrolase is the human dicarboxylic acid thioesterase, acot8, which exhibits activity on glutaryl-CoA, adipyl-CoA, suberyl-CoA, sebacyl-CoA, and dodecanedioyl-CoA (Westin et al., *J Biol. Chem.* 280:38125-38132 (2005)) and the closest *E. coli* homolog, tesB, which can also hydrolyze a broad range of CoA thioesters (Naggert et al., *J Biol. Chem.* 266:11044-11050 (1991)). A similar enzyme has also been characterized in the rat liver (Deana et al., *Biochem. Int.* 26:767-773 (1992)). Other potential *E. coli* thioester hydrolases include the gene products of tesA (Bonner et al., *Chem.* 247:3123-3133 (1972)), ybgC (Kuznetsova et al., *FEMS Microbiol Rev* 29:263-279 (2005); and (Zhuang et al., *FEBS Lett.* 516:161-163 (2002)), paaI (Song et al., *J Biol. Chem.* 281:11028-11038 (2006)), and ybdB (Leduc et al., *J Bacteriol.* 189:7112-7126 (2007)). These genes/proteins are identified below in Table 8.

TABLE 8

| Gene | GenBank ID | GI Number | Organism |
| --- | --- | --- | --- |
| tesB | NP_414986 | 16128437 | Escherichia coli |
| acot8 | CAA15502 | 3191970 | Homo sapiens |
| acot8 | NP_570112 | 51036669 | Rattus norvegicus |
| tesA | NP_415027 | 16128478 | Escherichia coli |
| ybgC | NP_415264 | 16128711 | Escherichia coli |
| paaI | NP_415914 | 16129357 | Escherichia coli |
| ybdB | NP_415129 | 16128580 | Escherichia coli |

Yet another candidate hydrolase is the glutaconate CoA-transferase from *Acidaminococcus fermentans*. This enzyme was transformed by site-directed mutagenesis into an acyl-CoA hydrolase with activity on glutaryl-CoA, acetyl-CoA and 3-butenoyl-CoA (Mack et al., *FEBS. Lett.* 405:209-212 (1997)). This suggests that the enzymes encoding succinyl-CoA:3-ketoacid-CoA transferases and acetoacetyl-CoA: acetyl-CoA transferases may also serve as candidates for this reaction step but would require certain mutations to change their function. These genes/proteins are identified below in Table 9.

TABLE 9

| Gene | GenBank ID | GI Number | Organism |
|---|---|---|---|
| gctA | CAA57199 | 559392 | *Acidaminococcus fermentans* |
| gctB | CAA57200 | 559393 | *Acidaminococcus fermentans* |

Acetoacetate Decarboxylase

Acetoacetate decarboxylase converts acetoacetate into carbon dioxide and acetone. Exemplary acetoacetate decarboxylase enzymes are encoded by the gene products of adc from *C. acetobutylicum* (Petersen and Bennett, *Appl Environ. Microbiol* 56:3491-3498 (1990)) and adc from *Clostridium saccharoperbutylacetonicum* (Kosaka et al., *Biosci. Biotechnol Biochem.* 71:58-68 (2007)). The enzyme from *C. beijerinkii* can be inferred from sequence similarity. These genes/proteins are identified below in Table 10.

TABLE 10

| Gene | GenBank ID | GI Number | Organism |
|---|---|---|---|
| Adc | NP_149328.1 | 15004868 | *Clostridium acetobutylicum* |
| Adc | AAP42566.1 | 31075386 | *Clostridium saccharoperbutylacetonicum* |
| Adc | YP_001310906.1 | 150018652 | *Clostridium beijerinckii* |

Isopropanol Dehydrogenase

The final step in the isopropanol synthesis pathway involves the reduction of acetone to isopropanol. Exemplary alcohol dehydrogenase enzymes capable of this transformation include adh from *C. beijerinckii* (Hanai et al., *Appl Environ Microbiol* 73:7814-7818 (2007); Jojima et al., *Appl Microbiol Biotechnol* 77:1219-1224 (2008)) and adh from *Thermoanaerobacter brockii* (Hanai et al., *Appl Environ Microbiol* 73:7814-7818 (2007); Peretz et al., *Anaerobe* 3:259-270 (1997)). Additional characterized enzymes include alcohol dehydrogenases from *Ralstonia eutropha* (formerly *Alcaligenes eutrophus*) (Steinbuchel and Schlegel et al., *Eur. J. Biochem.* 141:555-564 (1984)) and *Phytomonas* species (Uttaro and Opperdoes et al., *Mol. Biochem. Parasitol.* 85:213-219 (1997)). These genes/proteins are identified below in Table 11.

TABLE 11

| Gene | GenBank ID | GI Number | Organism |
|---|---|---|---|
| sadh | CAD36475 | 21615553 | *Rhodococcus rubber* |
| adhA | AAC25556 | 3288810 | *Pyrococcus furiosus* |

TABLE 11-continued

| Gene | GenBank ID | GI Number | Organism |
|---|---|---|---|
| Adh | P14941.1 | 113443 | *Thermoanaerobobacter brockii* |
| Adh | AAA23199.2 | 60592974 | *Clostridium beijerinckii* |

Production of n-Propanol Utilizing Propionyl-CoA

The pathways described herein for production of n-propanol utilize reduction of propionyl-CoA into propionaldehyde by a CoA-dependent aldehyde dehydrogenase that is then reduced further to form n-propanol (FIGS. 1-4). This conversion is carried out by two different enzymes: an aldehyde and alcohol dehydrogenase or in one step by a bifunctional aldehyde/alcohol dehydrogenase. Alternatively, propionyl CoA can be converted into propionyl phosphate and then transformed into propionaldehyde by an acyl phosphate reductase.

Propionaldehyde Dehydrogenase and Propanol Dehydrogenase

The conversion of propionyl-CoA to propanol is catalyzed by either a bifunctional enzyme that has both the CoA-dependent aldehyde dehydrogenase and the alcohol dehydrogenase activities or by two different enzymes with the aldehyde and alcohol dehydrogenase activities.

Exemplary two-step oxidoreductases that convert an acyl-CoA to alcohol include those that transform substrates such as acetyl-CoA to ethanol (e.g., adhE from *E. coli*) (Kessler, *FEBS. Lett.* 281:59-63 (1991)) and butyryl-CoA to butanol (e.g. adhE2 from *C. acetobutylicum*). (Fontaine et al., *J. Bacteriol.* 184:821-830 (2002)). In addition to reducing acetyl-CoA to ethanol, the enzyme encoded by adhE in *Leuconostoc mesenteroides* has been shown to oxidize the branched chain compound isobutyraldehyde to isobutyryl-CoA (Kazahaya, *Microbiol.* 18:43-55 (1972); and Koo et al., *Biotechnol Lett.* 27:505-510 (2005)). These genes/proteins are identified below in Table 12.

TABLE 12

| Gene | GenBank ID | GI Number | Organism |
|---|---|---|---|
| adhE | NP_415757.1 | 16129202 | *Escherichia coli* |
| adhE2 | AAK09379.1 | 12958626 | *Clostridium acetobutylicum* |
| adhE | AAV66076.1 | 55818563 | *Leuconostoc mesenteroides* |

Another exemplary enzyme can convert malonyl-CoA to 3-HP. An NADPH-dependent enzyme with this activity has been characterized in *Chloroflexus aurantiacus* where it participates in the 3-hydroxypropionate cycle (Hugler, *J. Bacteriol.* 184:2404-2410 (2002); and Strauss, *Eur. J. Biochem.* 215:633-643 (1993)). This enzyme, with a mass of 300 kDa, is highly substrate-specific and shows little sequence similarity to other known oxidoreductases (Hugler, *J. Bacteriol.* 184:2404-2410 (2002)). No enzymes in other organisms have been shown to catalyze this specific reaction; however there is bioinformatic evidence that other organisms may have similar pathways (Klatt, *Environ. Microbiol.* 9:2067-2078 (2007)). Enzyme candidates in other organisms including *Roseiflexus castenholzii*, *Erythrobacter* sp. NAP1 and marine gamma proteobacterium HTCC2080 can be inferred by sequence similarity. These genes/proteins are identified below in Table 13.

TABLE 13

| Gene | GenBank ID | GI Number | Organism |
|---|---|---|---|
| mcr | AAS20429.1 | 42561982 | *Chloroflexus aurantiacus* |
| Rcas_2929 | YP_001433009.1 | 156742880 | *Roseiflexus castenholzii* |
| NAP1_02720 | ZP_01039179.1 | 85708113 | *Erythrobacter* sp. NAP1 |
| MGP2080_00535 | ZP_01626393.1 | 119504313 | marine gamma proteobacterium HTCC2080 |

Longer chain acyl-CoA molecules can be reduced by enzymes such as the jojoba (*Simmondsia chinensis*) FAR which encodes an alcohol-forming fatty acyl-CoA reductase. Its overexpression in *E. coli* resulted in FAR activity and the accumulation of fatty alcohol (Metz, *Plant Physiology* 122: 635-644 (2000). These genes/proteins are identified below in Table 14.

TABLE 14

| Gene | GenBank ID | GI Number | Organism |
|---|---|---|---|
| FAR | AAD38039.1 | 5020215 | *Simmondsia chinensis* |

Several acyl-CoA dehydrogenases are capable of reducing an acyl-CoA to its corresponding aldehyde. Exemplary genes that encode such enzymes include the *Acinetobacter calcoaceticus* acr1 encoding a fatty acyl-CoA reductase, (Reiser, *Journal of Bacteriology* 179:2969-2975 (1997)) the *Acinetobacter* sp. M-1 fatty acyl-CoA reductase, (Ishige et al., *Appl. Environ. Microbiol.* 68:1192-1195 (2002)) and a CoA- and NADP-dependent succinate semialdehyde dehydrogenase encoded by the sucD gene in *Clostridium kluyveri* (Sohling, *J. Bacteriol.* 178:871-880 (1996)). SucD of *P. gingivalis* is another succinate semialdehyde dehydrogenase (Takahashi, *J. Bacteriol* 182:4704-4710 (2000)). The enzyme acylating acetaldehyde dehydrogenase in *Pseudomonas* sp, encoded by bphG, is yet another candidate as it has been demonstrated to oxidize and acylate acetaldehyde, propionaldehyde, butyraldehyde, isobutyraldehyde and formaldehyde (Powlowski, *J. Bacteriol.* 175:377-385 (1993)). In addition to reducing acetyl-CoA to ethanol, the enzyme encoded by adhE in *Leuconostoc mesenteroides* has been shown to oxidize the branched chain compound isobutyraldehyde to isobutyryl-CoA (Kazahaya, *J. Gen. Appl. Microbiol.* 18:43-55 (1972); and Koo et al., *Biotechnol Lett.* 27:505-510 (2005)). These genes/proteins are identified below in Table 15.

TABLE 15

| Gene | GenBank ID | GI Number | Organism |
|---|---|---|---|
| acr1 | YP_047869.1 | 50086359 | *Acinetobacter calcoaceticus* |
| acr1 | AAC45217 | 1684886 | *Acinetobacter baylyi* |
| acr1 | BAB85476.1 | 18857901 | *Acinetobacter* sp. Strain M-1 |
| sucD | P38947.1 | 172046062 | *Clostridium kluyveri* |
| sucD | NP_904963.1 | 34540484 | *Porphyromonas gingivalis* |
| bphG | BAA03892.1 | 425213 | *Pseudomonas* sp |
| adhE | AAV66076.1 | 55818563 | *Leuconostoc mesenteroides* |

An additional enzyme type that converts an acyl-CoA to its corresponding aldehyde is malonyl-CoA reductase which transforms malonyl-CoA to malonic semialdehyde. Malonyl-CoA reductase is a key enzyme in autotrophic carbon fixation via the 3-hydroxypropionate cycle in thermoacidophilic archaeal bacteria (Berg, *Science* 318:1782-1786 (2007); and Thauer, *Science* 318:1732-1733 (2007)). The enzyme utilizes NADPH as a cofactor and has been characterized in *Metallosphaera* and *Sulfolobus* spp. (Alber et al., *J. Bacteriol.* 188:8551-8559 (2006); and Hugler, *J. Bacteriol.* 184:2404-2410 (2002)). The enzyme is encoded by Msed_0709 in *Metallosphaera sedula* (Alber et al., *J. Bacteriol.* 188:8551-8559 (2006); and Berg, *Science* 318:1782-1786 (2007)). A gene encoding a malonyl-CoA reductase from *Sulfolobus tokodaii* was cloned and heterologously expressed in *E. coli* (Alber et al., *J. Bacteriol* 188:8551-8559 (2006). This enzyme has also been shown to catalyze the conversion of methylmalonyl-CoA to its corresponding aldehyde (WO2007141208 (2007)). Although the aldehyde dehydrogenase functionality of these enzymes is similar to the bifunctional dehydrogenase from *Chloroflexus aurantiacus*, there is little sequence similarity. Both malonyl-CoA reductase enzyme candidates have high sequence similarity to aspartate-semialdehyde dehydrogenase, an enzyme catalyzing the reduction and concurrent dephosphorylation of aspartyl-4-phosphate to aspartate semialdehyde. Additional gene candidates can be found by sequence homology to proteins in other organisms including *Sulfolobus solfataricus* and *Sulfolobus acidocaldarius* and have been listed below. Yet another candidate for CoA-acylating aldehyde dehydrogenase is the ald gene from *Clostridium beijerinckii* (Toth, *Appl. Environ. Microbiol.* 65:4973-4980 (1999). This enzyme has been reported to reduce acetyl-CoA and butyryl-CoA to their corresponding aldehydes. This gene is very similar to eutE that encodes acetaldehyde dehydrogenase of *Salmonella typhimurium* and *E. coli* (Toth, *Appl. Environ. Microbiol.* 65:4973-4980 (1999). These genes/proteins are identified below in Table 16.

TABLE 16

| Gene | GenBank ID | GI Number | Organism |
|---|---|---|---|
| Msed_0709 | YP_001190808.1 | 146303492 | *Metallosphaera sedula* |
| mcr | NP_378167.1 | 15922498 | *Sulfolobus tokodaii* |
| asd-2 | NP_343563.1 | 15898958 | *Sulfolobus solfataricus* |
| Saci_2370 | YP_256941.1 | 70608071 | *Sulfolobus acidocaldarius* |
| Ald | AAT66436 | 49473535 | *Clostridium beijerinckii* |
| eutE | AAA80209 | 687645 | *Salmonella typhimurium* |
| eutE | P77445 | 2498347 | *Escherichia coli* |

Exemplary genes encoding enzymes that catalyze the conversion of an aldehyde to alcohol (i.e., alcohol dehydrogenase or equivalently aldehyde reductase) include alrA encoding a medium-chain alcohol dehydrogenase for C2-C14, (Tani, *Appl. Environ. Microbiol.* 66:5231-5235 (2000)) ADH2 from *Saccharomyces cerevisiae*, (Atsumi, *Nature* 451:86-89 (2008)) yqhD from *E. coli* which has preference for molecules longer than C3, (Sulzenbacher et al., *Journal of Molecular Biology* 342:489-502 (2004)) and bdh I and bdh II from *C. acetobutylicum* which converts butyraldehyde into butanol (Walter, *Journal of Bacteriology* 174: 7149-7158 (1992)). The gene product of yqhD catalyzes the reduction of acetaldehyde, malondialdehyde, propionaldehyde, butyraldehyde, and acrolein using NADPH as the cofactor (Perez, *J. Biol. Chem.* 283:7346-7353 (2008)). ADH1 from *Zymomonas mobilis* has been demonstrated to have activity on a number of aldehydes including formaldehyde, acetaldehyde, propionaldehyde, butyraldehyde, and acrolein (Kinoshita, *Appl. Microbiol. Biotechnol.* 22:249-254 (1985)). These genes/proteins are identified below in Table 17.

TABLE 17

| Gene | GenBank ID | GI Number | Organism |
| --- | --- | --- | --- |
| alrA | BAB12273.1 | 9967138 | *Acinetobacter* sp. Strain M-1 |
| ADH2 | NP_014032.1 | 6323961 | *Saccharomyces cerevisiae* |
| yqhD | NP_417484.1 | 16130909 | *Escherichia coli* |
| bdh I | NP_349892.1 | 15896543 | *Clostridium acetobutylicum* |
| bdh II | NP_349891.1 | 15896542 | *Clostridium acetobutylicum* |
| adhA | YP_162971.1 | 56552132 | *Zymomonas mobilis* |

Enzymes exhibiting 3-hydroxybutyraldehyde reductase activity (EC 1.1.1.61) also fall into this category. Such enzymes have been characterized in *Ralstonia eutropha*, (Bravo J. *Forensic Sci.* 49:379-387 (2004)) *Clostridium kluyveri* (Wolff, *Protein Expr. Purif.* 6:206-212 (1995)) and *Arabidopsis thaliana* (Breitkreuz et al., *J. Biol. Chem.* 278: 41552-41556 (2003)). Yet another gene candidate is the alcohol dehydrogenase adhI from *Geobacillus thermoglucosidasius* (Jeon et al., *J. Biotechnal* 135:127-133 (2008)). These genes/proteins are identified below in Table 18.

TABLE 18

| Gene | GenBank ID | GI Number | Organism |
| --- | --- | --- | --- |
| 4hbd | YP_726053.1 | 113867564 | *Ralstonia eutropha* H16 |
| 4hbd | L21902.1 | 146348486 | *Clostridium kluyveri* DSM 555 |
| 4hbd | Q94B07 | 75249805 | *Arabidopsis thaliana* |
| adhI | AAR91477.1 | 40795502 | *Geobacillus thermoglucosidasius* M10EXG |

Another exemplary enzyme is 3-hydroxyisobutyrate dehydrogenase which catalyzes the reversible oxidation of 3-hydroxyisobutyrate to methylmalonate semialdehyde. This enzyme participates in valine, leucine and isoleucine degradation and has been identified in bacteria, eukaryotes, and mammals. The enzyme encoded by P84067 from *Therms thermophilus* HB8 has been structurally characterized (Lokanath et al., *J Mol Biol* 352:905-917 (2005)). The reversibility of the human 3-hydroxyisobutyrate dehydrogenase was demonstrated using isotopically-labeled substrate (Manning, *Biochem J* 231:481-484 (1985)). Additional genes encoding this enzyme include 3hidh in *Homo sapiens* (Hawes et al., *Methods Enzymol.* 324:218-228 (2000)) and *Oryctolagus cuniculus*, (Hawes et al., *Methods Enzymol.* 324:218-228 (2000); and Chowdhury, *Biosci. Biotechnol Biochem.* 60:2043-2047 (1996)) (mmsb in *Pseudomonas aeruginosa*, and dhat in *Pseudomonas putida* (Aberhart, *J Chem. Soc.* 6:1404-1406 (1979); Chowdhury, *Biosci. Biotechnol Biochem.* 60:2043-2047 (1996) and Chowdhury, *Biosci. Biotechnol Biochem.* 67:438-441 (2003)). These genes/proteins are identified below in Table 19.

TABLE 19

| Gene | GenBank ID | GI Number | Organism |
| --- | --- | --- | --- |
| P84067 | P84067 | 75345323 | *Thermus thermophilus* |
| mmsb | P28811.1 | 127211 | *Pseudomonas aeruginosa* |
| dhat | Q59477.1 | 2842618 | *Pseudomonas putida* |
| 3hidh | P31937.2 | 12643395 | *Homo sapiens* |
| 3hidh | P32185.1 | 416872 | *Oryctolagus cuniculus* |

Propionyl-CoA:Phosphate Propanoyltransferase

The conversion of propanoyl-CoA to propanoyl phosphate can be catalyzed by a phosphate transferase. Among the phosphate acetyltransferases (EC 2.3.1.8), several enzymes including those from *Bacillus subtilis*, (Rado, *Biochem. Biophys. Acta* 321:114-125 (1973)) *Clostridium kluyveri*, (Stadtman, *Methods Enzymol* 1:596-599 (1955)) and *Thermotoga maritima* (Bock, *J Bacteriol.* 181:1861-1867 (1999)) have been shown to have activity on propionyl-CoA. Therefore, the genes coding for these phosphate acetyltransferases as well as *Escherichia coli* pta gene will be utilized to catalyze this step. These genes/proteins are identified below in Table 20.

TABLE 20

| Gene | GenBank ID | GI Number | Organism |
| --- | --- | --- | --- |
| pta | P39646 | 730415 | *Bacillus subtilis* |
| pta | A5N801 | 146346896 | *Clostridium kluyveri* |
| pta | Q9X0L4 | 6685776 | *Thermotoga maritima* |
| pta | P0A9M8 | 71152910 | *Escherichia coli* K12 |

Propionyl Phosphate Reductase

The conversion of propanoyl phosphate to propionaldehyde is catalyzed by the propionyl phosphate reductase. Even though such direct conversion has not been demonstrated yet, similar transformations were well documented including glyceraldehyde-3-phosphate dehydrogenase and aspartate-semialdehyde dehydrogenase. The following genes encoding glyceraldehyde-3-phosphate dehydrogenase and aspartate-semialdehyde dehydrogenase will be considered for catalyzing this step. These genes/proteins are identified below in Table 21.

TABLE 21

| Gene | GenBank ID | GI Number | Organism |
| --- | --- | --- | --- |
| asd | NP_417891 | 16131307 | *Escherichia coli* K12 |
| gapA | NP_785996 | 28379104 | *Lactobacillus plantarum* WCFS1 |
| gapA | NP_416293 | 71159358 | *Escherichia coli* K12 |
| gapA | NP_347346 | 15893997 | *Clostridium acetobutylicum* ATCC 824 |
| gapN | NP_350239 | 15896890 | *Clostridium acetobutylicum* ATCC 824 |

Propionyl-CoA Hydrolase

Propionyl-CoA can be converted to propionate by a CoA hydrolase, synthetase or transferase. The hydrolysis of propionyl-CoA to propionate occurs in organic acid degradation pathways that proceed through the intermediate 2-oxobutanoate. This reaction is catalyzed by acyl-CoA hydrolase enzymes (EC 3.1.2.18). Propionyl-CoA is the preferred substrate of the short chin acyl-CoA hydrolase found in rat liver mitochondria (Alexson et al., *Biochim Biophys. Acta.*, 1105 (1):13-9 (1989)). This enzyme has been characterized but the sequence encoding the gene is not yet identified (Garras et al., *Biochim. Biophys. Acta.*, 1255:154-160 (1995)). Another enzyme exhibiting CoA hydrolase activity on propionyl-CoA is found in the mitochondrion of the pea leaf. Though its sequence has not been reported, this enzyme has a broad substrate specificity, with demonstrated activity on acetyl-CoA, propionyl-CoA, butyryl-CoA, palmitoyl-CoA, oleoyl-CoA, succinyl-CoA, and crotonyl-CoA (Zeiher et al., *Plant. Physiol.* 94:20-27 (1990)). Additional propionyl-CoA hydrolase candidates include 3-hydroxyisobutyryl-CoA hydrolase, acetyl-CoA hydrolase, and dicarboxylic acid thioesterase.

3-Hydroxyisobutyryl-CoA hydrolase efficiently catalyzes the conversion of 3-hydroxyisobutyryl-CoA to 3-hydroxyisobutyrate during valine degradation (Shimomura et al., *J Biol Chem.* 269:14248-14253 (1994)). Genes encoding this enzyme include hibch of *Rattus norvegicus* (Shimomura et al., supra; Shimomura et al., *Methods Enzymol.* 324:229-240 (2000)) and *Homo sapiens* (Shimomura et al., supra). The *H. sapiens* enzyme also accepts 3-hydroxybutyryl-CoA and 3-hydroxypropionyl-CoA as substrates (Shimomura et al., supra). Candidate genes by sequence homology include hibch of *Saccharomyces cerevisiae* and BC_2292 of *Bacillus cereus*. These genes/proteins are identified below in Table 22.

TABLE 22

| Gene | GenBank ID | GI Number | Organism |
| --- | --- | --- | --- |
| hibch | Q5XIE6.2 | 146324906 | *Rattus norvegicus* |
| hibch | Q6NVY1.2 | 146324905 | *Homo sapiens* |
| hibch | P28817.2 | 2506374 | *Saccharomyces cerevisiae* |
| BC_2292 | AP09256 | 29895975 | *Bacillus cereus* |

Several eukaryotic acetyl-CoA hydrolases (EC 3.1.2.1) have broad substrate specificity and thus represent suitable candidate enzymes. For example, the enzyme from *Rattus norvegicus* brain (Robinson et al., *Res. Commun.* 71:959-965 (1976)) can react with butyryl-CoA, hexanoyl-CoA and malonyl-CoA. The acetyl-CoA hydrolase, ACH1, from *S. cerevisiae* represents another candidate hydrolase (Buu et al., *J. Biol. Chem.* 278:17203-17209 (2003)). These genes/proteins are identified below in Table 23.

TABLE 23

| Gene | GenBank ID | GI Number | Organism |
| --- | --- | --- | --- |
| acot12 | NP_570103.1 | 18543355 | *Rattus norvegicus* |
| ACH1 | NP_009538 | 6319456 | *Saccharomyces cerevisiae* |

Another candidate hydrolase is the human dicarboxylic acid thioesterase, acot8, which exhibits activity on glutaryl-CoA, adipyl-CoA, suberyl-CoA, sebacyl-CoA, and dodecanedioyl-CoA (Westin et al., *J Biol. Chem.* 280:38125-38132 (2005)) and the closest *E. coli* homolog, tesB, which can also hydrolyze a broad range of CoA thioesters (Naggert et al., *J Biol. Chem.* 266:11044-11050 (1991)). A similar enzyme has also been characterized in the rat liver (Deana et al., *Biochem. Int.* 26:767-773 (1992)). Other potential *E. coli* thioester hydrolases include the gene products of tesA (Bonner et al., *Chem.* 247:3123-3133 (1972)), ybgC (Kuznetsova et al., *FEMS Microbiol Rev* 29:263-279 (2005); and (Zhuang et al., *FEBS Lett.* 516:161-163 (2002)), paaI (Song et al., *J Biol. Chem.* 281:11028-11038 (2006)), and ybdB (Leduc et al., *J Bacteriol.* 189:7112-7126 (2007)). These genes/proteins are identified below in Table 24.

TABLE 24

| Gene | GenBank ID | GI Number | Organism |
| --- | --- | --- | --- |
| tesB | NP_414986 | 16128437 | *Escherichia coli* |
| acot8 | CAA15502 | 3191970 | *Homo sapiens* |
| acot8 | NP_570112 | 51036669 | *Rattus norvegicus* |
| tesA | NP_415027 | 16128478 | *Escherichia coli* |
| ybgC | NP_415264 | 16128711 | *Escherichia coli* |
| paaI | NP_415914 | 16129357 | *Escherichia coli* |
| ybdB | NP_415129 | 16128580 | *Escherichia coli* |

Yet another candidate hydrolase is the glutaconate CoA-transferase from *Acidaminococcus fermentans*. This enzyme was transformed by site-directed mutagenesis into an acyl-CoA hydrolase with activity on glutaryl-CoA, acetyl-CoA and 3-butenoyl-CoA (Mack et al., *FEBS. Lett.* 405:209-212 (1997)). This suggests that the enzymes encoding succinyl-CoA:3-ketoacid-CoA transferases and acetoacetyl-CoA: acetyl-CoA transferases may also serve as candidates for this reaction step but would require certain mutations to change their function. These genes/proteins are identified below in Table 25.

TABLE 25

| Gene | GenBank ID | GI Number | Organism |
| --- | --- | --- | --- |
| gctA | CAA57199 | 559392 | *Acidaminococcus fermentans* |
| gctB | CAA57200 | 559393 | *Acidaminococcus fermentans* |

Propionyl-CoA Synthetase

A CoA synthetase can also catalyze the removal of the CoA moiety from propionyl-CoA. One candidate enzyme, ADP-forming acetyl-CoA synthetase (ACD, EC 6.2.1.13), couples the conversion of acyl-CoA esters to their corresponding acids with the concurrent synthesis of ATP. Several enzymes with broad substrate specificities have been described in the literature. ACD I from *Archaeoglobus fulgidus*, encoded by AF1211, was shown to operate on a variety of linear and branched-chain substrates including acetyl-CoA, propionyl-CoA, butyryl-CoA, acetate, propionate, butyrate, isobutyrate, isovalerate, succinate, fumarate, phenylacetate, indoleacetate (Musfeldt et al., *J Bacteriol* 184:636-644 (2002)). The enzyme from *Haloarcula marismortui* (annotated as a succinyl-CoA synthetase) accepts propionate, butyrate, and branched-chain acids (isovalerate and isobutyrate) as substrates, and was shown to operate in the forward and reverse directions (Brasen et al., *Arch Microbiol* 182:277-287 (2004)). The ACD encoded by PAE3250 from hyperthermophilic crenarchaeon *Pyrobaculum aerophilum* showed the broadest substrate range of all characterized ACDs, reacting with acetyl-CoA, isobutyryl-CoA (preferred substrate) and phenylacetyl-CoA (Brasen et al., supra). The enzymes from *A. fulgidus, H. marismortui* and *P. aerophilum* have all been cloned, functionally expressed, and characterized in *E. coli* (Musfeldt et al., supra; Brasen et al., supra). These genes/proteins are identified below in Table 26.

TABLE 26

| Gene | GenBank ID | GI Number | Organism |
| --- | --- | --- | --- |
| AF1211 | NP_070039.1 | 11498810 | *Archaeoglobus fulgidus* DSM 4304 |
| scs | YP_135572.1 | 55377722 | *Haloarcula marismortui* ATCC 43049 |
| PAE3250 | NP_560604.1 | 18313937 | *Pyrobaculum aerophilum* str. IM2 |

Another candidate CoA synthetase is succinyl-CoA synthetase. The sucCD genes of *E. coli* form a succinyl-CoA synthetase complex which naturally catalyzes the formation of succinyl-CoA from succinate with the concaminant consumption of one ATP, a reaction which is reversible in vivo (Buck et al., *Biochem.* 24:6245-6252 (1985)). These genes/proteins are identified below in Table 27.

TABLE 27

| Gene | GenBank ID | GI Number | Organism |
| --- | --- | --- | --- |
| sucC | NP_415256.1 | 16128703 | *Escherichia coli* |
| sucD | AAC73823.1 | 1786949 | *Escherichia coli* |

Additional exemplary CoA-ligases include the rat dicarboxylate-CoA ligase for which the sequence is yet uncharacterized (Vamecq et al., *Biochemical Journal* 230:683-693 (1985)), either of the two characterized phenylacetate-CoA ligases from *P. chrysogenum* (Lamas-Maceiras et al., *Biochem. J.* 395:147-155 (2005); Wang et al., *Biochem Biophy Res Commun* 360(2):453-458 (2007)), the phenylacetate-CoA ligase from *Pseudomonas putida* (Martinez-Blanco et al., *J. Biol. Chem.* 265:7084-7090 (1990)), and the 6-carboxyhexanoate-CoA ligase from *Bacilis subtilis* (Bower et al., *J. Bacteriol.* 178(14):4122-4130 (1996)). Additional candidate enzymes are acetoacetyl-CoA synthetases from *Mus musculus* (Hasegawa et al., *Biochim Biophys Acta* 1779:414-419 (2008)) and *Homo sapiens* (Ohgami et al., *Biochem Pharmacol* 65:989-994 (2003)) which naturally catalyze the ATP-dependant conversion of acetoacetate into acetoacetyl-CoA. These genes/proteins are identified below in Table 28.

TABLE 28

| Gene | GenBank ID | GI Number | Organism |
|---|---|---|---|
| phl | CAJ15517.1 | 77019264 | *Penicillium chrysogenum* |
| phlB | ABS19624.1 | 152002983 | *Penicillium chrysogenum* |
| paaF | AAC24333.2 | 22711873 | *Pseudomonas putida* |
| bioW | NP_390902.2 | 50812281 | *Bacillus subtilis* |
| AACS | NP_084486.1 | 21313520 | *Mus musculus* |
| AACS | NP_076417.2 | 31982927 | *Homo sapiens* |

Propionyl-CoA Transferase

Propionyl-CoA transferase catalyzes the conversion of propionyl-CoA to propionate while transferring the CoA moiety to a CoA acceptor molecule. Many transferases have broad specificity and thus may utilize CoA acceptors as diverse as acetate, succinate, propionate, butyrate, 2-methylacetoacetate, 3-ketohexanoate, 3-ketopentanoate, valerate, crotonate, 3-mercaptopropionate, propionate, vinylacetate, butyrate, among others.

Several genes have been identified that have propionyl-CoA transferase activity. The enzyme from *Roseburia* sp. A2-183 was shown to have butyryl-CoA:acetate:CoA transferase and propionyl-CoA:acetate:CoA transferase activity (Charrier et al., *Microbiology* 152, 179-185 (2006)). Close homologs can be found in, for example, *Roseburia intestinalis* L1-82, *Roseburia inulinivorans* DSM 16841, *Eubacterium rectale* ATCC 33656. Another enzyme with propionyl-CoA transferase activity can be found in *Clostridium propionicum* (Selmer et al., *Eur J Biochem* 269, 372-380 (2002)). This enzyme can use acetate, (R)-lactate, (S)-lactate, acrylate, and butyrate as the CoA acceptor (Selmer et al., *Eur J Biochem* 269, 372-380 (2002); Schweiger and Buckel, *FEBS Letters*, 171(1) 79-84 (1984)). Close homologs can be found in, for example, *Clostridium novyi* NT, *Clostridium beijerinckii* NCIMB 8052, and *Clostridium botulinum* C str. Eklund. YgfH encodes a propionyl CoA:succinate CoA transferase in *E. coli* (Haller et al., *Biochemistry*, 39(16) 4622-4629). Close homologs can be found in, for example, *Citrobacter youngae* ATCC 29220, *Salmonella enterica* subsp. *arizonae serovar*, and *Yersinia intermedia* ATCC 29909. These genes/proteins are identified below in Table 29.

TABLE 29

| Gene | GenBank ID | GI Number | Organism |
|---|---|---|---|
| Ach1 | AAX19660.1 | 60396828 | *Roseburia* sp. A2-183 |
| ROSINTL182_07121 | ZP_04743841.2 | 257413684 | *Roseburia intestinalis* L1-82 |
| ROSEINA2194_03642 | ZP_03755203.1 | 225377982 | *Roseburia inulinivorans* DSM 16841 |
| EUBREC_3075 | YP_002938937.1 | 238925420 | *Eubacterium rectale* ATCC 33656 |
| pct | CAB77207.1 | 7242549 | *Clostridium propionicum* |
| NT01CX_2372 | YP_878445.1 | 118444712 | *Clostridium novyi* NT |
| Cbei_4543 | YP_001311608.1 | 150019354 | *Clostridium beijerinckii* NCIMB 8052 |
| CBC_A0889 | ZP_02621218.1 | 168186583 | *Clostridium botulinum* C str. Eklund |
| ygfH | NP_417395.1 | 16130821 | *Escherichia coli* str. K-12 substr. MG1655 |
| CIT292_04485 | ZP_03838384.1 | 227334728 | *Citrobacter youngae* ATCC 29220 |
| SARI_04582 | YP_001573497.1 | 161506385 | *Salmonella enterica* subsp. *arizonae serovar* |
| yinte0001_14430 | ZP_04635364.1 | 238791727 | *Yersinia intermedia* ATCC 29909 |

An additional candidate enzyme is the two-unit enzyme encoded by pcaI and pcaJ in *Pseudomonas*, which has been shown to have 3-oxoadipyl-CoA/succinate transferase activity (Kaschabek et al., supra). Similar enzymes based on homology exist in *Acinetobacter* sp. ADP1 (Kowalchuk et al., *Gene* 146:23-30 (1994)) and *Streptomyces coelicolor*. Additional exemplary succinyl-CoA:3:oxoacid-CoA transferases are present in *Helicobacter pylori* (Corthesy-Theulaz et al., *J. Biol. Chem.* 272:25659-25667 (1997)) and *Bacillus subtilis* (Stols et al., *Protein. Expr. Purif.* 53:396-403 (2007)). These genes/proteins are identified below in Table 30.

TABLE 30

| Gene | GenBank ID | GI Number | Organism |
|---|---|---|---|
| pcaI | AAN69545.1 | 24985644 | *Pseudomonas putida* |
| pcaJ | NP_746082.1 | 26990657 | *Pseudomonas putida* |
| pcaI | YP_046368.1 | 50084858 | *Acinetobacter* sp. ADP1 |
| pcaJ | AAC37147.1 | 141776 | *Acinetobacter* sp. ADP1 |
| pcaI | NP_630776.1 | 21224997 | *Streptomyces coelicolor* |
| pcaJ | NP_630775.1 | 21224996 | *Streptomyces coelicolor* |
| HPAG1_0676 | YP_627417 | 108563101 | *Helicobacter pylori* |
| HPAG1_0677 | YP_627418 | 108563102 | *Helicobacter pylori* |
| ScoA | NP_391778 | 16080950 | *Bacillus subtilis* |
| ScoB | NP_391777 | 16080949 | *Bacillus subtilis* |

A CoA transferase that can utilize acetate as the CoA acceptor is acetoacetyl-CoA transferase, encoded by the *E. coli* atoA (alpha subunit) and atoD (beta subunit) genes (Vanderwinkel et al., *Biochem. Biophys. Res. Commun.* 33:902-908 (1968); Korolev et al., *Acta Crystallogr. D Biol*

Crystallogr. 58:2116-2121 (2002)). This enzyme has also been shown to transfer the CoA moiety to acetate from a variety of branched and linear acyl-CoA substrates, including isobutyrate (Matthies et al., Appl Environ Microbiol 58:1435-1439 (1992)), valerate (Vanderwinkel et al., supra) and butanoate (Vanderwinkel et al., supra). Similar enzymes exist in Corynebacterium glutamicum ATCC 13032 (Duncan et al., Appl Environ Microbiol 68:5186-5190 (2002)), Clostridium acetobutylicum (Cary et al., Appl Environ Microbiol 56:1576-1583 (1990)), and Clostridium saccharoperbutylacetonicum (Kosaka et al., Biosci. Biotechnol Biochem. 71:58-68 (2007)). These genes/proteins are identified below in Table 31.

TABLE 31

| Gene | GenBank ID | GI Number | Organism |
|---|---|---|---|
| atoA | P76459.1 | 2492994 | Escherichia coli K12 |
| atoD | P76458.1 | 2492990 | Escherichia coli K12 |
| actA | YP_226809.1 | 62391407 | Corynebacterium glutamicum ATCC 13032 |
| cg0592 | YP_224801.1 | 62389399 | Corynebacterium glutamicum ATCC 13032 |
| ctfA | NP_149326.1 | 15004866 | Clostridium acetobutylicum |
| ctfB | NP_149327.1 | 15004867 | Clostridium acetobutylicum |
| ctfA | AAP42564.1 | 31075384 | Clostridium saccharoperbutylacetonicum |
| ctfB | AAP42565.1 | 31075385 | Clostridium saccharoperbutylacetonicum |

The above enzymes may also exhibit the desired activities on propionyl-CoA. Additional exemplary transferase candidates are catalyzed by the gene products of cat1, cat2, and cat3 of Clostridium kluyveri which have been shown to exhibit succinyl-CoA, 4-hydroxybutyryl-CoA, and butyryl-CoA transferase activity, respectively (Seedorf et al., supra; Sohling et al., Eur. J. Biochem. 212:121-127 (1993); Sohling et al., J Bacteriol. 178:871-880 (1996)). Similar CoA transferase activities are also present in Trichomonas vaginalis (van Grinsven et al., J. Biol. Chem. 283:1411-1418 (2008)) and Trypanosoma brucei (Riviere et al., J. Biol. Chem. 279: 45337-45346 (2004)). These genes/proteins are identified below in Table 32.

TABLE 32

| Gene | GenBank ID | GI Number | Organism |
|---|---|---|---|
| cat1 | P38946.1 | 729048 | Clostridium kluyveri |
| cat2 | P38942.2 | 172046066 | Clostridium kluyveri |
| cat3 | EDK35586.1 | 146349050 | Clostridium kluyveri |
| TVAG_395550 | XP_001330176 | 123975034 | Trichomonas vaginalis G3 |
| Tb11.02.0290 | XP_828352 | 71754875 | Trypanosoma brucei |

The glutaconate-CoA-transferase (EC 2.8.3.12) enzyme from anaerobic bacterium Acidaminococcus fermentans reacts with diacid glutaconyl-CoA and 3-butenoyl-CoA (Mack et al., FEBS Lett. 405:209-212 (1997)). The genes encoding this enzyme are gctA and gctB. This enzyme has reduced but detectable activity with other CoA derivatives including glutaryl-CoA, 2-hydroxyglutaryl-CoA, adipyl-CoA and acrylyl-CoA (Buckel et al., Eur. J. Biochem. 118: 315-321 (1981)). The enzyme has been cloned and expressed in E. coli (Mack et al., Eur. J. Biochem. 226:41-51 (1994)). These genes/proteins are identified below in Table 33.

TABLE 33

| Gene | GenBank ID | GI Number | Organism |
|---|---|---|---|
| gctA | CAA57199.1 | 559392 | Acidaminococcus fermentans |
| gctB | CAA57200.1 | 559393 | Acidaminococcus fermentans |

Propionate Kinase

Propionate is activated to propionyl-phosphate by an enzyme with propionate kinase activity. Butyrate kinase (EC 2.7.2.7) carries out the reversible conversion of butyryl-phosphate to butyrate during acidogenesis in C. acetobutylicum (Cary et al., Appl. Environ. Microbiol 56:1576-1583 (1990)). This enzyme is encoded by either of the two buk gene products (Huang et al., J Mol. Microbiol Biotechnol 2:33-38 (2000)). This enzyme was shown to accept propionate, isobutanoate and valerate as alternate substrates (Hartmanis, J. Biol. Chem., 262(2):617-21 (1987)). Other butyrate kinase enzymes are found in C. butyricum and C. tetanomorphum (Twarog et al., J Bacteriol. 86:112-117 (1963)). These enzymes also accept propionate, isobutanoate and valerate as secondary substrates. Related enzyme isobutyrate kinase from Thermotoga maritima has also been expressed in E. coli and crystallized (Diao et al., E. Biol. Crystallogr. 59:1100-1102 (2003); and Diao et al., J Bacteriol. 191:2521-2529 (2009)). Aspartokinase catalyzes the ATP-dependent phosphorylation of aspartate and participates in the synthesis of several amino acids. The aspartokinase III enzyme in E. coli, encoded by lysC, has a broad substrate range and the catalytic residues involved in substrate specificity have been elucidated (Keng et al., Arch. Biochem. Biophys. 335:73-81 (1996)). Two additional kinases in E. coli are also good candidates: acetate kinase and gamma-glutamyl kinase. The E. coli acetate kinase, encoded by ackA (Skarstedt et al., J. Biol. Chem. 251:6775-6783 (1976)), phosphorylates propionate in addition to acetate (Hesslinger et al., Mol. Microbiol 27:477-492 (1998)). The E. coli gamma-glutamyl kinase, encoded by proB (Smith et al., J. Bacteriol. 157:545-551 (1984)), phosphorylates the gamma carbonic acid group of glutamate. These genes/proteins are identified below in Table 34.

TABLE 34

| Gene | GenBank ID | GI Number | Organism |
|---|---|---|---|
| buk1 | NP_349675 | 15896326 | Clostridium acetobutylicum |
| buk2 | Q97II1 | 20137415 | Clostridium acetobutylicum |
| buk2 | Q9X278.1 | 6685256 | Thermotoga maritima |
| lysC | NP_418448.1 | 16131850 | Escherichia coli |
| ackA | NP_416799.1 | 16130231 | Escherichia coli |
| proB | NP_414777.1 | 16128228 | Escherichia coli |

Propionate Reductase

The reduction of propionate to propionic semialdehyde is catalyzed by a carboxylic acid reductase. Exemplary enzyme candidates for succinate reductase and 4-hydroxybutyrate reductase enzyme, described below, are also applicable here.

Example II

Pathways for Production of Acetyl-CoA from Glucose

Figure 2:
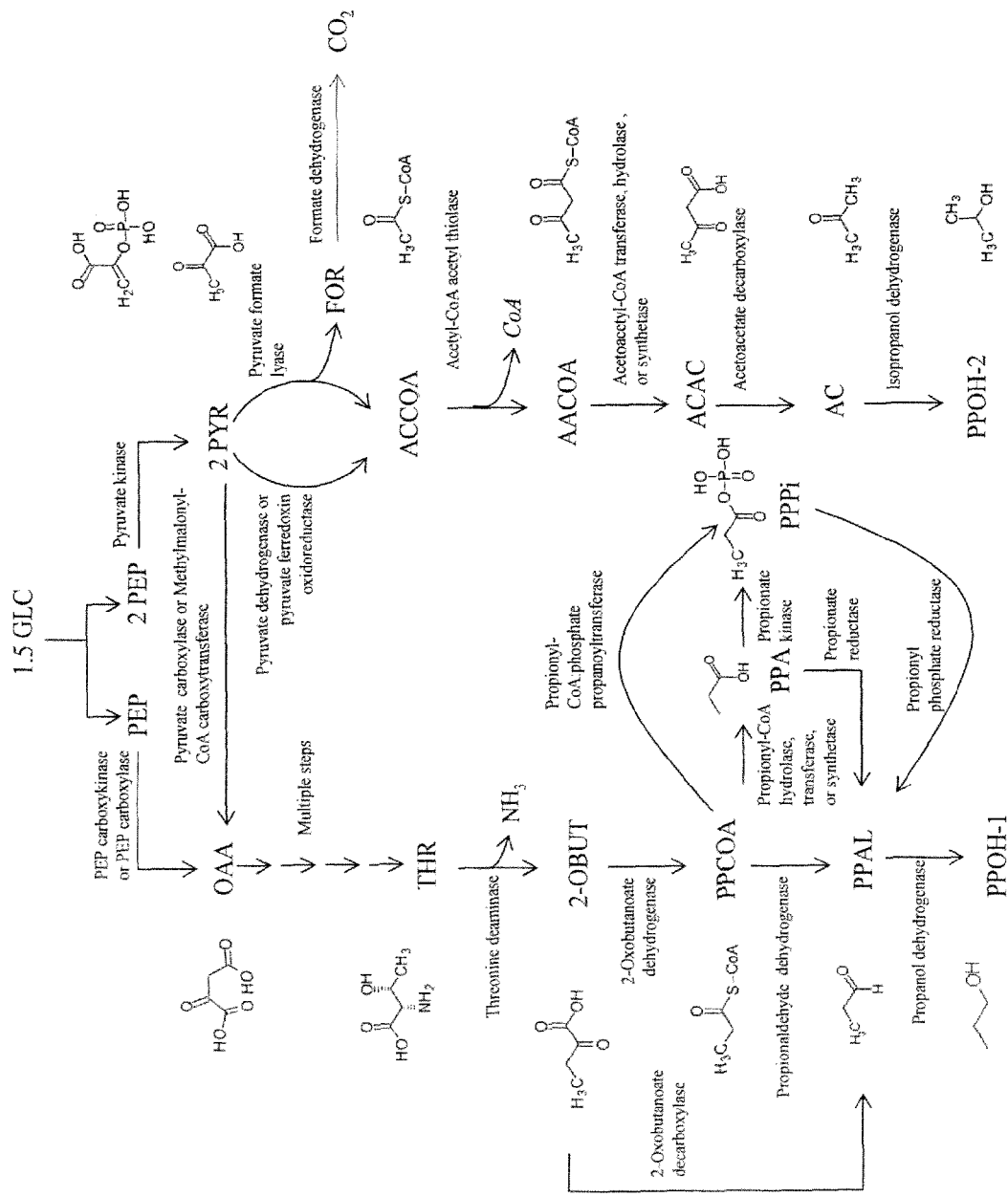
FIG. 2 shows an exemplary pathway for co-production of n-propanol and isopropanol from glucose. Abbreviations: Glc—glucose, PEP—phosphoenolpyruvate, PYR—pyruvate, FOR—formate, ACCOA—acetyl-CoA, AACOA—acetoacetyl-CoA, ACAC—acetoacetate, AC—acetone, PPOH-2—isopropanol, OAA—oxaloacetate, THR—threonine, 2-OBUT—2-oxobutanoate, PPCOA—propionyl-CoA, PPA—propionate, PPAL—propionaldehyde, PPPi—propionyl phosphate, PPOH-1—n-propanol.
Figure 3:
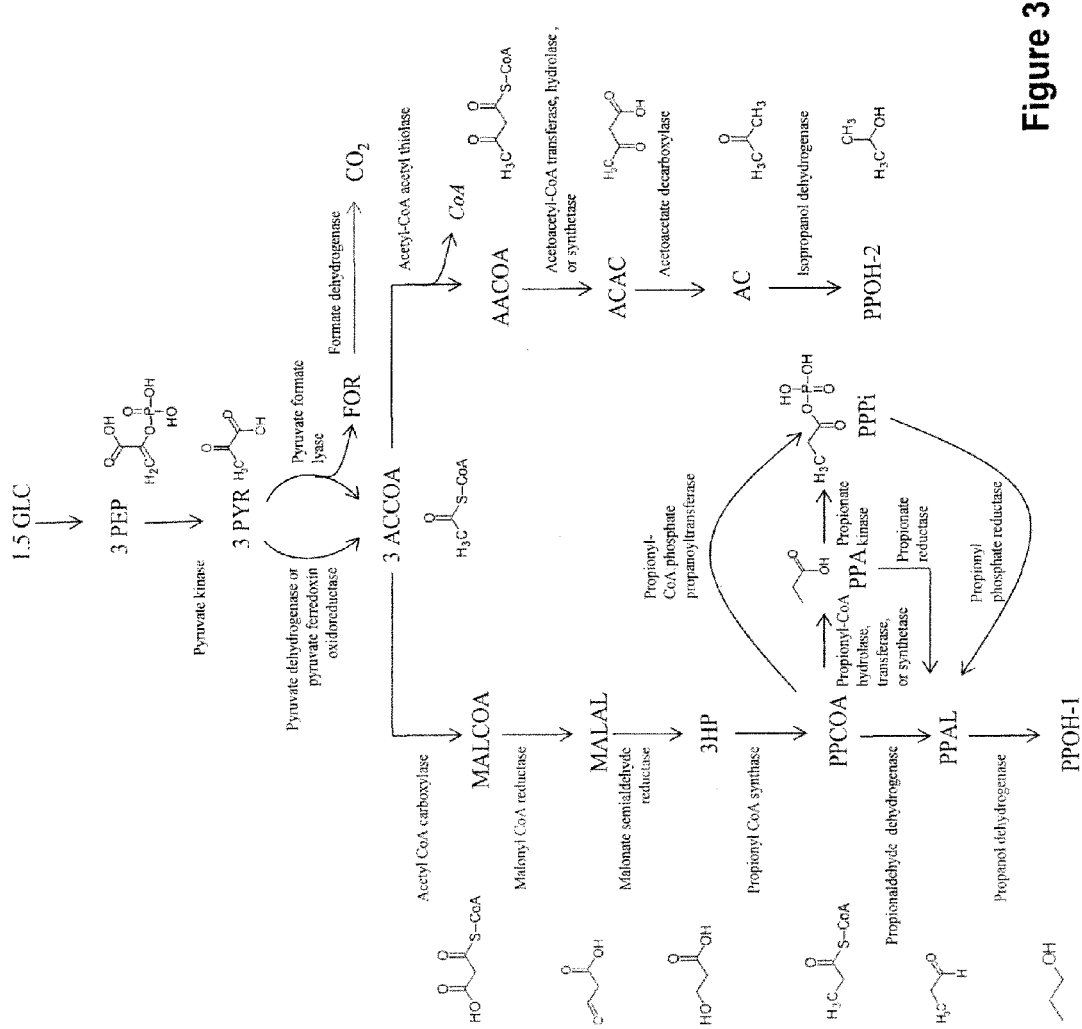
FIG. 3 shows an exemplary pathway for co-production of n-propanol and isopropanol from glucose. Abbreviations: Glc—glucose, PEP—phosphoenolpyruvate, PYR—pyruvate, FOR—formate, ACCOA—acetyl-CoA, AACOA—acetoacetyl-CoA, ACAC—acetoacetate, AC—acetone, PPOH-2—isopropanol, MALCOA—malonyl-CoA, MALAL—malonate semialdehyde, 3HP-3-hydroxypropionate, PPCOA—propionyl-CoA, PPA—propionate, PPAL—propionaldehyde, PPPi—propionyl phosphate, PPOH-1—n-propanol.

Further to Example I, the pathway for production of acetyl-CoA from glucose proceeds via phosphoenolpyruvate (PEP) (FIGS. 1-4). Glucose is converted into PEP by the native glycolysis pathway of the microbial organism. PEP is converted to pyruvate by pyruvate kinase and then to acetyl-CoA by pyruvate dehydrogenase or pyruvate ferredoxin oxidoreductase. Alternatively, pyruvate is converted to acetyl-CoA and formate by pyruvate formate lyase. Formate is then converted to carbon dioxide by a formate dehydrogenase that also produces NADH. The acetyl-CoA produced by these pathways are then utilized for production of isopropanol as described in Example I or utilized for production of both n-propanol and isopropanol as described in Example V below (FIG. 3).

Pyruvate Dehydrogenase

The pyruvate dehydrogenase complex, catalyzing the conversion of pyruvate to acetyl-CoA, has been extensively studied. The S. cerevisiae complex consists of an E2 (LAT1) core that binds E1 (PDA1, PDB1), E3 (LPD1), and Protein X (PDX1) components (Pronk, Yeast 12:1607-1633 (1996)). In the E. coli enzyme, specific residues in the E1 component are responsible for substrate specificity (Bisswanger, J. Biol Chem. 256:815-822 (1981); Bremer, Eur. J Biochem. 8:535-540 (1969) and Gong et al., J. Biol Chem. 275:13645-13653 (2000)). Engineering efforts have improved the E. coli PDH enzyme activity under anaerobic conditions (Kim, J. Bacteriol 190:3851-3858 (2008); Kim, Appl. Environ. Microbiol. 73:1766-1771 (2007) and Zhou, Biotechnol. Lett. 30:335-342 (2008)). In contrast to the E. coli PDH, the B. subtilis complex is active and required for growth under anaerobic conditions (Nakano, J. Bacteriol 179:6749-6755 (1997)). The Klebsiella pneumoniae PDH, characterized during growth on glycerol, is also active under anaerobic conditions (Menzel, J. Biotechnol. 56:135-142 (1997)). Crystal structures of the enzyme complex from bovine kidney (Zhou, Proc. Natl. Acad. Sci. U.S.A. 98:14802-14807 (2001)) and the E2 catalytic domain from Azotobacter vinelandii are available (Mattevi et al., Science. 255:1544-1550 (1992)). Some mammalian PDH enzymes complexes can react on alternate substrates such as 2-oxobutanoate (Paxton, J Bacteriol. 179:5684-5692 (1997)). These genes/proteins are identified below in Table 35.

TABLE 35

| Gene | GenBank ID | GI Number | Organism |
| --- | --- | --- | --- |
| LAT1 | NP_014328 | 6324258 | Saccharomyces cerevisiae |
| PDA1 | NP_011105 | 37362644 | Saccharomyces cerevisiae |
| PDB1 | NP_009780 | 6319698 | Saccharomyces cerevisiae |
| LPD1 | NP_116635 | 14318501 | Saccharomyces cerevisiae |
| PDX1 | NP_011709 | 6321632 | Saccharomyces cerevisiae |
| aceE | NP_414656.1 | 16128107 | Escherichia coli str. K12 substr. MG1655 |
| aceF | NP_414657.1 | 16128108 | Escherichia coli str. K12 substr. MG1655 |
| lpd | NP_414658.1 | 16128109 | Escherichia coli str. K12 substr. MG1655 |
| pdhA | P21881.1 | 3123828 | Bacillus subtilis |
| pdhB | P21882.1 | 129068 | Bacillus subtilis |
| pdhC | P21883.2 | 129054 | Bacillus subtilis |
| pdhD | P21880.1 | 118672 | Bacillus subtilis |
| aceE | YP_001333808.1 | 152968699 | Klebsiella pneumonia MGH78578 |
| aceF | YP_001333809.1 | 152968700 | Klebsiella pneumonia MGH78578 |
| lpdA | YP_001333810.1 | 152968701 | Klebsiella pneumonia MGH78578 |
| Pdha1 | NP_001004072.2 | 124430510 | Rattus norvegicus |
| Pdha2 | NP_446446.1 | 16758900 | Rattus norvegicus |
| Dlat | NP_112287.1 | 78365255 | Rattus norvegicus |
| Dld | NP_955417.1 | 40786469 | Rattus norvegicus |

Pyruvate Ferredoxin Oxidoreductase

Pyruvate ferredoxin oxidoreductase (PFOR) catalyzes the oxidation of pyruvate to form acetyl-CoA. The PFOR from Desulfovibrio africanus has been cloned and expressed in E. coli resulting in an active recombinant enzyme that was stable for several days in the presence of oxygen (Pieulle, J Bacteriol 179:5684-5692 (1997)). Oxygen stability is relatively uncommon in PFORs and is believed to be conferred by a 60 residue extension in the polypeptide chain of the D. africanus enzyme. The M. thermoacetica PFOR is also well characterized (Menon, Biochemistry 36:8484-8494 (1997)) and was even shown to have high activity in the direction of pyruvate synthesis during autotrophic growth (Furdui, J Biol Chem. 275:28494-28499 (2000)). Further, E. coli possesses an uncharacterized open reading frame, ydbK, that encodes a protein that is 51% identical to the M. thermoacetica PFOR. Evidence for pyruvate oxidoreductase activity in E. coli has been described (Blaschkowski, Eur. J Biochem. 123:563-569 (1982)). Several additional PFOR enzymes are described in the following review (Ragsdale, Chem. Rev. 103:2333-2346 (2003)). Finally, flavodoxin reductases (e.g., fqrB from Helicobacter pylori or Campylobacter jejuni) (St Maurice et al., J. Bacteriol. 189:4764-4773 (2007)) or Rnf-type proteins (Seedorf et al., Proc. Natl. Acad. Sci. U.S.A. 105:2128-2133 (2008); and Herrmann, J. Bacteriol 190:784-791 (2008)) provide a means to generate NADH or NADPH from the reduced ferredoxin generated by PFOR. These genes/proteins are identified below in Table 36.

TABLE 36

| Gene | GenBank ID | GI Number | Organism |
| --- | --- | --- | --- |
| por | CAA70873.1 | 1770208 | Desulfovibrio africanus |
| por | YP_428946.1 | 83588937 | Moorella thermoacetica |
| ydbK | NP_415896.1 | 16129339 | Escherichia coli |
| fqrB | NP_207955.1 | 15645778 | Helicobacter pylori |
| fqrB | YP_001482096.1 | 157414840 | Campylobacter jejuni |
| RnfC | EDK33306.1 | 146346770 | Clostridium kluyveri |
| RnfD | EDK33307.1 | 146346771 | Clostridium kluyveri |
| RnfG | EDK33308.1 | 146346772 | Clostridium kluyveri |
| RnfE | EDK33309.1 | 146346773 | Clostridium kluyveri |
| RnfA | EDK33310.1 | 146346774 | Clostridium kluyveri |
| RnfB | EDK33311.1 | 146346775 | Clostridium kluyveri |

Pyruvate Formate Lyase

Pyruvate formate lyase is an enzyme that catalyzes the conversion of pyruvate and CoA into acetyl-CoA and formate. Pyruvate formate lyase is a common enzyme in prokaryotic organisms that is used to help modulate anaerobic redox balance. Exemplary enzymes can be found in Escherichia coli (Knappe, FEMS. Microbiol Rev. 6:383-398 (1990)), Lactococcus lactis (Melchiorsen, Appl Microbiol Biotechnol 58:338-344 (2002)), and Streptococcus mutans. (Takahashi-Abbe, Oral. Microbiol Immunol. 18:293-297 (2003)). A mitochondrial pyruvate formate lyase has also been identified in the eukaryote, Chlamydomonas reinhardtii. (Hemschemeier, Eukaryot. Cell 7:518-526 (2008); and Atteia, J. Biol. Chem. 281:9909-9918 (2008)). These genes/proteins are identified below in Table 37.

TABLE 37

| Gene | GenBank ID | GI Number | Organism |
| --- | --- | --- | --- |
| pflB | NP_415423 | 16128870 | Escherichia coli |
| pfl | CAA03993 | 2407931 | Lactococcus lactis |
| pfl | BAA09085 | 1129082 | Streptococcus mutans |
| PFL1 | EDP09457 | 158283707 | Chlamydomonas reinhardtii |

Formate Hydrogen Lyase

A formate hydrogen lyase enzyme can be employed to convert formate to carbon dioxide and hydrogen. An exemplary formate hydrogen lyase enzyme can be found in Escherichia coli. The E. coli formate hydrogen lyase consists of hydrogenase 3 and formate dehydrogenase-H (Maeda, *Appl Microbiol Biotechnol* 77:879-890 (2007)). It is activated by the gene product of fhlA (Maeda, *Appl Microbiol Biotechnol* 77:879-890 (2007)). The addition of the trace elements, selenium, nickel and molybdenum, to a fermentation broth has been shown to enhance formate hydrogen lyase activity (Soini, *Microb. Cell Fact.* 7:26 (2008)). These genes/proteins are identified below in Table 38.

TABLE 38

| Gene | GenBank ID | GI Number | Organism |
|---|---|---|---|
| Hydrogenase 3: | | | |
| hycD | NP_417202 | 16130629 | *Escherichia coli* |
| hycC | NP_417203 | 16130630 | *Escherichia coli* |
| hycF | NP_417200 | 16130627 | *Escherichia coli* |
| hycG | NP_417199 | 16130626 | *Escherichia coli* |
| hycB | NP_417204 | 16130631 | *Escherichia coli* |
| hycE | NP_417201 | 16130628 | *Escherichia coli* |
| Formate dehydrogenase-H: | | | |
| fdhF | NP_418503 | 16131905 | *Escherichia coli* |
| Activator: | | | |
| fhlA | NP_417211 | 16130638 | *Escherichia coli* |

A formate hydrogen lyase enzyme also exists in the hyperthermophilic archaeon, *Thermococcus litoralis* (Takacs et al., *BMC. Microbiol* 8:88 (2008)). These genes/proteins are identified below in Table 39.

TABLE 39

| Gene | GenBank ID | GI Number | Organism |
|---|---|---|---|
| mhyC | ABW05543 | 157954626 | *Thermococcus litoralis* |
| mhyD | ABW05544 | 157954627 | *Thermococcus litoralis* |
| mhyE | ABW05545 | 157954628 | *Thermococcus litoralis* |
| myhF | ABW05546 | 157954629 | *Thermococcus litoralis* |
| myhG | ABW05547 | 157954630 | *Thermococcus litoralis* |
| myhH | ABW05548 | 157954631 | *Thermococcus litoralis* |
| fdhA | AAB94932 | 2746736 | *Thermococcus litoralis* |
| fdhB | AAB94931 | 157954625 | *Thermococcus litoralis* |

Additional formate hydrogen lyase systems have been found in *Salmonella typhimurium*, *Klebsiella pneumoniae*, *Rhodospirillum rubrum*, *Methanobacterium formicicum* (Vardar-Schara, *Microbial Biotechnology* 1:107-125 (2008)).

Formate Dehydrogenase

Formate dehydrogenase activity is present in both *E. coli* and *Saccharomyces cerevisiae* among other organisms. *S. cerevisiae* contains two formate dehydrogenases, FDH1 and FDH2, that catalyze the oxidation of formate to $CO_2$. (Overkamp et al., *Yeast* 19:509-520 (2002)) In *Moorella thermoacetica*, the loci, Moth_2312 and Moth_2313, are actually one gene that is responsible for encoding the alpha subunit of formate dehydrogenase while the beta subunit is encoded by Moth_2314 (Pierce et al., *Environ. Microbiol* (2008); Andreesen, *J. Bacteriol.* 116:867-873 (1973); Li, *J. Bacteriol* 92:405-412 (1966) and Yamamoto, *J. Biol. Chem.* 258:1826-1832 (1983)) Another set of genes encoding formate dehydrogenase activity is encoded by Sfum_2703 through Sfum_2706 in *Syntrophobacter fumaroxidans* (Reda, *Proc. Natl. Acad. Sci. U.S.A.* 105:10654-10658 (2008); and de Bok et al., *Eur. J. Biochem.* 270:2476-2485 (2003)). Similar to their *M. thermoacetica* counterparts, Sfum_2705 and Sfum_2706 are actually one gene. *E. coli* contains multiple formate dehydrogenases. These genes/proteins are identified below in Table 40.

TABLE 40

| Gene | GenBank ID | GI Number | Organism |
|---|---|---|---|
| FDH1 | NP_015033 | 6324964 | *Saccharomyces cerevisiae* |
| FDH2 | Q08987 | 88909613 | *Saccharomyces cerevisiae* |
| Moth_2312 | YP_431142 | 148283121 | *Moorella thermoacetica* |
| Moth_2313 | YP_431143 | 83591134 | *Moorella thermoacetica* |
| Moth_2314 | YP_431144 | 83591135 | *Moorella thermoacetica* |
| Sfum_2703 | YP_846816.1 | 116750129 | *Syntrophobacter fumaroxidans* |
| Sfum_2704 | YP_846817.1 | 116750130 | *Syntrophobacter fumaroxidans* |
| Sfum_2705 | YP_846818.1 | 116750131 | *Syntrophobacter fumaroxidans* |
| Sfum_2706 | YP_846819.1 | 116750132 | *Syntrophobacter fumaroxidans* |
| fdnG, H, I | NP_415991-993.1 | 16129433 16129434 16129435 | *Escherichia coli* |
| fdoG, H, I | NP_418330, 29, 28.1 | 16131734 16131733 16131732 | *Escherichia coli* |

Example III

Pathways for Production of Propionyl-CoA from Glucose Utilizing the Reductive TCA Cycle Further to Examples I and II, the pathway for production of propionyl-CoA proceeds via oxaloacetate (FIG. 1). PEP is converted into oxaloacetate either via PEP carboxykinase or PEP carboxylase. Alternatively, PEP is converted first to pyruvate by pyruvate kinase and then to oxaloacetate by methylmalonyl-CoA carboxytransferase or pyruvate carboxylase. Oxaloacetate is converted to propionyl-CoA by means of the reductive TCA cycle, a methylmutase, a decarboxylase, an epimerase and a decarboxylase.

PEP Carboxykinase

Although the net conversion of phosphoenolpyruvate to oxaloacetate is redox-neutral, the mechanism of this conversion is important to the overall energetics of the co-production pathway. The most desirable enzyme for the conversion of PEP to oxaloacetate is PEP carboxykinase which simultaneously forms an ATP while carboxylating PEP. In most organisms, however, PEP carboxykinase serves a gluconeogenic function and converts oxaloacetate to PEP at the expense of one ATP. *S. cerevisiae* is one such organism whose native PEP carboxykinase, PCK1, serves a gluconeogenic role (Valdes-Hevia, *FEBS. Lett.* 258:313-316 (1989)). *E. coli* is another such organism, as the role of PEP carboxykinase in producing oxaloacetate is believed to be minor when compared to PEP carboxylase, which does not form ATP, possibly due to the higher $K_m$ for bicarbonate of PEP carboxykinase (Kim, *Appl Environ Microbiol* 70:1238-1241 (2004)). Nevertheless, activity of the native *E. coli* PEP carboxykinase from PEP towards oxaloacetate has been recently demonstrated in ppc mutants of *E. coli* K-12 (Kwon, *Journal of Microbiology and Biotechnology* 16:1448-1452 (2006)). These strains exhibited no growth defects and had increased succinate production at high $NaHCO_3$ concentrations. In some organisms, particularly rumen bacteria, PEP carboxykinase is quite efficient in producing oxaloacetate from PEP and generating ATP. Examples of PEP carboxykinase genes that have been cloned into *E. coli* include those from *Mannheimia succiniciproducens* (Lee, *Biotechnol. Bioprocess Eng.* 7:95-99 (2002)), *Anaerobiospirillum succiniciproducens* (Laivenieks, *Appl Environ Microbiol* 63:2273-2280 (1997)), and

*Actinobacillus succinogenes* (Kim, *Appl Environ Microbiol* 70:1238-1241 (2004)). Internal experiments have also found that the PEP carboxykinase enzyme encoded by *Haemophilus influenza* is highly efficient at forming oxaloacetate from PEP. These genes/proteins are identified below in Table 41.

TABLE 41

| Gene | GenBank ID | GI Number | Organism |
|---|---|---|---|
| PCK1 | NP_013023 | 6322950 | *Saccharomyces cerevisiae* |
| pck | NP_417862.1 | 16131280 | *Escherichia coli* |
| pckA | YP_089485.1 | 52426348 | *Mannheimia succiniciproducens* |
| pckA | O09460.1 | 3122621 | *Anaerobiospirillum succiniciproducens* |
| pckA | Q6W6X5 | 75440571 | *Actinobacillus succinogenes* |
| pckA | P43923.1 | 1172573 | *Haemophilus influenza* |

These sequences and sequences for subsequent enzymes listed in this report can be used to identify homologue proteins in GenBank or other databases through sequence similarity searches (e.g. BLASTp). The resulting homologue proteins and their corresponding gene sequences provide additional DNA sequences for transformation into the host organism of choice.

PEP Carboxylase

PEP carboxylase represents an alternative enzyme for the formation of oxaloacetate from PEP. Since the enzyme does not generate ATP upon decarboxylating oxaloacetate, its utilization decreases the maximum ATP yield of the production pathway and represents a less favorable alternative for converting oxaloacetate to PEP. Nevertheless, the maximum theoretical C3 alcohols yield of 1.33 mol/mol will remain unchanged if PEP carboxylase is utilized to convert PEP to oxaloacetate. *S. cerevisiae* does not naturally encode a PEP carboxylase, but exemplary organisms that possess genes that encode PEP carboxylase include *E. coli* (Kai, *Arch. Biochem. Biophys.* 414:170-179 (2003)), *Methylobacterium extorquens* AM1 (Arps, *J. Bacteriol.* 175:3776-3783 (1993)), and *Corynebacterium glutamicum* (Eikmanns, *Mol. Gen. Genet.* 218:330-339 (1989)). These genes/proteins are identified below in Table 42.

TABLE 42

| Gene | GenBank ID | GI Number | Organism |
|---|---|---|---|
| ppc | NP_418391 | 16131794 | *Escherichia coli* |
| ppcA | AAB58883 | 28572162 | *Methylobacterium extorquens* |
| ppc | ABB53270 | 80973080 | *Corynebacterium glutamicum* |

Pyruvate Kinase and Methylmalonyl-CoA Carboxyltransferase

An additional energetically efficient route to oxaloacetate from PEP requires two enzymatic activities: pyruvate kinase and methylmalonyl-CoA carboxytransferase. Pyruvate kinase catalyzes the ATP-generating conversion of PEP to pyruvate and is encoded by the PYK1 (Burke, *J. Biol. Chem.* 258:2193-2201 (1983)) and PYK2 (Boles et al., *J. Bacteriol.* 179:2987-2993 (1997)) genes in *S. cerevisiae*. In *E. coli*, this activity is catalyzed by the gene product of pykF and pykA. Methylmalonyl-CoA carboxytransferase catalyzes the conversion of pyruvate to oxaloacetate. Importantly, this reaction also simultaneously catalyzes the conversion of (S)-methylmalonyl-CoA to propionyl-CoA (see FIGS. 1 and 2). An exemplary methylmalonyl-CoA carboxytransferase which is comprised of 1.3 S, 5 S, and 12 S subunits can be found in *Propionibacterium freudenreichii* (Thornton et al., *J. Bacteriol* 175:5301-5308 (1993)). These genes/proteins are identified below in Table 43.

TABLE 43

| Gene | GenBank ID | GI Number | Organism |
|---|---|---|---|
| PYK1 | NP_009362 | 6319279 | *Saccharomyces cerevisiae* |
| PYK2 | NP_014992 | 6324923 | *Saccharomyces cerevisiae* |
| pykF | NP_416191.1 | 16129632 | *Escherichia coli* |
| pykA | NP_416368.1 | 16129807 | *Escherichia coli* |
| 1.3S subunit | P02904 | 114847 | *Propionibacterium freudenreichii* |
| 5S subunit | Q70AC7 | 62901478 | *Propionibacterium freudenreichii* |
| 12S subunit | Q8GBW6 | 62901481 | *Propionibacterium freudenreichii* |

Pyruvate Kinase and Pyruvate Carboxylase

A combination of enzymes can convert PEP to oxaloacetate with a stoichiometry identical to that of PEP carboxylase. These enzymes are encoded by pyruvate kinase, PYK1 (Burke, *J. Biol. Chem.* 258:2193-2201 (1983)) or PYK2 (Boles et al., *J. Bacteriol,* 179:2987-2993 (1997)) and pyruvate carboxylase, PYC1 (Walker, *Biochem. Biophys. Res. Commun.* 176:1210-1217 (1991)) or PYC2 (Walker, *Biochem. Biophys. Res. Commun.* 176:1210-1217 (1991)). The latter genes/proteins are identified below in Table 44.

TABLE 44

| Gene | GenBank ID | GI Number | Organism |
|---|---|---|---|
| PYC1 | NP_011453 | 6321376 | *Saccharomyces cerevisiae* |
| PYC2 | NP_009777 | 6319695 | *Saccharomyces cerevisiae* |
| Pyc | YP_890857.1 | 118470447 | *Mycobacterium smegmatis* |

Malate Dehydrogenase, Fumarase, Fumarate Reductase

Oxaloacetate can be converted to succinate by malate dehydrogenase, fumarase and fumarate reductase when the TCA cycle is operating in the reductive cycle. *S. cerevisiae* possesses three copies of malate dehydrogenase, MDH1 (McAlister-Henn, *J. Bacteriol* 169:5157-5166 (1987)) MDH2 (Minard, *Mol. Cell. Biol.* 11:370-380 (1991); and Gibson, *J. Biol. Chem.* 278:25628-25636 (2003)), and MDH3 (Steffan, *J. Biol. Chem.* 267:24708-24715 (1992)), which localize to the mitochondrion, cytosol, and peroxisome, respectively. *S. cerevisiae* contains one copy of a fumarase-encoding gene, FUM1, whose product localizes to both the cytosol and mitochondrion (Sass, *J. Biol. Chem.* 278:45109-45116 (2003)). Fumarate reductase is encoded by two soluble enzymes, FRDS1 (Enomoto, *DNA. Res.* 3:263-267 (1996)) and FRDS2 (Muratsubaki, *Arch. Biochem. Biophys.* 352:175-181 (1998)), which localize to the cytosol and promitochondrion, respectively, and are required for anaerobic growth on glucose (Arikawa, *Microbiol Lett.* 165:111-116 (1998)). *E. coli* is known to have an active malate dehydrogenase. It has three fumarases encoded by fumA, B and C, each one of which is active under different conditions of oxygen availability. The fumarate reductase in *E. coli* is composed of four subunits. These genes/proteins are identified below in Table 45.

TABLE 45

| Gene | GenBank ID | GI Number | Organism |
|---|---|---|---|
| MDH1 | NP_012838 | 6322765 | *Saccharomyces cerevisiae* |
| MDH2 | NP_014515 | 116006499 | *Saccharomyces cerevisiae* |
| MDH3 | NP_010205 | 6320125 | *Saccharomyces cerevisiae* |
| FUM1 | NP_015061 | 6324993 | *Saccharomyces cerevisiae* |
| FRDS1 | P32614 | 418423 | *Saccharomyces cerevisiae* |
| FRDS2 | NP_012585 | 6322511 | *Saccharomyces cerevisiae* |

TABLE 45-continued

| Gene | GenBank ID | GI Number | Organism |
|---|---|---|---|
| frdA | NP_418578.1 | 16131979 | Escherichia coli |
| frdB | NP_418577.1 | 16131978 | Escherichia coli |
| frdC | NP_418576.1 | 16131977 | Escherichia coli |
| frdD | NP_418475.1 | 16131877 | Escherichia coli |
| Mdh | NP_417703.1 | 16131126 | Escherichia coli |
| FumA | NP_416129.1 | 16129570 | Escherichia coli |
| FumB | NP_418546.1 | 16131948 | Escherichia coli |
| FumC | NP_416128.1 | 16129569 | Escherichia coli |

Succinyl-CoA Transferase

Succinyl-CoA transferase catalyzes the conversion of succinyl-CoA to succinate while transferring the CoA moiety to a CoA acceptor molecule. Many transferases have broad specificity and thus may utilize CoA acceptors as diverse as acetate, succinate, propionate, butyrate, 2-methylacetoacetate, 3-ketohexanoate, 3-ketopentanoate, valerate, crotonate, 3-mercaptopropionate, propionate, vinylacetate, butyrate, among others.

The conversion of succinate to succinyl-CoA is ideally carried by a transferase which does not require the direct consumption of an ATP or GTP. This type of reaction is common in a number of organisms. Perhaps the top candidate enzyme for this reaction step is succinyl-CoA:3-ketoacid-CoA transferase. This enzyme converts succinate to succinyl-CoA while converting a 3-ketoacyl-CoA to a 3-ketoacid. Exemplary succinyl-CoA:3:ketoacid-CoA transferases are present in *Helicobacter pylori* (Corthesy-Theulaz et al., *J. Biol. Chem.* 272:25659-25667 (1997)), *Bacillus subtilis* (Stols et al., *Protein. Expr. Purif.* 53:396-403 (2007)), and *Homo sapiens* (Fukao et al., *Genomics*, 68:144-151 (2000); and Tanaka, *Mol. Hum. Reprod.* 8:16-23 (2002)). These genes/proteins are identified below in Table 46.

TABLE 46

| Gene | GenBank ID | GI Number | Organism |
|---|---|---|---|
| HPAG1_0676 | YP_627417 | 108563101 | Helicobacter pylori |
| HPAG1_0677 | YP_627418 | 108563102 | Helicobacter pylori |
| ScoA | NP_391778 | 16080950 | Bacillus subtilis |
| ScoB | NP_391777 | 16080949 | Bacillus subtilis |
| OXCT1 | NP_000427 | 4557817 | Homo sapiens |
| OXCT2 | NP_071403 | 11545841 | Homo sapiens |

The conversion of succinate to succinyl-CoA can also be catalyzed by succinyl-CoA: Acetyl-CoA transferase. The gene product of cat1 of *Clostridium kluyveri* has been shown to exhibit succinyl-CoA: acetyl-CoA transferase activity (Sohling, *J Bacteriol.* 178:871-880 (1996)). In addition, the activity is present in *Trichomonas vaginalis* (van Grinsven et al., *J. Biol. Chem.* 283:1411-1418 (2008)) and *Trypanosoma brucei* (Riviere et al., *J. Biol. Chem.* 279:45337-45346 (2004)). These genes/proteins are identified below in Table 47.

TABLE 47

| Gene | GenBank ID | GI Number | Organism |
|---|---|---|---|
| cat1 | P38946.1 | 729048 | Clostridium kluyveri |
| TVAG_395550 | XP_001330176 | 123975034 | Trichomonas vaginalis G3 |
| Tb11.02.0290 | XP_828352 | 71754875 | Trypanosoma brucei |

Yet another possible CoA acceptor is benzylsuccinate. Succinyl-CoA:(R)-Benzylsuccinate CoA-Transferase functions as part of an anaerobic degradation pathway for toluene in organisms such as *Thauera aromatica* (Leutwein and Heider, *J. Bact.* 183(14) 4288-4295 (2001)). Homologs can be found in *Azoarcus* sp. T, *Aromatoleum aromaticum* EbN1, and *Geobacter metallireducens* GS-15. These genes/proteins are identified below in Table 48.

TABLE 48

| Gene | GenBank ID | GI Number | Organism |
|---|---|---|---|
| bbsE | AAF89840 | 9622535 | Thauera aromatica |
| bbsf | AAF89841 | 9622536 | Thauera aromatica |
| bbsE | AAU45405.1 | 52421824 | Azoarcus sp. T |
| bbsF | AAU45406.1 | 52421825 | Azoarcus sp. T |
| bbsE | YP_158075.1 | 56476486 | Aromatoleum aromaticum EbN1 |
| bbsF | YP_158074.1 | 56476485 | Aromatoleum aromaticum EbN1 |
| Gmet_1521 | YP_384480.1 | 78222733 | Geobacter metallireducens GS-15 |
| Gmet_1522 | YP_384481.1 | 78222734 | Geobacter metallireducens GS-15 |

Finally, ygfH encodes a propionyl CoA:succinate CoA transferase in *E. coli* (Haller et al., *Biochemistry*, 39(16) 4622-4629). Close homologs can be found in, for example, *Citrobacter youngae* ATCC 29220, *Salmonella enterica* subsp. *arizonae serovar*, and *Yersinia intermedia* ATCC 29909. These genes/proteins are identified below in Table 49.

TABLE 49

| Gene | GenBank ID | GI Number | Organism |
|---|---|---|---|
| ysfH | NP_417395.1 | 16130821 | Escherichia coli str. K-12 substr. MG1655 |
| CIT292_04485 | ZP_03838384.1 | 227334728 | Citrobacter youngae ATCC 29220 |
| SARI_04582 | YP_001573497.1 | 161506385 | Salmonella enterica subsp. arizonae serovar |
| yinte0001_14430 | ZP_04635364.1 | 238791727 | Yersinia intermedia ATCC 29909 |

Succinyl-CoA Synthetase

The product of the LSC1 and LSC2 genes of *S. cerevisiae* and the sucC and sucD genes of *E. coli* naturally form a succinyl-CoA synthetase complex that catalyzes the formation of succinyl-CoA from succinate with the concomitant consumption of one ATP, a reaction which is reversible in vivo (Przybyla-Zawilask et al., *Eur. J. Biochem.* 258(2):736-743 (1998) and Buck et al., *J. Gen. Microbiol.* 132(6):1753-1762 (1986)). These genes/proteins are identified below in Table 50.

TABLE 50

| Gene | GenBank ID | GI Number | Organism |
|---|---|---|---|
| LSC1 | NP_014785 | 6324716 | Saccharomyces cerevisiae |
| LSC2 | NP_011760 | 6321683 | Saccharomyces cerevisiae |
| sucC | NP_415256.1 | 16128703 | Escherichia coli |
| sucD | AAC73823.1 | 1786949 | Escherichia coli |

Methylmalonyl-CoA Mutase

Succinyl-CoA can be converted into (R)-methylmalonyl-CoA by methylmalonyl-CoA mutase (MCM). In *E. coli*, the reversible adenosylcobalamin-dependant mutase participates in a three-step pathway leading to the conversion of succinate to propionate (Haller, *Biochemistry* 39:4622-9 (2000)). MCM is encoded by genes scpA in *Escherichia coli* (Haller,

*Biochemistry* 39: 4622-4629 (2000); and Bobik, *Anal. Bioanal. Chem.* 375:344-349 (2003)) and mutA in *Homo sapiens* (Padovani, *Biochemistry* 45:9300-9306 (2006)). In several other organisms MCM contains alpha and beta subunits and is encoded by two genes. Exemplary gene candidates encoding the two-subunit protein are *Propionibacterium fredenreichii* sp. *shermani* mutA and mutB (Korotkova, *J Biol Chem.* 279: 13652-13658 (2004)) and *Methylobacterium extorquens* mcmA and mcmB (Korotkova, *J Biol Chem.* 279:13652-13658 (2004)). These genes/proteins are identified below in Table 51.

TABLE 51

| Gene | GenBank ID | GI Number | Organism |
|---|---|---|---|
| scpA | NP_417392.1 | 16130818 | *Escherichia coli* K12 |
| mutA | P22033.3 | 67469281 | *Homo sapiens* |
| mutA | P11652.3 | 127549 | *Propionibacterium fredenreichii* sp. *shermanii* |
| mutB | P11653.3 | 127550 | *Propionibacterium fredenreichii* sp. *shermanii* |
| mcmA | Q84FZ1 | 75486201 | *Methylobacterium extorquens* |
| mcmB | Q6TMA2 | 75493131 | *Methylobacterium extorquens* |

Additional enzyme candidates identified based on high homology to the *E. coli* spcA gene product are identified below in Table 52.

TABLE 52

| Gene | GenBank ID | GI Number | Organism |
|---|---|---|---|
| sbm | NP_838397.1 | 30064226 | *Shigella flexneri* |
| SARI_04585 | ABX24358.1 | 160867735 | *Salmonella enterica* |
| YfreA_01000861 | ZP_00830776.1 | 77975240 | *Yersinia frederiksenii* |

There further exists evidence that genes adjacent to the methylmalonyl-CoA mutase catalytic genes are also required for maximum activity. For example, it has been demonstrated that the meaB gene from *M. extorquens* forms a complex with methylmalonyl-CoA mutase, stimulates in vitro mutase activity, and possibly protects it from irreversible inactivation (Korotkova, *J Biol Chem.* 279:13652-13658 (2004)). The *M. extorquens* meaB gene product is highly similar to the product of the *E. coli* argK gene (BLASTp: 45% identity, e-value: 4e-67) which is adjacent to scpA on the chromosome. No sequence for a meaB homolog in *P. freudenreichii* is catalogued in GenBank. However, the *Propionibacterium acnes* KPA171202 gene product, YP_055310.1, is 51% identical to the *M. extorquens* meaB protein and its gene is also adjacent to the methylmalonyl-CoA mutase gene on the chromosome. These genes/proteins are identified below in Table 53.

TABLE 53

| Gene | GenBank ID | GI Number | Organism |
|---|---|---|---|
| argK | AAC75955.1 | 1789285 | *Escherichia coli* K12 |
| KPA171202 | YP_055310.1 | 50842083 | *Propionibacterium acnes* |
| meaB | 2QM8_B | 158430328 | *Methylobacterium extorquens* |

Methylmalonyl-CoA Epimerase

Methylmalonyl-CoA epimerase (MMCE) is the enzyme that interconverts (R)-methylmalonyl-CoA and (S)-methylmalonyl-CoA. MMCE is an essential enzyme in the breakdown of odd-numbered fatty acids and of the amino acids valine, isoleucine, and methionine. Methylmalonyl-CoA epimerase is present in organisms such as *Bacillus subtilis* (YqjC) (Haller, *Biochemistry.* 39:4622-4629 (2000)), *Homo sapiens* (YqjC) (Fuller, *Biochem. J* 213:643-650 (1983)), *Rattus norvegicus* (Mcee) (Bobik, *J Biol Chem.* 276:37194-37198 (2001)), *Propionibacterium shermanii* (AF454511) (Haller, *Biochemistry* 39:4622-9 (2000); McCarthy, *Structure* 9:637-46 (2001) and (Fuller, *Biochem. J* 213:643-650 (1983)) and *Caenorhabditis elegans* (mmce) (Kuhnl et al., *FEBS J* 272:1465-1477 (2005)). The additional gene candidate, AE016877 in *Bacillus cereus*, has high sequence homology to the other characterized enzymes. MMCE activity is required if the employed methylmalonyl-CoA decarboxylase or methylmalonyl-CoA carboxytransferase requires the (S) stereoisomer of methylmalonyl-CoA. These genes/proteins are identified below in Table 54.

TABLE 54

| Gene | GenBank ID | GI Number | Organism |
|---|---|---|---|
| YqjC | NP_390273 | 255767522 | *Bacillus subtilis* |
| MCEE | Q96PE7.1 | 50401130 | *Homo sapiens* |

| Gene | GenBank ID | GI Number | Organism |
|---|---|---|---|
| Mcee_predicted | NP_001099811.1 | 157821869 | *Rattus norvegicus* |
| AF454511 | AAL57846.1 | 18042135 | *Propionibacterium fredenreichii* sp. *shermanii* |
| mmce | AAT92095.1 | 51011368 | *Caenorhabditis elegans* |
| AE016877 | AAP08811.1 | 29895524 | *Bacillus cereus* ATCC 14579 |

Methylmalonyl-CoA Decarboxylase

Methylmalonyl-CoA decarboxylase, is a biotin-independent enzyme that catalyzes the conversion of methylmalonyl-CoA to propionyl-CoA in *E. coli* (Benning, *Biochemistry.* 39:4630-4639 (2000); and Haller, *Biochemistry.* 39:4622-4629 (2000)). The stereo specificity of the *E. coli* enzyme was not reported, but the enzyme in *Propionigenium modestum* (Bott et al., *Eur. J. Biochem.* 250:590-599 (1997)) and *Veillonella parvula* (Huder, *J. Biol. Chem.* 268:24564-24571 (1993)) catalyzes the decarboxylation of the (S)-stereoisomer of methylmalonyl-CoA (Hoffmann, *FEBS. Lett.* 220:121-125 (1987). The enzymes from *P. modestum* and *V. parvula* are comprised of multiple subunits that not only decarboxylate (S)-methylmalonyl-CoA, but also create a pump that transports sodium ions across the cell membrane as a means to generate energy. These genes/proteins are identified below in Table 55.

TABLE 55

| Gene | GenBank ID | GI Number | Organism |
|---|---|---|---|
| YgfG | NP_417394 | 90111512 | *Escherichia coli* |
| mmdA | CAA05137 | 2706398 | *Propionigenium modestum* |
| mmdD | CAA05138 | 2706399 | *Propionigenium modestum* |
| mmdC | CAA05139 | 2706400 | *Propionigenium modestum* |
| mmdB | CAA05140 | 2706401 | *Propionigenium modestum* |
| mmdA | CAA80872 | 415915 | *Veillonella parvula* |
| mmdC | CAA80873 | 415916 | *Veillonella parvula* |
| mmdE | CAA80874 | 415917 | *Veillonella parvula* |
| mmdD | CAA80875 | 415918 | *Veillonella parvula* |
| mmdB | CAA80876 | 415919 | *Veillonella parvula* |

Example IV

Pathways for Production of Propionyl-CoA from Glucose via Threonine

Further to Examples I and II, the pathway for production of propionyl-CoA via threonine is exemplified in FIG. 2. PEP is converted into oxaloacetate either via PEP carboxykinase or PEP carboxylase as described in Example III. Alternatively, PEP is converted first to pyruvate by pyruvate kinase and then to oxaloacetate by methylmalonyl-CoA carboxytransferase or pyruvate carboxylase as described in Example III. Oxaloacetate is converted into threonine by the native threonine pathway engineered for high yields. It is then deaminated to form 2-oxobutanoate and subsequently converted into propionyl-CoA. In one alternative, 2-oxobutanoate is converted to propionaldehyde by a decarboxylase, which is then reduced to n-propanol by a propanol dehydrogenase.

Threonine Deaminase

The conversion of threonine to 2-oxobutanoate (or 2-ketobutyrate) can be accomplished by a threonine deaminase. It is encoded by one or more genes selected from ilvA (Calhoun et al., J. Biol. Chem. 248(10):3511-6, (1973)) and tdcB (Umbarger et al., J. Bacteriol. 73(1):105-12, (1957); Datta et al., Proc. Natl. Acad. Sci. USA 84(2): 393-7 (1987)). Rhodospirillum rubrum represents an additional exemplary organism containing threonine deaminase (Feldberg et al., Eur. J. Biochem. 21(3): 438-46 (1971); U.S. Pat. No. 5,958,745). Details for exemplary enzymes for carrying out this transformation are shown below. These genes/proteins are identified below in Table 56.

TABLE 56

| Gene | GenBank ID | GI Number | Organism |
| --- | --- | --- | --- |
| ilvA | AAC77492 | 1790207 | Escherichia coli |
| tdcB | AAC76152 | 1789505 | Escherichia coli |
| Rru_A2877 | YP_427961.1 | 83594209 | Rhodospirillum rubrum |
| Rru_A0647 | YP_425738.1 | 83591986 | Rhodospirillum rubrum |

2-Oxobutanoate Dehydrogenase 2-oxobutanoate (2-ketobutyrate) can be converted to propionyl-CoA via a pyruvate formate lyase and a pyruvate formate lyase activating enzyme. The pyruvate formate lyase is encoded by gene selected from pflB and tdcE, while the pyruvate formate lyase activating enzyme is encoded by a pflA gene. Details for these exemplary genes for carrying out this transformation are already listed.

Alternatively, 2-oxobutanoate can be converted to propionyl-CoA by means of pyruvate dehydrogenase, pyruvate ferredoxin oxidoreductase (PFOR), or any other enzyme with 2-ketoacid dehydrogenase functionality. Such enzymes are also capable of converting pyruvate to acetyl-CoA. Exemplary pyruvate dehydrogenase enzymes are present in E. coli (Bisswanger, H., J. Biol. Chem. 256:815-822 (1981); Bremer, J., Eur. J. Biochem. 8:535-540 (1969); Gong et al., J. Biol. Chem. 275:13645-13653 (2000)), B. subtilis (Nakano et al., J. Bacteriol. 179:6749-6755 (1997)), K. pneumonia (Menzel et al., J. Biotechnol. 56:135-142 (1997)), R. norvegicus (Paxton et al., Biochem. J. 234:295-303 (1986)), for example. Exemplary gene information is provided below. These genes/proteins are identified below in Table 57.

TABLE 57

| Gene | GenBank ID | GI Number | Organism |
| --- | --- | --- | --- |
| aceE | NP_414656.1 | 16128107 | Escherichia coli str. K12 substr. MG1655 |
| aceF | NP_414657.1 | 16128108 | Escherichia coli str. K12 substr. MG1655 |
| lpd | NP_414658.1 | 16128109 | Escherichia coli str. K12 substr. MG1655 |
| pdhA | P21881.1 | 3123238 | Bacillus subtilis |
| pdhB | P21882.1 | 129068 | Bacillus subtilis |
| pdhC | P21883.2 | 129054 | Bacillus subtilis |
| pdhD | P21880.1 | 118672 | Bacillus subtilis |
| aceE | YP_001333808.1 | 152968699 | Klebsiella pneumonia MGH78578 |
| aceF | YP_001333809.1 | 152968700 | Klebsiella pneumonia MGH78578 |
| lpdA | YP_001333810.1 | 152968701 | Klebsiella pneumonia MGH78578 |
| Pdha1 | NP_001004072.2 | 124430510 | Rattus norvegicus |
| Pdha2 | NP_446446.1 | 16758900 | Rattus norvegicus |
| Dlat | NP_112287.1 | 78365255 | Rattus norvegicus |
| Dld | NP_955417.1 | 40786469 | Rattus norvegicus |

Exemplary PFOR enzymes include, for example, the enzyme from Desulfovibrio africanus which has been cloned and expressed in E. coli, resulting in an active recombinant enzyme that was stable for several days in the presence of oxygen (Pieulle et al., J. Bacteriol. 179:5684-5692 (1997)). Oxygen stability is relatively uncommon in PFORs and is reported to be conferred by a 60 residue extension in the polypeptide chain of the D. africanus enzyme. The M. thermoacetica PFOR is also well characterized (Menon et al. Biochemistry 36:8484-8494 (1997)) and was shown to have high activity in the direction of pyruvate synthesis during autotrophic growth (Furdui et al. J. Biol. Chem. 275:28494-28499 (2000)). Further, E. coli possesses an uncharacterized open reading frame, ydbK, that encodes a protein that is 51% identical to the M. thermoacetica PFOR. Evidence for pyruvate oxidoreductase activity in E. coli has been described (Blaschkowski et al., Eur. J. Biochem. 123:563-569 (1982)). The protein sequences of these exemplary PFOR enzymes can be identified by the following GenBank accession and/or GI numbers as shown below. Several additional PFOR enzymes have been described (Ragsdale, Chem. Rev. 103: 2333-2346 (2003)). These genes/proteins are identified below in Table 58.

TABLE 58

| Gene | GenBank ID | GI Number | Organism |
| --- | --- | --- | --- |
| Por | CAA70873.1 | 1770208 | Desulfovibrio africanus |
| Por | YP_428946.1 | 83588937 | Moorella thermoacetica |
| YdbK | NP_415896.1 | 16129339 | Escherichia coli |

Additional routes for producing propionyl-CoA are disclosed in U.S. Pat. No. 5,958,745 which is incorporated by reference herein in its entirety. One such route involves converting 2-ketobutyrate to propionate by pyruvate oxidase, and converting propionate to propionyl-CoA via an acyl-CoA synthetase.

2-Oxobutanoate Decarboxylase

A keto acid decarboxylase can catalyze the conversion of 2-oxobutanoate to propionaldehyde. Several 2-keto acid decarboxylases have been identified. Enzyme candidates for this step are pyruvate decarboxylase (EC 4.1.1.1), benzoyl-formate decarboxylase (4.1.1.7), alpha-ketoglutarate decarboxylase (EC 4.1.1.71), branched-chain alpha-keto-acid decarboxylase (4.1.1.72), and indolepyruvate decarboxylase (EC 4.1.1.74). These classes of decarboxylases are NADH-independent, they utilize thiamine diphosphate as a cofactor, and the interaction of the substrate with the enzyme-bound cofactor is thought to be the rate-limiting step for enzyme activation (Hubner, Eur. J Biochem. 92:175-181 (1978)). Pyruvate decarboxylase and benzoylformate decarboxylase have broad substrate ranges for diverse keto-acids and have been characterized in structural detail. Fewer alpha-ketoglutarate and branched-chain alpha-ketoacid decarboxylases have been characterized experimentally; however these enzymes also appear to decarboxylate a variety of keto-acid substrates.

Pyruvate decarboxylase (PDC), also termed keto-acid decarboxylase, is a key enzyme in alcoholic fermentation, catalyzing the decarboxylation of pyruvate to acetaldehyde. The enzyme from *Saccharomyces cerevisiae* has a broad substrate range for aliphatic 2-keto acids including 2-ketobutyrate, 2-ketovalerate, 3-hydroxypyruvate and 2-phenylpyruvate (22). The PDC from *Zymomonas mobilis*, encoded by pdc, has been a subject of directed engineering studies that altered the affinity for different substrates (Siegert et al., *Protein Eng Des Sel* 18:345-357 (2005)). The PDC from *Saccharomyces cerevisiae* has also been extensively studied, engineered for altered activity, and functionally expressed in *E. coli* (Li, *Biochemistry.* 38:10004-10012 (1999); ter Schure, *Appl. Environ. Microbiol.* 64:1303-1307 (1998) and Killenberg-Jabs, *Eur. J. Biochem.* 268:1698-1704 (2001)). The crystal structure of this enzyme is available (Killenberg-Jabs, *Eur. J. Biochem.* 268:1698-1704 (2001)). Other well-characterized PDC candidates include the enzymes from *Acetobacter pasteurians* (Chandra, *Arch. Microbiol.* 176:443-451 (2001)) and *Kluyveromyces lactis* (Krieger, *Eur. J. Biochem.* 269:3256-3263 (2002)). These genes/proteins are identified below in Table 59.

TABLE 59

| Gene | GenBank ID | GI Number | Organism |
| --- | --- | --- | --- |
| pdc | P06672.1 | 118391 | *Zymomonas mobilis* |
| pdc1 | P06169 | 30923172 | *Saccharomyces cerevisiae* |
| pdc | Q8L388 | 20385191 | *Acetobacter pasteurians* |
| pdc1 | Q12629 | 52788279 | *Kluyveromyces lactis* |

Like PDC, benzoylformate decarboxylase has a broad substrate range and has been the target of enzyme engineering studies. The enzyme from *Pseudomonas putida* has been extensively studied and crystal structures of this enzyme are available (Polovnikova et al, *Biochemistry* 42:1820-1830 (2003); and Hasson et al., *Biochemistry* 37:9918-9930 (1998)). Site-directed mutagenesis of two residues in the active site of the *Pseudomonas putida* enzyme altered the affinity (Km) of naturally and non-naturally occurring substrates (Siegert et al., *Protein Eng Des Sel* 18:345-357 (2005)). The properties of this enzyme have been further modified by directed engineering (Lingen et al., *Chembiochem.* 4:721-726 (2003); and Lingen, *Protein Eng* 15:585-593 (2002)). The enzyme from *Pseudomonas aeruginosa*, encoded by mdlC, has also been characterized experimentally (Barrowman, *FEMS Microbiology Letters* 34:57-60 (1986)). Additional gene candidates from *Pseudomonas stutzeri*, *Pseudomonas fluorescens* and other organisms can be inferred by sequence homology or identified using a growth selection system developed in *Pseudomonas putida* (Henning et al., *Appl. Environ. Microbiol.* 72:7510-7517 (2006)). These genes/proteins are identified below in Table 60.

TABLE 60

| Gene | GenBank ID | GI Number | Organism |
| --- | --- | --- | --- |
| mdlC | P20906.2 | 3915757 | *Pseudomonas putida* |
| mdlC | Q9HUR2.1 | 81539678 | *Pseudomonas aeruginosa* |
| dpgB | ABN80423.1 | 126202187 | *Pseudomonas stutzeri* |
| ilvB-1 | YP_260581.1 | 70730840 | *Pseudomonas fluorescens* |

A third enzyme capable of decarboxylating 2-oxoacids is alpha-ketoglutarate decarboxylase (KGD). The substrate range of this class of enzymes has not been studied to date. The KDC from *Mycobacterium tuberculosis* (Tian, *Proc Natl Acad Sci U S. A* 102:10670-10675 (2005)) has been cloned and functionally expressed in other internal projects at Genomatica. However, it is not an ideal candidate for strain engineering because it is large (~130 kD) and GC-rich. KDC enzyme activity has been detected in several species of Rhizobia including *Bradyrhizobium japonicum* and *Mesorhizobium loti* (Green, *J. Bacteriol.* 182:2838-2844 (2000)). Although the KDC-encoding gene(s) have not been isolated in these organisms, the genome sequences are available and several genes in each genome are annotated as putative KDCs. A KDC from *Euglena gracilis* has also been characterized but the gene associated with this activity has not been identified to date (Shigeoka, *Arch. Biochem. Biophys.* 288: 22-28 (1991)). The first twenty amino acids starting from the N-terminus were sequenced MTYKAPVKDVKFLLD-KVFKV (SEQ ID NO: 2) (Shigeoka, *Arch. Biochem. Biophys.* 288:22-28 (1991)). The gene could be identified by testing candidate genes containing this N-terminal sequence for KDC activity. These genes/proteins are identified below in Table 61.

TABLE 61

| Gene | GenBank ID | GI Number | Organism |
| --- | --- | --- | --- |
| kgd | O50463.4 | 160395583 | *Mycobacterium tuberculosis* |
| kgd | NP_767092.1 | 27375563 | *Bradyrhizobium japonicum* USDA110 |
| kgd | NP_105204.1 | 13473636 | *Mesorhizobium loti* |

A fourth candidate enzyme for catalyzing this step is branched chain alpha-ketoacid decarboxylase (BCKA). This class of enzyme has been shown to act on a variety of compounds varying in chain length from 3 to 6 carbons (Oku, *J Biol Chem.* 263:18386-18396 (1988); and Smit et al., *Appl Environ Microbiol* 71:303-311 (2005)). The enzyme in *Lactococcus lactis* has been characterized on a variety of branched and linear substrates including 2-oxobutanoate, 2-oxohexanoate, 2-oxopentanoate, 3-methyl-2-oxobutanoate, 4-methyl-2-oxobutanoate and isocaproate (Smit et al., *Appl Environ Microbiol* 71:303-311 (2005)). The enzyme has been structurally characterized (Berthold et al., *Acta Crystallogr. D Biol Crystallogr.* 63:1217-1224 (2007)). Sequence alignments between the *Lactococcus lactis* enzyme and the pyruvate decarboxylase of *Zymomonas mobilis* indicate that the catalytic and substrate recognition residues are nearly identical (Siegert et al., *Protein Eng Des Sel* 18:345-357 (2005)), so this enzyme would be a promising candidate for directed engineering. Decarboxylation of alpha-ketoglutarate by a BCKA was detected in *Bacillus subtilis*; however, this activity was low (5%) relative to activity on other branched-chain substrates (Oku, *J Biol Chem.* 263:18386-18396 (1988)) and the gene encoding this enzyme has not been identified to date. Additional BCKA gene candidates can be identified by homology to the *Lactococcus lactis* protein sequence. Many of the high-scoring BLASTp hits to this enzyme are annotated as indolepyruvate decarboxylases (EC 4.1.1.74). Indolepyruvate decarboxylase (IPDA) is an enzyme that catalyzes the decarboxylation of indolepyruvate to indoleacetaldehyde in plants and plant bacteria. This gene/protein is identified below in Table 62.

TABLE 62

| Gene | GenBank ID | GI Number | Organism |
|------|------------|-----------|----------|
| kdcA | AAS49166.1 | 44921617 | *Lactococcus lactis* |

Recombinant branched chain alpha-keto acid decarboxylase enzymes derived from the E1 subunits of the mitochondrial branched-chain keto acid dehydrogenase complex from *Homo sapiens* and *Bos taurus* have been cloned and functionally expressed in *E. coli* (Wynn, *J. Biol. Chem.* 267:12400-12403 (1992); Davie, *J. Biol. Chem.* 267:16601-16606 (1992) and Wynn et al., *J. Biol. Chem.* 267:1881-1887 (1992)). In these studies, the authors found that co-expression of chaperonins GroEL and GroES enhanced the specific activity of the decarboxylase by 500-fold (Wynn, *J. Biol. Chem.* 267:12400-12403 (1992)). These enzymes are composed of two alpha and two beta subunits. These genes/proteins are identified below in Table 63.

TABLE 63

| Gene | GenBank ID | GI Number | Organism |
|------|------------|-----------|----------|
| BCKDHB | NP_898871.1 | 34101272 | *Homo sapiens* |
| BCKDHA | NP_000700.1 | 11386135 | *Homo sapiens* |
| BCKDHB | P21839 | 115502434 | *Bos taurus* |
| BCKDHA | P11178 | 129030 | *Bos taurus* |

Example V

Pathways for Production of Propionyl-CoA from Glucose via Malonyl-CoA

Further to Examples I and II, the pathway for production of propionyl-CoA via malonyl-CoA is exemplified in FIG. 3. Acetyl CoA is carboxylated to form malonyl-CoA. This is then reduced to malonate semialdehyde, and subsequently transformed into 3-hydroxypropionate (3HP). 3HP is converted into propionyl-CoA via propionyl-CoA synthase.

Acetyl-CoA Carboxylase

The multisubunit acetyl-CoA carboxylase complex (ACC), broadly conserved among bacteria, catalyzes the ATP-dependent formation of malonyl-CoA by acetyl-CoA and bicarbonate. This reaction serves as the first committed step in fatty acid biosynthesis, and the enzyme has been targeted in efforts to develop antibacterial drugs and inhibitors in *E. coli* (Freiberg et al., *J. Biol. Chem.* 279: 26066-26073 (2004)), yeast (Zhang, *Proc. Natl. Acad. Sci. U.S.A.* 101:5910-5915 (2004)), *Bacillus subtilis* (Freiberg et al., *J. Biol. Chem.* 279:26066-26073 (2004)) and other organisms (Barber, *Biochim. Biophys. Acta* 1733:1-28 (2005)). In *E. coli* and many other bacteria, ACC is composed of four subunits encoded by accA, accB, accC and accD (Choi-Rhee, *J. Biol. Chem.* 278:30806-30812 (2003)). Expression of two subunits, accB and accC, is autoregulated by the gene product of accB (James, *J. Biol. Chem.* 279:2520-2527 (2004)). In yeast, the enzyme is encoded by two genes, hfa1 and acc1. The gene bpl1, encoding a biotin:apoprotein ligase, is required for enzyme function.

Autotrophic members of the archael taxonomic group *Sulfolobales* exhibit high levels of acetyl-CoA carboxylase activity in the context of the 3-hydroxypropionate cycle (Chuakrut, *J. Bacteriol.* 185:938-947 (2003); and Hugler, *Eur. J. Biochem.* 270:736-744 (2003)). In *Metallosphaera sedula*, the acyl-CoA carboxylase holoenzyme is a multimer composed of subunits encoded by three genes: Msed_0148 (biotin/lipoyl attachment), Msed_0147 (biotin carboxylase), and Msed_1375 (carboxyl transferase). The enzyme has been purified and characterized and was found to be bifunctional, reacting with acetyl-CoA and propionyl-CoA (Hugler, *Eur. J. Biochem.* 270:736-744 (2003)). A bifunctional archael acetyl-CoA carboxylase enzyme from *Acidanus brierleyi*, encoded by three genes, has been cloned into *E. coli* and characterized (Chuakrut, *J. Bacteriol.* 185:938-947 (2003). The sequences of *A. brierleyi* acyl-CoA carboxylase genes and flanking regions were submitted to the DNA Data Bank of Japan (DDBJ) under accession no. AB088419. Although these archael enzymes exhibit high activity it should be noted that the optimum temperature is 65° C. (Chuakrut, *J. Bacteriol.* 185:938-947 (2003)). These genes/proteins are identified below in Table 64.

TABLE 64

| Gene | GenBank ID | GI Number | Organism |
|------|------------|-----------|----------|
| accA | NP_414727 | 16128178 | *Escherichia coli* K12 str. MG1655 |
| accB | NP_417721 | 16131143 | *Escherichia coli* K12 str. MG1655 |
| accC | NP_417722 | 16131144 | *Escherichia coli* K12 str. MG1655 |
| accD | NP_416819 | 16130251 | *Escherichia coli* K12 str. MG1655 |
| accA | NP_390798.1 | 16079972 | *Bacillus subtilis* subsp. subtilis str. 168 |
| accB | NP_390315.1 | 16079491 | *Bacillus subtilis* subsp. subtilis str. 168 |
| accC | NP_390314.1 | 16079490 | *Bacillus subtilis* subsp. subtilis str. 168 |
| accD | NP_390799.1 | 16079973 | *Bacillus subtilis* subsp. subtilis str. 168 |
| bpl1 | NP_010140.1 | 6320060 | *Saccharomyces cerevisiae* |
| hfa1 | NP_013934.1 | 6323863 | *Saccharomyces cerevisiae* |
| acc1 | NP_014413.1 | 6324343 | *Saccharomyces cerevisiae* |
| accB Msed_0148 | Q8J2Z3 | 74499802 | *Metallosphaera sedula* |
| accC Msed_0147 | Q8J2Z4 | 74499032 | *Metallosphaera sedula* |
| pccB Msed_1375 | Q8J2Z5 | 74499033 | *Metallosphaera sedula* |
| accB | BAC55868.1 | 27877098 | *Acidanus brierleyi* |
| accC | BAC55867.1 | 27877097 | *Acidanus brierleyi* |
| pccB | BAC55869.1 | 27877099 | *Acidanus brierleyi* |

Malonyl-CoA Reductase and Malonate Semialdehyde Reductase

The reduction of malonyl-CoA to 3-HP can be accomplished by a bifunctional malonyl-CoA reductase with aldehyde dehydrogenase and alcohol dehydrogenase functionality. An NADPH-dependent enzyme with this activity has been characterized in *Chloroflexus aurantiacus* where it participates in the 3-hydroxypropionate cycle (Hugler, *J. Bacteriol.* 184:2404-2410 (2002); and Strauss, *Eur. J. Biochem.* 215: 633-643 (1993)). This enzyme, with a mass of 300 kDa, is highly substrate-specific and shows little sequence similarity to other known oxidoreductases (Hugler, *J. Bacteriol.* 184: 2404-2410 (2002)). No enzymes in other organisms have been shown to catalyze this specific reaction; however there is bioinformatic evidence that other organisms may have similar pathways (Klatt, *Environ. Microbiol.* 9:2067-2078 (2007).

Enzyme candidates in other organisms including *Roseiflexus castenholzii*, *Erythrobacter* sp. NAP1 and marine gamma proteobacterium HTCC2080 can be inferred by sequence similarity. These genes/proteins are identified below in Table 65.

TABLE 65

| Gene | GenBank ID | GI Number | Organism |
| --- | --- | --- | --- |
| mcr | AAS20429.1 | 42561982 | *Chloroflexus aurantiacus* |
| Rcas_2929 | YP_001433009.1 | 156742880 | *Roseiflexus castenholzii* |
| NAP1_02720 | ZP_01039179.1 | 85708113 | *Erythrobacter* sp. NAP1 |
| MGP2080_00535 | ZP_01626393.1 | 119504313 | marine gamma proteobacterium HTCC2080 |

Alternatively, the reduction of malonyl-CoA to 3-HP can be catalyzed by two separate enzymes: a CoA-acylating aldehyde dehydrogenase and a primary alcohol dehydrogenase. By this route, malonyl-CoA is first reduced to malonate semialdehyde (MSA) by malonate-semialdehyde dehydrogenase or malonyl-CoA reductase. MSA is subsequently converted to 3-HP by 3-HP-dehydrogenase.

Malonyl-CoA reductase is a key enzyme in autotrophic carbon fixation via the 3-hydroxypropionate cycle in thermoacidophilic archael bacteria (Berg, *Science.* 318:1782-1786 (2007); and Thauer, *Science.* 318:1732-1733 (2007)). The enzyme utilizes NADPH as a cofactor and has been characterized in *Metallosphaera* and *Sulfolobus* spp (Alber et al, *J. Bacteriol.* 188:8551-8559 (2006); and Hugler, *J. Bacteriol.* 184:2404-2410 (2002)). The enzyme encoded by Msed_0709 in *Metallosphaera sedula* is known to convert malonyl-CoA to malonic semialdehyde and operate in the direction of interest (Alber et al., *J. Bacteriol.* 188:8551-8559 (2006); and (Berg, *Science.* 318:1782-1786 (2007)). A gene encoding a malonyl-CoA reductase from *Sulfolobus tokodaii* was cloned and heterologously expressed in *E. coli* (Alber et al., *J. Bacteriol.* 188:8551-8559 (2006). Although the aldehyde dehydrogenase functionality of these enzymes is similar to the bifunctional dehydrogenase from *Chloroflexus aurantiacus*, there is little sequence similarity. Both malonyl-CoA reductase enzyme candidates have high sequence similarity to aspartate-semialdehyde dehydrogenase, an enzyme catalyzing the reduction and concurrent dephosphorylation of aspartyl-4-phosphate to aspartate semialdehyde. Additional gene candidates can be found by sequence homology to proteins in other organisms including *Sulfolobus solfataricus* and *Sulfolobus acidocaldarius*. These genes/proteins are identified below in Table 66.

TABLE 66

| Gene | GenBank ID | GI Number | Organism |
| --- | --- | --- | --- |
| Msed_0709 | YP_001190808.1 | 146303492 | *Metallosphaera sedula* |
| mcr | NP_378167.1 | 15922498 | *Sulfolobus tokodaii* |
| asd-2 | NP_343563.1 | 15898958 | *Sulfolobus solfataricus* |
| Saci_2370 | YP_256941.1 | 70608071 | *Sulfolobus acidocaldarius* |

The subsequent conversion of malonic semialdehyde to 3-HP can be accomplished by an enzyme with 3-HP dehydrogenase activity. Three enzymes are known to catalyze this conversion: NADH-dependent 3-hydroxypropionate dehydrogenase, NADPH-dependent malonate semialdehyde reductase, and NADH-dependent 3-hydroxyisobutyrate dehydrogenases. An NADH-dependent 3-hydroxypropionate dehydrogenase is thought to participate in beta-alanine biosynthesis pathways from propionate in bacteria and plants (Rathinasabapathi, *Journal of Plant Pathology* 159:671-674 (2002); and Stadtman, A. *J. Am. Chem. Soc.* 77:5765-5766 (1955)). This enzyme has not been associated with a gene in any organism to date. NADPH-dependent malonate semialdehyde reductase catalyzes the reverse reaction in autotrophic CO2-fixing bacteria. Although the enzyme activity has been detected in *Metallosphaera sedula*, the identity of the gene is not known (Alber et al., *J. Bacteriol.* 188:8551-8559 (2006)).

Several 3-hydroxyisobutyrate dehydrogenase enzymes have also been shown to convert malonic semialdehyde to 3-HP. Three gene candidates exhibiting this activity are mmsB from *Pseudomonas aeruginosa* PAO1 (Gokam et al., U.S. Pat. No. 7,393,676 (2008)). mmsB from *Pseudomonas putida* KT2440 (Liao, U.S. Patent Publication 2005-0221466 (2005) and mmsB from *Pseudomonas putida* E23 (Chowdhury, *Biosci. Biotechnol. Biochem.* 60:2043-2047 (1996)). The protein from *Pseudomonas putida* E23 has been characterized and functionally expressed in *E. coli*; however, its activity on 3-HP was relatively low (Chowdhury, *Biosci. Biotechnol. Biochem.* 60:2043-2047 (1996)). An enzyme with 3-hydroxybutyrate dehydrogenase activity in *Alcaligenes faecalis* M3A has also been identified (Liao, U.S. Patent Publication 2005-0221466 (2005); and Liao, U.S. Patent Publication 2005-0221466 (2005)). Additional gene candidates from other organisms including *Rhodobacter spaeroides* can be inferred by sequence similarity. These genes/proteins are identified below in Table 67.

TABLE 67

| Gene | GenBank ID | GI Number | Organism |
| --- | --- | --- | --- |
| mmsB | AAA25892.1 | 151363 | *Pseudomonas aeruginosa* |
| mmsB | NP_252259.1 | 15598765 | *Pseudomonas aeruginosa* PAO1 |
| mmsB | NP_746775.1 | 26991350 | *Pseudomonas putida* KT2440 |
| mmsB | JC7926 | 60729613 | *Pseudomonas putida* E23 |
| orfB1 | AAL26884 | 16588720 | *Rhodobacter spaeroides* |

Enzymes exhibiting a 4-hydroxybutyrate activity (EC 1.1.1.61) may also be able to convert malonic semialdehyde to 3-HP, as the chemical transformation is very similar. Such enzymes have been characterized in *Ralstonia eutropha* (Bravo, *J. Forensic Sci.* 49:379-387 (2004)), *Clostridium kluyveri* (Wolff, *Protein Expr. Purif.* 6:206-212 (1995)) and *Arabidopsis thaliana* (Breitkreuz et al., *J. Biol. Chem.* 278:41552-41556 (2003)). Activity of these enzymes on malonic semialdehyde has not been demonstrated experimentally to date. However, since these enzymes have been studied in other internal projects at Genomatica they could easily be tested for 3-HP dehydrogenase activity. These genes/proteins are identified below in Table 68.

TABLE 68

| Gene | GenBank ID | GI Number | Organism |
| --- | --- | --- | --- |
| 4hbd | YP_726053.1 | 113867564 | *Ralstonia eutropha* H16 |
| 4hbd | L21902.1 | 146348486 | *Clostridium kluyveri* DSM 555 |
| 4hbd | Q94B07 | 75249805 | *Arabidopsis thaliana* |

Propionyl-CoA Synthase

The conversion of 3-hydroxypropionate (3HP) to propionyl-CoA is accomplished by a propionyl-CoA synthase. This step is known to be catalyzed by a single fusion protein of 201 KDa in *Chloroflexus aurantiacus* (Alber, *J Biol. Chem.* 277:12137-12143 (2002)). The protein is comprised of a CoA ligase, an enoyl-CoA hydratase and an enoyl-CoA reductase. The enzyme has been purified 30-fold to near homogeneity and has a very large native molecular mass between 500 and 800 kDa. In thermoacidophilic *Metallosphaera sedula* (and members of the Sulfolobaceae family), this function is catalyzed by three different enzymes, a 3-hydroxypropionyl-CoA synthetase that activates 3HP to its CoA ester, a 3-hydroxypropionyl-CoA dehydratase that converts 3-HP-CoA to acryloyl-CoA followed by the reduction of the latter to form propionyl-CoA. A 3-HP-CoA synthetase had been reported (Alber, *J Bacteriol.* 190:1383-1389 (2008)). The gene encoding the protein has been sequenced and gene encoding a homologous protein identified in the genome of *Sulfolobus tokodaii*; similar genes were found in *S. solfataricus* and *S. acidocaldarius*. The gene was heterologously expressed in *Escherichia coli*. These genes/proteins are identified below in Table 69.

TABLE 69

| Gene | GenBank ID | GI Number | Organism |
| --- | --- | --- | --- |
| Msed_1456 | YP_001191537 | 146304221 | M. sedula |
| ST0783 | NP_376686 | 15921017 | S. tokodaii |
| acsA-10 | NP_344510 | 15899905 | S. solfataricus |
| Saci_1184 | YP_255824 | 70606954 | S. acidocaldarius |
| pcs | AAL47820 | 29126583 | C. aurantiacus |

Recently, 3-hydroxypropionyl-CoA dehydratase and acryloyl-CoA reductase were purified from *M. sedula* (Teufel, *J Bacteriol.* 191:4572-4581 (2009)), the coding genes were identified from the genome of *M. sedula* and other members of the *Sulfolobales*, and recombinant enzymes were produced as a proof of function. It was concluded that the genes coding for 3-hydroxypropionyl-CoA dehydratase and acryloyl-CoA reductase are not clustered on the *Metallosphaera* or the *Sulfolobus* genome. Comparison of the respective domains of propionyl-CoA synthase in these two organisms has revealed that the enzyme(s) catalyzing the conversion of 3HP to propionyl-CoA has evolved independently in these two phyla. The GenBank accession and/or GI numbers for the 3-HP-CoA dehydratase from *M. sedula* are identified below in Table 70.

TABLE 70

| Gene | GenBank ID | GI Number | Organism |
| --- | --- | --- | --- |
| Msed_2001 | YP_001192065.1 | 146304749 | M. sedula |

The GenBank IDs for acryloyl-CoA reductasees are identified below in Table 71.

TABLE 71

| Gene | GenBank ID | GI Number | Organism |
| --- | --- | --- | --- |
| Msed_1426 | YP_001191508.1 | 146304192 | M. sedula |
| ST0480 | NP_376364 | 15920695 | S. tokodaii |

Other gene candidates encoding these two enzymes can be obtained by sequence homology searches.

Example VI

Pathways for Production of Propionyl-CoA from Glucose Via Lactate

Figure 4:
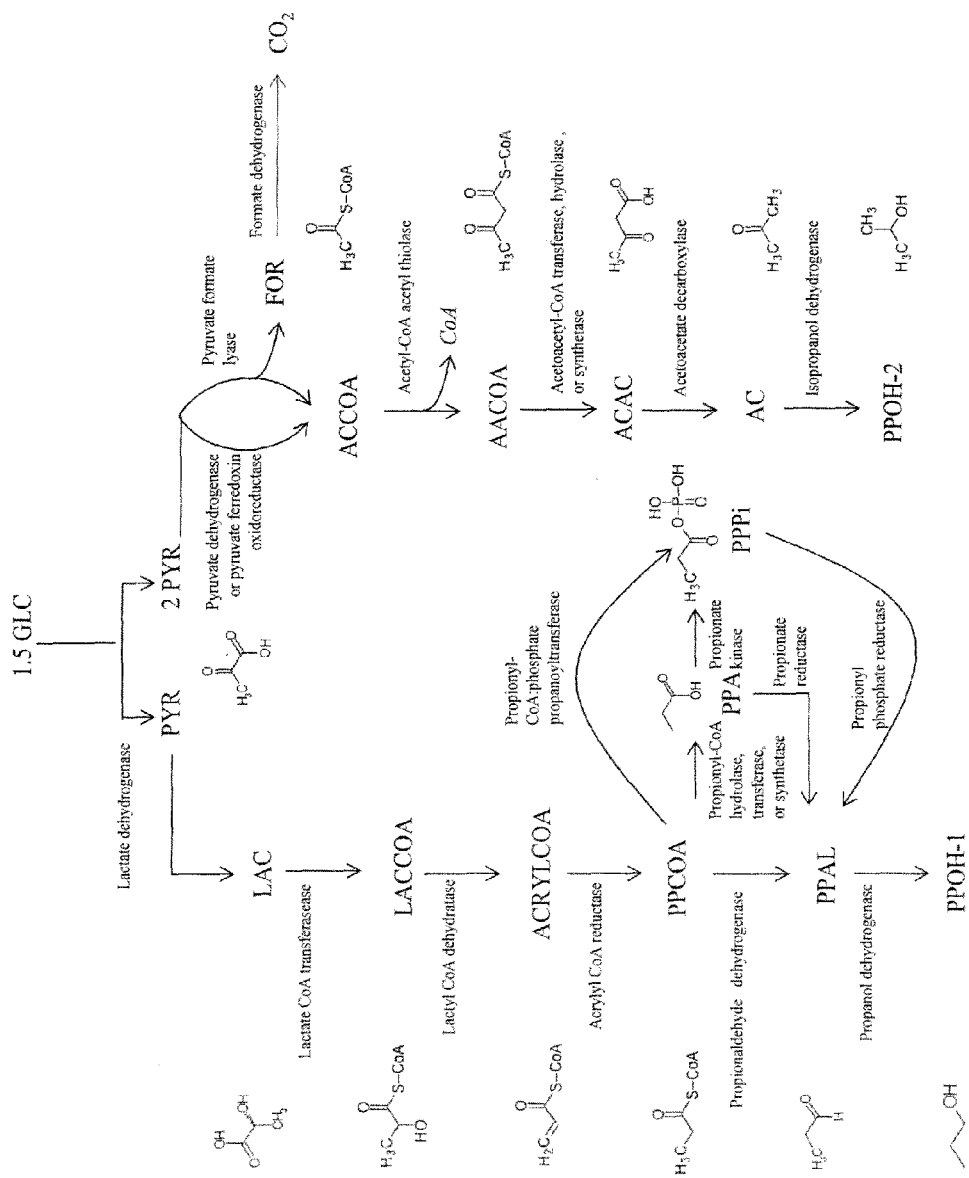
FIG. 4 shows an exemplary pathway for co-production of n-propanol and isopropanol from glucose. Abbreviations: Glc—glucose, PEP—phosphoenolpyruvate, PYR—pyruvate, FOR—formate, ACCOA—acetyl-CoA, AACOA—acetoacetyl-CoA, ACAC—acetoacetate, AC—acetone, PPOH-2—isopropanol, LAC—D-lactate, LACCOA—lactoyl-CoA, ACRYLCOA—acryloyl-CoA, PPCOA—propionyl-CoA, PPA—propionate, PPAL—propionaldehyde, PPPi—propionyl phosphate, PPOH-1—n-propanol.
Figure 5:
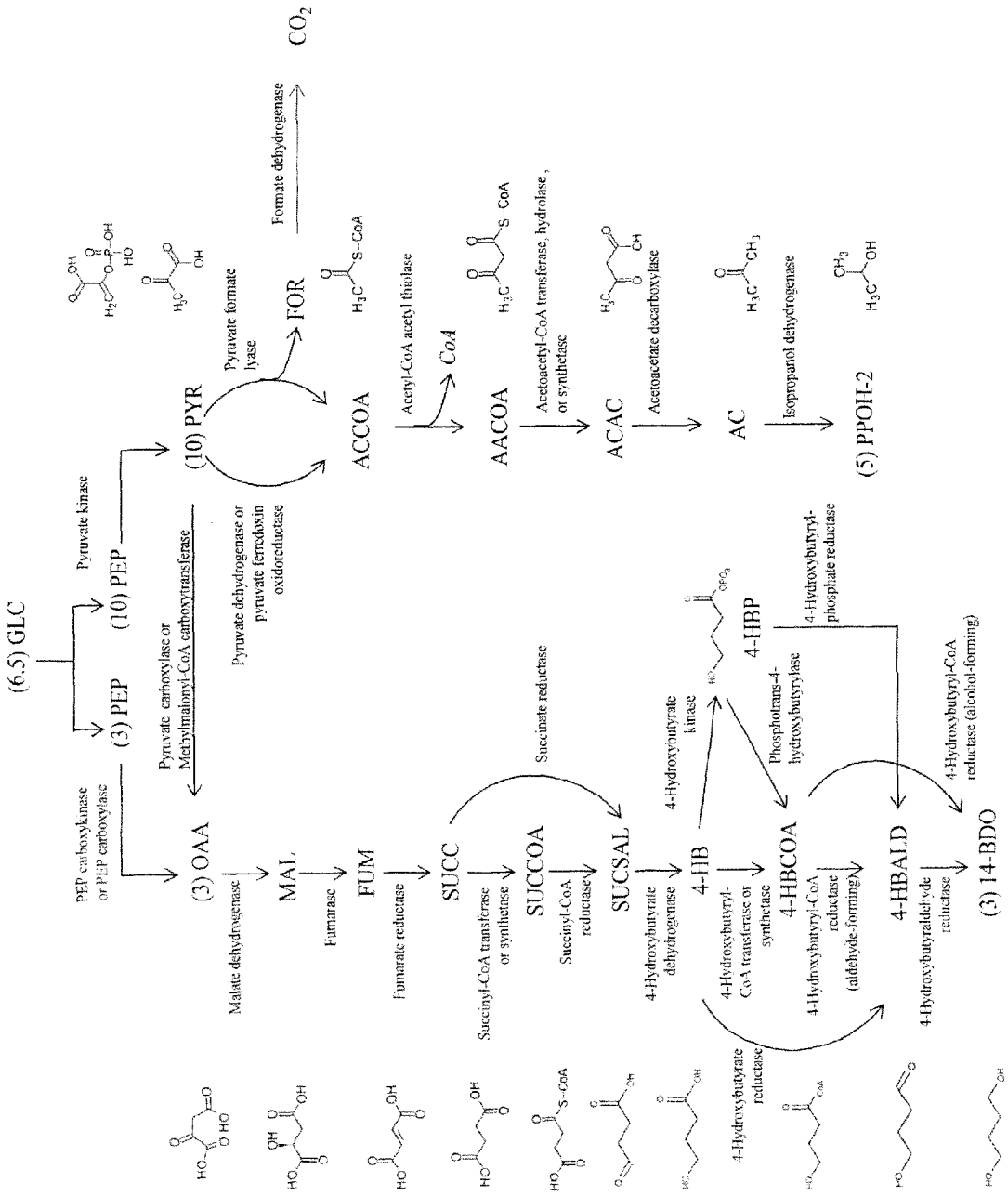
FIG. 5 shows an exemplary pathway for coproduction of 1,4-BDO and isopropanol from glucose. Abbreviations: Glc—glucose, PEP—phosphoenolpyruvate, PYR—pyruvate, FOR—formate, ACCOA—acetyl-CoA, AACOA—acetoacetyl-CoA, ACAC—acetoacetate, AC—acetone, PPOH-2—isopropanol, OAA—oxaloacetate, MAL—malate, FUM—fumarate, SUCC—succinate, SUCCOA—succinyl-CoA, SUCSAL—succinic semialdehyde, 4-HB—4-hydroxybutyrate, 4-HBCOA—4-hydroxybutyryl-CoA, 4-HBALD—4-hydroxybutyraldehyde, 14-BDO—1,4-butanediol, 4-HBP—4-hydroxybutyryl-phosphate.
Figure 6:
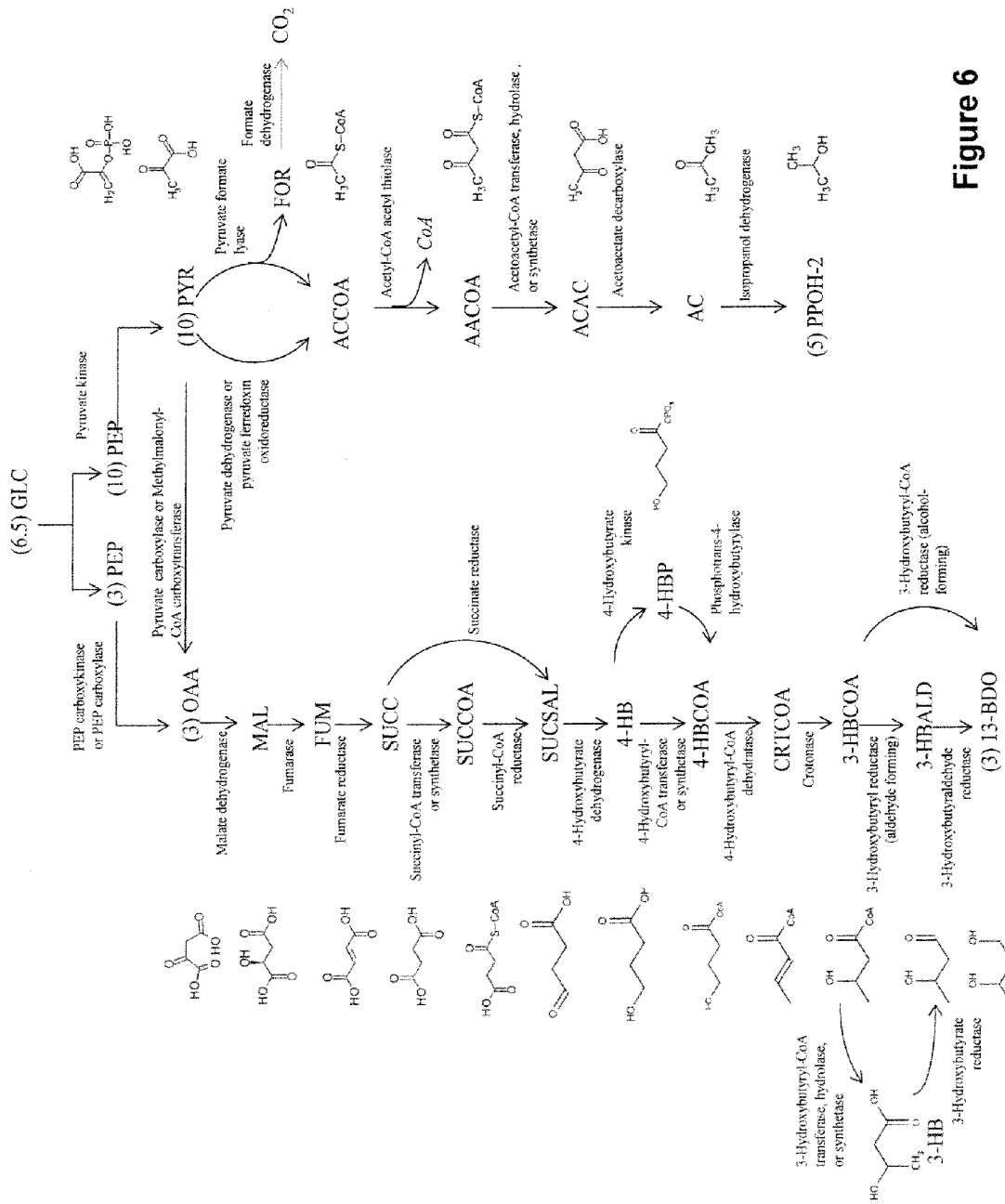
FIG. 6 shows an exemplary pathway for coproduction of 1,3-BDO and isopropanol from glucose. Abbreviations: Glc—glucose, PEP—phosphoenolpyruvate, PYR—pyruvate, FOR—formate, ACCOA—acetyl-CoA, AACOA—acetoacetyl-CoA, ACAC—acetoacetate, AC—acetone, PPOH-2—isopropanol, OAA—oxaloacetate, MAL—malate, FUM—fumarate, SUCC—succinate, SUCCOA—succinyl-CoA, SUCSAL—succinic semialdehyde, 3-HB—3-hydroxybutyrate, 4-HB—4-hydroxybutyrate, 4-HBCOA—4-hydroxybutyryl-CoA, CRTCOA—crotonyl-CoA, 3-HBCOA—3-hydroxybutyryl-CoA, 3-HBALD—3-hydroxybutyraldehyde, 13-BDO—1,3-butanediol.

Further to Examples I and II, the pathway for production of propionyl-CoA via lactate is exemplified in FIG. 4. This pathway presents yet another redox balanced route for the formation of propionyl-CoA. Pyruvate is reduced to form lactate which is then activated to form lactoyl-CoA. The lactoyl-CoA is dehydrated to form acryloyl-CoA and then reduced to generate propionyl-CoA.

Lactate Dehydrogenase

The conversion of pyruvate to lactate is catalyzed by lactate dehydrogenase (EC 1.1.1.27). Many lactate dehydrogenases have been described in detail (Garvie, *Microbiol Rev* 44:106-139 (1980)). The fermentative lactate dehydrogenase of *Escherichia coli* will be the first candidate to be overexpressed for converting pyruvate to lactate (Bunch, *Microbiology* 143 (Pt 1), 187-195 (1997)). Other lactate dehydrogenase candidates will be utilized for this step including those with low Km for pyruvate that favors the formation of lactate, such as lactate dehydrogease from: *Lactobacillus casei* (Gordon, *Eur. J Biochem.* 67:543-555 (1976)), *Plasmodium falciparum* (Brown et al., *Biochemistry* 43:6219-6229 (2004)), and *Thermotoga maritime* (Auerbach et al., *Structure.* 6:769-781 (1998)). These genes/proteins are identified below in Table 72.

TABLE 72

| Gene | GenBank ID | GI Number | Organism |
| --- | --- | --- | --- |
| ldh | P52643 | 1730102 | Escherichia coli |
| ldh | P00343 | 126063 | Lactobacillus casei |
| ldh | Q6JH32 | 74911026 | Plasmodium ovale |
| ldh | P16115 | 547837 | Thermotoga maritima |

Lactate-CoA Transferase

The activation of lactate to lactoyl-CoA can be catalyzed by lactate-CoA transferase activity associated with propionate CoA-transferase (EC 2.8.3.1). *Clostridium propionicum* ferments alanine via the nonrandomising pathway with acryloyl-CoA as characteristic intermediate. In this pathway, lactate is activated to lactoyl-CoA by the enzyme propionate:acetyl-CoA CoA-transferase (EC 2.8.3.1, or propionate CoA-transferase) using propionyl-CoA or acetyl-CoA as a coenzyme A donor (Schweiger, *FEBS Lett.* 171:79-84 (1984)). The enzyme exhibited rather broad substrate specificities for monocarboxylic acids including acrylate, propionate and butyrate whereas dicarboxylic acids were not used. Gene coding for this enzyme was cloned (Selmer, *Eur. J Biochem.* 269:372-380 (2002)). Other propionate CoA-transferase can be candidates for this step include homologues of *Clostridium propionicum* propionate CoA-transferase. These genes/proteins are identified below in Table 73.

TABLE 73

| Gene | GenBank ID | GI Number | Organism |
| --- | --- | --- | --- |
| Pct | Q9L3F7 | 75416255 | Clostridium propionicum |
| Pct | YP_002270763.1 | 209397911 | Escherichia coli O157:H7 |
| Pct | Q220N6 | 122479931 | Rhodoferax ferrireducens DSM 15236 |
| Pct | Q46MA6 | 123621528 | Ralstonia eutropha |

Lactoyl-CoA Dehydratase

The dehydration of lactoyl-CoA to acryloyl-CoA is catalyzed by lactoyl-CoA dehydratase (EC 4.2.1.54). *Clostridium propionicum* ferments alanine via the nonrandomising pathway with acryloyl-CoA as characteristic intermediate (Schweiger, *FEBS Lett.* 171:79-84 (1984)). In this pathway, lactoyl-CoA is dehydrated to acryloyl-CoA by the lactoyl-CoA dehydratase (Hofmeister, *Eur. J Biochem.* 206:547-552 (1992)). Cloning of the propionate CoA-transferase also identified a second ORF (lcdB) likely encoding one subunit of the lactoyl-CoA dehydratase required in the pathway. The lcdB is similar to the 2-hydroxyglutaryl-CoA dehydratase β subunit. Homologues of lcdB will be tested for their activity in this step. These genes/proteins are identified below in Table 74.

TABLE 74

| Gene | GenBank ID | GI Number | Organism |
|---|---|---|---|
| CBC_A0885 | ZP_02621214 | 168186579 | *Clostridium botulinum* C str. Eklund |
| CBC_A0886 | ZP_02621215 | 168186580 | *Clostridium botulinum* C str. Eklund |
| hgdB | YP_878441 | 118444181 | *Clostridium novyi*-NT |
| hgdA | YP_878442 | 118444701 | *Clostridium novyi*-NT |

Acryloyl-CoA Reductase

The conversion of acryloyl-CoA to propionyl-CoA is catalyzed by the acryloyl-CoA reductase. In alanine-fermenting *Clostridium propionicum*, acryloyl-CoA reductase catalyses the irreversible NADH-dependent formation of propionyl-CoA from acryloyl-CoA. The enzyme has been purified and the N-termini of the subunits of the enzyme have been determined (Hetzel et al., *Eur. J Biochem.* 270:902-910 (2003)). The N-terminus of the dimeric propionyl-CoA dehydsrogenase subunit is similar to those of butyryl-CoA dehydrogenases from several *Clostridia* and related anaerobes (up to 55% sequence identity). The N-termini of the β and γ subunits share 40% and 35% sequence identities with those of the A and B subunits of the electron-transferring flavoprotein (ETF) from *Megasphaera elsdenii*, respectively, and up to 60% with those of putative ETFs from other anaerobes. Since the complete genome sequence of *Clostridium propionicum* is not available, the N-terminus of the propionyl-CoA dehydrogenase subunit "MDFKLTKTQVLQQWLFAEFAGIGIK-PIAE" (SEQ ID NO: 1) was used in similarity search and resulted in the following homologues of the propionyl-CoA dehydrogenase for their activities in this step. These genes/proteins are identified below in Table 75.

TABLE 75

| Gene | GenBank ID | GI Number | Organism |
|---|---|---|---|
| bcdA | CAQ53135 | 188027001 | *Clostridium saccharobutylicum* |
| Cbei_2035 | ABR34203 | 149903370 | *Clostridium beijerinckii* |
| ANACAC_00471 | EDR98937 | 167654808 | *Anaerostipes caccae* DSM 14662 |

Additionally, a tri-functional propionyl-CoA synthase (pcs) gene was identified from the phototrophic green non-sulfur eubacterium *Chloroflexus aurantiacus* (Alber, *J Biol. Chem.* 277:12137-12143 (2002)). The propionyl-CoA synthase is a natural fusion protein of 201 kDa consisting of a CoA ligase, an enoyl-CoA hydratase, and an enoyl-CoA reductase. The enzyme catalyzes the conversion from 3-hydroxypropionate to 3-hydroxypropionyl-CoA to acryloyl-CoA then to propionyl-CoA. This enzyme can be utilized in whole or in part for its enoyl-CoA reductase activity. The gene/protein is identified below in Table 76.

TABLE 76

| Gene | GenBank ID | GI Number | Organism |
|---|---|---|---|
| pcs | AAL47820 | 29126583 | *Chloroflexus aurantiacus* |

Example VII

Pathways for Co-Production of 1,4-Butanediol (1,4-BDO) and Isopropanol from Glucose This example describes exemplary pathways for co-production of 1,4-butanediol (1,4-BDO) and isopropanol.

Novel pathways for co-producing 1,4-butanediol (1,4-BDO) and isopropanol and related products are described herein. In the 1,4-butanediol (1,4-BDO) and isopropanol co-production pathway of FIG. 5, central metabolism intermediates are first channeled into succinyl-CoA. For formation of succinyl-CoA, phosphoenolpyruvate (PEP) is converted into oxaloacetate either via PEP carboxykinase or PEP carboxylase. Alternatively, PEP is converted first to pyruvate by pyruvate kinase and then to oxaloacetate by methylmalonyl-CoA carboxytransferase or pyruvate carboxylase. Oxaloacetate is then converted to succinyl-CoA by means of the reductive TCA cycle. Succinyl-CoA is then converted to succinic semialdehyde by a CoA-dependent aldehyde dehydrogenase. Alternatively, succinate can be converted to succinic semialdehyde by a succinate reductase. Next, succinic semialdehyde is reduced to 4-hydroxybutyrate by 4-hydroxybutyrate dehydrogenase. Activation of 4-HB to its acyl-CoA is catalyzed by a CoA transferase or synthetase. Alternatively, 4-HB can be converted into 4-hydroxybutyryl-phosphate and subsequently transformed into 4-HB-CoA by a phosphotrans-4-hydroxybutyrylase. 4-HB-CoA is then converted to 14-BDO by either a bifunctional CoA-dependent aldehyde/alcohol dehydrogenase, or by two separate enzymes with aldehyde and alcohol dehydrogenase activity. Yet another alternative that bypasses the 4-HB-CoA intermediate is direct reduction of 4-HB to 4-hydroxybutyrylaldehyde by a carboxylic acid reductase. 4-Hydroxybutyrylaldehyde is subsequently reduced to 14-BDO by an alcohol dehydrogenase. Yet another route that bypasses the CoA intermediate is reduction of 4-hydroxybutyryl-phosphate to 4-hydroxybutyryaldehyde by a phosphate reductase. Pathways for production of isopropanol proceed as described above in Examples I and II.

The maximum theoretical yield of a 14-BDO and isopropanol producing organism is 0.77 moles isopropanol and 0.46 moles 14-BDO per mole glucose consumed (0.26 g/g IPA and 0.23 g/g 14-BDO), per the following equation:

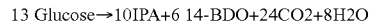

13 Glucose→10IPA+6 14-BDO+24CO2+8H2O

Example VIII

Pathways for Co-Production of 1,3-Butanediol (1,3-BDO) and Isopropanol from Glucose This example describes exemplary pathways for co-production of 1,3-butanediol (13-BDO) and isopropanol.

Novel pathways for co-producing 1,3-butanediol (13-BDO) and isopropanol and related products are described herein. The coproduction route to 1,3-butanediol (13-BDO) and isopropanol, shown in FIG. 6, also proceeds through 4-hydroxybutyryl-CoA, formed as described in Example VI. In this route, 4-hydroxybutyryl-CoA is dehydrated and isomerized to form crotonyl-CoA. The dehydration and vinylisomerisation reactions are catalyzed by a bifunctional enzyme, 4-hydroxybutyryl-CoA dehydratase. Crotonyl-CoA is then hydrated to 3-hydroxybutyryl-CoA. Removal of the CoA moiety and concurrent reduction yields 3-hydroxybutyraldehyde. Finally reduction of the aldehyde by 3-hydroxybutyraldehyde reductase yields 13-BDO. Alternately, 3-hydroxybutyryl-CoA can be converted to 13-BDO directly by a 3-hydroxybutyryl-CoA reductase (alcohol forming). Several other alternate routes are possible in this pathway. Succinate can be converted to succinic semialdehyde by a carboxylic acid reductase, bypassing the formation of succinyl-CoA. 4-HB can be phosphorylated to 4-HB-phosphate by a kinase, then subsequently converted to 4-HB-CoA. Finally 3-hydroxybutyryl-CoA can be de-acylated by a CoA hydrolase, transferase or synthetase, then subsequently reduced to 3-hydroxybutyraldehyde by a carboxylic acid reductase.

Pathways for production of isopropanol proceed as described above in Examples I and II.

The maximum theoretical yield of 13-BDO and isopropanol via this pathway is 0.77 moles isopropanol and 0.46 moles 13-BDO per mole glucose consumed (0.26 g/g IPA and 0.23 g/g 13-BDO), per the following equation:

$$13\ \text{Glucose} \rightarrow 10\text{IPA} + 6\ 13\text{-BDO} + 24\text{CO}_2 + 8\text{H}_2\text{O}$$

Example IX

Pathways for Co-Production of Methylacrylic Acid (MAA) and Isopropanol from Glucose This example describes exemplary pathways for co-production of methylacrylic acid (MAA) and isopropanol.

Figure 7:
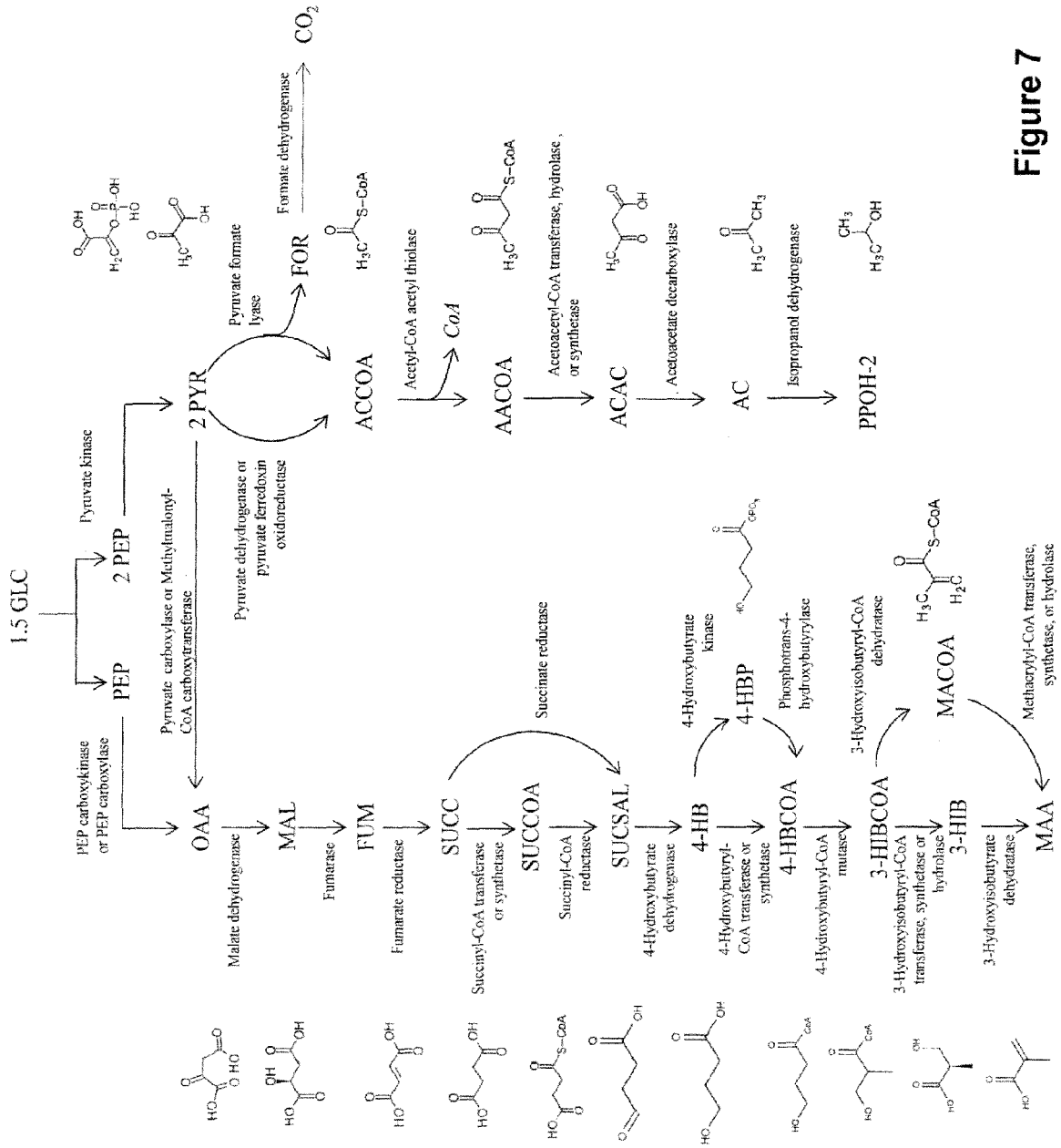
FIG. 7 shows an exemplary pathway for coproduction of methyacrylic acid and isopropanol from glucose. Abbreviations: Glc—glucose, PEP—phosphoenolpyruvate, PYR—pyruvate, FOR—formate, ACCOA—acetyl-CoA, AACOA—acetoacetyl-CoA, ACAC—acetoacetate, AC—acetone, PPOH-2—isopropanol, OAA—oxaloacetate, MACOA—methacrylyl-CoA, MAL—malate, FUM—fumarate, SUCC—succinate, SUCCOA—succinyl-CoA, SUCSAL—succinic semialdehyde, 4-HB—4-hydroxybutyrate, 4-HBCOA—4-hydroxybutyryl-CoA, 3-HIBCOA—3-hydroxyisobutyryl-CoA, 3-HIB—3-hydroxyisobutyrate, MAA—methylacrylic acid.
Figure 8:
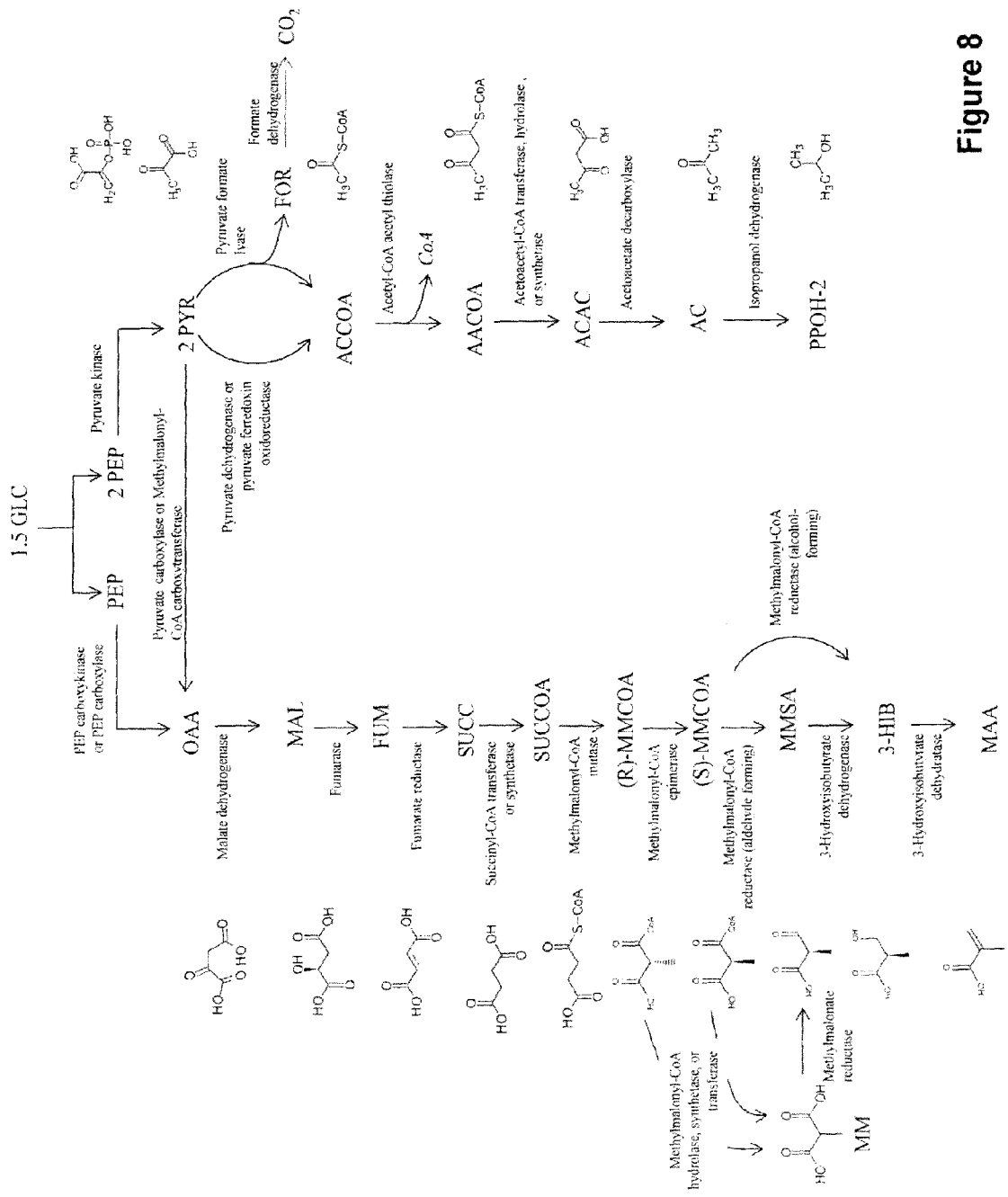
FIG. 8 shows an exemplary pathway for coproduction of methyacrylic acid and isopropanol from glucose. Abbreviations: Glc—glucose, PEP—phosphoenolpyruvate, PYR—pyruvate, FOR—formate, ACCOA—acetyl-CoA, AACOA—acetoacetyl-CoA, ACAC—acetoacetate, AC—acetone, PPOH-2—isopropanol, OAA—oxaloacetate, MAL—malate, FUM—fumarate, SUCC—succinate, SUCCOA—succinyl-CoA, MM—methylmalonate, MMCOA—methylmalonyl-CoA, MMSA—methylmalonate semialdehyde, 3-HIB—3-hydroxyisobutyrate, MAA—methylacrylic acid.

Novel pathways for co-producing methylacrylic acid (MAA) and isopropanol and related products are described herein. Two coproduction routes to methylacrylic acid (MAA) are shown in FIGS. 7 and 8. The route shown in FIG. 7 proceeds through 4-hydroxybutyryl-CoA, formed as described previously. 4-Hydroxybutyryl-CoA is converted to 3-hydroxyisobutyryl-CoA by a methyl mutase. The CoA moiety of 3-Hydroxyisobutyryl-CoA is then removed by a CoA transferase, hydrolase or synthetase. Finally, dehydration of the 3-hydroxy group yields MAA. Several of the key steps in this route can be bypassed by alternate routes. Succinate, for example, can be directly converted to succinic semialdehyde by a succinate reductase, bypassing the formation of succinyl-CoA. The conversion of 4-HB to 4-HB-CoA can proceed through the intermediate 4-hydroxybutyrylphosphate, via the enzymes 4-hydroxybutyrate kinase and phosphotrans-4-hydroxybutyrylase. 3-HIBCOA can be converted to MAA via the intermediate methacrylyl-CoA. Pathways for production of isopropanol proceed as described above in Examples I and II.

In the alternate MAA coproduction route shown in FIG. 8, succinyl-CoA is formed through the reductive TCA cycle, then converted to methylmalonyl-CoA by methylmalonyl-CoA mutase. An epimerase may be required to convert the (R) stereoisomer of methylmalonyl-CoA to the (S) configuration. A CoA-dependent aldehyde dehydrogenase then converts methylmalonyl-CoA to methylmalonate semialdehyde. Reduction of the aldehyde to 3-hydroxyisobutyrate, followed by dehydration, yields MAA. Alternately, methylmalonyl-CoA is converted to 3-hydroxyisobutyrate by an alcohol-forming CoA reductase. In yet another alternate route, methylmalonyl-CoA is converted to methylmalonate by a CoA hydrolase, transferase or synthetase. Methylmalonate is subsequently converted to methylmalonate semialdehyde by a carboxylic acid reductase. Methylmalonate semialdehyde is converted to MAA as described previously. Pathways for production of isopropanol proceed as described above in Examples I and II.

Both MAA coproduction pathways achieve yields 0.67 moles each of isopropanol and MAA per mole glucose utilized (0.22 g/g isopropanol and 0.32 g/g MAA) per the equation:

$$3\ \text{Glucose} \rightarrow 2\text{IPA} + 2\ \text{MAA} + 4\text{CO}_2 + 4\text{H}_2\text{O}$$

Example X

Enzyme Classification System for Production of Isopronaol and 1,4-Butanediol (1,4-BDO), 1,3-Butanediol (1,3-BDO) or Methylacrylic Acid (MAA)

This example describes the enzyme classification system for the exemplary pathways described in Examples VII and IX for production of 1,4-butanediol (1,4-BDO), 1,3-butanediol (1,3-BDO) or methylacrylic acid (MAA). Exemplary enzymes for production of isopropanol from acetyl-CoA are described in Example I and exemplary enzymes for production acetyl-CoA from glucose are described in Example II.

PEP Carboxykinase

Although the net conversion of phosphoenolpyruvate to oxaloacetate is redox-neutral, the mechanism of this conversion is important to the overall energetics of the co-production pathway. The most desirable enzyme for the conversion of PEP to oxaloacetate is PEP carboxykinase which simultaneously forms an ATP while carboxylating PEP. In most organisms, however, PEP carboxykinase serves a gluconeogenic function and converts oxaloacetate to PEP at the expense of one ATP. S. cerevisiae is one such organism whose native PEP carboxykinase, PCK1, serves a gluconeogenic role (Valdes-Hevia et al., FEBS. Lett. 258:313-316 (1989)). E. coli is another such organism, as the role of PEP carboxykinase in producing oxaloacetate is believed to be minor when compared to PEP carboxylase, which does not form ATP, possibly due to the higher $K_m$ for bicarbonate of PEP carboxykinase (Kim, et al., Appl Environ Microbiol 70:1238-1241 (2004)). Nevertheless, activity of the native E. coli PEP carboxykinase from PEP towards oxaloacetate has been recently demonstrated in ppc mutants of E. coli K-12 (Kwon et al., Journal of Microbiology and Biotechnology 16:1448-1452 (2006)). These strains exhibited no growth defects and had increased succinate production at high $NaHCO_3$ concentrations. In some organisms, particularly rumen bacteria, PEP carboxykinase is quite efficient in producing oxaloacetate from PEP and generating ATP. Examples of PEP carboxykinase genes that have been cloned into E. coli include those from Mannheimia succiniciproducens (Lee et al., Gene. Biotechnol. Bioprocess Eng. 7:95-99 (2002)), Anaerobiospirillum succiniciproducens (Laivenieks et al., Appl Environ Microbiol 63:2273-2280 (1997)), and Actinobacillus succinogenes (Kim et al., Appl Environ Microbiol 70:1238-1241 (2004)). Internal experiments have also found that the PEP carboxykinase enzyme encoded by Haemophilus influenza is highly efficient at forming oxaloacetate from PEP. These genes/proteins are identified below in Table 77.

TABLE 77

| Gene | GenBank ID | GI Number | Organism |
| --- | --- | --- | --- |
| PCK1 | NP_013023 | 6322950 | Saccharomyces cerevisiae |
| pck | NP_417862.1 | 16131280 | Escherichia coli |
| pckA | YP_089485.1 | 52426348 | Mannheimia succiniciproducens |

TABLE 77-continued

| Gene | GenBank ID | GI Number | Organism |
|---|---|---|---|
| pckA | O09460.1 | 3122621 | Anaerobicspirillum succiniciproducens |
| pckA | Q6W6X5 | 75440571 | Actinobacillus succinogenes |
| pckA | P43923.1 | 1172573 | Haemophilus influenza |

These sequences and sequences for subsequent enzymes listed in this report can be used to identify homologue proteins in GenBank or other databases through sequence similarity searches (e.g. BLASTp). The resulting homologue proteins and their corresponding gene sequences provide additional DNA sequences for transformation into the host organism of our choice.

PEP Carboxylase

PEP carboxylase represents an alternative enzyme for the formation of oxaloacetate from PEP. *S. cerevisiae* does not naturally encode a PEP carboxylase, but exemplary organisms that possess genes that encode PEP carboxylase include *E. coli* (Kai et al., *Arch. BioChem. Biophys.* 414:170-179 (2003)), *Methylobacterium extorquens* AM1 (Arps et al., *J. Bacteriol.* 175:3776-3783 (1993)), and *Corynebacterium glutamicum* (Eikmanns et al., *Mol. Gen. Genet.* 218:330-339 (1989)). These genes/proteins are identified below in Table 78.

TABLE 78

| Gene | GenBank ID | GI Number | Organism |
|---|---|---|---|
| ppc | NP_418391 | 16131794 | Escherichia coli |
| ppcA | AAB58883 | 28572162 | Methylobacterium extorquens |
| ppc | ABB53270 | 80973080 | Corynebacterium glutamicum |

Pyruvate Kinase and Methylmalonyl-CoA Carboxytransferase

An additional energetically efficient route to oxaloacetate from PEP requires two enzymatic activities: pyruvate kinase and methylmalonyl-CoA carboxytransferase. Pyruvate kinase catalyzes the ATP-generating conversion of PEP to pyruvate and is encoded by the PYK1 (Burke et al., *J. Biol. Chem.* 258:2193-2201 (1983)) and PYK2 (Boles et al., *J. Bacteriol.* 179:2987-2993 (1997)) genes in *S. cerevisiae*. In *E. coli*, this activity is catalyzed by the gene product of pykF and pykA. Methylmalonyl-CoA carboxytransferase catalyzes the conversion of pyruvate to oxaloacetate. Importantly, this reaction also simultaneously catalyzes the conversion of (S)-methylmalonyl-CoA to propionyl-CoA (see FIGS. 1 and 2). An exemplary methylmalonyl-CoA carboxytransferase which is comprised of 1.3 S, 5 S, and 12 S subunits can be found in *Propionibacterium freudenreichii* (Thornton et al., *J. Bacteriol.* 175:5301-5308 (1993)). These genes/proteins are identified below in Table 79.

TABLE 79

| Gene | GenBank ID | GI Number | Organism |
|---|---|---|---|
| PYK1 | NP_009362 | 6319279 | Saccharomyces cerevisiae |
| PYK2 | NP_014992 | 6324923 | Saccharomyces cerevisiae |
| pykF | NP_416191.1 | 16129632 | Escherichia coli |
| pykA | NP_416368.1 | 16129807 | Escherichia coli |
| 1.3S subunit | P02904 | 114847 | Propionibacterium freudenreichii |
| 5S subunit | Q70AC7 | 62901478 | Propionibacterium freudenreichii |
| 12S subunit | Q8GBW6 | 62901481 | Propionibacterium freudenreichii |

Pyruvate Kinase and Pyruvate Carboxylase

A combination of enzymes can convert PEP to oxaloacetate with a stoichiometry identical to that of PEP carboxylase. These enzymes are encoded by pyruvate kinase, PYK1 (Burke et al., *J. Biol. Chem.* 258:2193-2201 (1983)) or PYK2 (Boles et al., *J. Bacteriol.* 179:2987-2993 (1997)), and pyruvate carboxylase, PYC1 (Walker et al., *BioChem. Biophys. Res. Commun.* 176:1210-1217 (1991)) or PYC2 (224). Some candidates for pyruvate carboxylase function are identified below in Table 80.

TABLE 80

| Gene | GenBank ID | GI Number | Organism |
|---|---|---|---|
| PYC1 | NP_011453 | 6321376 | Saccharomyces cerevisiae |
| PYC2 | NP_009777 | 6319695 | Saccharomyces cerevisiae |
| Pyc | YP_890857.1 | 118470447 | Mycobacterium smegmatis |

Malate Dehydrogenase, Fumarase, Fumarate Reductase

Oxaloacetate can be converted to succinate by malate dehydrogenase, fumarase and fumarate reductase when the TCA cycle is operating in the reductive cycle. *S. cerevisiae* possesses three copies of malate dehydrogenase, MDH1 (McAlister-Henn et al., *J. Bacteriol.* 169:5157-5166 (1987)), MDH2 (Gibson *J. Biol. Chem.* 278:25628-25636 (2003); and Minard et al., *Mol. Cell Biol.* 11:370-380 (1991)), and MDH3 (Steffan et al., *J. Biol. Chem.* 267:24708-24715 (1992)), which localize to the mitochondrion, cytosol, and peroxisome, respectively. *S. cerevisiae* contains one copy of a fumarase-encoding gene, FUM1, whose product localizes to both the cytosol and mitochondrion (Sass et al., *J. Biol. Chem.* 278:45109-45116 (2003)). Fumarate reductase is encoded by two soluble enzymes, FRDS1 (Enomoto et al., *DNA. Res.* 3:263-267 (1996)) and FRDS2 (Muratsubaki et al., *Arch. BioChem. Biophys.* 352:175-181 (1998)), which localize to the cytosol and promitochondrion, respectively, and are required for anaerobic growth on glucose (Arikawa et al., *Microbiol Lett.* 165:111-116 (1998)). *E. coli* is known to have an active malate dehydrogenase. It has three fumarases encoded by fumA, B and C, each one of which is active under different conditions of oxygen availability. The fumarate reductase in *E. coli* is composed of four subunits. These genes/proteins are identified below in Table 81.

TABLE 81

| Gene | GenBank ID | GI Number | Organism |
|---|---|---|---|
| MDH1 | NP_012838 | 6322765 | Saccharomyces cerevisiae |
| MDH2 | NP_014515 | 116006499 | Saccharomyces cerevisiae |
| MDH3 | NP_010205 | 6320125 | Saccharomyces cerevisiae |
| FUM1 | NP_015061 | 6324993 | Saccharomyces cerevisiae |
| FRDS1 | P32614 | 418423 | Saccharomyces cerevisiae |
| FRDS2 | NP_012585 | 6322511 | Saccharomyces cerevisiae |
| frdA | NP_418578.1 | 16131979 | Escherichia coli |
| frdB | NP_418577.1 | 16131978 | Escherichia coli |
| frdC | NP_418576.1 | 16131977 | Escherichia coli |
| frdD | NP_418475.1 | 16131877 | Escherichia coli |
| Mdh | NP_417703.1 | 16131126 | Escherichia coli |
| FumA | NP_416129.1 | 16129570 | Escherichia coli |
| FumB | NP_418546.1 | 16131948 | Escherichia coli |
| FumC | NP_416128.1 | 16129569 | Escherichia coli |

Succinyl-CoA Transferase

Succinyl-CoA transferase catalyzes the conversion of succinyl-CoA to succinate while transferring the CoA moiety to a CoA acceptor molecule. Many transferases have broad specificity and thus may utilize CoA acceptors as diverse as acetate, succinate, propionate, butyrate, 2-methylacetoacetate, 3-ketohexanoate, 3-ketopentanoate, valerate, crotonate, 3-mercaptopropionate, propionate, vinylacetate, butyrate, among others.

The conversion of succinate to succinyl-CoA is ideally carried by a transferase which does not require the direct consumption of an ATP or GTP. This type of reaction is common in a number of organisms. Perhaps the top candidate enzyme for this reaction step is succinyl-CoA:3-ketoacid-CoA transferase. This enzyme converts succinate to succinyl-CoA while converting a 3-ketoacyl-CoA to a 3-ketoacid. Exemplary succinyl-CoA:3:ketoacid-CoA transferases are present in *Helicobacter pylori* (Corthesy-Theulaz et al., *J. Biol. Chem.* 272:25659-25667 (1997)), *Bacillus subtilis* (Stols et al., *Protein. Expr. Purif.* 53:396-403 (2007)), and *Homo sapiens* (Fukao et al., *Genomics.* 68:144-151 (2000); and Tanaka et al., *Mol. Hum. Reprod.* 8:16-23 (2002)). These genes/proteins are identified below in Table 82.

TABLE 82

| Gene | GenBank ID | GI Number | Organism |
| --- | --- | --- | --- |
| HPAG1_0676 | YP_627417 | 108563101 | *Helicobacter pylori* |
| HPAG1_0677 | YP_627418 | 108563102 | *Helicobacter pylori* |
| ScoA | NP_391778 | 16080950 | *Bacillus subtilis* |
| ScoB | NP_391777 | 16080949 | *Bacillus subtilis* |
| OXCT1 | NP_000427 | 4557817 | *Homo sapiens* |
| OXCT2 | NP_071403 | 11545841 | *Homo sapiens* |

The conversion of succinate to succinyl-CoA can also be catalyzed by succinyl-CoA: Acetyl-CoA transferase. The gene product of cat1 of *Clostridium kluyveri* has been shown to exhibit succinyl-CoA: acetyl-CoA transferase activity (Sohling et al., *J Bacteriol.* 178:871-880 (1996)). In addition, the activity is present in *Trichomonas vaginalis* (van Grinsven et al., *J. Biol. Chem.* 283:1411-1418 (2008)) and *Trypanosoma brucei* (Riviere et al., *J. Biol. Chem.* 279:45337-45346 (2004)). These genes/proteins are identified below in Table 83.

TABLE 83

| Gene | GenBank ID | GI Number | Organism |
| --- | --- | --- | --- |
| cat1 | P38946.1 | 729048 | *Clostridium kluyveri* |
| TVAG_395550 | XP_001330176 | 123975034 | *Trichomonas vaginalis* G3 |
| Tb11.02.0290 | XP_828352 | 71754875 | *Trypanosoma brucei* |

Yet another possible CoA acceptor is benzylsuccinate. Succinyl-CoA:(R)-Benzylsuccinate CoA-Transferase functions as part of an anaerobic degradation pathway for toluene in organisms such as *Thauera aromatica* (Leutwein and Heider, *J. Bact.* 183(14) 4288-4295 (2001)). Homologs can be found in *Azoarcus* sp. T, *Aromatoleum aromaticum* EbN1, and *Geobacter metallireducens* GS-15. These genes/proteins are identified below in Table 84.

TABLE 84

| Gene | GenBank ID | GI Number | Organism |
| --- | --- | --- | --- |
| bbsE | AAF89840 | 9622535 | *Thauera aromatica* |
| bbsf | AAF89841 | 9622536 | *Thauera aromatica* |
| bbsE | AAU45405.1 | 52421824 | *Azoarcus* sp. T |
| bbsF | AAU45406.1 | 52421825 | *Azoarcus* sp. T |
| bbsE | YP_158075.1 | 56476486 | *Aromatoleum aromaticum* EbN1 |
| bbsF | YP_158074.1 | 56476485 | *Aromatoleum aromaticum* EbN1 |
| Gmet_1521 | YP_384480.1 | 78222733 | *Geobacter metallireducens* GS-15 |
| Gmet_1522 | YP_384481.1 | 78222734 | *Geobacter metallireducens* GS-15 |

Finally, ygfH encodes a propionyl CoA:succinate CoA transferase in *E. coli* (Haller et al., *Biochemistry*, 39(16) 4622-4629). Close homologs can be found in, for example, *Citrobacter youngae* ATCC 29220, *Salmonella enterica* subsp. *arizonae serovar*, and *Yersinia intermedia* ATCC 29909. These genes/proteins are identified below in Table 85.

TABLE 85

| Gene | GenBank ID | GI Number | Organism |
| --- | --- | --- | --- |
| ygfH | NP_417395.1 | 16130821 | *Escherichia coli* str. K-12 substr. MG1655 |
| CIT292_04485 | ZP_03838384.1 | 227334728 | *Citrobacter youngae* ATCC 29220 |
| SARI_04582 | YP_001573497.1 | 161506385 | *Salmonella enterica* subsp. *arizonae* serovar |
| yinte0001_14430 | ZP_04635364.1 | 238791727 | *Yersinia intermedia* ATCC 29909 |

Succinyl-CoA Synthetase

The product of the LSC1 and LSC2 genes of *S. cerevisiae* and the sucC and sucD genes of *E. coli* naturally form a succinyl-CoA synthetase complex that catalyzes the formation of succinyl-CoA from succinate with the concomitant consumption of one ATP, a reaction which is reversible in vivo (Bravo et al., *J. Forensic Sci.* 49:379-387 (2004)). These genes/proteins are identified below in Table 86.

TABLE 86

| Gene | GenBank ID | GI Number | Organism |
| --- | --- | --- | --- |
| LSC1 | NP_014785 | 6324716 | *Saccharomyces cerevisiae* |
| LSC2 | NP_011760 | 6321683 | *Saccharomyces cerevisiae* |
| sucC | NP_415256.1 | 16128703 | *Escherichia coli* |
| sucD | AAC73823.1 | 1786949 | *Escherichia coli* |

Pyruvate Formate Lyase

Pyruvate formate lyase is an enzyme that catalyzes the conversion of pyruvate and CoA into acetyl-CoA and formate. Pyruvate formate lyase is a common enzyme in prokaryotic organisms that is used to help modulate anaerobic redox balance. Exemplary enzymes can be found in *Escherichia coli* (Knappe et al., *FEMS. Microbiol Rev.* 6:383-398 (1990)), *Lactococcus lactis* (Melchiorsen et al., *Appl Microbiol Biotechnol* 58:338-344 (2002)), and *Streptococcus mutans* (Takahashi-Abbe et al., *Oral. Microbiol Immunol.* 18:293-297 (2003)). A mitochondrial pyruvate formate lyase has also been identified in the eukaryote, *Chlamydomonas reinhardtii* (Atteia et al., *J. Biol. Chem.* 281:9909-9918 (2006); and Hemschemeier et al., *Eukaryot. Cell* 7:518-526 (2008)). These genes/proteins are identified below in Table 87.

TABLE 87

| Gene | GenBank ID | GI Number | Organism |
|---|---|---|---|
| pflB | NP_415423 | 16128870 | *Escherichia coli* |
| pfl | CAA03993 | 2407931 | *Lactococcus lactis* |
| pfl | BAA09085 | 1129082 | *Streptococcus mutans* |
| PFL1 | EDP09457 | 158283707 | *Chlamydomonas reinhardtii* |

Formate Hydrogen Lyase

A formate hydrogen lyase enzyme can be employed to convert formate to carbon dioxide and hydrogen. An exemplary formate hydrogen lyase enzyme can be found in *Escherichia coli*. The *E. coli* formate hydrogen lyase consists of hydrogenase 3 and formate dehydrogenase-H (Maeda et al., *Appl Microbiol Biotechnol* 77:879-890 (2007)). It is activated by the gene product of fhlA (Maeda et al., *Appl Microbiol Biotechnol* 77:879-890 (2007)). The addition of the trace elements, selenium, nickel and molybdenum, to a fermentation broth has been shown to enhance formate hydrogen lyase activity (Soini, et al., *Microb. Cell Fact.* 7:26 (2008)). These genes/proteins are identified below in Table 88.

TABLE 88

| Gene | GenBank ID | GI Number | Organism |
|---|---|---|---|
| Hydrogenase 3: | | | |
| hycD | NP_417202 | 16130629 | *Escherichia coli* |
| hycC | NP_417203 | 16130630 | *Escherichia coli* |
| hycF | NP_417200 | 16130627 | *Escherichia coli* |
| hycG | NP_417199 | 16130626 | *Escherichia coli* |
| hycB | NP_417204 | 16130631 | *Escherichia coli* |
| hycE | NP_417201 | 16130628 | *Escherichia coli* |
| Formate dehydrogenase-H: | | | |
| fdhF | NP_418503 | 16131905 | *Escherichia coli* |
| Activator: | | | |
| fhlA | NP_417211 | 16130638 | *Escherichia coli* |

A formate hydrogen lyase enzyme also exists in the hyperthermophilic archaeon, *Thermococcus litoralis* (Takacs et al., *Microbiol* 8:88 2008)). These genes/proteins are identified below in Table 89.

TABLE 89

| Gene | GenBank ID | GI Number | Organism |
|---|---|---|---|
| mhyC | ABW05543 | 157954626 | *Thermococcus litoralis* |
| mhyD | ABW05544 | 157954627 | *Thermococcus litoralis* |
| mhyE | ABW05545 | 157954628 | *Thermococcus litoralis* |
| myhF | ABW05546 | 157954629 | *Thermococcus litoralis* |
| myhG | ABW05547 | 157954630 | *Thermococcus litoralis* |
| myhH | ABW05548 | 157954631 | *Thermococcus litoralis* |
| fdhA | AAB94932 | 2746736 | *Thermococcus litoralis* |
| fdhB | AAB94931 | 157954625 | *Thermococcus litoralis* |

Additional formate hydrogen lyase systems have been found in *Salmonella typhimurium*, *Klebsiella pneumoniae*, *Rhodospirillum rubrum*, *Methanobacterium formicicum* (Vardar-Schara et al., *Microbial Biotechnology* 1:107-125)).

Formate Dehydrogenase

Formate dehydrogenase activity is present in both *E. coli* and *Saccharomyces cerevisiae* among other organisms. *S. cerevisiae* contains two formate dehydrogenases, FDH1 and FDH2, that catalyze the oxidation of formate to $CO_2$ (Overkamp et al., *Yeast* 19:509-520 (2002)). In *Moorella thermoacetica*, the loci, Moth_2312 and Moth_2313, are actually one gene that is responsible for encoding the alpha subunit of formate dehydrogenase while the beta subunit is encoded by Moth_2314 (Andreesen et al., *J. Bacteriol.* 116:867-873 (1973); Li et al., *J. Bacteriol.* 92:405-412 (1966); Pierce et al., *Environ. Microbiol* (2008) and Yamamoto et al., *J. Biol. Chem.* 258:1826-1832 (1983)). Another set of genes encoding formate dehydrogenase activity is encoded by Sfum_2703 through Sfum_2706 in *Syntrophobacter fumaroxidans* (de Bok, et al., *Eur. J. BioChem.* 270:2476-2485 (2003); and Reda et al., *Proc. Natl. Acad. Sci. U.S.A.* 105:10654-10658 (2008)). Similar to their *M. thermoacetica* counterparts, Sfum_2705 and Sfum_2706 are actually one gene. *E. coli* contains multiple formate dehydrogenases. These genes/proteins are identified below in Table 90.

TABLE 90

| Gene | GenBank ID | GI Number | Organism |
|---|---|---|---|
| FDH1 | NP_015033 | 6324964 | *Saccharomyces cerevisiae* |
| FDH2 | Q08987 | 88909613 | *Saccharomyces cerevisiae* |
| Moth_2312 | YP_431142 | 148283121 | *Moorella thermoacetica* |
| Moth_2313 | YP_431143 | 83591134 | *Moorella thermoacetica* |
| Moth_2314 | YP_431144 | 83591135 | *Moorella thermoacetica* |
| Sfum_2703 | YP_846816.1 | 116750129 | *Syntrophobacter fumaroxidans* |
| Sfum_2704 | YP_846817.1 | 116750130 | *Syntrophobacter fumaroxidans* |
| Sfum_2705 | YP_846818.1 | 116750131 | *Syntrophobacter fumaroxidans* |
| Sfum_2706 | YP_846819.1 | 116750132 | *Syntrophobacter fumaroxidans* |
| fdnG, H, I | NP_415991-993.1 | 16129433 16129434 16129435 | *Escherichia coli* |
| fdoG, H, I | NP_418330, 29, 28.1 | 16131734 16131733 16131732 | *Escherichia coli* |

Pyruvate Dehydrogenase

The pyruvate dehydrogenase complex, catalyzing the conversion of pyruvate to acetyl-CoA, has been extensively studied. The *S. cerevisiae* complex consists of an E2 (LAT1) core that binds E1 (PDA1, PDB1), E3 (LPD1), and Protein X (PDX1) components (Pronk et al., *Yeast* 12:1607-1633 (1996)). In the *E. coli* enzyme, specific residues in the E1 component are responsible for substrate specificity (Bisswanger *J Biol Chem.* 256:815-822. (1981); Bremer *J Biochem.* 8:535-540 (1969) and Gong et al., *J Biol Chem.* 275:13645-13653 (2000)). Engineering efforts have improved the *E. coli* PDH enzyme activity under anaerobic conditions (Kim et al., *Appl. Environ. Microbiol.* 73:1766-1771 (2007); Kim et al., *J. Bacteriol.* 190:3851-3858 (2008) and Zhou et al., *Biotechnol. Lett.* 30:335-342 (2008)). In contrast to the *E. coli* PDH, the *B. subtilis* complex is active and required for growth under anaerobic conditions (Nakano et al., *J. Bacteriol.* 179:6749-6755 (1997)). The *Klebsiella pneumoniae* PDH, characterized during growth on glycerol, is also active under anaerobic conditions (Menzel et al., *J. Biotechnol.* 56:135-142 (1997)). Crystal structures of the enzyme complex from bovine kidney (Zhou et al., *Proc. Natl. Acad. Sci. U.S. A* 98:14802-14807 (2001)) and the E2 catalytic domain from *Azotobacter vinelandii* are available (Mattevi et al., *Science.* 255:1544-1550 (1992)). Some maMAAlian PDH enzymes complexes can react on alternate substrates such as 2-oxobutanoate (Paxton et al., BioChem. J. 234:295-303 (1986)). These genes/proteins are identified below in Table 91.

TABLE 91

| Gene | GenBank ID | GI Number | Organism |
|---|---|---|---|
| LAT1 | NP_014328 | 6324258 | Saccharomyces cerevisiae |
| PDA1 | NP_011105 | 37362644 | Saccharomyces cerevisiae |
| PDB1 | NP_009780 | 6319698 | Saccharomyces cerevisiae |
| LPD1 | NP_116635 | 14318501 | Saccharomyces cerevisiae |
| PDX1 | NP_011709 | 6321632 | Saccharomyces cerevisiae |
| aceE | NP_414656.1 | 16128107 | Escherichia coli str. K12 substr. MG1655 |
| aceF | NP_414657.1 | 16128108 | Escherichia coli str. K12 substr. MG1655 |
| Lpd | NP_414658.1 | 16128109 | Escherichia coli str. K12 substr. MG1655 |
| pdhA | P21881.1 | 3123238 | Bacillus subtilis |
| pdhB | P21882.1 | 129068 | Bacillus subtilis |
| pdhC | P21883.2 | 129054 | Bacillus subtilis |
| pdhD | P21880.1 | 118672 | Bacillus subtilis |
| aceE | YP_001333808.1 | 152968699 | Klebsiella pneumonia MGH78578 |
| aceF | YP_001333809.1 | 152968700 | Klebsiella pneumonia MGH78578 |
| lpdA | YP_001333810.1 | 152968701 | Klebsiella pneumonia MGH78578 |
| Pdha1 | NP_001004072.2 | 124430510 | Rattus norvegicus |
| Pdha2 | NP_446446.1 | 16758900 | Rattus norvegicus |
| Dlat | NP_112287.1 | 78365255 | Rattus norvegicus |
| Dld | NP_955417.1 | 40786469 | Rattus norvegicus |

Pyruvate Ferredoxin Oxidoreductase

Pyruvate ferredoxin oxidoreductase (PFOR) catalyzes the oxidation of pyruvate to form acetyl-CoA. The PFOR from Desulfovibrio africanus has been cloned and expressed in E. coli resulting in an active recombinant enzyme that was stable for several days in the presence of oxygen (Pieulle et al., J Bacteriol. 179:5684-5692 (1997)). Oxygen stability is relatively uncommon in PFORs and is believed to be conferred by a 60 residue extension in the polypeptide chain of the D. africanus enzyme. The M. thermoacetica PFOR is also well characterized (Menon et al., BioChemistry 36:8484-8494 (1997)) and was even shown to have high activity in the direction of pyruvate synthesis during autotrophic growth (Furdui et al., J Biol Chem. 275:28494-28499 (2000)). Further, E. coli possesses an uncharacterized open reading frame, ydbK, encoding a protein that is 51% identical to the M. thermoacetica PFOR. Evidence for pyruvate oxidoreductase activity in E. coli has been described (Blaschkowski et al., J BioChem. 123:563-569 (1982)). Several additional PFOR enzymes are described in the following review (Ragsdale, Chem. Rev. 103:2333-2346 (2003)). Finally, flavodoxin reductases (e.g., fqrB from Helicobacter pylori or Campylobacter jejuni (St Maurice et al., J. Bacteriol. 189:4764-4773 (2007)) or Rnf-type proteins (Herrmann et al., J. Bacteriol. 190:784-791 (2008); and Seedorf et al., Proc. Natl. Acad. Sci. U.S.A. 105:2128-2133 (2008)) provide a means to generate NADH or NADPH from the reduced ferredoxin generated by PFOR. These genes/proteins are identified below in Table 92.

TABLE 92

| Gene | GenBank ID | GI Number | Organism |
|---|---|---|---|
| Por | CAA70873.1 | 1770208 | Desulfovibrio africanus |
| Por | YP_428946.1 | 83588937 | Moorella thermoacetica |
| ydbK | NP_415896.1 | 16129339 | Escherichia coli |
| fqrB | NP_207955.1 | 15645778 | Helicobacter pylori |
| fqrB | YP_001482096.1 | 157414840 | Campylobacter jejuni |
| RnfC | EDK33306.1 | 146346770 | Clostridium kluyveri |

TABLE 92-continued

| Gene | GenBank ID | GI Number | Organism |
|---|---|---|---|
| RnfD | EDK33307.1 | 146346771 | Clostridium kluyveri |
| RnfG | EDK33308.1 | 146346772 | Clostridium kluyveri |
| RnfE | EDK33309.1 | 146346773 | Clostridium kluyveri |
| RnfA | EDK33310.1 | 146346774 | Clostridium kluyveri |
| RnfB | EDK33311.1 | 146346775 | Clostridium kluyveri |

Succinic Semialdehyde Dehydrogenase (CoA-Dependent)

Succinic semialdehyde dehydrogenase (CoA-dependent), also referred to as succinyl-CoA reductase, is a CoA- and NAD(P)H-dependent oxidoreductase that reduces succinyl-CoA to its corresponding aldehyde. Exemplary enzymes are encoded by the sucD gene in Clostridium kluyveri (Sohling et al., J Bacteriol 178:871-80 (1996); and Sohling et al., J Bacteriol. 178:871-880 (1996)) and the sucD gene of P. gingivalis (Takahashi et al., J. Bacteriol. 182:4704-4710 (2000)). Other enzymes that catalyze similar reactions are the fatty acyl-CoA reductases of Acinetobacter calcoaceticus (Reiser et al., Journal of Bacteriology 179:2969-2975 (2007)) and Acinetobacter sp. M-1 (Ishige et al., Appl. Environ. Microbiol. 68:1192-1195 (2002)), and the acylating acetaldehyde dehydrogenase in Pseudomonas sp, which has been demonstrated to oxidize and acylate acetaldehyde, propionaldehyde, butyraldehyde, isobutyraldehyde and formaldehyde (Powlowski et al., J Bacteriol. 175:377-385 (1993)). In addition to reducing acetyl-CoA to ethanol, the enzyme encoded by adhE in Leuconostoc mesenteroides has been shown to oxidize the branched chain compound isobutyraldehyde to isobutyryl-CoA (Koo et al., Biotechnol Lett. 27:505-510 (2005)). These genes/proteins are identified below in Table 93.

TABLE 93

| Gene | GenBank ID | GI Number | Organism |
|---|---|---|---|
| sucD | P38947.1 | 172046062 | Clostridium kluyveri |
| sucD | NP_904963.1 | 34540484 | Porphyromonas gingivalis |
| acr1 | YP_047869.1 | 50086359 | Acinetobacter calcoaceticus |
| acr1 | AAC45217 | 1684886 | Acinetobacter baylyi |
| acr1 | BAB85476.1 | 18857901 | Acinetobacter sp. Strain M-1 |
| bphG | BAA03892.1 | 425213 | Pseudomonas sp |
| adhE | AAV66076.1 | 55818563 | Leuconostoc mesenteroides |

4-Hydroxybutyrate Dehydrogenase

4-Hydroxybutyrate dehydrogenase catalyzes the NAD(P)H dependent reduction of succinic semialdehyde to 4-HB. Enzymes exhibiting this activity are found in Ralstonia eutropha (Bravo et al., J. Forensic Sci. 49:379-387 (2004)), Clostridium kluyveri (Wolff et al., Protein Expr. Purif. 6:206-212 (1995)) and Arabidopsis thaliana (Breitkreuz et al., J. Biol. Chem. 278:41552-41556 (2003)). Yet another gene is the alcohol dehydrogenase adhI from Geobacillus thermoglucosidasius (Jeon et al., J Biotechnol 135:127-133 (2008)). These genes/proteins are identified below in Table 94.

TABLE 94

| Gene | GenBank ID | GI Number | Organism |
|---|---|---|---|
| 4hbd | YP_726053.1 | 113867564 | Ralstonia eutropha H16 |
| 4hbd | EDK35022.1 | 146348486 | Clostridium kluyveri |
| 4hbd | Q94B07 | 75249805 | Arabidopsis thaliana |
| adhI | AAR91477.1 | 40795502 | Geobacillus thermoglucosidasius |

4-Hydroxybutyryl-CoA Transferase

The conversion of 4-HB to 4-hydroxybutyryl-CoA is catalyzed by an enzyme with 4-hydroxybutyryl-CoA transferase activity. Candidate enzymes include the gene products of cat1, cat2, and cat3 of *Clostridium kluyveri* which have been shown to exhibit succinyl-CoA, 4-hydroxybutyryl-CoA, and butyryl-CoA transferase activity, respectively (Gerhardt et al., *Arch. Microbiol.* 174:189-199 (2000); Arikawa et al., *Microbiol Lett.* 165:111-116 (1998) and Sohling et al., *J Bacteriol.* 178:871-880 (1996)). Similar CoA transferase activities are also present in *Trichomonas vaginalis* (van Grinsven et al., *J. Biol. Chem.* 283:1411-1418 (2008)) and *Trypanosoma brucei* (Riviere et al., *J. Biol. Chem.* 279: 45337-45346 (2004)). The atoA and atoD genes of *E. coli* encode an acetoacetyl-CoA transferase with a broad substrate range (Sramek et al., *Arch. BioChem. Biophys.* 171:14-26 (1975)). This enzyme has been shown to transfer a CoA moiety from acetyl-CoA to a variety of branched and linear substrates including isobutyrate (Matthies et al., *Appl Environ. Microbiol* 58:1435-1439 (1992)), valerate (Vanderwinkel et al., *BioChem. Biophys. Res. Commun.* 33:902-908 (1968)) and butanoate (Vanderwinkel et al., *BioChem. Biophys. Res. Commun.* 33:902-908 (1968)). These genes/proteins are identified below in Table 95.

TABLE 95

| Gene | GenBank ID | GI Number | Organism |
| --- | --- | --- | --- |
| cat1 | P38946.1 | 729048 | *Clostridium kluyveri* |
| cat2 | P38942.2 | 172046066 | *Clostridium kluyveri* |
| cat3 | EDK35586.1 | 146349050 | *Clostridium kluyveri* |
| TVAG_395550 | XP_001330176 | 123975034 | *Trichomonas vaginalis* G3 |
| Tb11.02.0290 | XP_828352 | 71754875 | *Trypanosoma brucei* |
| atoA | P76459.1 | 2492994 | *Escherichia coli* |
| atoD | P76458.1 | 2492990 | *Escherichia coli* |

4-Hydroxybutyryl-CoA Synthetase

The conversion of 4-HB to 4-hydroxybutyryl-CoA can also be catalyzed by a CoA acid-thiol ligase, also known as a CoA synthetase. Enzymes catalyzing this exact transformation have not been characterized to date; however, several enzymes with broad substrate specificities have been described in the literature. An exemplary candidate is the enzyme encoded by sucCD in *E. coli*, which naturally catalyzes the formation of succinyl-CoA from succinate with the concomitant consumption of one ATP, a reaction which is reversible in vivo (Buck et al., *BioChemistry* 24:6245-6252 (1985)). Additional CoA-ligase candidates include the ADP-forming phenylacetate-CoA ligases from *P. chrysogenum* (Lamas-Maceiras et al., *BioChem. J* 395:147-155 (2006); and Wang et al., *BioChem. Biophys. Res. Commun.* 360:453-458 (2007)) and the pimeloyl-CoA ligase from *Pseudomonas mendocina*. The AMP-forming enzyme from *Pseudomonas mendocina*, cloned into *E. coli*, was shown to accept the alternate substrates hexanedioate and nonanedioate (Binieda et al., *BioChem. J* 340 (Pt 3):793-801 (1999)). These genes/proteins are identified below in Table 96. CoA synthetase enzyme candidates identified for acetoacetyl-CoA synthetase, succinyl-CoA synthetase, propionyl-CoA synthetase, 3-hydroxybutyryl-CoA synthetase, 3-hydroxyisobutyryl-CoA synthetase, methylmalonyl-CoA synthetase and methacrylyl-CoA synthase are also applicable here.

TABLE 96

| Gene | GenBank ID | GI Number | Organism |
| --- | --- | --- | --- |
| sucC | NP_415256.1 | 16128703 | *Escherichia coli* |
| sucD | AAC73823.1 | 1786949 | *Escherichia coli* |
| phl | CAJ15517.1 | 77019264 | *Penicillium chrysogenum* |
| pauA | NP_249708.1 | 15596214 | *Pseudomonas mendocina* |

4-Hydroxybutyryl-CoA Reductase (Aldehyde Forming)

4-Hydroxybutyryl-CoA reductase catalyzes the NAD(P)H dependent reduction of 4-hydroxybutyryl-CoA to 4-hydroxybutyraldehyde. Enzymes that exhibit this activity include succinate semialdehyde dehydrogenase enzymes encoded by the sucD gene in *Clostridium kluyveri* (Sohling et al., *J Bacteriol* 178:871-80 (1996); and Sohling et al., *J Bacteriol.* 178:871-880 (1996)) and sucD of *P. gingivalis* (Takahashi et al., *J. Bacteriol.* 182:4704-4710 (2000)). Butyraldehyde dehydrogenase enzymes, found in solventogenic organisms such as *Clostridium* saccharoperbutylacetonicum (Kosaka et al., *Biosci. Biotechnol BioChem.* 71:58-68 (2007)), catalyzes a similar reaction: conversion of butyryl-CoA to butyraldehyde. The enzyme acylating acetaldehyde dehydrogenase in *Pseudomonas* sp, encoded by bphG, is yet another candidate as it has been demonstrated to oxidize and acylate acetaldehyde, propionaldehyde, butyraldehyde, isobutyraldehyde and formaldehyde (Powlowski et al., *J Bacteriol.* 175:377-385 (1993)). Fatty acyl-CoA reductase enzymes from *Acinetobacter calcoaceticus* (Reiser et al., *Journal of Bacteriology* 179:2969-2975 (1997)) and the *Acinetobacter* sp. M-1 (Ishige, et al., *Appl. Environ. Microbiol.* 68:1192-1195 (2002)) catalyze similar reactions. In addition to reducing acetyl-CoA to ethanol, the enzyme encoded by adhE in *Leuconostoc mesenteroides* has been shown to oxidize the branched chain compound isobutyraldehyde to isobutyryl-CoA (Koo et al., *Biotechnol Lett.* 27:505-510 (2005)). These genes/proteins are identified below in Table 97.

TABLE 97

| Gene | GenBank ID | GI Number | Organism |
| --- | --- | --- | --- |
| sucD | P38947.1 | 172046062 | *Clostridium kluyveri* |
| sucD | NP_904963.1 | 34540484 | *Porphyromonas gingivalis* |
| bld | AAP42563.1 | 31075383 | *Clostridium saccharoperbutylacetonicum* |
| bphG | BAA03892.1 | 425213 | *Pseudomonas* sp |
| acr1 | YP_047869.1 | 50086359 | *Acinetobacter calcoaceticus* |
| acr1 | AAC45217 | 1684886 | *Acinetobacter baylyi* |
| acr1 | BAB85476.1 | 18857901 | *Acinetobacter* sp. Strain M-1 |
| adhE | AAV66076.1 | 55818563 | *Leuconostoc mesenteroides* |

4-Hydroxybutyraldehyde Reductase

The conversion of 4-hydroxybutyrylaldehyde to 14-BDO is catalyzed by an alcohol dehydrogenase. Several native dehydrogenases in *E. coli* such as yqhD (Sulzenbacher et al., *Journal of Molecular Biology* 342:489-502 (2004)) exhibit broad substrate specificity and are able to catalyze this reaction. The gene product of yqhD catalyzes the reduction of acetaldehyde, malondialdehyde, propionaldehyde, butyraldehyde, and acrolein using NADPH as the cofactor (Perez et al., *J Biol. Chem.* 283:7346-7353 (2008); and Perez et al., *J Biol. Chem.* 283:7346-7353 (2008)). Additional enzyme candidates that catalyze the conversion of an aldehyde to alcohol include alrA encoding a medium-chain alcohol dehydrogenase for C2-C14 (Tani et al., *Appl. Environ. Microbiol.* 66:5231-5235 (2000)), ADH2 from *Saccharomyces cerevisiae* (Atsumi et al., *Nature* 451:86-89 (2008)) and bdh I and bdh II from *C. acetobutylicum* which converts butyraldehyde into butanol (Walter et al., *Journal of Bacteriology* 174:7149-7158 (1992)). The adhA gene product from *Zymomonas mobilis* has been demonstrated to have activity on a number of aldehydes including formaldehyde, acetaldehyde, propionaldehyde, butyraldehyde, and acrolein (Kinoshita et al., *Appl Microbiol Biotechnol* 22:249-254 (1985)). These genes/proteins are identified below in Table 98.

TABLE 98

| Gene | GenBank ID | GI Number | Organism |
|---|---|---|---|
| yqhD | NP_417484.1 | 16130909 | *Escherichia coli* |
| alrA | BAB12273.1 | 9967138 | *Acinetobacter* sp. Strain M-1 |
| ADH2 | NP_014032.1 | 6323961 | *Saccharomyces cerevisiae* |
| bdh I | NP_349892.1 | 15896543 | *Clostridium acetobutylicum* |
| bdh II | NP_349891.1 | 15896542 | *Clostridium acetobutylicum* |
| adhA | YP_162971.1 | 56552132 | *Zymomonas mobilis* |

4-Hydroxybutyryl-CoA Reductase (Alcohol Forming)

The conversion of 4-hydroxybutyryl-CoA to 14-BDO can also be catalyzed by a bifunctional oxidoreductase with aldehyde dehydrogenase and alcohol dehydrogenase capabilities. For example, the adheE2 gene product from *Clostridium acetobutylicum* converts butyryl-CoA to butanol (Fontaine et al., *J. Bacteriol.* 184:821-830 (2002)). This enzyme also accepts 4-hydroxybutyryl-CoA as a substrate. Additional bifunctional alcohol-forming reductase enzymes include the gene products of adhE in *Leuconostoc mesenteroides* (Kazahaya et al., *J. Gen. Appl. Microbiol.* 18:43-55 (1972); and Koo et al., *Biotechnol Lett.* 27:505-510 (2005)) and FAR from *Simmondsia chinensis* (Metz et al., *Plant Physiology* 122: 635-644 (2000)). Another exemplary enzyme is the NADPH-dependent malonyl-CoA reductase in *Chloroflexus aurantiacus* encoded by mcr (Hugler et al., *J. Bacteriol.* 184:2404-2410 (2002); and Strauss et al., *Eur. J. BioChem.* 215:633-643 (1993)). These genes/proteins are identified below in Table 99.

TABLE 99

| Gene | GenBank ID | GI Number | Organism |
|---|---|---|---|
| adhE2 | AAK09379.1 | 12958626 | *Clostridium acetobutylicum* |
| adhE | AAV66076.1 | 55818563 | *Leuconostoc mesenteroides* |
| FAR | AAD38039.1 | 5020215 | *Simmondsia chinensis* |
| mcr | AAS20429.1 | 42561982 | *Chloroflexus aurantiacus* |

4-Hydroxybutyrate Phosphotransferase (aka. Kinase)

4-Hydroxybutyrate phosphotransferase, also known as 4-hydroxybutyrate kinase, transforms 4-HB to 4-hydroxybutyryl phosphate with concurrent hydrolysis of one ATP. Candidate enzymes for catalyzing these transformations include butyrate kinase, aspartokinase, acetate kinase and gaMAA-glutamyl kinase. Butyrate kinase (EC 2.7.2.7) enzymes carry out the reversible conversion of butyryl-phosphate to butyrate during acidogenesis in *C. acetobutylicum* (Cary et al., *Appl. Environ. Microbiol* 56:1576-1583 (1990)). This enzyme is encoded by either of the two buk gene products (Huang et al., *J Mol. Microbiol. Biotechnol* 2:33-38 (2000)). Other butyrate kinase enzymes are found in *C. butyricum* and *C. tetanomorphum* (TWAROG et al., *J Bacteriol.* 86:112-117 (1963)). Related enzyme isobutyrate kinase from *Thermotoga maritima* has also been expressed in *E. coli* and crystallized (Diao et al., *D. Biol. Crystallogr.* 59:1100-1102 (2003); and Diao et al., *J. Bacteriol.* 191:2521-2529 (2009)). Aspartokinase catalyzes the ATP-dependent phosphorylation of aspartate and participates in the synthesis of several amino acids. The aspartokinase III enzyme in *E. coli*, encoded by lysC, has a broad substrate range and the catalytic residues involved in substrate specificity have been elucidated (Keng et al., *Arch. BioChem. Biophys.* 335:73-81 (1996)). Two additional kinases in *E. coli* are also good candidates: acetate kinase and gaMAA-glutamyl kinase. The *E. coli* acetate kinase, encoded by ackA (Skarstedt et al., *J. Biol. Chem.* 251:6775-6783 (1976)), phosphorylates propionate in addition to acetate (Hesslinger et al., *Mol. Microbiol* 27:477-492 (1998)). The *E. coli* gaMAA-glutamyl kinase, encoded by proB (Smith et al., *J. Bacteriol.* 157:545-551 (1984)), phosphorylates the gaMAA carbonic acid group of glutamate. These genes/proteins are identified below in Table 100.

TABLE 100

| Gene | GenBank ID | GI Number | Organism |
|---|---|---|---|
| buk1 | NP_349675 | 15896326 | *Clostridium acetobutylicum* |
| buk2 | Q97II1 | 20137415 | *Clostridium acetobutylicum* |
| buk2 | Q9X278.1 | 6685256 | *Thermotoga maritima* |
| lysC | NP_418448.1 | 16131850 | *Escherichia coli* |
| ackA | NP_416799.1 | 16130231 | *Escherichia coli* |
| proB | NP_414777.1 | 16128228 | *Escherichia coli* |

Phosphotrans-4-Hydroxybutyrylase

Phosphotrans-4-hydroxybutyrylase exchanges the phosphate moiety of 4-hydroxybutyryl-phosphate for a CoA moiety, forming 4-hydroxybutyryl-CoA. A candidate enzyme for this transformation is phosphotransbutyrylase (EC 2.3.1.19) an enzyme that reversibly converts butyryl-CoA into butyryl-phosphate. This enzyme is encoded by ptb genes found in *C. acetobutylicum* (Walter et al., *Gene* 134:107-111 (1993); and Wiesenborn et al., *Appl Environ. Microbiol* 55:317-322 (1989)), butyrate-producing bacterium L2-50 (Louis et al., *J. Bacteriol.* 186:2099-2106 (2004)) and *Bacillus megaterium* (Vazquez et al., *Curr. Microbiol* 42:345-349 (2001)). These genes/proteins are identified below in Table 101.

TABLE 101

| Gene | GenBank ID | GI Number | Organism |
|---|---|---|---|
| ptb | NP_349676 | 34540484 | *Clostridium acetobutylicum* |
| ptb | AAR19757.1 | 38425288 | butyrate-producing bacterium L2-50 |
| ptb | CAC07932.1 | 10046659 | *Bacillus megaterium* |

4-Hydroxybutyryl-Phosphate Reductase

The reduction of 4-hydroxybutyryl-phosphate to its corresponding aldehyde is catalyzed by phosphate reductase. This reaction is not catalyzed by known enzymes, but a similar reaction is catalyzed by aspartate semialdehyde dehydrogenase (ASD, EC 1.2.1.11): the NADPH-dependent reduction of 4-aspartyl phosphate to aspartate-4-semialdehyde. ASD participates in amino acid biosynthesis and recently has been studied as an antimicrobial target (Hadfield et al., *Biochemistry* 40:14475-14483 (2001)). The *E. coli* ASD structure has been solved (Hadfield et al., *J Mol. Biol.* 289:991-1002 (1999)) and the enzyme has been shown to accept the alternate substrate beta-3-methylaspartyl phosphate (Shames et al., *J Biol. Chem.* 259:15331-15339 (1984)). The *Haemophilus influenzae* enzyme has been the subject of enzyme engineering studies to alter substrate binding affinities at the active site (Blanco et al., *Acta Crystallogr. D. Biol. Crystallogr.* 60:1388-1395 (2004); and Blanco et al., *Acta Crystallogr. D. Biol. Crystallogr.* 60:1808-1815 (2004)). Other ASD candidates are found in *Mycobacterium tuberculosis* (Shafiani et al., *J Appl Microbiol* 98:832-838 (2005)), *Methanococcus jannaschii* (Faehnle et al., *J Mol. Biol.* 353:1055-1068 (2005)), and the infectious microorganisms *Vibrio cholera* and *Heliobacter pylori* (Moore et al., *Protein Expr. Purif.* 25:189-194 (2002)). A related enzyme candidate is acetylglutamylphosphate reductase (EC 1.2.1.38), an enzyme that naturally reduces acetylglutamylphosphate to acetylglutamate-5-semialdehyde, found in *S. cerevisiae* (Pauwels et al., *Eur. J Biochem.* 270:1014-1024 (2003)), *B. subtilis* (O'Reilly and Devine, *Microbiology* 140 (Pt 5):1023-1025 (1994)) and other organisms. These genes/proteins are identified below in Table 102.

TABLE 102

| Gene | GenBank ID | GI Number | Organism |
| --- | --- | --- | --- |
| asd | NP_417891.1 | 16131307 | *Escherichia coli* |
| asd | YP_248335.1 | 68249223 | *Haemophilus influenzae* |
| asd | AAB49996 | 1899206 | *Mycobacterium tuberculosis* |
| VC2036 | NP_231670 | 15642038 | *Vibrio cholera* |
| asd | YP_002301787.1 | 210135348 | *Heliobacter pylori* |
| ARG5,6 | NP_010992.1 | 6320913 | *Saccharomyces cerevisiae* |
| argC | NP_389001.1 | 16078184 | *Bacillus subtilis* |

Other exemplary phosphate reductase enzymes include glyceraldehyde 3-phosphate dehydrogenase which converts glyceraldehyde-3-phosphate into D-glycerate 1,3-bisphosphate (e.g., *E. coli* gapA (Branlant et al., *Eur. J. Biochem.* 150:61-66 (1985))), N-acetyl-gamma-glutamyl-phosphate reductase which converts N-acetyl-L-glutamate-5-semialdehyde into N-acetyl-L-glutamyl-5-phosphate (e.g., *E. coli* argC (Parsot et al. *Gene,* 68: 275-283 (1988))), and glutamate-5-semialdehyde dehydrogenase which converts L-glutamate-5-semialdehyde into L-glutamyl-5-phospate (e.g., *E. coli* proA (Smith et al., *J. Bacteriol.,* 157:545-551 (1984))). Genes encoding glutamate-5-semialdehyde dehydrogenase enzymes from *Salmonella typhimurium* (Mahan et al., *J. Bacteriol.,* 156: 1249-1262 (1983)) and *Campylobacter jejuni* (Louie et al., *Mol. Gen. Genet.,* 240:29-35 (1993)) were cloned and expressed in *E. coli*. These genes/proteins are identified below in Table 103.

TABLE 103

| Gene | GenBank ID | GI Number | Organism |
| --- | --- | --- | --- |
| gapA | P0A9B2.2 | 71159358 | *Escherichia coli* |
| argC | NP_418393.1 | 16131796 | *Escherichia coli* |
| proA | NP_414778.1 | 16128229 | *Escherichia coli* |
| proA | NP_459319.1 | 16763704 | *Salmonella typhimurium* |
| proA | P53000.2 | 9087222 | *Campylobacter jejuni* |

Succinate Reductase and 4-Hydroxybutyrate Reductase

The direct reduction of succinate to succinic semialdehyde or 4-HB to 4-hydroxybutyraldehyde can be catalyzed by a carboxylic acid reductase. The carboxylic acid reductase of *Nocardia iowensis*, known equivalently as aryl-aldehyde dehydrogenase, catalyzes the magnesium, ATP and NADPH-dependent reduction of carboxylic acids to their corresponding aldehydes (Venkitasubramanian et al., J Biol. Chem. 282: 478-485 (2007)) and is capable of catalyzing the conversion of 4-hydroxybutyrate to 4-hydroxybutanal. This enzyme, encoded by car, was cloned and functionally expressed in *E. coli* (Venkitasubramanian et al., J Biol. Chem. 282:478-485 (2007)). Expression of the npt gene product improved activity of the enzyme via post-transcriptional modification. The npt gene encodes a specific phosphopantetheine transferase (PPTase) that converts the inactive apo-enzyme to the active holo-enzyme. The natural substrate of this enzyme is vanillic acid and the enzyme exhibits broad acceptance of aromatic and aliphatic substrates (Venkitasubramanian et al. "Biocatalytic Reduction of Carboxylic Acids: Mechanism and Applications" Chapter 15 in Biocatalysis in the Pharmaceutical and Biotechnology Industries, ed. R. N. Patel, CRC Press LLC, Boca Raton, Fla. (2006)). These genes/proteins are identified below in Table 104.

TABLE 104

| Gene | GenBank ID | GI Number | Organism |
| --- | --- | --- | --- |
| car | AAR91681.1 | 40796035 | *Nocardia iowensis* (sp. NRRL 5646) |
| npt | ABI83656.1 | 114848891 | *Nocardia iowensis* (sp. NRRL 5646) |

Additional car and npt genes can be identified based on sequence homology. Non-limiting examples of proteins encoded by these genes are shown in Table 105.

TABLE 105

| Gene | GenBank ID | GI Number | Organism |
| --- | --- | --- | --- |
| fadD9 | YP_978699.1 | 121638475 | *Mycobacterium bovis* BCG |
| BCG_2812c | YP_978898.1 | 121638674 | *Mycobacterium bovis* BCG |
| nfa20150 | YP_118225.1 | 54023983 | *Nocardia farcinica* IFM 10152 |
| nfa40540 | YP_120266.1 | 54026024 | *Nocardia farcinica* IFM 10152 |
| SGR_6790 | YP_001828302.1 | 182440583 | *Streptomyces griseus* subsp. *griseus* NBRC 13350 |
| SGR_665 | YP_001822177.1 | 182434458 | *Streptomyces griseus* subsp. *griseus* NBRC 13350 |
| MSMEG_2956 | YP_887275.1 | YP_887275.1 | *Mycobacterium smegmatis* MC2 155 |
| MSMEG_5739 | YP_889972.1 | 118469671 | *Mycobacterium smegmatis* MC2 155 |
| MSMEG_2648 | YP_886985.1 | 118471293 | *Mycobacterium smegmatis* MC2 155 |
| MAP1040c | NP_959974.1 | 41407138 | *Mycobacterium avium* subsp. *paratuberculosis* K-10 |
| MAP2899c | NP_961833.1 | 41408997 | *Mycobacterium avium* subsp. *paratuberculosis* K-10 |
| MMAR_2117 | YP_001850422.1 | 183982131 | *Mycobacterium marinum* M |
| MMAR_2936 | YP_001851230.1 | 183982939 | *Mycobacterium marinum* M |
| MMAR_1916 | YP_001850220.1 | 183981929 | *Mycobacterium marinum* M |
| TpauDRAFT_33060 | ZP_04027864.1 | 227980601 | *Tsukamurella paurometabola* DSM 20162 |
| TpauDRAFT_20920 | ZP_04026660.1 | 227979396 | *Tsukamurella paurometabola* DSM 20162 |

An additional enzyme candidate found in *Streptomyces griseus* is encoded by the griC and griD genes. This enzyme is believed to convert 3-amino-4-hydroxybenzoic acid to 3-amino-4-hydroxybenzaldehyde as deletion of either griC or griD led to accumulation of extracellular 3-acetylamino-4-hydroxybenzoic acid, a shunt product of 3-amino-4-hydroxybenzoic acid metabolism (Suzuki, et al., *J. Antibiot.* 60(6): 380-387 (2007)). Co-expression of griC and griD with SGR_665, an enzyme similar in sequence to the *Nocardia iowensis* npt, may be beneficial. These genes/proteins are identified below in Table 106.

TABLE 106

| Gene | GenBank ID | GI Number | Organism |
|---|---|---|---|
| griC | YP_001825755.1 | 182438036 | *Streptomyces griseus* subsp. *griseus* NBRC 13350 |
| griD | YP_001825756.1 | 182438037 | *Streptomyces griseus* subsp. *griseus* NBRC 13350 |

An enzyme with similar characteristics, alpha-aminoadipate reductase (AAR, EC 1.2.1.31), participates in lysine biosynthesis pathways in some fungal species. This enzyme naturally reduces alpha-aminoadipate to alpha-aminoadipate semialdehyde. The carboxyl group is first activated through the ATP-dependent formation of an adenylate that is then reduced by NAD(P)H to yield the aldehyde and AMP. Like CAR, this enzyme utilizes magnesium and requires activation by a PPTase. Enzyme candidates for AAR and its corresponding PPTase are found in *Saccharomyces cerevisiae* (Morris et al., *Gene* 98:141-145 (1991)), *Candida albicans* (Guo et al., *Mol. Genet. Genomics* 269:271-279 (2003)), and *Schizosaccharomyces pombe* (Ford et al., *Curr. Genet.* 28:131-137 (1995)). The AAR from *S. pombe* exhibited significant activity when expressed in *E. coli* (Guo et al., *Yeast* 21:1279-1288 (2004)). The AAR from *Penicillium chrysogenum* accepts S-carboxymethyl-L-cysteine as an alternate substrate, but did not react with adipate, L-glutamate or diaminopimelate (Hijarrubia et al., *J Biol. Chem* 278:8250-8256 (2003)). The gene encoding the *P. chrysogenum* PPTase has not been identified to date and no high-confidence hits were identified by sequence comparison homology searching. These genes/proteins are identified below in Table 107.

TABLE 107

| Gene | GenBank ID | GI Number | Organism |
|---|---|---|---|
| LYS2 | AAA34747.1 | 171867 | *Saccharomyces cerevisiae* |
| LYS5 | P50113.1 | 1708896 | *Saccharomyces cerevisiae* |
| LYS2 | AAC02241.1 | 2853226 | *Candida albicans* |
| LYS5 | AAO26020.1 | 28136195 | *Candida albicans* |
| Lys1p | P40976.3 | 13124791 | *Schizosaccharomyces pombe* |
| Lys7p | Q10474.1 | 1723561 | *Schizosaccharomyces pombe* |
| Lys2 | CAA74300.1 | 3282044 | *Penicillium chrysogenum* |

4-Hydroxybutyryl-CoA dehydratase

4-Hydroxybutyryl-CoA dehydratase catalyzes the reversible conversion of 4-hydroxybutyryl-CoA to crotonyl-CoA. This enzyme possesses an intrinsic vinylacetyl-CoA Δ-isomerase activity, shifting the double bond from the 3,4 position to the 2,3 position (Scherf et al., *Eur. J BioChem.* 215:421-429 (1993); and Scherf et al., *Arch. Microbiol* 161: 239-245 (1994)). 4-Hydroxybutyrul-CoA dehydratase enzymes from *C. aminobutyricum* and *C. kluyveri* were purified, characterized, and sequenced at the N-terminus (Scherf et al., *Eur. J BioChem.* 215:421-429 (1993); and Scherf et al., *Arch. Microbiol* 161:239-245 (1994)). The *C. kluyveri* enzyme, encoded by abfD, was cloned, sequenced and expressed in *E. coli* (Gerhardt et al., *Arch. Microbiol* 174:189-199 (2000)). The abfD gene product from *Porphyromonas gingivalis* ATCC 33277 is closely related by sequence homology to the Clostridial gene products. These genes/proteins are identified below in Table 108.

TABLE 108

| Gene | GenBank ID | GI Number | Organism |
|---|---|---|---|
| abfD | YP_001396399.1 | 153955634 | *Clostridium kluyveri* DSM 555 |
| abfD | P55792 | 84028213 | *Clostridium aminobutyricum* |
| abfD | YP_001928843 | 188994591 | *Porphyromonas gingivalis* ATCC 33277 |

Crotonase

3-Hydroxybutyryl-CoA dehydratase (EC 4.2.1.55), also called crotonase, is an enoyl-CoA hydratase that reversibly dehydrates 3-hydroxyisobutyryl-CoA to form crotonyl-CoA. Crotonase enzymes are required for n-butanol formation in some organisms, particularly Clostridial species, and also comprise one step of the 3-hydroxypropionate/4-hydroxybutyrate cycle in thermoacidophilic Archaea of the genera *Sulfolobus*, *Acidianus*, and *Metallosphaera*. Exemplary genes encoding crotonase enzymes can be found in *C. acetobutylicum* (Atsumi et al., *Metab Eng* 10:305-311 (2008); and Boynton et al., *J Bacteriol.* 178:3015-3024 (1996)), *C. kluyveri* (Hillmer et al., *FEBS Lett.* 21:351-354 (1972)), and *Metallosphaera sedula* (Berg et al., *Science.* 318:1782-1786 (2007)) though the sequence of the latter gene is not known. The enoyl-CoA hydratase of *Pseudomonas putida*, encoded by ech, catalyzes the conversion of crotonyl-CoA to 3-hydroxybutyryl-CoA (Roberts et al., *Arch. Microbiol* 117:99-108 (1978)). Additional enoyl-CoA hydratase candidates are phaA and phaB, of *P. putida*, and paaA and paaB from *P. fluorescens* (Olivera et al., *Proc. Natl. Acad. Sci U.S. A* 95:6419-6424 (1998)). Lastly, a number of *Escherichia coli* genes have been shown to demonstrate enoyl-CoA hydratase functionality including maoC (Park et al., *J Bacteriol.* 185: 5391-5397 (2003)), paaF (Ismail et al., *Eur. J BioChem.* 270: 3047-3054 (2003); Park et al., *Appl. BioChem. Biotechnol* 113-116:335-346 (2004) and Park et al., *Biotechnol Bioeng* 86:681-686 (2004)) and paaG (Ismail et al., *Eur. J BioChem.* 270:3047-3054 (2003); Park et al., *Appl. BioChem. Biotechnol* 113-116:335-346 (2004) and Park et al., *Biotechnol Bioeng* 86:681-686 (2004)). These genes/proteins are identified below in Table 109.

TABLE 109

| Gene | GenBank ID | GI Number | Organism |
|---|---|---|---|
| crt | NP_349318.1 | 15895969 | *Clostridium acetobutylicum* |
| crt1 | YP_001393856.1 | 153953091 | *Clostridium kluyveri* |
| ech | NP_745498.1 | 26990073 | *Pseudomonas putida* |
| paaA | NP_745427.1 | 26990002 | *Pseudomonas putida* |
| paaB | NP_745426.1 | 26990001 | *Pseudomonas putida* |
| phaA | ABF82233.1 | 106636093 | *Pseudomonas fluorescens* |
| phaB | ABF82234.1 | 106636094 | *Pseudomonas fluorescens* |
| maoC | NP_415905.1 | 16129348 | *Escherichia coli* |
| paaF | NP_415911.1 | 16129354 | *Escherichia coli* |
| paaG | NP_415912.1 | 16129355 | *Escherichia coli* |

3-Hydroxybutyryl-CoA Reductase (Aldehyde Forming)

3-Hydroxybutyryl-CoA dehydrogenase catalyzes the NAD(P)H dependent reduction of 3-hydroxybutyryl-CoA to 3-hydroxybutyraldehyde. An enzyme catalyzing this transformation has not been identified to date. An exemplary CoA-acylating aldehyde dehydrogenase is the ald gene from *Clostridium beijerinckii* (Toth et al., *Appl Environ. Microbiol* 65:4973-4980 (1999)). This enzyme has been reported to reduce acetyl-CoA and butyryl-CoA to their corresponding aldehydes. Another enzyme that converts an acyl-CoA to its corresponding aldehyde is malonyl-CoA reductase which transforms malonyl-CoA to malonic semialdehyde. Malonyl-CoA reductase is a key enzyme in autotrophic carbon fixation via the 3-hydroxypropionate cycle in thermoacidophilic archael bacteria (Berg et al., *Science.* 318:1782-1786 (2007); and Thauer, *Science.* 318:1732-1733 (2007)). The enzyme utilizes NADPH as a cofactor and has been characterized in *Metallosphaera* and *Sulfolobus* spp (Alber et al., *J. Bacteriol.* 188:8551-8559 (2006); and Hugler et al., *J. Bacteriol.* 184:2404-2410 (2002)). The enzyme is encoded by Msed_0709 in *Metallosphaera sedula* (Alber et al., *J. Bacteriol.* 188:8551-8559 (2006); Berg et al., *Science.* 318:1782-1786 (2007)). A gene encoding a malonyl-CoA reductase from *Sulfolobus tokodaii* was cloned and heterologously expressed in *E. coli* (Alber et al., *J. Bacteriol.* 188:8551-8559 (2006)). This enzyme has also been shown to catalyze the conversion of methylmalonyl-CoA to its corresponding aldehyde (WO/2007/141208). Aldehyde dehydrogenase enzyme candidates for converting 4-hydroxybutyryl-CoA to 4-hydroxybutyraldehyde, described above, are also applicable here. These genes/proteins are identified below in Table 110.

TABLE 110

| Gene | GenBank ID | GI Number | Organism |
|---|---|---|---|
| Ald | AAT66436 | 49473535 | *Clostridium beijerinckii* |
| Msed_0709 | YP_001190808.1 | 146303492 | *Metallosphaera sedula* |
| mcr | NP_378167.1 | 15922498 | *Sulfolobus tokodaii* |

3-Hydroxybutyraldehyde Reductase

An enzyme with 3-hydroxybutyraldehyde reductase activity is required to convert 3-hydroxybutyraldehyde to 1,3-butanediol. Exemplary genes encoding enzymes that catalyze the conversion of an aldehyde to alcohol (i.e., alcohol dehydrogenase or equivalently aldehyde reductase) include alrA encoding a medium-chain alcohol dehydrogenase for C2-C14 (Tani et al., *Appl. Environ. Microbiol.* 66:5231-5235 (2000)), ADH2 from *Saccharomyces cerevisiae* (Atsumi et al., *Nature* 451:86-89 (2008)), yqhD from *E. coli* which has preference for molecules longer than C(3) (Sulzenbacher et al., *Journal of Molecular Biology* 342:489-502 (2004)), and bdh I and bdh II from *C. acetobutylicum* which converts butyraldehyde into butanol (Walter et al., *Journal of Bacteriology* 174:7149-7158 (1992)). The gene product of yqhD catalyzes the reduction of acetaldehyde, malondialdehyde, propionaldehyde, butyraldehyde, and acrolein using NADPH as the cofactor (Perez et al., *J Biol. Chem.* 283:7346-7353 (2008); and Perez et al., *J Biol. Chem.* 283:7346-7353 (2008)). The adhA gene product from *Zymomonas* mobilis has been demonstrated to have activity on a number of aldehydes including formaldehyde, acetaldehyde, propionaldehyde, butyraldehyde, and acrolein (Kinoshita et al., *Appl Microbiol Biotechnol* 22:249-254 (1985)). These genes/proteins are identified below in Table 111.

TABLE 111

| Gene | GenBank ID | GI Number | Organism |
|---|---|---|---|
| alrA | BAB12273.1 | 9967138 | *Acinetobacter* sp. Strain M-1 |
| ADH2 | NP_014032.1 | 6323961 | *Saccharomyces cerevisiae* |
| yqhD | NP_417484.1 | 16130909 | *Escherichia coli* |
| bdh I | NP_349892.1 | 15896543 | *Clostridium acetobutylicum* |
| bdh II | NP_349891.1 | 15896542 | *Clostridium acetobutylicum* |
| adhA | YP_162971.1 | 56552132 | *Zymomonas mobilis* |

Additional candidates include 4-hydroxybutyrate dehydrogenase and 3-hydroxyisobutyrate dehydrogenase enzymes. 4-Hydroxybutyrate dehydrogenase enzymes naturally convert 4-hydroxybutyraldehyde to 4-HB and have been characterized in *Ralstonia eutropha* (Bravo et al., *J. Forensic Sci.* 49:379-387 (2004)), *Clostridium* kluyveri (Wolff et al., *Protein Expr. Purif.* 6:206-212 (1995)) and *Arabidopsis thaliana* (Breitkreuz, et al., *J. Biol. Chem.* 278:41552-41556 (2003)). 3-Hydroxyisobutyrate dehydrogenase enzyme candidates include mmsB from *Pseudomonas aeruginosa* PAO1 (Gokam et al., U.S. Pat. No. 7,393,676 (2008)), mmsB from *Pseudomonas putida* KT2440 (118) and mmsB from *Pseudomonas putida* E23 (Chowdhury, et al., *Biosci. Biotechnol. BioChem.* 60:2043-2047 (1996)). These genes/proteins are identified below in Table 112.

TABLE 112

| Gene | GenBank ID | GI Number | Organism |
|---|---|---|---|
| 4hbd | YP_726053.1 | 113867564 | *Ralstonia eutropha* H16 |
| 4hbd | EDK35022.1 | 146348486 | *Clostridium kluyveri* |
| 4hbd | Q94B07 | 75249805 | *Arabidopsis thaliana* |
| mmsB | NP_252259.1 | 15598765 | *Pseudomonas aeruginosa* PAO1 |
| mmsB | NP_746775.1 | 26991350 | *Pseudomonas putida* KT2440 |
| mmsB | JC7926 | 60729613 | *Pseudomonas putida* E23 |

3-Hydroxybutyryl-CoA Reductase (Alcohol Forming)

A bifunctional oxidoreductase is required for the direct conversion of 3-hydroxybutyryl-CoA to 1,3-butanediol. Exemplary enzymes that convert an acyl-CoA to alcohol include those that transform substrates such as acetyl-CoA to ethanol (e.g., adhE from *E. coli* (Kessler et al., *FEBS. Lett.* 281:59-63 (1991))), butyryl-CoA to butanol (e.g. adhE2 from *C. acetobutylicum* (Fontaine et al., *J. Bacteriol.* 184:821-830 (2002))) and 4-hydroxybutyryl-CoA to 1,4-butanediol (see candidates in previous section). The jojoba (*Simmondsia chinensis*) FAR encodes an alcohol-forming fatty acyl-CoA reductase. This gene was cloned and overexpressed in *E. coli*, resulting in FAR activity and the accumulation of fatty alcohol (Metz et al., *Plant Physiology* 122:635-644 (2000)). Another exemplary enzyme convert malonyl-CoA to 3-hydroxypropionate. An NADPH-dependent enzyme with this activity has characterized in *Chloroflexus aurantiacus* where it participates in the 3-hydroxypropionate cycle (Hugler et al., *J. Bacteriol.* 184:2404-2410 (2002); and Strauss et al., *Eur. J.*

*BioChem.* 215:633-643 (1993)). This enzyme, with a mass of 300 kDa, is highly substrate-specific and shows little sequence similarity to other known oxidoreductases (Hugler et al., *J. Bacteriol.* 184:2404-2410 (2002)). These genes/proteins are identified below in Table 113.

TABLE 113

| Gene | GenBank ID | GI Number | Organism |
|---|---|---|---|
| adhE | NP_415757.1 | 16129202 | *Escherichia coli* |
| adhE2 | AAK09379.1 | 12958626 | *Clostridium acetobutylicum* |
| adhE | AAV66076.1 | 55818563 | *Leuconostoc mesenteroides* |
| FAR | AAD38039.1 | 5020215 | *Simmondsia chinensis* |
| mcr | AAS20429.1 | 42561982 | *Chloroflexus aurantiacus* |

3-Hydroxybutyryl-CoA Transferase

The conversion of 3-hydroxybutyryl-CoA to 3-hydroxybutyrate (3-HB) is catalyzed by a CoA transferase, hydrolase or synthetase. A CoA transferase enzyme catalyzing this specific transformation has not been identified to date. The *E. coli* enzyme acyl-CoA:acetate-CoA transferase, also known as acetate-CoA transferase (EC 2.8.3.8), has been shown to transfer the CoA moiety to acetate from a variety of branched and linear acyl-CoA substrates, including isobutyrate (Matthies et al., *Appl Environ Microbiol* 58:1435-1439 (1992)), valerate (Vanderwinkel et al., *BioChem. Biophys. Res Commun.* 33:902-908 (1968)) and butanoate (Vanderwinkel et al., *BioChem. Biophys. Res Commun.* 33:902-908 (1968)). This enzyme is encoded by atoA (alpha subunit) and atoD (beta subunit) in *E. coli* sp. K12 (Korolev et al., *D Biol Crystallogr.* 58:2116-2121 (2002); and Vanderwinkel et al., *BioChem. Biophys. Res Commun.* 33:902-908 (1968)) and actA and cg0592 in *Corynebacterium glutamicum* ATCC 13032 (Duncan et al., *Appl Environ Microbiol* 68:5186-5190 (2002)). Similar enzymes exist in *Corynebacterium glutamicum* ATCC 13032 (Eikmanns et al., *Mol. Gen. Genet.* 218:330-339 (1989)), *Clostridium acetobutylicum* (Cary et al., *Appl. Environ. Microbiol* 56:1576-1583 (1990); and Wiesenborn et al., *Appl. Environ. Microbiol* 55:323-329 (1989)), and *Clostridium* saccharoperbutylacetonicum (Kosaka et al., *Biosci. Biotechnol BioChem.* 71:58-68 (2007)). These genes/proteins are identified below in Table 114.

TABLE 114

| Gene | GenBank ID | GI Number | Organism |
|---|---|---|---|
| atoA | P76459.1 | 2492994 | *Escherichia coli* |
| atoD | P76458.1 | 2492990 | *Escherichia coli* |
| actA | YP_226809.1 | 62391407 | *Corynebacterium glutamicum* |
| cg0592 | YP_224801.1 | 62389399 | *Corynebacterium glutamicum* |
| ctfA | NP_149326.1 | 15004866 | *Clostridium acetobutylicum* |
| ctfB | NP_149327 | 15004867 | *Clostridium acetobutylicum* |
| ctfA | AAP42564.1 | 31075384 | *Clostridium saccharoperbutylacetonicum* |
| ctfB | AAP42565.1 | 31075385 | *Clostridium saccharoperbutylacetonicum* |

CoA transferase gene candidates described for propionyl-CoA transferase, methylmalonyl-CoA transferase, acetoacetyl-CoA transferase, methacrylyl-CoA transferase, 3-hydroxyisobutyryl-CoA transferase, 4-hydroxybutyryl-CoA transferase and succinyl-CoA transferase are also applicable here.

3-Hydroxybutyryl-CoA Synthetase

3-Hydroxybutyryl-CoA can also be converted to 3-HB by a CoA synthetase (also known as ligase or synthase). A candidate ATP synthase is ADP-forming acetyl-CoA synthetase (ACD, EC 6.2.1.13), an enzyme that couples the conversion of acyl-CoA esters to their corresponding acids with the concurrent synthesis of ATP. Although this enzyme has not been shown to react with 3-hydroxybutyryl-CoA as a substrate, several enzymes with broad substrate specificities have been described in the literature. ACD I from *Archaeoglobus fulgidus*, encoded by AF1211, was shown to operate on a variety of linear and branched-chain substrates including isobutyrate, isopentanoate, and fumarate (Musfeldt et al., *J Bacteriol.* 184:636-644 (2002)). A second reversible ACD in *Archaeoglobus fulgidus*, encoded by AF1983, was also shown to have a broad substrate range with high activity on cyclic compounds phenylacetate and indoleacetate (Musfeldt, et al., *J Bacteriol.* 184:636-644 (2002)). The enzyme from *Haloarcula marismortui* (annotated as a succinyl-CoA synthetase) accepts propionate, butyrate, and branched-chain acids (isovalerate and isobutyrate) as substrates, and was shown to operate in the forward and reverse directions (Brasen et al., *Arch. Microbiol* 182:277-287 (2004)). The ACD encoded by PAE3250 from hyperthermophilic crenarchaeon *Pyrobaculum aerophilum* showed the broadest substrate range of all characterized ACDs, reacting with acetyl-CoA, isobutyryl-CoA (preferred substrate) and phenylacetyl-CoA (Brasen et al., *Arch. Microbiol* 182:277-287 (2004)). However, directed evolution or engineering may be necessary for this enzyme to operate at the physiological temperature of the host organism. The enzymes from *A. fulgidus, H. marismortui* and *P. aerophilum* have all been cloned, functionally expressed, and characterized in *E. coli* (Brasen et al., *Arch. Microbiol* 182:277-287 (2004); and Musfeldt et al., *J Bacteriol.* 184:636-644 (2002)). An additional candidate is the enzyme encoded by sucCD in *E. coli*, which naturally catalyzes the formation of succinyl-CoA from succinate with the concomitant consumption of one ATP, a reaction which is reversible in vivo (Buck et al., *BioChemistry* 24:6245-6252 (1984)). These genes/proteins are identified below in Table 115.

TABLE 115

| Gene | GenBank ID | GI Number | Organism |
|---|---|---|---|
| AF1211 | NP_070039.1 | 11498810 | *Archaeoglobus fulgidus* DSM 4304 |
| AF1983 | NP_070807.1 | 11499565 | *Archaeoglobus fulgidus* DSM 4304 |
| scs | YP_135572.1 | 55377722 | *Haloarcula marismortui* |
| PAE3250 | NP_560604.1 | 18313937 | *Pyrobaculum aerophilum* str. IM2 |
| sucC | NP_415256.1 | 16128703 | *Escherichia coli* |
| sucD | AAC73823.1 | 1786949 | *Escherichia coli* |

CoA synthetase gene candidates described for propionyl-CoA synthetase, methylmalonyl-CoA synthetase, methacrylyl-CoA synthetase, acetoacetyl-CoA synthetase, 3-hydroxyisobutyryl-CoA synthetase, 4-hydroxybutyryl-CoA synthetase and succinyl-CoA synthetase are also applicable here.

3-Hydroxybutyryl-CoA Hydrolase

A 3-hydroxybutyryl-CoA hydrolase is required to convert 3-hydroxybutyryl-CoA to 3-HB. The enzyme 3-hydroxyisobutyryl-CoA hydrolase (EC 3.1.2.4) catalyzes a related transformation: the hydrolysis of 3-hydroxyisobutyryl-CoA. The 3-hydroxyisobutyryl-CoA hydrolase from *Homo sapiens* also accepts 3-hydroxybutyryl-CoA as a substrate (Shimomura et al., *Methods Enzymol.* 324:229-240 (2000)). This enzyme has also been characterized in *Rattus norvegicus* (Shimomura et al., *J Biol Chem.* 269:14248-14253 (1994); and Shimomura et al., *Methods Enzymol.* 324:229-240 (2000)). Candidate genes by sequence homology include hibch of *Saccharomyces cerevisiae* and BC_2292 of *Bacillus* cereus. These proteins are identified below in Table 116. Additional CoA hydrolase enzyme candidates identified for propionyl-CoA hydrolase, methylmalonyl-CoA hydrolase, methacrylyl-CoA hydrolase, acetoacetyl-CoA hydrolase and 3-hydroxyisobutyryl-CoA are also applicable here. These genes/proteins are identified below in Table 116.

TABLE 116

| Gene | GenBank ID | GI Number | Organism |
|---|---|---|---|
| hibch | Q5XIE6.2 | 146324906 | Rattus norvegicus |
| hibch | Q6NVY1.2 | 146324905 | Homo sapiens |
| hibch | P28817.2 | 2506374 | Saccharomyces cerevisiae |
| BC_2292 | AP09256 | 29895975 | Bacillus cereus |

3-Hydroxybutyrate Reductase

The reduction of 3-hydroxybutyrate to 3-hydroxybutyraldehyde is catalyzed by a carboxylic acid reductase. Exemplary enzyme candidates for succinate reductase and 4-hydroxybutyrate reductase enzymes are also applicable here.

4-Hydroxybutyryl-CoA Mutase

The conversion of 4HB-CoA to 3-hydroxyisobutyryl-CoA is catalyzed by a methylmutase. Such a conversion has yet to be demonstrated experimentally. However, two methylmutases (i.e., isobutyryl-CoA mutase and methylmalonyl-CoA mutase) that catalyze similar reactions are promising candidates given the structural similarity of their corresponding substrates.

Methylmalonyl-CoA mutase (MCM) is a cobalamin-dependent enzyme that naturally converts succinyl-CoA to methylmalonyl-CoA. In E. coli, the reversible adenosylcobalamin-dependant mutase participates in a three-step pathway leading to the conversion of succinate to propionate (Haller et al., BioChemistry 39:4622-9 (2000)). MCM is encoded by genes scpA in Escherichia coli (Bobik et al., Anal. Bioanal. Chem. 375:344-349 (2003); and Haller et al., BioChemistry 39:4622-4629 (2000)) and mutA in Homo sapiens (Padovani et al., BioChemistry 45:9300-9306 (2006)). In several other organisms MCM contains alpha and beta subunits and is encoded by two genes. Exemplary gene candidates encoding the two-subunit protein are Propionibacterium freudenreichii sp. shermanii mutA and mutB (Korotkova et al., J Biol Chem. 279:13652-13658 (2004)) and Methylobacterium extorquens mcmA and mcmB (Korotkova et al., J Biol Chem. 279:13652-13658 (2004)). These genes/proteins are identified below in Table 117.

TABLE 117

| Gene | GenBank ID | GI Number | Organism |
|---|---|---|---|
| scpA | NP_417392.1 | 16130818 | Escherichia coli K12 |
| mutA | P22033.3 | 67469281 | Homo sapiens |
| mutA | P11652.3 | 127549 | Propionibacterium freudenreichii sp. shermanii |
| mutB | P11653.3 | 127550 | Propionibacterium freudenreichii sp. shermanii |
| mcmA | Q84FZ1 | 75486201 | Methylobacterium extorquens |
| mcmB | Q6TMA2 | 75493131 | Methylobacterium extorquens |

Additional enzyme candidates identified based on high homology to the E. coli spcA gene product include those identified below in Table 118.

TABLE 118

| Gene | GenBank ID | GI Number | Organism |
|---|---|---|---|
| sbm | NP_838397.1 | 30064226 | Shigella flexneri |
| SARI_04585 | ABX24358.1 | 160867735 | Salmonella enterica |
| YfreA_01000861 | ZP_00830776.1 | 77975240 | Yersinia frederiksenii |

There further exists evidence that genes adjacent to the methylmalonyl-CoA mutase catalytic genes are also required for maximum activity. For example, it has been demonstrated that the meaB gene from M. extorquens forms a complex with methylmalonyl-CoA mutase, stimulates in vitro mutase activity, and possibly protects it from irreversible inactivation (Korotkova et al., J Biol Chem. 279:13652-13658 (2004)). The M. extorquens meaB gene product is highly similar to the product of the E. coli argK gene (BLASTp: 45% identity, e-value: 4e-67) which is adjacent to scpA on the chromosome. No sequence for a meaB homolog in P. freudenreichii is catalogued in GenBank. However, the Propionibacterium acnes KPA171202 gene product at the locus PPA0597 is 51% identical to the M. extorquens meaB protein and its gene is also adjacent to the methylmalonyl-CoA mutase gene on the chromosome. These genes/proteins are identified below in Table 119.

TABLE 119

| Gene | GenBank ID | GI Number | Organism |
|---|---|---|---|
| argK | AAC75955.1 | 1789285 | Escherichia coli K12 |
| PPA0597 | YP_055310.1 | 50842083 | Propionibacterium acnes |
| KPA171202 | 2QM8_B | 158430328 | Methylobacterium extorquens |

Alternatively, isobutyryl-CoA mutase (ICM) could catalyze the proposed transformation. ICM is a cobalamin-dependent methylmutase in the MCM family that reversibly rearranges the carbon backbone of butyryl-CoA into isobutyryl-CoA (FIG. 7B of Ratnatilleke, J Biol Chem. 274:31679-31685 (1999)). A recent study of a novel ICM in Methylibium petroleiphilum, along with previous work, provides evidence that changing a single amino acid near the active site alters the substrate specificity of the enzyme (Ratnatilleke et al., J Biol Chem. 274:31679-31685 (1999); and Rohwerder et al., Appl Environ Microbiol 72:4128-4135 (2006)). This implies that if a native enzyme is unable to catalyze the conversion of 4HB-CoA to 3HIB-CoA, the enzyme could undergo rational engineering. Exemplary ICM genes encoding homodimeric enzymes include icmA in Streptomyces coelicolor A3 (2) and Mpe_B0541 in Methylibium petroleiphilum PM1 (Ratnatilleke et al., J Biol Chem. 274:31679-31685 (1999); and Rohwerder et al., Appl Environ Microbiol 72:4128-4135 (2006)). Genes encoding heterodimeric enzymes include icm and icmB in Streptomyces cinnamonensis (Ratnatilleke, et al., J Biol Chem. 274:31679-31685 (1999); Vrijbloed et al., J Bacteriol. 181:5600-5605 (1999) and Zerbe-Burkhardt et al., J Biol Chem. 273:6508-6517 (1998)). Enzymes encoded by icmA and icmB genes in Streptomyces avermitilis MA-4680 show high sequence similarity to known ICMs. These genes/proteins are identified below in Table 120.

TABLE 120

| Gene | GenBank ID | GI Number | Organism |
|---|---|---|---|
| icmA | CAB40912.1 | 4585853 | Streptomyces coelicolor A3(2) |
| Mpe_B0541 | YP_001023546.1 | 124263076 | Methylibium petroleiphilum PM1 |
| icm | AAC08713.1 | 3002492 | Streptomyces cinnamonensis |
| icmB | CAB59633.1 | 6137077 | Streptomyces cinnamonensis |
| icmA | NP_824008.1 | 29829374 | Streptomyces avermitilis |
| icmB | NP_824637.1 | 29830003 | Streptomyces avermitilis |

3-Hydroxyisobutyryl-CoA Transferase

The next step in this pathway entails the conversion of 3-hydroxyisobutyryl-CoA into 3-hydroxyisobutyrate (3-HIB) by a CoA transferase. An enzyme catalyzing this specific transformation has not been identified to date. The *E. coli* enzyme acyl-CoA:acetate-CoA transferase, also known as acetate-CoA transferase (EC 2.8.3.8), has been shown to transfer the CoA moiety to acetate from a variety of branched and linear acyl-CoA substrates, including isobutyrate (Matthies et al., *Appl Environ Microbiol* 58:1435-1439 (1992)), valerate (Vanderwinkel et al., *BioChem. Biophys. Res Commun.* 33:902-908 (1968)) and butanoate (Vanderwinkel et al., *BioChem. Biophys. Res Commun.* 33:902-908 (1968)). This enzyme is encoded by atoA (alpha subunit) and atoD (beta subunit) in *E. coli* sp. $K_{12}$ (Korolev et al., *D Biol Crystallogr.* 58:2116-2121 (2002); and Vanderwinkel et al., *BioChem. Biophys. Res Commun.* 33:902-908 (1968)) and actA and cg0592 in *Corynebacterium glutamicum* ATCC 13032 (Duncan et al., *Appl Environ Microbiol* 68:5186-5190 (2002)). Similar enzymes exist in *Corynebacterium glutamicum* ATCC 13032 (Eikmanns et al., *Mol. Gen. Genet.* 218:330-339 (1989)), *Clostridium acetobutylicum* (Cary et al., *Appl. Environ. Microbiol* 56:1576-1583 (1990); and Wiesenborn et al., *Appl. Environ. Microbiol* 55:323-329 (1989)), and *Clostridium* saccharoperbutylacetonicum (Kosaka et al., *Biosci. Biotechnol BioChem.* 71:58-68 (2007)). 4-Hydroxybutyryl-CoA transferase enzyme candidates, described previously, are also applicable here. These genes/proteins are identified below in Table 121.

TABLE 121

| Gene | GenBank ID | GI Number | Organism |
|---|---|---|---|
| atoA | P76459.1 | 2492994 | Escherichia coli |
| atoD | P76458.1 | 2492990 | Escherichia coli |
| actA | YP_226809.1 | 62391407 | Corynebacterium glutamicum |
| cg0592 | YP_224801.1 | 62389399 | Corynebacterium glutamicum |
| ctfA | NP_149326.1 | 15004866 | Clostridium acetobutylicum |
| ctfB | NP_149327 | 15004867 | Clostridium acetobutylicum |
| ctfA | AAP42564.1 | 31075384 | Clostridium saccharoperbutylacetonicum |
| ctfB | AAP42565.1 | 31075385 | Clostridium saccharoperbutylacetonicum |

3-Hydroxyisobutyryl-CoA Synthetase

3-Hydroxyisobutyryl-CoA can also be converted to 3-HIB by a CoA synthetase (also known as ligase or synthase). A candidate ATP synthase is ADP-forming acetyl-CoA synthetase (ACD, EC 6.2.1.13), an enzyme that couples the conversion of acyl-CoA esters to their corresponding acids with the concurrent synthesis of ATP. Although this enzyme has not been shown to react with 3-hydroxyisobutyryl-CoA as a substrate, several enzymes with broad substrate specificities have been described in the literature. ACD I from *Archaeoglobus fulgidus*, encoded by AF1211, was shown to operate on a variety of linear and branched-chain substrates including isobutyrate, isopentanoate, and fumarate (Musfeldt et al., *J Bacteriol.* 184:636-644 (2002)). A second reversible ACD in *Archaeoglobus fulgidus*, encoded by AF1983, was also shown to have a broad substrate range with high activity on cyclic compounds phenylacetate and indoleacetate (Musfeldt, et al., *J Bacteriol.* 184:636-644 (2002)). The enzyme from *Haloarcula marismortui* (annotated as a succinyl-CoA synthetase) accepts propionate, butyrate, and branched-chain acids (isovalerate and isobutyrate) as substrates, and was shown to operate in the forward and reverse directions (Brasen et al., *Arch. Microbiol* 182:277-287 (2004)). The ACD encoded by PAE3250 from hyperthermophilic crenarchaeon *Pyrobaculum aerophilum* showed the broadest substrate range of all characterized ACDs, reacting with acetyl-CoA, isobutyryl-CoA (preferred substrate) and phenylacetyl-CoA (Brasen et al., *Arch. Microbiol* 182:277-287 (2004)). However, directed evolution or engineering may be necessary for this enzyme to operate at the physiological temperature of the host organism. The enzymes from *A. fulgidus*, *H. marismortui* and *P. aerophilum* have all been cloned, functionally expressed, and characterized in *E. coli* (Brasen et al., *Arch. Microbiol* 182:277-287 (2004); and Musfeldt et al., *J Bacteriol.* 184:636-644 (2002)). An additional candidate is the enzyme encoded by sucCD in *E. coli*, which naturally catalyzes the formation of succinyl-CoA from succinate with the concomitant consumption of one ATP, a reaction which is reversible in vivo (Buck et al., *BioChemistry* 24:6245-6252 (1984)). These genes/proteins are identified below in Table 122.

TABLE 122

| Gene | GenBank ID | GI Number | Organism |
|---|---|---|---|
| AF1211 | NP_070039.1 | 11498810 | Archaeoglobus fulgidus DSM 4304 |
| AF1983 | NP_070807.1 | 11499565 | Archaeoglobus fulgidus DSM 4304 |
| scs | YP_135572.1 | 55377722 | Haloarcula marismortui |
| PAE3250 | NP_560604.1 | 18313937 | Pyrobaculum aerophilum str. IM2 |
| sucC | NP_415256.1 | 16128703 | Escherichia coli |
| sucD | AAC73823.1 | 1786949 | Escherichia coli |

3-Hydroxyisobutyryl-CoA Hydrolase

The enzyme 3-hydroxyisobutyryl-CoA hydrolase selectively converts 3-hydroxyisobutyryl-CoA to 3-HIB during valine degradation (Shimomura et al., *J Biol Chem* 269:14248-53 (1994)). Genes encoding this enzyme were described previously. 3-Hydroxybutyryl-CoA hydrolase and propionyl-CoA gene candidates, described previously, are also applicable here.

3-Hydroxyisobutyrate Dehydratase

The dehydration of 3-hydroxyisobutyrate to methylacrylic acid is catalyzed by an enzyme with 3-hydroxyisobutyrate dehydratase activity. No direct evidence for this specific enzymatic transformation has been identified. However, most dehydratases catalyze the alpha, beta-elimination of water which involves activation of the alpha-hydrogen by an electron-withdrawing carbonyl, carboxylate, or CoA-thiol ester group and removal of the hydroxyl group from the beta-position (Buckel et al., *J Bacteriol.* 117:1248-1260 (1974); and Martins, et al., *Proc Natl Acad Sci USA* 101:15645-9 (2004)). This is the exact type of transformation proposed for the final step in the methylacrylic acid pathway. The proposed transformation is highly similar to the 2-(hydroxymethyl) glutarate dehydratase of *Eubacterium barkeri* (FIG. 3A). This enzyme has been studied in the context of nicotinate catabolism and is encoded by hmd (Alhapel et al., *Proc Natl Acad Sci USA* 103:12341-6 (2006)). An enzyme with similar functionality in *E. barkeri* is dimethylmaleate hydratase, a reversible $Fe^{2+}$-dependent and oxygen-sensitive enzyme in the aconitase family that hydrates dimethylmaleate to form (2R,3S)-2,3-dimethylmalate. This enzyme is encoded by dmdAB (Alhapel et al., *Proc Natl Acad Sci USA* 103:12341-6 (2006); and Kollmann-Koch et al., *Hoppe Seylers. Z. Physiol Chem.* 365:847-857 (1984)). These genes/proteins are identified below in Table 123.

TABLE 123

| Gene | GenBank ID | GI Number | Organism |
|---|---|---|---|
| hmd | ABC88407.1 | 86278275 | Eubacterium barkeri |
| dmdA | ABC88408 | 86278276 | Eubacterium barkeri |
| dmdB | ABC88409.1 | 86278277 | Eubacterium barkeri |

An additional enzyme candidate is 2-methylmalate dehydratase, also called citramalate hydrolyase, a reversible hydrolyase that catalyzes the alpha, beta elimination of water from citramalate to form mesaconate. This enzyme has been studied in *Methanocaldococcus jannaschii* in the context of the pyruvate pathway to 2-oxobutanoate, where it has been shown to have a broad substrate specificity (Drevland et al., *J Bacteriol.* 189:4391-4400 (2007)). This enzyme activity was also detected in *Clostridium tetanomorphum, Morganella morganii, Citrobacter amalonaticus* where it is thought to participate in glutamate degradation (Kato et al., *Arch. Microbiol* 168:457-463 (1997)). The *M. jannaschii* protein sequence does not bear significant homology to genes in these organisms. This genes/proteins is identified below in Table 124.

TABLE 124

| Gene | GenBank ID | GI Number | Organism |
|---|---|---|---|
| leuD | Q58673.1 | 3122345 | Methanocaldococcus jannaschii |

Fumarate hydratase enzymes, which naturally catalyze the dehydration of malate to fumarate, represent an additional set of candidates. Although the ability of fumarate hydratase to react on 3-hydroxyisobutyrate as a substrate has not been described, a wealth of structural information is available for this enzyme and other researchers have successfully engineered the enzyme to alter activity, inhibition and localization (Weaver, *D Biol Crystallogr.* 61:1395-1401 (2005)). *E. coli* has three fumarases: FumA, FumB, and FumC that are regulated by growth conditions. FumB is oxygen sensitive and only active under anaerobic conditions. FumA is active under microanaerobic conditions, and FumC is the only active enzyme in aerobic growth (Guest et al., *J Gen Microbiol* 131:2971-2984 (1985); Tseng et al., *J Bacteriol* 183:461-467 (2001) and Woods et al., *Biochim Biophys Acta* 954:14-26 (1988)). Additional enzyme candidates are found in *Campylobacter jejuni* (Smith et al., *Int. J BioChem. Cell Biol* 31:961-975 (1999)), *Therms thermophilus* (Mizobata et al., *Arch. BioChem. Biophys.* 355:49-55 (1998)) and *Rattus norvegicus* (Kobayashi et al., *J BioChem.* 89:1923-1931 (1981)). The MmcBC fumarase from *Pelotomaculum thermopropionicum* is another class of fumarase with two subunits (Shimoyama et al., *FEMS Microbiol Lett* 270:207-213 (2007)). These genes/proteins are identified below in Table 125.

TABLE 125

| Gene | GenBank ID | GI Number | Organism |
|---|---|---|---|
| fumA | P0AC33 | 81175318 | Escherichia coli K12 |
| fumB | P14407 | 33112655 | Escherichia coli K12 |
| fumC | P05042.1 | 120601 | Escherichia coli K12 |
| fumC | O69294.1 | 9789756 | Campylobacter jejuni |
| fumC | P84127 | 75427690 | Thermus thermophilus |
| fumH | P14408.1 | 120605 | Rattus norvegicus |
| MmcB | YP_001211906 | 147677691 | Pelotomaculum thermopropionicum |
| MmcC | YP_001211907 | 147677692 | Pelotomaculum thermopropionicum |

3-Hydroxyisobutyryl-CoA Dehydratase

Dehydration of 3-hydroxyisobutyryl-CoA by a CoA dehydratase yields methacrylyl-CoA. Enoyl-CoA hydratases (EC 4.2.1.17) catalyze the dehydration of 3-hydroxyacyl-CoA substrates (Agnihotri and Liu., *J. Bacteriol.* 188:8551-8559 (2003); Conrad et al., *J. Bacteriol.* 118:103-111 (1974); and Roberts et al., *Arch. Microbiol* 117:99-108 (1978)). The enoyl-CoA hydratase (ECH) found in bovine liver accepts a variety of substrates including methacrylyl-CoA, 2- and 3-methyl-crotonoyl-CoA, acryloyl-CoA and 1-carboxycyclohexenoyl-CoA (Agnihotri et al., *Bioorg Med Chem.,* 11(1):9-20 (2003)). A recombinant bovine liver ECH enzyme has been overexpressed in *E. coli* and found to have similar catalytic properties (Dakoji et al., *J Am Chem Soc.,* 123:9749 (2001)). The enoyl-CoA hydratase of *Pseudomonas putida*, encoded by ech, catalyzes the conversion of 3-hydroxybutyryl-CoA to crotonoyl-CoA (Roberts et al., *Arch. Microbiol* 117:99-108 (1978)). Additional enoyl-CoA hydratase candidates are phaA and phaB, of *P. putida*, and paaA and paaB from *P. fluorescens* (Olivera et al., *Proc. Natl. Acad. Sci U.S.A* 95:6419-6424 (1998)). The gene product of pimF in *Rhodopseudomonas palustris* is predicted to encode an enoyl-CoA hydratase that participates in pimeloyl-CoA degradation (Harrison and Harwood, *Microbiology* 151:727-736 (2005)). Lastly, a number of *Escherichia coli* genes have been shown to demonstrate enoyl-CoA hydratase functionality including maoC (Park and Lee, *J. Bacteriol.* 185:5391-5397 (2003)), paaF (Ismail et al., *J Biochem.* 270:3047-3054 (2003); Park and Lee, *Appl. Biochem. Biotechnol* 113-116: 335-346 (2004); and Park and Yup, *Biotechnol Bioeng* 86:681-686 (2004)) and paaG (Ismail et al., *J Biochem.* 270: 3047-3054 (2003); Park and Lee, *Appl. Biochem. Biotechnol* 113-116:335-346 (2004); and Park and Yup, *Biotechnol Bioeng* 86:681-686 (2004)). These genes/proteins are identified below in Table 126.

TABLE 126

| Gene | GenBank ID | GI Number | Organism |
|---|---|---|---|
| ECHS1 | NP_001020377.2 | 70778822 | Bos taurus |
| ech | NP_745498.1 | 26990073 | Pseudomonas putida |
| paaA | NP_745427.1 | 26990002 | Pseudomonas putida |
| paaB | NP_745426.1 | 26990001 | Pseudomonas putida |
| phaA | ABF82233.1 | 106636093 | Pseudomonas fluorescens |
| phaB | ABF82234.1 | 106636094 | Pseudomonas fluorescens |
| pimF | CAE29158 | 39650635 | Rhodopseudomonas palustris |
| maoC | NP_415905.1 | 16129348 | Escherichia coli |
| paaF | NP_415911.1 | 16129354 | Escherichia coli |
| paaG | NP_415912.1 | 16129355 | Escherichia coli |

Another exemplary enzyme candidate for catalyzing this reaction is crotonase. Gene candidates for this enzyme are described above. Alternatively, the *E. coli* gene products of fadA and fadB encode a multienzyme complex involved in fatty acid oxidation that exhibits enoyl-CoA hydratase activity (Nakahigashi and Inokuchi, *Nucleic Acids Res.* 18:4937 (1990); Yang, *J. Bacteriol.* 173:7405-7406 (1991); and Yang et al., *Biochemistry* 30:6788-6795 (1991)). Knocking out a negative regulator encoded by fadR can be utilized to activate the fadB gene product (Sato et al., *J Biosci. Bioeng* 103:38-44 (2007)). The fadI and fadJ genes encode similar functions and are naturally expressed under anaerobic conditions (Campbell et al., *Mol. Microbiol.* 47:793-805 (2003)). These genes/proteins are identified below in Table 127.

TABLE 127

| Gene | GenBank ID | GI Number | Organism |
| --- | --- | --- | --- |
| fadA | YP_026272.1 | 49176430 | *Escherichia coli* |
| fadB | NP_418288.1 | 16131692 | *Escherichia coli* |
| fadI | NP_416844.1 | 16130275 | *Escherichia coli* |
| fadJ | NP_416843.1 | 16130274 | *Escherichia coli* |
| fadR | NP_415705.1 | 16129150 | *Escherichia coli* |

Methacrylyl-CoA Hydrolase

Conversion of methacrylyl-CoA to MAA is catalyzed by a CoA transferase, synthetase or hydrolase. CoA hydrolase gene candidates described for propionyl-CoA hydrolase, methylmalonyl-CoA hydrolase, acetoacetyl-CoA hydrolase, 3-hydroxybutyryl-CoA hydrolase and 3-hydroxyisobutyryl-CoA hydrolase are also applicable here.

Methacrylyl-CoA Transferase

Conversion of methacrylyl-CoA to MAA is catalyzed by a CoA transferase, synthetase or hydrolase. CoA transferase gene candidates described for propionyl-CoA transferase, methylmalonyl-CoA transferase, acetoacetyl-CoA transferase, 3-hydroxybutyryl-CoA transferase, 3-hydroxyisobutyryl-CoA transferase, 4-hydroxybutyryl-CoA transferase and succinyl-CoA transferase are applicable here.

Methacrylyl-CoA Synthetase

Conversion of methacrylyl-CoA to MAA is catalyzed by a CoA transferase, synthetase or hydrolase. CoA synthetase gene candidates described for propionyl-CoA synthetase, methylmalonyl-CoA synthetase, acetoacetyl-CoA synthetase, 3-hydroxybutyryl-CoA synthetase, 3-hydroxyisobutyryl-CoA synthetase, 4-hydroxybutyryl-CoA synthetase and succinyl-CoA synthetase are applicable here.

Methylmalonyl-CoA Hydrolase

Methylmalonyl-CoA is converted to methylmalonate by methylmalonyl-CoA hydrolase (EC 3.1.2.17). This enzyme, isolated from *Rattus norvegicus* liver, is also active on malonyl-CoA and propionyl-CoA as alternative substrates (Kovachy et al., *J. Biol. Chem.*, 258: 11415-11421 (1983)). The gene associated with this enzyme is not known. Other CoA hydrolase enzyme candidates for propionyl-CoA hydrolase, methacrylyl-CoA hydrolase, acetoacetyl-CoA hydrolase, 3-hydroxybutyryl-CoA hydrolase and 3-hydroxyisobutyryl-CoA hydrolase, described in previous sections, are applicable here.

Methylmalonyl-CoA Transferase

Alternately, methylmalonyl-CoA is converted to methylmalonate by a CoA transferase. CoA transferase gene candidates described for propionyl-CoA transferase, methacrylyl-CoA transferase, acetoacetyl-CoA transferase, 3-hydroxybutyryl-CoA transferase, 3-hydroxyisobutyryl-CoA transferase, 4-hydroxybutyryl-CoA transferase and succinyl-CoA transferase are also applicable here Methylmalonyl-CoA Synthetase Yet another enzyme that forms methylmalonate from methylmalonyl-CoA is methylmalonyl-CoA synthetase. CoA synthetase gene candidates described for propionyl-CoA synthetase, methacrylyl-CoA synthetase, acetoacetyl-CoA synthetase, 3-hydroxybutyryl-CoA synthetase, 3-hydroxyisobutyryl-CoA synthetase, 4-hydroxybutyryl-CoA synthetase and succinyl-CoA synthetase are applicable here.

Methylmalonate Reductase

The reduction of methylmalonate to methylmalonate semialdehyde is catalyzed by a carboxylic acid reductase. Exemplary enzyme candidates for succinate reductase and 4-hydroxybutyrate reductase enzymes are also applicable here.

Throughout this application various publications have been referenced. The disclosures of these publications in their entireties, including GenBank and GI number publications, are hereby incorporated by reference in this application in order to more fully describe the state of the art to which this invention pertains. Although the invention has been described with reference to the examples provided above, it should be understood that various modifications can be made without departing from the spirit of the invention.

What is claimed is:

1. A non-naturally occurring microbial organism having a 1,4-butanediol pathway and an isopropanol pathway, comprising at least one exogenous nucleic acid encoding a 1,4-butanediol pathway enzyme expressed in a sufficient amount to produce 1,4-butanediol and at least one exogenous nucleic acid encoding an isopropanol pathway enzyme expressed in a sufficient amount to produce isopropanol, wherein said 1,4-butanediol pathway comprises:

(1) a succinyl-CoA reductase, a 4-hydroxybutyrate dehydrogenase, a 4-hydroxybutyryl-CoA transferase, a 4-hydroxybutyryl-CoA reductase (aldehyde-forming) and a 4-hydroxybutyraldehyde reductase;

(2) a succinyl-CoA reductase, a 4-hydroxybutyrate dehydrogenase, a 4-hydroxybutyryl-CoA synthetase, a 4-hydroxybutyryl-CoA reductase (aldehyde-forming) and a 4-hydroxybutyraldehyde reductase;

(3) a succinyl-CoA reductase, a 4-hydroxybutyrate dehydrogenase, a 4-hydroxybutyrate reductase and a 4-hydroxybutyraldehyde reductase;

(4) a succinyl-CoA reductase, a 4-hydroxybutyrate dehydrogenase, a 4-hydroxybutyrate kinase, a phosphotrans-4-hydroxybutyrylase, a 4-hydroxybutyryl-CoA reductase (aldehyde-forming) and a 4-hydroxybutyraldehyde reductase; or (5) a succinyl-CoA reductase, a 4-hydroxybutyrate dehydrogenase, a 4-hydroxybutyrate kinase, a 4-hydroxybutyryl-phosphate reductase and a 4-hydroxybutyraldehyde reductase, and wherein said isopropanol pathway comprises:

(6) an acetyl-CoA acetyl thiolase, an acetoacetyl-CoA transferase, an acetoacetate decarboxylase and an isopropanol dehydrogenase;

(7) an acetyl-CoA acetyl thiolase, an acetoacetyl-CoA hydrolase, an acetoacetate decarboxylase and an isopropanol dehydrogenase; or (8) an acetyl-CoA acetyl thiolase, an acetoacetyl-CoA synthetase, an acetoacetate decarboxylase and an isopropanol dehydrogenase.

2. The non-naturally occurring microbial organism of claim 1, further comprising an acetyl-CoA pathway comprising at least one exogenous nucleic acid encoding an acetyl-CoA pathway enzyme expressed in a sufficient amount to produce acetyl-CoA, said acetyl-CoA pathway comprising:

a pyruvate kinase, a pyruvate dehydrogenase, or a pyruvate ferredoxin oxidoreductase.

3. The non-naturally occurring microbial organism of claim 1, further comprising a succinyl-CoA pathway comprising at least one exogenous nucleic acid encoding a succinyl-CoA pathway enzyme expressed in a sufficient amount to produce succinyl-CoA, said succinyl-CoA pathway comprising:

a PEP carboxykinase, a PEP carboxylase, a malate dehydrogenase, a fumarase, a fumarate reductase, a succinyl-CoA transferase or a succinyl-CoA synthetase.

4. The non-naturally occurring microbial organism of claim 3, wherein said succinyl-CoA pathway comprises one, two, three, four, five, six or seven exogenous nucleic acids each encoding a succinyl-CoA pathway enzyme.

5. The non-naturally occurring microbial organism of claim 1, wherein said exogenous nucleic acid is a heterologous nucleic acid.

6. The non-naturally occurring microbial organism of claim 1, wherein said non-naturally occurring microbial organism is in a substantially anaerobic culture medium.

7. A method for producing 1,4-butanediol and isopropanol, comprising culturing a non-naturally occurring microbial organism of claim 1 under conditions and for a sufficient period of time to produce 1,4-butanediol and isopropanol.

8. The method of claim 7, wherein said conditions comprise substantially anaerobic culture conditions.

9. The method of claim 7, wherein said exogenous nucleic acid is a heterologous nucleic acid.

10. The non-naturally occurring microbial organism of claim 1, wherein said microbial organism comprises one, two, three, four or five exogenous nucleic acids each encoding a 1,4-butanediol pathway enzyme.

11. The non-naturally occurring microbial organism of claim 1, wherein said microbial organism comprises one, two, three or four exogenous nucleic acids each encoding a isopropanol pathway enzyme.

12. The non-naturally occurring microbial organism of claim 1, wherein said microbial organism comprises one, two, three, four or five exogenous nucleic acids each encoding a 1,4-butanediol pathway enzyme, and one, two, three or four exogenous nucleic acids each encoding a isopropanol pathway enzyme.

13. The non-naturally occurring microbial organism of claim 12, wherein said microbial organism comprises exogenous nucleic acids encoding each of the enzymes of at least one of the 1,4-butanediol pathway comprising (1)-(5), and exogenous nucleic acids encoding each of the enzymes of at least one of the isopropanol pathway comprising (6)-(8).

14. The non-naturally occurring microbial organism of claim 1, wherein said 1,4-butanediol pathway comprises (1) a succinyl-CoA reductase, a 4-hydroxybutyrate dehydrogenase, a 4-hydroxybutyryl-CoA transferase, a 4-hydroxybutyryl-CoA reductase (aldehyde-forming) and a 4-hydroxybutyraldehyde reductase; and said isopropanol pathway comprises (6) an acetyl-CoA acetyl thiolase, an acetoacetyl-CoA transferase, an acetoacetate decarboxylase and an isopropanol dehydrogenase.

15. The non-naturally occurring microbial organism of claim 1, wherein said 1,4-butanediol pathway comprises (1) a succinyl-CoA reductase, a 4-hydroxybutyrate dehydrogenase, a 4-hydroxybutyryl-CoA transferase, a 4-hydroxybutyryl-CoA reductase (aldehyde-forming) and a 4-hydroxybutyraldehyde reductase; and said isopropanol pathway comprises (7) an acetyl-CoA acetyl thiolase, an acetoacetyl-CoA hydrolase, an acetoacetate decarboxylase and an isopropanol dehydrogenase.

16. The non-naturally occurring microbial organism of claim 1, wherein said 1,4-butanediol pathway comprises (1) a succinyl-CoA reductase, a 4-hydroxybutyrate dehydrogenase, a 4-hydroxybutyryl-CoA transferase, a 4-hydroxybutyryl-CoA reductase (aldehyde-forming) and a 4-hydroxybutyraldehyde reductase; and said isopropanol pathway comprises (8) an acetyl-CoA acetyl thiolase, an acetoacetyl-CoA synthetase, an acetoacetate decarboxylase and an isopropanol dehydrogenase.

17. The non-naturally occurring microbial organism of claim 1, wherein said 1,4-butanediol pathway comprises (2) a succinyl-CoA reductase, a 4-hydroxybutyrate dehydrogenase, a 4-hydroxybutyryl-CoA synthetase, a 4-hydroxybutyryl-CoA reductase (aldehyde-forming) and a 4-hydroxybutyraldehyde reductase; and said isopropanol pathway comprises (6) an acetyl-CoA acetyl thiolase, an acetoacetyl-CoA transferase, an acetoacetate decarboxylase and an isopropanol dehydrogenase.

18. The non-naturally occurring microbial organism of claim 1, wherein said 1,4-butanediol pathway comprises (2) a succinyl-CoA reductase, a 4-hydroxybutyrate dehydrogenase, a 4-hydroxybutyryl-CoA synthetase, a 4-hydroxybutyryl-CoA reductase (aldehyde-forming) and a 4-hydroxybutyraldehyde reductase; and said isopropanol pathway comprises (7) an acetyl-CoA acetyl thiolase, an acetoacetyl-CoA hydrolase, an acetoacetate decarboxylase and an isopropanol dehydrogenase.

19. The non-naturally occurring microbial organism of claim 1, wherein said 1,4-butanediol pathway comprises (2) a succinyl-CoA reductase, a 4-hydroxybutyrate dehydrogenase, a 4-hydroxybutyryl-CoA synthetase, a 4-hydroxybutyryl-CoA reductase (aldehyde-forming) and a 4-hydroxybutyraldehyde reductase; and said isopropanol pathway comprises (8) an acetyl-CoA acetyl thiolase, an acetoacetyl-CoA synthetase, an acetoacetate decarboxylase and an isopropanol dehydrogenase.

20. The non-naturally occurring microbial organism of claim 1, wherein said 1,4-butanediol pathway comprises (3) a succinyl-CoA reductase, a 4-hydroxybutyrate dehydrogenase, a 4-hydroxybutyrate reductase and a 4-hydroxybutyraldehyde reductase; and said isopropanol pathway comprises (6) an acetyl-CoA acetyl thiolase, an acetoacetyl-CoA transferase, an acetoacetate decarboxylase and an isopropanol dehydrogenase.

21. The non-naturally occurring microbial organism of claim 1, wherein said 1,4-butanediol pathway comprises (3) a succinyl-CoA reductase, a 4-hydroxybutyrate dehydrogenase, a 4-hydroxybutyrate reductase and a 4-hydroxybutyraldehyde reductase; and said isopropanol pathway comprises (7) an acetyl-CoA acetyl thiolase, an acetoacetyl-CoA hydrolase, an acetoacetate decarboxylase and an isopropanol dehydrogenase.

22. The non-naturally occurring microbial organism of claim 1, wherein said 1,4-butanediol pathway comprises (3) a succinyl-CoA reductase, a 4-hydroxybutyrate dehydrogenase, a 4-hydroxybutyrate reductase and a 4-hydroxybutyraldehyde reductase; and said isopropanol pathway comprises (8) an acetyl-CoA acetyl thiolase, an acetoacetyl-CoA synthetase, an acetoacetate decarboxylase and an isopropanol dehydrogenase.

23. The non-naturally occurring microbial organism of claim 1, wherein said 1,4-butanediol pathway comprises (4) a succinyl-CoA reductase, a 4-hydroxybutyrate dehydrogenase, a 4-hydroxybutyrate kinase, a phosphotrans-4-hydroxybutyrylase, a 4-hydroxybutyryl-CoA reductase (aldehyde-forming) and a 4-hydroxybutyraldehyde reductase; and said isopropanol pathway comprises (6) an acetyl-CoA acetyl thiolase, an acetoacetyl-CoA transferase, an acetoacetate decarboxylase and an isopropanol dehydrogenase.

24. The non-naturally occurring microbial organism of claim 1, wherein said 1,4-butanediol pathway comprises (4) a succinyl-CoA reductase, a 4-hydroxybutyrate dehydrogenase, a 4-hydroxybutyrate kinase, a phosphotrans-4-hydroxybutyrylase, a 4-hydroxybutyryl-CoA reductase (aldehyde-forming) and a 4-hydroxybutyraldehyde reductase; and said isopropanol pathway comprises (7) an acetyl-CoA acetyl thiolase, an acetoacetyl-CoA hydrolase, an acetoacetate decarboxylase and an isopropanol dehydrogenase.

25. The non-naturally occurring microbial organism of claim 24, wherein said 1,4-butanediol pathway comprises (4) a succinyl-CoA reductase, a 4-hydroxybutyrate dehydrogenase, a 4-hydroxybutyrate kinase, a phosphotrans-4-hydroxybutyrylase, a 4-hydroxybutyryl-CoA reductase (aldehyde-forming) and a 4-hydroxybutyraldehyde reductase; and said isopropanol pathway comprises (8) an acetyl-CoA acetyl thiolase, an acetoacetyl-CoA synthetase, an acetoacetate decarboxylase and an isopropanol dehydrogenase.

26. The non-naturally occurring microbial organism of claim 1, wherein said 1,4-butanediol pathway comprises (5) a succinyl-CoA reductase, a 4-hydroxybutyrate dehydrogenase, a 4-hydroxybutyrate kinase, a 4-hydroxybutyryl-phosphate reductase and a 4-hydroxybutyraldehyde reductase; and said isopropanol pathway comprises (6) an acetyl-CoA acetyl thiolase, an acetoacetyl-CoA transferase, an acetoacetate decarboxylase and an isopropanol dehydrogenase.

27. The non-naturally occurring microbial organism of claim 1, wherein said 1,4-butanediol pathway comprises (5) a succinyl-CoA reductase, a 4-hydroxybutyrate dehydrogenase, a 4-hydroxybutyrate kinase, a 4-hydroxybutyryl-phosphate reductase and a 4-hydroxybutyraldehyde reductase; and said isopropanol pathway comprises (7) an acetyl-CoA acetyl thiolase, an acetoacetyl-CoA hydrolase, an acetoacetate decarboxylase and an isopropanol dehydrogenase.

28. The non-naturally occurring microbial organism of claim 1, wherein said 1,4-butanediol pathway comprises (5) a succinyl-CoA reductase, a 4-hydroxybutyrate dehydrogenase, a 4-hydroxybutyrate kinase, a 4-hydroxybutyryl-phosphate reductase and a 4-hydroxybutyraldehyde reductase; and said isopropanol pathway comprises (8) an acetyl-CoA acetyl thiolase, an acetoacetyl-CoA synthetase, an acetoacetate decarboxylase and an isopropanol dehydrogenase.

* * * * *

SEQUENCE LISTING

```
<160> NUMBER OF SEQ ID NOS: 2

<210> SEQ ID NO 1
<211> LENGTH: 29
<212> TYPE: PRT
<213> ORGANISM: Clostridium saccharobutylicum

<400> SEQUENCE: 1

Met Asp Phe Lys Leu Thr Lys Thr Gln Val Leu Gln Gln Trp Leu Phe
 1               5                  10                  15

Ala Glu Phe Ala Gly Ile Gly Ile Lys Pro Ile Ala Glu
            20                  25

<210> SEQ ID NO 2
<211> LENGTH: 20
<212> TYPE: PRT
<213> ORGANISM: Euglena gracilis
<220> FEATURE:
<223> OTHER INFORMATION: first 20 amino acid from N-terminus from KDC
      gene
```

-continued

```
<400> SEQUENCE: 2

Met Thr Tyr Lys Ala Pro Val Lys Asp Val Lys Phe Leu Leu Asp Lys
1               5                   10                  15

Val Phe Lys Val
            20
```